US007645597B2

(12) United States Patent
Metz et al.

(10) Patent No.: US 7,645,597 B2
(45) Date of Patent: Jan. 12, 2010

(54) PUFA POLYKETIDE SYNTHASE SYSTEMS AND USES THEREOF

(75) Inventors: James G. Metz, Longmont, CO (US); Craig A. Weaver, Boulder, CO (US); William R. Barclay, Boulder, CO (US); James H. Flatt, Colorado Springs, CO (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

(21) Appl. No.: 11/778,608

(22) Filed: Jul. 16, 2007

(65) Prior Publication Data

US 2008/0044871 A1   Feb. 21, 2008

Related U.S. Application Data

(60) Division of application No. 11/676,971, filed on Feb. 20, 2007, which is a division of application No. 10/810,352, filed on Mar. 26, 2004, now Pat. No. 7,211,418, and a continuation-in-part of application No. 10/124,800, filed on Apr. 16, 2002, now Pat. No. 7,247,461, and a continuation-in-part of application No. 09/231,899, filed on Jan. 14, 1999, now Pat. No. 6,566,583.

(60) Provisional application No. 60/457,979, filed on Mar. 26, 2003, provisional application No. 60/284,066, filed on Apr. 16, 2001, provisional application No. 60/298,796, filed on Jun. 15, 2001, provisional application No. 60/323,269, filed on Sep. 18, 2001.

(51) Int. Cl.
C12N 15/53 (2006.01)
C12N 15/74 (2006.01)
C12N 15/79 (2006.01)
C12N 15/82 (2006.01)
C12P 7/64 (2006.01)

(52) U.S. Cl. .................. 435/134; 435/419; 435/189; 435/252.3; 435/320.1; 435/410; 536/23.2

(58) Field of Classification Search .................. None
See application file for complete search history.

(56) References Cited

U.S. PATENT DOCUMENTS 5,130,242 A   7/1992   Barclay et al.

(Continued)

FOREIGN PATENT DOCUMENTS

CA   2520795   10/2004

(Continued)

OTHER PUBLICATIONS

Abbadi et al., Eur. J. Lipid Sci. Technol., 103:106-113 (2001).

(Continued)

*Primary Examiner*—Anand U Desai
*Assistant Examiner*—William W Moore
(74) *Attorney, Agent, or Firm*—Sheridan Ross P.C.

(57) ABSTRACT

The invention generally relates to polyunsaturated fatty acid (PUFA) polyketide synthase (PKS) systems, to homologues thereof, to isolated nucleic acid molecules and recombinant nucleic acid molecules encoding biologically active domains of such a PUFA PKS system, to genetically modified organisms comprising PUFA PKS systems, to methods of making and using such systems for the production of bioactive molecules of interest, and to novel methods for identifying new bacterial and non-bacterial microorganisms having such a PUFA PKS system.

21 Claims, 3 Drawing Sheets

U.S. PATENT DOCUMENTS

| | | |
|---|---|---|
| 5,246,841 A | 9/1993 | Yazawa et al. |
| 5,310,242 A | 5/1994 | Golder |
| 5,639,790 A | 6/1997 | Voelker et al. |
| 5,672,491 A | 9/1997 | Khosia et al. |
| 5,683,898 A | 11/1997 | Yazawa et al. |
| 5,798,259 A | 8/1998 | Yazawa et al. |
| 5,908,622 A | 6/1999 | Barclay |
| 6,033,883 A | 3/2000 | Barr et al. |
| 6,140,486 A | 10/2000 | Facciotti et al. |
| 6,503,706 B1 | 1/2003 | Abken et al. |
| 6,566,583 B1 | 5/2003 | Facciotti et al. |
| 7,001,772 B2 | 2/2006 | Roessler et al. |
| 7,125,672 B2 | 10/2006 | Picataggio et al. |
| 7,211,418 B2 | 5/2007 | Metz et al. |
| 7,214,853 B2 | 5/2007 | Facciotti et al. |
| 7,217,856 B2 | 5/2007 | Weaver et al. |
| 7,256,022 B2 | 8/2007 | Metz et al. |
| 7,256,023 B2 | 8/2007 | Metz et al. |
| 7,259,295 B2 | 8/2007 | Metz et al. |
| 7,271,315 B2 | 9/2007 | Metz et al. |
| 2002/0138874 A1 | 9/2002 | Mukerji et al. |
| 2002/0156254 A1 | 10/2002 | Qiu et al. |
| 2002/0194641 A1 | 12/2002 | Metz et al. |
| 2004/0005672 A1 | 1/2004 | Santi et al. |
| 2004/0010817 A1 | 1/2004 | Shockey et al. |
| 2004/0139498 A1 | 7/2004 | Jaworski et al. |
| 2004/0172682 A1 | 9/2004 | Kinney et al. |
| 2005/0014231 A1 | 1/2005 | Mukerji et al. |
| 2005/0089865 A1 | 4/2005 | Napier et al. |
| 2005/0164192 A1 | 7/2005 | Graham et al. |
| 2007/0244192 A1 | 10/2007 | Metz |
| 2007/0245431 A1 | 10/2007 | Metz et al. |
| 2007/0256146 A1 | 11/2007 | Metz et al. |
| 2007/0270494 A1 | 11/2007 | Metz et al. |
| 2008/0022422 A1 | 1/2008 | Weaver et al. |
| 2008/0026434 A1 | 1/2008 | Weaver et al. |
| 2008/0026435 A1 | 1/2008 | Weaver et al. |
| 2008/0026438 A1 | 1/2008 | Metz et al. |
| 2008/0026439 A1 | 1/2008 | Metz et al. |
| 2008/0026440 A1 | 1/2008 | Metz et al. |
| 2008/0032351 A1 | 2/2008 | Metz et al. |
| 2008/0038378 A1 | 2/2008 | Metz et al. |
| 2008/0038379 A1 | 2/2008 | Metz et al. |
| 2008/0038790 A1 | 2/2008 | Metz et al. |
| 2008/0038791 A1 | 2/2008 | Metz et al. |
| 2008/0038792 A1 | 2/2008 | Metz et al. |
| 2008/0038793 A1 | 2/2008 | Metz et al. |
| 2008/0038794 A1 | 2/2008 | Metz et al. |
| 2008/0038795 A1 | 2/2008 | Metz et al. |
| 2008/0038796 A1 | 2/2008 | Metz et al. |
| 2008/0038797 A1 | 2/2008 | Metz et al. |
| 2008/0040822 A1 | 2/2008 | Metz et al. |
| 2008/0044867 A1 | 2/2008 | Metz et al. |
| 2008/0044868 A1 | 2/2008 | Metz et al. |
| 2008/0044869 A1 | 2/2008 | Metz et al. |
| 2008/0044870 A1 | 2/2008 | Metz et al. |
| 2008/0044872 A1 | 2/2008 | Metz et al. |
| 2008/0044873 A1 | 2/2008 | Metz et al. |
| 2008/0050790 A1 | 2/2008 | Metz et al. |
| 2008/0148433 A1 | 6/2008 | Metz et al. |

FOREIGN PATENT DOCUMENTS

| | | |
|---|---|---|
| EP | 0594868 | 5/1994 |
| EP | 0823475 | 2/1998 |
| WO | 9323545 | 11/1993 |
| WO | 9621735 | 7/1996 |
| WO | 9846764 | 10/1998 |
| WO | 9855625 | 12/1998 |
| WO | 0042195 | 7/2000 |
| WO | WO 02/083870 | 10/2002 |
| WO | WO 2004/087879 | 10/2004 |
| WO | WO 2006/008099 | 1/2006 |
| WO | WO 2006/034228 | 3/2006 |

OTHER PUBLICATIONS

Allen et al., Appl. Envir. Microbiol., 65(4):1710-1720 (1999).
Bateman et al., Nucl. Acids Res., 30(1):276-280 (2002).
Bentley et al., Annu. Rev. Microbiol., 53:411-46 (1999).
Bisang et al., Nature, 401:502-505 (1999).
Bork, TIG, 12(10):425-427 (1996).
Brenner, TIG, 15(4):132-133 (1999).
Broun et al., Science, 282:1315-1317 (1998).
Creelman et al., Annu. Rev. Plan Physiol. Plant Mol. Biol., 48:355-81 (1997).
DeLong & Yayanos, Appl. Environ. Microbiol., 51(4):730-737 (1986).
Doerks, TIG, 14(6):248-250 (1998).
Facciotti et al., "Cloning and Characterization of Polyunsaturated Fatty Acids (PUFA) Genes from Marine Bacteria" in Proceedings of the international symposium on progress and prospect of marine biotechnology (China Ocean Pres 1999), pp. 404-405 Abstract.
Heath et al., J. Biol. Chem., 271(44):27795-27801 (1996).
Hopwood & Sherman, Annu. Rev. Genet., 24:37-66 (1990).
Hutchinson, Annu. Rev. Microbiol., 49:201-238 (1995).
Jostensen & Landfald, FEMS Microbiology Letters, 151:95-101 (1997).
Katz & Donadio, Annu. Rev. Microbiol., 47:875-912 (1993).
Kealing et al., Curr. Opin. Chem. Biol., 3:598-606 (1999).
Kyle et al., HortScience, 25:1523-26 (1990).
Magnuson, Microbil. Rev., 57(3):522-542 (1993) Abstract.
Metz et al., Science, 293:290-293 (2001).
Nakahara, Yukagaku, 44(10):821-7 (1995).
Nasu et al., J. Ferment. Bioeng., 122:467-473 (1997).
Nichols et al., Curr. Opin Biotechnol., 10:240-246 (1999).
Nogi et al., Extremophiles, 2:1-7 (1998).
Parker-Barnes et al., PNAS, 97(15):8284-8289 (2000).
Sánchez et al., Chemistry & Biolosy, 8:725-738 (2001).
Shanklin et al., Annu. Rev. Plant Physiol. Plant Mol. Biol., 49:611-41 (1998).
Smith et al., Nature Biotechnol., 15:1222-1223 (1997).
Somerville Am. J. Clin. Nutr., 58(2 supp):270S-275S (1993).
Van de Loo, Proc. Natl. Acad. Sci. USA, 92:6743-6747 (1995).
Watanabe et al., J. Biochem., 122:467-473 (1997).
Yalpani et al., The Plant Cell, 13:1401-1409 (2001).
Yazawa, Lipids, 31(supp):S297-S300 (1996).
Metz et al. Production of Polyunsaturated Fatty Acids by Polyketide Synthase in Both Prokaryotes and Eukaryotes. Science Jul. 12, 2001, vol. 293, pp. 290-293.
Qiu et al. Identification of a delta4 fatty acid desaturase from *Thraustochytrium* sp. involved in the biosynthesis. J. Biol. Chem. Aug. 24, 2001, vol. 276, No. 34, pp. 31561-31566.
Yokochi et al. Optimization of docosahexaenoic acid production. App. Microbiol. Biotechnol. 1998, vol. 49, pp. 72-76.
Nakahara et al. Production of docosahexaenoic and docosapentaenoic acids by *Schizochytrium* sp. isolated from Yap Islands. 1996 J. Am. Oil Chem. Soc. 1996, vol. 73, No. 11, pp. 1421-1426.
Weete et al. Lipids and Ultrasctructure of *Thrauchytrium* sp. ATCC26185. 1997, Am Oil Chem. Soc. vol. 32, No. 8, pp. 839-845.
Singh et al. Microbial Production of Docosahexaenoic Acid (DHA, C22:6) Adv. Appl. Microbial, 1997. vol. 45, pp. 271-312.
Napier, Trends Plant Sci. Feb. 2002; 7(2): 51-4.
International Search Report for International (PCT) Patent Application No. PCT/US04/09323, mailed Apr. 4, 2007.
Written Opinion for International (PCT) Patent Application No. PCT/US04/09323, mailed Apr. 4, 2007.
International Preliminary Report on Patentability for International (PCT) Patent Application No. PCT/US04/09323, mailed May 9, 2007.
Examiner's First Report for Australian Patent Application No. 2004225485, mailed Nov. 17, 2006.

First Examination Report for Indian Patent Application No. 4359/DELNP/2005, dated Mar. 14, 2007.
U.S. Appl. No. 11/674,574, Facciotti et al. (Feb. 13, 2007).
U.S. Appl. No. 11/777,277, Metz et al. (Jul. 12, 2007).
U.S. Appl. No. 11/778,594, Metz et al. (Jul. 16, 2007).
Allen E.A. et al. 2002 "Structure and regulation of the omega-3 polyunsaturated fatty acid synthase genes from the deep-sea bacterium *Photobacterium profundum* strain SS9" Microbiology vol. 148 pp. 1903-1913.
Cane et al., "Harnessing the Biosynthetic Code: Combinations, Permutations, and Mutations." Science 1998, vol. 282, pp. 63-68.
Chuck et al., "Molecular recognition of diketide substrates by a beta-ketoacyl-acyl carrier protein synthase domain within a bimodular polyketide synthase", Chem and Bio, Current Bio, (London), GB,, vol. 4, No. 10, 1997, pp. 757-766, XP000884721.
Database Geneseq 'Online! Dec. 11, 2000,"S. aggregatum PKS cluster ORF6 homolog DNA." XP002368912, retrieved from EBI accession No. GSN:AAA71567Database accession No. AAA71567—& Database Geneseq 'Online! Dec. 11, 2000, "S. aggregatum PKS cluster ORF6 homolog protein." XP002368914 retrieved from EBI accession No. GSP:AAB10482 Database accession No. AAB10482 & WO 00/42195 A (Calgene, LLC) Jul. 20, 2000.
GenBank Accession No. AF4091 00, (Allen et al.) 2002.
GenBank Accession No. U09865. Alcaligenes eutrophus pyruvate dehydrogenase (pdhA), dihydrolipoamide acetyltransferase (pdhB), dihydrolipoamide dehydrogenase (pdhL), and ORF3 genes, complete cds (1994).
Harlow et al. Antibodies: A Laboratory Manual (1988) Cold Spring Harbor Laboratory Press, p. 76.
Jez et al., "Structural control of polyketide formation in plant-specific polyketide synthases", Chem and Bio (London), vol. 7, No. 12, Dec. 2000, pp. 919-930, XP002338564.
Kaulmann et al. "Biosynthesis of Polyunsaturated Fatty Acids by Polyketide Synthases", Angew. Chem. Int. Ed. 2002, 41, No. 11, pp. 1866-1869.
Kealey et al., "Production of a polyketide natural product in non-polyketide-producing prokaryotic and eukaryotic hosts", Proceedings of the Natural Academy of Sciences of the United States of America, vol. 95, No. 2, Jan. 20, 1998, pp. 505-509, XP002338563.
Khosla et al., "Tolerance and Specificity of Polyketide Synthases", Annu. Rev. Biochem. 1999. 68:219-253.
Leadlay PF. "Combinatorial Approaches to Polyketides Biosynthesis" Current Opinion in Chemical Biology (1997) 1: 162-168.
Nasu et al., "Efficient Transformation of *Marchantia polymorpha* That is Haploid and Has Very Small Genome DNA," Journal of Fermentation and Bioengineering vol. 84, No. 6, 519-523 1997.
Nicholson et al., "Design and utility of oligonucleotide gene probes for fungal polyketide synthases", Chem & Bio (London) vol. 8, No. 2, Feb. 2001, pp. 157-178, XP002338562.
Oliynuk et al. "A hybrid modular polyketide synthase obtained by domain swapping." Chemistry & Biology (1996) 3: 833-839.
Orikasa et al. Characterization of the eicosapentaenoic acid biosynthesis gene cluster from *Shewanella* sp. strain SCRC-2738, Cellular and Molecular Biology (Noisy-le-grand), Jul. 2004, vol. 50, No. 5, pp. 625-630.
Satomi et al. *Shewanelia marinintesina* sp. nov., *Shewanella schlegeliana* sp. nov. and *Shewanelia sairae* sp. nov., novel eicosapentaenoic-acid-producing marine bacteria isolated from see-animal intestines. Internat. J. Syst. Evol. Microbiol. 2003, vol. 53, pp. 491-499.
Takeyama et al. Expression of eicosapentaenoic acid synthesis gene clustter from *Shewanella* sp. in transgenic marine cyanobacterium. *Synechecoccus* sp. Microbiology. 1997, vol. 143, pp. 2725-2731.
UniProt Accession No. Q93CG6_PHOPR, (Allen et al.) 2002.
Wallis et al., "Polyunsaturated fatty acid synthesis: what will they think of next?", Tibs Trends in Bio Sciences, Elsevier Publ., Cambridge, EN, vol. 27, No. 9, Sep. 2002, pp. 467-473, XP004378766.
Wiesmann et al. "The molecular basis of Celmer's rules: the stereochemistry of the condensation step in chain extension on the erythromycin polyketide synthase." Biochemistry (1997) 36: 13849-13855.
Wiesmann et al. "Origin of starter units for erythromycin biosynthesis." Biochemistry (1998) 37: 11012-11017.
Wiesmann et al. "Polyketide synthesis in vitro on a modular polyketide synthase." Chemistry & Biology (Sep. 1995) 2: 583-589.
International Search Report for International (PCT) Patent Application No. PCT/US02/12254, mailed Nov. 15, 2002.
International Preliminary Examination Report for International (PCT) Patent Application No. PCT/US02/12254, mailed Oct. 16, 2006.
International Search Report for International (PCT) Patent Application No. PCT/US00/00956, mailed Jul. 6, 2000.
Written Opinion for International (PCT) Patent Application No. PCT/US00/00956, mailed Dec. 19, 2000.
International Preliminary Examination Report for International (PCT) Patent Application No. PCT/US00/00956, mailed Apr. 19, 2001.
International Search Report for International (PCT) Patent Application No. PCT/US05/36998, mailed Mar. 22, 2007.
Written Opinion for International (PCT) Patent Application No. PCT/US05/36998, mailed Mar. 22, 2007.
International Search Report for International (PCT) Patent Application No. PCT/US08/63835, mailed Nov. 3, 2008.
Written Opinion for International (PCT) Patent Application No. PCT/US08/63835, mailed Nov. 3, 2008.
International Search Report for International (PCT) Patent Application No. PCT/US06/22893, mailed Feb. 29, 2008.
Written Opinion for International (PCT) Patent Application No. PCT/US06/22893, mailed Feb. 29, 2008.
International Search Report for International (PCT) Patent Application No. PCT/US07/64105, mailed Nov. 23, 2007.
Written Opinion for International (PCT) Patent Application No. PCT/US07/64105, mailed Nov. 23, 2007.
International Preliminary Report on Patentability for International (PCT) Patent Application No. PCT/US07/64105, mailed Sep. 25, 2008.
International Search Report for International (PCT) Patent Application No. PCT/US07/64104, mailed Dec. 5, 2008.
Written Opinion for International (PCT) Patent Application No. PCT/US07/64104, mailed Dec. 5, 2008.
International Search Report for International (PCT) Patent Application No. PCT/US2007/064106, mailed Sep. 16, 2008.
Written Opinion for International (PCT) Patent Application No. PCT/US2007/064106, mailed Sep. 16, 2008.
International Preliminary Report on Patentability for International (PCT) Patent Application No. PCT/US2007/064106, mailed Oct. 30, 2008.
Fan K W et al: "Eicosapentaenoic and docosahexaenoic acids production by and okara-utilizing potential of thraustochytrids" Journal of Industrial Microbiology and Biotechnology, Basingstoke, GB, vol. 27, No. 4, Oct. 1, 2001 (Oct. 1, 2001), pp. 199-202, XP002393382 ISSN: 1367-5435.
Wolff et al, Arachidonic, Eicosapentaenoic and Biosynthetically Related Fatty Acids in Seed Lipids from a primitive Gymnosperm, *Agathis robusta*. Lipids 34(10), 1994, 1083-1097.
Grimsley et al, "Fatty acid composition of mutants of the moss *Physcomitrella patens*" Phytochemistry 20(7): 1519-1524, 1981.
Bedford et al, "A functional chimeric modular polyketide synthase generated via domain replacement." Chemistry & Biology 3: 827-831, Oct 1996.

Comparison of PKS Orfs/domains:
*Schizochytrium* vs *Shewanella*

Amino acid sequence homology

■ = 20-35%   ▨ = 35-50%   ▧ = > 50%

PUFA POLYKETIDE SYNTHASE SYSTEMS AND USES THEREOF

CROSS-REFERENCE TO RELATED APPLICATIONS

This application is a divisional of U.S. application Ser. No. 11/676,971, filed Feb. 20, 2007, which is a divisional of U.S. application Ser. No. 10/810,352, filed Mar. 26, 2004, now U.S. Pat. No. 7,211,418, which claims the benefit of priority under 35 U.S.C. § 119(e) from U.S. Provisional Application Ser. No. 60/457,979, filed Mar. 26, 2003, entitled "Modification of a *Schizochytrium* PKS System to Facilitate Production of Lipids Rich in Polyunsaturated Fatty Acids". U.S. application Ser. No. 10/810,352 is also a continuation-in-part of U.S. patent application Ser. No. 10/124,800, filed Apr. 16, 2002, now U.S. Pat. No. 7,247,461, which claims the benefit of priority under 35 U.S.C. § 119(e) to: U.S. Provisional Application Ser. No. 60/284,066, filed Apr. 16, 2001; U.S. Provisional Application Ser. No. 60/298,796, filed Jun. 15, 2001; and U.S. Provisional Application Ser. No. 60/323,269, filed Sep. 18, 2001. U.S. patent application Ser. No. 10/124,800, supra, is also a continuation-in-part of U.S. application Ser. No. 09/231,899, filed Jan. 14, 1999, now U.S. Pat. No. 6,566,583. Each of the above-identified patent applications is incorporated herein by reference in its entirety.

This application does not claim the benefit of priority from U.S. application Ser. No. 09/090,793, filed Jun. 4, 1998, now U.S. Pat. No. 6,140,486, although U.S. application Ser. No. 09/090,793 is incorporated herein by reference in its entirety.

REFERENCE TO SEQUENCE LISTING

This application contains a Sequence Listing submitted as an electronic text file named "Sequence_Listing.txt", having a size in bytes of 593 kb, and created on 26 Mar. 2004. The information contained in this electronic file is hereby incorporated by reference in its entirety pursuant to 37 CFR §1.52 (e)(5).

FIELD OF THE INVENTION

This invention relates to polyunsaturated fatty acid (PUFA) polyketide synthase (PKS) systems from microorganisms, including eukaryotic organisms, such as Thraustochytrid microorganisms. More particularly, this invention relates to nucleic acids encoding non-bacterial PUFA PKS systems, to non-bacterial PUFA PKS systems, to genetically modified organisms comprising non-bacterial PUFA PKS systems, and to methods of making and using the non-bacterial PUFA PKS systems disclosed herein. This invention also relates to genetically modified microorganisms and methods to efficiently produce lipids (triacylglycerols (TAG), as well as membrane-associated phospholipids (PL)) enriched in various polyunsaturated fatty acids (PUFAs) and particularly, eicosapentaenoic acid (C20:5, ω-3; EPA) by manipulation of a PUFA polyketide synthase (PKS) system.

BACKGROUND OF THE INVENTION

Polyketide synthase (PKS) systems are generally known in the art as enzyme complexes derived from fatty acid synthase (FAS) systems, but which are often highly modified to produce specialized products that typically show little resemblance to fatty acids. It has now been shown, however, that polyketide synthase systems exist in marine bacteria and certain microalgae that are capable of synthesizing PUFAs from malonyl-CoA. The PKS pathways for PUFA synthesis in *Shewanella* and another marine bacteria, *Vibrio marinus*, are described in detail in U.S. Pat. No. 6,140,486. The PKS pathways for PUFA synthesis in the eukaryotic Thraustochytrid, *Schizochytrium* is described in detail in U.S. Pat. No. 6,566,583. Finally, the PKS pathways for PUFA synthesis in eukaryotes such as members of Thraustochytriales, including the complete structural description of the PUFA PKS pathway in *Schizochytrium* and the identification of the PUFA PKS pathway in *Thraustochytrium*, including details regarding uses of these pathways, are described in detail in U.S. Patent Application Publication No. 20020194641, published Dec. 19, 2002 (corresponding to U.S. patent application Ser. No. 10/124,800, filed Apr. 16, 2002).

Researchers have attempted to exploit polyketide synthase (PKS) systems that have been described in the literature as falling into one of three basic types, typically referred to as: Type II, Type I and modular. The Type II system is characterized by separable proteins, each of which carries out a distinct enzymatic reaction. The enzymes work in concert to produce the end product and each individual enzyme of the system typically participates several times in the production of the end product. This type of system operates in a manner analogous to the fatty acid synthase (FAS) systems found in plants and bacteria. Type I PKS systems are similar to the Type II system in that the enzymes are used in an iterative fashion to produce the end product. The Type I differs from Type II in that enzymatic activities, instead of being associated with separable proteins, occur as domains of larger proteins. This system is analogous to the Type I FAS systems found in animals and fungi.

In contrast to the Type I and II systems, in modular PKS systems, each enzyme domain is used only once in the production of the end product. The domains are found in very large proteins and the product of each reaction is passed on to another domain in the PKS protein. Additionally, in all of the PKS systems described above, if a carbon-carbon double bond is incorporated into the end product, it is always in the trans configuration.

In the Type I and Type II PKS systems described above, the same set of reactions is carried out in each cycle until the end product is obtained. There is no allowance for the introduction of unique reactions during the biosynthetic procedure. The modular PKS systems require huge proteins that do not utilize the economy of iterative reactions (i.e., a distinct domain is required for each reaction). Additionally, as stated above, carbon-carbon double bonds are introduced in the trans configuration in all of the previously described PKS systems.

Polyunsaturated fatty acids (PUFAs) are critical components of membrane lipids in most eukaryotes (Lauritzen et al., *Prog. Lipid Res.* 40 1 (2001); McConn et al., *Plant J.* 15, 521 (1998)) and are precursors of certain hormones and signaling molecules (Heller et al., *Drugs* 55, 487 (1998); Creelman et al., *Annu. Rev. Plant Physiol. Plant Mol. Biol.* 48, 355 (1997)). Known pathways of PUFA synthesis involve the processing of saturated 16:0 or 18:0 fatty acids (the abbreviation X:Y indicates an acyl group containing X carbon atoms and Y double bonds (usually cis in PUFAs); double-bond positions of PUFAs are indicated relative to the methyl carbon of the fatty acid chain (ω3 or ω6) with systematic methylene interruption of the double bonds) derived from fatty acid synthase (FAS) by elongation and aerobic desaturation reactions (Sprecher, *Curr. Opin. Clin. Nutr. Metab. Care* 2, 135 (1999); Parker-Barnes et al., *Proc. Natl. Acad. Sci. USA* 97, 8284 (2000); Shanklin et al., *Annu. Rev. Plant Physiol. Plant Nol. Biol.* 49, 611 (1998)). Starting from acetyl-CoA, the synthesis of docosahexaenoic acid (DHA) requires approximately 30 distinct enzyme activities and nearly 70 reactions including the four repetitive steps of the fatty acid synthesis cycle. Polyketide synthases (PKSs) carry out some of the same reactions as FAS (Hopwood et al., *Annu. Rev. Genet.* 24, 37 (1990); Bentley et al., *Annu. Rev. Microbiol.* 53, 411 (1999)) and use the same small protein (or domain), acyl carrier protein (ACP), as a covalent attachment site for the growing carbon chain. However, in these enzyme systems, the complete cycle of reduction, dehydration and reduction seen in FAS is often abbreviated so that a highly derivatized carbon chain is produced, typically containing many keto- and hydroxy-groups as well as carbon-carbon double bonds in the trans configuration. The linear products of PKSs are often cyclized to form complex biochemicals that include antibiotics and many other secondary products (Hopwood et al., (1990) supra; Bentley et al., (1999), supra; Keating et al., *Curr. Opin. Chem. Biol.* 3, 598 (1999)).

Very long chain PUFAs such as docosahexaenoic acid (DHA; 22:6ω3) and eicosapentaenoic acid (EPA; 20:5ω3) have been reported from several species of marine bacteria, including *Shewanella* sp (Nichols et al., *Curr. Op. Biotechnol.* 10, 240 (1999); Yazawa, *Lipids* 31, S (1996); DeLong et al., *Appl. Environ. Microbiol.* 51, 730 (1986)). Analysis of a genomic fragment (cloned as plasmid pEPA) from *Shewanella* sp. strain SCRC2738 led to the identification of five open reading frames (Orfs), totaling 20 Kb, that are necessary and sufficient for EPA production in *E. coli* (Yazawa, (1996), supra). Several of the predicted protein domains were homologues of FAS enzymes, while other regions showed no homology to proteins of known function. At least 11 regions within the five Orfs were identifiable as putative enzyme domains (See Metz et al., *Science* 293:290-293 (2001)). When compared with sequences in the gene databases, seven of these were more strongly related to PKS proteins than to FAS proteins. Included in this group were domains putatively encoding malonyl-CoA:ACP acyltransferase (MAT), β-ketoacyl-ACP synthase (KS), β-ketoacyl-ACP reductase (KR), acyltransferase (AT), phosphopantetheine transferase, chain length (or chain initiation) factor (CLF) and a highly unusual cluster of six ACP domains (i.e., the presence of more than two clustered ACP domains had not previously been reported in PKS or FAS sequences). It is likely that the PKS pathway for PUFA synthesis that has been identified in *Shewanella* is widespread in marine bacteria. Genes with high homology to the *Shewanella* gene cluster have been identified in *Photobacterium profundum* (Allen et al., *Appli. Environ. Microbiol.* 65:1710 (1999)) and in *Moritella marina* (*Vibrio marinus*) (see U.S. Pat. No. 6,140,486, ibid., and Tanaka et al., *Biotechnol. Lett.* 21:939 (1999)).

Polyunsaturated fatty acids (PUFAs) are considered to be useful for nutritional, pharmaceutical, industrial, and other purposes. An expansive supply of PUFAs from natural sources and from chemical synthesis are not sufficient for commercial needs. A major current source for PUFAs is from marine fish; however, fish stocks are declining, and this may not be a sustainable resource. Additionally, contamination, both heavy metal and toxic organic molecules, is a serious issue with oil derived from marine fish. Vegetable oils derived from oil seed crops are relatively inexpensive and do not have the contamination issues associated with fish oils. However, the PUFAs found in commercially developed plant oils are typically limited to linoleic acid (eighteen carbons with 2 double bonds, in the delta 9 and 12 positions—18:2 delta 9,12) and linolenic acid (18:3 delta 9,12,15). In the conventional pathway for PUFA synthesis, medium chain-length saturated fatty acids (products of a fatty acid synthase (FAS) system) are modified by a series of elongation and desaturation reactions. Because a number of separate desaturase and elongase enzymes are required for fatty acid synthesis from linoleic and linolenic acids to produce the more saturated and longer chain PUFAs, engineering plant host cells for the expression of PUFAs such as EPA and docosahexaenoic acid (DHA) may require expression of several separate enzymes to achieve synthesis. Additionally, for production of useable quantities of such PUFAs, additional engineering efforts may be required, for example, engineering the down regulation of enzymes that compete for substrate, engineering of higher enzyme activities such as by mutagenesis or targeting of enzymes to plastid organelles. Therefore it is of interest to obtain genetic material involved in PUFA biosynthesis from species that naturally produce these fatty acids and to express the isolated material alone or in combination in a heterologous system which can be manipulated to allow production of commercial quantities of PUFAs.

The discovery of a PUFA PKS system in marine bacteria such as *Shewanella* and *Vibrio marinus* (see U.S. Pat. No. 6,140,486, ibid.) provides a resource for new methods of commercial PUFA production. However, these marine bacteria have limitations which may ultimately restrict their usefulness on a commercial level. First, although U.S. Pat. No. 6,140,486 discloses that these marine bacteria PUFA PKS systems can be used to genetically modify plants, the marine bacteria naturally live and grow in cold marine environments and the enzyme systems of these bacteria do not function well above 22° C. In contrast, many crop plants, which are attractive targets for genetic manipulation using the PUFA PKS system, have normal growth conditions at temperatures above 22° C. and ranging to higher than 40° C. Therefore, the PUFA PKS systems from these marine bacteria are not predicted to be readily adaptable to plant expression under normal growth conditions. Additionally, the known marine bacteria PUFA PKS systems do not directly produce triacylglyerols (TAG), whereas direct production of TAG would be desirable because TAG are a lipid storage product, and as a result, can be accumulated at very high levels in cells, as opposed to a "structural" lipid product (e.g. phospholipids), which can generally only accumulate at low levels.

With regard to the production of eicosapentaenoic acid (EPA) in particular, researchers have tried to produce EPA with microbes by growing them in both photosynthetic and heterotrophic cultures. They have also used both classical and directed genetic approaches in attempts to increase the productively of the organisms under culture conditions. Other researchers have attempted to produce EPA in oil-seed crop plants by introduction of genes encoding various desaturase and elongase enzymes.

Researchers have attempted to use cultures of red microalgae (Monodus), diatoms (e.g. *Phaeodactylum*), other microalgae and fungi (e.g. *Mortierella* cultivated at low temperatures). However, in all cases, productivity was low compared to existing commercial microbial production systems for other long chain PUFAs such as DHA. In many cases, the EPA occurred primarily in the phospholipids (PL) rather than the triacylglycerols (TAG). Since productivity of microalgae under heterotrophic growth conditions can be much higher than under phototrophic conditions, researchers have attempted, and achieved, trophic conversion by introduction of genes encoding specific sugar transporters. However, even with the newly acquired heterotrophic capability, productivity in terms of oil remained relatively low.

Efforts to produce EPA in oil-seed crop plants by modification of the endogenous fatty acid biosynthesis pathway have only yielded plants with very low levels of the PUFA in their oils. As discussed above, several marine bacteria have been shown to produce PUFAs (EPA as well as DHA). However, these bacteria do not produce TAG and the EPA is found primarily in the PL membranes. The levels of EPA produced as well as the growth characteristics of these particular marine bacteria (discussed above) limit their utility for commercial production of EPA.

Therefore, there is a need in the art for other PUFA PKS systems having greater flexibility for commercial use, and for a biological system that efficiently produces quantities of lipids (PL and TAG) enriched in desired PUFAs, such as EPA, in a commercially useful production process.

SUMMARY OF THE INVENTION

One embodiment of the present invention relates to an isolated nucleic acid molecule. The nucleic acid molecule comprises a nucleic acid sequence selected from: (a) a nucleic acid sequence encoding an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; (b) a nucleic acid sequence encoding an amino acid sequence that is at least about 60% identical, and more preferably at least about 70% identical, and more preferably at least about 80% identical, and more preferably at least about 90% identical, to an amino acid sequence selected from the group consisting of: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a polyunsaturated fatty acid (PUFA) polyketide synthase (PKS) system; (c) a nucleic acid sequence encoding an amino acid sequence that is at least about 65% identical, and more preferably at least about 70% identical, and more preferably at least about 80% identical, and more preferably at least about 90% identical, to SEQ ID NO:54, wherein the amino acid sequence has a biological activity of at least one domain of a polyunsaturated fatty acid (PUFA) polyketide synthase (PKS) system; (d) a nucleic acid sequence encoding an amino acid sequence that is at least about 70% identical, and more preferably at least about 80% identical, and more preferably at least about 90% identical, to an amino acid sequence selected from the group consisting of: SEQ ID NO:45, SEQ ID NO:48, SEQ ID NO:60, SEQ ID NO:62 and SEQ ID NO:64, wherein the amino acid sequence has a biological activity of at least one domain of a polyunsaturated fatty acid (PUFA) polyketide synthase (PKS) system; (e) a nucleic acid sequence encoding an amino acid sequence that is at least about 80% identical, and more preferably at least about 90% identical, to an amino acid sequence selected from the group consisting of: SEQ ID NO:41, SEQ ID NO:66, SEQ ID NO:68, wherein the amino acid sequence has a biological activity of at least one domain of a polyunsaturated fatty acid (PUFA) polyketide synthase (PKS) system; and/or (f) a nucleic acid sequence that is fully complementary to the nucleic acid sequence of (a), (b), (c), (d), or (e). In one aspect, the nucleic acid sequence encodes an amino acid sequence selected from: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, and biologically active fragments thereof. In one aspect, the nucleic acid sequence is selected from the group consisting of: SEQ ID NO:38, SEQ ID NO:40, SEQ ID NO:42, SEQ ID NO:44, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, and SEQ ID NO:67.

Another embodiment of the present invention relates to a recombinant nucleic acid molecule comprising any of the above-described nucleic acid molecules, operatively linked to at least one transcription control sequence.

Yet another embodiment of the present invention relates to a recombinant cell transfected with any of the above-described recombinant nucleic acid molecules.

Another embodiment of the present invention relates to a genetically modified microorganism, wherein the microorganism expresses a PKS system comprising at least one biologically active domain of a polyunsaturated fatty acid (PUFA) polyketide synthase (PKS) system, wherein the at least one domain of the PUFA PKS system comprises an amino acid sequence selected from: (a) an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; (b) an amino acid sequence that is at least about 60% identical, and more preferably at least about 70% identical, and more preferably at least about 80% identical, and more preferably at least about 90% identical, to an amino acid sequence selected from the group consisting of: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a polyunsaturated fatty acid (PUFA) polyketide synthase (PKS) system; (c) an amino acid sequence that is at least about 65% identical, and more preferably at least about 70% identical, and more preferably at least about 80% identical, and more preferably at least about 90% identical, to SEQ ID NO:54, wherein the amino acid sequence has a biological activity of at least one domain of a polyunsaturated fatty acid (PUFA) polyketide synthase (PKS) system; (d) an amino acid sequence that is at least about 70% identical, and more preferably at least about 80% identical, and more preferably at least about 90% identical, to an amino acid sequence selected from the group consisting of: SEQ ID NO:45, SEQ ID NO:48, SEQ ID NO:60, SEQ ID NO:62 and SEQ ID NO:64, wherein the amino acid sequence has a biological activity of at least one domain of a polyunsaturated fatty acid (PUFA) polyketide synthase (PKS) system; and/or (e) an amino acid sequence that is at least about 80% identical, and more preferably at least about 90% identical, to an amino acid sequence selected from the group consisting of: SEQ ID NO:41, SEQ ID NO:66, SEQ ID NO:68, wherein the amino acid sequence has a biological activity of at least one domain of a polyunsaturated fatty acid (PUFA) polyketide synthase (PKS) system. The microorganism is genetically modified to affect the activity of the PKS system.

In one aspect, the microorganism is genetically modified by transfection with a recombinant nucleic acid molecule encoding the at least one domain of a polyunsaturated fatty acid (PUFA) polyketide synthase (PKS) system. For example, the microorganism can include a Thraustochytrid, such as a *Schizochytrium*. In one aspect, such a microorganism has been further genetically modified to recombinantly express at least one nucleic acid molecule encoding at least one biologically active domain from a PKS system selected from the group consisting of: a bacterial PUFA PKS system, a Type I PKS system, a Type II PKS system, a modular PKS system, and a non-bacterial PUFA PKS system. The non-bacterial PUFA PKS system can include a Thraustochytrid PUFA PKS system and in one aspect, a *Schizochytrium* PUFA PKS system.

In another aspect, the microorganism endogenously expresses a PKS system comprising the at least one domain of the PUFA PKS system, and wherein the genetic modification is in a nucleic acid sequence encoding at least one domain of the PUFA PKS system. In another aspect, such a microorganism has been further genetically modified to recombinantly express at least one nucleic acid molecule encoding at least one biologically active domain from a PKS system selected from the group consisting of: a bacterial PUFA PKS system, a Type I PKS system, a Type II PKS system, a modular PKS system, and a non-bacterial PUFA PKS system (e.g., a Thraustochytrid PUFA PKS system, such as a *Schizochytrium* PUFA PKS system).

In another aspect, the microorganism endogenously expresses a PUFA PKS system comprising the at least one biologically active domain of a PUFA PKS system, and wherein the genetic modification comprises expression of a recombinant nucleic acid molecule selected from the group consisting of a recombinant nucleic acid molecule encoding at least one biologically active domain from a second PKS system and a recombinant nucleic acid molecule encoding a protein that affects the activity of the endogenous PUFA PKS system. The biologically active domain from a second PKS system can include, but is not limited to: (a) a domain of a polyunsaturated fatty acid (PUFA) polyketide synthase (PKS) system from a Thraustochytrid microorganism; (b) a domain of a PUFA PKS system from a microorganism identified by the following method: (i) selecting a microorganism that produces at least one PUFA; and, (ii) identifying a microorganism from (i) that has an ability to produce increased PUFAs under dissolved oxygen conditions of less than about 5% of saturation in the fermentation medium, as compared to production of PUFAs by the microorganism under dissolved oxygen conditions of greater than about 5% of saturation in the fermentation medium; (c) a domain comprising an amino acid sequence selected from the group consisting of: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and biologically active fragments thereof; and (d) a domain comprising an amino acid sequence that is at least about 60% identical, and more preferably at least about 70% identical, and more preferably at least about 80% identical, and more preferably at least about 90% identical, to the amino acid sequence of (c), wherein the amino acid sequence has a biological activity of at least one domain of a polyunsaturated fatty acid (PUFA) polyketide synthase (PKS) system. In one aspect, recombinant nucleic acid molecule encodes a phosphopantetheine transferase. In one aspect, the second PKS system is selected from the group consisting of: a bacterial PUFA PKS system, a type I PKS system, a type II PKS system, a modular PKS system, and a non-bacterial PUFA PKS system (e.g., a eukaryotic PUFA PKS system, such as a Thraustochytrid PUFA PKS system, including, but not limited to a *Schizochytrium* PUFA PKS system).

Yet another embodiment of the present invention relates to a genetically modified plant, wherein the plant has been genetically modified to recombinantly express a PKS system comprising at least one biologically active domain of a polyunsaturated fatty acid (PUFA) polyketide synthase (PKS) system, wherein the domain comprises an amino acid sequence selected from the group consisting of: (a) an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; (b) an amino acid sequence that is at least about 60% identical, and more preferably at least about 70% identical, and more preferably at least about 80% identical, and more preferably at least about 90% identical, to an amino acid sequence selected from the group consisting of: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a polyunsaturated fatty acid (PUFA) polyketide synthase (PKS) system; (c) an amino acid sequence that is at least about 65% identical, and more preferably at least about 70% identical, and more preferably at least about 80% identical, and more preferably at least about 90% identical, to SEQ ID NO:54, wherein the amino acid sequence has a biological activity of at least one domain of a polyunsaturated fatty acid (PUFA) polyketide synthase (PKS) system; (d) an amino acid sequence that is at least about 70% identical, and more preferably at least about 80% identical, and more preferably at least about 90% identical, to an amino acid sequence selected from the group consisting of: SEQ ID NO:45, SEQ ID NO:48, SEQ ID NO:60, SEQ ID NO:62 and SEQ ID NO:64, wherein the amino acid sequence has a biological activity of at least one domain of a polyunsaturated fatty acid (PUFA) polyketide synthase (PKS) system; and/or (e) an amino acid sequence that is at least about 80% identical, and more preferably at least about 90% identical, to an amino acid sequence selected from the group consisting of: SEQ ID NO:41, SEQ ID NO:66, SEQ ID NO:68, wherein the amino acid sequence has a biological activity of at least one domain of a polyunsaturated fatty acid (PUFA) polyketide synthase (PKS) system. In one aspect, the at least one domain of the PUFA PKS system comprises an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66 and SEQ ID NO:68 and biologically active fragments thereof. In one aspect, the plant has been further genetically modified to recombinantly express at least one nucleic acid molecule encoding at least one biologically active domain from a PKS system selected from the group consisting of: a bacterial PUFA PKS system, a Type I PKS system, a Type II PKS system, a modular PKS system, and a non-bacterial PUFA PKS system (e.g., a Thraustochytrid PUFA PKS system, such as a *Schizochytrium* PUFA PKS system).

Yet another embodiment of the present invention relates to a method to produce a bioactive molecule that is produced by a polyketide synthase system, comprising culturing under conditions effective to produce the bioactive molecule a genetically modified organism that expresses a PKS system comprising at least one biologically active domain of a polyunsaturated fatty acid (PUFA) polyketide synthase (PKS) system, wherein the at least one domain of the PUFA PKS system comprises an amino acid sequence selected from the group consisting of: (a) an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; (b) an amino acid sequence that is at least about 60% identical, and more preferably at least about 70% identical, and more preferably at least about 80% identical, and more preferably at least about 90% identical, to an amino acid sequence selected from the group consisting of: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a polyunsaturated fatty acid (PUFA) polyketide synthase (PKS) system; (c) an amino acid sequence that is at least about 65% identical, and more preferably at least about 70% identical, and more preferably at least about 80% identical, and more preferably at least about 90% identical, to SEQ ID NO:54, wherein the amino acid sequence has a biological activity of at least one domain of a polyunsaturated fatty acid (PUFA) polyketide synthase (PKS) system; (d) an amino acid sequence that is at least about 70% identical, and more preferably at least about 80% identical, and more preferably at least about 90% identical, to an amino acid sequence selected from the group consisting of: SEQ ID NO:45, SEQ ID NO:48, SEQ ID NO:60, SEQ ID NO:62 and SEQ ID NO:64, wherein the amino acid sequence has a biological activity of at least one domain of a polyunsaturated fatty acid (PUFA) polyketide synthase (PKS) system; and/or (e) an amino acid sequence that is at least about 80% identical, and more preferably at least about 90% identical, to an amino acid sequence selected from the group consisting of: SEQ ID NO:41, SEQ ID NO:66, SEQ ID NO:68, wherein the amino acid sequence has a biological activity of at least one domain of a polyunsaturated fatty acid (PUFA) polyketide synthase (PKS) system.

In one aspect, the organism endogenously expresses a PKS system comprising the at least one domain of the PUFA PKS system, and wherein the genetic modification is in a nucleic acid sequence encoding the at least one domain of the PUFA PKS system. In one aspect, the genetic modification changes at least one product produced by the endogenous PKS system, as compared to an organism wherein the PUFA PKS system has not been genetically modified.

In another aspect, the organism endogenously expresses a PKS system comprising the at least one biologically active domain of the PUFA PKS system, and the genetic modification comprises transfection of the organism with a recombinant nucleic acid molecule selected from the group consisting of: a recombinant nucleic acid molecule encoding at least one biologically active domain from a second PKS system and a recombinant nucleic acid molecule encoding a protein that affects the activity of the PUFA PKS system. In one aspect, the genetic modification changes at least one product produced by the endogenous PKS system, as compared to an organism that has not been genetically modified to affect PUFA production.

In another aspect, the organism is genetically modified by transfection with a recombinant nucleic acid molecule encoding the at least one domain of the polyunsaturated fatty acid (PUFA) polyketide synthase (PKS) system.

In another aspect, the organism produces a polyunsaturated fatty acid (PUFA) profile that differs from the naturally occurring organism without a genetic modification.

In another aspect, the organism endogenously expresses a non-bacterial PUFA PKS system, and wherein the genetic modification comprises substitution of a domain from a different PKS system for a nucleic acid sequence encoding at least one domain of the non-bacterial PUFA PKS system.

In yet another aspect, the organism endogenously expresses a non-bacterial PUFA PKS system that has been modified by transfecting the organism with a recombinant nucleic acid molecule encoding a protein that regulates the chain length of fatty acids produced by the PUFA PKS system.

In another aspect, the bioactive molecule is selected from: an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and/or a cholesterol lowering formulation. In one aspect, the bioactive molecule is an antibiotic. In another aspect, the bioactive molecule is a polyunsaturated fatty acid (PUFA). In yet another aspect, the bioactive molecule is a molecule including carbon-carbon double bonds in the cis configuration. In one aspect, the bioactive molecule is a molecule including a double bond at every third carbon. In one aspect, the organism is a microorganism. In another aspect, the organism is a plant.

Another embodiment of the present invention relates to a method to produce a plant that has a polyunsaturated fatty acid (PUFA) profile that differs from the naturally occurring plant, comprising genetically modifying cells of the plant to express a PKS system comprising at least one recombinant nucleic acid molecule comprising a nucleic acid sequence encoding at least one biologically active domain of a PUFA PKS system, wherein the at least one domain of the PUFA PKS system comprises an amino acid sequence selected from the group consisting of: (a) an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; (b) an amino acid sequence that is at least about 60% identical, and more preferably at least about 70% identical, and more preferably at least about 80% identical, and more preferably at least about 90% identical, to an amino acid sequence selected from the group consisting of: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a polyunsaturated fatty acid (PUFA) polyketide synthase (PKS) system; (c) an amino acid sequence that is at least about 65% identical, and more preferably at least about 70% identical, and more preferably at least about 80% identical, and more preferably at least about 90% identical, to SEQ ID NO:54, wherein the amino acid sequence has a biological activity of at least one domain of a polyunsaturated fatty acid (PUFA) polyketide synthase (PKS) system; (d) an amino acid sequence that is at least about 70% identical, and more preferably at least about 80% identical, and more preferably at least about 90% identical, to an amino acid sequence selected from the group consisting of: SEQ ID NO:45, SEQ ID NO:48, SEQ ID NO:60, SEQ ID NO:62 and SEQ ID NO:64, wherein the amino acid sequence has a biological activity of at least one domain of a polyunsaturated fatty acid (PUFA) polyketide synthase (PKS) system; and (e) an amino acid sequence that is at least about 80% identical, and more preferably at least about 90% identical, to an amino acid sequence selected from the group consisting of: SEQ ID NO:41, SEQ ID NO:66, SEQ ID NO:68, wherein the amino acid sequence has a biological activity of at least one domain of a polyunsaturated fatty acid (PUFA) polyketide synthase (PKS) system.

Another embodiment of the present invention relates to a method to modify an endproduct containing at least one fatty acid, comprising adding to the endproduct an oil produced by a recombinant host cell that expresses at least one recombinant nucleic acid molecule comprising a nucleic acid sequence encoding at least one biologically active domain of a PUFA PKS system, wherein the at least one domain of a PUFA PKS system comprises an amino acid sequence selected from the group consisting of: (a) an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; (b) an amino acid sequence that is at least about 60% identical, and more preferably at least about 70% identical, and more preferably at least about 80% identical, and more preferably at least about 90% identical, to an amino acid sequence selected from the group consisting of: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a polyunsaturated fatty acid (PUFA) polyketide synthase (PKS) system; (c) an amino acid sequence that is at least about 65% identical, and more preferably at least about 70% identical, and more preferably at least about 80% identical, and more preferably at least about 90% identical, to SEQ ID NO:54, wherein the amino acid sequence has a biological activity of at least one domain of a polyunsaturated fatty acid (PUFA) polyketide synthase (PKS) system; (d) an amino acid sequence that is at least about 70% identical, and more preferably at least about 80% identical, and more preferably at least about 90% identical, to an amino acid sequence selected from the group consisting of: SEQ ID NO:45, SEQ ID NO:48, SEQ ID NO:60, SEQ ID NO:62 and SEQ ID NO:64, wherein the amino acid sequence has a biological activity of at least one domain of a polyunsaturated fatty acid (PUFA) polyketide synthase (PKS) system; and (e) an amino acid sequence that is at least about 80% identical, and more preferably at least about 90% identical, to an amino acid sequence selected from the group consisting of: SEQ ID NO:41, SEQ ID NO:66, SEQ ID NO:68, wherein the amino acid sequence has a biological activity of at least one domain of a polyunsaturated fatty acid (PUFA) polyketide synthase (PKS) system. In one aspect, the endproduct is selected from: a dietary supplement, a food product, a pharmaceutical formulation, a humanized animal milk, and an infant formula. In one aspect, the pharmaceutical formulation is selected from the group consisting of an anti-inflammatory formulation, a chemotherapeutic agent, an active excipient, an osteoporosis drug, an anti-depressant, an anti-convulsant, an anti-*Heliobactor pylon* drug, a drug for treatment of neurodegenerative disease, a drug for treatment of degenerative liver disease, an antibiotic, and a cholesterol lowering formulation. In one aspect, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Yet another embodiment of the present invention relates to a method to produce a humanized animal milk, comprising genetically modifying milk-producing cells of a milk-producing animal with at least one recombinant nucleic acid molecule comprising a nucleic acid sequence encoding at least one biologically active domain of a PUFA PKS system, wherein the at least one domain of the PUFA PKS system comprises an amino acid sequence selected from the group consisting of: (a) an amino acid sequence selected from the group consisting of: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; (b) an amino acid sequence that is at least about 60% identical, and more preferably at least about 70% identical, and more preferably at least about 80% identical, and more preferably at least about 90% identical, to an amino acid sequence selected from the group consisting of: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a polyunsaturated fatty acid (PUFA) polyketide synthase (PKS) system; (c) an amino acid sequence that is at least about 65% identical, and more preferably at least about 70% identical, and more preferably at least about 80% identical, and more preferably at least about 90% identical, to SEQ ID NO:54, wherein the amino acid sequence has a biological activity of at least one domain of a polyunsaturated fatty acid (PUFA) polyketide synthase (PKS) system; (d) an amino acid sequence that is at least about 70% identical, and more preferably at least about 80% identical, and more preferably at least about 90% identical, to an amino acid sequence selected from the group consisting of: SEQ ID NO:45, SEQ ID NO:48, SEQ ID NO:60, SEQ ID NO:62 and SEQ ID NO:64, wherein the amino acid sequence has a biological activity of at least one domain of a polyunsaturated fatty acid (PUFA) polyketide synthase (PKS) system; and (e) an amino acid sequence that is at least about 80% identical, and more preferably at least about 90% identical, to an amino acid sequence selected from the group consisting of: SEQ ID NO:41, SEQ ID NO:66, SEQ ID NO:68, wherein the amino acid sequence has a biological activity of at least one domain of a polyunsaturated fatty acid (PUFA) polyketide synthase (PKS) system.

Another embodiment of the present invention relates to a genetically modified Thraustochytrid microorganism, wherein the microorganism has an endogenous polyunsaturated fatty acid (PUFA) polyketide synthase (PKS) system, and wherein the endogenous PUFA PKS system has been genetically modified to alter the expression profile of a polyunsaturated fatty acid (PUFA) by the Thraustochytrid microorganism as compared to the Thraustochytrid microorganism in the absence of the genetic modification.

In one aspect, the endogenous PUFA PKS system has been modified by mutagenesis of a nucleic acid sequence that encodes at least one domain of the endogenous PUFA PKS system. In one aspect, the modification is produced by targeted mutagenesis. In another aspect, the modification is produced by classical mutagenesis and screening.

In another aspect, the endogenous PUFA PKS system has been modified by deleting at least one nucleic acid sequence that encodes at least one domain of the endogenous PUFA PKS system and inserting therefore a nucleic acid sequence encoding a homologue of the endogenous domain to alter the PUFA production profile of the Thraustochytrid microorganism, wherein the homologue has a biological activity of at least one domain of a PKS system. In one aspect, the homologue of the endogenous domain comprises a modification, as compared to the endogenous domain, selected from the group consisting of at least one deletion, insertion or substitution that results in an alteration of PUFA production profile by the microorganism. In another aspect, the amino acid sequence of the homologue is at least about 60% identical, and more preferably about 70% identical, and more preferably about 80% identical, and more preferably about 90% identical to the amino acid sequence of the endogenous domain. In one aspect, homologue of the endogenous domain is a domain from a PUFA PKS system of another Thraustochytrid microorganism.

In another aspect, the endogenous PUFA PKS system has been modified by deleting at least one nucleic acid sequence that encodes at least one domain of the endogenous PUFA PKS system and inserting therefore a nucleic acid sequence encoding at least one domain of a PKS system from a different microorganism. In one aspect, the nucleic acid sequence encoding at least one domain of a PKS system from a different microorganism is from a bacterial PUFA PKS system. For example, the different microorganism can be a marine bacteria having a PUFA PKS system that naturally produces PUFAs at a temperature of about 25° C. or greater. In one aspect, the marine bacteria is selected from the group consisting of *Shewanella olleyana* and *Shewanella japonica*. In one aspect, the domain of a PKS system from a different microorganism is from a PKS system selected from the group consisting of: a Type I PKS system, a Type II PKS system, a modular PKS system, and a PUFA PKS system from a different Thraustochytrid microorganism.

In any of the above aspects, the domain of the endogenous PUFA PKS system can include, but is not limited to, a domain having a biological activity of at least one of the following proteins: malonyl-CoA:ACP acyltransferase (MAT), β-keto acyl-ACP synthase (KS), ketoreductase (KR), acyltransferase (AT), FabA-like β-hydroxy acyl-ACP dehydrase (DH), phosphopantetheine transferase, chain length factor (CLF), acyl carrier protein (ACP), enoyl ACP-reductase (ER), an enzyme that catalyzes the synthesis of trans-2-acyl-ACP, an enzyme that catalyzes the reversible isomerization of trans-2-acyl-ACP to cis-3-acyl-ACP, and an enzyme that catalyzes the elongation of cis-3-acyl-ACP to cis-5-β-keto-acyl-ACP. In any of the above aspects, the domain of the endogenous PUFA PKS system can include an amino acid sequence selected from the group consisting of: (a) an amino acid sequence selected from the group consisting of: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68 and biologically active fragments thereof; and (b) an amino acid sequence that is at least about 60% identical, and more preferably at least about 70% identical, and more preferably at least about 80% identical, and more preferably at least about 90% identical, to an amino acid sequence of (a), wherein the amino acid sequence has a biological activity of at least one domain of a polyunsaturated fatty acid (PUFA) polyketide synthase (PKS) system.

In one aspect, the PUFA production profile is altered to initiate, increase or decrease production of eicosapentaenoic acid (EPA) by the microorganism. In another aspect, the PUFA production profile is altered to initiate, increase or decrease production of docosahexaenoic acid (DHA) by the microorganism. In another aspect, the PUFA production profile is altered to initiate, increase or decrease production of one or both isomers of docosapentaenoic acid (DPA) by the microorganism. In another aspect, the PUFA production profile is altered to initiate, increase or decrease production of arachidonic acid (ARA) by the microorganism. In another aspect, the Thraustochytrid is from a genus selected from the group consisting of *Schizochytrium, Thraustochytrium*, and *Japonochytrium*. In another aspect, the Thraustochytrid is from the genus *Schizochytrium*. In another aspect, the Thraustochytrid is from a *Schizochytrium* species selected from the group consisting of: *Schizochytrium aggregatum, Schizochytrium limacinum*, and *Schizochytrium minutum*. In another aspect, the Thraustochytrid is from the genus *Thraustochytrium*.

Yet another embodiment of the present invention relates to a genetically modified *Schizochytrium* that produces eicosapentaenoic acid (EPA), wherein the *Schizochytrium* has an endogenous polyunsaturated fatty acid (PUFA) polyketide synthase (PKS) system comprising a genetic modification in at least one nucleic acid sequence that encodes at least one domain of the endogenous PUFA PKS system that results in the production of EPA by the *Schizochytrium*. In one aspect, the *Schizochytrium* comprises a genetic modification in at least one nucleic acid sequence encoding at least one domain having a biological activity of at least one of the following proteins: malonyl-CoA:ACP acyltransferase (MAT), β-keto acyl-ACP synthase (KS), ketoreductase (KR), acyltransferase (AT), FabA-like β-hydroxy acyl-ACP dehydrase (DH), phosphopantetheine transferase, chain length factor (CLF), acyl carrier protein (ACP), enoyl ACP-reductase (ER), an enzyme that catalyzes the synthesis of trans-2-acyl-ACP, an enzyme that catalyzes the reversible isomerization of trans-2-acyl-ACP to cis-3-acyl-ACP, and an enzyme that catalyzes the elongation of cis-3-acyl-ACP to cis-5-β-keto-acyl-ACP. In one aspect, the *Schizochytrium* comprises a genetic modification in at least one nucleic acid sequence encoding at least one domain from the open reading frame encoding SEQ ID NO:2 of the endogenous PUFA PKS system. In one aspect, the *Schizochytrium* comprises a genetic modification in at least one nucleic acid sequence encoding at least one domain from the open reading frame encoding SEQ ID NO:4 of the endogenous PUFA PKS system. In one aspect, the *Schizochytrium* comprises a genetic modification in at least one nucleic acid sequence encoding at least one domain from the open reading frame encoding SEQ ID NO:6 of the endogenous PUFA PKS system. In one aspect, the *Schizochytrium* comprises a genetic modification in at least one nucleic acid sequence encoding at least one domain having a biological activity of at least one of the following proteins: β-keto acyl-ACP synthase (KS), FabA-like β-hydroxy acyl-ACP dehydrase (DH), chain length factor (CLF), an enzyme that catalyzes the synthesis of trans-2-acyl-ACP, an enzyme that catalyzes the reversible isomerization of trans-2-acyl-ACP to cis-3-acyl-ACP, and an enzyme that catalyzes the elongation of cis-3-acyl-ACP to cis-5-β-keto-acyl-ACP. In one aspect, the *Schizochytrium* comprises a genetic modification in at least one nucleic acid sequence encoding an amino acid sequence selected from the group consisting of SEQ ID NO:20, SEQ ID NO:22, SEQ ID NO:28 and SEQ ID NO:30 of the endogenous PUFA PKS system. In one aspect, the *Schizochytrium* has been modified by deleting at least one nucleic acid sequence that encodes at least one domain of the endogenous PUFA PKS system and inserting therefore a nucleic acid sequence encoding at least one domain of a PKS system from a non-*Schizochytrium* microorganism. In one aspect, the non-*Schizochytrium* microorganism grows and produces PUFAs at temperature of at least about 15° C., and more preferably at least about 20° C., and more preferably at least about 25° C., and more preferably at least about 30° C., and more preferably between about 20° C. and about 40° C. In one aspect, the nucleic acid sequence encoding at least one domain of a PKS system from a non-*Schizochytrium* microorganism is from a bacterial PUFA PKS system. In one aspect, the bacterial PUFA PKS system is from a bacterium selected from the group consisting of *Shewanella olleyana* and *Shewanella japonica*. In another aspect, the nucleic acid sequence encoding at least one domain of a PKS system is selected from the group consisting of a Type I PKS system, a Type II PKS system, a modular PKS system, and a non-bacterial PUFA PKS system (e.g., a eukaryotic PUFA PKS system, such as a Thraustochytrid PUFA PKS system).

Another embodiment of the present invention relates to a genetically modified *Schizochytrium* that produces increased amounts of docosahexaenoic acid (DHA) as compared to a non-genetically modified *Schizochytrium*, wherein the *Schizochytrium* has an endogenous polyunsaturated fatty acid (PUFA) polyketide synthase (PKS) system comprising a genetic modification in at least one nucleic sequence that encodes at least one domain of the endogenous PUFA PKS system that results in increased the production of DHA by the *Schizochytrium*. In one aspect, at least one domain of the endogenous PUFA PKS system has been modified by substitution for at least one domain of a PUFA PKS system from *Thraustochytrium*. In one aspect, the ratio of DHA to DPA produced by the *Schizochytrium* is increased as compared to a non-genetically modified *Schizochytrium*.

Another embodiment of the present invention relates to a method to produce lipids enriched for at least one selected polyunsaturated fatty acid (PUFA), comprising culturing under conditions effective to produce the lipids a genetically modified Thraustochytrid microorganism as described above or a genetically modified *Schizochytrium* as described above. In one aspect, the selected PUFA is eicosapentaenoic acid (EPA).

Yet another embodiment of the present invention relates to a method to produce eicosapentaenoic acid (EPA)-enriched lipids, comprising culturing under conditions effective to produce the EPA-enriched lipids a genetically modified Thraustochytrid microorganism, wherein the microorganism has an endogenous polyunsaturated fatty acid (PUFA) polyketide synthase (PKS) system, and wherein the endogenous PUFA PKS system has been genetically modified in at least one domain to initiate or increase the production of EPA in the lipids of the microorganism as compared to in the absence of the modification.

DETAILED DESCRIPTION OF THE INVENTION

Figure 1:
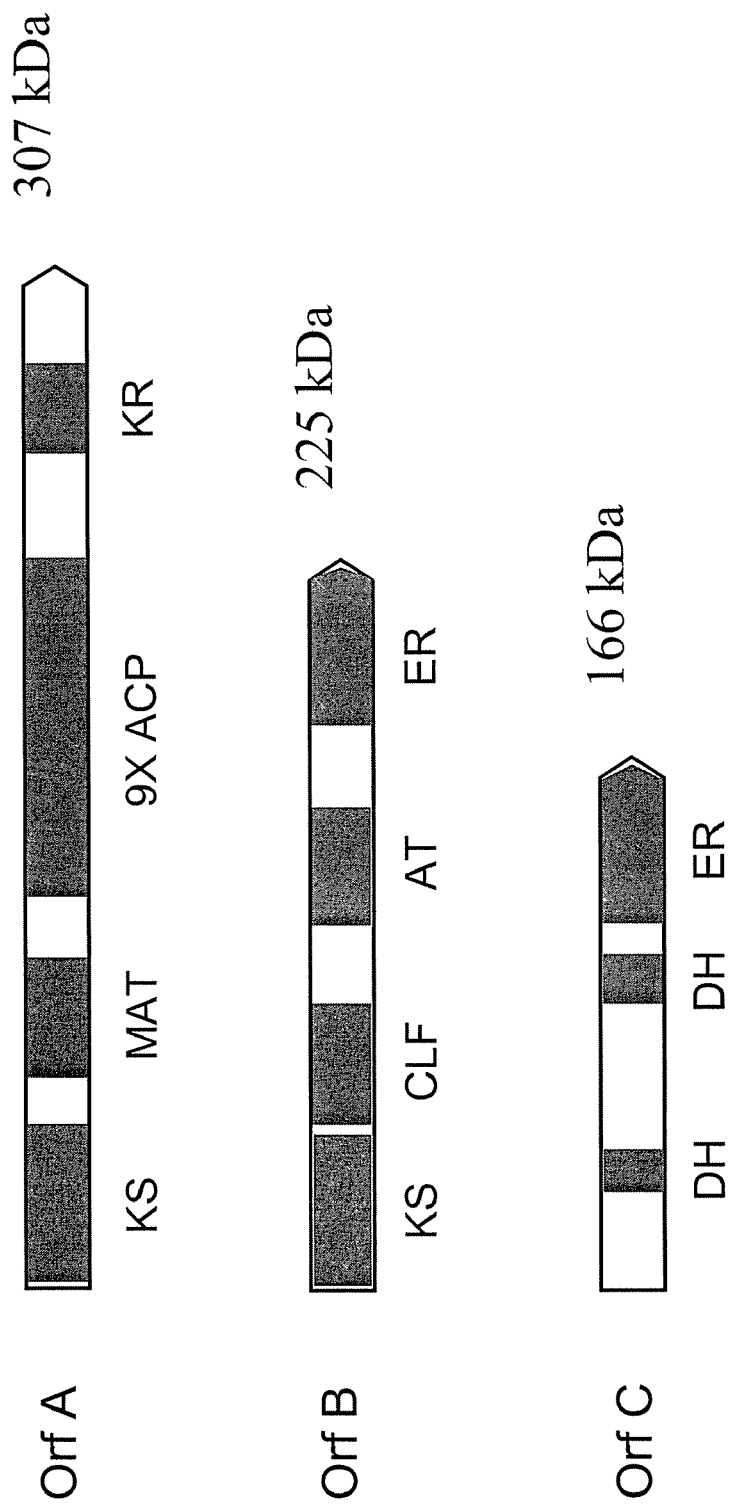
FIG. 1 is a graphical representation of the domain structure of the *Schizochytrium* PUFA PKS system.

The present invention generally relates to polyunsaturated fatty acid (PUFA) polyketide synthase (PKS) systems, to genetically modified organisms comprising such PUFA PKS systems, to methods of making and using such systems for the production of products of interest, including bioactive molecules and particularly, PUFAs, such as DHA, DPA and EPA. As used herein, a PUFA PKS system generally has the following identifying features: (1) it produces PUFAs as a natural product of the system; and (2) it comprises several multifunctional proteins assembled into a complex that conducts both iterative processing of the fatty acid chain as well non-iterative processing, including trans-cis isomerization and enoyl reduction reactions in selected cycles (See FIG. 1, for example). Reference to a PUFA PKS system refers collectively to all of the genes and their encoded products that work in a complex to produce PUFAs in an organism. Therefore, the PUFA PKS system refers specifically to a PKS system for which the natural products are PUFAs.

More specifically, first, a PUFA PKS system that forms the basis of this invention produces polyunsaturated fatty acids (PUFAs) as products (i.e., an organism that endogenously (naturally) contains such a PKS system makes PUFAs using this system). The PUFAs referred to herein are preferably polyunsaturated fatty acids with a carbon chain length of at least 16 carbons, and more preferably at least 18 carbons, and more preferably at least 20 carbons, and more preferably 22 or more carbons, with at least 3 or more double bonds, and preferably 4 or more, and more preferably 5 or more, and even more preferably 6 or more double bonds, wherein all double bonds are in the cis configuration. It is an object of the present invention to find or create via genetic manipulation or manipulation of the endproduct, PKS systems which produce polyunsaturated fatty acids of desired chain length and with desired numbers of double bonds. Examples of PUFAs include, but are not limited to, DHA (docosahexaenoic acid (C22:6, ω-3)), ARA (eicosatetraenoic acid or arachidonic acid (C20:4, n-6)), DPA (docosapentaenoic acid (C22:5, ω-6 or ω-3)), and EPA (eicosapentaenoic acid (C20:5, ω-3)).

Second, the PUFA PKS system described herein incorporates both iterative and non-iterative reactions, which distinguish the system from previously described PKS systems (e.g., type I, type II or modular). More particularly, the PUFA PKS system described herein contains domains that appear to function during each cycle as well as those which appear to function during only some of the cycles. A key aspect of this functionality may be related to the domains showing homology to the bacterial Fab-A enzymes. For example, the Fab-A enzyme of *E. coli* has been shown to possess two enzymatic activities. It possesses a dehydration activity in which a water molecule ($H_2O$) is abstracted from a carbon chain containing a hydroxy group, leaving a trans double bond in that carbon chain. In addition, it has an isomerase activity in which the trans double bond is converted to the cis configuration. This isomerization is accomplished in conjunction with a migration of the double bond position to adjacent carbons. In PKS (and FAS) systems, the main carbon chain is extended in 2 carbon increments. One can therefore predict the number of extension reactions required to produce the PUFA products of these PKS systems. For example, to produce DHA (C22:6, all cis) requires 10 extension reactions. Since there are only 6 double bonds in the end product, it means that during some of the reaction cycles, a double bond is retained (as a cis isomer), and in others, the double bond is reduced prior to the next extension.

Before the discovery of a PUFA PKS system in marine bacteria (see U.S. Pat. No. 6,140,486), PKS systems were not known to possess this combination of iterative and selective enzymatic reactions, and they were not thought of as being able to produce carbon-carbon double bonds in the cis configuration. However, the PUFA PKS system described by the present invention has the capacity to introduce cis double bonds and the capacity to vary the reaction sequence in the cycle.

The present inventors propose to use these features of the PUFA PKS system to produce a range of bioactive molecules that could not be produced by the previously described (Type II, Type I and modular) PKS systems. These bioactive molecules include, but are not limited to, polyunsaturated fatty acids (PUFAs), antibiotics or other bioactive compounds, many of which will be discussed below. For example, using the knowledge of the PUFA PKS gene structures described herein, any of a number of methods can be used to alter the PUFA PKS genes, or combine portions of these genes with other synthesis systems, including other PKS systems, such that new products are produced. The inherent ability of this particular type of system to do both iterative and selective reactions will enable this system to yield products that would not be found if similar methods were applied to other types of PKS systems.

Much of the structure of the PKS system for PUFA synthesis in the eukaryotic Thraustochytrid, *Schizochytrium* has been described in detail in U.S. Pat. No. 6,566,583. Complete sequencing of cDNA and genomic clones in *Schizochytrium* by the present inventors allowed the identification of the full-length genomic sequence of each of OrfA, OrfB and OrfC and the complete identification of the specific domains in these *Schizochytrium* Orfs with homology to those in *Shewanella* (see FIG. 2 and U.S. patent application Ser. No. 10/124,800, supra). In U.S. patent application Ser. No. 10/124,800, the inventors also identified a *Thraustochytrium* species as meeting the criteria for having a PUFA PKS system and then demonstrated that this organism was likely to contain genes with homology to *Schizochytrium* PUFA PKS genes by Southern blot analysis. However, the isolation and determination of the structure of such genes and the domain organization of the genes was not described in U.S. patent application Ser. No. 10/124,800. In the present invention, the inventors have now cloned and sequenced the full-length genomic sequence of homologous open reading frames (Orfs) in this Thraustochytrid of the genus *Thraustochytrium* (specifically, *Thraustochytrium* sp. 23B (ATCC 20892)), and have identified the domains comprising the PUFA PKS system in this *Thraustochytrium*. Therefore, the present invention solves the above-mentioned problem of providing additional PUFA PKS systems that have the flexibility for commercial use. The *Thraustochytrium* PUFA PKS system is described in detail below.

The present invention also solves the above-identified problem for production of commercially valuable lipids enriched in a desired PUFA, such as EPA, by the present inventors' development of genetically modified microorganisms and methods for efficiently producing lipids (triacylglycerols (TAG) as well as membrane-associated phospholipids (PL)) enriched in PUFAs by manipulation of the polyketide synthase-like system that produces PUFAs in eukaryotes, including members of the order Thraustochytriales such as *Schizochytrium* and *Thraustochytrium*. Specifically, and by way of example, the present inventors describe herein a strain of *Schizochytrium* that has previously been optimized for commercial production of oils enriched in PUFA, primarily docosahexaenoic acid (DHA; C22:6 n-3) and docosapentaenoic acid (DPA; C22:5 n-6), and that will now be genetically modified such that EPA (C20:5 n-3) production (or other PUFA production) replaces the DHA production, without sacrificing the oil productivity characteristics of the organism. In addition, the present inventors describe herein the genetic modification of *Schizochytrium* with PUFA PKS genes from *Thraustochytrium* to improve the DHA production by the *Schizochytrium* organism, specifically by altering the ratio of DHA to DPA produced by the microorganism through the modification of the PUFA PKS system. These are only a few examples of the technology encompassed by the invention, as the concepts of the invention can readily be applied to other production organisms and other desired PUFAs as described in detail below.

In one embodiment, a PUFA PKS system according to the present invention comprises at least the following biologically active domains: (a) at least two enoyl-ACP reductase (ER) domains; (b) at least six acyl carrier protein (ACP) domains; (c) at least two β-ketoacyl-ACP synthase (KS) domains; (d) at least one acyltransferase (AT) domain; (e) at least one β-ketoacyl-ACP reductase (KR) domain; (f) at least two FabA-like β-hydroxyacyl-ACP dehydrase (DH) domains; (g) at least one chain length factor (CLF) domain; and (h) at least one malonyl-CoA:ACP acyltransferase (MAT) domain. The functions of these domains are generally individually known in the art and will be described in detail below with regard to the PUFA PKS system of the present invention.

In another embodiment, the PUFA PKS system comprises at least the following biologically active domains: (a) at least one enoyl-ACP reductase (ER) domain; (b) multiple acyl carrier protein (ACP) domains (at least from one to four, and preferably at least five, and more preferably at least six, and even more preferably seven, eight, nine, or more than nine); (c) at least two β-ketoacyl-ACP synthase (KS) domains; (d) at least one acyltransferase (AT) domain; (e) at least one β-ketoacyl-ACP reductase (KR) domain; (f) at least two FabA-like β-hydroxyacyl-ACP dehydrase (DH) domains; (g) at least one chain length factor (CLF) domain; and (h) at least one malonyl-CoA:ACP acyltransferase (MAT) domain. Preferably, such a PUFA PKS system is a non-bacterial PUFA-PKS system.

In one embodiment, a PUFA PKS system of the present invention is a non-bacterial PUFA PKS system. In other words, in one embodiment, the PUFA PKS system of the present invention is isolated from an organism that is not a bacterium, or is a homologue of, or derived from, a PUFA PKS system from an organism that is not a bacterium, such as a eukaryote or an archaebacterium. Eukaryotes are separated from prokaryotes based on the degree of differentiation of the cells, with eukaryotes having more highly differentiated cells and prokaryotes having less differentiated cells. In general, prokaryotes do not possess a nuclear membrane, do not exhibit mitosis during cell division, have only one chromosome, their cytoplasm contains 70S ribosomes, they do not possess any mitochondria, endoplasmic reticulum, chloroplasts, lysosomes or Golgi apparatus, their flagella (if present) consists of a single fibril. In contrast, eukaryotes have a nuclear membrane, they do exhibit mitosis during cell division, they have many chromosomes, their cytoplasm contains 80S ribosomes, they do possess mitochondria, endoplasmic reticulum, chloroplasts (in algae), lysosomes and Golgi apparatus, and their flagella (if present) consists of many fibrils. In general, bacteria are prokaryotes, while algae, fungi, protist, protozoa and higher plants are eukaryotes.

The PUFA PKS systems of the marine bacteria (e.g., *Shewanella* sp. strain SCRC2738 and *Vibrio marinus*) are not the basis of the present invention, although the present invention does contemplate the use of domains from these bacterial PUFA PKS systems in conjunction with domains from the non-bacterial PUFA PKS systems of the present invention. In addition, the present invention does contemplate the isolation and use of PUFA PKS gene sets (and proteins and domains encoded thereby) isolated from other bacteria (e.g. *Shewanella olleyana* and *Shewanella japonica*) that will be particularly suitable for use as sources of PUFA PKS genes for modifying or combining with the non-bacterial PUFA PKS genes described herein to produce hybrid constructs and genetically modified microorganisms and plants. For example, according to the present invention, genetically modified organisms can be produced which incorporate non-bacterial PUFA PKS functional domains with bacterial PUFA PKS functional domains, as well as PKS functional domains or proteins from other PKS systems (type I, type II, modular) or FAS systems. As discussed in more detail below, PUFA PKS genes from two species of *Shewanella*, namely *Shewanella olleyana* or *Shewanella japonica*, are exemplary bacterial genes that are preferred for use in genetically modified microorganisms, plants, and methods of the invention. PUFA PKS systems (genes and the proteins and domains encoded thereby) from such marine bacteria (e.g., *Shewanella olleyana* or *Shewanella japonica*) are encompassed by the present invention as novel PUFA PKS sequences.

According to the present invention, the terms/phrases "Thraustochytrid", "Thraustochytriales microorganism" and "microorganism of the order Thraustochytriales" can be used interchangeably and refer to any members of the order Thraustochytriales, which includes both the family Thraustochytriaceae and the family Labyrinthulaceae. The terms "Labyrinthulid" and "Labyrinthulaceae" are used herein to specifically refer to members of the family Labyrinthulaceae. To specifically reference Thraustochytrids that are members of the family Thraustochytriaceae, the term "Thraustochytriaceae" is used herein. Thus, for the present invention, members of the *Labyrinthulids* are considered to be included in the Thraustochytrids.

Developments have resulted in frequent revision of the taxonomy of the Thraustochytrids. Taxonomic theorists generally place Thraustochytrids with the algae or algae-like protists. However, because of taxonomic uncertainty, it would be best for the purposes of the present invention to consider the strains described in the present invention as Thraustochytrids to include the following organisms: Order: Thraustochytriales; Family: Thraustochytriaceae (Genera: *Thraustochytrium, Schizochytrium, Japonochytrium, Aplanochytrium*, or *Elina*) or Labyrinthulaceae (Genera *Labyrinthula, Labyrinthuloides*, or *Labyrinthomyxa*). Also, the following genera are sometimes included in either family Thraustochytriaceae or Labyrinthulaceae: *Althornia, Corallochytrium, Diplophyrys*, and *Pyrrhosorus*), and for the purposes of this invention are encompassed by reference to a Thraustochytrid or a member of the order Thraustochytriales. It is recognized that at the time of this invention, revision in the taxonomy of Thraustochytrids places the genus *Labyrinthuloides* in the family of Labyrinthulaceae and confirms the placement of the two families Thraustochytriaceae and Labyrinthulaceae within the Stramenopile lineage. It is noted that the Labyrinthulaceae are sometimes commonly called *labyrinthulids* or *labyrinthula*, or *labyrinthuloides* and the Thraustochytriaceae are commonly called thraustochytrids, although, as discussed above, for the purposes of clarity of this invention, reference to Thraustochytrids encompasses any member of the order Thraustochytriales and/or includes members of both Thraustochytriaceae and Labyrinthulaceae. Recent taxonomic changes are summarized below.

Strains of certain unicellular microorganisms disclosed herein are members of the order Thraustochytriales. Thraustochytrids are marine eukaryotes with an evolving taxonomic history. Problems with the taxonomic placement of the Thraustochytrids have been reviewed by Moss (1986), Bahnweb and Jackle (1986) and Chamberlain and Moss (1988).

For convenience purposes, the Thraustochytrids were first placed by taxonomists with other colorless zoosporic eukaryotes in the Phycomycetes (algae-like fungi). The name Phycomycetes, however, was eventually dropped from taxonomic status, and the Thraustochytrids were retained in the Oomycetes (the biflagellate zoosporic fungi). It was initially assumed that the Oomycetes were related to the heterokont algae, and eventually a wide range of ultrastructural and biochemical studies, summarized by Barr (Barr, 1981, *Biosystems* 14:359-370) supported this assumption. The Oomycetes were in fact accepted by Leedale (Leedale, 1974, *Taxon* 23:261-270) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis, 1970, *Origin of Eukaryotic Cells*. Yale University Press, New Haven); e.g., mitochondria were derived from bacterial endosymbionts, chloroplasts from cyanophytes, and flagella from spirochaetes. The other theory suggests a gradual evolution of the membrane-bound organelles from the non-membrane-bounded systems of the prokaryote ancestor via an autogenous process (Cavalier-Smith, 1975, *Nature* (Lond.) 256:462-468). Both groups of evolutionary biologists however, have removed the Oomycetes and Thraustochytrids from the fungi and place them either with the chromophyte algae in the kingdom Chromophyta (Cavalier-Smith, 1981, *BioSystems* 14:461-481) (this kingdom has been more recently expanded to include other protists and members of this kingdom are now called Stramenopiles) or with all algae in the kingdom Protoctista (Margulis and Sagen, 1985, Biosystems 18:141-147).

With the development of electron microscopy, studies on the ultrastructure of the zoospores of two genera of Thraustochytrids, *Thraustochytrium* and *Schizochytrium*, (Perkins, 1976, pp. 279-312 in "Recent Advances in Aquatic Mycology" (ed. E. B. G. Jones), John Wiley & Sons, New York; Kazama, 1980, *Can. J. Bot.* 58:2434-2446; Barr, 1981, *Biosystems* 14:359-370) have provided good evidence that the Thraustochytriaceae are only distantly related to the Oomycetes. Additionally, genetic data representing a correspondence analysis (a form of multivariate statistics) of 5-S ribosomal RNA sequences indicate that Thraustochytriales are clearly a unique group of eukaryotes, completely separate from the fungi, and most closely related to the red and brown algae, and to members of the Oomycetes (Mannella, et al., 1987, *Mol. Evol.* 24:228-235). Most taxonomists have agreed to remove the Thraustochytrids from the Oomycetes (Bartnicki-Garcia, 1987, pp. 389-403 in "Evolutionary Biology of the Fungi" (eds. Rayner, A. D. M., Brasier, C. M. & Moore, D.), Cambridge University Press, Cambridge).

In summary, employing the taxonomic system of Cavalier-Smith (Cavalier-Smith, 1981, *BioSystems* 14:461-481, 1983; Cavalier-Smith, 1993, *Microbiol Rev.* 57:953-994), the Thraustochytrids are classified with the chromophyte algae in the kingdom Chromophyta (Stramenopiles). This taxonomic placement has been more recently reaffirmed by Cavalier-Smith et al. using the 18s rRNA signatures of the Heterokonta to demonstrate that Thraustochytrids are chromists not Fungi (Cavalier-Smith et al., 1994, *Phil. Tran. Roy. Soc. London Series BioSciences* 346:387-397). This places the Thraustochytrids in a completely different kingdom from the fungi, which are all placed in the kingdom Eufungi.

Currently, there are 71 distinct groups of eukaryotic organisms (Patterson 1999) and within these groups four major lineages have been identified with some confidence: (1) Alveolates, (2) Stramenopiles, (3) a Land Plant-green algae-Rhodophyte_Glaucophyte ("plant") clade and (4) an Opisthokont clade (Fungi and Animals). Formerly these four major lineages would have been labeled Kingdoms but use of the "kingdom" concept is no longer considered useful by some researchers.

As noted by Armstrong, Stramenopile refers to three-parted tubular hairs, and most members of this lineage have flagella bearing such hairs. Motile cells of the Stramenopiles (unicellular organisms, sperm, zoopores) are asymmetrical having two laterally inserted flagella, one long, bearing three-parted tubular hairs that reverse the thrust of the flagellum, and one short and smooth. Formerly, when the group was less broad, the Stramenopiles were called Kingdom Chromista or the heterokont (=different flagella) algae because those groups consisted of the Brown Algae or Phaeophytes, along with the yellow-green Algae, Golden-brown Algae, Eustigmatophytes and Diatoms. Subsequently some heterotrophic, fungal-like organisms, the water molds, and *labyrinthulids* (slime net amoebas), were found to possess similar motile cells, so a group name referring to photosynthetic pigments or algae became inappropriate. Currently, two of the families within the Stramenopile lineage are the Labyrinthulaceae and the Thraustochytriaceae. Historically, there have been numerous classification strategies for these unique microorganisms and they are often classified under the same order (i.e., Thraustochytriales). Relationships of the members in these groups are still developing. Porter and Leander have developed data based on 18S small subunit ribosomal DNA indicating the thraustochytrid-*labyrinthulid* clade in monophyletic. However, the clade is supported by two branches; the first contains three species of *Thraustochytrium* and *Ulkenia profunda*, and the second includes three species of *Labyrinthula*, two species of *Labyrinthuloides* and *Schizochytrium aggregatum*.

The taxonomic placement of the Thraustochytrids as used in the present invention is therefore summarized below:
Kingdom: Chromophyta (Stramenopiles)
Phylum: Heterokonta
Order: Thraustochytriales (Thraustochytrids)
Family: Thraustochytriaceae or Labyrinthulaceae
Genera: *Thraustochytrium, Schizochytrium, Japonochytrium, Aplanochytrium, Elina, Labyrinthula, Labyrinthuloides*, or *Labyrinthulomyxa*

Some early taxonomists separated a few original members of the genus *Thraustochytrium* (those with an amoeboid life stage) into a separate genus called *Ulkenia*. However it is now known that most, if not all, Thraustochytrids (including *Thraustochytrium* and *Schizochytrium*), exhibit amoeboid stages and as such, *Ulkenia* is not considered by some to be a valid genus. As used herein, the genus *Thraustochytrium* will include *Ulkenia*.

Despite the uncertainty of taxonomic placement within higher classifications of Phylum and Kingdom, the Thraustochytrids remain a distinctive and characteristic grouping whose members remain classifiable within the order Thraustochytriales.

*Schizochytrium* is a Thraustochytrid marine microorganism that accumulates large quantities of triacylglycerols rich in DHA and docosapentaenoic acid (DPA; 22:5 ω-6); e.g., 30% DHA+DPA by dry weight (Barclay et al., *J. Appl. Phycol.* 6, 123 (1994)). In eukaryotes that synthesize 20- and 22-carbon PUFAs by an elongation/desaturation pathway, the pools of 18-, 20- and 22-carbon intermediates are relatively large so that in vivo labeling experiments using [$^{14}$C]-acetate reveal clear precursor-product kinetics for the predicted intermediates (Gellerman et al., *Biochim. Biophys. Acta* 573:23 (1979)). Furthermore, radiolabeled intermediates provided exogenously to such organisms are converted to the final PUFA products. The present inventors have shown that [1-$^{14}$C]-acetate was rapidly taken up by *Schizochytrium* cells and incorporated into fatty acids, but at the shortest labeling time (1 min), DHA contained 31% of the label recovered in fatty acids, and this percentage remained essentially unchanged during the 10-15 min of [$^{14}$C]-acetate incorporation and the subsequent 24 hours of culture growth. Similarly, DPA represented 10% of the label throughout the experiment. There is no evidence for a precursor-product relationship between 16- or 18-carbon fatty acids and the 22-carbon polyunsaturated fatty acids. These results are consistent with rapid synthesis of DHA from [$^{14}$C]-acetate involving very small (possibly enzyme-bound) pools of intermediates. A cell-free homogenate derived from *Schizochytrium* cultures incorporated [1-$^{14}$C]-malonyl-CoA into DHA, DPA, and saturated fatty acids. The same biosynthetic activities were retained by a 100,000×g supernatant fraction but were not present in the membrane pellet. Thus, DHA and DPA synthesis in *Schizochytrium* does not involve membrane-bound desaturases or fatty acid elongation enzymes like those described for other eukaryotes (Parker-Barnes et al., 2000, supra; Shanklin et al., 1998, supra). These fractionation data contrast with those obtained from the *Shewanella* enzymes (See Metz et al., 2001, supra) and may indicate use of a different (soluble) acyl acceptor molecule, such as CoA, by the *Schizochytrium* enzyme. It is expected that *Thraustochytrium* will have a similar biochemistry.

In U.S. Pat. No. 6,566,583, a cDNA library from *Schizochytrium* was constructed and approximately 8500 random clones (ESTs) were sequenced. Sequences that exhibited homology to 8 of the 11 domains of the *Shewanella* PKS genes shown in FIG. 2 were all identified at frequencies of 0.2-0.5%. In U.S. Pat. No. 6,566,583, several cDNA clones from *Schizochytrium* showing homology to the *Shewanella* PKS genes were sequenced, and various clones were assembled into nucleic acid sequences representing two partial open reading frames and one complete open reading frame.

Figure 2:
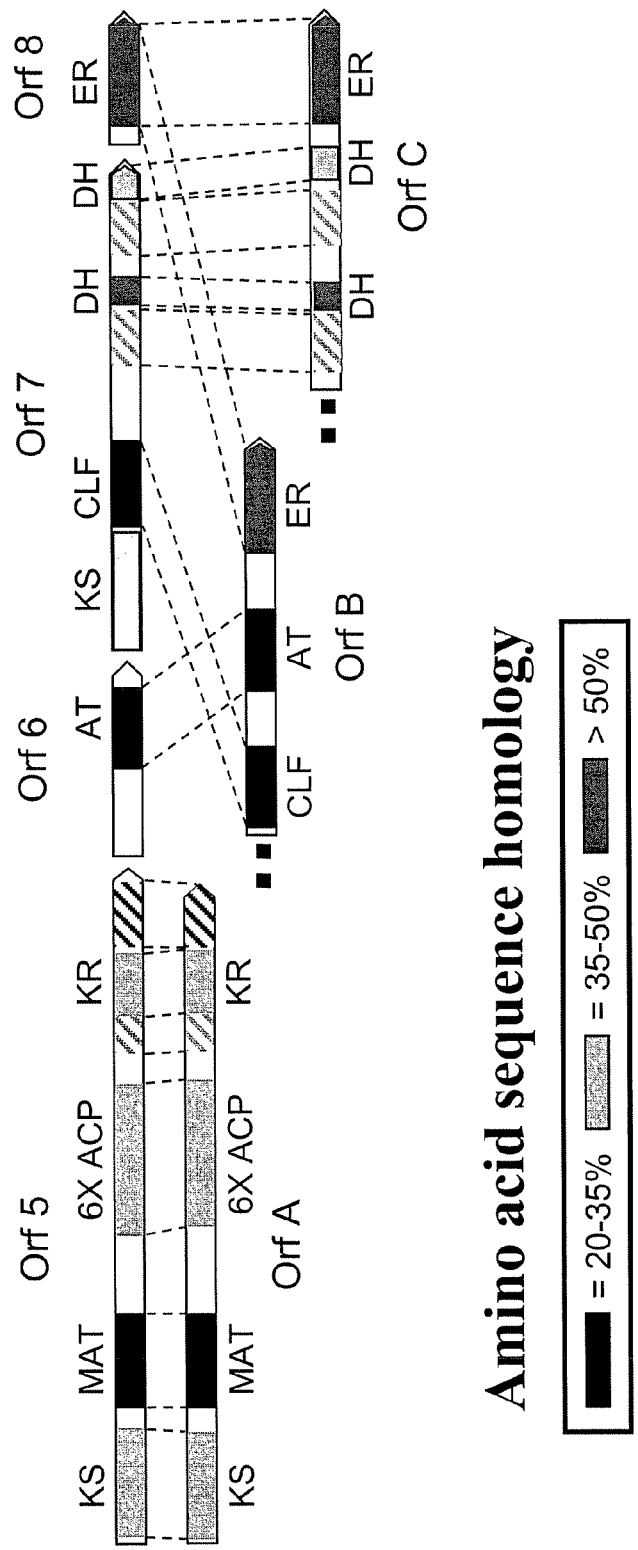
FIG. 2 shows a comparison of domains of PUFA PKS systems from *Schizochytrium* and *Shewanella*.
Figure 3:
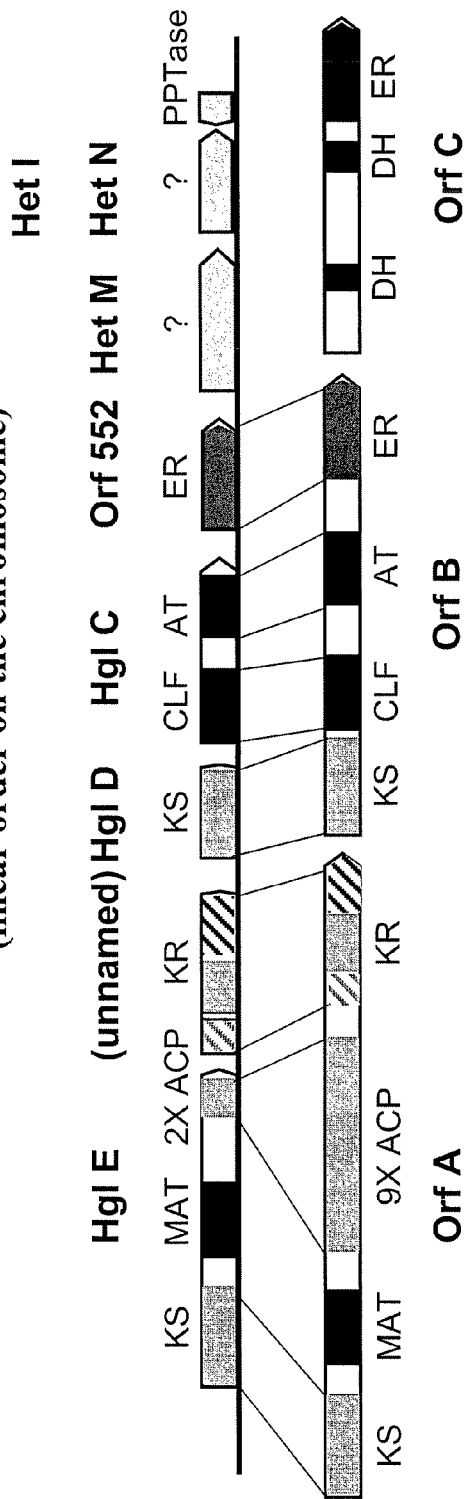
FIG. 3 shows a comparison of domains of PUFA PKS systems from *Schizochytrium* and a related PKS system from *Nostoc* whose product is a long chain fatty acid that does not contain any double bonds.

Further sequencing of cDNA and genomic clones by the present inventors allowed the identification of the full-length genomic sequence of each of OrfA, OrfB and OrfC in *Schizochytrium* and the complete identification of the domains in *Schizochytrium* with homology to those in *Shewanella* (see FIG. 2). These genes are described in detail in U.S. patent application Ser. No. 10/124,800, supra and are described in some detail below.

The present inventors have now identified, cloned, and sequenced the full-length genomic sequence of homologous Orfs in a Thraustochytrid of the genus *Thraustochytrium* (specifically, *Thraustochytrium* sp. 23B (ATCC 20892)) and have identified the domains comprising the PUFA PKS system in this *Thraustochytrium*.

Based on the comparison of the domains of the PUFA PKS system of *Schizochytrium* with the domains of the PUFA PKS system of *Shewanella*, clearly, the *Schizochytrium* genome encodes proteins that are highly similar to the proteins in *Shewanella* that are capable of catalyzing EPA synthesis. The proteins in *Schizochytrium* constitute a PUFA PKS system that catalyzes DHA and DPA synthesis. Simple modification of the reaction scheme identified for *Shewanella* will allow for DHA synthesis in *Schizochytrium*. The homology between the prokaryotic *Shewanella* and eukaryotic *Schizochytrium* genes suggests that the PUFA PKS has undergone lateral gene transfer.

A similar comparison can be made for *Thraustochytrium*. In all cases, comparison of the *Thraustochytrium* 23B (*Th.* 23B) PUFA PKS proteins or domains to other known sequences revealed that the closest match was one of the *Schizochytrium* PUFA PKS proteins (OrfA, B or C, or a domain therefrom) as described in U.S. patent application Ser. No. 10/124,800, supra. The next closest matches in all cases were to one of the PUFA PKS proteins from marine bacteria (*Shewanella* SCRC-2738, *Shewanella oneidensis*, *Photobacter profundum* and *Moritella marina*) or from a related system found in nitrogen fixing cyanobacteria (e.g., *Nostoc punctiforme* and *Nostoc* sp. PCC 7120). The products of the cyanobacterial enzyme systems lack double bonds and the proteins lack domains related to the DH domains implicated in cis double bond formation (i.e., the FabA related DH domains).

According to the present invention, the phrase "open reading frame" is denoted by the abbreviation "Orf". It is noted that the protein encoded by an open reading frame can also be denoted in all upper case letters as "ORF" and a nucleic acid sequence for an open reading frame can also be denoted in all lower case letters as "orf", but for the sake of consistency, the spelling "Orf" is preferentially used herein to describe either the nucleic acid sequence or the protein encoded thereby. It will be obvious from the context of the usage of the term whether a protein or nucleic acid sequence is referenced.

*Schizochytrium* PUFA PKS

FIG. 1 is a graphical representation of the three open reading frames from the *Schizochytrium* PUFA PKS system, and includes the domain structure of this PUFA PKS system. As described in detail in U.S. patent application Ser. No. 10/124,800, the domain structure of each open reading frame is as follows:

Open Reading Frame A (OrfA):

The complete nucleotide sequence for OrfA is represented herein as SEQ ID NO:1. OrfA is a 8730 nucleotide sequence (not including the stop codon) which encodes a 2910 amino acid sequence, represented herein as SEQ ID NO:2. Within OrfA are twelve domains: (a) one β-ketoacyl-ACP synthase (KS) domain; (b) one malonyl-CoA:ACP acyltransferase (MAT) domain; (c) nine acyl carrier protein (ACP) domains; and (d) one β-ketoacyl-ACP reductase (KR) domain. The nucleotide sequence for OrfA has been deposited with GenBank as Accession No. AF378327 (amino acid sequence Accession No. AAK728879).

The first domain in *Schizochytrium* OrfA is a β-ketoacyl-ACP synthase (KS) domain, also referred to herein as OrfA-KS. This domain is contained within the nucleotide sequence spanning from a starting point of between about positions 1 and 40 of SEQ ID NO:1 (OrfA) to an ending point of between about positions 1428 and 1500 of SEQ ID NO:1. The nucleotide sequence containing the sequence encoding the OrfA-KS domain is represented herein as SEQ ID NO:7 (positions 1-1500 of SEQ ID NO:1). The amino acid sequence containing the KS domain spans from a starting point of between about positions 1 and 14 of SEQ ID NO:2 (OrfA) to an ending point of between about positions 476 and 500 of SEQ ID NO:2. The amino acid sequence containing the OrfA-KS domain is represented herein as SEQ ID NO:8 (positions 1-500 of SEQ ID NO:2). It is noted that the OrfA-KS domain contains an active site motif: DXAC* (*acyl binding site $C_{215}$).

According to the present invention, a domain or protein having β-ketoacyl-ACP synthase (KS) biological activity (function) is characterized as the enzyme that carries out the initial step of the FAS (and PKS) elongation reaction cycle. The term "β-ketoacyl-ACP synthase" can be used interchangeably with the terms "3-keto acyl-ACP synthase", "β-keto acyl-ACP synthase", and "keto-acyl ACP synthase", and similar derivatives. The acyl group destined for elongation is linked to a cysteine residue at the active site of the enzyme by a thioester bond. In the multi-step reaction, the acyl-enzyme undergoes condensation with malonyl-ACP to form -ketoacyl-ACP, $CO_2$ and free enzyme. The KS plays a key role in the elongation cycle and in many systems has been shown to possess greater substrate specificity than other enzymes of the reaction cycle. For example, *E. coli* has three distinct KS enzymes—each with its own particular role in the physiology of the organism (Magnuson et al., *Microbiol. Rev.* 57, 522 (1993)). The two KS domains of the PUFA-PKS systems could have distinct roles in the PUFA biosynthetic reaction sequence.

As a class of enzymes, KS's have been well characterized. The sequences of many verified KS genes are known, the active site motifs have been identified and the crystal structures of several have been determined. Proteins (or domains of proteins) can be readily identified as belonging to the KS family of enzymes by homology to known KS sequences.

The second domain in OrfA is a malonyl-CoA:ACP acyltransferase (MAT) domain, also referred to herein as OrfA-MAT. This domain is contained within the nucleotide sequence spanning from a starting point of between about positions 1723 and 1798 of SEQ ID NO:1 (OrfA) to an ending point of between about positions 2805 and 3000 of SEQ ID NO:1. The nucleotide sequence containing the sequence encoding the OrfA-MAT domain is represented herein as SEQ ID NO:9 (positions 1723-3000 of SEQ ID NO:1). The amino acid sequence containing the MAT domain spans from a starting point of between about positions 575 and 600 of SEQ ID NO:2 (OrfA) to an ending point of between about positions 935 and 1000 of SEQ ID NO:2. The amino acid sequence containing the OrfA-MAT domain is represented herein as SEQ ID NO:10 (positions 575-1000 of SEQ ID NO:2). It is noted that the OrfA-MAT domain contains an active site motif: GHS*XG (*acyl binding site $S_{706}$), represented herein as SEQ ID NO:11.

According to the present invention, a domain or protein having malonyl-CoA:ACP acyltransferase (MAT) biological activity (function) is characterized as one that transfers the malonyl moiety from malonyl-CoA to ACP. The term "malonyl-CoA:ACP acyltransferase" can be used interchangeably with "malonyl acyltransferase" and similar derivatives. In addition to the active site motif (GxSxG), these enzymes possess an extended motif (R and Q amino acids in key positions) that identifies them as MAT enzymes (in contrast to the AT domain of *Schizochytrium* Orf B). In some PKS systems (but not the PUFA PKS domain) MAT domains will preferentially load methyl- or ethyl-malonate on to the ACP group (from the corresponding CoA ester), thereby introducing branches into the linear carbon chain. MAT domains can be recognized by their homology to known MAT sequences and by their extended motif structure.

Domains 3-11 of OrfA are nine tandem acyl carrier protein (ACP) domains, also referred to herein as OrfA-ACP (the first domain in the sequence is OrfA-ACP1, the second domain is OrfA-ACP2, the third domain is OrfA-ACP3, etc.). The first ACP domain, OrfA-ACP1, is contained within the nucleotide sequence spanning from about position 3343 to about position 3600 of SEQ ID NO:1 (OrfA). The nucleotide sequence containing the sequence encoding the OrfA-ACP1 domain is represented herein as SEQ ID NO:12 (positions 3343-3600 of SEQ ID NO:1). The amino acid sequence containing the first ACP domain spans from about position 1115 to about position 1200 of SEQ ID NO:2. The amino acid sequence containing the OrfA-ACP1 domain is represented herein as SEQ ID NO:13 (positions 1115-1200 of SEQ ID NO:2). It is noted that the OrfA-ACP1 domain contains an active site motif: LGIDS* (*pantetheine binding motif $S_{1157}$), represented herein by SEQ ID NO:14.

The nucleotide and amino acid sequences of all nine ACP domains are highly conserved and therefore, the sequence for each domain is not represented herein by an individual sequence identifier. However, based on the information disclosed herein, one of skill in the art can readily determine the sequence containing each of the other eight ACP domains (see discussion below).

All nine ACP domains together span a region of OrfA of from about position 3283 to about position 6288 of SEQ ID NO:1, which corresponds to amino acid positions of from about 1095 to about 2096 of SEQ ID NO:2. The nucleotide sequence for the entire ACP region containing all nine domains is represented herein as SEQ ID NO:16. The region represented by SEQ ID NO:16 includes the linker segments between individual ACP domains. The repeat interval for the nine domains is approximately every 330 nucleotides of SEQ ID NO:16 (the actual number of amino acids measured between adjacent active site serines ranges from 104 to 116 amino acids). Each of the nine ACP domains contains a pantetheine binding motif LGIDS* (represented herein by SEQ ID NO:14), wherein S* is the pantetheine binding site serine (S). The pantetheine binding site serine (S) is located near the center of each ACP domain sequence. At each end of the ACP domain region and between each ACP domain is a region that is highly enriched for proline (P) and alanine (A), which is believed to be a linker region. For example, between ACP domains 1 and 2 is the sequence: APAPVKAAA-PAAPVASAPAPA, represented herein as SEQ ID NO:15. The locations of the active site serine residues (i.e., the pantetheine binding site) for each of the nine ACP domains, with respect to the amino acid sequence of SEQ ID NO:2, are as follows: ACP1=$S_{1157}$; ACP2=$S_{1266}$; ACP3=$S_{1377}$; ACP4=$S_{1488}$; ACP5=$S_{1604}$; ACP6=$S_{1715}$; ACP7=$S_{1819}$; ACP8=$S_{1930}$; and ACP9=$S_{2034}$. Given that the average size of an ACP domain is about 85 amino acids, excluding the linker, and about 110 amino acids including the linker, with the active site serine being approximately in the center of the domain, one of skill in the art can readily determine the positions of each of the nine ACP domains in OrfA.

According to the present invention, a domain or protein having acyl carrier protein (ACP) biological activity (function) is characterized as being small polypeptides (typically, 80 to 100 amino acids long), that function as carriers for growing fatty acyl chains via a thioester linkage to a covalently bound co-factor of the protein. They occur as separate units or as domains within larger proteins. ACPs are converted from inactive apo-forms to functional holo-forms by transfer of the phosphopantetheinyl moeity of CoA to a highly conserved serine residue of the ACP. Acyl groups are attached to ACP by a thioester linkage at the free terminus of the phosphopantetheinyl moiety. ACPs can be identified by labeling with radioactive pantetheine and by sequence homology to known ACPs. The presence of variations of the above mentioned motif (LGIDS*) is also a signature of an ACP.

Domain 12 in OrfA is a β-ketoacyl-ACP reductase (KR) domain, also referred to herein as OrfA-KR. This domain is contained within the nucleotide sequence spanning from a starting point of about position 6598 of SEQ ID NO:1 to an ending point of about position 8730 of SEQ ID NO:1. The nucleotide sequence containing the sequence encoding the OrfA-KR domain is represented herein as SEQ ID NO:17 (positions 6598-8730 of SEQ ID NO:1). The amino acid sequence containing the KR domain spans from a starting point of about position 2200 of SEQ ID NO:2 (OrfA) to an ending point of about position 2910 of SEQ ID NO:2. The amino acid sequence containing the OrfA-KR domain is represented herein as SEQ ID NO:18 (positions 2200-2910 of SEQ ID NO:2). Within the KR domain is a core region with homology to short chain aldehyde-dehydrogenases (KR is a member of this family). This core region spans from about position 7198 to about position 7500 of SEQ ID NO:1, which corresponds to amino acid positions 2400-2500 of SEQ ID NO:2.

According to the present invention, a domain or protein having β-ketoacyl-ACP reductase (KR) activity is characterized as one that catalyzes the pyridine-nucleotide-dependent reduction of 3-ketoacyl forms of ACP. The term "β-ketoacyl-ACP reductase" can be used interchangeably with the terms "ketoreductase", "3-ketoacyl-ACP reductase", "keto-acyl ACP reductase" and similar derivatives of the term. It is the first reductive step in the de novo fatty acid biosynthesis elongation cycle and a reaction often performed in polyketide biosynthesis. Significant sequence similarity is observed with one family of enoyl-ACP reductases (ER), the other reductase of FAS (but not the ER family present in the PUFA PKS system), and the short-chain alcohol dehydrogenase family. Pfam analysis of the PUFA PKS region indicated above reveals the homology to the short-chain alcohol dehydrogenase family in the core region. Blast analysis of the same region reveals matches in the core area to known KR enzymes as well as an extended region of homology to domains from the other characterized PUFA PKS systems.

Open Reading Frame B (OrfB):

The complete nucleotide sequence for OrfB is represented herein as SEQ ID NO:3. OrfB is a 6177 nucleotide sequence (not including the stop codon) which encodes a 2059 amino acid sequence, represented herein as SEQ ID NO:4. Within OrfB are four domains: (a) one β-ketoacyl-ACP synthase (KS) domain; (b) one chain length factor (CLF) domain; (c) one acyltransferase (AT) domain; and, (d) one enoyl-ACP reductase (ER) domain. The nucleotide sequence for OrfB has been deposited with GenBank as Accession No. AF378328 (amino acid sequence Accession No. AAK728880).

The first domain in OrfB is a β-ketoacyl-ACP synthase (KS) domain, also referred to herein as OrfB-KS. This domain is contained within the nucleotide sequence spanning from a starting point of between about positions 1 and 43 of SEQ ID NO:3 (OrfB) to an ending point of between about positions 1332 and 1350 of SEQ ID NO:3. The nucleotide sequence containing the sequence encoding the OrfB-KS domain is represented herein as SEQ ID NO:19 (positions 1-1350 of SEQ ID NO:3). The amino acid sequence containing the KS domain spans from a starting point of between about positions 1 and 15 of SEQ ID NO:4 (OrfB) to an ending point of between about positions 444 and 450 of SEQ ID NO:4. The amino acid sequence containing the OrfB-KS domain is represented herein as SEQ ID NO:20 (positions 1-450 of SEQ ID NO:4). It is noted that the OrfB-KS domain contains an active site motif: DXAC* (*acyl binding site $C_{196}$). KS biological activity and methods of identifying proteins or domains having such activity is described above.

The second domain in OrfB is a chain length factor (CLF) domain, also referred to herein as OrfB-CLF. This domain is contained within the nucleotide sequence spanning from a starting point of between about positions 1378 and 1402 of SEQ ID NO:3 (OrfB) to an ending point of between about positions 2682 and 2700 of SEQ ID NO:3. The nucleotide sequence containing the sequence encoding the OrfB-CLF domain is represented herein as SEQ ID NO:21 (positions 1378-2700 of SEQ ID NO:3). The amino acid sequence containing the CLF domain spans from a starting point of between about positions 460 and 468 of SEQ ID NO:4 (OrfB) to an ending point of between about positions 894 and 900 of SEQ ID NO:4. The amino acid sequence containing the OrfB-CLF domain is represented herein as SEQ ID NO:22 (positions 460-900 of SEQ ID NO:4). It is noted that the OrfB-CLF domain contains a KS active site motif without the acyl-binding cysteine.

According to the present invention, a domain or protein is referred to as a chain length factor (CLF) based on the following rationale. The CLF was originally described as characteristic of Type II (dissociated enzymes) PKS systems and was hypothesized to play a role in determining the number of elongation cycles, and hence the chain length, of the end product. CLF amino acid sequences show homology to KS domains (and are thought to form heterodimers with a KS protein), but they lack the active site cysteine. CLF's role in PKS systems is currently controversial. New evidence (C. Bisang et al., Nature 401, 502 (1999)) suggests a role in priming (providing the initial acyl group to be elongated) the PKS systems. In this role the CLF domain is thought to decarboxylate malonate (as malonyl-ACP), thus forming an acetate group that can be transferred to the KS active site. This acetate therefore acts as the 'priming' molecule that can undergo the initial elongation (condensation) reaction. Homologues of the Type II CLF have been identified as 'loading' domains in some modular PKS systems. A domain with the sequence features of the CLF is found in all currently identified PUFA PKS systems and in each case is found as part of a multidomain protein.

The third domain in OrfB is an AT domain, also referred to herein as OrfB-AT. This domain is contained within the nucleotide sequence spanning from a starting point of between about positions 2701 and 3598 of SEQ ID NO:3 (OrfB) to an ending point of between about positions 3975 and 4200 of SEQ ID NO:3. The nucleotide sequence containing the sequence encoding the OrfB-AT domain is represented herein as SEQ ID NO:23 (positions 2701-4200 of SEQ ID NO:3). The amino acid sequence containing the AT domain spans from a starting point of between about positions 901 and 1200 of SEQ ID NO:4 (OrfB) to an ending point of between about positions 1325 and 1400 of SEQ ID NO:4. The amino acid sequence containing the OrfB-AT domain is represented herein as SEQ ID NO:24 (positions 901-1400 of SEQ ID NO:4). It is noted that the OrfB-AT domain contains an active site motif of GxS*xG (*acyl binding site $S_{1140}$) that is characteristic of acyltransferase (AT) proteins.

An "acyltransferase" or "AT" refers to a general class of enzymes that can carry out a number of distinct acyl transfer reactions. The term "acyltransferase" can be used interchangeably with the term "acyl transferase". The Schizochytrium domain shows good homology to a domain present in all of the other PUFA PKS systems currently examined and very weak homology to some acyltransferases whose specific functions have been identified (e.g. to malonyl-CoA:ACP acyltransferase, MAT). In spite of the weak homology to MAT, this AT domain is not believed to function as a MAT because it does not possess an extended motif structure characteristic of such enzymes (see MAT domain description, above). For the purposes of this disclosure, the functions of the AT domain in a PUFA PKS system include, but are not limited to: transfer of the fatty acyl group from the OrfA ACP domain(s) to water (i.e. a thioesterase—releasing the fatty acyl group as a free fatty acid), transfer of a fatty acyl group to an acceptor such as CoA, transfer of the acyl group among the various ACP domains, or transfer of the fatty acyl group to a lipophilic acceptor molecule (e.g. to lysophosphadic acid).

The fourth domain in OrfB is an ER domain, also referred to herein as OrfB-ER. This domain is contained within the nucleotide sequence spanning from a starting point of about position 4648 of SEQ ID NO:3 (OrfB) to an ending point of about position 6177 of SEQ ID NO:3. The nucleotide sequence containing the sequence encoding the OrfB-ER domain is represented herein as SEQ ID NO:25 (positions 4648-6177 of SEQ ID NO:3). The amino acid sequence containing the ER domain spans from a starting point of about position 1550 of SEQ ID NO:4 (OrfB) to an ending point of about position 2059 of SEQ ID NO:4. The amino acid sequence containing the OrfB-ER domain is represented herein as SEQ ID NO:26 (positions 1550-2059 of SEQ ID NO:4).

According to the present invention, this domain has enoyl-ACP reductase (ER) biological activity. According to the present invention, the term "enoyl-ACP reductase" can be used interchangeably with "enoyl reductase", "enoyl ACP-reductase" and "enoyl acyl-ACP reductase". The ER enzyme reduces the trans-double bond (introduced by the DH activity) in the fatty acyl-ACP, resulting in fully saturating those carbons. The ER domain in the PUFA-PKS shows homology to a newly characterized family of ER enzymes (Heath et al., Nature 406, 145 (2000)). Heath and Rock identified this new class of ER enzymes by cloning a gene of interest from Streptococcus pneumoniae, purifying a protein expressed from that gene, and showing that it had ER activity in an in vitro assay. The sequence of the Schizochytrium ER domain of OrfB shows homology to the S. pneumoniae ER protein. All of the PUFA PKS systems currently examined contain at least one domain with very high sequence homology to the Schizochytrium ER domain. The Schizochytrium PUFA PKS system contains two ER domains (one on OrfB and one on OrfC).

Open Reading Frame C (OrfC):

The complete nucleotide sequence for OrfC is represented herein as SEQ ID NO:5. OrfC is a 4509 nucleotide sequence (not including the stop codon) which encodes a 1503 amino acid sequence, represented herein as SEQ ID NO:6. Within OrfC are three domains: (a) two FabA-like β-hydroxyacyl-ACP dehydrase (DH) domains; and (b) one enoyl-ACP reductase (ER) domain. The nucleotide sequence for OrfC has been deposited with GenBank as Accession No. AF378329 (amino acid sequence Accession No. AAK728881).

The first domain in OrfC is a DH domain, also referred to herein as OrfC-DH1. This is one of two DH domains in OrfC, and therefore is designated DH1. This domain is contained within the nucleotide sequence spanning from a starting point of between about positions 1 and 778 of SEQ ID NO:5 (OrfC) to an ending point of between about positions 1233 and 1350 of SEQ ID NO:5. The nucleotide sequence containing the sequence encoding the OrfC-DH1 domain is represented herein as SEQ ID NO:27 (positions 1-1350 of SEQ ID NO:5). The amino acid sequence containing the DH1 domain spans from a starting point of between about positions 1 and 260 of SEQ ID NO:6 (OrfC) to an ending point of between about positions 411 and 450 of SEQ ID NO:6. The amino acid sequence containing the OrfC-DH1 domain is represented herein as SEQ ID NO:28 (positions 1-450 of SEQ ID NO:6).

According to the present invention, this domain has FabA-like β-hydroxyacyl-ACP dehydrase (DH) biological activity. The term "FabA-like β-hydroxyacyl-ACP dehydrase" can be used interchangeably with the terms "FabA-like β-hydroxy acyl-ACP dehydrase", "β-hydroxyacyl-ACP dehydrase", "dehydrase" and similar derivatives. The characteristics of both the DH domains (see below for DH 2) in the PUFA PKS systems have been described in the preceding sections. This class of enzyme removes HOH from a β-ketoacyl-ACP and leaves a trans double bond in the carbon chain. The DH domains of the PUFA PKS systems show homology to bacterial DH enzymes associated with their FAS systems (rather than to the DH domains of other PKS systems). A subset of bacterial DH's, the FabA-like DH's, possesses cis-trans isomerase activity (Heath et al., *J. Biol. Chem.*, 271, 27795 (1996)). It is the homologies to the FabA-like DH's that indicate that one or both of the DH domains is responsible for insertion of the cis double bonds in the PUFA PKS products.

The second domain in OrfC is a DH domain, also referred to herein as OrfC-DH2. This is the second of two DH domains in OrfC, and therefore is designated DH2. This domain is contained within the nucleotide sequence spanning from a starting point of between about positions 1351 and 2437 of SEQ ID NO:5 (OrfC) to an ending point of between about positions 2607 and 2850 of SEQ ID NO:5. The nucleotide sequence containing the sequence encoding the OrfC-DH2 domain is represented herein as SEQ ID NO:29 (positions 1351-2850 of SEQ ID NO:5). The amino acid sequence containing the DH2 domain spans from a starting point of between about positions 451 and 813 of SEQ ID NO:6 (OrfC) to an ending point of between about positions 869 and 950 of SEQ ID NO:6. The amino acid sequence containing the OrfC-DH2 domain is represented herein as SEQ ID NO:30 (positions 451-950 of SEQ ID NO:6). DH biological activity has been described above.

The third domain in OrfC is an ER domain, also referred to herein as OrfC-ER. This domain is contained within the nucleotide sequence spanning from a starting point of about position 2998 of SEQ ID NO:5 (OrfC) to an ending point of about position 4509 of SEQ ID NO:5. The nucleotide sequence containing the sequence encoding the OrfC-ER domain is represented herein as SEQ ID NO:31 (positions 2998-4509 of SEQ ID NO:5). The amino acid sequence containing the ER domain spans from a starting point of about position 1000 of SEQ ID NO:6 (OrfC) to an ending point of about position 1502 of SEQ ID NO:6. The amino acid sequence containing the OrfC-ER domain is represented herein as SEQ ID NO:32 (positions 1000-1502 of SEQ ID NO:6). ER biological activity has been described above.

*Thraustochytrium* 23B PUFA PKS

Th. 23B Open Reading Frame A (OrfA):

The complete nucleotide sequence for Th. 23B OrfA is represented herein as SEQ ID NO:38. SEQ ID NO:38 encodes the following domains in Th. 23B OrfA: (a) one β-ketoacyl-ACP synthase (KS) domain; (b) one malonyl-CoA:ACP acyltransferase (MAT) domain; (c) eight acyl carrier protein (ACP) domains; and (d) one β-ketoacyl-ACP reductase (KR) domain. This domain organization is the same as is present in *Schizochytrium* OrfA (SEQ ID NO:1) with the exception that the Th. 23B OrfA has 8 adjacent ACP domains, while *Schizochytrium* OrfA has 9 adjacent ACP domains. Th. 23B OrfA is a 8433 nucleotide sequence (not including the stop codon) which encodes a 2811 amino acid sequence, represented herein as SEQ ID NO:39. The Th. 23B OrfA amino acid sequence (SEQ ID NO:39) was compared with known sequences in a standard BLAST search (BLAST parameters: Blastp, low complexity filter Off, program—BLOSUM62, Gap cost—Existence: 11, Extension 1; (BLAST described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety))). At the amino acid level, the sequences with the greatest degree of homology to Th. 23B OrfA was *Schizochytrium* Orf A (gb AAK72879.1) (SEQ ID NO:2). The alignment extends over the entire query but is broken into 2 pieces (due to the difference in numbers of ACP repeats). SEQ ID NO:39 first aligns at positions 6 through 1985 (including 8 ACP domains) with SEQ ID NO:2 and shows a sequence identity to SEQ ID NO:2 of 54% over 2017 amino acids. SEQ ID NO:39 also aligns at positions 980 through 2811 with SEQ ID NO:2 and shows a sequence identity to SEQ ID NO:2 of 43% over 1861 amino acids. In this second alignment, the match is evident for the Th. 23B 8×ACPs in the regions of the conserved pantetheine attachment site motif, but is very poor over the 1st *Schizochytrium* ACP domain (i.e., there is not a $9^{th}$ ACP domain in the Th. 23B query sequence, but the Blastp output under theses conditions attempts to align them anyway). SEQ ID NO:39 shows the next closest identity with sequences from *Shewanella oneidensis* (Accession No. NP_717214) and *Photobacter profundum* (Accession No. AAL01060).

The first domain in Th. 23B OrfA is a KS domain, also referred to herein as Th. 23B OrfA-KS. KS domain function has been described in detail above. This domain is contained within the nucleotide sequence spanning from about position 1 to about position 1500 of SEQ ID NO:38, represented herein as SEQ ID NO:40. The amino acid sequence containing the Th. 23B KS domain is a region of SEQ ID NO:39 spanning from about position 1 to about position 500 of SEQ ID NO:39, represented herein as SEQ ID NO:41. This region of SEQ ID NO:39 has a Pfam match to FabB (β-ketoacyl-ACP synthase) spanning from position 1 to about position 450 of SEQ ID NO:39 (also positions 1 to about 450 of SEQ ID NO:41). It is noted that the Th. 23B OrfA-KS domain contains an active site motif: DXAC* (*acyl binding site $C_{207}$). Also, a characteristic motif at the end of the Th. 23B KS region, GFGG, is present in positions 453-456 of SEQ ID NO:39 (also positions 453-456 of SEQ ID NO:41). The amino acid sequence spanning positions 1-500 of SEQ ID NO:39 is about 79% identical to *Schizochytrium* OrfA (SEQ ID NO:2) over 496 amino acids. The amino acid sequence spanning positions 1-450 of SEQ ID NO:39 is about 81% identical to *Schizochytrium* OrfA (SEQ ID NO:2) over 446 amino acids.

The second domain in Th. 23B OrfA is a MAT domain, also referred to herein as Th. 23B OrfA-MAT. MAT domain function has been described in detail above. This domain is contained within the nucleotide sequence spanning from between about position 1503 and about position 3000 of SEQ ID NO:38, represented herein as SEQ ID NO:42. The amino acid sequence containing the Th. 23B MAT domain is a region of SEQ ID NO:39 spanning from about position 501 to about position 1000, represented herein by SEQ ID NO:43. This region of SEQ ID NO:39 has a Pfam match to FabD (malonyl-CoA:ACP acyltransferase) spanning from about position 580 to about position 900 of SEQ ID NO:39 (positions 80-400 of SEQ ID NO:43). It is noted that the Th. 23B OrfA-MAT domain contains an active site motif: GHS*XG (*acyl binding site $S_{697}$), represented by positions 695-699 of SEQ ID NO:39. The amino acid sequence spanning positions 501-1000 of SEQ ID NO:39 is about 46% identical to *Schizochytrium* OrfA (SEQ ID NO:2) over 481 amino acids. The amino acid sequence spanning positions 580-900 of SEQ ID NO:39 is about 50% identical to *Schizochytrium* OrfA (SEQ ID NO:2) over 333 amino acids.

Domains 3-10 of Th. 23B OrfA are eight tandem ACP domains, also referred to herein as Th. 23B OrfA-ACP (the first domain in the sequence is OrfA-ACP1, the second domain is OrfA-ACP2, the third domain is OrfA-ACP3, etc.). The function of ACP domains has been described in detail above. The first Th. 23B ACP domain, Th. 23B OrfA-ACP1, is contained within the nucleotide sequence spanning from about position 3205 to about position 3555 of SEQ ID NO:38 (OrfA), represented herein as SEQ ID NO:44. The amino acid sequence containing the first Th. 23B ACP domain is a region of SEQ ID NO:39 spanning from about position 1069 to about position 1185 of SEQ ID NO:39, represented herein by SEQ ID NO:45. The amino acid sequence spanning positions 1069-1185 of SEQ ID NO:39 is about 65% identical to *Schizochytrium* OrfA (SEQ ID NO:2) over 85 amino acids. Th. 23B OrfA-ACP1 has a similar identity to any one of the nine ACP domains in *Schizochytrium* OrfA.

The eight ACP domains in Th. 23B OrfA are adjacent to one another and can be identified by the presence of the phosphopantetheine binding site motif, LGXDS* (represented by SEQ ID NO:46), wherein the S* is the phosphopantetheine attachment site. The amino acid position of each of the eight S* sites, with reference to SEQ ID NO:39, are 1128 (ACP1), 1244 (ACP2), 1360 (ACP3), 1476 (ACP4), 1592 (ACP5), 1708 (ACP6), 1824 (ACP7) and 1940 (ACP8). The nucleotide and amino acid sequences of all eight Th. 23B ACP domains are highly conserved and therefore, the sequence for each domain is not represented herein by an individual sequence identifier. However, based on the information disclosed herein, one of skill in the art can readily determine the sequence containing each of the other seven ACP domains in SEQ ID NO:38 and SEQ ID NO:39.

All eight Th. 23B ACP domains together span a region of Th. 23B OrfA of from about position 3205 to about position 5994 of SEQ ID NO:38, which corresponds to amino acid positions of from about 1069 to about 1998 of SEQ ID NO:39. The nucleotide sequence for the entire ACP region containing all eight domains is represented herein as SEQ ID NO:47. SEQ ID NO:47 encodes an amino acid sequence represented herein by SEQ ID NO:48. SEQ ID NO:48 includes the linker segments between individual ACP domains. The repeat interval for the eight domains is approximately every 116 amino acids of SEQ ID NO:48, and each domain can be considered to consist of about 116 amino acids centered on the active site motif (described above). It is noted that the linker regions between the nine adjacent ACP domains in OrfA in *Schizochytrium* are highly enriched in proline and alanine residues, while the linker regions between the eight adjacent ACP domains in OrfA of *Thraustochytrium* are highly enriched in serine residues (and not proline or alanine residues).

The last domain in Th. 23B OrfA is a KR domain, also referred to herein as Th. 23B OrfA-KR. KR domain function has been discussed in detail above. This domain is contained within the nucleotide sequence spanning from between about position 6001 to about position 8433 of SEQ ID NO:38, represented herein by SEQ ID NO:49. The amino acid sequence containing the Th. 23B KR domain is a region of SEQ ID NO:39 spanning from about position 2001 to about position 2811 of SEQ ID NO:39, represented herein by SEQ ID NO:50. This region of SEQ ID NO:39 has a Pfam match to FabG (β-ketoacyl-ACP reductase) spanning from about position 2300 to about 2550 of SEQ ID NO:39 (positions 300-550 of SEQ ID NO:50). The amino acid sequence spanning positions 2001-2811 of SEQ ID NO:39 is about 40% identical to *Schizochytrium* OrfA (SEQ ID NO:2) over 831 amino acids. The amino acid sequence spanning positions 2300-2550 of SEQ ID NO:39 is about 51% identical to *Schizochytrium* OrfA (SEQ ID NO:2) over 235 amino acids.

Th. 23B Open Reading Frame B (Or/B):

The complete nucleotide sequence for Th. 23B OrfB is represented herein as SEQ ID NO:51. SEQ ID NO:51 encodes the following domains in Th. 23B OrfB: (a) one β-ketoacyl-ACP synthase (KS) domain; (b) one chain length factor (CLF) domain; (c) one acyltransferase (AT) domain; and, (d) one enoyl-ACP reductase (ER) domain. This domain organization is the same as in *Schizochytrium* Orf B (SEQ ID NO:3) with the exception that the linker region between the AT and ER domains of the *Schizochytrium* protein is longer than that of Th. 23B by about 50-60 amino acids. Also, this linker region in *Schizochytrium* has a specific area that is highly enriched in serine residues (it contains 15 adjacent serine residues, in addition to other serines in the region), whereas the corresponding linker region in Th. 23B OrfB is not enriched in serine residues. This difference in the AT/ER linker region most likely accounts for a break in the alignment between *Schizochytrium* OrfB and Th. 23B OrfB at the start of this region.

Th. 23B OrfB is a 5805 nucleotide sequence (not including the stop codon) which encodes a 1935 amino acid sequence, represented herein as SEQ ID NO:52. The Th. 23B OrfB amino acid sequence (SEQ ID NO:52) was compared with known sequences in a standard BLAST search (BLAST parameters: Blastp, low complexity filter Off, program—BLOSUM62, Gap cost—Existence: 11, Extension 1; (BLAST described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety))). At the amino acid level, the sequences with the greatest degree of homology to Th. 23B OrfB were *Schizochytrium* Orf B (gb AAK72880.1) (SEQ ID NO:4), over most of OrfB; and *Schizochytrium* OrfC (gb AAK728881.1) (SEQ ID NO:6), over the last domain (the alignment is broken into 2 pieces, as mentioned above). SEQ ID NO:52 first aligns at positions 10 through about 1479 (including the KS, CLF and AT domains) with SEQ ID NO:4 and shows a sequence identity to SEQ ID NO:4 of 52% over 1483 amino acids. SEQ ID NO:52 also aligns at positions 1491 through 1935 (including the ER domain) with SEQ ID NO:6 and shows a sequence identity to SEQ ID NO:4 of 64% over 448 amino acids.

The first domain in the Th. 23B OrfB is a KS domain, also referred to herein as Th. 23B OrfB-KS. KS domain function has been described in detail above. This domain is contained within the nucleotide sequence spanning from between about position 1 and about position 1500 of SEQ ID NO:51 (Th. 23B OrfB), represented herein as SEQ ID NO:53. The amino acid sequence containing the Th. 23B KS domain is a region of SEQ ID NO: 52 spanning from about position 1 to about position 500 of SEQ ID NO:52, represented herein as SEQ ID NO:54. This region of SEQ ID NO:52 has a Pfam match to FabB (β-ketoacyl-ACP synthase) spanning from about position 1 to about position 450 (positions 1-450 of SEQ ID NO:54). It is noted that the Th. 23B OrfB-KS domain contains an active site motif: DXAC*, where C* is the site of acyl group attachment and wherein the C* is at position 201 of SEQ ID NO:52. Also, a characteristic motif at the end of the KS region, GFGG is present in amino acid positions 434-437 of SEQ ID NO:52. The amino acid sequence spanning positions 1-500 of SEQ ID NO:52 is about 64% identical to *Schizochytrium* OrfB (SEQ ID NO:4) over 500 amino acids.

The amino acid sequence spanning positions 1-450 of SEQ ID NO:52 is about 67% identical to *Schizochytrium* OrfB (SEQ ID NO:4) over 442 amino acids.

The second domain in Th. 23B OrfB is a CLF domain, also referred to herein as Th. 23B OrfB-CLF. CLF domain function has been described in detail above. This domain is contained within the nucleotide sequence spanning from between about position 1501 and about position 3000 of SEQ ID NO:51 (OrfB), represented herein as SEQ ID NO:55. The amino acid sequence containing the CLF domain is a region of SEQ ID NO: 52 spanning from about position 501 to about position 1000 of SEQ ID NO:52, represented herein as SEQ ID NO:56. This region of SEQ ID NO:52 has a Pfam match to FabB (β-ketoacyl-ACP synthase) spanning from about position 550 to about position 910 (positions 50-410 of SEQ ID NO:56). Although CLF has homology to KS proteins, it lacks an active site cysteine to which the acyl group is attached in KS proteins. The amino acid sequence spanning positions 501-1000 of SEQ ID NO:52 is about 49% identical to *Schizochytrium* OrfB (SEQ ID NO:4) over 517 amino acids. The amino acid sequence spanning positions 550-910 of SEQ ID NO:52 is about 54% identical to *Schizochytrium* OrfB (SEQ ID NO:4) over 360 amino acids.

The third domain in Th. 23B OrfB is an AT domain, also referred to herein as Th. 23B OrfB-AT. AT domain function has been described in detail above. This domain is contained within the nucleotide sequence spanning from between about position 3001 and about position 4500 of SEQ ID NO:51 (Th. 23B OrfB), represented herein as SEQ ID NO:58. The amino acid sequence containing the Th. 23B AT domain is a region of SEQ ID NO: 52 spanning from about position 1001 to about position 1500 of SEQ ID NO:52, represented herein as SEQ ID NO:58. This region of SEQ ID NO:52 has a Pfam match to FabD (malonyl-CoA:ACP acyltransferase) spanning from about position 1100 to about position 1375 (positions 100-375 of SEQ ID NO:58). Although this AT domain of the PUFA synthases has homology to MAT proteins, it lacks the extended motif of the MAT (key arginine and glutamine residues) and it is not thought to be involved in malonyl-CoA transfers. The GXS*XG motif of acyltransferases is present, with the S* being the site of acyl attachment and located at position 1123 with respect to SEQ ID NO:52. The amino acid sequence spanning positions 1001-1500 of SEQ ID NO:52 is about 44% identical to *Schizochytrium* OrfB (SEQ ID NO:4) over 459 amino acids. The amino acid sequence spanning positions 1100-1375 of SEQ ID NO:52 is about 45% identical to *Schizochytrium* OrfB (SEQ ID NO:4) over 283 amino acids.

The fourth domain in Th. 23B OrfB is an ER domain, also referred to herein as Th. 23B OrfB-ER. ER domain function has been described in detail above. This domain is contained within the nucleotide sequence spanning from between about position 4501 and about position 5805 of SEQ ID NO:51 (OrfB), represented herein as SEQ ID NO:59. The amino acid sequence containing the Th. 23B ER domain is a region of SEQ ID NO: 52 spanning from about position 1501 to about position 1935 of SEQ ID NO:52, represented herein as SEQ ID NO:60. This region of SEQ ID NO:52 has a Pfam match to a family of dioxygenases related to 2-nitropropane dioxygenases spanning from about position 1501 to about position 1810 (positions 1-310 of SEQ ID NO:60). That this domain functions as an ER can be further predicted due to homology to a newly characterized ER enzyme from *Streptococcus pneumoniae*. The amino acid sequence spanning positions 1501-1935 of SEQ ID NO:52 is about 66% identical to *Schizochytrium* OrfB (SEQ ID NO:4) over 433 amino acids. The amino acid sequence spanning positions 1501-1810 of SEQ ID NO:52 is about 70% identical to *Schizochytrium* OrfB (SEQ ID NO:4) over 305 amino acids.

Th. 23B Open Reading Frame C (OrfC):

The complete nucleotide sequence for Th. 23B OrfC is represented herein as SEQ ID NO:61. SEQ ID NO:61 encodes the following domains in Th. 23B OrfC: (a) two FabA-like β-hydroxyacyl-ACP dehydrase (DH) domains, both with homology to the FabA protein (an enzyme that catalyzes the synthesis of trans-2-decenoyl-ACP and the reversible isomerization of this product to cis-3-decenoyl-ACP); and (b) one enoyl-ACP reductase (ER) domain with high homology to the ER domain of *Schizochytrium* OrfB. This domain organization is the same as in *Schizochytrium* Orf C (SEQ ID NO:5).

Th. 23B OrfC is a 4410 nucleotide sequence (not including the stop codon) which encodes a 1470 amino acid sequence, represented herein as SEQ ID NO:62. The Th. 23B OrfC amino acid sequence (SEQ ID NO:62) was compared with known sequences in a standard BLAST search (BLAST parameters: Blastp, low complexity filter Off, program—BLOSUM62, Gap cost—Existence: 11, Extension 1; (BLAST described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety))). At the amino acid level, the sequences with the greatest degree of homology to Th. 23B OrfC was *Schizochytrium* OrfC (gb AAK728881.1) (SEQ ID NO:6). SEQ ID NO:52 is 66% identical to *Schizochytrium* OrfC (SEQ ID NO:6).

The first domain in Th. 23B OrfC is a DH domain, also referred to herein as Th. 23B OrfC-DH1. DH domain function has been described in detail above. This domain is contained within the nucleotide sequence spanning from between about position 1 to about position 1500 of SEQ ID NO:61 (OrfC), represented herein as SEQ ID NO:63. The amino acid sequence containing the Th. 23B DH1 domain is a region of SEQ ID NO: 62 spanning from about position 1 to about position 500 of SEQ ID NO:62, represented herein as SEQ ID NO:64. This region of SEQ ID NO:62 has a Pfam match to FabA, as mentioned above, spanning from about position 275 to about position 400 (positions 275-400 of SEQ ID NO:64). The amino acid sequence spanning positions 1-500 of SEQ ID NO:62 is about 66% identical to *Schizochytrium* OrfC (SEQ ID NO:6) over 526 amino acids. The amino acid sequence spanning positions 275-400 of SEQ ID NO:62 is about 81% identical to *Schizochytrium* OrfC (SEQ ID NO:6) over 126 amino acids.

The second domain in Th. 23B OrfC is also a DH domain, also referred to herein as Th. 23B OrfC-DH2. This is the second of two DH domains in OrfC, and therefore is designated DH2. This domain is contained within the nucleotide sequence spanning from between about position 1501 to about 3000 of SEQ ID NO:61 (OrfC), represented herein as SEQ ID NO:65. The amino acid sequence containing the Th. 23B DH2 domain is a region of SEQ ID NO: 62 spanning from about position 501 to about position 1000 of SEQ ID NO:62, represented herein as SEQ ID NO:66. This region of SEQ ID NO:62 has a Pfam match to FabA, as mentioned above, spanning from about position 800 to about position 925 (positions 300-425 of SEQ ID NO:66). The amino acid sequence spanning positions 501-1000 of SEQ ID NO:62 is about 56% identical to *Schizochytrium* OrfC (SEQ ID NO:6) over 518 amino acids. The amino acid sequence spanning positions 800-925 of SEQ ID NO:62 is about 58% identical to *Schizochytrium* OrfC (SEQ ID NO:6) over 124 amino acids.

The third domain in Th. 23B OrfC is an ER domain, also referred to herein as Th. 23B OrfC-ER. ER domain function has been described in detail above. This domain is contained within the nucleotide sequence spanning from between about position 3001 to about position 4410 of SEQ ID NO:61 (OrfC), represented herein as SEQ ID NO:67. The amino acid sequence containing the Th. 23B ER domain is a region of SEQ ID NO: 62 spanning from about position 1001 to about position 1470 of SEQ ID NO:62, represented herein as SEQ ID NO:68. This region of SEQ ID NO:62 has a Pfam match to the dioxygenases related to 2-nitropropane dioxygenases, as mentioned above, spanning from about position 1025 to about position 1320 (positions 25-320 of SEQ ID NO:68). This domain function as an ER can also be predicted due to homology to a newly characterized ER enzyme from *Streptococcus pneumoniae*. The amino acid sequence spanning positions 1001-1470 of SEQ ID NO:62 is about 75% identical to *Schizochytrium* OrfB (SEQ ID NO:4) over 474 amino acids. The amino acid sequence spanning positions 1025-1320 of SEQ ID NO:62 is about 81% identical to *Schizochytrium* OrfB (SEQ ID NO:4) over 296 amino acids.

One embodiment of the present invention relates to an isolated protein or domain from a non-bacterial PUFA PKS system, a homologue thereof, and/or a fragment thereof. Also included in the invention are isolated nucleic acid molecules encoding any of the proteins, domains or peptides described herein (discussed in detail below). According to the present invention, an isolated protein or peptide, such as a protein or peptide from a PUFA PKS system, is a protein or a fragment thereof (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. An isolated peptide can be produced synthetically (e.g., chemically, such as by peptide synthesis) or recombinantly. In addition, and by way of example, a "*Thraustochytrium* PUFA PKS protein" refers to a PUFA PKS protein (generally including a homologue of a naturally occurring PUFA PKS protein) from a *Thraustochytrium* microorganism, or to a PUFA PKS protein that has been otherwise produced from the knowledge of the structure (e.g., sequence), and perhaps the function, of a naturally occurring PUFA PKS protein from *Thraustochytrium*. In other words, general reference to a *Thraustochytrium* PUFA PKS protein includes any PUFA PKS protein that has substantially similar structure and function of a naturally occurring PUFA PKS protein from *Thraustochytrium* or that is a biologically active (i.e., has biological activity) homologue of a naturally occurring PUFA PKS protein from *Thraustochytrium* as described in detail herein. As such, a *Thraustochytrium* PUFA PKS protein can include purified, partially purified, recombinant, mutated/modified and synthetic proteins. The same description applies to reference to other proteins or peptides described herein, such as the PUFA PKS proteins and domains from *Schizochytrium* or from other microorganisms.

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with another compound. Such modifications can be considered to be mutations, for example, if the modification is different than the post-translational modification that occurs in the natural, wild-type protein or peptide.

As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. A homologue can have either enhanced, decreased, or substantially similar properties as compared to the naturally occurring protein or peptide. Preferred homologues of a PUFA PKS protein or domain are described in detail below. It is noted that homologues can include synthetically produced homologues, naturally occurring allelic variants of a given protein or domain, or homologous sequences from organisms other than the organism from which the reference sequence was derived.

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* (1982) 157: 105-132), or on the basis of the ability to assume similar polypeptide secondary structure (Chou and Fasman, *Adv. Enzymol.* (1978) 47: 45-148, 1978).

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications or mutations in protein homologues, as compared to the wild-type protein, either increase, decrease, or do not substantially change, the basic biological activity of the homologue as compared to the naturally occurring (wild-type) protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Biological activities of PUFA PKS systems and the individual proteins/domains that make up a PUFA PKS system have been described in detail elsewhere herein. Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action (or activity) of a protein. Similarly, modifications which result in an increase in protein expression or an increase in the activity of the protein, can be referred to as amplification, overproduction, activation, enhancement, up-regulation or increased action (or activity) of a protein. It is noted that general reference to a homologue having the biological activity of the wild-type protein does not necessarily mean that the homologue has identical biological activity as the wild-type protein, particularly with regard to the level of biological activity. Rather, a homologue can perform the same biological activity as the wild-type protein, but at a reduced or increased level of activity as compared to the wild-type protein. A functional domain of a PUFA PKS system is a domain (i.e., a domain can be a portion of a protein) that is capable of performing a biological function (i.e., has biological activity).

Methods of detecting and measuring PUFA PKS protein or domain biological activity include, but are not limited to, measurement of transcription of a PUFA PKS protein or domain, measurement of translation of a PUFA PKS protein or domain, measurement of posttranslational modification of a PUFA PKS protein or domain, measurement of enzymatic activity of a PUFA PKS protein or domain, and/or measurement production of one or more products of a PUFA PKS system (e.g., PUFA production). It is noted that an isolated protein of the present invention (including a homologue) is not necessarily required to have the biological activity of the wild-type protein. For example, a PUFA PKS protein or domain can be a truncated, mutated or inactive protein, for example. Such proteins are useful in screening assays, for example, or for other purposes such as antibody production. In a preferred embodiment, the isolated proteins of the present invention have biological activity that is similar to that of the wild-type protein (although not necessarily equivalent, as discussed above).

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichrosim, or nuclear magnetic resonance (NMR).

In one embodiment, the present invention relates to an isolated protein comprising an amino acid sequence selected from the group consisting of: (a) an amino acid sequence selected from the group consisting of: SEQ ID NO:39, SEQ ID NO:52, SEQ ID NO:62, and biologically active fragments thereof; (b) an amino acid sequence selected from the group consisting of: SEQ ID NO:41, SEQ ID NO:43, SEQ ID NO:45, SEQ ID NO:48, SEQ ID NO:50, SEQ ID NO:54, SEQ ID NO:56, SEQ ID NO:58, SEQ ID NO:60, SEQ ID NO:64, SEQ ID NO:66, SEQ ID NO:68 and biologically active fragments thereof; (c) an amino acid sequence that is at least about 60% identical to at least 500 consecutive amino acids of the amino acid sequence of (a), wherein the amino acid sequence has a biological activity of at least one domain of a polyunsaturated fatty acid (PUFA) polyketide synthase (PKS) system; and/or (d) an amino acid sequence that is at least about 60% identical to the amino acid sequence of (b), wherein the amino acid sequence has a biological activity of at least one domain of a polyunsaturated fatty acid (PUFA) polyketide synthase (PKS) system. In a further embodiment, an amino acid sequence including the active site domains or other functional motifs described above for several of the PUFA PKS domains are encompassed by the invention. In one embodiment, the amino acid sequence described above does not include any of the following amino acid sequences: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32.

In one aspect of the invention, a PUFA PKS protein or domain encompassed by the present invention, including a homologue of a particular PUFA PKS protein or domain described herein, comprises an amino acid sequence that is at least about 60% identical to at least 500 consecutive amino acids of an amino acid sequence chosen from: SEQ ID NO:39, SEQ ID NO:52, or SEQ ID NO:62, wherein the amino acid sequence has a biological activity of at least one domain of a PUFA PKS system. In a further aspect, the amino acid sequence of the protein is at least about 60% identical to at least about 600 consecutive amino acids, and more preferably to at least about 700 consecutive amino acids, and more preferably to at least about 800 consecutive amino acids, and more preferably to at least about 900 consecutive amino acids, and more preferably to at least about 1000 consecutive amino acids, and more preferably to at least about 1100 consecutive amino acids, and more preferably to at least about 1200 consecutive amino acids, and more preferably to at least about 1300 consecutive amino acids, and more preferably to at least about 1400 consecutive amino acids of any of SEQ ID NO:39, SEQ ID NO:52, or SEQ ID NO:62, or to the full length of SEQ ID NO:62. In a further aspect, the amino acid sequence of the protein is at least about 60% identical to at least about 1500 consecutive amino acids, and more preferably to at least about 1600 consecutive amino acids, and more preferably to at least about 1700 consecutive amino acids, and more preferably to at least about 1800 consecutive amino acids, and more preferably to at least about 1900 consecutive amino acids, of any of SEQ ID NO:39 or SEQ ID NO:52, or to the full length of SEQ ID NO:52. In a further aspect, the amino acid sequence of the protein is at least about 60% identical to at least about 2000 consecutive amino acids, and more preferably to at least about 2100 consecutive amino acids, and more preferably to at least about 2200 consecutive amino acids, and more preferably to at least about 2300 consecutive amino acids, and more preferably to at least about 2400 consecutive amino acids, and more preferably to at least about 2500 consecutive amino acids, and more preferably to at least about 2600 consecutive amino acids, and more preferably to at least about 2700 consecutive amino acids, and more preferably to at least about 2800 consecutive amino acids, and even more preferably, to the full length of SEQ ID NO:39. In one embodiment, the amino acid sequence described above does not include any of the following amino acid sequences: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32.

In another aspect, a PUFA PKS protein or domain encompassed by the present invention, including homologues as described above, comprises an amino acid sequence that is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:39, SEQ ID NO:52, or SEQ ID NO:62, over any of the consecutive amino acid lengths described in the paragraph above, wherein the amino acid sequence has a biological activity of at least one domain of a PUFA PKS system. In one embodiment, the amino acid sequence described above does not include any of the following amino acid sequences: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32.

In one aspect of the invention, a PUFA PKS protein or domain encompassed by the present invention, including a homologue as described above, comprises an amino acid sequence that is at least about 60% identical to an amino acid sequence chosen from: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, wherein the amino acid sequence has a biological activity of at least one domain of a PUFA PKS system. In a further aspect, the amino acid sequence of the protein is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, wherein the amino acid sequence has a biological activity of at least one domain of a PUFA PKS system. In one embodiment, the amino acid sequence described above does not include any of the following amino acid sequences: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32.

In another aspect, a PUFA PKS protein or domain encompassed by the present invention, including a homologue as described above, comprises an amino acid sequence that is at least about 50% identical to an amino acid sequence chosen from: SEQ ID NO:39, SEQ ID NO:43, SEQ ID NO:50, SEQ ID NO:52, and SEQ ID NO:58, wherein the amino acid sequence has a biological activity of at least one domain of a PUFA PKS system. In another aspect, the amino acid sequence of the protein is at least about 55% identical, and more preferably at least about 60% identical, to an amino acid sequence chosen from: SEQ ID NO:39, SEQ ID NO:43, SEQ ID NO:50, SEQ ID NO:52, SEQ ID NO:56 and SEQ ID NO:58, wherein the amino acid sequence has a biological activity of at least one domain of a PUFA PKS system. In a further aspect, the amino acid sequence of the protein is at least about 65% identical to an amino acid sequence chosen from SEQ ID NO:39, SEQ ID NO:43, SEQ ID NO:50, SEQ ID NO:52, SEQ ID NO:54, SEQ ID NO:56 and SEQ ID NO:58, wherein the amino acid sequence has a biological activity of at least one domain of a PUFA PKS system. In another aspect, the amino acid sequence of the protein is at least about 70% identical, and more preferably at least about 75% identical, to an amino acid sequence chosen from: SEQ ID NO:39, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, and SEQ ID NO:64, wherein the amino acid sequence has a biological activity of at least one domain of a PUFA PKS system. In another aspect, the amino acid sequence of the protein is at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical, to an amino acid sequence chosen from: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, wherein the amino acid sequence has a biological activity of at least one domain of a PUFA PKS system. In one embodiment, the amino acid sequence described above does not include any of the following amino acid sequences: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32.

In a preferred embodiment an isolated protein or domain of the present invention comprises, consists essentially of, or consists of, an amino acid sequence chosen from: SEQ ID NO:39, SEQ ID NO:41, SEQ ID NO:43, SEQ ID NO:45, SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, or any biologically active fragments thereof, including any fragments that have a biological activity of at least one domain of a PUFA PKS system.

In one aspect of the present invention, the following *Schizochytrium* proteins and domains are useful in one or more embodiments of the present invention, all of which have been previously described in detail in U.S. patent application Ser. No. 10/124,800, supra. In one aspect of the invention, a PUFA PKS protein or domain useful in the present invention comprises an amino acid sequence that is at least about 60% identical to at least 500 consecutive amino acids of an amino acid sequence chosen from: SEQ ID NO:2, SEQ ID NO:4, and SEQ ID NO:6; wherein the amino acid sequence has a biological activity of at least one domain of a PUFA PKS system. In a further aspect, the amino acid sequence of the protein is at least about 60% identical to at least about 600 consecutive amino acids, and more preferably to at least about 700 consecutive amino acids, and more preferably to at least about 800 consecutive amino acids, and more preferably to at least about 900 consecutive amino acids, and more preferably to at least about 1000 consecutive amino acids, and more preferably to at least about 1100 consecutive amino acids, and more preferably to at least about 1200 consecutive amino acids, and more preferably to at least about 1300 consecutive amino acids, and more preferably to at least about 1400 consecutive amino acids, and more preferably to at least about 1500 consecutive amino acids of any of SEQ ID NO:2, SEQ ID NO:4 and SEQ ID NO:6, or to the full length of SEQ ID NO:6. In a further aspect, the amino acid sequence of the protein is at least about 60% identical to at least about 1600 consecutive amino acids, and more preferably to at least about 1700 consecutive amino acids, and more preferably to at least about 1800 consecutive amino acids, and more preferably to at least about 1900 consecutive amino acids, and more preferably to at least about 2000 consecutive amino acids of any of SEQ ID NO:2 or SEQ ID NO:4, or to the full length of SEQ ID NO:4. In a further aspect, the amino acid sequence of the protein is at least about 60% identical to at least about 2100 consecutive amino acids, and more preferably to at least about 2200 consecutive amino acids, and more preferably to at least about 2300 consecutive amino acids, and more preferably to at least about 2400 consecutive amino acids, and more preferably to at least about 2500 consecutive amino acids, and more preferably to at least about 2600 consecutive amino acids, and more preferably to at least about 2700 consecutive amino acids, and more preferably to at least about 2800 consecutive amino acids, and even more preferably, to the full length of SEQ ID NO:2.

In another aspect, a PUFA PKS protein or domain useful in one or more embodiments of the present invention comprises an amino acid sequence that is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:2, SEQ ID NO:4, or SEQ ID NO:6, over any of the consecutive amino acid lengths described in the paragraph above, wherein the amino acid sequence has a biological activity of at least one domain of a PUFA PKS system.

In another aspect of the invention, a PUFA PKS protein or domain useful in one or more embodiments of the present invention comprises an amino acid sequence that is at least about 60% identical to an amino acid sequence chosen from: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, wherein the amino acid sequence has a biological activity of at least one domain of a PUFA PKS system. In a further aspect, the amino acid sequence of the protein is at least about 65% identical, and more preferably at least about 70% identical, and more preferably at least about 75% identical, and more preferably at least about 80% identical, and more preferably at least about 85% identical, and more preferably at least about 90% identical, and more preferably at least about 95% identical, and more preferably at least about 96% identical, and more preferably at least about 97% identical, and more preferably at least about 98% identical, and more preferably at least about 99% identical to an amino acid sequence chosen from: SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32, wherein the amino acid sequence has a biological activity of at least one domain of a PUFA PKS system.

In yet another aspect of the invention, a PUFA PKS protein or domain useful in one or more embodiments of the present invention comprises, consists essentially of, or consists of, an amino acid sequence chosen from: SEQ ID NO:2, SEQ ID NO:4, SEQ ID NO:6, SEQ ID NO:8, SEQ ID NO:10, SEQ ID NO:13, SEQ ID NO:18, SEQ ID NO:20, SEQ ID NO:22, SEQ ID NO:24, SEQ ID NO:26, SEQ ID NO:28, SEQ ID NO:30, SEQ ID NO:32 or any biologically active fragments thereof, including any fragments that have a biological activity of at least one domain of a PUFA PKS system.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

As used herein, unless otherwise specified, reference to a percent (%) identity refers to an evaluation of homology which is performed using: (1) a BLAST 2.0 Basic BLAST homology search using blastp for amino acid searches, blastn for nucleic acid searches, and blastX for nucleic acid searches and searches of translated amino acids in all 6 open reading frames, all with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST). It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174, 247, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For Blastn, using 0 BLOSUM62 Matrix:
  Reward for match=1
  Penalty for mismatch=−2
  Open gap (5) and extension gap (2) penalties
  gap x_dropoff (50) expect (10) word size (11) filter (on)

For Blastp, using 0 BLOSUM62 Matrix:
  Open gap (11) and extension gap (1) penalties
  gap x_dropoff (50) expect (10) word size (3) filter (on).

According to the present invention, an amino acid sequence that has a biological activity of at least one domain of a PUFA PKS system is an amino acid sequence that has the biological activity of at least one domain of the PUFA PKS system described in detail herein, as previously exemplified by the *Schizochytrium* PUFA PKS system or as additionally exemplified herein by the *Thraustochytrium* PUFA PKS system. The biological activities of the various domains within the *Schizochytrium* or *Thraustochytrium* PUFA PKS systems have been described in detail above. Therefore, an isolated protein useful in the present invention can include the translation product of any PUFA PKS open reading frame, any PUFA PKS domain, biologically active fragment thereof, or any homologue of a naturally occurring PUFA PKS open reading frame product or domain which has biological activity.

In another embodiment of the invention, an amino acid sequence having the biological activity of at least one domain of a PUFA PKS system of the present invention includes an amino acid sequence that is sufficiently similar to a naturally occurring PUFA PKS protein or polypeptide that a nucleic acid sequence encoding the amino acid sequence is capable of hybridizing under moderate, high, or very high stringency conditions (described below) to (i.e., with) a nucleic acid molecule encoding the naturally occurring PUFA PKS protein or polypeptide (i.e., to the complement of the nucleic acid strand encoding the naturally occurring PUFA PKS protein or polypeptide). Preferably, an amino acid sequence having the biological activity of at least one domain of a PUFA PKS system of the present invention is encoded by a nucleic acid sequence that hybridizes under moderate, high or very high stringency conditions to the complement of a nucleic acid sequence that encodes any of the above-described amino acid sequences for a PUFA PKS protein or domain. Methods to deduce a complementary sequence are known to those skilled in the art. It should be noted that since amino acid sequencing and nucleic acid sequencing technologies are not entirely error-free, the sequences presented herein, at best, represent apparent sequences of PUFA PKS domains and proteins of the present invention.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

The present invention also includes a fusion protein that includes any PUFA PKS protein or domain or any homologue or fragment thereof attached to one or more fusion segments. Suitable fusion segments for use with the present invention include, but are not limited to, segments that can: enhance a protein's stability; provide other desirable biological activity; and/or assist with the purification of the protein (e.g., by affinity chromatography). A suitable fusion segment can be a domain of any size that has the desired function (e.g., imparts increased stability, solubility, biological activity; and/or simplifies purification of a protein). Fusion segments can be joined to amino and/or carboxyl termini of the protein and can be susceptible to cleavage in order to enable straight-forward recovery of the desired protein. Fusion proteins are preferably produced by culturing a recombinant cell transfected with a fusion nucleic acid molecule that encodes a protein including the fusion segment attached to either the carboxyl and/or amino terminal end of the protein of the invention as discussed above.

In one embodiment of the present invention, any of the above-described PUFA PKS amino acid sequences, as well as homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

The minimum size of a protein or domain and/or a homologue or fragment thereof of the present invention is, in one aspect, a size sufficient to have the requisite biological activity, or sufficient to serve as an antigen for the generation of an antibody or as a target in an in vitro assay. In one embodiment, a protein of the present invention is at least about 8 amino acids in length (e.g., suitable for an antibody epitope or as a detectable peptide in an assay), or at least about 25 amino acids in length, or at least about 50 amino acids in length, or at least about 100 amino acids in length, or at least about 150 amino acids in length, or at least about 200 amino acids in length, or at least about 250 amino acids in length, or at least about 300 amino acids in length, or at least about 350 amino acids in length, or at least about 400 amino acids in length, or at least about 450 amino acids in length, or at least about 500 amino acids in length, or at least about 750 amino acids in length, and so on, in any length between 8 amino acids and up to the full length of a protein or domain of the invention or longer, in whole integers (e.g., 8, 9, 10, . . . 25, 26, . . . 500, 501, . . . 1234, 1235, . . .). There is no limit, other than a practical limit, on the maximum size of such a protein in that the protein can include a portion of a PUFA PKS protein, domain, or biologically active or useful fragment thereof, or a full-length PUFA PKS protein or domain, plus additional sequence (e.g., a fusion protein sequence), if desired.

Further embodiments of the present invention include isolated nucleic acid molecules comprising, consisting essentially of, or consisting of nucleic acid sequences that encode any of the above-identified proteins or domains, including a homologue or fragment thereof, as well as nucleic acid sequences that are fully complementary thereto. In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on PUFA PKS system biological activity as described herein. Protein homologues (e.g., proteins encoded by nucleic acid homologues) have been discussed in detail above.

A nucleic acid molecule homologue can be produced using a number of methods known to those skilled in the art (see, for example, Sambrook et al., *Molecular Cloning: A Laboratory Manual*, Cold Spring Harbor Labs Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to form a probe or oligonucleotide primer that is capable of forming a stable hybrid (e.g., under moderate, high or very high stringency conditions) with the complementary sequence of a nucleic acid molecule useful in the present invention, or of a size sufficient to encode an amino acid sequence having a biological activity of at least one domain of a PUFA PKS system according to the present invention. As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a sequence sufficient to encode a biologically active fragment of a domain of a PUFA PKS system, an entire domain of a PUFA PKS system, several domains within an open reading frame (Orf) of a PUFA PKS system, an entire Orf of a PUFA PKS system, or more than one Orf of a PUFA PKS system.

In one embodiment of the present invention, an isolated nucleic acid molecule comprises, consists essentially of, or consists of a nucleic acid sequence encoding any of the above-described amino acid sequences, including any of the amino acid sequences, or homologues thereof, from a *Schizochytrium* or *Thraustochytrium* described herein. In one aspect, the nucleic acid sequence is selected from the group of: SEQ ID NO:1, SEQ ID NO:3, SEQ ID NO:5, SEQ ID NO:7, SEQ ID NO:9, SEQ ID NO:12, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:38, SEQ ID NO:40, SEQ ID NO:42, SEQ ID NO:44, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, or SEQ ID NO:67, or homologues (including sequences that are at least about 50%, 55%, 60%, 65%, 70%, 75%, 80%, 85%, 90%, 95%, 96%, 97%, 98%, or 99% identical to such sequences), or fragments thereof, or any complementary sequences thereof.

Another embodiment of the present invention includes a recombinant nucleic acid molecule comprising a recombinant vector and a nucleic acid sequence encoding protein or peptide having a biological activity of at least one domain (or homologue or fragment thereof) of a PUFA PKS system as described herein. Such nucleic acid sequences are described in detail above. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a PUFA PKS domain) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to bind to the target gene such that the target gene and the insert undergo homologous recombination, whereby the endogenous target gene is deleted, inactivated or attenuated (i.e., by at least a portion of the endogenous target gene being mutated or deleted). The use of this type of recombinant vector to replace an endogenous *Schizochytrium* gene with a recombinant gene is described in the Examples section, and the general technique for genetic transformation of Thraustochytrids is described in detail in U.S. patent application Ser. No. 10/124,807, published as U.S. Patent Application Publication No. 20030166207, published Sep. 4, 2003.

Typically, a recombinant nucleic acid molecule includes at least one nucleic acid molecule of the present invention operatively linked to one or more expression control sequences. As used herein, the phrase "recombinant molecule" or "recombinant nucleic acid molecule" primarily refers to a nucleic acid molecule or nucleic acid sequence operatively linked to a expression control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to an expression control sequence (e.g., a transcription control sequence and/or a translation control sequence) in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a host cell or organism into which the recombinant nucleic acid molecule is to be introduced.

Recombinant nucleic acid molecules of the present invention can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

The present inventors have found that the *Schizochytrium* PUFA PKS Orfs A and B are closely linked in the genome and region between the Orfs has been sequenced. The Orfs are oriented in opposite directions and 4244 base pairs separate the start (ATG) codons (i.e. they are arranged as follows: 3'OrfA5'—4244 bp—5'OrfB3'). Examination of the 4244 bp intergenic region did not reveal any obvious Orfs (no significant matches were found on a BlastX search). Both Orfs A and B are highly expressed in *Schizochytrium*, at least during the time of oil production, implying that active promoter elements are embedded in this intergenic region. These genetic elements are believed to have utility as a bi-directional promoter sequence for transgenic applications. For example, in a preferred embodiment, one could clone this region, place any genes of interest at each end and introduce the construct into *Schizochytrium* (or some other host in which the promoters can be shown to function). It is predicted that the regulatory elements, under the appropriate conditions, would provide for coordinated, high level expression of the two introduced genes. The complete nucleotide sequence for the regulatory region containing *Schizochytrium* PUFA PKS regulatory elements (e.g., a promoter) is represented herein as SEQ ID NO:36.

In a similar manner, OrfC is highly expressed in *Schizochytrium* during the time of oil production and regulatory elements are expected to reside in the region upstream of its start codon. A region of genomic DNA upstream of OrfC has been cloned and sequenced and is represented herein as (SEQ ID NO:37). This sequence contains the 3886 nt immediately upstream of the OrfC start codon. Examination of this region did not reveal any obvious Orfs (i.e., no significant matches were found on a BlastX search). It is believed that regulatory elements contained in this region, under the appropriate conditions, will provide for high-level expression of a gene placed behind them. Additionally, under the appropriate conditions, the level of expression may be coordinated with genes under control of the A-B intergenic region (SEQ ID NO:36).

Therefore, in one embodiment, a recombinant nucleic acid molecule useful in the present invention, as disclosed herein, can include a PUFA PKS regulatory region contained within SEQ ID NO:36 and/or SEQ ID NO:37. Such a regulatory region can include any portion (fragment) of SEQ ID NO:36 and/or SEQ ID NO:37 that has at least basal PUFA PKS transcriptional activity.

One or more recombinant molecules of the present invention can be used to produce an encoded product (e.g., a PUFA PKS domain, protein, or system) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. In one embodiment of the invention, a preferred host cell is a Thraustochytrid host cell (described in detail below) or a plant host cell. Host cells can be either untransfected cells or cells that are already transfected with at least one other recombinant nucleic acid molecule.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast, or into plants. In microbial systems, the term "transformation" is used to describe an inherited change due to the acquisition of exogenous nucleic acids by the microorganism or plant and is essentially synonymous with the term "transfection." However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass transfection of animal cells, and transformation of microbial cells or plant cells, to the extent that the terms pertain to the introduction of exogenous nucleic acids into a cell. Therefore, transfection techniques include, but are not limited to, transformation, particle bombardment, diffusion, active transport, bath sonication, electroporation, microinjection, lipofection, adsorption, infection and protoplast fusion.

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

General discussion above with regard to recombinant nucleic acid molecules and transfection of host cells is intended to be applied to any recombinant nucleic acid molecule discussed herein, including those encoding any amino acid sequence having a biological activity of at least one domain from a PUFA PKS, those encoding amino acid sequences from other PKS systems, and those encoding other proteins or domains.

Polyunsaturated fatty acids (PUFAs) are essential membrane components in higher eukaryotes and the precursors of many lipid-derived signaling molecules. The PUFA PKS system of the present invention uses pathways for PUFA synthesis that do not require desaturation and elongation of saturated fatty acids. The pathways catalyzed by PUFA PKSs that are distinct from previously recognized PKSs in both structure and mechanism. Generation of cis double bonds is suggested to involve position-specific isomerases; these enzymes are believed to be useful in the production of new families of antibiotics.

To produce significantly high yields of one or more desired polyunsaturated fatty acids or other bioactive molecules, an organism, preferably a microorganism or a plant, and most preferably a Thraustochytrid microorganism, can be genetically modified to alter the activity and particularly, the end product, of the PUFA PKS system in the microorganism or plant.

Therefore, one embodiment of the present invention relates to a genetically modified microorganism, wherein the microorganism expresses a PKS system comprising at least one biologically active domain of a polyunsaturated fatty acid (PUFA) polyketide synthase (PKS) system. The domain of the PUFA PKS system can include any of the domains, including homologues thereof, for PUFA PKS systems as described above (e.g., for *Schizochytrium* and *Thraustochytrium*), and can also include any domain of a PUFA PKS system from any other non-bacterial microorganism, including any eukaryotic microorganism, including any Thraustochytrid microorganism or any domain of a PUFA PKS system from a microorganism identified by a screening method as described in U.S. patent application Ser. No. 10/124,800, supra. The genetic modification affects the activity of the PKS system in the organism. The screening process described in U.S. patent application Ser. No. 10/124,800 includes the steps of: (a) selecting a microorganism that produces at least one PUFA; and, (b) identifying a microorganism from (a) that has an ability to produce increased PUFAs under dissolved oxygen conditions of less than about 5% of saturation in the fermentation medium, as compared to production of PUFAs by the microorganism under dissolved oxygen conditions of greater than about 5% of saturation, and preferably about 10%, and more preferably about 15%, and more preferably about 20% of saturation in the fermentation medium.

In one aspect, such an organism can endogenously contain and express a PUFA PKS system, and the genetic modification can be a genetic modification of one or more of the functional domains of the endogenous PUFA PKS system, whereby the modification has some effect on the activity of the PUFA PKS system. In another aspect, such an organism can endogenously contain and express a PUFA PKS system, and the genetic modification can be an introduction of at least one exogenous nucleic acid sequence (e.g., a recombinant nucleic acid molecule), wherein the exogenous nucleic acid sequence encodes at least one biologically active domain or protein from a second PKS system and/or a protein that affects the activity of the PUFA PKS system (e.g., a phosphopantetheinyl transferases (PPTase), discussed below). In yet another aspect, the organism does not necessarily endogenously (naturally) contain a PUFA PKS system, but is genetically modified to introduce at least one recombinant nucleic acid molecule encoding an amino acid sequence having the biological activity of at least one domain of a PUFA PKS system. In this aspect, PUFA PKS activity is affected by introducing or increasing PUFA PKS activity in the organism. Various embodiments associated with each of these aspects will be discussed in greater detail below.

It is to be understood that a genetic modification of a PUFA PKS system or an organism comprising a PUFA PKS system can involve the modification of at least one domain of a PUFA PKS system (including a portion of a domain), more than one or several domains of a PUFA PKS system (including adjacent domains, non-contiguous domains, or domains on different proteins in the PUFA PKS system), entire proteins of the PUFA PKS system, and the entire PUFA PKS system (e.g., all of the proteins encoded by the PUFA PKS genes). As such, modifications can include a small modification to a single domain of an endogenous PUFA PKS system; to substitution, deletion or addition to one or more domains or proteins of a given PUFA PKS system; up to replacement of the entire PUFA PKS system in an organism with the PUFA PKS system from a different organism. One of skill in the art will understand that any genetic modification to a PUFA PKS system is encompassed by the invention.

As used herein, a genetically modified microorganism can include a genetically modified bacterium, protist, microalgae, fungus, or other microbe, and particularly, any of the genera of the order Thraustochytriales (e.g., a Thraustochytrid) described herein (e.g., *Schizochytrium, Thraustochytrium, Japonochytrium, Labyrinthula, Labyrinthuloides*, etc.). Such a genetically modified microorganism has a genome which is modified (i.e., mutated or changed) from its normal (i.e., wild-type or naturally occurring) form such that the desired result is achieved (i.e., increased or modified PUFA PKS activity and/or production of a desired product using the PKS system). Genetic modification of a microorganism can be accomplished using classical strain development and/or molecular genetic techniques. Such techniques known in the art are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Preferred microorganism host cells to modify according to the present invention include, but are not limited to, any bacteria, protist, microalga, fungus, or protozoa. In one aspect, preferred microorganisms to genetically modify include, but are not limited to, any microorganism of the order Thraustochytriales, including any microorganism in the families Thraustochytriaceae and Labyrinthulaceae. Particularly preferred host cells for use in the present invention could include microorganisms from a genus including, but not limited to: *Thraustochytrium, Japonochytrium, Aplanochytrium, Elina* and *Schizochytrium* within the Thraustochytriaceae and *Labyrinthula, Labyrinthuloides,* and *Labyrinthomyxa* within the Labyrinthulaceae. Preferred species within these genera include, but are not limited to: any species within *Labyrinthula*, including *Labrinthula sp., Labyrinthula algeriensis, Labyrinthula cienkowskii, Labyrinthula chattonii, Labyrinthula coenocystis, Labyrinthula macrocystis, Labyrinthula macrocystis atlantica, Labyrinthula macrocystis macrocystis, Labyrinthula magnifica, Labyrinthula minuta, Labyrinthula roscoffensis, Labyrinthula valkanovii, Labyrinthula vitellina, Labyrinthula vitellina pacifica, Labyrinthula vitellina vitellina, Labyrinthula zopfii*; any *Labyrinthuloides* species, including *Labyrinthuloides sp., Labyrinthuloides minuta, Labyrinthuloides schizochytrops*; any *Labyrinthomyxa* species, including *Labyrinthomyxa sp., Labyrinthomyxa pohlia, Labyrinthomyxa sauvageaui,* any *Aplanochytrium* species, including *Aplanochytrium sp.* and *Aplanochytrium kerguelensis*; any *Elina* species, including *Elina sp., Elina marisalba, Elina sinorifica*; any *Japanochytrium* species, including *Japanochytrium sp., Japanochytrium marinum*; any *Schizochytrium* species, including *Schizochytrium sp., Schizochytrium aggregatum, Schizochytrium limacinum, Schizochytrium minutum, Schizochytrium octosporum*; and any *Thraustochytrium* species, including *Thraustochytrium sp., Thraustochytrium aggregatum, Thraustochytrium arudimentale, Thraustochytrium aureum, Thraustochytrium benthicola, Thraustochytrium globosum, Thraustochytrium kinnei, Thraustochytrium motivum, Thraustochytrium pachydermum, Thraustochytrium proliferum, Thraustochytrium roseum, Thraustochytrium striatum, Ulkenia sp., Ulkenia minuta, Ulkenia profunda, Ulkenia radiate, Ulkenia sarkariana,* and *Ulkenia visurgensis.* Particularly preferred species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31) (ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207). Other examples of suitable host microorganisms for genetic modification include, but are not limited to, yeast including *Saccharomyces cerevisiae, Saccharomyces carlsbergensis,* or other yeast such as *Candida, Kluyveromyces,* or other fungi, for example, filamentous fungi such as *Aspergillus, Neurospora, Penicillium,* etc. Bacterial cells also may be used as hosts. These include, but are not limited to, *Escherichia coli,* which can be useful in fermentation processes. Alternatively, and only by way of example, a host such as a *Lactobacillus* species or *Bacillus* species can be used as a host.

Another embodiment of the present invention relates to a genetically modified plant, wherein the plant has been genetically modified to recombinantly express a PKS system comprising at least one biologically active domain of a polyunsaturated fatty acid (PUFA) polyketide synthase (PKS) system. The domain of the PUFA PKS system can include any of the domains, including homologues thereof, for PUFA PKS systems as described above (e.g., for *Schizochytrium* and/or *Thraustochytrium*), and can also include any domain of a PUFA PKS system from any non-bacterial microorganism (including any eukaryotic microorganism and any other Thraustochytrid microorganism) or any domain of a PUFA PKS system from a microorganism identified by a screening method as described in U.S. patent application Ser. No. 10/124,800, supra. The plant can also be further modified with at least one domain or biologically active fragment thereof of another PKS system, including, but not limited to, bacterial PUFA PKS or PKS systems, Type I PKS systems, Type II PKS systems, modular PKS systems, and/or any non-bacterial PUFA PKS system (e.g., eukaryotic, Thraustochytrid, Thraustochytriaceae or Labyrinthulaceae, *Schizochytrium,* etc.).

As used herein, a genetically modified plant can include any genetically modified plant including higher plants and particularly, any consumable plants or plants useful for producing a desired bioactive molecule of the present invention. Such a genetically modified plant has a genome which is modified (i.e., mutated or changed) from its normal (i.e., wild-type or naturally occurring) form such that the desired result is achieved (i.e., increased or modified PUFA PKS activity and/or production of a desired product using the PKS system). Genetic modification of a plant can be accomplished using classical strain development and/or molecular genetic techniques. Methods for producing a transgenic plant, wherein a recombinant nucleic acid molecule encoding a desired amino acid sequence is incorporated into the genome of the plant, are known in the art. A preferred plant to genetically modify according to the present invention is preferably a plant suitable for consumption by animals, including humans.

Preferred plants to genetically modify according to the present invention (i.e., plant host cells) include, but are not limited to any higher plants, and particularly consumable plants, including crop plants and especially plants used for their oils. Such plants can include, for example: canola, soybeans, rapeseed, linseed, corn, safflowers, sunflowers and tobacco. Other preferred plants include those plants that are known to produce compounds used as pharmaceutical agents, flavoring agents, neutraceutical agents, functional food ingredients or cosmetically active agents or plants that are genetically engineered to produce these compounds/agents.

According to the present invention, a genetically modified microorganism or plant includes a microorganism or plant that has been modified using recombinant technology or by classical mutagenesis and screening techniques. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications that result in an increase in gene expression or function can be referred to as amplification, overproduction, overexpression, activation, enhancement, addition, or up-regulation of a gene.

The genetic modification of a microorganism or plant according to the present invention preferably affects the activity of the PKS system expressed by the microorganism or plant, whether the PKS system is endogenous and genetically modified, endogenous with the introduction of recombinant nucleic acid molecules into the organism (with the option of modifying the endogenous system or not), or provided completely by recombinant technology. To alter the PUFA production profile of a PUFA PKS system or organism expressing such system includes causing any detectable or measurable change in the production of any one or more PUFAs by the host microorganism or plant as compared to in the absence of the genetic modification (i.e., as compared to the unmodified, wild-type microorganism or plant or the microorganism or plant that is unmodified at least with respect to PUFA synthesis—i.e., the organism might have other modifications not related to PUFA synthesis). To affect the activity of a PKS system includes any genetic modification that causes any detectable or measurable change or modification in the PKS system expressed by the organism as compared to in the absence of the genetic modification. A detectable change or modification in the PKS system can include, but is not limited to: a change or modification (introduction of, increase or decrease) of the expression and/or biological activity of any one or more of the domains in a modified PUFA PKS system as compared to the endogenous PUFA PKS system in the absence of genetic modification, the introduction of PKS system activity into an organism such that the organism now has measurable/detectable PKS system activity (i.e., the organism did not contain a PKS system prior to the genetic modification), the introduction into the organism of a functional domain from a different PKS system than a PKS system endogenously expressed by the organism such that the PKS system activity is modified (e.g., a bacterial PUFA PKS domain or a type I PKS domain is introduced into an organism that endogenously expresses a non-bacterial PUFA PKS system), a change in the amount of a bioactive molecule (e.g., a PUFA) produced by the PKS system (e.g., the system produces more (increased amount) or less (decreased amount) of a given product as compared to in the absence of the genetic modification), a change in the type of a bioactive molecule (e.g., a change in the type of PUFA) produced by the PKS system (e.g., the system produces an additional or different PUFA, a new or different product, or a variant of a PUFA or other product that is naturally produced by the system), and/or a change in the ratio of multiple bioactive molecules produced by the PKS system (e.g., the system produces a different ratio of one PUFA to another PUFA, produces a completely different lipid profile as compared to in the absence of the genetic modification, or places various PUFAs in different positions in a triacylglycerol as compared to the natural configuration). Such a genetic modification includes any type of genetic modification and specifically includes modifications made by recombinant technology and by classical mutagenesis.

It should be noted that reference to increasing the activity of a functional domain or protein in a PUFA PKS system refers to any genetic modification in the organism containing the domain or protein (or into which the domain or protein is to be introduced) which results in increased functionality of the domain or protein system and can include higher activity of the domain or protein (e.g., specific activity or in vivo enzymatic activity), reduced inhibition or degradation of the domain or protein system, and overexpression of the domain or protein. For example, gene copy number can be increased, expression levels can be increased by use of a promoter that gives higher levels of expression than that of the native promoter, or a gene can be altered by genetic engineering or classical mutagenesis to increase the activity of the domain or protein encoded by the gene.

Similarly, reference to decreasing the activity of a functional domain or protein in a PUFA PKS system refers to any genetic modification in the organism containing such domain or protein (or into which the domain or protein is to be introduced) which results in decreased functionality of the domain or protein and includes decreased activity of the domain or protein, increased inhibition or degradation of the domain or protein and a reduction or elimination of expression of the domain or protein. For example, the action of domain or protein of the present invention can be decreased by blocking or reducing the production of the domain or protein, "knocking out" the gene or portion thereof encoding the domain or protein, reducing domain or protein activity, or inhibiting the activity of the domain or protein. Blocking or reducing the production of a domain or protein can include placing the gene encoding the domain or protein under the control of a promoter that requires the presence of an inducing compound in the growth medium. By establishing conditions such that the inducer becomes depleted from the medium, the expression of the gene encoding the domain or protein (and therefore, of protein synthesis) could be turned off. The present inventors demonstrate the ability to delete (knock out) targeted genes in a Thraustochytrid microorganism in the Examples section. Blocking or reducing the activity of domain or protein could also include using an excision technology approach similar to that described in U.S. Pat. No. 4,743,546, incorporated herein by reference. To use this approach, the gene encoding the protein of interest is cloned between specific genetic sequences that allow specific, controlled excision of the gene from the genome. Excision could be prompted by, for example, a shift in the cultivation temperature of the culture, as in U.S. Pat. No. 4,743,546, or by some other physical or nutritional signal.

In one embodiment of the present invention, a genetic modification includes a modification of a nucleic acid sequence encoding an amino acid sequence that has a biological activity of at least one domain of a non-bacterial PUFA PKS system as described herein (e.g., a domain, more than one domain, a protein, or the entire PUFA PKS system, of an endogenous PUFA PKS system of a Thraustochytrid host). Such a modification can be made to an amino acid sequence within an endogenously (naturally) expressed non-bacterial PUFA PKS system, whereby a microorganism that naturally contains such a system is genetically modified by, for example, classical mutagenesis and selection techniques and/or molecular genetic techniques, include genetic engineering techniques. Genetic engineering techniques can include, for example, using a targeting recombinant vector to delete a portion of an endogenous gene (demonstrated in the Examples), or to replace a portion of an endogenous gene with a heterologous sequence (demonstrated in the Examples). Examples of heterologous sequences that could be introduced into a host genome include sequences encoding at least one functional domain from another PKS system, such as a different non-bacterial PUFA PKS system (e.g., from a eukaryote, including another Thraustochytrid), a bacterial PUFA PKS system, a type I PKS system, a type II PKS system, or a modular PKS system. A heterologous sequence can also include an entire PUFA PKS system (e.g., all genes associated with the PUFA PKS system) that is used to replace the entire endogenous PUFA PKS system (e.g., all genes of the endogenous PUFA PKS system) in a host. A heterologous sequence can also include a sequence encoding a modified functional domain (a homologue) of a natural domain from a PUFA PKS system of a host Thraustochytrid (e.g., a nucleic acid sequence encoding a modified domain from OrfB of a *Schizochytrium*, wherein the modified domain will, when used to replace the naturally occurring domain expressed in the *Schizochytrium*, alter the PUFA production profile by the *Schizochytrium*). Other heterologous sequences to introduce into the genome of a host includes a sequence encoding a protein or functional domain that is not a domain of a PKS system, but which will affect the activity of the endogenous PKS system. For example, one could introduce into the host genome a nucleic acid molecule encoding a phosphopantetheinyl transferase (discussed below). Specific modifications that could be made to an endogenous PUFA PKS system are discussed in detail herein.

In another aspect of this embodiment of the invention, the genetic modification can include: (1) the introduction of a recombinant nucleic acid molecule encoding an amino acid sequence having a biological activity of at least one domain of a PUFA PKS system; and/or (2) the introduction of a recombinant nucleic acid molecule encoding a protein or functional domain that affects the activity of a PUFA PKS system, into a host. The host can include: (1) a host cell that does not express any PKS system, wherein all functional domains of a PKS system are introduced into the host cell, and wherein at least one functional domain is from a non-bacterial PUFA PKS system; (2) a host cell that expresses a PKS system (endogenous or recombinant) having at least one functional domain of a non-bacterial PUFA PKS system, wherein the introduced recombinant nucleic acid molecule can encode at least one additional non-bacterial PUFA PKS domain function or another protein or domain that affects the activity of the host PKS system; and (3) a host cell that expresses a PKS system (endogenous or recombinant) which does not necessarily include a domain function from a non-bacterial PUFA PKS, and wherein the introduced recombinant nucleic acid molecule includes a nucleic acid sequence encoding at least one functional domain of a non-bacterial PUFA PKS system. In other words, the present invention intends to encompass any genetically modified organism (e.g., microorganism or plant), wherein the organism comprises at least one non-bacterial PUFA PKS domain function (either endogenously or introduced by recombinant modification), and wherein the genetic modification has a measurable effect on the non-bacterial PUFA PKS domain function or on the PKS system when the organism comprises a functional PKS system.

The present invention encompasses many possible non-bacterial and bacterial microorganisms as either possible host cells for the PUFA PKS systems described herein and/or as sources for additional genetic material encoding PUFA PKS system proteins and domains for use in the genetic modifications and methods described herein. For example, microbial organisms with a PUFA PKS system similar to that found in *Schizochytrium*, such as the *Thraustochytrium* microorganism discovered by the present inventors and described in Example 1, can be readily identified/isolated/screened by methods to identify other non-bacterial microorganisms that have a polyunsaturated fatty acid (PUFA) polyketide synthase (PKS) system that are described in detail in U.S. Patent Application Publication No. 20020194641, supra (corresponding to U.S. patent application Ser. No. 10/124,800).

Locations for collection of the preferred types of microbes for screening for a PUFA PKS system according to the present invention include any of the following: low oxygen environments (or locations near these types of low oxygen environments including in the guts of animals including invertebrates that consume microbes or microbe-containing foods (including types of filter feeding organisms), low or non-oxygen containing aquatic habitats (including freshwater, saline and marine), and especially at-or near-low oxygen environments (regions) in the oceans. The microbial strains would preferably not be obligate anaerobes but be adapted to live in both aerobic and low or anoxic environments. Soil environments containing both aerobic and low oxygen or anoxic environments would also excellent environments to find these organisms in and especially in these types of soil in aquatic habitats or temporary aquatic habitats.

A particularly preferred non-bacterial microbial strain to screen for use as a host and/or a source of PUFA PKS genes according to the present invention would be a strain (selected from the group consisting of algae, fungi (including yeast), protozoa or protists) that, during a portion of its life cycle, is capable of consuming whole bacterial cells (bacterivory) by mechanisms such as phagocytosis, phagotrophic or endocytic capability and/or has a stage of its life cycle in which it exists as an amoeboid stage or naked protoplast. This method of nutrition would greatly increase the potential for transfer of a bacterial PKS system into a eukaryotic cell if a mistake occurred and the bacterial cell (or its DNA) did not get digested and instead are functionally incorporated into the eukaryotic cell.

Included in the present invention as sources of PUFA PKS genes (and proteins and domains encoded thereby) are any Thraustochytrids other than those specifically described herein that contain a PUFA PKS system. Such Thraustochytrids include, but are not limited to, but are not limited to, any microorganism of the order Thraustochytriales, including any microorganism in the families Thraustochytriaceae and Labyrinthulaceae, which further comprise a genus including, but not limited to: *Thraustochytrium, Japonochytrium, Aplanochytrium, Elina* and *Schizochytrium* within the Thraustochytriaceae and *Labyrinthula, Labyrinthuloides*, and *Labyrinthomyxa* within the Labyrinthulaceae. Preferred species within these genera include, but are not limited to: any species within *Labyrinthula*, including *Labrinthula* sp., *Labyrinthula algeriensis, Labyrinthula cienkowskii, Labyrinthula chattonii, Labyrinthula coenocystis, Labyrinthula macrocystis, Labyrinthula macrocystis atlantica, Labyrinthula macrocystis macrocystis, Labyrinthula magnifica, Labyrinthula minuta, Labyrinthula roscoffensis, Labyrinthula valkanovii, Labyrinthula vitellina, Labyrinthula vitellina pacifica, Labyrinthula vitellina vitellina, Labyrinthula zopfii*; any *Labyrinthuloides* species, including *Labyrinthuloides* sp., *Labyrinthuloides minuta, Labyrinthuloides schizochytrops*; any *Labyrinthomyxa* species, including *Labyrinthomyxa* sp., *Labyrinthomyxa pohlia, Labyrinthomyxa sauvageaui*, any *Aplanochytrium* species, including *Aplanochytrium* sp. and *Aplanochytrium kerguelensis*; any

*Elina* species, including *Elina* sp., *Elina marisalba, Elina sinorifica*; any *Japanochytrium* species, including *Japanochytrium* sp., *Japanochytrium marinum*; any *Schizochytrium* species, including *Schizochytrium* sp., *Schizochytrium aggregatum, Schizochytrium limacinum, Schizochytrium minutum, Schizochytrium octosporum*; and any *Thraustochytrium* species, including *Thraustochytrium* sp., *Thraustochytrium aggregatum, Thraustochytrium arudimentale, Thraustochytrium aureum, Thraustochytrium benthicola, Thraustochytrium globosum, Thraustochytrium kinnei, Thraustochytrium motivum, Thraustochytrium pachydermum, Thraustochytrium proliferum, Thraustochytrium roseum, Thraustochytrium striatum, Ulkenia* sp., *Ulkenia minuta, Ulkenia profunda, Ulkenia radiate, Ulkenia sarkariana*, and *Ulkenia visurgensis*.

It is noted that, without being bound by theory, the present inventors consider *Labyrinthula* and other Labyrinthulaceae as sources of PUFA PKS genes because the Labyrinthulaceae are closely related to the Thraustochytriaceae which are known to possess PUFA PKS genes, the Labyrinthulaceae are known to be bactivorous/phagocytotic, and some members of the Labyrinthulaceae have fatty acid/PUFA profiles consistent with having a PUFA PKS system.

Strains of microbes (other than the members of the Thraustochytrids) capable of bacterivory (especially by phagocytosis or endocytosis) can be found in the following microbial classes (including but not limited to example genera):

In the algae and algae-like microbes (including Stramenopiles): of the class Euglenophyceae (for example genera *Euglena*, and *Peranema*), the class Chrysophyceae (for example the genus *Ochromonas*), the class Dinobryaceae (for example the genera *Dinobryon, Platychrysis*, and *Chrysochromulina*), the Dinophyceae (including the genera *Crypthecodinium, Gymnodinium, Peridinium, Ceratium, Gyrodinium*, and *Oxyrrhis*), the class Cryptophyceae (for example the genera *Cryptomonas*, and *Rhodomonas*), the class Xanthophyceae (for example the genus *Olisthodiscus*) (and including forms of algae in which an amoeboid stage occurs as in the flagellates Rhizochloridaceae, and zoospores/gametes of *Aphanochaete pascheri, Bumilleria stigeoclonium* and *Vaucheria geminata*), the class Eustigmatophyceae, and the class Prymnesiopyceae (including the genera *Prymnesium* and *Diacronema*).

In the Stramenopiles including the: Proteromonads, Opalines, *Developayella*, Diplophorys, *Labyrinthulids*, Thraustochytrids, Bicosecids, Oomycetes, Hypochytridiomycetes, *Commation, Reticulosphaera, Pelagomonas*, Pelapococcus, *Ollicola*, Aureococcus, Parmales, Raphidiophytes, Synurids, Rhizochromulinaales, Pedinellales, Dictyochales, Chrysomeridales, Sarcinochrysidales, Hydrurales, Hibberdiales, and Chromulinales.

In the Fungi: Class Myxomycetes (form myxamoebae)—slime molds, class Acrasieae including the orders Acrasiceae (for example the genus *Sappinia*), class Guttulinaceae (for example the genera *Guttulinopsis*, and *Guttulina*), class Dictysteliaceae (for example the genera *Acrasis, Dictyostelium, Polysphondylium*, and *Coenonia*), and class Phycomyceae including the orders Chytridiales, Ancylistales, Blastocladiales, Monoblepharidales, Saprolegniales, Peronosporales, Mucorales, and Entomophthorales.

In the Protozoa: Protozoa strains with life stages capable of bacterivory (including by phageocytosis) can be selected from the types classified as ciliates, flagellates or amoebae. Protozoan ciliates include the groups: Chonotrichs, Colpodids, Cyrtophores, Haptorids, Karyorelicts, Oligohymenophora, Polyhymenophora (spirotrichs), Prostomes and Suctoria. Protozoan flagellates include the Biosoecids, Bodonids, Cercomonads, Chrysophytes (for example the genera *Anthophysa, Chrysamoemba, Chrysosphaerella, Dendromonas, Dinobryon, Mallomonas, Ochromonas, Paraphysomonas, Poterioochromonas, Spumella, Syncrypta, Synura*, and *Uroglena*), Collar flagellates, Cryptophytes (for example the genera *Chilomonas, Cryptomonas, Cyanomonas*, and *Goniomonas*), Dinoflagellates, Diplomonads, Euglenoids, Heterolobosea, Pedinellids, Pelobionts, Phalansteriids, Pseudodendromonads, Spongomonads and Volvocales (and other flagellates including the unassigned flagellate genera of *Artodiscus, Clautriavia, Helkesimastix, Kathablepharis* and *Multicilia*). Amoeboid protozoans include the groups: Actinophryids, Centrohelids, Desmothoricids, Diplophryids, Eumamoebae, Heterolobosea, Leptomyxids, Nucleariid filose amoebae, Pelebionts, Testate amoebae and Vampyrellids (and including the unassigned amoebid genera *Gymnophrys, Biomyxa, Microcometes, Reticulomyxa, Belonocystis, Elaeorhanis, Allelogromia, Gromia* or *Lieberkuhnia*). The protozoan orders include the following: Percolomonadeae, Heterolobosea, Lyromonadea, Pseudociliata, Trichomonadea, Hypermastigea, Heteromiteae, Telonemea, Cyathobodonea, Ebridea, Pyytomyxea, Opalinea, Kinetomonadea, Hemimastigea, Protostelea, Myxagastrea, Dictyostelea, Choanomonadea, Apicomonadea, Eogregarinea, Neogregarinea, Coelotrolphea, Eucoccidea, Haemosporea, Piroplasmea, Spirotrichea, Prostomatea, Litostomatea, Phyllopharyngea, Nassophorea, Oligohymenophorea, Colpodea, Karyorelicta, Nucleohelea, Centrohelea, Acantharea, Sticholonchea, Polycystinea, Phaeodarea, Lobosea, Filosea, Athalamea, Monothalamea, Polythalamea, Xenophyophorea, Schizocladea, Holosea, Entamoebae, Myxosporea, Actinomyxea, Halosporea, Paramyxea, Rhombozoa and Orthonectea.

A preferred embodiment of the present invention includes strains of the microorganisms listed above that have been collected from one of the preferred habitats listed above.

In some embodiments of this method of the present invention, PUFA PKS systems from bacteria, including genes and portions thereof (encoding entire PUFA PKS systems, proteins thereof and/or domains thereof) can be used to genetically modify other PUFA PKS systems (e.g., any non-bacterial PUFA PKS system) and/or microorganisms containing the same (or vice versa) in the embodiments of the invention. In one aspect, novel PUFA PKS systems can be identified in bacteria that are expected to be particularly useful for creating genetically modified microorganisms (e.g., genetically modified Thraustochytrids) and/or novel hybrid constructs encoding PUFA PKS systems for use in the methods and genetically modified microorganisms and plants of the present invention. In one aspect, bacteria that may be particularly useful in the embodiments of the present invention have PUFA PKS systems, wherein the PUFA PKS system is capable of producing PUFAs at temperatures exceeding about 20° C., preferably exceeding about 25° C. and even more preferably exceeding about 30° C. As described previously herein, the marine bacteria, *Shewanella* and *Vibrio marinus*, described in U.S. Pat. No. 6,140,486, do not produce PUFAs at higher temperatures, which limits the usefulness of PUFA PKS systems derived from these bacteria, particularly in plant applications under field conditions. Therefore, in one embodiment, the screening method of the present invention can be used to identify bacteria that have a PUFA PKS system, wherein the bacteria are capable of growth and PUFA production at higher temperatures (e.g., above about 15° C., 20° C., 25° C., or 30° C. or even higher). However, even if the bacteria sources do not grow well and/or produce PUFAs at the higher temperatures, the present invention encompasses the identification, isolation and use of the PUFA PKS systems (genes and proteins/domains encoded thereby), wherein the PUFA PKS systems from the bacteria have enzymatic/biological activity at temperatures above about 15° C., 20° C., 25° C., or 30° C. or even higher. In one aspect of this embodiment, inhibitors of eukaryotic growth such as nystatin (antifungal) or cycloheximide (inhibitor of eukaryotic protein synthesis) can be added to agar plates used to culture/select initial strains from water samples/soil samples collected from the types of habitats/niches such as marine or estuarian habits, or any other habitat where such bacteria can be found. This process would help select for enrichment of bacterial strains without (or minimal) contamination of eukaryotic strains. This selection process, in combination with culturing the plates at elevated temperatures (e.g. 30° C.), and then selecting strains that produce at least one PUFA would initially identify candidate bacterial strains with a PUFA PKS system that is operative at elevated temperatures (as opposed to those bacterial strains in the prior art which only exhibit PUFA production at temperatures less than about 20° C. and more preferably below about 5° C.).

However, even in bacteria that do not grow well (or at all) at higher temperatures, or that do not produce at least one PUFA at higher temperatures, such strains can be identified and selected as comprising a PUFA PKS system by the identification of the ability of the bacterium to produce PUFAs under any conditions and/or by screening the genome of the bacterium for genes that are homologous to other known PUFA PKS genes from bacteria or non-bacterial organisms (e.g., see Example 7). To evaluate PUFA PKS function at higher temperatures for genes from any bacterial source, one can produce cell-free extracts and test for PUFA production at various temperatures, followed by selection of microorganisms that contain PUFA PKS genes that have enzymatic/biological activity at higher temperature ranges (e.g., 15° C., 20° C., 25° C., or 30° C. or even higher).

Suitable bacteria to use as hosts for genetic modification include any bacterial strain as discussed above. Particularly suitable bacteria to use as a source of PUFA PKS genes (and proteins and domains encoded thereby) for the production of genetically modified sequences and organisms according to the present invention include any bacterium that comprises a PUFA PKS system. Such bacteria are typically isolated from marine or estuarian habitats and can be readily identified by their ability to product PUFAs and/or by the presence of one or more genes having homology to known PUFA PKS genes in the organism. Such bacteria can include, but are not limited to, bacteria of the genera *Shewanella* and *Vibrio*. Preferred bacteria for use in the present invention include those with PUFA PKS systems that are biologically active at higher temperatures (e.g., above about 15° C., 20° C., 25° C., or 30° C. or even higher). The present inventors have identified two exemplary bacteria (e.g. *Shewanella olleyana* and *Shewanella japonica*; see Examples 7 and 8) that will be particularly suitable for use as sources of PUFA PKS genes, and others can be readily identified or are known to comprise PUFA PKS genes and may be useful in an embodiment of the present invention (e.g., *Shewanella gelidimarina*).

Furthermore, it is recognized that not all bacterial or non-bacterial microorganisms can be readily cultured from natural habitats. However, genetic characteristics of such un-culturable microorganisms can be evaluated by isolating genes from DNA prepared en mass from mixed or crude environmental samples. Particularly suitable to the present invention, PUFA PKS genes derived from un-culturable microorganisms can be isolated from environmental DNA samples by degenerate PCR using primers designed to generally match regions of high similarity in known PUFA PKS genes (e.g., see Example 7). Alternatively, whole DNA fragments can be cloned directly from purified environmental DNA by any of several methods known to the art. Sequence of the DNA fragments thus obtained can reveal homologs to known genes such as PUFA PKS genes. Homologs of OrfB and OrfC (referring to the domain structure of *Schizochytrium* and *Thraustochytrium*, for example) may be particularly useful in defining the PUFA PKS end product. Whole coding regions of PUFA PKS genes can then be expressed in host organisms (such as *Escherichia coli* or yeast) in combination with each other or with known PUFA PKS gene or gene fragment combinations to evaluate their effect on PUFA production. As described above, activity in cell-free extracts can be used to determine function at desired temperatures. Isolated PUFA PKS genes can also be transformed directly into appropriate *Schizochytrium* or other suitable strains to measure function. PUFA PKS system-encoding constructs identified or produced in such a manner, including hybrid constructs, can also be used to transform other organisms, such as plants.

Therefore, using the non-bacterial PUFA PKS systems of the present invention, which, for example, makes use of genes from Thraustochytrid PUFA PKS systems, as well as PUFA PKS systems and PKS systems from bacteria, gene mixing can be used to extend the range of PUFA products to include EPA, DHA, ARA, GLA, SDA and others (described in detail below), as well as to produce a wide variety of bioactive molecules, including antibiotics, other pharmaceutical compounds, and other desirable products. The method to obtain these bioactive molecules includes not only the mixing of genes from various organisms but also various methods of genetically modifying the non-bacterial PUFA PKS genes disclosed herein. Knowledge of the genetic basis and domain structure of the non-bacterial PUFA PKS system of the present invention provides a basis for designing novel genetically modified organisms which produce a variety of bioactive molecules. Although mixing and modification of any PKS domains and related genes are contemplated by the present inventors, by way of example, various possible manipulations of the PUFA-PKS system are discussed below with regard to genetic modification and bioactive molecule production.

Accordingly, encompassed by the present invention are methods to genetically modify microbial or plant cells by: genetically modifying at least one nucleic acid sequence in the organism that encodes an amino acid sequence having the biological activity of at least one functional domain of a non-bacterial PUFA PKS system according to the present invention, and/or expressing at least one recombinant nucleic acid molecule comprising a nucleic acid sequence encoding such amino acid sequence. Various embodiments of such sequences, methods to genetically modify an organism, and specific modifications have been described in detail above. Typically, the method is used to produce a particular genetically modified organism that produces a particular bioactive molecule or molecules.

One embodiment of the present invention relates to a genetically modified Thraustochytrid microorganism, wherein the microorganism has an endogenous polyunsaturated fatty acid (PUFA) polyketide synthase (PKS) system, and wherein the endogenous PUFA PKS system has been genetically modified to alter the expression profile of a polyunsaturated fatty acid (PUFA) by the microorganism as compared to the Thraustochytrid microorganism in the absence of the modification. Thraustochytrid microorganisms useful as host organisms in the present invention endogenously contain and express a PUFA PKS system. The genetic modification can be a genetic modification of one or more of the functional domains of the endogenous PUFA PKS system, whereby the modification alters the PUFA production profile of the endogenous PUFA PKS system. In addition, or as an alternative, the genetic modification can be an introduction of at least one exogenous nucleic acid sequence (e.g., a recombinant nucleic acid molecule) to the microorganism, wherein the exogenous nucleic acid sequence encodes at least one biologically active domain or protein from a second PKS system and/or a protein that affects the activity of the PUFA PKS system (e.g., a phosphopantetheinyl transferases (PPTase)). The second PKS system can be any PKS system, including other PUFA PKS systems and including homologues of genes from the Thraustochytrid PUFA PKS system to be genetically modified.

This embodiment of the invention is particularly useful for the production of commercially valuable lipids enriched in a desired PUFA, such as EPA, via the present inventors' development of genetically modified microorganisms and methods for efficiently producing lipids (triacylglyerols (TAG) as well as membrane-associated phospholipids (PL)) enriched in PUFAs.

This particular embodiment of the present invention is derived in part from the following knowledge: (1) utilization of the inherent TAG production capabilities of selected microorganisms, and particularly, of Thraustochytrids, such as the commercially developed Schizochytrium strain described herein; (2) the present inventors' detailed understanding of PUFA PKS biosynthetic pathways (i.e., PUFA PKS systems) in eukaryotes and in particular, in members of the order Thraustochytriales; and, (3) utilization of a homologous genetic recombination system in Schizochytrium. Based on the inventors' knowledge of the systems involved, the same general approach may be exploited to produce PUFAs other than EPA.

In one embodiment of the invention, the endogenous Thraustochytrid PUFA PKS genes, such as the Schizochytrium genes encoding PUFA PKS enzymes that normally produce DHA and DPA, are modified by random or targeted mutagenesis, replaced with genes from other organisms that encode homologous PKS proteins (e.g., from bacteria or other sources), or replaced with genetically modified Schizochytrium, Thraustochytrium or other Thraustochytrid PUFA PKS genes. The product of the enzymes encoded by these introduced and/or modified genes can be EPA, for example, or it could be some other related molecule, including other PUFAs. One feature of this method is the utilization of endogenous components of Thraustochytrid PUFA synthesis and accumulation machinery that is essential for efficient production and incorporation of the PUFA into PL and TAG. In particular, this embodiment of the invention is directed to the modification of the type of PUFA produced by the organism, while retaining the high oil productivity of the parent strain.

Although some of the following discussion uses the organism Schizochytrium as an exemplary host organism, any Thraustochytrid can be modified according to the present invention, including members of the genera Thraustochytrium, Labyrinthuloides, and Japonochytrium. For example, the genes encoding the PUFA PKS system for a species of Thraustochytrium have been identified (see Example 6), and this organism can also serve as a host organism for genetic modification using the methods described herein, although it is more likely that the Thraustochytrium PKS genes will be used to modify the endogenous PUFA PKS genes of another Thraustochytrid, such as Schizochytrium. Furthermore, using methods for screening organisms as set forth in U.S. application Ser. No. 10/124,800, supra, one can identify other organisms useful in the present method and all such organisms are encompassed herein.

This embodiment of the present invention can be illustrated as follows. By way of example, based on the present inventors' current understanding of PUFA synthesis and accumulation in Schizochytrium, the overall biochemical process can be divided into three parts.

First, the PUFAs that accumulate in Schizochytrium oil (DHA and DPA) are the product of a PUFA PKS system as discussed above. The PUFA PKS system in Schizochytrium converts malonyl-CoA into the end product PUFA without release of significant amounts of intermediate compounds. In Schizochytrium, three genes have been identified (Orfs A, B and C; also represented by SEQ ID NO:1, SEQ ID NO:3 and SEQ ID NO:5, respectively) that encode all of the enzymatic domains known to be required for actual synthesis of PUFAs. Similar sets of genes (encoding proteins containing homologous sets of enzymatic domains) have been cloned and characterized from several other non-eukaryotic organisms that produce PUFAs, namely, several strains of marine bacteria. In addition, the present inventors have identified and now sequenced PUFA PKS genes in at least one other marine protist (Thraustochytrium strain 23B) (described in detail below).

The PUFA products of marine bacteria include EPA (e.g., produced by Shewanella SRC2738 and Photobacter profundum) as well as DHA (Vibrio marinus, now known as Moritella marina) (described in U.S. Pat. No. 6,140,486, supra; and in U.S. Pat. No. 6,566,583, supra). It is an embodiment of the invention that any PUFA PKS gene set could be envisioned to substitute for the Schizochytrium genes described in the example herein, as long as the physiological growth requirements of the production organism (e.g., Schizochytrium) in fermentation conditions were satisfied. In particular, the PUFA-producing bacterial strains described above grow only at relatively low temperatures (typically less than 20° C.) which further indicates that their PUFA PKS gene products will not function at standard growth temperatures for Schizochytrium (25-30° C.). However, the inventors have recently identified at least two other marine bacteria that grow and produce EPA at standard growth temperatures for Schizochytrium and other Thraustochytrids (see Example 7). These alternate marine bacteria have been shown to possess PUFA-PKS-like genes that will serve as material for modification of Schizochytrium and other Thraustochytrids by methods described herein. It will be apparent to those skilled in the art from this disclosure that other currently unstudied or unidentified PUFA-producing bacteria could also contain PUFA PKS genes useful for modification of Thraustochytrids.

Second, in addition to the genes that encode the enzymes directly involved in PUFA synthesis, an "accessory" enzyme is required. The gene encodes a phosphopantetheine transferase (PPTase) that activates the acyl-carrier protein (ACP) domains present in the PUFA PKS complex. Activation of the ACP domains by addition of this co-factor is required for the PUFA PKS enzyme complex to function. All of the ACP domains of the PUFA PKS systems identified so far show a high degree of amino acid sequence conservation and, without being bound by theory, the present inventors believe that the PPTase of Schizochytrium and other Thraustochytrids will recognize and activate ACP domains from other PUFA PKS systems. As proof of principle that heterologous PPTases and PUFA PKS genes can function together to produce a PUFA product, the present inventors demonstrate herein the use of two different heterologous PPTases with the PUFA PKS genes from *Schizochytrium* to produce a PUFA in a bacterial host cell.

Third, in *Schizochytrium*, the products of the PUFA PKS system are efficiently channeled into both the phospholipids (PL) and triacylglycerols (TAG). The present inventors' data suggest that the PUFA is transferred from the ACP domains of the PKS complex to coenzyme A (CoA). As in other eukaryotic organisms, this acyl-CoA would then serve as the substrate for the various acyl-transferases that form the PL and TAG molecules. In contrast, the data indicate that in bacteria, transfer to CoA does not occur; rather, there is a direct transfer from the ACP domains of the PKS complex to the acyl-transferases that form PL. The enzymatic system in *Schizochytrium* that transfers PUFA from ACP to CoA clearly can recognize both DHA and DPA and therefore, the present inventors believe that it is predictable that any PUFA product of the PUFA PKS system (as attached to the PUFA PKS ACP domains) will serve as a substrate.

Therefore, in one embodiment of the present invention, the present inventors propose to alter the genes encoding the components of the PUFA PKS enzyme complex (part 1) while utilizing the endogenous PPTase from *Schizochytrium* or another Thraustochytrid host (part 2) and PUFA-ACP to PUFA-CoA transferase activity and TAG/PL synthesis systems (or other endogenous PUFA ACP to TAG/PL mechanism) (part 3). These methods of the present invention are supported by experimental data, some of which are presented in the Examples section in detail.

First, the present inventors have found that the PUFA PKS system can be transferred between organisms, and that some parts are interchangeable. More particularly, it has been previously shown that the PUFA PKS pathways of the marine bacteria, *Shewanella* SCR2738 (Yazawa, 1996, *Lipids* 31:S297-300) and *Vibrio marinus* (along with the PPTase from *Shewanella*) (U.S. Pat. No. 6,140,486), can be successfully transferred to a heterologous host (i.e., to *E. coli*). Additionally, the degree of structural homology between the subunits of the PUFA PKS enzymes from these two organisms (*Shewanella* SCRC2738 and *Vibrio marinus*) is such that it has been possible to mix and match genes from the two systems (U.S. Pat. No. 6,140,486, supra). The PUFA end product of the mixed sets of genes varied depending on the origins of the specific gene homologues. At least one open reading frame (*Shewanella*'s Orf 7 and its *Vibrio marinus* homologue; see FIG. 13 of U.S. Pat. No. 6,140,486; note that the nomenclature for this Orf has changed; it is labeled as Orf 8 in the patent, but was submitted to Genbank as Orf 7, and is now referred to by its GenBank designation) could be associated with determination of whether DHA or EPA would be the product of the composite system. The functional domains of all of the PUFA PKS enzymes identified so far show sequence homology to one another. Similarly, these data indicated that PUFA PKS systems, including those from the marine bacteria, can be transferred to, and will function in, *Schizochytrium* and other Thraustochytrids.

The present inventors have now expressed the PUFA PKS genes (Orfs A, B and C) from *Schizochytrium* in an *E. coli* host and have demonstrated that the cells made DHA and DPA in about the same ratio as the endogenous production of these PUFAs in *Schizochytrium* (see Example 2). Therefore, it has been demonstrated that the recombinant *Schizochytrium* PUFA PKS genes encode a functional PUFA synthesis system. Additionally, all or portions of the *Thraustochytrium* 23B OrfA and OrfC genes have been shown to function in *Schizochytrium* (see Example 6).

Second, the present inventors have previously found that PPTases can activate heterologous PUFA PKS ACP domains. Production of DHA in *E. coli* transformed with the PUFA PKS genes from *Vibrio marinus* occurred only when an appropriate PPTase gene (in this case, from *Shewanella* SCRC2738) was also present (see U.S. Pat. No. 6,140,486, supra). This demonstrated that the *Shewanella* PPTase was able to activate the *Vibrio* PUFA PKS ACP domains. Additionally, the present inventors have now demonstrated the activation (pantetheinylation) of ACP domains from *Schizochytrium* Orf A using a PPTase (sfp) from *Bacillus subtilus* (see Example 2). The present inventors have also demonstrated activation (pantetheinylation) of ACP domains from *Schizochytrium* Orf A by a PPTase called Het I from *Nostoc* (see Example 2). The HetI enzyme was additionally used as the PPTase in the experiments discussed above for the production of DHA and DPA in *E. coli* using the recombinant *Schizochytrium* PUFA PKS genes (Example 2).

Third, data indicate that DHA-CoA and DPA-CoA may be metabolic intermediates in the *Schizochytrium* TAG and PL synthesis pathway. Published biochemical data suggest that in bacteria, the newly synthesized PUFAs are transferred directly from the PUFA PKS ACP domains to the phospholipid synthesis enzymes. In contrast, the present inventors' data indicate that in *Schizochytrium*, a eukaryotic organism, there may be an intermediate between the PUFA on the PUFA PKS ACP domains and the target TAG and PL molecules. The typical carrier of fatty acids in the eukaryotic cytoplasm is CoA. The inventors examined extracts of *Schizochytrium* cells and found significant levels of compounds that co-migrated during HPLC fractionation with authentic standards of DHA-CoA, DPA-CoA, 16:0-CoA and 18:1-CoA. The identity of the putative DHA-CoA and DPA-CoA peaks were confirmed using mass spectroscopy. In contrast, the inventors were not able to detect DHA-CoA in extracts of *Vibrio marinus*, again suggesting that a different mechanism exists in bacteria for transfer of the PUFA to its final target (e.g., direct transfer to PL). The data indicate a mechanism likely exists in *Schizochytrium* for transfer of the newly synthesized PUFA to CoA (probably via a direct transfer from the ACP to CoA). Both TAG and PL synthesis enzymes could then access this PUFA-CoA. The observation that both DHA and DPA CoA are produced suggests that the enzymatic transfer machinery may recognize a range of PUFAs.

Fourth, the present inventors have now created knockouts of OrfA, OrfB, and OrfC in *Schizochytrium* (see Example 3). The knockout strategy relies on the homologous recombination that has been demonstrated to occur in *Schizochytrium* (see U.S. patent application Ser. No. 10/124,807, supra). Several strategies can be employed in the design of knockout constructs. The specific strategy used to inactivate these three genes utilized insertion of a Zeocin™ resistance gene coupled to a tubulin promoter (derived from pMON50000, see U.S. patent application Ser. No. 10/124,807) into a cloned portion of the Orf. The new construct containing the interrupted coding region was then used for the transformation of wild type *Schizochytrium* cells via particle bombardment (see U.S. patent application Ser. No. 10/124,807). Bombarded cells were spread on plates containing both Zeocin™ and a supply of PUFA (see below). Colonies that grew on these plates were then streaked onto Zeocin™ plates that were not supplemented with PUFAs. Those colonies that required PUFA supplementation for growth were candidates for having had the PUFA PKS Orf inactivated via homologous recombination. In all three cases, this presumption was confirmed by rescuing the knockout by transforming the cells with a full-length genomic DNA clones of the respective Schizochytrium Orfs. Furthermore, in some cases, it was found that the Zeocin™ resistance gene had been removed (see Example 5), indicating that the introduced functional gene had integrated into the original site by double homologous recombination (i.e. deleting the resistance marker). One key to the success of this strategy was supplementation of the growth medium with PUFAs. In the present case, an effective means of supplementation was found to be sequestration of the PUFA by mixing with partially methylated beta-cyclodextrin prior to adding to the growth medium (see Example 5). Together, these experiments demonstrate the principle that one of skill in the art, given the guidance provided herein, can inactivate one or more of the PUFA PKS genes in a PUFA PKS-containing microorganism such as *Schizochytrium*, and create a PUFA auxotroph which can then be used for further genetic modification (e.g., by introducing other PKS genes) according to the present invention (e.g., to alter the fatty acid profile of the recombinant organism).

One important element of the genetic modification of the organisms of the present invention is the ability to directly transform a Thraustochytrid genome. In U.S. application Ser. No. 10/124,807, supra, transformation of *Schizochytrium* via single crossover homologous recombination and targeted gene replacement via double crossover homologous recombination were demonstrated. As discussed above, the present inventors have now used this technique for homologous recombination to inactivate Orf A, Orf B and OrfC of the PUFA-PKA system in *Schizochytrium*. The resulting mutants are dependent on supplementation of the media with PUFA. Several markers of transformation, promoter elements for high level expression of introduced genes and methods for delivery of exogenous genetic material have been developed and are available. Therefore, the tools are in place for knocking out endogenous PUFA PKS genes in Thraustochytrids and other eukaryotes having similar PUFA PKS systems and replacing them with genes from other organisms (or with modified *Schizochytrium* genes) as proposed above.

In one approach for production of EPA-rich TAG, the PUFA PKS system of *Schizochytrium* can be altered by the addition of heterologous genes encoding a PUFA PKS system whose product is EPA. It is anticipated that the endogenous PPTase will activate the ACP domains of that heterologous PUFA PKS system. Additionally, it is anticipated that the EPA will be converted to EPA-CoA and will readily be incorporated into *Schizochytrium* TAG and PL membranes. In one modification of this approach, techniques can be used to modify the relevant domains of the endogenous *Schizochytrium* system (either by introduction of specific regions of heterologous genes or by mutagenesis of the *Schizochytrium* genes themselves) such that its end product is EPA rather than DHA and DPA. This is an exemplary approach, as this technology can be applied to the production of other PUFA end products and to any eukaryotic microorganism that comprises a PUFA PKS system and that has the ability to efficiently channel the products of the PUFA PKS system into both the phospholipids (PL) and triacylglycerols (TAG). In particular, the invention is applicable to any Thraustochytrid microorganism or any other eukaryote that has an endogenous PUFA PKS system, which is described in detail below by way of example. In addition, the invention is applicable to any suitable host organism, into which the modified genetic material for production of various PUFA profiles as described herein can be transformed. For example, in the Examples, the PUFA PKS system from *Schizochytrium* is transformed into an *E. coli*. Such a transformed organism could then be further modified to alter the PUFA production profile using the methods described herein.

The present invention can make use of genes and nucleic acid sequences which encode proteins or domains from PKS systems other than the PUFA PKS system described herein and in U.S. patent application Ser. No. 10/124,800, and include genes and nucleic acid sequences from bacterial and non-bacterial PKS systems, including PKS systems of Type II, Type I and modular, described above. Organisms which express each of these types of PKS systems are known in the art and can serve as sources for nucleic acids useful in the genetic modification process of the present invention.

In a preferred embodiment, genes and nucleic acid sequences which encode proteins or domains from PKS systems other than the PUFA PKS system or from other PUFA PKS systems are isolated or derived from organisms which have preferred growth characteristics for production of PUFAs. In particular, it is desirable to be able to culture the genetically modified Thraustochytrid microorganism at temperatures greater than about 15° C., greater than 20° C., greater than 25° C., greater than 30° C., greater than 35° C., greater than 40° C., or in one embodiment, at any temperature between about 20° C. and 40° C. Therefore, PKS proteins or domains having functional enzymatic activity at these temperatures are preferred. For example, the present inventors describe herein the use of PKS genes from *Shewanella olleyana* or *Shewanella japonica*, which are marine bacteria that naturally produce EPA and grow at temperatures up to 30° C. and 35° C., respectively (see Example 7). PKS proteins or domains from these organisms are examples of proteins and domains that can be mixed with Thraustochytrid PUFA PKS proteins and domains as described herein to produce a genetically modified organism that has a specifically designed or modified PUFA production profile.

In another preferred embodiment, the genes and nucleic acid sequences that encode proteins or domains from a PUFA PKS system that produces one fatty acid profile are used to modify another PUFA PKS system and thereby alter the fatty acid profile of the host. For example, *Thraustochytrium* 23B (ATCC 20892) is significantly different from *Schizochytrium* sp. (ATCC 20888) in its fatty acid profile. *Thraustochytrium* 23B can have DHA:DPA(n-6) ratios as high as 40:1 compared to only 2-3:1 in *Schizochytrium* (ATCC 20888). *Thraustochytrium* 23B can also have higher levels of C20:5(n-3). However, *Schizochytrium* (ATCC 20888) is an excellent oil producer as compared to *Thraustochytrium* 23B. *Schizochytrium* accumulates large quantities of triacylglycerols rich in DHA and docosapentaenoic acid (DPA; 22:5ω6); e.g., 30% DHA+DPA by dry weight. Therefore, the present inventors describe herein the modification of the *Schizochytrium* endogenous PUFA PKS system with *Thraustochytrium* 23B PUFA PKS genes to create a genetically modified *Schizochytrium* with a DHA:DPA profile more similar to *Thraustochytrium* 23B (i.e., a "super-DHA-producer" *Schizochytrium*, wherein the production capabilities of the *Schizochytrium* combine with the DHA:DPA ratio of *Thraustochytrium*).

Therefore, the present invention makes use of genes from Thraustochytrid PUFA PKS systems, and further utilizes gene mixing to extend and/or alter the range of PUFA products to include EPA, DHA, DPA, ARA, GLA, SDA and others. The method to obtain these altered PUFA production profiles includes not only the mixing of genes from various organisms into the Thrasustochytrid PUFA PKS genes, but also various methods of genetically modifying the endogenous Thraustochytrid PUFA PKS genes disclosed herein. Knowledge of the genetic basis and domain structure of the Thraustochytrid PUFA PKS system of the present invention (e.g., described in detail for *Schizochytrium* above) provides a basis for designing novel genetically modified organisms which produce a variety of PUFA profiles. Novel PUFA PKS constructs prepared in microorganisms such as a Thraustochytrid can be isolated and used to transform plants to impart similar PUFA production properties onto the plants.

Any one or more of the endogenous Thraustochytrid PUFA PKS domains can be altered or replaced according to the present invention, provided that the modification produces the desired result (i.e., alteration of the PUFA production profile of the microorganism). Particularly preferred domains to alter or replace include, but are not limited to, any of the domains corresponding to the domains in *Schizochytrium* OrfB or OrfC (β-keto acyl-ACP synthase (KS), acyltransferase (AT), FabA-like β-hydroxy acyl-ACP dehydrase (DH), chain length factor (CLF), enoyl ACP-reductase (ER), an enzyme that catalyzes the synthesis of trans-2-acyl-ACP, an enzyme that catalyzes the reversible isomerization of trans-2-acyl-ACP to cis-3-acyl-ACP, and an enzyme that catalyzes the elongation of cis-3-acyl-ACP to cis-5-β-keto-acyl-ACP). In one embodiment, preferred domains to alter or replace include, but are not limited to, β-keto acyl-ACP synthase (KS), FabA-like β-hydroxy acyl-ACP dehydrase (DH), and chain length factor (CLF).

In one aspect of the invention, Thraustochytrid PUFA-PKS PUFA production is altered by modifying the CLF (chain length factor) domain. This domain is characteristic of Type II (dissociated enzymes) PKS systems. Its amino acid sequence shows homology to KS (keto synthase pairs) domains, but it lacks the active site cysteine. CLF may function to determine the number of elongation cycles, and hence the chain length, of the end product. In this embodiment of the invention, using the current state of knowledge of FAS and PKS synthesis, a rational strategy for production of ARA by directed modification of the non-bacterial PUFA-PKS system is provided. There is controversy in the literature concerning the function of the CLF in PKS systems (Bisang et al., *Nature* 401, 502 (1999); Yi et al., *J. Am. Chem. Soc.* 125, 12708 (2003)) and it is realized that other domains may be involved in determination of the chain length of the end product. However, it is significant that *Schizochytrium* produces both DHA (C22:6, ω-3) and DPA (C22:5, ω-6). In the PUFA-PKS system the cis double bonds are introduced during synthesis of the growing carbon chain. Since placement of the ω-3 and ω-6 double bonds occurs early in the synthesis of the molecules, one would not expect that they would affect subsequent end-product chain length determination. Thus, without being bound by theory, the present inventors believe that introduction of a factor (e.g. CLF) that directs synthesis of C20 units (instead of C22 units) into the *Schizochytrium* PUFA-PKS system will result in the production of EPA (C20:5, ω-3) and ARA (C20:4, ω-6). For example, in heterologous systems, one could exploit the CLF by directly substituting a CLF from an EPA producing system (such as one from *Photobacterium*, or preferably from a microorganism with the preferred growth requirements as described below) into the *Schizochytrium* gene set. The fatty acids of the resulting transformants can then be analyzed for alterations in profiles to identify the transformants producing EPA and/or ARA.

By way of example, in this aspect of the invention, one could construct a clone with the CLF of OrfB replaced with a CLF from a C20 PUFA-PKS system. A marker gene could be inserted downstream of the coding region. More specifically, one can use the homologous recombination system for transformation of Thraustochytrids as described herein and in detail in U.S. patent application Ser. No. 10/124,807, supra. One can then transform the wild type Thraustochytrid cells (e.g., *Schizochytrium* cells), select for the marker phenotype, and then screen for those that had incorporated the new CLF. Again, one would analyze these transformants for any effects on fatty acid profiles to identify transformants producing EPA and/or ARA. If some factor other than those associated with the CLF is found to influence the chain length of the end product, a similar strategy could be employed to alter those factors.

In another aspect of the invention, modification or substitution of the β-hydroxy acyl-ACP dehydrase/keto synthase pairs is contemplated. During cis-vaccenic acid (C18:1, Δ11) synthesis in *E. coli*, creation of the cis double bond is believed to depend on a specific DH enzyme, β-hydroxy acyl-ACP dehydrase, the product of the fabA gene. This enzyme removes HOH from a β-keto acyl-ACP and leaves a trans double bond in the carbon chain. A subset of DH's, FabA-like, possess cis-trans isomerase activity (Heath et al., 1996, supra). A novel aspect of bacterial and non-bacterial PUFA-PKS systems is the presence of two FabA-like DH domains. Without being bound by theory, the present inventors believe that one or both of these DH domains will possess cis-trans isomerase activity (manipulation of the DH domains is discussed in greater detail below).

Another aspect of the unsaturated fatty acid synthesis in *E. coli* is the requirement for a particular KS enzyme, β-ketoacyl-ACP synthase, the product of the fabB gene. This is the enzyme that carries out condensation of a fatty acid, linked to a cysteine residue at the active site (by a thio-ester bond), with a malonyl-ACP. In the multi-step reaction, $CO_2$ is released and the linear chain is extended by two carbons. It is believed that only this KS can extend a carbon chain that contains a double bond. This extension occurs only when the double bond is in the cis configuration; if it is in the trans configuration, the double bond is reduced by enoyl-ACP reductase (ER) prior to elongation (Heath et al., 1996, supra). All of the PUFA-PKS systems characterized so far have two KS domains, one of which shows greater homology to the FabB-like KS of *E. coli* than the other. Again, without being bound by theory, the present inventors believe that in PUFA-PKS systems, the specificities and interactions of the DH (FabA-like) and KS (FabB-like) enzymatic domains determine the number and placement of cis double bonds in the end products. Because the number of 2-carbon elongation reactions is greater than the number of double bonds present in the PUFA-PKS end products, it can be determined that in some extension cycles complete reduction occurs. Thus the DH and KS domains can be used as targets for alteration of the DHA/DPA ratio or ratios of other long chain fatty acids. These can be modified and/or evaluated by introduction of homologous domains from other systems or by mutagenesis of these gene fragments.

In another embodiment, the ER (enoyl-ACP reductase—an enzyme which reduces the trans-double bond in the fatty acyl-ACP resulting in fully saturated carbons) domains can be modified or substituted to change the type of product made by the PKS system. For example, the present inventors know that *Schizochytrium* PUFA-PKS system differs from the previously described bacterial systems in that it has two (rather than one) ER domains. Without being bound by theory, the present inventors believe these ER domains can strongly influence the resulting PKS production product. The resulting PKS product could be changed by separately knocking out the individual domains or by modifying their nucleotide sequence or by substitution of ER domains from other organisms.

In another aspect of the invention, substitution of one of the DH (FabA-like) domains of the PUFA-PKS system for a DH domain that does not posses isomerization activity is contemplated, potentially creating a molecule with a mix of cis- and trans-double bonds. The current products of the *Schizochytrium* PUFA PKS system are DHA and DPA (C22:5 ω6). If one manipulated the system to produce C20 fatty acids, one would expect the products to be EPA and ARA (C20:4 ω6). This could provide a new source for ARA. One could also substitute domains from related PUFA-PKS systems that produced a different DHA to DPA ratio—for example by using genes from *Thraustochytrium* 23B (the PUFA PKS system of which is identified in U.S. patent application Ser. No. 10/124,800, supra).

Additionally, in one embodiment, one of the ER domains is altered in the Thraustochytrid PUFA PKS system (e.g. by removing or inactivating) to alter the end product profile. Similar strategies could be attempted in a directed manner for each of the distinct domains of the PUFA-PKS proteins using more or less sophisticated approaches. Of course one would not be limited to the manipulation of single domains. Finally, one could extend the approach by mixing domains from the PUFA-PKS system and other PKS or FAS systems (e.g., type I, type II, modular) to create an entire range of new PUFA end products.

It is recognized that many genetic alterations, either random or directed, which one may introduce into a native (endogenous, natural) PKS system, will result in an inactivation of enzymatic functions. Therefore, in order to test for the effects of genetic manipulation of a Thraustochytrid PUFA PKS system in a controlled environment, one could first use a recombinant system in another host, such as *E. coli*, to manipulate various aspects of the system and evaluate the results. For example, the FabB-strain of *E. coli* is incapable of synthesizing unsaturated fatty acids and requires supplementation of the medium with fatty acids that can substitute for its normal unsaturated fatty acids in order to grow (see Metz et al., 2001, supra). However, this requirement (for supplementation of the medium) can be removed when the strain is transformed with a functional PUFA-PKS system (i.e. one that produces a PUFA product in the *E. coli* host—see (Metz et al., 2001, supra, FIG. 2A). The transformed FabB-strain now requires a functional PUFA-PKS system (to produce the unsaturated fatty acids) for growth without supplementation. The key element in this example is that production of a wide range of unsaturated fatty acid will suffice (even unsaturated fatty acid substitutes such as branched chain fatty acids). Therefore, in another preferred embodiment of the invention, one could create a large number of mutations in one or more of the PUFA PKS genes disclosed herein, and then transform the appropriately modified FabB-strain (e.g. create mutations in an expression construct containing an ER domain and transform a FabB-strain having the other essential domains on a separate plasmid—or integrated into the chromosome) and select only for those transformants that grow without supplementation of the medium (i.e., that still possessed an ability to produce a molecule that could complement the FabB-defect).

One test system for genetic modification of a PUFA PKS is exemplified in the Examples section. Briefly, a host microorganism such as *E. coli* is transformed with genes encoding a PUFA PKS system including all or a portion of a Thraustochytrid PUFA PKS system (e.g., Orfs A, B and C of *Schizochytrium*) and a gene encoding a phosphopanteheinyl transferases (PPTase), which is required for the attachment of a phosphopantetheine cofactor to produce the active, holo-ACP in the PKS system. The genes encoding the PKS system can be genetically engineered to introduce one or more modifications to the Thraustochytrid PUFA PKS genes and/or to introduce nucleic acids encoding domains from other PKS systems into the Thraustochytrid genes (including genes from non-Thraustochytrid microorganisms and genes from different Thraustochytrid microorganisms). The PUFA PKS system can be expressed in the *E. coli* and the PUFA production profile measured. In this manner, potential genetic modifications can be evaluated prior to manipulation of the Thraustochytrid PUFA production organism.

The present invention includes the manipulation of endogenous nucleic acid molecules and/or the use of isolated nucleic acid molecules comprising a nucleic acid sequence from a Thraustochytrid PUFA PKS system or a homologue thereof. In one aspect, the present invention relates to the modification and/or use of a nucleic acid molecule comprising a nucleic acid sequence encoding a domain from a PUFA PKS system having a biological activity of at least one of the following proteins: malonyl-CoA:ACP acyltransferase (MAT), β-keto acyl-ACP synthase (KS), ketoreductase (KR), acyltransferase (AT), FabA-like β-hydroxy acyl-ACP dehydrase (DH), phosphopantetheine transferase, chain length factor (CLF), acyl carrier protein (ACP), enoyl ACP-reductase (ER), an enzyme that catalyzes the synthesis of trans-2-acyl-ACP, an enzyme that catalyzes the reversible isomerization of trans-2-acyl-ACP to cis-3-acyl-ACP, and/or an enzyme that catalyzes the elongation of cis-3-acyl-ACP to cis-5-β-keto-acyl-ACP. Preferred domains to modify in order to alter the PUFA production profile of a host Thraustochytrid have been discussed previously herein.

The genetic modification of a Thraustochytrid microorganism according to the present invention preferably affects the type, amounts, and/or activity of the PUFAs produced by the microorganism, whether the endogenous PUFA PKS system is genetically modified and/or whether recombinant nucleic acid molecules are introduced into the organism. According to the present invention, to affect an activity of a PUFA PKS system, such as to affect the PUFA production profile, includes any genetic modification in the PUFA PKS system or genes that interact with the PUFA PKS system that causes any detectable or measurable change or modification in any biological activity the PUFA PKS system expressed by the organism as compared to in the absence of the genetic modification. According to the present invention, the phrases "PUFA profile", "PUFA expression profile" and "PUFA production profile" can be used interchangeably and describe the overall profile of PUFAs expressed/produced by a microorganism. The PUFA expression profile can include the types of PUFAs expressed by the microorganism, as well as the absolute and relative amounts of the PUFAs produced. Therefore, a PUFA profile can be described in terms of the ratios of PUFAs to one another as produced by the microorganism, in terms of the types of PUFAs produced by the microorganism, and/or in terms of the types and absolute or relative amounts of PUFAs produced by the microorganism.

As discussed above, while the host microorganism can include any eukaryotic microorganism with an endogenous PUFA PKS system and the ability to efficiently channel the products of the PUFA PKS system into both the phospholipids (PL) and triacylglycerols (TAG), the preferred host microorganism is any member of the order Thraustochytriales, including the families Thraustochytriaceae and Labyrinthulaceae. Particularly preferred host cells for use in the present invention could include microorganisms from a genus including, but not limited to: *Thraustochytrium, Japonochytrium, Aplanochytrium, Elina,* and *Schizochytrium* within the Thraustochytriaceae, and *Labyrinthula, Labyrinthuloides,* and *Labyrinthomyxa* within the Labyrinthulaceae. Preferred species within these genera include, but are not limited to: any species within *Labyrinthula,* including *Labrinthula* sp.,

*Labyrinthula algeriensis, Labyrinthula cienkowskii, Labyrinthula chattonii, Labyrinthula coenocystis, Labyrinthula macrocystis, Labyrinthula macrocystis atlantica, Labyrinthula macrocystis macrocystis, Labyrinthula magnifica, Labyrinthula minuta, Labyrinthula roscoffensis, Labyrinthula valkanovii, Labyrinthula vitellina, Labyrinthula vitellina pacifica, Labyrinthula vitellina vitellina, Labyrinthula zopfii;* any *Labyrinthuloides* species, including *Labyrinthuloides* sp., *Labyrinthuloides minuta, Labyrinthuloides schizochytrops;* any *Labyrinthomyxa* species, including *Labyrinthomyxa* sp., *Labyrinthomyxa pohlia, Labyrinthomyxa sauvageaui,* any *Aplanochytrium* species, including *Aplanochytrium* sp. and *Aplanochytrium kerguelensis;* any *Elina* species, including *Elina* sp., *Elina marisalba, Elina sinorifica;* any *Japanochytrium* species, including *Japanochytrium* sp., *Japanochytrium marinum;* any *Schizochytrium* species, including *Schizochytrium* sp., *Schizochytrium aggregatum, Schizochytrium limacinum, Schizochytrium minutum, Schizochytrium octosporum;* and any *Thraustochytrium* species, including *Thraustochytrium* sp., *Thraustochytrium aggregatum, Thraustochytrium arudimentale, Thraustochytrium aureum, Thraustochytrium benthicola, Thraustochytrium globosum, Thraustochytrium kinnei, Thraustochytrium motivum, Thraustochytrium pachydermum, Thraustochytrium proliferum, Thraustochytrium roseum, Thraustochytrium striatum, Ulkenia* sp., *Ulkenia minuta, Ulkenia profunda, Ulkenia radiate, Ulkenia sarkariana,* and *Ulkenia visurgensis.* Particularly preferred species within these genera include, but are not limited to: any *Schizochytrium* species, including *Schizochytrium aggregatum, Schizochytrium limacinum, Schizochytrium minutum;* any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum;* and any *Japonochytrium* species. Particularly preferred strains of Thraustochytriales include, but are not limited to: *Schizochytrium* sp. (S31) (ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207).

In one embodiment of the present invention, it is contemplated that a mutagenesis program could be combined with a selective screening process to obtain a Thraustochytrid microorganism with the PUFA production profile of interest. The mutagenesis methods could include, but are not limited to: chemical mutagenesis, gene shuffling, switching regions of the genes encoding specific enzymatic domains, or mutagenesis restricted to specific regions of those genes, as well as other methods.

For example, high throughput mutagenesis methods could be used to influence or optimize production of the desired PUFA profile. Once an effective model system has been developed, one could modify these genes in a high throughput manner. Utilization of these technologies can be envisioned on two levels. First, if a sufficiently selective screen for production of a product of interest (e.g., EPA) can be devised, it could be used to attempt to alter the system to produce this product (e.g., in lieu of, or in concert with, other strategies such as those discussed above). Additionally, if the strategies outlined above resulted in a set of genes that did produce the PUFA profile of interest, the high throughput technologies could then be used to optimize the system. For example, if the introduced domain only functioned at relatively low temperatures, selection methods could be devised to permit removing that limitation.

In one embodiment of the present invention, a genetically modified Thraustochytrid microorganism has an enhanced ability to synthesize desired PUFAs and/or has a newly introduced ability to synthesize a different profile of PUFAs. According to the present invention, "an enhanced ability to synthesize" a product refers to any enhancement, or up-regulation, in a pathway related to the synthesis of the product such that the microorganism produces an increased amount of the product (including any production of a product where there was none before) as compared to the wild-type microorganism, cultured or grown, under the same conditions. Methods to produce such genetically modified organisms have been described in detail above.

As described above, in one embodiment of the present invention, a genetically modified microorganism or plant includes a microorganism or plant which has an enhanced ability to synthesize desired bioactive molecules (products) or which has a newly introduced ability to synthesize specific products (e.g., to synthesize a specific antibiotic). According to the present invention, "an enhanced ability to synthesize" a product refers to any enhancement, or up-regulation, in a pathway related to the synthesis of the product such that the microorganism or plant produces an increased amount of the product (including any production of a product where there was none before) as compared to the wild-type microorganism or plant, cultured or grown, under the same conditions. Methods to produce such genetically modified organisms have been described in detail above.

One embodiment of the present invention is a method to produce desired bioactive molecules (also referred to as products or compounds) by growing or culturing a genetically modified microorganism or plant of the present invention (described in detail above). Such a method includes the step of culturing in a fermentation medium or growing in a suitable environment, such as soil, a microorganism or plant, respectively, that has a genetic modification as described previously herein and in accordance with the present invention. Preferred host cells for genetic modification related to the PUFA PKS system of the invention are described above.

One embodiment of the present invention is a method to produce desired PUFAs by culturing a genetically modified Thraustochytrid microorganism of the present invention (described in detail above). Such a method includes the step of culturing in a fermentation medium and under conditions effective to produce the PUFA(s) a Thraustochytrid microorganism that has a genetic modification as described previously herein and in accordance with the present invention. An appropriate, or effective, medium refers to any medium in which a genetically modified microorganism of the present invention, including Thraustochytrids and other microorganisms, when cultured, is capable of producing the desired PUFA product(s). Such a medium is typically an aqueous medium comprising assimilable carbon, nitrogen and phosphate sources. Such a medium can also include appropriate salts, minerals, metals and other nutrients. Any microorganisms of the present invention can be cultured in conventional fermentation bioreactors. The microorganisms can be cultured by any fermentation process which includes, but is not limited to, batch, fed-batch, cell recycle, and continuous fermentation. Preferred growth conditions for Thraustochytrid microorganisms according to the present invention are well known in the art and are described in detail, for example, in U.S. Pat. No. 5,130,242, U.S. Pat. No. 5,340,742, and U.S. Pat. No. 5,698,244, each of which is incorporated herein by reference in its entirety.

In one embodiment, the genetically modified microorganism is cultured at a temperature of greater than about 15° C., and in another embodiment, greater than about 20° C., and in another embodiment, greater than about 25° C., and in another embodiment, greater than about 30° C., and in another embodiment, greater than about 35° C., and in another embodiment, greater than about 40° C., and in one embodiment, at any temperature between about 20° C. and 40° C.

The desired PUFA(s) and/or other bioactive molecules produced by the genetically modified microorganism can be recovered from the fermentation medium using conventional separation and purification techniques. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, phase separation, membrane separation, electrodialysis, reverse osmosis, distillation, chemical derivatization and crystallization. Alternatively, microorganisms producing the PUFA(s), or extracts and various fractions thereof, can be used without removal of the microorganism components from the product.

Preferably, a genetically modified Thraustochytrid microorganism of the invention produces one or more polyunsaturated fatty acids including, but not limited to, EPA (C20:5, ω-3), DHA (C22:6, ω-3), DPA (C22:5, ω-6), ARA (C20:4, ω-6), GLA (C18:3, n-6), and SDA (C18:4, n-3)). In one preferred embodiment, a *Schizochytrium* that, in wild-type form, produces high levels of DHA and DPA, is genetically modified according to the invention to produce high levels of EPA. As discussed above, one advantage of using genetically modified Thraustochytrid microorganisms to produce PUFAs is that the PUFAs are directly incorporated into both the phospholipids (PL) and triacylglycerides (TAG).

Preferably, PUFAs are produced in an amount that is greater than about 5% of the dry weight of the microorganism, and in one aspect, in an amount that is greater than 6%, and in another aspect, in an amount that is greater than 7%, and in another aspect, in an amount that is greater than 8%, and in another aspect, in an amount that is greater than 9%, and in another aspect, in an amount that is greater than 10%, and so on in whole integer percentages, up to greater than 90% dry weight of the microorganism (e.g., 15%, 20%, 30%, 40%, 50%, and any percentage in between).

In the method for production of desired bioactive compounds of the present invention, a genetically modified plant is cultured in a fermentation medium or grown in a suitable medium such as soil. An appropriate, or effective, fermentation medium has been discussed in detail above. A suitable growth medium for higher plants includes any growth medium for plants, including, but not limited to, soil, sand, any other particulate media that support root growth (e.g. vermiculite, perlite, etc.) or hydroponic culture, as well as suitable light, water and nutritional supplements which optimize the growth of the higher plant. The genetically modified plants of the present invention are engineered to produce significant quantities of the desired product through the activity of the PKS system that is genetically modified according to the present invention. The compounds can be recovered through purification processes which extract the compounds from the plant. In a preferred embodiment, the compound is recovered by harvesting the plant. In this embodiment, the plant can be consumed in its natural state or further processed into consumable products.

Many genetic modifications useful for producing bioactive molecules will be apparent to those of skill in the art, given the present disclosure, and various other modifications have been discussed previously herein. The present invention contemplates any genetic modification related to a PUFA PKS system as described herein which results in the production of a desired bioactive molecule.

Bioactive molecules, according to the present invention, include any molecules (compounds, products, etc.) that have a biological activity, and that can be produced by a PKS system that comprises at least one amino acid sequence having a biological activity of at least one functional domain of a non-bacterial PUFA PKS system as described herein. Such bioactive molecules can include, but are not limited to: a polyunsaturated fatty acid (PUFA), an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. One advantage of the non-bacterial PUFA PKS system of the present invention is the ability of such a system to introduce carbon-carbon double bonds in the cis configuration, and molecules including a double bond at every third carbon. This ability can be utilized to produce a variety of compounds.

Preferably, bioactive compounds of interest are produced by the genetically modified microorganism in an amount that is greater than about 0.05%, and preferably greater than about 0.1%, and more preferably greater than about 0.25%, and more preferably greater than about 0.5%, and more preferably greater than about 0.75%, and more preferably greater than about 1%, and more preferably greater than about 2.5%, and more preferably greater than about 5%, and more preferably greater than about 10%, and more preferably greater than about 15%, and even more preferably greater than about 20% of the dry weight of the microorganism. For lipid compounds, preferably, such compounds are produced in an amount that is greater than about 5% of the dry weight of the microorganism. For other bioactive compounds, such as antibiotics or compounds that are synthesized in smaller amounts, those strains possessing such compounds at of the dry weight of the microorganism are identified as predictably containing a novel PKS system of the type described above. In some embodiments, particular bioactive molecules (compounds) are secreted by the microorganism, rather than accumulating. Therefore, such bioactive molecules are generally recovered from the culture medium and the concentration of molecule produced will vary depending on the microorganism and the size of the culture.

One embodiment of the present invention relates to a method to modify an endproduct containing at least one fatty acid, comprising adding to the endproduct an oil produced by a recombinant host cell that expresses at least one recombinant nucleic acid molecule comprising a nucleic acid sequence encoding at least one biologically active domain of a PUFA PKS system. The PUFA PKS system includes any suitable bacterial or non-bacterial PUFA PKS system described herein, including the PUFA PKS systems from *Thraustochytrium* and *Schizochytrium*, or any PUFA PKS system from bacteria that normally (i.e., under normal or natural conditions) are capable of growing and producing PUFAs at temperatures above 22° C., such as *Shewanella olleyana* or *Shewanella japonica*.

Preferably, the endproduct is selected from the group consisting of a food, a dietary supplement, a pharmaceutical formulation, a humanized animal milk, and an infant formula. Suitable pharmaceutical formulations include, but are not limited to, an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. In one embodiment, the endproduct is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

Suitable food products include, but are not limited to, fine bakery wares, bread and rolls, breakfast cereals, processed and unprocessed cheese, condiments (ketchup, mayonnaise, etc.), dairy products (milk, yogurt), puddings and gelatin desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks.

Yet another embodiment of the present invention relates to a method to produce a humanized animal milk. This method includes the steps of genetically modifying milk-producing cells of a milk-producing animal with at least one recombinant nucleic acid molecule comprising a nucleic acid sequence encoding at least one biologically active domain of a PUFA PKS system as described herein.

Methods to genetically modify a host cell and to produce a genetically modified non-human, milk-producing animal, are known in the art. Examples of host animals to modify include cattle, sheep, pigs, goats, yaks, etc., which are amenable to genetic manipulation and cloning for rapid expansion of a transgene expressing population. For animals, PKS-like transgenes can be adapted for expression in target organelles, tissues and body fluids through modification of the gene regulatory regions. Of particular interest is the production of PUFAs in the breast milk of the host animal.

The following examples are provided for the purpose of illustration and are not intended to limit the scope of the present invention.

EXAMPLES

Example 1

The following example, from U.S. patent application Ser. No. 10/124,800, describes the use of the screening process of the present invention to identify other non-bacterial organisms comprising a PUFA PKS system according to the present invention.

*Thraustochytrium* sp. 23B (ATCC 20892) was cultured as described in detail herein.

A frozen vial of *Thraustochytrium* sp. 23B (ATCC 20892) was used to inoculate a 250 mL shake flask containing 50 mL of RCA medium. The culture was shaken on a shaker table (200 rpm) for 72 hr at 25° C. RCA medium contains the following:

| RCA Medium | |
|---|---|
| Deionized water | 1000 mL |
| Reef Crystals ® sea salts | 40 g/L |
| Glucose | 20 g/L |
| Monosodium glutamate (MSG) | 20 g/L |
| Yeast extract | 1 g/L |
| PII metals* | 5 mL/L |
| Vitamin mix* | 1 mL/L |
| pH | 7.0 |

*PII metal mix and vitamin mix are same as those outlined in U.S. Pat. No. 5,130,742, incorporated herein by reference in its entirety.

25 mL of the 72 hr old culture was then used to inoculate another 250 mL shake flask containing 50 mL of low nitrogen RCA medium (10 g/L MSG instead of 20 g/L) and the other 25 mL of culture was used to inoculate a 250 mL shake flask containing 175 mL of low-nitrogen RCA medium. The two flasks were then placed on a shaker table (200 rpm) for 72 hr at 25° C. The cells were then harvested via centrifugation and dried by lyophilization. The dried cells were analyzed for fat content and fatty acid profile and content using standard gas chromatograph procedures.

The screening results for *Thraustochytrium* 23B under low oxygen conditions relative to high oxygen conditions were as follows:

| | |
|---|---|
| Did DHA as % FAME increase? | Yes (38->44%) |
| C14:0 + C16:0 + C16:1 greater than about 40% TFA? | Yes (44%) |
| No C18:3(n − 3) or C18:3(n − 6)? | Yes (0%) |
| Did fat content increase? | Yes (2-fold increase) |
| Did DHA (or other HUFA content increase)? | Yes (2.3-fold increase) |

The results, especially the significant increase in DHA content (as % FAME) under low oxygen conditions, conditions, strongly indicates the presence of a PUFA producing PKS system in this strain of *Thraustochytrium*.

In order to provide additional data confirming the presence of a PUFA PKS system, a Southern blot of *Thraustochytrium* 23B was conducted using PKS probes from *Schizochytrium* strain 20888, a strain which has already been determined to contain a PUFA producing PKS system (i.e., SEQ ID Nos:1-32 described above). Fragments of *Thraustochytrium* 23B genomic DNA which are homologous to hybridization probes from PKS PUFA synthesis genes were detected using the Southern blot technique. *Thraustochytrium* 23B genomic DNA was digested with either ClaI or KpnI restriction endonucleases, separated by agarose gel electrophoresis (0.7% agarose, in standard tris-acetate-EDTA buffer), and blotted to a Schleicher & Schuell Nytran Supercharge membrane by capillary transfer. Two digoxigenin labeled hybridization probes were used—one specific for the enoyl-ACP reductase (ER) region of *Schizochytrium* PKS Orf B (nucleotides 5012-5511 of Orf B; SEQ ID NO:3), and the other specific for a conserved region at the beginning of *Schizochytrium* PKS Orf C (nucleotides 76-549 of OrfC; SEQ ID NO:5).

The OrfB-ER probe detected an approximately 13 kb ClaI fragment and an approximately 3.6 kb KpnI fragment in the *Thraustochytrium* 23B genomic DNA. The OrfC probe detected an approximately 7.5 kb ClaI fragment and an approximately 4.6 kb KpnI fragment in the *Thraustochytrium* 23B genomic DNA.

Finally, a recombinant genomic library, consisting of DNA fragments from *Thraustochytrium* 23B genomic DNA inserted into vector lambda FIX II (Stratagene), was screened using digoxigenin labeled probes corresponding to the following segments of *Schizochytrium* 20888 PUFA-PKS genes: nucleotides 7385-7879 of Orf A (SEQ ID NO:1), nucleotides 5012-5511 of Orf B (SEQ ID NO:3), and nucleotides 76-549 of Orf C (SEQ ID NO:5). Each of these probes detected positive plaques from the *Thraustochytrium* 23B library, indicating extensive homology between the *Schizochytrium* PUFA-PKS genes and the genes of *Thraustochytrium* 23B.

These results demonstrate that *Thraustochytrium* 23B genomic DNA contains sequences that are homologous to PKS genes from *Schizochytrium* 20888.

Example 2

The following example demonstrates that *Schizochytrium* Orfs A, B and C encode a functional DHA/DPA synthesis enzyme via functional expression in *E. coli*.

General Preparation of *E. coli* Transformants

The three genes encoding the *Schizochytrium* PUFA PKS system that produces DHA and DPA in *Schizochytrium* (Orfs A, B & C; SEQ ID NO:1, SEQ ID NO:3 and SEQ ID NO:5, respectively) were cloned into a single *E. coli* expression vector (derived from pET21c (Novagen)). The genes are transcribed as a single message (by the T7 RNA-polymerase), and a ribosome-binding site cloned in front of each of the genes initiates translation. Modification of the Orf B coding sequence was needed to obtain production of a full-length Orf B protein in *E. coli* (see below). An accessory gene, encoding a PPTase (see below) was cloned into a second plasmid (derived from pACYC184, New England Biolabs).

OrfB

The Orf B gene is predicted to encode a protein with a mass of ~224 kDa. Initial attempts at expression of the gene in *E. coli* resulted in accumulation of a protein with an apparent molecular mass of ~165 kDa (as judged by comparison to proteins of known mass during SDS-PAGE). Examination of the Orf B nucleotide sequence revealed a region containing 15 sequential serine codons—all of them being the TCT codon. The genetic code contains 6 different serine codons, and three of these are used frequently in *E. coli*. The present inventors used four overlapping oligonucleotides in combination with a polymerase chain reaction protocol to resynthesize a small portion of the Orf B gene (a ~195 base pair, BspHI to SacII restriction enzyme fragment) that contained the serine codon repeat region. In the synthetic Orf B fragment, a random mixture of the 3 serine codons commonly used by *E. coli* was used, and some other potentially problematic codons were changed as well (i.e., other codons rarely used by *E. coli*). The BspHI to SacII fragment present in the original Orf B was replaced by the resynthesized fragment (to yield Orf B*) and the modified gene was cloned into the relevant expression vectors. The modified OrfB* still encodes the amino acid sequence of SEQ ID NO:4. Expression of the modified OrfB* clone in *E. coli* resulted in the appearance of a ~224 kDa protein, indicating that the full-length product of OrfB was produced. The sequence of the resynthesized Orf B* BspHI to SacII fragment is shown in SEQ ID NO:80. Referring to SEQ ID NO:80, the nucleotide sequence of the resynthesized BspHI to SacII region of Orf B is shown. The BspHI restriction site and the SacII restriction site are identified. The BspHI site starts at nucleotide 4415 of the Orf B CDS (SEQ ID NO:3) (note: there are a total of three BspHI sites in the Orf B CDS, while the SacII site is unique). The sequence of the unmodified Orf B CDS is given in GenBank Accession number AF378328 and in SEQ ID NO:3.

PPTase

The ACP domains of the Orf A protein (SEQ ID NO:2 in *Schizochytrium*) must be activated by addition of phosphopantetheine group in order to function. The enzymes that catalyze this general type of reaction are called phosphopantetheine transferases (PPTases). *E. coli* contains two endogenous PPTases, but it was anticipated that they would not recognize the Orf A ACP domains from *Schizochytrium*. This was confirmed by expressing Orfs A, B* (see above) and C in *E. coli* without an additional PPTase. In this transformant, no DHA production was detected. The inventors tested two heterologous PPTases in the *E. coli* PUFA PKS expression system: (1) sfp (derived from *Bacillus subtilis*) and (2) Het I (from the cyanobacterium *Nostoc* strain 7120).

The sfp PPTase has been well characterized and is widely used due to its ability to recognize a broad range of substrates. Based on published sequence information (Nakana, et al., 1992, *Molecular and General Genetics* 232: 313-321), an expression vector for sfp was built by cloning the coding region, along with defined up- and downstream flanking DNA sequences, into a pACYC-184 cloning vector. The oligonucleotides:

```
                          (forward; SEQ ID NO:73)
CGGGGTACCCGGGAGCCGCCTTGGCTTTGT;
and
                          (reverse; SEQ ID NO:74)
AAACTGCAGCCCGGGTCCAGCTGGCAGGCACCCTG,
``` were used to amplify the region of interest from genomic *B. subtilus* DNA. Convenient restriction enzyme sites were included in the oligonucleotides to facilitate cloning in an intermediate, high copy number vector and finally into the EcoRV site of pACYC184 to create the plasmid: pBR301. Examination of extracts of *E. coli* transformed with this plasmid revealed the presence of a novel protein with the mobility expected for sfp. Co-expression of the sfp construct in cells expressing the Orf A, B*, C proteins, under certain conditions, resulted in DHA production. This experiment demonstrated that sfp was able to activate the *Schizochytrium* Orf A ACP domains. In addition, the regulatory elements associated with the sfp gene were used to create an expression cassette into which other genes could be inserted. Specifically, the sfp coding region (along with three nucleotides immediately upstream of the ATG) in pBR301 was replaced with a 53 base pair section of DNA designed so that it contains several unique (for this construct) restriction enzyme sites. The initial restriction enzyme site in this region is NdeI (CATATG; SEQ ID NO:79). The ATG sequence embedded in this site is utilized as the initiation methionine codon for introduced genes. The additional restriction sites (BglLL, NotI, SmaI, PmeII, HindIII, SpeI and XhoI) were included to facilitate the cloning process. The functionality of this expression vector cassette was tested by using PCR to generate a version of sfp with a NdeI site at the 5' end and an XhoI site at the 3' end. This fragment was cloned into the expression cassette and transferred into *E. coli* along with the Orf A, B* and C expression vector. Under appropriate conditions, these cells accumulated DHA, demonstrating that a functional sfp had been produced.

To the present inventors' knowledge, Het I has not been tested previously in a heterologous situation. Het I is present in a cluster of genes in *Nostoc* known to be responsible for the synthesis of long chain hydroxy-fatty acids that are a component of a glyco-lipid layer present in heterocysts of that organism. The present inventors, without being bound by theory, believe that Het I activates the ACP domains of a protein, Hgl E, present in that cluster. The two ACP domains of Hgl E have a high degree of sequence homology to the ACP domains found in *Schizochytrium* Orf A. The endogenous start codon of Het I has not been identified (there is no methionine present in the putative protein). There are several potential alternative start codons (e.g., TTG and ATT) near the 5' end of the open reading frame. The sequence of the region of *Nostoc* DNA encoding the HetI gene is shown in SEQ ID NO:81. SEQ ID NO:82 represents the amino acid sequence encoded by SEQ ID NO:81. Referring to SEQ ID NO:81, limit to the upstream coding region indicated by the inframe nonsense triplet (TAA) at positions 1-3 of SEQ ID NO: 81 and ends with the stop codon (TGA) at positions 715-717 of SEQ ID NO:81. No methionine codons (ATG) are present in the sequence. Potential alternative initiation codons are: 3 TTG codons (positions 4-6, 7-9 and 49-51 of SEQ ID NO:81), ATT (positions 76-78 of SEQ ID NO:81) and GTG (positions 235-237 of SEQ ID NO:81). A Het I expression construct was made by using PCR to replace the furthest 5' potential alternative start codon (TTG) with a methionine codon (ATG, as part of the above described NdeI restriction enzyme recognition site), and introducing an XhoI site at the 3' end of the coding sequence. The modified HetI coding sequence was then inserted into the NdeI and XhoI sites of the pACYC184 vector construct containing the sfp regulatory elements. Expression of this Het I construct in *E. coli* resulted in the appearance of a new protein of the size expected from the sequence data. Co-expression of Het I with *Schizochytrium* Orfs A, B*, C in *E. coli* under several conditions resulted in the accumulation of DHA and DPA in those cells. In all of the experiments in which sfp and Het I were compared, more DHA and DPA accumulated in the cells containing the Het I construct than in cells containing the sfp construct.

Production of DHA and DPA in *E. coli* Transformants

The two plasmids encoding: (1) the *Schizochytrium* PUFA PKS genes (Orfs A, B* and C) and (2) the PPTase (from sfp or from Het I) were transformed into *E. coli* strain BL21 which contains an inducible T7 RNA polymerase gene. Synthesis of the *Schizochytrium* proteins was induced by addition of IPTG to the medium, while PPTase expression was controlled by a separate regulatory element (see above). Cells were grown under various defined conditions and using either of the two heterologous PPTase genes. The cells were harvested and the fatty acids were converted to methyl-esters (FAME) and analyzed using gas-liquid chromatography.

Under several conditions, DHA and DPA were detected in *E. coli* cells expressing the *Schizochytrium* PUFA PKS genes, plus either of the two heterologous PPTases. No DHA or DPA was detected in FAMEs prepared from control cells (i.e., cells transformed with a plasmid lacking one of the Orfs). The ratio of DHA to DPA observed in *E. coli* approximates that of the endogenous DHA and DPA production observed in *Schizochytrium*. The highest level of PUFA (DHA plus DPA), representing ~17% of the total FAME, was found in cells grown at 32° C. in 765 medium (recipe available from the American Type Culture Collection) supplemented with 10% (by weight) glycerol. Note that PUFA accumulation was also observed when cells were grown in Luria Broth supplemented with 5 or 10% glycerol, and when grown at 20° C. Selection for the presence of the respective plasmids was maintained by inclusion of the appropriate antibiotics during the growth and IPTG (to a final concentration of 0.5 mM) was used to induce expression of Orfs A, B* and C.

FIG. 4 shows an example chromatogram from gas-liquid chromatographic analysis of FAMEs derived from control cells and from cells expressing the *Schizochytrium* PUFA PKS genes plus a PPTase (in this case Het I). Identity of the labeled FAMEs has been confirmed using mass spectroscopy.

Example 3

The following example shows demonstrates that genes encoding the *Schizochytrium* PUFA PKS enzyme complex can be selectively inactivated (knocked out), and that it is a lethal phenotype unless the medium is supplemented with polyunsaturated fatty acids.

Homologous recombination has been demonstrated in *Schizochytrium* (see copending U.S. patent application Ser. No. 10/124,807, incorporated herein by reference in its entirety). A plasmid designed to inactivate *Schizochytrium* Orf A (SEQ ID NO:1) was made by inserting a Zeocin™ resistance marker into the Sma I site of a clone containing the Orf A coding sequence. The Zeocin™ resistance marker was obtained from the plasmid pMON50000—expression of the Zeocin™ resistance gene is driven by a *Schizochytrium* derived tubulin promoter element (see U.S. patent application Ser. No. 10/124,807, ibid.). The knock-out construct thus consists of: 5' *Schizochytrium* Orf A coding sequence, the tub-Zeocin™ resistance element and 3' *Schizochytrium* Orf A coding sequence, all cloned into pBluescript II SK (+) vector (Stratagene).

The plasmid was introduced into *Schizochytrium* cells by particle bombardment and transformants were selected on plates containing Zeocin™ and supplemented with polyunsaturated fatty acids (PUFA) (see Example 4). Colonies that grew on the Zeocin™ plus PUFA plates were tested for ability to grow on plates without the PUFA supplementation and several were found that required the PUFA. These PUFA auxotrophs are putative Orf A knockouts. Northern blot analysis of RNA extracted from several of these mutants confirmed that a full-length Orf A message was not produced in these mutants.

These experiments demonstrate that a *Schizochytrium* gene (e.g., Orf A) can be inactivated via homologous recombination, that inactivation of Orf A results in a lethal phenotype, and that those mutants can be rescued by supplementation of the media with PUFA.

Similar sets of experiments directed to the inactivation of *Schizochytrium* Orf B (SEQ ID NO:3) and Orf C (SEQ ID NO:5) have yielded similar results. That is, Orf B and Orf C can be individually inactivated by homologous recombination and those cells require PUFA supplementation for growth.

Example 4

The following example shows that PUFA auxotrophs can be maintained on medium supplemented with EPA, demonstrating that EPA can substitute for DHA in *Schizochytrium*.

As indicated in Example 3, *Schizochytrium* cells in which the PUFA PKS complex has been inactivated required supplementation with PUFA to survive. Aside from demonstrating that *Schizochytrium* is dependent on the products of this system for growth, this experimental system permits the testing of various fatty acids for their ability to rescue the mutants. It was discovered that the mutant cells (in which any of the three genes have been inactivated) grew as well on media supplemented with EPA as they did on media supplemented with DHA. This result indicates that, if the endogenous PUFA PKS complex which produces DHA were replaced with one whose product was EPA, the cells would be viable. Additionally, these mutant cells could be rescued by supplementation with either ARA or GLA, demonstrating the feasibility of producing genetically modified *Schizochytrium* that produce these products. It is noted that a preferred method for supplementation with PUFAs involves combining the free fatty acids with partially methylated beta-cyclodextrin prior to addition of the PUFAs to the medium.

Example 5

The following example shows that inactivated PUFA genes can be replaced at the same site with active forms of the genes in order to restore PUFA synthesis.

Double homologous recombination at the acetolactate synthase gene site has been demonstrated in *Schizochytrium* (see U.S. patent application Ser. No. 10/124,807, supra). The present inventors tested this concept for replacement of the *Schizochytrium* PUFA PKS genes by transformation of a *Schizochytrium* Orf A knockout strain (described in Example 2) with a full-length *Schizochytrium* Orf A genomic clone. The transformants were selected by their ability to grow on media without supplemental PUFAs. These PUFA prototrophs were then tested for resistance to Zeocin™ and several were found that were sensitive to the antibiotic. These results indicate that the introduced *Schizochytrium* Orf A has replaced the Zeocin™ resistance gene in the knockout strain via double homologous recombination. This experiment demonstrates the proof of concept for gene replacement within the PUFA PKS genes. Similar experiments for *Schizochytrium* Orf B and Orf C knock-outs have given identical results.

Example 6

This example shows that all or some portions of the *Thraustochytrium* 23B PUFA PKS genes can function in *Schizochytrium*.

As described in U.S. patent application Ser. No. 10/124,800 (supra), the DHA-producing protist *Thraustochytrium* 23B (Th. 23B) has been shown to contain orfA, orfB, and orfC homologs. Complete genomic clones of the three Th. 23B genes were used to transform the *Schizochytrium* strain containing the cognate orf "knock-out". Direct selection for complemented transformants was carried out in the absence of PUFA supplementation. By this method, it was shown that the Th. 23B orfA and orfC genes could complement the *Schizochytrium* orfA and orfC knock-out strains, respectively, to PUFA prototrophy. Complemented transformants were found that either retained or lost Zeocin™ resistance (the marker inserted into the *Schizochytrium* genes thereby defining the knock-outs). The Zeocin™-resistant complemented transformants are likely to have arisen by a single cross-over integration of the entire *Thraustochytrium* gene into the *Schizochytrium* genome outside of the respective orf region. This result suggests that the entire *Thraustochytrium* gene is functioning in *Schizochytrium*. The Zeocin™-sensitive complemented transformants are likely to have arisen by double cross-over events in which portions (or conceivably all) of the *Thraustochytrium* genes functionally replaced the cognate regions of the *Schizochytrium* genes that had contained the disruptive Zeocin™ resistance marker. This result suggests that a fraction of the *Thraustochytrium* gene is functioning in *Schizochytrium*.

Example 7

The following example shows that certain EPA-producing bacteria contain PUFA PKS-like genes that appear to be suitable for modification of *Schizochytrium*.

Two EPA-producing marine bacterial strains of the genus *Shewanella* have been shown to grow at temperatures typical of *Schizochytrium* fermentations and to possess PUFA PKS-like genes. *Shewanella olleyana* (Australian Collection of Antarctic Microorganisms (ACAM) strain number 644; Skerratt et al., *Int. J. Syst. Evol. Microbiol.* 52, 2101 (2002)) produces EPA and grows up to 30° C. *Shewanella japonica* (American Type Culture Collection (ATCC) strain number BAA-316; Ivanova et al., *Int. J. Syst. Evol. Microbiol.* 51, 1027 (2001)) produces EPA and grows up to 35° C.

To identify and isolate the PUFA-PKS genes from these bacterial strains, degenerate PCR primer pairs for the KS-MAT region of bacterial orf5/pfaA genes and the DH-DH region of bacterial orf7/pfaC genes were designed based on published gene sequences for *Shewanella* SCRC-2738, *Shewanella oneidensis* MR-1; *Shewanella* sp. GA-22; *Photobacter profundum*, and *Moritella marina* (see discussion above). Specifically, the primers and PCR conditions were designed as follows:

Primers for the KS/AT region; based on the following published sequences: *Shewanella* sp. SCRC-2738; *Shewanella oneidensis* MR-1; *Photobacter profundum*; *Moritella marina*:

```
prRZ23
GGYATGMTGRTTGGTGAAGG      (forward; SEQ ID NO:69)

prRZ24
TRTTSASRTAYTGYGAACCTTG    (reverse; SEQ ID NO:70)
```

Primers for the DH region; based on the following published sequences: *Shewanella* sp. GA-22; *Shewanella* sp. SCRC-2738; *Photobacter profundum*; *Moritella marina*:

```
prRZ28
ATGKCNGAAGGTTGTGGCCA      (forward; SEQ ID NO:71)

prRZ29
CCWGARATRAAGCCRTTDGGTTG   (reverse; SEQ ID NO:72)
```

The PCR conditions (with bacterial chromosomal DNA as templates) were as follows:
  Reaction Mixture:
  0.2 µM dNTPs
  0.1 µM each primer
  8% DMSO
  250 ng chromosomal DNA
  2.5 U Herculase® DNA polymerase (Stratagene)
  1× Herculase® buffer
  50 µL total volume
  PCR Protocol: (1) 98° C. for 3 min.; (2) 98° C. for 40 sec.; (3) 56° C. for 30 sec.; (4) 72° C. for 90 sec.; (5) Repeat steps 2-4 for 29 cycles; (6) 72° C. for 10 min.; (7) Hold at 6° C.

For both primer pairs, PCR gave distinct products with expected sizes using chromosomal DNA templates from either *Shewanella olleyana* or *Shewanella japonica*. The four respective PCR products were cloned into pCR-BLUNT II-TOPO (Invitrogen) and insert sequences were determined using the M13 forward and reverse primers. In all cases, the DNA sequences thus obtained were highly homologous to known bacterial PUFA PKS gene regions.

The DNA sequences obtained from the bacterial PCR products were compared with known sequences and with PUFA PKS genes from *Schizochytrium* ATCC 20888 in a standard Blastx search (BLAST parameters: Low Complexity filter: On; Matrix: BLOSUM62; Word Size: 3; Gap Costs: Existance11, Extension 1 (BLAST described in Altschul, S.

F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety)).

At the amino acid level, the sequences with the greatest degree of homology to the *Shewanella olleyana* ACAM644 ketoacyl synthase/acyl transferase (KS-AT) deduced amino acid sequence encoded by SEQ ID NO:76 were: *Photobacter profundum* pfaA (identity=70%; positives=81%); *Shewanella oneidensis* MR-1 "multi-domain β-ketoacyl synthase" (identity=66%; positives=77%); and Moritella marina ORF8 (identity=56%; positives=71%). The *Schizochytrium* sp. ATCC20888 orfA was 41% identical and 56% positive to the deduced amino acid sequence encoded by SEQ ID NO:76.

At the amino acid level, the sequences with the greatest degree of homology to the *Shewanella japonica* ATCC BAA-316 ketoacyl synthase/acyl transferase (KS-AT) deduced amino acid sequence encoded by SEQ ID NO:78 were: *Shewanella oneidensis* MR-1 "multi-domain β-ketoacyl synthase" (identity=67%; positives=79%); *Shewanella* sp. SCRC-2738 orf5 (identity=69%; positives=77%); and Moritella marina ORF8 (identity=56%; positives=70%). The *Schizochytrium* sp. ATCC20888 orfA was 41% identical and 55% positive to the deduced amino acid sequence encoded by SEQ ID NO:78.

At the amino acid level, the sequences with the greatest degree of homology to the *Shewanella olleyana* ACAM644 dehydrogenase (DH) deduced amino acid sequence encoded by SEQ ID NO:75 were: *Shewanella* sp. SCRC-2738 orf7 (identity=77%; positives=86%); *Photobacter profundum* pfaC (identity=72%; positives 81%); and *Shewanella oneidensis* MR-1 "multi-domain β-ketoacyl synthase" (identity 75%; positives=83%). The *Schizochytrium* sp. ATCC20888 orfC was 26% identical and 42% positive to the deduced amino acid sequence encoded by SEQ ID NO:75.

At the amino acid level, the sequences with the greatest degree of homology to the *Shewanella japonica* ATCC BAA-316 dehydrogenase (DH) deduced amino acid sequence encoded by SEQ ID NO:77 were: *Shewanella* sp. SCRC-2738 orf7 (identity=77%; positives=86%); *Photobacter profundum* pfaC (identity=73%; positives=83%) and *Shewanella oneidensis* MR-1 "multi-domain β-ketoacyl synthase" (identity=74%; positives=81%). The *Schizochytrium* sp. ATCC20888 orfC was 27% identical and 42% positive to the deduced amino acid sequence encoded by SEQ ID NO:77.

It is expected that the PUFA PKS gene sets from these two *Shewanella* strains will provide beneficial sources of whole genes or individual domains for the modification of *Schizochytrium* PUFA production. PUFA PKS genes and the proteins and domains encoded thereby from either of *Shewanella olleyana* or *Shewanella japonica* are explicitly encompassed by the present invention.

Example 8

This example demonstrates how the bacterial PUFA PKS gene fragments described in Example 7 can be used to modify PUFA production in *Schizochytrium*.

All presently-known examples of PUFA PKS genes from bacteria exist as four closely linked genes that contain the same domains as in the three-gene *Schizochytrium* set. It is anticipated that the PUFA PKS genes from *Shewanella olleyana* and *Shewanella japonica* will likewise be found in this tightly clustered arrangement. The homologous regions identified in Example 7 are used to isolate the PUFA PKS gene clusters from clone banks of *Sh. olleyana* and *Sh. japonica* DNAs. Clone banks can be constructed in bacteriophage lambda vectors, cosmid vectors, bacterial artificial chromosome ("BAC") vectors, or by other methods known in the art. Desired clones containing bacterial PUFA PKS genes can be identified by colony or plaque hybridization (as described in Example 1) using probes generated by PCR of the partial gene sequences of Example 7 employing primers designed from these sequences. The complete DNA sequence of the new bacterial PUFA PKS gene sets are then used to design vectors for transformation of *Schizochytrium* strains defective in the endogenous PUFA PKS genes (e.g., see Examples 3, 5, and 6). Whole bacterial genes (coding sequences) may be used to replace whole *Schizochytrium* genes (coding sequences), thus utilizing the *Schizochytrium* gene expression regions, and the fourth bacterial gene may be targeted to a different location within the genome. Alternatively, individual bacterial PUFA PKS functional domains may be "swapped" or exchanged with the analogous *Schizochytrium* domains by similar techniques of homologous recombination. It is understood that the sequence of the bacterial PUFA PKS genes or domains may have to be modified to accommodate details of *Schizochytrium* codon usage, but this is within the ability of those of skill in the art.

Each publication cited or discussed herein is incorporated herein by reference in its entirety.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule comprising a nucleic acid sequence encoding an amino acid sequence that is at least 95% identical to SEQ ID NO:64, wherein said amino acid sequence has FabA-like β-hydroxy acyl-ACP dehydrase activity.

2. The isolated nucleic acid molecule of claim 1, consisting of a nucleic acid sequence encoding an amino acid sequence that is at least 95% identical to SEQ ID NO:64, wherein said amino acid sequence has FabA-like β-hydroxy acyl-ACP dehydrase activity.

3. The isolated nucleic acid molecule of claim 1, comprising a nucleic acid sequence encoding an amino acid sequence that is at least 96% identical to SEQ ID NO:64, wherein said amino acid sequence has FabA-like β-hydroxy acyl-ACP dehydrase activity.

4. The isolated nucleic acid molecule of claim 1, consisting of a nucleic acid sequence encoding an amino acid sequence that is at least 96% identical to SEQ ID NO:64, wherein said amino acid sequence has FabA-like β-hydroxy acyl-ACP dehydrase activity.

5. The isolated nucleic acid molecule of claim 1, comprising a nucleic acid sequence encoding an amino acid sequence that is at least 97% identical to SEQ ID NO:64, wherein said amino acid sequence has FabA-like β-hydroxy acyl-ACP dehydrase activity.

6. The isolated nucleic acid molecule of claim 1, consisting of a nucleic acid sequence encoding an amino acid sequence that is at least 97% identical to SEQ ID NO:64, wherein said amino acid sequence has FabA-like β-hydroxy acyl-ACP dehydrase activity.

7. The isolated nucleic acid molecule of claim 1, comprising a nucleic acid sequence encoding an amino acid sequence that is at least 98% identical to SEQ ID NO:64, wherein said amino acid sequence has FabA-like β-hydroxy acyl-ACP dehydrase activity.

8. The isolated nucleic acid molecule of claim 1, consisting of a nucleic acid sequence encoding an amino acid sequence that is at least 98% identical to SEQ ID NO:64, wherein said amino acid sequence has FabA-like β-hydroxy acyl-ACP dehydrase activity.

9. The isolated nucleic acid molecule of claim 1, comprising a nucleic acid sequence encoding an amino acid sequence that is at least 99% identical to SEQ ID NO:64, wherein said amino acid sequence has FabA-like β-hydroxy acyl-ACP dehydrase activity.

10. The isolated nucleic acid molecule of claim 1, consisting of a nucleic acid sequence encoding an amino acid sequence that is at least 99% identical to SEQ ID NO:64, wherein said amino acid sequence has FabA-like β-hydroxy acyl-ACP dehydrase activity.

11. The isolated nucleic acid molecule of claim 1, comprising a nucleic acid sequence encoding the amino acid sequence of SEQ ID NO:64.

12. The isolated nucleic acid molecule of claim 1, consisting of a nucleic acid sequence encoding the amino acid sequence of SEQ ID NO:64.

13. The isolated nucleic acid molecule of claim 1, wherein the nucleic acid molecule comprises SEQ ID NO:63.

14. The isolated nucleic acid molecule of claim 1, wherein the nucleic acid molecule consists of SEQ ID NO:63.

15. A recombinant nucleic acid molecule comprising the nucleic acid molecule of claim 1 and a transcription control sequence.

16. A recombinant plant cell that expresses the nucleic acid molecule of claim 1.

17. A recombinant microbial cell that expresses a recombinant vector comprising the nucleic acid molecule of claim 1 and a transcription control sequence.

18. The recombinant microbial cell of claim 17, wherein the microbial cell is a bacterium.

19. The recombinant microbial cell of claim 17, wherein the microbial cell is a Thraustochytriales microorganism.

20. The recombinant microbial cell of claim 19, wherein the Thraustochytriales microorganism is a *Schizochytrium* or a *Thraustochytrium*.

21. A method to produce at least one polyunsaturated fatty acid (PUFA), comprising culturing under conditions effective to produce the PUFA plant, a plant cell or a microbial cell that expresses a PKS system for production of PUFAs, wherein the plant cell or microbial cell expresses a recombinant vector comprising the nucleic acid molecule of claim 1.

\* \* \* \* \*

UNITED STATES PATENT AND TRADEMARK OFFICE
CERTIFICATE OF CORRECTION

PATENT NO. : 7,645,597 B2  Page 1 of 1
APPLICATION NO. : 11/778608
DATED : January 12, 2010
INVENTOR(S) : James G. Metz et al.

It is certified that error appears in the above-identified patent and that said Letters Patent is hereby corrected as shown below:

In Claim 21, column 408, line 53, delete the first occurence of the word "plant."

Signed and Sealed this

Twenty-third Day of March, 2010

David J. Kappos
*Director of the United States Patent and Trademark Office*

SEQUENCE LISTING

```
<160> NUMBER OF SEQ ID NOS: 82

<210> SEQ ID NO 1
<211> LENGTH: 8730
<212> TYPE: DNA
<213> ORGANISM: Schizochytrium sp.
<220> FEATURE:
<221> NAME/KEY: CDS
<222> LOCATION: (1)..(8730)

<400> SEQUENCE: 1 atg gcg gcc cgt ctg cag gag caa aag gga ggc gag atg gat acc cgc      48
Met Ala Ala Arg Leu Gln Glu Gln Lys Gly Gly Glu Met Asp Thr Arg
```

-continued

| | 1 | | | | 5 | | | | | 10 | | | | | 15 | | |
|---|---|---|---|---|---|---|---|---|---|---|---|---|---|---|---|---|---|

```
att gcc atc atc ggc atg tcg gcc atc ctc ccc tgc ggc acg acc gtg       96
Ile Ala Ile Ile Gly Met Ser Ala Ile Leu Pro Cys Gly Thr Thr Val
         20                  25                  30 cgc gag tcg tgg gag acc atc cgc gcc ggc atc gac tgc ctg tcg gat      144
Arg Glu Ser Trp Glu Thr Ile Arg Ala Gly Ile Asp Cys Leu Ser Asp
     35                  40                  45 ctc ccc gag gac cgc gtc gac gtg acg gcg tac ttt gac ccc gtc aag      192
Leu Pro Glu Asp Arg Val Asp Val Thr Ala Tyr Phe Asp Pro Val Lys
 50                  55                  60 acc acc aag gac aag atc tac tgc aag cgc ggt ggc ttc att ccc gag      240
Thr Thr Lys Asp Lys Ile Tyr Cys Lys Arg Gly Gly Phe Ile Pro Glu
 65                  70                  75                  80 tac gac ttt gac gcc cgc gag ttc gga ctc aac atg ttc cag atg gag      288
Tyr Asp Phe Asp Ala Arg Glu Phe Gly Leu Asn Met Phe Gln Met Glu
                 85                  90                  95 gac tcg gac gca aac cag acc atc tcg ctt ctc aag gtc aag gag gcc      336
Asp Ser Asp Ala Asn Gln Thr Ile Ser Leu Leu Lys Val Lys Glu Ala
             100                 105                 110 ctc cag gac gcc ggc atc gac gcc ctc ggc aag gaa aag aag aac atc      384
Leu Gln Asp Ala Gly Ile Asp Ala Leu Gly Lys Glu Lys Lys Asn Ile
         115                 120                 125 ggc tgc gtg ctc ggc att ggc ggc ggc caa aag tcc agc cac gag ttc      432
Gly Cys Val Leu Gly Ile Gly Gly Gly Gln Lys Ser Ser His Glu Phe
     130                 135                 140 tac tcg cgc ctt aat tat gtt gtc gtg gag aag gtc ctc cgc aag atg      480
Tyr Ser Arg Leu Asn Tyr Val Val Val Glu Lys Val Leu Arg Lys Met
145                 150                 155                 160 ggc atg ccc gag gag gac gtc aag gtc gcc gtc gaa aag tac aag gcc      528
Gly Met Pro Glu Glu Asp Val Lys Val Ala Val Glu Lys Tyr Lys Ala
                 165                 170                 175 aac ttc ccc gag tgg cgc ctc gac tcc ttc cct ggc ttc ctc ggc aac      576
Asn Phe Pro Glu Trp Arg Leu Asp Ser Phe Pro Gly Phe Leu Gly Asn
             180                 185                 190 gtc acc gcc ggt cgc tgc acc aac acc ttc aac ctc gac ggc atg aac      624
Val Thr Ala Gly Arg Cys Thr Asn Thr Phe Asn Leu Asp Gly Met Asn
         195                 200                 205 tgc gtt gtc gac gcc gca tgc gcc tcg tcc ctc atc gcc gtc aag gtc      672
Cys Val Val Asp Ala Ala Cys Ala Ser Ser Leu Ile Ala Val Lys Val
     210                 215                 220 gcc atc gac gag ctg ctc tac ggt gac tgc gac atg atg gtc acc ggt      720
Ala Ile Asp Glu Leu Leu Tyr Gly Asp Cys Asp Met Met Val Thr Gly
225                 230                 235                 240 gcc acc tgc acg gat aac tcc atc ggc atg tac atg gcc ttc tcc aag      768
Ala Thr Cys Thr Asp Asn Ser Ile Gly Met Tyr Met Ala Phe Ser Lys
                 245                 250                 255 acc ccc gtg ttc tcc acg gac ccc agc gtg cgc gcc tac gac gaa aag      816
Thr Pro Val Phe Ser Thr Asp Pro Ser Val Arg Ala Tyr Asp Glu Lys
             260                 265                 270 aca aag ggc atg ctc atc ggc gag ggc tcc gcc atg ctc gtc ctc aag      864
Thr Lys Gly Met Leu Ile Gly Glu Gly Ser Ala Met Leu Val Leu Lys
         275                 280                 285 cgc tac gcc gac gcc gtc cgc gac ggc gat gag atc cac gct gtt att      912
Arg Tyr Ala Asp Ala Val Arg Asp Gly Asp Glu Ile His Ala Val Ile
     290                 295                 300 cgc ggc tgc gcc tcc tcc agt gat ggc aag gcc gcc ggc atc tac acg      960
Arg Gly Cys Ala Ser Ser Ser Asp Gly Lys Ala Ala Gly Ile Tyr Thr
305                 310                 315                 320 ccc acc att tcg ggc cag gag gag gcc ctc cgc cgc gcc tac aac cgc     1008
```

```
                Pro Thr Ile Ser Gly Gln Glu Glu Ala Leu Arg Arg Ala Tyr Asn Arg
                                325                 330                 335 gcc tgt gtc gac ccg gcc acc gtc act ctc gtc gag ggt cac ggc acc            1056
Ala Cys Val Asp Pro Ala Thr Val Thr Leu Val Glu Gly His Gly Thr
                340                 345                 350 ggt act ccc gtt ggc gac cgc atc gag ctc acc gcc ttg cgc aac ctc            1104
Gly Thr Pro Val Gly Asp Arg Ile Glu Leu Thr Ala Leu Arg Asn Leu
                355                 360                 365 ttt gac aag gcc tac ggc gag ggc aac acc gaa aag gtc gct gtg ggc            1152
Phe Asp Lys Ala Tyr Gly Glu Gly Asn Thr Glu Lys Val Ala Val Gly
        370                 375                 380 agc atc aag tcc agc atc ggc cat ctc aag gcc gtc gcc ggt ctc gcc            1200
Ser Ile Lys Ser Ser Ile Gly His Leu Lys Ala Val Ala Gly Leu Ala
385                 390                 395                 400 ggt atg atc aag gtc atc atg gcg ctc aag cac aag act ctc ccg ggc            1248
Gly Met Ile Lys Val Ile Met Ala Leu Lys His Lys Thr Leu Pro Gly
                405                 410                 415 acc atc aac gtc gac aac cca ccc aac ctc tac gac aac acg ccc atc            1296
Thr Ile Asn Val Asp Asn Pro Pro Asn Leu Tyr Asp Asn Thr Pro Ile
                420                 425                 430 aac gag tcc tcg ctc tac att aac acc atg aac cgc ccc tgg ttc ccg            1344
Asn Glu Ser Ser Leu Tyr Ile Asn Thr Met Asn Arg Pro Trp Phe Pro
                435                 440                 445 ccc cct ggt gtg ccc cgc cgc gcc ggc att tcg agc ttt ggc ttt ggt            1392
Pro Pro Gly Val Pro Arg Arg Ala Gly Ile Ser Ser Phe Gly Phe Gly
        450                 455                 460 ggc gcc aac tac cac gcc gtc ctc gag gag gcc gag ccc gag cac acg            1440
Gly Ala Asn Tyr His Ala Val Leu Glu Glu Ala Glu Pro Glu His Thr
465                 470                 475                 480 acc gcg tac cgc ctc aac aag cgc ccg cag ccc gtg ctc atg atg gcc            1488
Thr Ala Tyr Arg Leu Asn Lys Arg Pro Gln Pro Val Leu Met Met Ala
                485                 490                 495 gcc acg ccc gcg gcc ctc cag tcg ctc tgc gag gcc cag ctc aag gag            1536
Ala Thr Pro Ala Ala Leu Gln Ser Leu Cys Glu Ala Gln Leu Lys Glu
                500                 505                 510 ttc gag gcc gcc atc aag gag aac gag acc gtc aag aac acc gcc tac            1584
Phe Glu Ala Ala Ile Lys Glu Asn Glu Thr Val Lys Asn Thr Ala Tyr
                515                 520                 525 atc aag tgc gtc aag ttc ggc gag cag ttc aaa ttc cct ggc tcc atc            1632
Ile Lys Cys Val Lys Phe Gly Glu Gln Phe Lys Phe Pro Gly Ser Ile
        530                 535                 540 ccg gcc aca aac gcg cgc ctc ggc ttc ctc gtc aag gat gct gag gat            1680
Pro Ala Thr Asn Ala Arg Leu Gly Phe Leu Val Lys Asp Ala Glu Asp
545                 550                 555                 560 gcc tgc tcc acc ctc cgt gcc atc tgc gcc caa ttc gcc aag gat gtc            1728
Ala Cys Ser Thr Leu Arg Ala Ile Cys Ala Gln Phe Ala Lys Asp Val
                565                 570                 575 acc aag gag gcc tgg cgc ctc ccc cgc gag ggc gtc agc ttc cgc gcc            1776
Thr Lys Glu Ala Trp Arg Leu Pro Arg Glu Gly Val Ser Phe Arg Ala
                580                 585                 590 aag ggc atc gcc acc aac ggc gct gtc gcc gcg ctc ttc tcc ggc cag            1824
Lys Gly Ile Ala Thr Asn Gly Ala Val Ala Ala Leu Phe Ser Gly Gln
                595                 600                 605 ggc gcg cag tac acg cac atg ttt agc gag gtg gcc atg aac tgg ccc            1872
Gly Ala Gln Tyr Thr His Met Phe Ser Glu Val Ala Met Asn Trp Pro
        610                 615                 620 cag ttc cgc cag agc att gcc gcc atg gac gcc gcc cag tcc aag gtc            1920
Gln Phe Arg Gln Ser Ile Ala Ala Met Asp Ala Ala Gln Ser Lys Val
625                 630                 635                 640
```

```
                                            -continued gct gga agc gac aag gac ttt gag cgc gtc tcc cag gtc ctc tac ccg    1968
Ala Gly Ser Asp Lys Asp Phe Glu Arg Val Ser Gln Val Leu Tyr Pro
                645                 650                 655 cgc aag ccg tac gag cgt gag ccc gag cag aac ccc aag aag atc tcc    2016
Arg Lys Pro Tyr Glu Arg Glu Pro Glu Gln Asn Pro Lys Lys Ile Ser
            660                 665                 670 ctc acc gcc tac tcg cag ccc tcg acc ctg gcc tgc gct ctc ggt gcc    2064
Leu Thr Ala Tyr Ser Gln Pro Ser Thr Leu Ala Cys Ala Leu Gly Ala
        675                 680                 685 ttt gag atc ttc aag gag gcc ggc ttc acc ccg gac ttt gcc gcc ggc    2112
Phe Glu Ile Phe Lys Glu Ala Gly Phe Thr Pro Asp Phe Ala Ala Gly
    690                 695                 700 cat tcg ctc ggt gag ttc gcc gcc ctc tac gcc gcg ggc tgc gtc gac    2160
His Ser Leu Gly Glu Phe Ala Ala Leu Tyr Ala Ala Gly Cys Val Asp
705                 710                 715                 720 cgc gac gag ctc ttt gag ctt gtc tgc cgc cgc gcc cgc atc atg ggc    2208
Arg Asp Glu Leu Phe Glu Leu Val Cys Arg Arg Ala Arg Ile Met Gly
                725                 730                 735 ggc aag gac gca ccg gcc acc ccc aag gga tgc atg gcc gcc gtc att    2256
Gly Lys Asp Ala Pro Ala Thr Pro Lys Gly Cys Met Ala Ala Val Ile
            740                 745                 750 ggc ccc aac gcc gag aac atc aag gtc cag gcc gcc aac gtc tgg ctc    2304
Gly Pro Asn Ala Glu Asn Ile Lys Val Gln Ala Ala Asn Val Trp Leu
        755                 760                 765 ggc aac tcc aac tcg cct tcg cag acc gtc atc acc ggc tcc gtc gaa    2352
Gly Asn Ser Asn Ser Pro Ser Gln Thr Val Ile Thr Gly Ser Val Glu
    770                 775                 780 ggt atc cag gcc gag agc gcc cgc ctc cag aag gag ggc ttc cgc gtc    2400
Gly Ile Gln Ala Glu Ser Ala Arg Leu Gln Lys Glu Gly Phe Arg Val
785                 790                 795                 800 gtg cct ctt gcc tgc gag agc gcc ttc cac tcg ccc cag atg gag aac    2448
Val Pro Leu Ala Cys Glu Ser Ala Phe His Ser Pro Gln Met Glu Asn
                805                 810                 815 gcc tcg tcg gcc ttc aag gac gtc atc tcc aag gtc tcc ttc cgc acc    2496
Ala Ser Ser Ala Phe Lys Asp Val Ile Ser Lys Val Ser Phe Arg Thr
            820                 825                 830 ccc aag gcc gag acc aag ctc ttc agc aac gtc tct ggc gag acc tac    2544
Pro Lys Ala Glu Thr Lys Leu Phe Ser Asn Val Ser Gly Glu Thr Tyr
        835                 840                 845 ccc acg gac gcc cgc gag atg ctt acg cag cac atg acc agc agc gtc    2592
Pro Thr Asp Ala Arg Glu Met Leu Thr Gln His Met Thr Ser Ser Val
    850                 855                 860 aag ttc ctc acc cag gtc cgc aac atg cac cag gcc ggt gcg cgc atc    2640
Lys Phe Leu Thr Gln Val Arg Asn Met His Gln Ala Gly Ala Arg Ile
865                 870                 875                 880 ttt gtc gag ttc gga ccc aag cag gtg ctc tcc aag ctt gtc tcc gag    2688
Phe Val Glu Phe Gly Pro Lys Gln Val Leu Ser Lys Leu Val Ser Glu
                885                 890                 895 acc ctc aag gat gac ccc tcg gtt gtc acc gtc tct gtc aac ccg gcc    2736
Thr Leu Lys Asp Asp Pro Ser Val Val Thr Val Ser Val Asn Pro Ala
            900                 905                 910 tcg ggc acg gat tcg gac atc cag ctc cgc gac gcg gcc gtc cag ctc    2784
Ser Gly Thr Asp Ser Asp Ile Gln Leu Arg Asp Ala Ala Val Gln Leu
        915                 920                 925 gtt gtc gct ggc gtc aac ctt cag ggc ttt gac aag tgg gac gcc ccc    2832
Val Val Ala Gly Val Asn Leu Gln Gly Phe Asp Lys Trp Asp Ala Pro
    930                 935                 940 gat gcc acc cgc atg cag gcc atc aag aag aag cgc act acc ctc cgc    2880
Asp Ala Thr Arg Met Gln Ala Ile Lys Lys Lys Arg Thr Thr Leu Arg
945                 950                 955                 960
```

```
ctt tcg gcc gcc acc tac gtc tcg gac aag acc aag aag gtc cgc gac      2928
Leu Ser Ala Ala Thr Tyr Val Ser Asp Lys Thr Lys Lys Val Arg Asp
            965                 970                 975 gcc gcc atg aac gat ggc cgc tgc gtc acc tac ctc aag ggc gcc gca      2976
Ala Ala Met Asn Asp Gly Arg Cys Val Thr Tyr Leu Lys Gly Ala Ala
        980                 985                 990 ccg ctc atc aag gcc ccg gag ccc gtt gtc gac gag gcc gcc aag cgc      3024
Pro Leu Ile Lys Ala Pro Glu Pro Val Val Asp Glu Ala Ala Lys Arg
            995                 1000                1005 gag gcc gag cgt ctc cag aag gag ctt cag gat gcc cag cgc cag          3069
Glu Ala Glu Arg Leu Gln Lys Glu Leu Gln Asp Ala Gln Arg Gln
        1010                1015                1020 ctc gac gac gcc aag cgc gcc gcc gcc gag gcc aac tcc aag ctc          3114
Leu Asp Asp Ala Lys Arg Ala Ala Ala Glu Ala Asn Ser Lys Leu
        1025                1030                1035 gcc gct gcc aag gag gag gcc aag acc gcc gct gct tcg gcc aag          3159
Ala Ala Ala Lys Glu Glu Ala Lys Thr Ala Ala Ala Ser Ala Lys
        1040                1045                1050 ccc gca gtt gac act gct gtt gtc gaa aag cat cgt gcc atc ctc          3204
Pro Ala Val Asp Thr Ala Val Val Glu Lys His Arg Ala Ile Leu
        1055                1060                1065 aag tcc atg ctc gcg gag ctc gat ggc tac gga tcg gtc gac gct          3249
Lys Ser Met Leu Ala Glu Leu Asp Gly Tyr Gly Ser Val Asp Ala
        1070                1075                1080 tct tcc ctc cag cag cag cag cag cag cag acg gcc ccc gcc ccg          3294
Ser Ser Leu Gln Gln Gln Gln Gln Gln Gln Thr Ala Pro Ala Pro
        1085                1090                1095 gtc aag gct gct gcg cct gcc gcc ccc gtt gcc tcg gcc cct gcc          3339
Val Lys Ala Ala Ala Pro Ala Ala Pro Val Ala Ser Ala Pro Ala
        1100                1105                1110 ccg gct gtc tcg aac gag ctt ctt gag aag gcc gag act gtc gtc          3384
Pro Ala Val Ser Asn Glu Leu Leu Glu Lys Ala Glu Thr Val Val
        1115                1120                1125 atg gag gtc ctc gcc gcc aag acc ggc tac gag acc gac atg atc          3429
Met Glu Val Leu Ala Ala Lys Thr Gly Tyr Glu Thr Asp Met Ile
        1130                1135                1140 gag gct gac atg gag ctc gag acc gag ctc ggc att gac tcc atc          3474
Glu Ala Asp Met Glu Leu Glu Thr Glu Leu Gly Ile Asp Ser Ile
        1145                1150                1155 aag cgt gtc gag atc ctc tcc gag gtc cag gcc atg ctc aat gtc          3519
Lys Arg Val Glu Ile Leu Ser Glu Val Gln Ala Met Leu Asn Val
        1160                1165                1170 gag gcc aag gat gtc gat gcc ctc agc cgc act cgc act gtt ggt          3564
Glu Ala Lys Asp Val Asp Ala Leu Ser Arg Thr Arg Thr Val Gly
        1175                1180                1185 gag gtt gtc aac gcc atg aag gcc gag atc gct ggc agc tct gcc          3609
Glu Val Val Asn Ala Met Lys Ala Glu Ile Ala Gly Ser Ser Ala
        1190                1195                1200 ccg gcg cct gct gcc gct gct ccg gct ccg gcc aag gct gcc cct          3654
Pro Ala Pro Ala Ala Ala Pro Ala Pro Ala Lys Ala Ala Pro
        1205                1210                1215 gcc gcc gct gcg cct gct gtc tcg aac gag ctt ctc gag aag gcc          3699
Ala Ala Ala Ala Pro Ala Val Ser Asn Glu Leu Leu Glu Lys Ala
        1220                1225                1230 gag acc gtc gtc atg gag gtc ctc gcc gcc aag act ggc tac gag          3744
Glu Thr Val Val Met Glu Val Leu Ala Ala Lys Thr Gly Tyr Glu
        1235                1240                1245 act gac atg atc gag tcc gac atg gag ctc gag act gag ctc ggc          3789
Thr Asp Met Ile Glu Ser Asp Met Glu Leu Glu Thr Glu Leu Gly
```

```
                    1250                1255                1260
att gac tcc atc aag cgt gtc gag atc ctc tcc gag gtt cag gcc      3834
Ile Asp Ser Ile Lys Arg Val Glu Ile Leu Ser Glu Val Gln Ala
    1265                1270                1275 atg ctc aac gtc gag gcc aag gac gtc gac gct ctc agc cgc act      3879
Met Leu Asn Val Glu Ala Lys Asp Val Asp Ala Leu Ser Arg Thr
        1280                1285                1290 cgc act gtg ggt gag gtc gtc aac gcc atg aag gct gag atc gct      3924
Arg Thr Val Gly Glu Val Val Asn Ala Met Lys Ala Glu Ile Ala
    1295                1300                1305 ggt ggc tct gcc ccg gcg cct gcc gcc gct gcc cca ggt ccg gct      3969
Gly Gly Ser Ala Pro Ala Pro Ala Ala Ala Ala Pro Gly Pro Ala
    1310                1315                1320 gct gcc gcc cct gcg cct gcc gcc gcc gcc cct gct gtc tcg aac      4014
Ala Ala Ala Pro Ala Pro Ala Ala Ala Ala Pro Ala Val Ser Asn
    1325                1330                1335 gag ctt ctt gag aag gcc gag acc gtc gtc atg gag gtc ctc gcc      4059
Glu Leu Leu Glu Lys Ala Glu Thr Val Val Met Glu Val Leu Ala
    1340                1345                1350 gcc aag act ggc tac gag act gac atg atc gag tcc gac atg gag      4104
Ala Lys Thr Gly Tyr Glu Thr Asp Met Ile Glu Ser Asp Met Glu
    1355                1360                1365 ctc gag acc gag ctc ggc att gac tcc atc aag cgt gtc gag att      4149
Leu Glu Thr Glu Leu Gly Ile Asp Ser Ile Lys Arg Val Glu Ile
    1370                1375                1380 ctc tcc gag gtc cag gcc atg ctc aac gtc gag gcc aag gac gtc      4194
Leu Ser Glu Val Gln Ala Met Leu Asn Val Glu Ala Lys Asp Val
    1385                1390                1395 gac gct ctc agc cgc acc cgc act gtt ggc gag gtc gtc gat gcc      4239
Asp Ala Leu Ser Arg Thr Arg Thr Val Gly Glu Val Val Asp Ala
    1400                1405                1410 atg aag gcc gag atc gct ggt ggc tct gcc ccg gcg cct gcc gcc      4284
Met Lys Ala Glu Ile Ala Gly Gly Ser Ala Pro Ala Pro Ala Ala
    1415                1420                1425 gct gct cct gct ccg gct gct gcc gcc cct gcg cct gcc gcc cct      4329
Ala Ala Pro Ala Pro Ala Ala Ala Ala Pro Ala Pro Ala Ala Pro
    1430                1435                1440 gcg cct gct gtc tcg agc gag ctt ctc gag aag gcc gag act gtc      4374
Ala Pro Ala Val Ser Ser Glu Leu Leu Glu Lys Ala Glu Thr Val
    1445                1450                1455 gtc atg gag gtc ctc gcc gcc aag act ggc tac gag act gac atg      4419
Val Met Glu Val Leu Ala Ala Lys Thr Gly Tyr Glu Thr Asp Met
    1460                1465                1470 atc gag tcc gac atg gag ctc gag acc gag ctc ggc att gac tcc      4464
Ile Glu Ser Asp Met Glu Leu Glu Thr Glu Leu Gly Ile Asp Ser
    1475                1480                1485 atc aag cgt gtc gag att ctc tcc gag gtc cag gcc atg ctc aac      4509
Ile Lys Arg Val Glu Ile Leu Ser Glu Val Gln Ala Met Leu Asn
    1490                1495                1500 gtc gag gcc aag gac gtc gac gct ctc agc cgc acc cgc act gtt      4554
Val Glu Ala Lys Asp Val Asp Ala Leu Ser Arg Thr Arg Thr Val
    1505                1510                1515 ggc gag gtc gtc gat gcc atg aag gcc gag atc gct ggt ggc tct      4599
Gly Glu Val Val Asp Ala Met Lys Ala Glu Ile Ala Gly Gly Ser
    1520                1525                1530 gcc ccg gcg cct gcc gcc gct gct cct gct ccg gct gct gcc gcc      4644
Ala Pro Ala Pro Ala Ala Ala Ala Pro Ala Pro Ala Ala Ala Ala
    1535                1540                1545 cct gcg cct gcc gcc cct gcg cct gcc gcc cct gcg cct gct gtc      4689
```

```
Pro Ala  Pro Ala  Ala Pro  Ala Pro  Ala Pro  Ala Val
    1550         1555         1560 tcg agc  gag ctt  ctc gag  aag gcc  gag act  gtc gtc  atg gag gtc       4734
Ser Ser  Glu Leu  Leu Glu  Lys Ala  Glu Thr  Val Val  Met Glu Val
    1565         1570         1575 ctc gcc  gcc aag  act ggc  tac gag  act gac  atg att  gag tcc gac       4779
Leu Ala  Ala Lys  Thr Gly  Tyr Glu  Thr Asp  Met Ile  Glu Ser Asp
    1580         1585         1590 atg gag  ctc gag  acc gag  ctc ggc  att gac  tcc atc  aag cgt gtc       4824
Met Glu  Leu Glu  Thr Glu  Leu Gly  Ile Asp  Ser Ile  Lys Arg Val
    1595         1600         1605 gag att  ctc tcc  gag gtt  cag gcc  atg ctc  aac gtc  gag gcc aag       4869
Glu Ile  Leu Ser  Glu Val  Gln Ala  Met Leu  Asn Val  Glu Ala Lys
    1610         1615         1620 gac gtc  gac gct  ctc agc  cgc act  cgc act  gtt ggt  gag gtc gtc       4914
Asp Val  Asp Ala  Leu Ser  Arg Thr  Arg Thr  Val Gly  Glu Val Val
    1625         1630         1635 gat gcc  atg aag  gct gag  atc gct  ggc agc  tcc gcc  tcg gcg cct       4959
Asp Ala  Met Lys  Ala Glu  Ile Ala  Gly Ser  Ser Ala  Ser Ala Pro
    1640         1645         1650 gcc gcc  gct gct  cct gct  ccg gct  gct gcc  gct cct  gcg ccc gct       5004
Ala Ala  Ala Ala  Pro Ala  Pro Ala  Ala Ala  Ala Pro  Ala Pro Ala
    1655         1660         1665 gcc gcc  gcc cct  gct gtc  tcg aac  gag ctt  ctc gag  aaa gcc gag       5049
Ala Ala  Ala Pro  Ala Val  Ser Asn  Glu Leu  Leu Glu  Lys Ala Glu
    1670         1675         1680 act gtc  gtc atg  gag gtc  ctc gcc  gcc aag  act ggc  tac gag act       5094
Thr Val  Val Met  Glu Val  Leu Ala  Ala Lys  Thr Gly  Tyr Glu Thr
    1685         1690         1695 gac atg  atc gag  tcc gac  atg gag  ctc gag  act gag  ctc ggc att       5139
Asp Met  Ile Glu  Ser Asp  Met Glu  Leu Glu  Thr Glu  Leu Gly Ile
    1700         1705         1710 gac tcc  atc aag  cgt gtc  gag atc  ctc tcc  gag gtt  cag gcc atg       5184
Asp Ser  Ile Lys  Arg Val  Glu Ile  Leu Ser  Glu Val  Gln Ala Met
    1715         1720         1725 ctc aac  gtc gag  gcc aag  gac gtc  gat gcc  ctc agc  cgc acc cgc       5229
Leu Asn  Val Glu  Ala Lys  Asp Val  Asp Ala  Leu Ser  Arg Thr Arg
    1730         1735         1740 act gtt  ggc gag  gtt gtc  gat gcc  atg aag  gcc gag  atc gct ggt       5274
Thr Val  Gly Glu  Val Val  Asp Ala  Met Lys  Ala Glu  Ile Ala Gly
    1745         1750         1755 ggc tct  gcc ccg  gcg cct  gcc gcc  gct gcc  cct gct  ccg gct gcc       5319
Gly Ser  Ala Pro  Ala Pro  Ala Ala  Ala Ala  Pro Ala  Pro Ala Ala
    1760         1765         1770 gcc gcc  cct gct  gtc tcg  aac gag  ctt ctc  gag aag  gcc gag act       5364
Ala Ala  Pro Ala  Val Ser  Asn Glu  Leu Leu  Glu Lys  Ala Glu Thr
    1775         1780         1785 gtc gtc  atg gag  gtc ctc  gcc gcc  aag act  ggc tac  gag acc gac       5409
Val Val  Met Glu  Val Leu  Ala Ala  Lys Thr  Gly Tyr  Glu Thr Asp
    1790         1795         1800 atg atc  gag tcc  gac atg  gag ctc  gag acc  gag ctc  ggc att gac       5454
Met Ile  Glu Ser  Asp Met  Glu Leu  Glu Thr  Glu Leu  Gly Ile Asp
    1805         1810         1815 tcc atc  aag cgt  gtc gag  att ctc  tcc gag  gtt cag  gcc atg ctc       5499
Ser Ile  Lys Arg  Val Glu  Ile Leu  Ser Glu  Val Gln  Ala Met Leu
    1820         1825         1830 aac gtc  gag gcc  aag gac  gtc gat  gct ctc  agc cgc  act cgc act       5544
Asn Val  Glu Ala  Lys Asp  Val Asp  Ala Leu  Ser Arg  Thr Arg Thr
    1835         1840         1845
```

-continued

| | | |
|---|---|---|
| gtt ggc gag gtc gtc gat gcc atg aag gct gag atc gcc ggc agc<br>Val Gly Glu Val Val Asp Ala Met Lys Ala Glu Ile Ala Gly Ser<br>1850                             1855                            1860 | 5589 | |
| tcc gcc ccg gcg cct gcc gcc gct gct cct gct ccg gct gct gcc<br>Ser Ala Pro Ala Pro Ala Ala Ala Ala Pro Ala Pro Ala Ala Ala<br>1865                             1870                            1875 | 5634 | |
| gct cct gcg ccc gct gcc gct gcc cct gct gtc tcg agc gag ctt<br>Ala Pro Ala Pro Ala Ala Ala Ala Pro Ala Val Ser Ser Glu Leu<br>1880                             1885                            1890 | 5679 | |
| ctc gag aag gcc gag acc gtc gtc atg gag gtc ctc gcc gcc aag<br>Leu Glu Lys Ala Glu Thr Val Val Met Glu Val Leu Ala Ala Lys<br>1895                             1900                            1905 | 5724 | |
| act ggc tac gag act gac atg att gag tcc gac atg gag ctc gag<br>Thr Gly Tyr Glu Thr Asp Met Ile Glu Ser Asp Met Glu Leu Glu<br>1910                             1915                            1920 | 5769 | |
| act gag ctc ggc att gac tcc atc aag cgt gtc gag atc ctc tcc<br>Thr Glu Leu Gly Ile Asp Ser Ile Lys Arg Val Glu Ile Leu Ser<br>1925                             1930                            1935 | 5814 | |
| gag gtt cag gcc atg ctc aac gtc gag gcc aag gac gtc gat gcc<br>Glu Val Gln Ala Met Leu Asn Val Glu Ala Lys Asp Val Asp Ala<br>1940                             1945                            1950 | 5859 | |
| ctc agc cgc acc cgc act gtt ggc gag gtt gtc gat gcc atg aag<br>Leu Ser Arg Thr Arg Thr Val Gly Glu Val Val Asp Ala Met Lys<br>1955                             1960                            1965 | 5904 | |
| gcc gag atc gct ggt ggc tct gcc ccg gcg cct gcc gcc gct gcc<br>Ala Glu Ile Ala Gly Gly Ser Ala Pro Ala Pro Ala Ala Ala Ala<br>1970                             1975                            1980 | 5949 | |
| cct gct ccg gct gcc gcc gcc cct gct gtc tcg aac gag ctt ctt<br>Pro Ala Pro Ala Ala Ala Ala Pro Ala Val Ser Asn Glu Leu Leu<br>1985                             1990                            1995 | 5994 | |
| gag aag gcc gag acc gtc gtc atg gag gtc ctc gcc gcc aag act<br>Glu Lys Ala Glu Thr Val Val Met Glu Val Leu Ala Ala Lys Thr<br>2000                             2005                            2010 | 6039 | |
| ggc tac gag acc gac atg atc gag tcc gac atg gag ctc gag acc<br>Gly Tyr Glu Thr Asp Met Ile Glu Ser Asp Met Glu Leu Glu Thr<br>2015                             2020                            2025 | 6084 | |
| gag ctc ggc att gac tcc atc aag cgt gtc gag att ctc tcc gag<br>Glu Leu Gly Ile Asp Ser Ile Lys Arg Val Glu Ile Leu Ser Glu<br>2030                             2035                            2040 | 6129 | |
| gtt cag gcc atg ctc aac gtc gag gcc aag gac gtc gac gct ctc<br>Val Gln Ala Met Leu Asn Val Glu Ala Lys Asp Val Asp Ala Leu<br>2045                             2050                            2055 | 6174 | |
| agc cgc act cgc act gtt ggc gag gtc gtc gat gcc atg aag gct<br>Ser Arg Thr Arg Thr Val Gly Glu Val Val Asp Ala Met Lys Ala<br>2060                             2065                            2070 | 6219 | |
| gag atc gct ggt ggc tct gcc ccg gcg cct gcc gcc gct gct cct<br>Glu Ile Ala Gly Gly Ser Ala Pro Ala Pro Ala Ala Ala Ala Pro<br>2075                             2080                            2085 | 6264 | |
| gcc tcg gct ggc gcc gcg cct gcg gtc aag att gac tcg gtc cac<br>Ala Ser Ala Gly Ala Ala Pro Ala Val Lys Ile Asp Ser Val His<br>2090                             2095                            2100 | 6309 | |
| ggc gct gac tgt gat gat ctt tcc ctg atg cac gcc aag gtg gtt<br>Gly Ala Asp Cys Asp Asp Leu Ser Leu Met His Ala Lys Val Val<br>2105                             2110                            2115 | 6354 | |
| gac atc cgc cgc ccg gac gag ctc atc ctg gag cgc ccc gag aac<br>Asp Ile Arg Arg Pro Asp Glu Leu Ile Leu Glu Arg Pro Glu Asn<br>2120                             2125                            2130 | 6399 | |
| cgc ccc gtt ctc gtt gtc gat gac ggc agc gag ctc acc ctc gcc<br>Arg Pro Val Leu Val Val Asp Asp Gly Ser Glu Leu Thr Leu Ala<br>2135                             2140                            2145 | 6444 | |

| | | |
|---|---|---|
| ctg gtc cgc gtc ctc ggc gcc tgc gcc gtt gtc ctg acc ttt gag<br>Leu Val Arg Val Leu Gly Ala Cys Ala Val Val Leu Thr Phe Glu<br>2150                       2155                  2160 | 6489 |
| ggt ctc cag ctc gct cag cgc gct ggt gcc gct gcc atc cgc cac<br>Gly Leu Gln Leu Ala Gln Arg Ala Gly Ala Ala Ala Ile Arg His<br>2165                       2170                  2175 | 6534 |
| gtg ctc gcc aag gat ctt tcc gcg gag agc gcc gag aag gcc atc<br>Val Leu Ala Lys Asp Leu Ser Ala Glu Ser Ala Glu Lys Ala Ile<br>2180                       2185                  2190 | 6579 |
| aag gag gcc gag cag cgc ttt ggc gct ctc ggc ttc atc tcg<br>Lys Glu Ala Glu Gln Arg Phe Gly Ala Leu Gly Gly Phe Ile Ser<br>2195                       2200                  2205 | 6624 |
| cag cag gcg gag cgc ttc gag ccc gcc gaa atc ctc ggc ttc acg<br>Gln Gln Ala Glu Arg Phe Glu Pro Ala Glu Ile Leu Gly Phe Thr<br>2210                       2215                  2220 | 6669 |
| ctc atg tgc gcc aag ttc gcc aag gct tcc ctc tgc acg gct gtg<br>Leu Met Cys Ala Lys Phe Ala Lys Ala Ser Leu Cys Thr Ala Val<br>2225                       2230                  2235 | 6714 |
| gct ggc ggc cgc ccg gcc ttt atc ggt gtg gcg cgc ctt gac ggc<br>Ala Gly Gly Arg Pro Ala Phe Ile Gly Val Ala Arg Leu Asp Gly<br>2240                       2245                  2250 | 6759 |
| cgc ctc gga ttc act tcg cag ggc act tct gac gcg ctc aag cgt<br>Arg Leu Gly Phe Thr Ser Gln Gly Thr Ser Asp Ala Leu Lys Arg<br>2255                       2260                  2265 | 6804 |
| gcc cag cgt ggt gcc atc ttt ggc ctc tgc aag acc atc ggc ctc<br>Ala Gln Arg Gly Ala Ile Phe Gly Leu Cys Lys Thr Ile Gly Leu<br>2270                       2275                  2280 | 6849 |
| gag tgg tcc gag tct gac gtc ttt tcc cgc ggc gtg gac att gct<br>Glu Trp Ser Glu Ser Asp Val Phe Ser Arg Gly Val Asp Ile Ala<br>2285                       2290                  2295 | 6894 |
| cag ggc atg cac ccc gag gat gcc gcc gtg gcg att gtg cgc gag<br>Gln Gly Met His Pro Glu Asp Ala Ala Val Ala Ile Val Arg Glu<br>2300                       2305                  2310 | 6939 |
| atg gcg tgc gct gac att cgc att cgc gag gtc ggc att ggc gca<br>Met Ala Cys Ala Asp Ile Arg Ile Arg Glu Val Gly Ile Gly Ala<br>2315                       2320                  2325 | 6984 |
| aac cag cag cgc tgc acg atc cgt gcc gcc aag ctc gag acc ggc<br>Asn Gln Gln Arg Cys Thr Ile Arg Ala Ala Lys Leu Glu Thr Gly<br>2330                       2335                  2340 | 7029 |
| aac ccg cag cgc cag atc gcc aag gac gac gtg ctg ctc gtt tct<br>Asn Pro Gln Arg Gln Ile Ala Lys Asp Asp Val Leu Leu Val Ser<br>2345                       2350                  2355 | 7074 |
| ggc ggc gct cgc ggc atc acg cct ctt tgc atc cgg gag atc acg<br>Gly Gly Ala Arg Gly Ile Thr Pro Leu Cys Ile Arg Glu Ile Thr<br>2360                       2365                  2370 | 7119 |
| cgc cag atc gcg ggc ggc aag tac att ctg ctt ggc cgc agc aag<br>Arg Gln Ile Ala Gly Gly Lys Tyr Ile Leu Leu Gly Arg Ser Lys<br>2375                       2380                  2385 | 7164 |
| gtc tct gcg agc gaa ccg gca tgg tgc gct ggc atc act gac gag<br>Val Ser Ala Ser Glu Pro Ala Trp Cys Ala Gly Ile Thr Asp Glu<br>2390                       2395                  2400 | 7209 |
| aag gct gtg caa aag gct gct acc cag gag ctc aag cgc gcc ttt<br>Lys Ala Val Gln Lys Ala Ala Thr Gln Glu Leu Lys Arg Ala Phe<br>2405                       2410                  2415 | 7254 |
| agc gct ggc gag ggc ccc aag ccc acg ccc cgc gct gtc act aag<br>Ser Ala Gly Glu Gly Pro Lys Pro Thr Pro Arg Ala Val Thr Lys<br>2420                       2425                  2430 | 7299 |
| ctt gtg ggc tct gtt ctt ggc gct cgc gag gtg cgc agc tct att<br>Leu Val Gly Ser Val Leu Gly Ala Arg Glu Val Arg Ser Ser Ile | 7344 |

```
                  2435                2440                2445 gct gcg att gaa gcg ctc ggc ggc aag gcc atc tac tcg tcg tgc       7389
Ala Ala Ile Glu Ala Leu Gly Gly Lys Ala Ile Tyr Ser Ser Cys
    2450                2455                2460 gac gtg aac tct gcc gcc gac gtg gcc aag gcc gtg cgc gat gcc       7434
Asp Val Asn Ser Ala Ala Asp Val Ala Lys Ala Val Arg Asp Ala
    2465                2470                2475 gag tcc cag ctc ggt gcc cgc gtc tcg ggc atc gtt cat gcc tcg       7479
Glu Ser Gln Leu Gly Ala Arg Val Ser Gly Ile Val His Ala Ser
    2480                2485                2490 ggc gtg ctc cgc gac cgt ctc atc gag aag aag ctc ccc gac gag       7524
Gly Val Leu Arg Asp Arg Leu Ile Glu Lys Lys Leu Pro Asp Glu
    2495                2500                2505 ttc gac gcc gtc ttt ggc acc aag gtc acc ggt ctc gag aac ctc       7569
Phe Asp Ala Val Phe Gly Thr Lys Val Thr Gly Leu Glu Asn Leu
    2510                2515                2520 ctc gcc gcc gtc gac cgc gcc aac ctc aag cac atg gtc ctc ttc       7614
Leu Ala Ala Val Asp Arg Ala Asn Leu Lys His Met Val Leu Phe
    2525                2530                2535 agc tcg ctc gcc ggc ttc cac ggc aac gtc ggc cag tct gac tac       7659
Ser Ser Leu Ala Gly Phe His Gly Asn Val Gly Gln Ser Asp Tyr
    2540                2545                2550 gcc atg gcc aac gag gcc ctt aac aag atg ggc ctc gag ctc gcc       7704
Ala Met Ala Asn Glu Ala Leu Asn Lys Met Gly Leu Glu Leu Ala
    2555                2560                2565 aag gac gtc tcg gtc aag tcg atc tgc ttc ggt ccc tgg gac ggt       7749
Lys Asp Val Ser Val Lys Ser Ile Cys Phe Gly Pro Trp Asp Gly
    2570                2575                2580 ggc atg gtg acg ccg cag ctc aag aag cag ttc cag gag atg ggc       7794
Gly Met Val Thr Pro Gln Leu Lys Lys Gln Phe Gln Glu Met Gly
    2585                2590                2595 gtg cag atc atc ccc cgc gag ggc ggc gct gat acc gtg gcg cgc       7839
Val Gln Ile Ile Pro Arg Glu Gly Gly Ala Asp Thr Val Ala Arg
    2600                2605                2610 atc gtg ctc ggc tcc tcg ccg gct gag atc ctt gtc ggc aac tgg       7884
Ile Val Leu Gly Ser Ser Pro Ala Glu Ile Leu Val Gly Asn Trp
    2615                2620                2625 cgc acc ccg tcc aag aag gtc ggc tcg gac acc atc acc ctg cac       7929
Arg Thr Pro Ser Lys Lys Val Gly Ser Asp Thr Ile Thr Leu His
    2630                2635                2640 cgc aag att tcc gcc aag tcc aac ccc ttc ctc gag gac cac gtc       7974
Arg Lys Ile Ser Ala Lys Ser Asn Pro Phe Leu Glu Asp His Val
    2645                2650                2655 atc cag ggc cgc cgc gtg ctg ccc atg acg ctg gcc att ggc tcg       8019
Ile Gln Gly Arg Arg Val Leu Pro Met Thr Leu Ala Ile Gly Ser
    2660                2665                2670 ctc gcg gag acc tgc ctc ggc ctc ttc ccc ggc tac tcg ctc tgg       8064
Leu Ala Glu Thr Cys Leu Gly Leu Phe Pro Gly Tyr Ser Leu Trp
    2675                2680                2685 gcc att gac gac gcc cag ctc ttc aag ggt gtc act gtc gac ggc       8109
Ala Ile Asp Asp Ala Gln Leu Phe Lys Gly Val Thr Val Asp Gly
    2690                2695                2700 gac gtc aac tgc gag gtg acc ctc acc ccg tcg acg gcg ccc tcg       8154
Asp Val Asn Cys Glu Val Thr Leu Thr Pro Ser Thr Ala Pro Ser
    2705                2710                2715 ggc cgc gtc aac gtc cag gcc acg ctc aag acc ttt tcc agc ggc       8199
Gly Arg Val Asn Val Gln Ala Thr Leu Lys Thr Phe Ser Ser Gly
    2720                2725                2730 aag ctg gtc ccg gcc tac cgc gcc gtc atc gtg ctc tcc aac cag       8244
```

```
Lys Leu Val Pro Ala Tyr Arg Ala Val Ile Val Leu Ser Asn Gln
    2735                2740                2745 ggc gcg ccc ccg gcc aac gcc acc atg cag ccg ccc tcg ctc gat    8289
Gly Ala Pro Pro Ala Asn Ala Thr Met Gln Pro Pro Ser Leu Asp
    2750                2755                2760 gcc gat ccg gcg ctc cag ggc tcc gtc tac gac ggc aag acc ctc    8334
Ala Asp Pro Ala Leu Gln Gly Ser Val Tyr Asp Gly Lys Thr Leu
    2765                2770                2775 ttc cac ggc ccg gcc ttc cgc ggc atc gat gac gtg ctc tcg tgc    8379
Phe His Gly Pro Ala Phe Arg Gly Ile Asp Asp Val Leu Ser Cys
    2780                2785                2790 acc aag agc cag ctt gtg gcc aag tgc agc gct gtc ccc ggc tcc    8424
Thr Lys Ser Gln Leu Val Ala Lys Cys Ser Ala Val Pro Gly Ser
    2795                2800                2805 gac gcc gct cgc ggc gag ttt gcc acg gac act gac gcc cat gac    8469
Asp Ala Ala Arg Gly Glu Phe Ala Thr Asp Thr Asp Ala His Asp
    2810                2815                2820 ccc ttc gtg aac gac ctg gcc ttt cag gcc atg ctc gtc tgg gtg    8514
Pro Phe Val Asn Asp Leu Ala Phe Gln Ala Met Leu Val Trp Val
    2825                2830                2835 cgc cgc acg ctc ggc cag gct gcg ctc ccc aac tcg atc cag cgc    8559
Arg Arg Thr Leu Gly Gln Ala Ala Leu Pro Asn Ser Ile Gln Arg
    2840                2845                2850 atc gtc cag cac cgc ccg gtc ccg cag gac aag ccc ttc tac att    8604
Ile Val Gln His Arg Pro Val Pro Gln Asp Lys Pro Phe Tyr Ile
    2855                2860                2865 acc ctc cgc tcc aac cag tcg ggc ggt cac tcc cag cac aag cac    8649
Thr Leu Arg Ser Asn Gln Ser Gly Gly His Ser Gln His Lys His
    2870                2875                2880 gcc ctt cag ttc cac aac gag cag ggc gat ctc ttc att gat gtc    8694
Ala Leu Gln Phe His Asn Glu Gln Gly Asp Leu Phe Ile Asp Val
    2885                2890                2895 cag gct tcg gtc atc gcc acg gac agc ctt gcc ttc                8730
Gln Ala Ser Val Ile Ala Thr Asp Ser Leu Ala Phe
    2900                2905                2910

<210> SEQ ID NO 2
<211> LENGTH: 2910
<212> TYPE: PRT
<213> ORGANISM: Schizochytrium sp.

<400> SEQUENCE: 2

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
                20                  25                  30

Arg Glu Ser Trp Glu Thr Ile Arg Ala Gly Ile Asp Cys Leu Ser Asp
            35                  40                  45

Leu Pro Glu Asp Arg Val Asp Val Thr Ala Tyr Phe Asp Pro Val Lys
        50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

Asp Ser Asp Ala Asn Gln Thr Ile Ser Leu Leu Lys Val Lys Glu Ala
                100                 105                 110

Leu Gln Asp Ala Gly Ile Asp Ala Leu Gly Lys Glu Lys Lys Asn Ile
            115                 120                 125
```

-continued

```
Gly Cys Val Leu Gly Ile Gly Gly Gln Lys Ser His Glu Phe
        130             135             140
Tyr Ser Arg Leu Asn Tyr Val Val Glu Lys Val Leu Arg Lys Met
145             150             155                 160
Gly Met Pro Glu Glu Asp Val Lys Val Ala Val Glu Lys Tyr Lys Ala
            165             170             175
Asn Phe Pro Glu Trp Arg Leu Asp Ser Phe Pro Gly Phe Leu Gly Asn
        180             185             190
Val Thr Ala Gly Arg Cys Thr Asn Thr Phe Asn Leu Asp Gly Met Asn
    195             200             205
Cys Val Val Asp Ala Ala Cys Ala Ser Ser Leu Ile Ala Val Lys Val
    210             215             220
Ala Ile Asp Glu Leu Leu Tyr Gly Asp Cys Asp Met Met Val Thr Gly
225             230             235             240
Ala Thr Cys Thr Asp Asn Ser Ile Gly Met Tyr Met Ala Phe Ser Lys
            245             250             255
Thr Pro Val Phe Ser Thr Asp Pro Ser Val Arg Ala Tyr Asp Glu Lys
            260             265             270
Thr Lys Gly Met Leu Ile Gly Glu Gly Ser Ala Met Leu Val Leu Lys
            275             280             285
Arg Tyr Ala Asp Ala Val Arg Asp Gly Asp Glu Ile His Ala Val Ile
    290             295             300
Arg Gly Cys Ala Ser Ser Ser Asp Gly Lys Ala Ala Gly Ile Tyr Thr
305             310             315             320
Pro Thr Ile Ser Gly Gln Glu Glu Ala Leu Arg Arg Ala Tyr Asn Arg
            325             330             335
Ala Cys Val Asp Pro Ala Thr Val Thr Leu Val Glu Gly His Gly Thr
            340             345             350
Gly Thr Pro Val Gly Asp Arg Ile Glu Leu Thr Ala Leu Arg Asn Leu
        355             360             365
Phe Asp Lys Ala Tyr Gly Glu Gly Asn Thr Glu Lys Val Ala Val Gly
        370             375             380
Ser Ile Lys Ser Ser Ile Gly His Leu Lys Ala Val Ala Gly Leu Ala
385             390             395             400
Gly Met Ile Lys Val Ile Met Ala Leu Lys His Lys Thr Leu Pro Gly
            405             410             415
Thr Ile Asn Val Asp Asn Pro Asn Leu Tyr Asp Asn Thr Pro Ile
        420             425             430
Asn Glu Ser Ser Leu Tyr Ile Asn Thr Met Asn Arg Pro Trp Phe Pro
    435             440             445
Pro Pro Gly Val Pro Arg Arg Ala Gly Ile Ser Ser Phe Gly Phe Gly
    450             455             460
Gly Ala Asn Tyr His Ala Val Leu Glu Glu Ala Glu Pro Glu His Thr
465             470             475             480
Thr Ala Tyr Arg Leu Asn Lys Arg Pro Gln Pro Val Leu Met Met Ala
            485             490             495
Ala Thr Pro Ala Ala Leu Gln Ser Leu Cys Glu Ala Gln Leu Lys Glu
            500             505             510
Phe Glu Ala Ala Ile Lys Glu Asn Glu Thr Val Lys Asn Thr Ala Tyr
        515             520             525
Ile Lys Cys Val Lys Phe Gly Glu Gln Phe Lys Phe Pro Gly Ser Ile
        530             535             540
Pro Ala Thr Asn Ala Arg Leu Gly Phe Leu Val Lys Asp Ala Glu Asp
```

-continued

```
        545                 550                 555                 560
    Ala Cys Ser Thr Leu Arg Ala Ile Cys Ala Gln Phe Ala Lys Asp Val
                    565                 570                 575
    Thr Lys Glu Ala Trp Arg Leu Pro Arg Glu Gly Val Ser Phe Arg Ala
                    580                 585                 590
    Lys Gly Ile Ala Thr Asn Gly Ala Val Ala Leu Phe Ser Gly Gln
                    595                 600                 605
    Gly Ala Gln Tyr Thr His Met Phe Ser Glu Val Ala Met Asn Trp Pro
                    610                 615                 620
    Gln Phe Arg Gln Ser Ile Ala Ala Met Asp Ala Ala Gln Ser Lys Val
    625                 630                 635                 640
    Ala Gly Ser Asp Lys Asp Phe Glu Arg Val Ser Gln Val Leu Tyr Pro
                    645                 650                 655
    Arg Lys Pro Tyr Glu Arg Glu Pro Glu Gln Asn Pro Lys Lys Ile Ser
                    660                 665                 670
    Leu Thr Ala Tyr Ser Gln Pro Ser Thr Leu Ala Cys Ala Leu Gly Ala
                    675                 680                 685
    Phe Glu Ile Phe Lys Glu Ala Gly Phe Thr Pro Asp Phe Ala Ala Gly
                    690                 695                 700
    His Ser Leu Gly Glu Phe Ala Ala Leu Tyr Ala Ala Gly Cys Val Asp
    705                 710                 715                 720
    Arg Asp Glu Leu Phe Glu Leu Val Cys Arg Arg Ala Arg Ile Met Gly
                    725                 730                 735
    Gly Lys Asp Ala Pro Ala Thr Pro Lys Gly Cys Met Ala Ala Val Ile
                    740                 745                 750
    Gly Pro Asn Ala Glu Asn Ile Lys Val Gln Ala Ala Asn Val Trp Leu
                    755                 760                 765
    Gly Asn Ser Asn Ser Pro Ser Gln Thr Val Ile Thr Gly Ser Val Glu
                    770                 775                 780
    Gly Ile Gln Ala Glu Ser Ala Arg Leu Gln Lys Gly Phe Arg Val
    785                 790                 795                 800
    Val Pro Leu Ala Cys Glu Ser Ala Phe His Ser Pro Gln Met Glu Asn
                    805                 810                 815
    Ala Ser Ser Ala Phe Lys Asp Val Ile Ser Lys Val Ser Phe Arg Thr
                    820                 825                 830
    Pro Lys Ala Glu Thr Lys Leu Phe Ser Asn Val Ser Gly Glu Thr Tyr
                    835                 840                 845
    Pro Thr Asp Ala Arg Glu Met Leu Thr Gln His Met Thr Ser Ser Val
                    850                 855                 860
    Lys Phe Leu Thr Gln Val Arg Asn Met His Gln Ala Gly Ala Arg Ile
    865                 870                 875                 880
    Phe Val Glu Phe Gly Pro Lys Gln Val Leu Ser Lys Leu Val Ser Glu
                    885                 890                 895
    Thr Leu Lys Asp Asp Pro Ser Val Val Thr Val Ser Val Asn Pro Ala
                    900                 905                 910
    Ser Gly Thr Asp Ser Asp Ile Gln Leu Arg Asp Ala Ala Val Gln Leu
                    915                 920                 925
    Val Val Ala Gly Val Asn Leu Gln Gly Phe Asp Lys Trp Asp Ala Pro
                    930                 935                 940
    Asp Ala Thr Arg Met Gln Ala Ile Lys Lys Lys Arg Thr Thr Leu Arg
    945                 950                 955                 960
    Leu Ser Ala Ala Thr Tyr Val Ser Asp Lys Thr Lys Lys Val Arg Asp
                    965                 970                 975
```

-continued

```
Ala Ala Met Asn Asp Gly Arg Cys Val Thr Tyr Leu Lys Gly Ala Ala
         980                 985                 990

Pro Leu Ile Lys Ala Pro Glu Pro  Val Val Asp Glu Ala  Ala Lys Arg
         995                 1000                1005

Glu Ala  Glu Arg Leu Gln Lys  Glu Leu Gln Asp Ala  Gln Arg Gln
    1010              1015                1020

Leu Asp  Asp Ala Lys Arg Ala  Ala Ala Glu Ala Asn  Ser Lys Leu
    1025              1030                1035

Ala Ala  Ala Lys Glu Glu Ala  Lys Thr Ala Ala Ala  Ser Ala Lys
    1040              1045                1050

Pro Ala  Val Asp Thr Ala Val  Val Glu Lys His Arg  Ala Ile Leu
    1055              1060                1065

Lys Ser  Met Leu Ala Glu Leu  Asp Gly Tyr Gly Ser  Val Asp Ala
    1070              1075                1080

Ser Ser  Leu Gln Gln Gln Gln  Gln Gln Gln Thr Ala  Pro Ala Pro
    1085              1090                1095

Val Lys  Ala Ala Ala Pro Ala  Ala Pro Val Ala Ser  Ala Pro Ala
    1100              1105                1110

Pro Ala  Val Ser Asn Glu Leu  Leu Glu Lys Ala Glu  Thr Val Val
    1115              1120                1125

Met Glu  Val Leu Ala Ala Lys  Thr Gly Tyr Glu Thr  Asp Met Ile
    1130              1135                1140

Glu Ala  Asp Met Glu Leu Glu  Thr Glu Leu Gly Ile  Asp Ser Ile
    1145              1150                1155

Lys Arg  Val Glu Ile Leu Ser  Glu Val Gln Ala Met  Leu Asn Val
    1160              1165                1170

Glu Ala  Lys Asp Val Asp Ala  Leu Ser Arg Thr Arg  Thr Val Gly
    1175              1180                1185

Glu Val  Val Asn Ala Met Lys  Ala Glu Ile Ala Gly  Ser Ser Ala
    1190              1195                1200

Pro Ala  Pro Ala Ala Ala Ala  Pro Ala Pro Ala Lys  Ala Ala Pro
    1205              1210                1215

Ala Ala  Ala Ala Pro Ala Val  Ser Asn Glu Leu Leu  Glu Lys Ala
    1220              1225                1230

Glu Thr  Val Val Met Glu Val  Leu Ala Ala Lys Thr  Gly Tyr Glu
    1235              1240                1245

Thr Asp  Met Ile Glu Ser Asp  Met Glu Leu Glu Thr  Glu Leu Gly
    1250              1255                1260

Ile Asp  Ser Ile Lys Arg Val  Glu Ile Leu Ser Glu  Val Gln Ala
    1265              1270                1275

Met Leu  Asn Val Glu Ala Lys  Asp Val Asp Ala Leu  Ser Arg Thr
    1280              1285                1290

Arg Thr  Val Gly Glu Val Val  Asn Ala Met Lys Ala  Glu Ile Ala
    1295              1300                1305

Gly Gly  Ser Ala Pro Ala Pro  Ala Ala Ala Ala Pro  Gly Pro Ala
    1310              1315                1320

Ala Ala  Ala Pro Ala Pro Ala  Ala Ala Pro Ala Val  Ser Asn
    1325              1330                1335

Glu Leu  Leu Glu Lys Ala Glu  Thr Val Val Met Glu  Val Leu Ala
    1340              1345                1350

Ala Lys  Thr Gly Tyr Glu Thr  Asp Met Ile Glu Ser  Asp Met Glu
    1355              1360                1365
```

-continued

```
Leu Glu Thr Glu Leu Gly Ile Asp Ser Ile Lys Arg Val Glu Ile
    1370            1375                1380

Leu Ser Glu Val Gln Ala Met Leu Asn Val Glu Ala Lys Asp Val
    1385            1390                1395

Asp Ala Leu Ser Arg Thr Arg Thr Val Gly Glu Val Val Asp Ala
    1400            1405                1410

Met Lys Ala Glu Ile Ala Gly Gly Ser Ala Pro Ala Pro Ala Ala
    1415            1420                1425

Ala Ala Pro Ala Pro Ala Ala Ala Pro Ala Pro Ala Ala Pro
    1430            1435                1440

Ala Pro Ala Val Ser Ser Glu Leu Leu Glu Lys Ala Glu Thr Val
    1445            1450                1455

Val Met Glu Val Leu Ala Ala Lys Thr Gly Tyr Glu Thr Asp Met
    1460            1465                1470

Ile Glu Ser Asp Met Glu Leu Glu Thr Glu Leu Gly Ile Asp Ser
    1475            1480                1485

Ile Lys Arg Val Glu Ile Leu Ser Glu Val Gln Ala Met Leu Asn
    1490            1495                1500

Val Glu Ala Lys Asp Val Asp Ala Leu Ser Arg Thr Arg Thr Val
    1505            1510                1515

Gly Glu Val Val Asp Ala Met Lys Ala Glu Ile Ala Gly Gly Ser
    1520            1525                1530

Ala Pro Ala Pro Ala Ala Ala Pro Ala Pro Ala Ala Ala Ala
    1535            1540                1545

Pro Ala Pro Ala Ala Pro Ala Pro Ala Ala Pro Ala Pro Ala Val
    1550            1555                1560

Ser Ser Glu Leu Leu Glu Lys Ala Glu Thr Val Val Met Glu Val
    1565            1570                1575

Leu Ala Ala Lys Thr Gly Tyr Glu Thr Asp Met Ile Glu Ser Asp
    1580            1585                1590

Met Glu Leu Glu Thr Glu Leu Gly Ile Asp Ser Ile Lys Arg Val
    1595            1600                1605

Glu Ile Leu Ser Glu Val Gln Ala Met Leu Asn Val Glu Ala Lys
    1610            1615                1620

Asp Val Asp Ala Leu Ser Arg Thr Arg Thr Val Gly Glu Val Val
    1625            1630                1635

Asp Ala Met Lys Ala Glu Ile Ala Gly Ser Ser Ala Ser Ala Pro
    1640            1645                1650

Ala Ala Ala Ala Pro Ala Pro Ala Ala Ala Ala Pro Ala Pro Ala
    1655            1660                1665

Ala Ala Ala Pro Ala Val Ser Asn Glu Leu Leu Glu Lys Ala Glu
    1670            1675                1680

Thr Val Val Met Glu Val Leu Ala Ala Lys Thr Gly Tyr Glu Thr
    1685            1690                1695

Asp Met Ile Glu Ser Asp Met Glu Leu Glu Thr Glu Leu Gly Ile
    1700            1705                1710

Asp Ser Ile Lys Arg Val Glu Ile Leu Ser Glu Val Gln Ala Met
    1715            1720                1725

Leu Asn Val Glu Ala Lys Asp Val Asp Ala Leu Ser Arg Thr Arg
    1730            1735                1740

Thr Val Gly Glu Val Val Asp Ala Met Lys Ala Glu Ile Ala Gly
    1745            1750                1755

Gly Ser Ala Pro Ala Pro Ala Ala Ala Ala Pro Ala Pro Ala Ala
```

-continued

```
            1760                1765                1770
Ala  Ala  Pro  Ala  Val  Ser  Asn  Glu  Leu  Leu  Glu  Lys  Ala  Glu  Thr
     1775                1780                1785

Val  Val  Met  Glu  Val  Leu  Ala  Ala  Lys  Thr  Gly  Tyr  Glu  Thr  Asp
     1790                1795                1800

Met  Ile  Glu  Ser  Asp  Met  Glu  Leu  Glu  Thr  Glu  Leu  Gly  Ile  Asp
     1805                1810                1815

Ser  Ile  Lys  Arg  Val  Glu  Ile  Leu  Ser  Glu  Val  Gln  Ala  Met  Leu
     1820                1825                1830

Asn  Val  Glu  Ala  Lys  Asp  Val  Asp  Ala  Leu  Ser  Arg  Thr  Arg  Thr
     1835                1840                1845

Val  Gly  Glu  Val  Val  Asp  Ala  Met  Lys  Ala  Glu  Ile  Ala  Gly  Ser
     1850                1855                1860

Ser  Ala  Pro  Ala  Pro  Ala  Ala  Ala  Pro  Ala  Pro  Ala  Ala  Ala
     1865                1870                1875

Ala  Pro  Ala  Pro  Ala  Ala  Ala  Pro  Ala  Val  Ser  Ser  Glu  Leu
     1880                1885                1890

Leu  Glu  Lys  Ala  Glu  Thr  Val  Val  Met  Glu  Val  Leu  Ala  Ala  Lys
     1895                1900                1905

Thr  Gly  Tyr  Glu  Thr  Asp  Met  Ile  Glu  Ser  Asp  Met  Glu  Leu  Glu
     1910                1915                1920

Thr  Glu  Leu  Gly  Ile  Asp  Ser  Ile  Lys  Arg  Val  Glu  Ile  Leu  Ser
     1925                1930                1935

Glu  Val  Gln  Ala  Met  Leu  Asn  Val  Glu  Ala  Lys  Asp  Val  Asp  Ala
     1940                1945                1950

Leu  Ser  Arg  Thr  Arg  Thr  Val  Gly  Glu  Val  Val  Asp  Ala  Met  Lys
     1955                1960                1965

Ala  Glu  Ile  Ala  Gly  Gly  Ser  Ala  Pro  Ala  Pro  Ala  Ala  Ala  Ala
     1970                1975                1980

Pro  Ala  Pro  Ala  Ala  Ala  Ala  Pro  Ala  Val  Ser  Asn  Glu  Leu  Leu
     1985                1990                1995

Glu  Lys  Ala  Glu  Thr  Val  Val  Met  Glu  Val  Leu  Ala  Ala  Lys  Thr
     2000                2005                2010

Gly  Tyr  Glu  Thr  Asp  Met  Ile  Glu  Ser  Asp  Met  Glu  Leu  Glu  Thr
     2015                2020                2025

Glu  Leu  Gly  Ile  Asp  Ser  Ile  Lys  Arg  Val  Glu  Ile  Leu  Ser  Glu
     2030                2035                2040

Val  Gln  Ala  Met  Leu  Asn  Val  Glu  Ala  Lys  Asp  Val  Asp  Ala  Leu
     2045                2050                2055

Ser  Arg  Thr  Arg  Thr  Val  Gly  Glu  Val  Val  Asp  Ala  Met  Lys  Ala
     2060                2065                2070

Glu  Ile  Ala  Gly  Gly  Ser  Ala  Pro  Ala  Pro  Ala  Ala  Ala  Pro
     2075                2080                2085

Ala  Ser  Ala  Gly  Ala  Ala  Pro  Ala  Val  Lys  Ile  Asp  Ser  Val  His
     2090                2095                2100

Gly  Ala  Asp  Cys  Asp  Asp  Leu  Ser  Leu  Met  His  Ala  Lys  Val  Val
     2105                2110                2115

Asp  Ile  Arg  Arg  Pro  Asp  Glu  Leu  Ile  Leu  Glu  Arg  Pro  Glu  Asn
     2120                2125                2130

Arg  Pro  Val  Leu  Val  Val  Asp  Asp  Gly  Ser  Glu  Leu  Thr  Leu  Ala
     2135                2140                2145

Leu  Val  Arg  Val  Leu  Gly  Ala  Cys  Ala  Val  Val  Leu  Thr  Phe  Glu
     2150                2155                2160
```

-continued

```
Gly Leu Gln Leu Ala Gln Arg Ala Gly Ala Ala Ala Ile Arg His
    2165                2170                2175

Val Leu Ala Lys Asp Leu Ser Ala Glu Ser Ala Glu Lys Ala Ile
    2180                2185                2190

Lys Glu Ala Glu Gln Arg Phe Gly Ala Leu Gly Gly Phe Ile Ser
    2195                2200                2205

Gln Gln Ala Glu Arg Phe Glu Pro Ala Glu Ile Leu Gly Phe Thr
    2210                2215                2220

Leu Met Cys Ala Lys Phe Ala Lys Ala Ser Leu Cys Thr Ala Val
    2225                2230                2235

Ala Gly Gly Arg Pro Ala Phe Ile Gly Val Ala Arg Leu Asp Gly
    2240                2245                2250

Arg Leu Gly Phe Thr Ser Gln Gly Thr Ser Asp Ala Leu Lys Arg
    2255                2260                2265

Ala Gln Arg Gly Ala Ile Phe Gly Leu Cys Lys Thr Ile Gly Leu
    2270                2275                2280

Glu Trp Ser Glu Ser Asp Val Phe Ser Arg Gly Val Asp Ile Ala
    2285                2290                2295

Gln Gly Met His Pro Glu Asp Ala Ala Val Ala Ile Val Arg Glu
    2300                2305                2310

Met Ala Cys Ala Asp Ile Arg Ile Arg Glu Val Gly Ile Gly Ala
    2315                2320                2325

Asn Gln Gln Arg Cys Thr Ile Arg Ala Ala Lys Leu Glu Thr Gly
    2330                2335                2340

Asn Pro Gln Arg Gln Ile Ala Lys Asp Asp Val Leu Leu Val Ser
    2345                2350                2355

Gly Gly Ala Arg Gly Ile Thr Pro Leu Cys Ile Arg Glu Ile Thr
    2360                2365                2370

Arg Gln Ile Ala Gly Gly Lys Tyr Ile Leu Leu Gly Arg Ser Lys
    2375                2380                2385

Val Ser Ala Ser Glu Pro Ala Trp Cys Ala Gly Ile Thr Asp Glu
    2390                2395                2400

Lys Ala Val Gln Lys Ala Ala Thr Gln Glu Leu Lys Arg Ala Phe
    2405                2410                2415

Ser Ala Gly Glu Gly Pro Lys Pro Thr Pro Arg Ala Val Thr Lys
    2420                2425                2430

Leu Val Gly Ser Val Leu Gly Ala Arg Glu Val Arg Ser Ser Ile
    2435                2440                2445

Ala Ala Ile Glu Ala Leu Gly Gly Lys Ala Ile Tyr Ser Ser Cys
    2450                2455                2460

Asp Val Asn Ser Ala Ala Asp Val Ala Lys Ala Val Arg Asp Ala
    2465                2470                2475

Glu Ser Gln Leu Gly Ala Arg Val Ser Gly Ile Val His Ala Ser
    2480                2485                2490

Gly Val Leu Arg Asp Arg Leu Ile Glu Lys Lys Leu Pro Asp Glu
    2495                2500                2505

Phe Asp Ala Val Phe Gly Thr Lys Val Thr Gly Leu Glu Asn Leu
    2510                2515                2520

Leu Ala Ala Val Asp Arg Ala Asn Leu Lys His Met Val Leu Phe
    2525                2530                2535

Ser Ser Leu Ala Gly Phe His Gly Asn Val Gly Gln Ser Asp Tyr
    2540                2545                2550
```

```
Ala Met Ala Asn Glu Ala Leu Asn Lys Met Gly Leu Glu Leu Ala
    2555                2560                2565

Lys Asp Val Ser Val Lys Ser Ile Cys Phe Gly Pro Trp Asp Gly
    2570                2575                2580

Gly Met Val Thr Pro Gln Leu Lys Lys Gln Phe Gln Glu Met Gly
    2585                2590                2595

Val Gln Ile Ile Pro Arg Glu Gly Ala Asp Thr Val Ala Arg
    2600                2605                2610

Ile Val Leu Gly Ser Ser Pro Ala Glu Ile Leu Val Gly Asn Trp
    2615                2620                2625

Arg Thr Pro Ser Lys Lys Val Gly Ser Asp Thr Ile Thr Leu His
    2630                2635                2640

Arg Lys Ile Ser Ala Lys Ser Asn Pro Phe Leu Glu Asp His Val
    2645                2650                2655

Ile Gln Gly Arg Arg Val Leu Pro Met Thr Leu Ala Ile Gly Ser
    2660                2665                2670

Leu Ala Glu Thr Cys Leu Gly Leu Phe Pro Gly Tyr Ser Leu Trp
    2675                2680                2685

Ala Ile Asp Asp Ala Gln Leu Phe Lys Gly Val Thr Val Asp Gly
    2690                2695                2700

Asp Val Asn Cys Glu Val Thr Leu Thr Pro Ser Thr Ala Pro Ser
    2705                2710                2715

Gly Arg Val Asn Val Gln Ala Thr Leu Lys Thr Phe Ser Ser Gly
    2720                2725                2730

Lys Leu Val Pro Ala Tyr Arg Ala Val Ile Val Leu Ser Asn Gln
    2735                2740                2745

Gly Ala Pro Pro Ala Asn Ala Thr Met Gln Pro Pro Ser Leu Asp
    2750                2755                2760

Ala Asp Pro Ala Leu Gln Gly Ser Val Tyr Asp Gly Lys Thr Leu
    2765                2770                2775

Phe His Gly Pro Ala Phe Arg Gly Ile Asp Asp Val Leu Ser Cys
    2780                2785                2790

Thr Lys Ser Gln Leu Val Ala Lys Cys Ser Ala Val Pro Gly Ser
    2795                2800                2805

Asp Ala Ala Arg Gly Glu Phe Ala Thr Asp Thr Asp Ala His Asp
    2810                2815                2820

Pro Phe Val Asn Asp Leu Ala Phe Gln Ala Met Leu Val Trp Val
    2825                2830                2835

Arg Arg Thr Leu Gly Gln Ala Ala Leu Pro Asn Ser Ile Gln Arg
    2840                2845                2850

Ile Val Gln His Arg Pro Val Pro Gln Asp Lys Pro Phe Tyr Ile
    2855                2860                2865

Thr Leu Arg Ser Asn Gln Ser Gly Gly His Ser Gln His Lys His
    2870                2875                2880

Ala Leu Gln Phe His Asn Glu Gln Gly Asp Leu Phe Ile Asp Val
    2885                2890                2895

Gln Ala Ser Val Ile Ala Thr Asp Ser Leu Ala Phe
    2900                2905                2910

<210> SEQ ID NO 3
<211> LENGTH: 6177
<212> TYPE: DNA
<213> ORGANISM: Schizochytrium sp.
<220> FEATURE:
<221> NAME/KEY: CDS
```

<222> LOCATION: (1)..(6177)

<400> SEQUENCE: 3

| | | |
|---|---|---|
| atg gcc gct cgg aat gtg agc gcc gcg cat gag atg cac gat gaa aag<br>Met Ala Ala Arg Asn Val Ser Ala Ala His Glu Met His Asp Glu Lys<br>1                    5                    10                  15 | 48 |
| cgc atc gcc gtc gtc ggc atg gcc gtc cag tac gcc gga tgc aaa acc<br>Arg Ile Ala Val Val Gly Met Ala Val Gln Tyr Ala Gly Cys Lys Thr<br>                    20                    25                    30 | 96 |
| aag gac gag ttc tgg gag gtg ctc atg aac ggc aag gtc gag tcc aag<br>Lys Asp Glu Phe Trp Glu Val Leu Met Asn Gly Lys Val Glu Ser Lys<br>                35                    40                    45 | 144 |
| gtg atc agc gac aaa cga ctc ggc tcc aac tac cgc gcc gag cac tac<br>Val Ile Ser Asp Lys Arg Leu Gly Ser Asn Tyr Arg Ala Glu His Tyr<br>50                    55                    60 | 192 |
| aaa gca gag cgc agc aag tat gcc gac acc ttt tgc aac gaa acg tac<br>Lys Ala Glu Arg Ser Lys Tyr Ala Asp Thr Phe Cys Asn Glu Thr Tyr<br>65                    70                    75                    80 | 240 |
| ggc acc ctt gac gag aac gag atc gac aac gag cac gaa ctc ctc ctc<br>Gly Thr Leu Asp Glu Asn Glu Ile Asp Asn Glu His Glu Leu Leu Leu<br>                          85                    90                    95 | 288 |
| aac ctc gcc aag cag gca ctc gca gag aca tcc gtc aaa gac tcg aca<br>Asn Leu Ala Lys Gln Ala Leu Ala Glu Thr Ser Val Lys Asp Ser Thr<br>                    100                 105               110 | 336 |
| cgc tgc ggc atc gtc agc ggc tgc ctc tcg ttc ccc atg gac aac ctc<br>Arg Cys Gly Ile Val Ser Gly Cys Leu Ser Phe Pro Met Asp Asn Leu<br>            115                    120                 125 | 384 |
| cag ggt gaa ctc ctc aac gtg tac caa aac cat gtc gag aaa aag ctc<br>Gln Gly Glu Leu Leu Asn Val Tyr Gln Asn His Val Glu Lys Lys Leu<br>130                     135                    140 | 432 |
| ggg gcc cgc gtc ttc aag gac gcc tcc cat tgg tcc gaa cgc gag cag<br>Gly Ala Arg Val Phe Lys Asp Ala Ser His Trp Ser Glu Arg Glu Gln<br>145                     150                    155                    160 | 480 |
| tcc aac aaa ccc gag gcc ggt gac cgc cgc atc ttc atg gac ccg gcc<br>Ser Asn Lys Pro Glu Ala Gly Asp Arg Arg Ile Phe Met Asp Pro Ala<br>                    165                 170               175 | 528 |
| tcc ttc gtc gcc gaa gaa ctc aac ctc ggc gcc ctt cac tac tcc gtc<br>Ser Phe Val Ala Glu Glu Leu Asn Leu Gly Ala Leu His Tyr Ser Val<br>                    180                 185               190 | 576 |
| gac gca gca tgc gcc acg gcg ctc tac gtg ctc cgc ctc gcg cag gat<br>Asp Ala Ala Cys Ala Thr Ala Leu Tyr Val Leu Arg Leu Ala Gln Asp<br>            195                    200                 205 | 624 |
| cat ctc gtc tcc ggc gcc gcc gac gtc atg ctc tgc ggt gcc acc tgc<br>His Leu Val Ser Gly Ala Ala Asp Val Met Leu Cys Gly Ala Thr Cys<br>210                     215                    220 | 672 |
| ctg ccg gag ccc ttt ttc atc ctt tcg ggc ttt tcc acc ttc cag gcc<br>Leu Pro Glu Pro Phe Phe Ile Leu Ser Gly Phe Ser Thr Phe Gln Ala<br>225                     230                    235                    240 | 720 |
| atg ccc gtc ggc acg ggc cag aac gtg tcc atg ccg ctg cac aag gac<br>Met Pro Val Gly Thr Gly Gln Asn Val Ser Met Pro Leu His Lys Asp<br>                    245                 250               255 | 768 |
| agc cag ggc ctc acc ccg ggt gag ggc ggc tcc atc atg gtc ctc aag<br>Ser Gln Gly Leu Thr Pro Gly Glu Gly Gly Ser Ile Met Val Leu Lys<br>            260                    265                 270 | 816 |
| cgt ctc gat gat gcc atc cgc gac ggc gac cac att tac ggc acc ctt<br>Arg Leu Asp Asp Ala Ile Arg Asp Gly Asp His Ile Tyr Gly Thr Leu<br>            275                    280                 285 | 864 |
| ctc ggc gcc aat gtc agc aac tcc ggc aca ggt ctg ccc ctc aag ccc<br>Leu Gly Ala Asn Val Ser Asn Ser Gly Thr Gly Leu Pro Leu Lys Pro<br>290                     295                    300 | 912 |

```
ctt ctc ccc agc gag aaa aag tgc ctc atg gac acc tac acg cgc att      960
Leu Leu Pro Ser Glu Lys Lys Cys Leu Met Asp Thr Tyr Thr Arg Ile
305                 310                 315                 320 aac gtg cac ccg cac aag att cag tac gtc gag tgc cac gcc acc ggc     1008
Asn Val His Pro His Lys Ile Gln Tyr Val Glu Cys His Ala Thr Gly
                325                 330                 335 acg ccc cag ggt gat cgt gtg gaa atc gac gcc gtc aag gcc tgc ttt     1056
Thr Pro Gln Gly Asp Arg Val Glu Ile Asp Ala Val Lys Ala Cys Phe
            340                 345                 350 gaa ggc aag gtc ccc cgt ttc ggt acc aca aag ggc aac ttt gga cac     1104
Glu Gly Lys Val Pro Arg Phe Gly Thr Thr Lys Gly Asn Phe Gly His
        355                 360                 365 acc cts gyc gca gcc ggc ttt gcc ggt atg tgc aag gtc ctc ctc tcc     1152
Thr Xaa Xaa Ala Ala Gly Phe Ala Gly Met Cys Lys Val Leu Leu Ser
    370                 375                 380 atg aag cat ggc atc atc ccg ccc acc ccg ggt atc gat gac gag acc     1200
Met Lys His Gly Ile Ile Pro Pro Thr Pro Gly Ile Asp Asp Glu Thr
385                 390                 395                 400 aag atg gac cct ctc gtc gtc tcc ggt gag gcc atc cca tgg cca gag     1248
Lys Met Asp Pro Leu Val Val Ser Gly Glu Ala Ile Pro Trp Pro Glu
                405                 410                 415 acc aac ggc gag ccc aag cgc gcc ggt ctc tcg gcc ttt ggc ttt ggt     1296
Thr Asn Gly Glu Pro Lys Arg Ala Gly Leu Ser Ala Phe Gly Phe Gly
                420                 425                 430 ggc acc aac gcc cat gcc gtc ttt gag gag cat gac ccc tcc aac gcc     1344
Gly Thr Asn Ala His Ala Val Phe Glu Glu His Asp Pro Ser Asn Ala
            435                 440                 445 gcc tgc acg ggc cac gac tcc att tct gcg ctc tcg gcc cgc tgc ggc     1392
Ala Cys Thr Gly His Asp Ser Ile Ser Ala Leu Ser Ala Arg Cys Gly
        450                 455                 460 ggt gaa agc aac atg cgc atc gcc atc act ggt atg gac gcc acc ttt     1440
Gly Glu Ser Asn Met Arg Ile Ala Ile Thr Gly Met Asp Ala Thr Phe
465                 470                 475                 480 ggc gct ctc aag gga ctc gac gcc ttc gag cgc gcc att tac acc ggc     1488
Gly Ala Leu Lys Gly Leu Asp Ala Phe Glu Arg Ala Ile Tyr Thr Gly
                485                 490                 495 gct cac ggt gcc atc cca ctc cca gaa aag cgc tgg cgc ttt ctc ggc     1536
Ala His Gly Ala Ile Pro Leu Pro Glu Lys Arg Trp Arg Phe Leu Gly
                500                 505                 510 aag gac aag gac ttt ctt gac ctc tgc ggc gtc aag gcc acc ccg cac     1584
Lys Asp Lys Asp Phe Leu Asp Leu Cys Gly Val Lys Ala Thr Pro His
            515                 520                 525 ggc tgc tac att gaa gat gtt gag gtc gac ttc cag cgc ctc cgc acg     1632
Gly Cys Tyr Ile Glu Asp Val Glu Val Asp Phe Gln Arg Leu Arg Thr
        530                 535                 540 ccc atg acc cct gaa gac atg ctc ctc cct cag cag ctt ctg gcc gtc     1680
Pro Met Thr Pro Glu Asp Met Leu Leu Pro Gln Gln Leu Leu Ala Val
545                 550                 555                 560 acc acc att gac cgc gcc atc ctc gac tcg gga atg aaa aag ggt ggc     1728
Thr Thr Ile Asp Arg Ala Ile Leu Asp Ser Gly Met Lys Lys Gly Gly
                565                 570                 575 aat gtc gcc gtc ttt gtc ggc ctc ggc acc gac ctc gag ctc tac cgt     1776
Asn Val Ala Val Phe Val Gly Leu Gly Thr Asp Leu Glu Leu Tyr Arg
                580                 585                 590 cac cgt gct cgc gtc gct ctc aag gag cgc gtc cgc cct gaa gcc tcc     1824
His Arg Ala Arg Val Ala Leu Lys Glu Arg Val Arg Pro Glu Ala Ser
            595                 600                 605 aag aag ctc aat gac atg atg cag tac att aac gac tgc ggc aca tcc     1872
Lys Lys Leu Asn Asp Met Met Gln Tyr Ile Asn Asp Cys Gly Thr Ser
```

-continued

```
            610                 615                 620
aca tcg tac acc tcg tac att ggc aac ctc gtc gcc acg cgc gtc tcg     1920
Thr Ser Tyr Thr Ser Tyr Ile Gly Asn Leu Val Ala Thr Arg Val Ser
625                 630                 635                 640 tcg cag tgg ggc ttc acg ggc ccc tcc ttt acg atc acc gag ggc aac     1968
Ser Gln Trp Gly Phe Thr Gly Pro Ser Phe Thr Ile Thr Glu Gly Asn
                645                 650                 655 aac tcc gtc tac cgc tgc gcc gag ctc ggc aag tac ctc ctc gag acc     2016
Asn Ser Val Tyr Arg Cys Ala Glu Leu Gly Lys Tyr Leu Leu Glu Thr
                660                 665                 670 ggc gag gtc gat ggc gtc gtc gtt gcg ggt gtc gat ctc tgc ggc agt     2064
Gly Glu Val Asp Gly Val Val Val Ala Gly Val Asp Leu Cys Gly Ser
675                 680                 685 gcc gaa aac ctt tac gtc aag tct cgc cgc ttc aag gtg tcc acc tcc     2112
Ala Glu Asn Leu Tyr Val Lys Ser Arg Arg Phe Lys Val Ser Thr Ser
690                 695                 700 gat acc ccg cgc gcc agc ttt gac gcc gcc gcc gat ggc tac ttt gtc     2160
Asp Thr Pro Arg Ala Ser Phe Asp Ala Ala Ala Asp Gly Tyr Phe Val
705                 710                 715                 720 ggc gag ggc tgc ggt gcc ttt gtg ctc aag cgt gag act agc tgc acc     2208
Gly Glu Gly Cys Gly Ala Phe Val Leu Lys Arg Glu Thr Ser Cys Thr
                725                 730                 735 aag gac gac cgt atc tac gct tgc atg gat gcc atc gtc cct ggc aac     2256
Lys Asp Asp Arg Ile Tyr Ala Cys Met Asp Ala Ile Val Pro Gly Asn
                740                 745                 750 gtc cct agc gcc tgc ttg cgc gag gcc ctc gac cag gcg cgc gtc aag     2304
Val Pro Ser Ala Cys Leu Arg Glu Ala Leu Asp Gln Ala Arg Val Lys
                755                 760                 765 ccg ggc gat atc gag atg ctc gag ctc agc gcc gac tcc gcc cgc cac     2352
Pro Gly Asp Ile Glu Met Leu Glu Leu Ser Ala Asp Ser Ala Arg His
770                 775                 780 ctc aag gac ccg tcc gtc ctg ccc aag gag ctc act gcc gag gag gaa     2400
Leu Lys Asp Pro Ser Val Leu Pro Lys Glu Leu Thr Ala Glu Glu Glu
785                 790                 795                 800 atc ggc ggc ctt cag acg atc ctt cgt gac gat gac aag ctc ccg cgc     2448
Ile Gly Gly Leu Gln Thr Ile Leu Arg Asp Asp Asp Lys Leu Pro Arg
                805                 810                 815 aac gtc gca acg ggc agt gtc aag gcc acc gtc ggt gac acc ggt tat     2496
Asn Val Ala Thr Gly Ser Val Lys Ala Thr Val Gly Asp Thr Gly Tyr
                820                 825                 830 gcc tct ggt gct gcc agc ctc atc aag gct gcg ctt tgc atc tac aac     2544
Ala Ser Gly Ala Ala Ser Leu Ile Lys Ala Ala Leu Cys Ile Tyr Asn
                835                 840                 845 cgc tac ctg ccc agc aac ggc gac gac tgg gat gaa ccc gcc cct gag     2592
Arg Tyr Leu Pro Ser Asn Gly Asp Asp Trp Asp Glu Pro Ala Pro Glu
850                 855                 860 gcg ccc tgg gac agc acc ctc ttt gcg tgc cag acc tcg cgc gct tgg     2640
Ala Pro Trp Asp Ser Thr Leu Phe Ala Cys Gln Thr Ser Arg Ala Trp
865                 870                 875                 880 ctc aag aac cct ggc gag cgt cgc tat gcg gcc gtc tcg ggc gtc tcc     2688
Leu Lys Asn Pro Gly Glu Arg Arg Tyr Ala Ala Val Ser Gly Val Ser
                885                 890                 895 gag acg cgc tcg tgc tat tcc gtg ctc ctc tcc gaa gcc gag ggc cac     2736
Glu Thr Arg Ser Cys Tyr Ser Val Leu Leu Ser Glu Ala Glu Gly His
                900                 905                 910 tac gag cgc gag aac cgc atc tcg ctc gac gag gag gcg ccc aag ctc     2784
Tyr Glu Arg Glu Asn Arg Ile Ser Leu Asp Glu Glu Ala Pro Lys Leu
915                 920                 925 att gtg ctt cgc gcc gac tcc cac gag gag atc ctt ggt cgc ctc gac     2832
```

-continued

```
                Ile Val Leu Arg Ala Asp Ser His Glu Glu Ile Leu Gly Arg Leu Asp
                    930                 935                 940 aag atc cgc gag cgc ttc ttg cag ccc acg ggc gcc gcc ccg cgc gag    2880
Lys Ile Arg Glu Arg Phe Leu Gln Pro Thr Gly Ala Ala Pro Arg Glu
945                 950                 955                 960 tcc gag ctc aag gcg cag gcc cgc cgc atc ttc ctc gag ctc ctc ggc    2928
Ser Glu Leu Lys Ala Gln Ala Arg Arg Ile Phe Leu Glu Leu Leu Gly
                965                 970                 975 gag acc ctt gcc cag gat gcc gct tct tca ggc tcg caa aag ccc ctc    2976
Glu Thr Leu Ala Gln Asp Ala Ala Ser Ser Gly Ser Gln Lys Pro Leu
            980                 985                 990 gct ctc agc ctc gtc tcc acg ccc tcc aag ctc cag cgc gag gtc gag    3024
Ala Leu Ser Leu Val Ser Thr Pro Ser Lys Leu Gln Arg Glu Val Glu
        995                 1000                1005 ctc gcg gcc aag ggt atc ccg cgc tgc ctc aag atg cgc cgc gat        3069
Leu Ala Ala Lys Gly Ile Pro Arg Cys Leu Lys Met Arg Arg Asp
    1010                1015                1020 tgg agc tcc cct gct ggc agc cgc tac gcg cct gag ccg ctc gcc        3114
Trp Ser Ser Pro Ala Gly Ser Arg Tyr Ala Pro Glu Pro Leu Ala
    1025                1030                1035 agc gac cgc gtc gcc ttc atg tac ggc gaa ggt cgc agc cct tac        3159
Ser Asp Arg Val Ala Phe Met Tyr Gly Glu Gly Arg Ser Pro Tyr
    1040                1045                1050 tac ggc atc acc caa gac att cac cgc att tgg ccc gaa ctc cac        3204
Tyr Gly Ile Thr Gln Asp Ile His Arg Ile Trp Pro Glu Leu His
    1055                1060                1065 gag gtc atc aac gaa aag acg aac cgt ctc tgg gcc gaa ggc gac        3249
Glu Val Ile Asn Glu Lys Thr Asn Arg Leu Trp Ala Glu Gly Asp
    1070                1075                1080 cgc tgg gtc atg ccg cgc gcc agc ttc aag tcg gag ctc gag agc        3294
Arg Trp Val Met Pro Arg Ala Ser Phe Lys Ser Glu Leu Glu Ser
    1085                1090                1095 cag cag caa gag ttt gat cgc aac atg att gaa atg ttc cgt ctt        3339
Gln Gln Gln Glu Phe Asp Arg Asn Met Ile Glu Met Phe Arg Leu
    1100                1105                1110 gga atc ctc acc tca att gcc ttc acc aat ctg gcg cgc gac gtt        3384
Gly Ile Leu Thr Ser Ile Ala Phe Thr Asn Leu Ala Arg Asp Val
    1115                1120                1125 ctc aac atc acg ccc aag gcc gcc ttt ggc ctc agt ctt ggc gag        3429
Leu Asn Ile Thr Pro Lys Ala Ala Phe Gly Leu Ser Leu Gly Glu
    1130                1135                1140 att tcc atg att ttt gcc ttt tcc aag aag aac ggt ctc atc tcc        3474
Ile Ser Met Ile Phe Ala Phe Ser Lys Lys Asn Gly Leu Ile Ser
    1145                1150                1155 gac cag ctc acc aag gat ctt cgc gag tcc gac gtg tgg aac aag        3519
Asp Gln Leu Thr Lys Asp Leu Arg Glu Ser Asp Val Trp Asn Lys
    1160                1165                1170 gct ctg gcc gtt gaa ttt aat gcg ctg cgc gag gcc tgg ggc att        3564
Ala Leu Ala Val Glu Phe Asn Ala Leu Arg Glu Ala Trp Gly Ile
    1175                1180                1185 cca cag agt gtc ccc aag gac gag ttc tgg caa ggc tac att gtg        3609
Pro Gln Ser Val Pro Lys Asp Glu Phe Trp Gln Gly Tyr Ile Val
    1190                1195                1200 cgc ggc acc aag cag gat atc gag gcg gcc atc gcc ccg gac agc        3654
Arg Gly Thr Lys Gln Asp Ile Glu Ala Ala Ile Ala Pro Asp Ser
    1205                1210                1215 aag tac gtg cgc ctc acc atc atc aat gat gcc aac acc gcc ctc        3699
Lys Tyr Val Arg Leu Thr Ile Ile Asn Asp Ala Asn Thr Ala Leu
    1220                1225                1230
```

```
                                      -continued att agc ggc aag ccc gac gcc tgc aag gct gcg atc gcg cgt ctc      3744
Ile Ser Gly Lys Pro Asp Ala Cys Lys Ala Ala Ile Ala Arg Leu
    1235            1240                1245 ggt ggc aac att cct gcg ctt ccc gtg acc cag ggc atg tgc ggc      3789
Gly Gly Asn Ile Pro Ala Leu Pro Val Thr Gln Gly Met Cys Gly
1250            1255                1260 cac tgc ccc gag gtg gga cct tat acc aag gat atc gcc aag atc      3834
His Cys Pro Glu Val Gly Pro Tyr Thr Lys Asp Ile Ala Lys Ile
        1265            1270                1275 cat gcc aac ctt gag ttc ccc gtt gtc gac ggc ctt gac ctc tgg      3879
His Ala Asn Leu Glu Phe Pro Val Val Asp Gly Leu Asp Leu Trp
            1280            1285                1290 acc aca atc aac cag aag cgc ctc gtg cca cgc gcc acg ggc gcc      3924
Thr Thr Ile Asn Gln Lys Arg Leu Val Pro Arg Ala Thr Gly Ala
                1295            1300                1305 aag gac gaa tgg gcc cct tct tcc ttt ggc gag tac gcc ggc cag      3969
Lys Asp Glu Trp Ala Pro Ser Ser Phe Gly Glu Tyr Ala Gly Gln
                    1310            1315                1320 ctc tac gag aag cag gct aac ttc ccc caa atc gtc gag acc att      4014
Leu Tyr Glu Lys Gln Ala Asn Phe Pro Gln Ile Val Glu Thr Ile
1325            1330                1335 tac aag caa aac tac gac gtc ttt gtc gag gtt ggg ccc aac aac      4059
Tyr Lys Gln Asn Tyr Asp Val Phe Val Glu Val Gly Pro Asn Asn
    1340            1345                1350 cac cgt agc acc gca gtg cgc acc acg ctt ggt ccc cag cgc aac      4104
His Arg Ser Thr Ala Val Arg Thr Thr Leu Gly Pro Gln Arg Asn
        1355            1360                1365 cac ctt gct ggc gcc atc gac aag cag aac gag gat gct tgg acg      4149
His Leu Ala Gly Ala Ile Asp Lys Gln Asn Glu Asp Ala Trp Thr
            1370            1375                1380 acc atc gtc aag ctt gtg gct tcg ctc aag gcc cac ctt gtt cct      4194
Thr Ile Val Lys Leu Val Ala Ser Leu Lys Ala His Leu Val Pro
                1385            1390                1395 ggc gtc acg atc tcg ccg ctg tac cac tcc aag ctt gtg gcg gag      4239
Gly Val Thr Ile Ser Pro Leu Tyr His Ser Lys Leu Val Ala Glu
                    1400            1405                1410 gct cag gct tgc tac gct gcg ctc tgc aag ggt gaa aag ccc aag      4284
Ala Gln Ala Cys Tyr Ala Ala Leu Cys Lys Gly Glu Lys Pro Lys
1415            1420                1425 aag aac aag ttt gtg cgc aag att cag ctc aac ggt cgc ttc aac      4329
Lys Asn Lys Phe Val Arg Lys Ile Gln Leu Asn Gly Arg Phe Asn
    1430            1435                1440 agc aag gcg gac ccc atc tcc tcg gcc gat ctt gcc agc ttt ccg      4374
Ser Lys Ala Asp Pro Ile Ser Ser Ala Asp Leu Ala Ser Phe Pro
        1445            1450                1455 cct gcg gac cct gcc att gaa gcc gcc atc tcg agc cgc atc atg      4419
Pro Ala Asp Pro Ala Ile Glu Ala Ala Ile Ser Ser Arg Ile Met
            1460            1465                1470 aag cct gtc gct ccc aag ttc tac gcg cgt ctc aac att gac gag      4464
Lys Pro Val Ala Pro Lys Phe Tyr Ala Arg Leu Asn Ile Asp Glu
                1475            1480                1485 cag gac gag acc cga gat ccg atc ctc aac aag gac aac gcg ccg      4509
Gln Asp Glu Thr Arg Asp Pro Ile Leu Asn Lys Asp Asn Ala Pro
                    1490            1495                1500 tct tct tct tct tct tct tct tct tct tct tct tct tct tct tct      4554
Ser Ser Ser Ser Ser Ser Ser Ser Ser Ser Ser Ser Ser Ser Ser
1505            1510                1515 ccg tcg cct gct cct tcg gcc ccc gtg caa aag aag gct gct ccc      4599
Pro Ser Pro Ala Pro Ser Ala Pro Val Gln Lys Lys Ala Ala Pro
    1520            1525                1530
```

| | | | | | | | | | | | | |
|---|---|---|---|---|---|---|---|---|---|---|---|---|
| gcc | gcg | gag | acc | aag | gct | gtt | gct | tcg | gct | gac | gca | ctt cgc agt | 4644 |
| Ala | Ala | Glu | Thr | Lys | Ala | Val | Ala | Ser | Ala | Asp | Ala | Leu Arg Ser |
| | 1535 | | | | 1540 | | | | | 1545 | | |
| gcc | ctg | ctc | gat | ctc | gac | agt | atg | ctt | gcg | ctg | agc | tct gcc agt | 4689 |
| Ala | Leu | Leu | Asp | Leu | Asp | Ser | Met | Leu | Ala | Leu | Ser | Ser Ala Ser |
| 1550 | | | | | 1555 | | | | | 1560 | | |
| gcc | tcc | ggc | aac | ctt | gtt | gag | act | gcg | cct | agc | gac | gcc tcg gtc | 4734 |
| Ala | Ser | Gly | Asn | Leu | Val | Glu | Thr | Ala | Pro | Ser | Asp | Ala Ser Val |
| 1565 | | | | | 1570 | | | | | 1575 | | |
| att | gtg | ccg | ccc | tgc | aac | att | gcg | gat | ctc | ggc | agc | cgc gcc ttc | 4779 |
| Ile | Val | Pro | Pro | Cys | Asn | Ile | Ala | Asp | Leu | Gly | Ser | Arg Ala Phe |
| 1580 | | | | | 1585 | | | | | 1590 | | |
| atg | aaa | acg | tac | ggt | gtt | tcg | gcg | cct | ctg | tac | acg | ggc gcc atg | 4824 |
| Met | Lys | Thr | Tyr | Gly | Val | Ser | Ala | Pro | Leu | Tyr | Thr | Gly Ala Met |
| | 1595 | | | | 1600 | | | | | 1605 | | |
| gcc | aag | ggc | att | gcc | tct | gcg | gac | ctc | gtc | att | gcc | gcc ggc cgc | 4869 |
| Ala | Lys | Gly | Ile | Ala | Ser | Ala | Asp | Leu | Val | Ile | Ala | Ala Gly Arg |
| 1610 | | | | | 1615 | | | | | 1620 | | |
| cag | ggc | atc | ctt | gcg | tcc | ttt | ggc | gcc | ggc | gga | ctt | ccc atg cag | 4914 |
| Gln | Gly | Ile | Leu | Ala | Ser | Phe | Gly | Ala | Gly | Gly | Leu | Pro Met Gln |
| 1625 | | | | | 1630 | | | | | 1635 | | |
| gtt | gtg | cgt | gag | tcc | atc | gaa | aag | att | cag | gcc | gcc | ctg ccc aat | 4959 |
| Val | Val | Arg | Glu | Ser | Ile | Glu | Lys | Ile | Gln | Ala | Ala | Leu Pro Asn |
| | 1640 | | | | 1645 | | | | | 1650 | | |
| ggc | ccg | tac | gct | gtc | aac | ctt | atc | cat | tct | ccc | ttt | gac agc aac | 5004 |
| Gly | Pro | Tyr | Ala | Val | Asn | Leu | Ile | His | Ser | Pro | Phe | Asp Ser Asn |
| | 1655 | | | | 1660 | | | | | 1665 | | |
| ctc | gaa | aag | ggc | aat | gtc | gat | ctc | ttc | ctc | gag | aag | ggt gtc acc | 5049 |
| Leu | Glu | Lys | Gly | Asn | Val | Asp | Leu | Phe | Leu | Glu | Lys | Gly Val Thr |
| 1670 | | | | | 1675 | | | | | 1680 | | |
| ttt | gtc | gag | gcc | tcg | gcc | ttt | atg | acg | ctc | acc | ccg | cag gtc gtg | 5094 |
| Phe | Val | Glu | Ala | Ser | Ala | Phe | Met | Thr | Leu | Thr | Pro | Gln Val Val |
| 1685 | | | | | 1690 | | | | | 1695 | | |
| cgg | tac | cgc | gcg | gct | ggc | ctc | acg | cgc | aac | gcc | gac | ggc tcg gtc | 5139 |
| Arg | Tyr | Arg | Ala | Ala | Gly | Leu | Thr | Arg | Asn | Ala | Asp | Gly Ser Val |
| | 1700 | | | | 1705 | | | | | 1710 | | |
| aac | atc | cgc | aac | cgt | atc | att | ggc | aag | gtc | tcg | cgc | acc gag ctc | 5184 |
| Asn | Ile | Arg | Asn | Arg | Ile | Ile | Gly | Lys | Val | Ser | Arg | Thr Glu Leu |
| 1715 | | | | | 1720 | | | | | 1725 | | |
| gcc | gag | atg | ttc | atg | cgt | cct | gcg | ccc | gag | cac | ctt | ctt cag aag | 5229 |
| Ala | Glu | Met | Phe | Met | Arg | Pro | Ala | Pro | Glu | His | Leu | Leu Gln Lys |
| | 1730 | | | | 1735 | | | | | 1740 | | |
| ctc | att | gct | tcc | ggc | gag | atc | aac | cag | gag | cag | gcc | gag ctc gcc | 5274 |
| Leu | Ile | Ala | Ser | Gly | Glu | Ile | Asn | Gln | Glu | Gln | Ala | Glu Leu Ala |
| 1745 | | | | | 1750 | | | | | 1755 | | |
| cgc | cgt | gtt | ccc | gtc | gct | gac | gac | atc | gcg | gtc | gaa | gct gac tcg | 5319 |
| Arg | Arg | Val | Pro | Val | Ala | Asp | Asp | Ile | Ala | Val | Glu | Ala Asp Ser |
| 1760 | | | | | 1765 | | | | | 1770 | | |
| ggt | ggc | cac | acc | gac | aac | cgc | ccc | atc | cac | gtc | att | ctg ccc ctc | 5364 |
| Gly | Gly | His | Thr | Asp | Asn | Arg | Pro | Ile | His | Val | Ile | Leu Pro Leu |
| 1775 | | | | | 1780 | | | | | 1785 | | |
| atc | atc | aac | ctt | cgc | gac | cgc | ctt | cac | cgc | gag | tgc | ggc tac ccg | 5409 |
| Ile | Ile | Asn | Leu | Arg | Asp | Arg | Leu | His | Arg | Glu | Cys | Gly Tyr Pro |
| 1790 | | | | | 1795 | | | | | 1800 | | |
| gcc | aac | ctt | cgc | gtc | cgt | gtg | ggc | gcc | ggt | ggc | att | ggg tgc | 5454 |
| Ala | Asn | Leu | Arg | Val | Arg | Val | Gly | Ala | Gly | Gly | Ile | Gly Cys |
| 1805 | | | | | 1810 | | | | | 1815 | | |
| ccc | cag | gcg | gcg | ctg | gcc | acc | ttc | aac | atg | ggt | gcc | tcc ttt att | 5499 |
| Pro | Gln | Ala | Ala | Leu | Ala | Thr | Phe | Asn | Met | Gly | Ala | Ser Phe Ile |

-continued

```
                  1820                1825                1830
gtc acc ggc acc gtg aac cag gtc gcc aag cag tcg ggc acg tgc       5544
Val Thr Gly Thr Val Asn Gln Val Ala Lys Gln Ser Gly Thr Cys
    1835                1840                1845 gac aat gtg cgc aag cag ctc gcg aag gcc act tac tcg gac gta       5589
Asp Asn Val Arg Lys Gln Leu Ala Lys Ala Thr Tyr Ser Asp Val
    1850                1855                1860 tgc atg gcc ccg gct gcc gac atg ttc gag gaa ggc gtc aag ctt       5634
Cys Met Ala Pro Ala Ala Asp Met Phe Glu Glu Gly Val Lys Leu
    1865                1870                1875 cag gtc ctc aag aag gga acc atg ttt ccc tcg cgc gcc aac aag       5679
Gln Val Leu Lys Lys Gly Thr Met Phe Pro Ser Arg Ala Asn Lys
    1880                1885                1890 ctc tac gag ctc ttt tgc aag tac gac tcg ttc gag tcc atg ccc       5724
Leu Tyr Glu Leu Phe Cys Lys Tyr Asp Ser Phe Glu Ser Met Pro
    1895                1900                1905 ccc gca gag ctt gcg cgc gtc gag aag cgc atc ttc agc cgc gcg       5769
Pro Ala Glu Leu Ala Arg Val Glu Lys Arg Ile Phe Ser Arg Ala
    1910                1915                1920 ctc gaa gag gtc tgg gac gag acc aaa aac ttt tac att aac cgt       5814
Leu Glu Glu Val Trp Asp Glu Thr Lys Asn Phe Tyr Ile Asn Arg
    1925                1930                1935 ctt cac aac ccg gag aag atc cag cgc gcc gag cgc gac ccc aag       5859
Leu His Asn Pro Glu Lys Ile Gln Arg Ala Glu Arg Asp Pro Lys
    1940                1945                1950 ctc aag atg tcg ctg tgc ttt cgc tgg tac ctg agc ctg gcg agc       5904
Leu Lys Met Ser Leu Cys Phe Arg Trp Tyr Leu Ser Leu Ala Ser
    1955                1960                1965 cgc tgg gcc aac act gga gct tcc gat cgc gtc atg gac tac cag       5949
Arg Trp Ala Asn Thr Gly Ala Ser Asp Arg Val Met Asp Tyr Gln
    1970                1975                1980 gtc tgg tgc ggt cct gcc att ggt tcc ttc aac gat ttc atc aag       5994
Val Trp Cys Gly Pro Ala Ile Gly Ser Phe Asn Asp Phe Ile Lys
    1985                1990                1995 gga act tac ctt gat ccg gcc gtc gca aac gag tac ccg tgc gtc       6039
Gly Thr Tyr Leu Asp Pro Ala Val Ala Asn Glu Tyr Pro Cys Val
    2000                2005                2010 gtt cag att aac aag cag atc ctt cgt gga gcg tgc ttc ttg cgc       6084
Val Gln Ile Asn Lys Gln Ile Leu Arg Gly Ala Cys Phe Leu Arg
    2015                2020                2025 cgt ctc gaa att ctg cgc aac gca cgc ctt tcc gat ggc gct gcc       6129
Arg Leu Glu Ile Leu Arg Asn Ala Arg Leu Ser Asp Gly Ala Ala
    2030                2035                2040 gct ctt gtg gcc agc atc gat gac aca tac gtc ccg gcc gag aag       6174
Ala Leu Val Ala Ser Ile Asp Asp Thr Tyr Val Pro Ala Glu Lys
    2045                2050                2055 ctg                                                                6177
Leu
```

<210> SEQ ID NO 4
<211> LENGTH: 2059
<212> TYPE: PRT
<213> ORGANISM: Schizochytrium sp.
<220> FEATURE:
<221> NAME/KEY: misc_feature
<222> LOCATION: (370)..(370)
<223> OTHER INFORMATION: The 'Xaa' at location 370 stands for Leu.
<220> FEATURE:
<221> NAME/KEY: misc_feature
<222> LOCATION: (371)..(371)
<223> OTHER INFORMATION: The 'Xaa' at location 371 stands for Ala, or
      Val.

```
<400> SEQUENCE: 4

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160

Ser Asn Lys Pro Glu Ala Gly Asp Arg Arg Ile Phe Met Asp Pro Ala
                165                 170                 175

Ser Phe Val Ala Glu Glu Leu Asn Leu Gly Ala Leu His Tyr Ser Val
            180                 185                 190

Asp Ala Ala Cys Ala Thr Ala Leu Tyr Val Leu Arg Leu Ala Gln Asp
        195                 200                 205

His Leu Val Ser Gly Ala Ala Asp Val Met Leu Cys Gly Ala Thr Cys
    210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
            260                 265                 270

Arg Leu Asp Asp Ala Ile Arg Asp Gly Asp His Ile Tyr Gly Thr Leu
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Xaa Xaa Ala Ala Gly Phe Ala Gly Met Cys Lys Val Leu Leu Ser
    370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
```

```
                405                 410                 415
Thr Asn Gly Glu Pro Lys Arg Ala Gly Leu Ser Ala Phe Gly Phe Gly
                420                 425                 430

Gly Thr Asn Ala His Ala Val Phe Glu Glu His Asp Pro Ser Asn Ala
            435                 440                 445

Ala Cys Thr Gly His Asp Ser Ile Ser Ala Leu Ser Ala Arg Cys Gly
        450                 455                 460

Gly Glu Ser Asn Met Arg Ile Ala Ile Thr Gly Met Asp Ala Thr Phe
465                 470                 475                 480

Gly Ala Leu Lys Gly Leu Asp Ala Phe Glu Arg Ala Ile Tyr Thr Gly
                485                 490                 495

Ala His Gly Ala Ile Pro Leu Pro Glu Lys Arg Trp Arg Phe Leu Gly
            500                 505                 510

Lys Asp Lys Asp Phe Leu Asp Leu Cys Gly Val Lys Ala Thr Pro His
        515                 520                 525

Gly Cys Tyr Ile Glu Asp Val Glu Val Asp Phe Gln Arg Leu Arg Thr
    530                 535                 540

Pro Met Thr Pro Glu Asp Met Leu Leu Pro Gln Gln Leu Leu Ala Val
545                 550                 555                 560

Thr Thr Ile Asp Arg Ala Ile Leu Asp Ser Gly Met Lys Lys Gly Gly
                565                 570                 575

Asn Val Ala Val Phe Val Gly Leu Gly Thr Asp Leu Glu Leu Tyr Arg
            580                 585                 590

His Arg Ala Arg Val Ala Leu Lys Glu Arg Val Arg Pro Glu Ala Ser
        595                 600                 605

Lys Lys Leu Asn Asp Met Met Gln Tyr Ile Asn Asp Cys Gly Thr Ser
    610                 615                 620

Thr Ser Tyr Thr Ser Tyr Ile Gly Asn Leu Val Ala Thr Arg Val Ser
625                 630                 635                 640

Ser Gln Trp Gly Phe Thr Gly Pro Ser Phe Thr Ile Thr Glu Gly Asn
                645                 650                 655

Asn Ser Val Tyr Arg Cys Ala Glu Leu Gly Lys Tyr Leu Leu Glu Thr
            660                 665                 670

Gly Glu Val Asp Gly Val Val Ala Gly Val Asp Leu Cys Gly Ser
        675                 680                 685

Ala Glu Asn Leu Tyr Val Lys Ser Arg Arg Phe Lys Val Ser Thr Ser
    690                 695                 700

Asp Thr Pro Arg Ala Ser Phe Asp Ala Ala Asp Gly Tyr Phe Val
705                 710                 715                 720

Gly Glu Gly Cys Gly Ala Phe Val Leu Lys Arg Glu Thr Ser Cys Thr
                725                 730                 735

Lys Asp Asp Arg Ile Tyr Ala Cys Met Asp Ala Ile Val Pro Gly Asn
            740                 745                 750

Val Pro Ser Ala Cys Leu Arg Glu Ala Leu Asp Gln Ala Arg Val Lys
        755                 760                 765

Pro Gly Asp Ile Glu Met Leu Glu Leu Ser Ala Asp Ser Ala Arg His
    770                 775                 780

Leu Lys Asp Pro Ser Val Leu Pro Lys Glu Leu Thr Ala Glu Glu
785                 790                 795                 800

Ile Gly Gly Leu Gln Thr Ile Leu Arg Asp Asp Lys Leu Pro Arg
                805                 810                 815

Asn Val Ala Thr Gly Ser Val Lys Ala Thr Val Gly Asp Thr Gly Tyr
            820                 825                 830
```

-continued

```
Ala Ser Gly Ala Ala Ser Leu Ile Lys Ala Ala Leu Cys Ile Tyr Asn
        835                 840                 845

Arg Tyr Leu Pro Ser Asn Gly Asp Asp Trp Asp Glu Pro Ala Pro Glu
    850                 855                 860

Ala Pro Trp Asp Ser Thr Leu Phe Ala Cys Gln Thr Ser Arg Ala Trp
865                 870                 875                 880

Leu Lys Asn Pro Gly Glu Arg Arg Tyr Ala Ala Val Ser Gly Val Ser
                885                 890                 895

Glu Thr Arg Ser Cys Tyr Ser Val Leu Leu Ser Glu Ala Glu Gly His
            900                 905                 910

Tyr Glu Arg Glu Asn Arg Ile Ser Leu Asp Glu Glu Ala Pro Lys Leu
        915                 920                 925

Ile Val Leu Arg Ala Asp Ser His Glu Glu Ile Leu Gly Arg Leu Asp
    930                 935                 940

Lys Ile Arg Glu Arg Phe Leu Gln Pro Thr Gly Ala Ala Pro Arg Glu
945                 950                 955                 960

Ser Glu Leu Lys Ala Gln Ala Arg Arg Ile Phe Leu Glu Leu Leu Gly
                965                 970                 975

Glu Thr Leu Ala Gln Asp Ala Ala Ser Ser Gly Ser Gln Lys Pro Leu
            980                 985                 990

Ala Leu Ser Leu Val Ser Thr Pro  Ser Lys Leu Gln Arg  Glu Val Glu
        995                 1000                1005

Leu Ala  Ala Lys Gly Ile Pro  Arg Cys Leu Lys Met  Arg Arg Asp
    1010            1015                1020

Trp Ser  Ser Pro Ala Gly Ser  Arg Tyr Ala Pro Glu  Pro Leu Ala
    1025            1030                1035

Ser Asp  Arg Val Ala Phe Met  Tyr Gly Glu Gly Arg  Ser Pro Tyr
    1040            1045                1050

Tyr Gly  Ile Thr Gln Asp Ile  His Arg Ile Trp Pro  Glu Leu His
    1055            1060                1065

Glu Val  Ile Asn Glu Lys Thr  Asn Arg Leu Trp Ala  Glu Gly Asp
    1070            1075                1080

Arg Trp  Val Met Pro Arg Ala  Ser Phe Lys Ser Glu  Leu Glu Ser
    1085            1090                1095

Gln Gln  Gln Glu Phe Asp Arg  Asn Met Ile Glu Met  Phe Arg Leu
    1100            1105                1110

Gly Ile  Leu Thr Ser Ile Ala  Phe Thr Asn Leu Ala  Arg Asp Val
    1115            1120                1125

Leu Asn  Ile Thr Pro Lys Ala  Ala Phe Gly Leu Ser  Leu Gly Glu
    1130            1135                1140

Ile Ser  Met Ile Phe Ala Phe  Ser Lys Lys Asn Gly  Leu Ile Ser
    1145            1150                1155

Asp Gln  Leu Thr Lys Asp Leu  Arg Glu Ser Asp Val  Trp Asn Lys
    1160            1165                1170

Ala Leu  Ala Val Glu Phe Asn  Ala Leu Arg Glu Ala  Trp Gly Ile
    1175            1180                1185

Pro Gln  Ser Val Pro Lys Asp  Glu Phe Trp Gln Gly  Tyr Ile Val
    1190            1195                1200

Arg Gly  Thr Lys Gln Asp Ile  Glu Ala Ala Ile Ala  Pro Asp Ser
    1205            1210                1215

Lys Tyr  Val Arg Leu Thr Ile  Ile Asn Asp Ala Asn  Thr Ala Leu
    1220            1225                1230
```

-continued

```
Ile Ser Gly Lys Pro Asp Ala Cys Lys Ala Ala Ile Ala Arg Leu
1235                1240                1245

Gly Gly Asn Ile Pro Ala Leu Pro Val Thr Gln Gly Met Cys Gly
1250                1255                1260

His Cys Pro Glu Val Gly Pro Tyr Thr Lys Asp Ile Ala Lys Ile
1265                1270                1275

His Ala Asn Leu Glu Phe Pro Val Val Asp Gly Leu Asp Leu Trp
1280                1285                1290

Thr Thr Ile Asn Gln Lys Arg Leu Val Pro Arg Ala Thr Gly Ala
1295                1300                1305

Lys Asp Glu Trp Ala Pro Ser Ser Phe Gly Glu Tyr Ala Gly Gln
1310                1315                1320

Leu Tyr Glu Lys Gln Ala Asn Phe Pro Gln Ile Val Glu Thr Ile
1325                1330                1335

Tyr Lys Gln Asn Tyr Asp Val Phe Val Glu Val Gly Pro Asn Asn
1340                1345                1350

His Arg Ser Thr Ala Val Arg Thr Thr Leu Gly Pro Gln Arg Asn
1355                1360                1365

His Leu Ala Gly Ala Ile Asp Lys Gln Asn Glu Asp Ala Trp Thr
1370                1375                1380

Thr Ile Val Lys Leu Val Ala Ser Leu Lys Ala His Leu Val Pro
1385                1390                1395

Gly Val Thr Ile Ser Pro Leu Tyr His Ser Lys Leu Val Ala Glu
1400                1405                1410

Ala Gln Ala Cys Tyr Ala Ala Leu Cys Lys Gly Glu Lys Pro Lys
1415                1420                1425

Lys Asn Lys Phe Val Arg Lys Ile Gln Leu Asn Gly Arg Phe Asn
1430                1435                1440

Ser Lys Ala Asp Pro Ile Ser Ser Ala Asp Leu Ala Ser Phe Pro
1445                1450                1455

Pro Ala Asp Pro Ala Ile Glu Ala Ala Ile Ser Ser Arg Ile Met
1460                1465                1470

Lys Pro Val Ala Pro Lys Phe Tyr Ala Arg Leu Asn Ile Asp Glu
1475                1480                1485

Gln Asp Glu Thr Arg Asp Pro Ile Leu Asn Lys Asp Asn Ala Pro
1490                1495                1500

Ser Ser Ser Ser Ser Ser Ser Ser Ser Ser Ser Ser Ser Ser Ser
1505                1510                1515

Pro Ser Pro Ala Pro Ser Ala Pro Val Gln Lys Lys Ala Ala Pro
1520                1525                1530

Ala Ala Glu Thr Lys Ala Val Ala Ser Ala Asp Ala Leu Arg Ser
1535                1540                1545

Ala Leu Leu Asp Leu Asp Ser Met Leu Ala Leu Ser Ser Ala Ser
1550                1555                1560

Ala Ser Gly Asn Leu Val Glu Thr Ala Pro Ser Asp Ala Ser Val
1565                1570                1575

Ile Val Pro Pro Cys Asn Ile Ala Asp Leu Gly Ser Arg Ala Phe
1580                1585                1590

Met Lys Thr Tyr Gly Val Ser Ala Pro Leu Tyr Thr Gly Ala Met
1595                1600                1605

Ala Lys Gly Ile Ala Ser Ala Asp Leu Val Ile Ala Ala Gly Arg
1610                1615                1620

Gln Gly Ile Leu Ala Ser Phe Gly Ala Gly Gly Leu Pro Met Gln
```

-continued

```
              1625                1630                1635

Val Val Arg Glu Ser Ile Glu Lys Ile Gln Ala Ala Leu Pro Asn
    1640                1645                1650

Gly Pro Tyr Ala Val Asn Leu Ile His Ser Pro Phe Asp Ser Asn
    1655                1660                1665

Leu Glu Lys Gly Asn Val Asp Leu Phe Leu Glu Lys Gly Val Thr
    1670                1675                1680

Phe Val Glu Ala Ser Ala Phe Met Thr Leu Thr Pro Gln Val Val
    1685                1690                1695

Arg Tyr Arg Ala Ala Gly Leu Thr Arg Asn Ala Asp Gly Ser Val
    1700                1705                1710

Asn Ile Arg Asn Arg Ile Ile Gly Lys Val Ser Arg Thr Glu Leu
    1715                1720                1725

Ala Glu Met Phe Met Arg Pro Ala Pro Glu His Leu Leu Gln Lys
    1730                1735                1740

Leu Ile Ala Ser Gly Glu Ile Asn Gln Glu Gln Ala Glu Leu Ala
    1745                1750                1755

Arg Arg Val Pro Val Ala Asp Asp Ile Ala Val Glu Ala Asp Ser
    1760                1765                1770

Gly Gly His Thr Asp Asn Arg Pro Ile His Val Ile Leu Pro Leu
    1775                1780                1785

Ile Ile Asn Leu Arg Asp Arg Leu His Arg Glu Cys Gly Tyr Pro
    1790                1795                1800

Ala Asn Leu Arg Val Arg Val Gly Ala Gly Gly Ile Gly Cys
    1805                1810                1815

Pro Gln Ala Ala Leu Ala Thr Phe Asn Met Gly Ala Ser Phe Ile
    1820                1825                1830

Val Thr Gly Thr Val Asn Gln Val Ala Lys Gln Ser Gly Thr Cys
    1835                1840                1845

Asp Asn Val Arg Lys Gln Leu Ala Lys Ala Thr Tyr Ser Asp Val
    1850                1855                1860

Cys Met Ala Pro Ala Ala Asp Met Phe Glu Glu Gly Val Lys Leu
    1865                1870                1875

Gln Val Leu Lys Lys Gly Thr Met Phe Pro Ser Arg Ala Asn Lys
    1880                1885                1890

Leu Tyr Glu Leu Phe Cys Lys Tyr Asp Ser Phe Glu Ser Met Pro
    1895                1900                1905

Pro Ala Glu Leu Ala Arg Val Glu Lys Arg Ile Phe Ser Arg Ala
    1910                1915                1920

Leu Glu Glu Val Trp Asp Glu Thr Lys Asn Phe Tyr Ile Asn Arg
    1925                1930                1935

Leu His Asn Pro Glu Lys Ile Gln Arg Ala Glu Arg Asp Pro Lys
    1940                1945                1950

Leu Lys Met Ser Leu Cys Phe Arg Trp Tyr Leu Ser Leu Ala Ser
    1955                1960                1965

Arg Trp Ala Asn Thr Gly Ala Ser Asp Arg Val Met Asp Tyr Gln
    1970                1975                1980

Val Trp Cys Gly Pro Ala Ile Gly Ser Phe Asn Asp Phe Ile Lys
    1985                1990                1995

Gly Thr Tyr Leu Asp Pro Ala Val Ala Asn Glu Tyr Pro Cys Val
    2000                2005                2010

Val Gln Ile Asn Lys Gln Ile Leu Arg Gly Ala Cys Phe Leu Arg
    2015                2020                2025
```

```
Arg Leu  Glu Ile Leu Arg Asn  Ala Arg Leu Ser Asp  Gly Ala Ala
    2030             2035              2040

Ala Leu  Val Ala Ser Ile Asp  Asp Thr Tyr Val Pro  Ala Glu Lys
    2045             2050              2055

Leu

<210> SEQ ID NO 5
<211> LENGTH: 4509
<212> TYPE: DNA
<213> ORGANISM: Schizochytrium sp.
<220> FEATURE:
<221> NAME/KEY: CDS
<222> LOCATION: (1)..(4509)

<400> SEQUENCE: 5
```

| | | | | | | | | | | | | | | | | |
|---|---|---|---|---|---|---|---|---|---|---|---|---|---|---|---|---|
| atg | gcg | ctc | cgt | gtc | aag | acg | aac | aag | aag | cca | tgc | tgg | gag | atg | acc | 48 |
| Met | Ala | Leu | Arg | Val | Lys | Thr | Asn | Lys | Lys | Pro | Cys | Trp | Glu | Met | Thr | |
| 1 | | | | 5 | | | | | 10 | | | | | 15 | | |
| aag | gag | gag | ctg | acc | agc | ggc | aag | acc | gag | gtg | ttc | aac | tat | gag | gaa | 96 |
| Lys | Glu | Glu | Leu | Thr | Ser | Gly | Lys | Thr | Glu | Val | Phe | Asn | Tyr | Glu | Glu | |
| | | | 20 | | | | | 25 | | | | | 30 | | | |
| ctc | ctc | gag | ttc | gca | gag | ggc | gac | atc | gcc | aag | gtc | ttc | gga | ccc | gag | 144 |
| Leu | Leu | Glu | Phe | Ala | Glu | Gly | Asp | Ile | Ala | Lys | Val | Phe | Gly | Pro | Glu | |
| | | 35 | | | | | 40 | | | | | 45 | | | | |
| ttc | gcc | gtc | atc | gac | aag | tac | ccg | cgc | cgc | gtg | cgc | ctg | ccc | gcc | cgc | 192 |
| Phe | Ala | Val | Ile | Asp | Lys | Tyr | Pro | Arg | Arg | Val | Arg | Leu | Pro | Ala | Arg | |
| 50 | | | | | 55 | | | | | 60 | | | | | | |
| gag | tac | ctg | ctc | gtg | acc | cgc | gtc | acc | ctc | atg | gac | gcc | gag | gtc | aac | 240 |
| Glu | Tyr | Leu | Leu | Val | Thr | Arg | Val | Thr | Leu | Met | Asp | Ala | Glu | Val | Asn | |
| 65 | | | | | 70 | | | | | 75 | | | | | 80 | |
| aac | tac | cgc | gtc | ggc | gcc | cgc | atg | gtc | acc | gag | tac | gat | ctc | ccc | gtc | 288 |
| Asn | Tyr | Arg | Val | Gly | Ala | Arg | Met | Val | Thr | Glu | Tyr | Asp | Leu | Pro | Val | |
| | | | | 85 | | | | | 90 | | | | | 95 | | |
| aac | gga | gag | ctc | tcc | gag | ggc | gga | gac | tgc | ccc | tgg | gcc | gtc | ctg | gtc | 336 |
| Asn | Gly | Glu | Leu | Ser | Glu | Gly | Gly | Asp | Cys | Pro | Trp | Ala | Val | Leu | Val | |
| | | | 100 | | | | | 105 | | | | | 110 | | | |
| gag | agt | ggc | cag | tgc | gat | ctc | atg | ctc | atc | tcc | tac | atg | ggc | att | gac | 384 |
| Glu | Ser | Gly | Gln | Cys | Asp | Leu | Met | Leu | Ile | Ser | Tyr | Met | Gly | Ile | Asp | |
| | | 115 | | | | | 120 | | | | | 125 | | | | |
| ttc | cag | aac | cag | ggc | gac | cgc | gtc | tac | cgc | ctg | ctc | aac | acc | acg | ctc | 432 |
| Phe | Gln | Asn | Gln | Gly | Asp | Arg | Val | Tyr | Arg | Leu | Leu | Asn | Thr | Thr | Leu | |
| | 130 | | | | | 135 | | | | | 140 | | | | | |
| acc | ttt | tac | ggc | gtg | gcc | cac | gag | ggc | gag | acc | ctc | gag | tac | gac | att | 480 |
| Thr | Phe | Tyr | Gly | Val | Ala | His | Glu | Gly | Glu | Thr | Leu | Glu | Tyr | Asp | Ile | |
| 145 | | | | | 150 | | | | | 155 | | | | | 160 | |
| cgc | gtc | acc | ggc | ttc | gcc | aag | cgt | ctc | gac | ggc | ggc | atc | tcc | atg | ttc | 528 |
| Arg | Val | Thr | Gly | Phe | Ala | Lys | Arg | Leu | Asp | Gly | Gly | Ile | Ser | Met | Phe | |
| | | | | 165 | | | | | 170 | | | | | 175 | | |
| ttc | ttc | gag | tac | gac | tgc | tac | gtc | aac | ggc | cgc | ctc | ctc | atc | gag | atg | 576 |
| Phe | Phe | Glu | Tyr | Asp | Cys | Tyr | Val | Asn | Gly | Arg | Leu | Leu | Ile | Glu | Met | |
| | | | 180 | | | | | 185 | | | | | 190 | | | |
| cgc | gat | ggc | tgc | gcc | ggc | ttc | ttc | acc | aac | gag | gag | ctc | gac | gcc | ggc | 624 |
| Arg | Asp | Gly | Cys | Ala | Gly | Phe | Phe | Thr | Asn | Glu | Glu | Leu | Asp | Ala | Gly | |
| | | 195 | | | | | 200 | | | | | 205 | | | | |
| aag | ggc | gtc | gtc | ttc | acc | cgc | ggc | gac | ctc | gcc | gcc | cgc | gcc | aag | atc | 672 |
| Lys | Gly | Val | Val | Phe | Thr | Arg | Gly | Asp | Leu | Ala | Ala | Arg | Ala | Lys | Ile | |
| | 210 | | | | | 215 | | | | | 220 | | | | | |
| cca | aag | cag | gac | gtc | tcc | ccc | tac | gcc | gtc | gcc | ccc | tgc | ctc | cac | aag | 720 |
| Pro | Lys | Gln | Asp | Val | Ser | Pro | Tyr | Ala | Val | Ala | Pro | Cys | Leu | His | Lys | |
| 225 | | | | | 230 | | | | | 235 | | | | | 240 | |

```
acc aag ctc aac gaa aag gag atg cag acc ctc gtc gac aag gac tgg        768
Thr Lys Leu Asn Glu Lys Glu Met Gln Thr Leu Val Asp Lys Asp Trp
            245                 250                 255 gca tcc gtc ttt ggc tcc aag aac ggc atg ccg gaa atc aac tac aaa        816
Ala Ser Val Phe Gly Ser Lys Asn Gly Met Pro Glu Ile Asn Tyr Lys
        260                 265                 270 ctc tgc gcg cgt aag atg ctc atg att gac cgc gtc acc agc att gac        864
Leu Cys Ala Arg Lys Met Leu Met Ile Asp Arg Val Thr Ser Ile Asp
    275                 280                 285 cac aag ggc ggt gtc tac ggc ctc ggt cag ctc gtc ggt gaa aag atc        912
His Lys Gly Gly Val Tyr Gly Leu Gly Gln Leu Val Gly Glu Lys Ile
290                 295                 300 ctc gag cgc gac cac tgg tac ttt ccc tgc cac ttt gtc aag gat cag        960
Leu Glu Arg Asp His Trp Tyr Phe Pro Cys His Phe Val Lys Asp Gln
305                 310                 315                 320 gtc atg gcc gga tcc ctc gtc tcc gac ggc tgc agc cag atg ctc aag       1008
Val Met Ala Gly Ser Leu Val Ser Asp Gly Cys Ser Gln Met Leu Lys
                325                 330                 335 atg tac atg atc tgg ctc ggc ctc cac ctc acc acc gga ccc ttt gac       1056
Met Tyr Met Ile Trp Leu Gly Leu His Leu Thr Thr Gly Pro Phe Asp
            340                 345                 350 ttc cgc ccg gtc aac ggc cac ccc aac aag gtc cgc tgc cgc ggc caa       1104
Phe Arg Pro Val Asn Gly His Pro Asn Lys Val Arg Cys Arg Gly Gln
        355                 360                 365 atc tcc ccg cac aag ggc aag ctc gtc tac gtc atg gag atc aag gag       1152
Ile Ser Pro His Lys Gly Lys Leu Val Tyr Val Met Glu Ile Lys Glu
    370                 375                 380 atg ggc ttc gac gag gac aac gac ccg tac gcc att gcc gac gtc aac       1200
Met Gly Phe Asp Glu Asp Asn Asp Pro Tyr Ala Ile Ala Asp Val Asn
385                 390                 395                 400 atc att gat gtc gac ttc gaa aag ggc cag gac ttt agc ctc gac cgc       1248
Ile Ile Asp Val Asp Phe Glu Lys Gly Gln Asp Phe Ser Leu Asp Arg
                405                 410                 415 atc agc gac tac ggc aag ggc gac ctc aac aag aag atc gtc gtc gac       1296
Ile Ser Asp Tyr Gly Lys Gly Asp Leu Asn Lys Lys Ile Val Val Asp
            420                 425                 430 ttt aag ggc atc gct ctc aag atg cag aag cgc tcc acc aac aag aac       1344
Phe Lys Gly Ile Ala Leu Lys Met Gln Lys Arg Ser Thr Asn Lys Asn
        435                 440                 445 ccc tcc aag gtt cag ccc gtc ttt gcc aac ggc gcc gcc act gtc ggc       1392
Pro Ser Lys Val Gln Pro Val Phe Ala Asn Gly Ala Ala Thr Val Gly
    450                 455                 460 ccc gag gcc tcc aag gct tcc tcc ggc gcc agc gcc agc gcc agc gcc       1440
Pro Glu Ala Ser Lys Ala Ser Ser Gly Ala Ser Ala Ser Ala Ser Ala
465                 470                 475                 480 gcc ccg gcc aag cct gcc ttc agc gcc gat gtt ctt gcg ccc aag ccc       1488
Ala Pro Ala Lys Pro Ala Phe Ser Ala Asp Val Leu Ala Pro Lys Pro
                485                 490                 495 gtt gcc ctt ccc gag cac atc ctc aag ggc gac gcc ctc gcc ccc aag       1536
Val Ala Leu Pro Glu His Ile Leu Lys Gly Asp Ala Leu Ala Pro Lys
            500                 505                 510 gag atg tcc tgg cac ccc atg gcc cgc atc ccg ggc aac ccg acg ccc       1584
Glu Met Ser Trp His Pro Met Ala Arg Ile Pro Gly Asn Pro Thr Pro
        515                 520                 525 tct ttt gcg ccc tcg gcc tac aag ccg cgc aac atc gcc ttt acg ccc       1632
Ser Phe Ala Pro Ser Ala Tyr Lys Pro Arg Asn Ile Ala Phe Thr Pro
    530                 535                 540 ttc ccc ggc aac ccc aac gat aac gac cac acc ccg ggc aag atg ccg       1680
Phe Pro Gly Asn Pro Asn Asp Asn Asp His Thr Pro Gly Lys Met Pro
```

```
                 545                 550                 555                 560
ctc acc tgg ttc aac atg gcc gag ttc atg gcc ggc aag gtc agc atg         1728
Leu Thr Trp Phe Asn Met Ala Glu Phe Met Ala Gly Lys Val Ser Met
                565                 570                 575 tgc ctc ggc ccc gag ttc gcc aag ttc gac gac tcg aac acc agc cgc         1776
Cys Leu Gly Pro Glu Phe Ala Lys Phe Asp Asp Ser Asn Thr Ser Arg
            580                 585                 590 agc ccc gct tgg gac ctc gct ctc gtc acc cgc gcc gtg tct gtg tct         1824
Ser Pro Ala Trp Asp Leu Ala Leu Val Thr Arg Ala Val Ser Val Ser
        595                 600                 605 gac ctc aag cac gtc aac tac cgc aac atc gac ctc gac ccc tcc aag         1872
Asp Leu Lys His Val Asn Tyr Arg Asn Ile Asp Leu Asp Pro Ser Lys
    610                 615                 620 ggt acc atg gtc ggc gag ttc gac tgc ccc gcg gac gcc tgg ttc tac         1920
Gly Thr Met Val Gly Glu Phe Asp Cys Pro Ala Asp Ala Trp Phe Tyr
625                 630                 635                 640 aag ggc gcc tgc aac gat gcc cac atg ccg tac tcg atc ctc atg gag         1968
Lys Gly Ala Cys Asn Asp Ala His Met Pro Tyr Ser Ile Leu Met Glu
                645                 650                 655 atc gcc ctc cag acc tcg ggt gtg ctc acc tcg gtg ctc aag gcg ccc         2016
Ile Ala Leu Gln Thr Ser Gly Val Leu Thr Ser Val Leu Lys Ala Pro
            660                 665                 670 ctg acc atg gag aag gac gac atc ctc ttc cgc aac ctc gac gcc aac         2064
Leu Thr Met Glu Lys Asp Asp Ile Leu Phe Arg Asn Leu Asp Ala Asn
        675                 680                 685 gcc gag ttc gtg cgc gcc gac ctc gac tac cgc ggc aag act atc cgc         2112
Ala Glu Phe Val Arg Ala Asp Leu Asp Tyr Arg Gly Lys Thr Ile Arg
    690                 695                 700 aac gtc acc aag tgc act ggc tac agc atg ctc ggc gag atg ggc gtc         2160
Asn Val Thr Lys Cys Thr Gly Tyr Ser Met Leu Gly Glu Met Gly Val
705                 710                 715                 720 cac cgc ttc acc ttt gag ctc tac gtc gat gat gtg ctc ttt tac aag         2208
His Arg Phe Thr Phe Glu Leu Tyr Val Asp Asp Val Leu Phe Tyr Lys
                725                 730                 735 ggc tcg acc tcg ttc ggc tgg ttc gtg ccc gag gtc ttt gcc gcc cag         2256
Gly Ser Thr Ser Phe Gly Trp Phe Val Pro Glu Val Phe Ala Ala Gln
            740                 745                 750 gcc ggc ctc gac aac ggc cgc aag tcg gag ccc tgg ttc att gag aac         2304
Ala Gly Leu Asp Asn Gly Arg Lys Ser Glu Pro Trp Phe Ile Glu Asn
        755                 760                 765 aag gtt ccg gcc tcg cag gtc tcc tcc ttt gac gtg cgc ccc aac ggc         2352
Lys Val Pro Ala Ser Gln Val Ser Ser Phe Asp Val Arg Pro Asn Gly
    770                 775                 780 agc ggc cgc acc gcc atc ttc gcc aac gcc ccc agc ggc gcc cag ctc         2400
Ser Gly Arg Thr Ala Ile Phe Ala Asn Ala Pro Ser Gly Ala Gln Leu
785                 790                 795                 800 aac cgc cgc acg gac cag ggc cag tac ctc gac gcc gtc gac att gtc         2448
Asn Arg Arg Thr Asp Gln Gly Gln Tyr Leu Asp Ala Val Asp Ile Val
                805                 810                 815 tcc ggc agc ggc aag aag agc ctc ggc tac gcc cac ggt tcc aag acg         2496
Ser Gly Ser Gly Lys Lys Ser Leu Gly Tyr Ala His Gly Ser Lys Thr
            820                 825                 830 gtc aac ccg aac gac tgg ttc ttc tcg tgc cac ttt tgg ttt gac tcg         2544
Val Asn Pro Asn Asp Trp Phe Phe Ser Cys His Phe Trp Phe Asp Ser
        835                 840                 845 gtc atg ccc gga agt ctc ggt gtc gag tcc atg ttc cag ctc gtc gag         2592
Val Met Pro Gly Ser Leu Gly Val Glu Ser Met Phe Gln Leu Val Glu
    850                 855                 860 gcc atc gcc gcc cac gag gat ctc gct ggc aaa gca cgg cat tgc caa         2640
```

-continued

```
Ala Ile Ala Ala His Glu Asp Leu Ala Gly Lys Ala Arg His Cys Gln
865                 870                 875                 880 ccc cac ctt tgt gca cgc ccc cgg gca aga tca agc tgg aag tac cgc    2688
Pro His Leu Cys Ala Arg Pro Arg Ala Arg Ser Ser Trp Lys Tyr Arg
                885                 890                 895 ggc cag ctc acg ccc aag agc aag aag atg gac tcg gag gtc cac atc    2736
Gly Gln Leu Thr Pro Lys Ser Lys Lys Met Asp Ser Glu Val His Ile
            900                 905                 910 gtg tcc gtg gac gcc cac gac ggc gtt gtc gac ctc gtc gcc gac ggc    2784
Val Ser Val Asp Ala His Asp Gly Val Val Asp Leu Val Ala Asp Gly
        915                 920                 925 ttc ctc tgg gcc gac agc ctc cgc gtc tac tcg gtg agc aac att cgc    2832
Phe Leu Trp Ala Asp Ser Leu Arg Val Tyr Ser Val Ser Asn Ile Arg
    930                 935                 940 gtg cgc atc gcc tcc ggt gag gcc cct gcc gcc gcc tcc tcc gcc gcc    2880
Val Arg Ile Ala Ser Gly Glu Ala Pro Ala Ala Ala Ser Ser Ala Ala
945                 950                 955                 960 tct gtg ggc tcc tcg gct tcg tcc gtc gag cgc acg cgc tcg agc ccc    2928
Ser Val Gly Ser Ser Ala Ser Ser Val Glu Arg Thr Arg Ser Ser Pro
                965                 970                 975 gct gtc gcc tcc ggc ccg gcc cag acc atc gac ctc aag cag ctc aag    2976
Ala Val Ala Ser Gly Pro Ala Gln Thr Ile Asp Leu Lys Gln Leu Lys
            980                 985                 990 acc gag ctc ctc gag ctc gat gcc ccg ctc tac ctc tcg cag gac ccg    3024
Thr Glu Leu Leu Glu Leu Asp Ala Pro Leu Tyr Leu Ser Gln Asp Pro
        995                 1000                1005 acc agc ggc cag ctc aag aag cac acc gac gtg gcc tcc ggc cag        3069
Thr Ser Gly Gln Leu Lys Lys His Thr Asp Val Ala Ser Gly Gln
    1010                1015                1020 gcc acc atc gtg cag ccc tgc acg ctc ggc gac ctc ggt gac cgc        3114
Ala Thr Ile Val Gln Pro Cys Thr Leu Gly Asp Leu Gly Asp Arg
1025                1030                1035 tcc ttc atg gag acc tac ggc gtc gtc gcc ccg ctg tac acg ggc        3159
Ser Phe Met Glu Thr Tyr Gly Val Val Ala Pro Leu Tyr Thr Gly
    1040                1045                1050 gcc atg gcc aag ggc att gcc tcg gcg gac ctc gtc atc gcc gcc        3204
Ala Met Ala Lys Gly Ile Ala Ser Ala Asp Leu Val Ile Ala Ala
1055                1060                1065 ggc aag cgc aag atc ctc ggc tcc ttt ggc gcc ggc ggc ctc ccc        3249
Gly Lys Arg Lys Ile Leu Gly Ser Phe Gly Ala Gly Gly Leu Pro
    1070                1075                1080 atg cac cac gtg cgc gcc gcc ctc gag aag atc cag gcc gcc ctg        3294
Met His His Val Arg Ala Ala Leu Glu Lys Ile Gln Ala Ala Leu
1085                1090                1095 cct cag ggc ccc tac gcc gtc aac ctc atc cac tcg cct ttt gac        3339
Pro Gln Gly Pro Tyr Ala Val Asn Leu Ile His Ser Pro Phe Asp
    1100                1105                1110 agc aac ctc gag aag ggc aac gtc gat ctc ttc ctc gag aag ggc        3384
Ser Asn Leu Glu Lys Gly Asn Val Asp Leu Phe Leu Glu Lys Gly
1115                1120                1125 gtc act gtg gtg gag gcc tcg gca ttc atg acc ctc acc ccg cag        3429
Val Thr Val Val Glu Ala Ser Ala Phe Met Thr Leu Thr Pro Gln
    1130                1135                1140 gtc gtc cgc tac cgc gcc gcc ggc ctc tcg cgc aac gcc gac ggt        3474
Val Val Arg Tyr Arg Ala Ala Gly Leu Ser Arg Asn Ala Asp Gly
1145                1150                1155 tcg gtc aac atc cgc aac cgc atc atc ggc aag gtc tcg cgc acc        3519
Ser Val Asn Ile Arg Asn Arg Ile Ile Gly Lys Val Ser Arg Thr
    1160                1165                1170
```

```
gag ctc gcc gag atg ttc atc cgc ccg gcc ccg gag cac ctc ctc    3564
Glu Leu Ala Glu Met Phe Ile Arg Pro Ala Pro Glu His Leu Leu
1175              1180                    1185 gag aag ctc atc gcc tcg ggc gag atc acc cag gag cag gcc gag    3609
Glu Lys Leu Ile Ala Ser Gly Glu Ile Thr Gln Glu Gln Ala Glu
1190              1195                    1200 ctc gcg cgc cgc gtt ccc gtc gcc gac gat atc gct gtc gag gct    3654
Leu Ala Arg Arg Val Pro Val Ala Asp Asp Ile Ala Val Glu Ala
1205              1210                    1215 gac tcg ggc ggc cac acc gac aac cgc ccc atc cac gtc atc ctc    3699
Asp Ser Gly Gly His Thr Asp Asn Arg Pro Ile His Val Ile Leu
1220              1225                    1230 ccg ctc atc atc aac ctc cgc aac cgc ctg cac cgc gag tgc ggc    3744
Pro Leu Ile Ile Asn Leu Arg Asn Arg Leu His Arg Glu Cys Gly
1235              1240                    1245 tac ccc gcg cac ctc cgc gtc cgc gtt ggc gcc ggc ggt ggc gtc    3789
Tyr Pro Ala His Leu Arg Val Arg Val Gly Ala Gly Gly Gly Val
1250              1255                    1260 ggc tgc ccg cag gcc gcc gcc gcc gcg ctc acc atg ggc gcc gcc    3834
Gly Cys Pro Gln Ala Ala Ala Ala Ala Leu Thr Met Gly Ala Ala
1265              1270                    1275 ttc atc gtc acc ggc act gtc aac cag gtc gcc aag cag tcc ggc    3879
Phe Ile Val Thr Gly Thr Val Asn Gln Val Ala Lys Gln Ser Gly
1280              1285                    1290 acc tgc gac aac gtg cgc aag cag ctc tcg cag gcc acc tac tcg    3924
Thr Cys Asp Asn Val Arg Lys Gln Leu Ser Gln Ala Thr Tyr Ser
1295              1300                    1305 gat atc tgc atg gcc ccg gcc gcc gac atg ttc gag gag ggc gtc    3969
Asp Ile Cys Met Ala Pro Ala Ala Asp Met Phe Glu Glu Gly Val
1310              1315                    1320 aag ctc cag gtc ctc aag aag gga acc atg ttc ccc tcg cgc gcc    4014
Lys Leu Gln Val Leu Lys Lys Gly Thr Met Phe Pro Ser Arg Ala
1325              1330                    1335 aac aag ctc tac gag ctc ttt tgc aag tac gac tcc ttc gac tcc    4059
Asn Lys Leu Tyr Glu Leu Phe Cys Lys Tyr Asp Ser Phe Asp Ser
1340              1345                    1350 atg cct cct gcc gag ctc gag cgc atc gag aag cgt atc ttc aag    4104
Met Pro Pro Ala Glu Leu Glu Arg Ile Glu Lys Arg Ile Phe Lys
1355              1360                    1365 cgc gca ctc cag gag gtc tgg gag gag acc aag gac ttt tac att    4149
Arg Ala Leu Gln Glu Val Trp Glu Glu Thr Lys Asp Phe Tyr Ile
1370              1375                    1380 aac ggt ctc aag aac ccg gag aag atc cag cgc gcc gag cac gac    4194
Asn Gly Leu Lys Asn Pro Glu Lys Ile Gln Arg Ala Glu His Asp
1385              1390                    1395 ccc aag ctc aag atg tcg ctc tgc ttc cgc tgg tac ctt ggt ctt    4239
Pro Lys Leu Lys Met Ser Leu Cys Phe Arg Trp Tyr Leu Gly Leu
1400              1405                    1410 gcc agc cgc tgg gcc aac atg ggc gcc ccg gac cgc gtc atg gac    4284
Ala Ser Arg Trp Ala Asn Met Gly Ala Pro Asp Arg Val Met Asp
1415              1420                    1425 tac cag gtc tgg tgt ggc ccg gcc att ggc gcc ttc aac gac ttc    4329
Tyr Gln Val Trp Cys Gly Pro Ala Ile Gly Ala Phe Asn Asp Phe
1430              1435                    1440 atc aag ggc acc tac ctc gac ccc gct gtc tcc aac gag tac ccc    4374
Ile Lys Gly Thr Tyr Leu Asp Pro Ala Val Ser Asn Glu Tyr Pro
1445              1450                    1455 tgt gtc gtc cag atc aac ctg caa atc ctc cgt ggt gcc tgc tac    4419
Cys Val Val Gln Ile Asn Leu Gln Ile Leu Arg Gly Ala Cys Tyr
1460              1465                    1470
```

```
ctg  cgc  cgt  ctc  aac  gcc  ctg  cgc  aac  gac  ccg  cgc  att  gac  ctc         4464
Leu  Arg  Arg  Leu  Asn  Ala  Leu  Arg  Asn  Asp  Pro  Arg  Ile  Asp  Leu
     1475                1480                     1485 gag  acc  gag  gat  gct  gcc  ttt  gtc  tac  gag  ccc  acc  aac  gcg  ctc         4509
Glu  Thr  Glu  Asp  Ala  Ala  Phe  Val  Tyr  Glu  Pro  Thr  Asn  Ala  Leu
1490                     1495                     1500
```

<210> SEQ ID NO 6
<211> LENGTH: 1503
<212> TYPE: PRT
<213> ORGANISM: Schizochytrium sp.

<400> SEQUENCE: 6

```
Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
            20                  25                  30

Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
    50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
        115                 120                 125

Phe Gln Asn Gln Gly Asp Arg Val Tyr Arg Leu Leu Asn Thr Thr Leu
    130                 135                 140

Thr Phe Tyr Gly Val Ala His Glu Gly Glu Thr Leu Glu Tyr Asp Ile
145                 150                 155                 160

Arg Val Thr Gly Phe Ala Lys Arg Leu Asp Gly Gly Ile Ser Met Phe
                165                 170                 175

Phe Phe Glu Tyr Asp Cys Tyr Val Asn Gly Arg Leu Leu Ile Glu Met
            180                 185                 190

Arg Asp Gly Cys Ala Gly Phe Phe Thr Asn Glu Glu Leu Asp Ala Gly
        195                 200                 205

Lys Gly Val Val Phe Thr Arg Gly Asp Leu Ala Ala Arg Ala Lys Ile
    210                 215                 220

Pro Lys Gln Asp Val Ser Pro Tyr Ala Val Ala Pro Cys Leu His Lys
225                 230                 235                 240

Thr Lys Leu Asn Glu Lys Glu Met Gln Thr Leu Val Asp Lys Asp Trp
                245                 250                 255

Ala Ser Val Phe Gly Ser Lys Asn Gly Met Pro Glu Ile Asn Tyr Lys
            260                 265                 270

Leu Cys Ala Arg Lys Met Leu Met Ile Asp Arg Val Thr Ser Ile Asp
        275                 280                 285

His Lys Gly Gly Val Tyr Gly Leu Gly Gln Leu Val Gly Glu Lys Ile
    290                 295                 300

Leu Glu Arg Asp His Trp Tyr Phe Pro Cys His Phe Val Lys Asp Gln
305                 310                 315                 320

Val Met Ala Gly Ser Leu Val Ser Asp Gly Cys Ser Gln Met Leu Lys
                325                 330                 335
```

```
Met Tyr Met Ile Trp Leu Gly Leu His Leu Thr Thr Gly Pro Phe Asp
        340                 345                 350

Phe Arg Pro Val Asn Gly His Pro Asn Lys Val Arg Cys Arg Gly Gln
        355                 360                 365

Ile Ser Pro His Lys Gly Lys Leu Val Tyr Val Met Glu Ile Lys Glu
        370                 375                 380

Met Gly Phe Asp Glu Asp Asn Asp Pro Tyr Ala Ile Ala Asp Val Asn
385                 390                 395                 400

Ile Ile Asp Val Asp Phe Glu Lys Gly Gln Asp Phe Ser Leu Asp Arg
                405                 410                 415

Ile Ser Asp Tyr Gly Lys Gly Asp Leu Asn Lys Lys Ile Val Val Asp
                420                 425                 430

Phe Lys Gly Ile Ala Leu Lys Met Gln Lys Arg Ser Thr Asn Lys Asn
            435                 440                 445

Pro Ser Lys Val Gln Pro Val Phe Ala Asn Gly Ala Ala Thr Val Gly
        450                 455                 460

Pro Glu Ala Ser Lys Ala Ser Ser Gly Ala Ser Ala Ser Ala Ser Ala
465                 470                 475                 480

Ala Pro Ala Lys Pro Ala Phe Ser Ala Asp Val Leu Ala Pro Lys Pro
                485                 490                 495

Val Ala Leu Pro Glu His Ile Leu Lys Gly Asp Ala Leu Ala Pro Lys
                500                 505                 510

Glu Met Ser Trp His Pro Met Ala Arg Ile Pro Gly Asn Pro Thr Pro
            515                 520                 525

Ser Phe Ala Pro Ser Ala Tyr Lys Pro Arg Asn Ile Ala Phe Thr Pro
        530                 535                 540

Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
            580                 585                 590

Ser Pro Ala Trp Asp Leu Ala Leu Val Thr Arg Ala Val Ser Val Ser
        595                 600                 605

Asp Leu Lys His Val Asn Tyr Arg Asn Ile Asp Leu Asp Pro Ser Lys
            610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
                645                 650                 655

Ile Ala Leu Gln Thr Ser Gly Val Leu Thr Ser Val Leu Lys Ala Pro
            660                 665                 670

Leu Thr Met Glu Lys Asp Asp Ile Leu Phe Arg Asn Leu Asp Ala Asn
            675                 680                 685

Ala Glu Phe Val Arg Ala Asp Leu Asp Tyr Arg Gly Lys Thr Ile Arg
        690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Asp Val Leu Phe Tyr Lys
                725                 730                 735

Gly Ser Thr Ser Phe Gly Trp Phe Val Pro Glu Val Phe Ala Ala Gln
                740                 745                 750
```

-continued

Ala Gly Leu Asp Asn Gly Arg Lys Ser Glu Pro Trp Phe Ile Glu Asn
        755                 760                 765

Lys Val Pro Ala Ser Gln Val Ser Ser Phe Asp Val Arg Pro Asn Gly
        770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
                805                 810                 815

Ser Gly Ser Gly Lys Lys Ser Leu Gly Tyr Ala His Gly Ser Lys Thr
                820                 825                 830

Val Asn Pro Asn Asp Trp Phe Phe Ser Cys His Phe Trp Phe Asp Ser
                835                 840                 845

Val Met Pro Gly Ser Leu Gly Val Glu Ser Met Phe Gln Leu Val Glu
                850                 855                 860

Ala Ile Ala Ala His Glu Asp Leu Ala Gly Lys Ala Arg His Cys Gln
865                 870                 875                 880

Pro His Leu Cys Ala Arg Pro Arg Ala Arg Ser Ser Trp Lys Tyr Arg
                885                 890                 895

Gly Gln Leu Thr Pro Lys Ser Lys Lys Met Asp Ser Glu Val His Ile
                900                 905                 910

Val Ser Val Asp Ala His Asp Gly Val Val Asp Leu Val Ala Asp Gly
                915                 920                 925

Phe Leu Trp Ala Asp Ser Leu Arg Val Tyr Ser Val Ser Asn Ile Arg
        930                 935                 940

Val Arg Ile Ala Ser Gly Glu Ala Pro Ala Ala Ser Ser Ala Ala
945                 950                 955                 960

Ser Val Gly Ser Ser Ala Ser Val Glu Arg Thr Arg Ser Ser Pro
                965                 970                 975

Ala Val Ala Ser Gly Pro Ala Gln Thr Ile Asp Leu Lys Gln Leu Lys
                980                 985                 990

Thr Glu Leu Leu Glu Leu Asp Ala Pro Leu Tyr Leu Ser Gln Asp Pro
        995                 1000                1005

Thr Ser Gly Gln Leu Lys Lys His Thr Asp Val Ala Ser Gly Gln
    1010                1015                1020

Ala Thr Ile Val Gln Pro Cys Thr Leu Gly Asp Leu Gly Asp Arg
    1025                1030                1035

Ser Phe Met Glu Thr Tyr Gly Val Val Ala Pro Leu Tyr Thr Gly
    1040                1045                1050

Ala Met Ala Lys Gly Ile Ala Ser Ala Asp Leu Val Ile Ala Ala
    1055                1060                1065

Gly Lys Arg Lys Ile Leu Gly Ser Phe Gly Ala Gly Gly Leu Pro
    1070                1075                1080

Met His His Val Arg Ala Ala Leu Glu Lys Ile Gln Ala Ala Leu
    1085                1090                1095

Pro Gln Gly Pro Tyr Ala Val Asn Leu Ile His Ser Pro Phe Asp
    1100                1105                1110

Ser Asn Leu Glu Lys Gly Asn Val Asp Leu Phe Leu Glu Lys Gly
    1115                1120                1125

Val Thr Val Val Glu Ala Ser Ala Phe Met Thr Leu Thr Pro Gln
    1130                1135                1140

Val Val Arg Tyr Arg Ala Ala Gly Leu Ser Arg Asn Ala Asp Gly
    1145                1150                1155

Ser Val Asn Ile Arg Asn Arg Ile Ile Gly Lys Val Ser Arg Thr

```
                      1160                1165                1170

Glu Leu Ala Glu Met Phe Ile Arg Pro Ala Pro Glu His Leu Leu
    1175                1180                1185

Glu Lys Leu Ile Ala Ser Gly Glu Ile Thr Gln Glu Gln Ala Glu
    1190                1195                1200

Leu Ala Arg Arg Val Pro Val Ala Asp Ile Ala Val Glu Ala
    1205                1210                1215

Asp Ser Gly Gly His Thr Asp Asn Arg Pro Ile His Val Ile Leu
    1220                1225                1230

Pro Leu Ile Ile Asn Leu Arg Asn Arg Leu His Arg Glu Cys Gly
    1235                1240                1245

Tyr Pro Ala His Leu Arg Val Arg Val Gly Ala Gly Gly Gly Val
    1250                1255                1260

Gly Cys Pro Gln Ala Ala Ala Ala Leu Thr Met Gly Ala Ala
    1265                1270                1275

Phe Ile Val Thr Gly Thr Val Asn Gln Val Ala Lys Gln Ser Gly
    1280                1285                1290

Thr Cys Asp Asn Val Arg Lys Gln Leu Ser Gln Ala Thr Tyr Ser
    1295                1300                1305

Asp Ile Cys Met Ala Pro Ala Ala Asp Met Phe Glu Glu Gly Val
    1310                1315                1320

Lys Leu Gln Val Leu Lys Lys Gly Thr Met Phe Pro Ser Arg Ala
    1325                1330                1335

Asn Lys Leu Tyr Glu Leu Phe Cys Lys Tyr Asp Ser Phe Asp Ser
    1340                1345                1350

Met Pro Pro Ala Glu Leu Glu Arg Ile Glu Lys Arg Ile Phe Lys
    1355                1360                1365

Arg Ala Leu Gln Glu Val Trp Glu Glu Thr Lys Asp Phe Tyr Ile
    1370                1375                1380

Asn Gly Leu Lys Asn Pro Glu Lys Ile Gln Arg Ala Glu His Asp
    1385                1390                1395

Pro Lys Leu Lys Met Ser Leu Cys Phe Arg Trp Tyr Leu Gly Leu
    1400                1405                1410

Ala Ser Arg Trp Ala Asn Met Gly Ala Pro Asp Arg Val Met Asp
    1415                1420                1425

Tyr Gln Val Trp Cys Gly Pro Ala Ile Gly Ala Phe Asn Asp Phe
    1430                1435                1440

Ile Lys Gly Thr Tyr Leu Asp Pro Ala Val Ser Asn Glu Tyr Pro
    1445                1450                1455

Cys Val Val Gln Ile Asn Leu Gln Ile Leu Arg Gly Ala Cys Tyr
    1460                1465                1470

Leu Arg Arg Leu Asn Ala Leu Arg Asn Asp Pro Arg Ile Asp Leu
    1475                1480                1485

Glu Thr Glu Asp Ala Ala Phe Val Tyr Glu Pro Thr Asn Ala Leu
    1490                1495                1500

<210> SEQ ID NO 7
<211> LENGTH: 600
<212> TYPE: DNA
<213> ORGANISM: Schizochytrium sp.
<220> FEATURE:
<221> NAME/KEY: CDS
<222> LOCATION: (1)..(600)

<400> SEQUENCE: 7
```

-continued

| | | |
|---|---|---|
| atg gcg gcc cgt ctg cag gag caa aag gga ggc gag atg gat acc cgc<br>Met Ala Ala Arg Leu Gln Glu Gln Lys Gly Gly Glu Met Asp Thr Arg<br>1                       5                      10                   15 | 48 |
| att gcc atc atc ggc atg tcg gcc atc ctc ccc tgc ggc acg acc gtg<br>Ile Ala Ile Ile Gly Met Ser Ala Ile Leu Pro Cys Gly Thr Thr Val<br>                    20                        25                  30 | 96 |
| cgc gag tcg tgg gag acc atc cgc gcc ggc atc gac tgc ctg tcg gat<br>Arg Glu Ser Trp Glu Thr Ile Arg Ala Gly Ile Asp Cys Leu Ser Asp<br>        35                      40                      45 | 144 |
| ctc ccc gag gac cgc gtc gac gtg acg gcg tac ttt gac ccc gtc aag<br>Leu Pro Glu Asp Arg Val Asp Val Thr Ala Tyr Phe Asp Pro Val Lys<br>      50                      55                      60 | 192 |
| acc acc aag gac aag atc tac tgc aag cgc ggt ggc ttc att ccc gag<br>Thr Thr Lys Asp Lys Ile Tyr Cys Lys Arg Gly Gly Phe Ile Pro Glu<br>65                      70                      75                  80 | 240 |
| tac gac ttt gac gcc cgc gag ttc gga ctc aac atg ttc cag atg gag<br>Tyr Asp Phe Asp Ala Arg Glu Phe Gly Leu Asn Met Phe Gln Met Glu<br>                          85                      90                  95 | 288 |
| gac tcg gac gca aac cag acc atc tcg ctt ctc aag gtc aag gag gcc<br>Asp Ser Asp Ala Asn Gln Thr Ile Ser Leu Leu Lys Val Lys Glu Ala<br>                    100                    105                  110 | 336 |
| ctc cag gac gcc ggc atc gac gcc ctc ggc aag gaa aag aag aac atc<br>Leu Gln Asp Ala Gly Ile Asp Ala Leu Gly Lys Glu Lys Lys Asn Ile<br>      115                    120                    125 | 384 |
| ggc tgc gtg ctc ggc att ggc ggc ggc caa aag tcc agc cac gag ttc<br>Gly Cys Val Leu Gly Ile Gly Gly Gly Gln Lys Ser Ser His Glu Phe<br>130                    135                    140 | 432 |
| tac tcg cgc ctt aat tat gtt gtc gtg gag aag gtc ctc cgc aag atg<br>Tyr Ser Arg Leu Asn Tyr Val Val Val Glu Lys Val Leu Arg Lys Met<br>145                    150                    155                  160 | 480 |
| ggc atg ccc gag gag gac gtc aag gtc gcc gtc gaa aag tac aag gcc<br>Gly Met Pro Glu Glu Asp Val Lys Val Ala Val Glu Lys Tyr Lys Ala<br>                    165                    170                  175 | 528 |
| aac ttc ccc gag tgg cgc ctc gac tcc ttc cct ggc ttc ctc ggc aac<br>Asn Phe Pro Glu Trp Arg Leu Asp Ser Phe Pro Gly Phe Leu Gly Asn<br>      180                    185                    190 | 576 |
| gtc acc gcc ggt cgc tgc acc aac<br>Val Thr Ala Gly Arg Cys Thr Asn<br>      195                    200 | 600 |

<210> SEQ ID NO 8
<211> LENGTH: 200
<212> TYPE: PRT
<213> ORGANISM: Schizochytrium sp.

<400> SEQUENCE: 8

Met Ala Ala Arg Leu Gln Glu Gln Lys Gly Gly Glu Met Asp Thr Arg
1               5                   10                  15

Ile Ala Ile Ile Gly Met Ser Ala Ile Leu Pro Cys Gly Thr Thr Val
            20                  25                  30

Arg Glu Ser Trp Glu Thr Ile Arg Ala Gly Ile Asp Cys Leu Ser Asp
        35                  40                  45

Leu Pro Glu Asp Arg Val Asp Val Thr Ala Tyr Phe Asp Pro Val Lys
    50                  55                  60

Thr Thr Lys Asp Lys Ile Tyr Cys Lys Arg Gly Gly Phe Ile Pro Glu
65                  70                  75                  80

Tyr Asp Phe Asp Ala Arg Glu Phe Gly Leu Asn Met Phe Gln Met Glu
                85                  90                  95

```
Asp Ser Asp Ala Asn Gln Thr Ile Ser Leu Leu Lys Val Lys Glu Ala
                100                 105                 110

Leu Gln Asp Ala Gly Ile Asp Ala Leu Gly Lys Glu Lys Lys Asn Ile
            115                 120                 125

Gly Cys Val Leu Gly Ile Gly Gly Gln Lys Ser Ser His Glu Phe
        130                 135                 140

Tyr Ser Arg Leu Asn Tyr Val Val Glu Lys Val Leu Arg Lys Met
145                 150                 155                 160

Gly Met Pro Glu Glu Asp Val Lys Val Ala Val Glu Lys Tyr Lys Ala
                165                 170                 175

Asn Phe Pro Glu Trp Arg Leu Asp Ser Phe Pro Gly Phe Leu Gly Asn
            180                 185                 190

Val Thr Ala Gly Arg Cys Thr Asn
        195                 200

<210> SEQ ID NO 9
<211> LENGTH: 1278
<212> TYPE: DNA
<213> ORGANISM: Schizochytrium sp.
<220> FEATURE:
<221> NAME/KEY: CDS
<222> LOCATION: (1)..(1278)

<400> SEQUENCE: 9 gat gtc acc aag gag gcc tgg cgc ctc ccc cgc gag ggc gtc agc ttc     48
Asp Val Thr Lys Glu Ala Trp Arg Leu Pro Arg Glu Gly Val Ser Phe
1               5                   10                  15 cgc gcc aag ggc atc gcc acc aac ggc gct gtc gcc gcg ctc ttc tcc     96
Arg Ala Lys Gly Ile Ala Thr Asn Gly Ala Val Ala Ala Leu Phe Ser
            20                  25                  30 ggc cag ggc gcg cag tac acg cac atg ttt agc gag gtg gcc atg aac    144
Gly Gln Gly Ala Gln Tyr Thr His Met Phe Ser Glu Val Ala Met Asn
        35                  40                  45 tgg ccc cag ttc cgc cag agc att gcc gcc atg gac gcc gcc cag tcc    192
Trp Pro Gln Phe Arg Gln Ser Ile Ala Ala Met Asp Ala Ala Gln Ser
    50                  55                  60 aag gtc gct gga agc gac aag gac ttt gag cgc gtc tcc cag gtc ctc    240
Lys Val Ala Gly Ser Asp Lys Asp Phe Glu Arg Val Ser Gln Val Leu
65                  70                  75                  80 tac ccg cgc aag ccg tac gag cgt gag ccc gag cag aac ccc aag aag    288
Tyr Pro Arg Lys Pro Tyr Glu Arg Glu Pro Glu Gln Asn Pro Lys Lys
                85                  90                  95 atc tcc ctc acc gcc tac tcg cag ccc tcg acc ctg gcc tgc gct ctc    336
Ile Ser Leu Thr Ala Tyr Ser Gln Pro Ser Thr Leu Ala Cys Ala Leu
            100                 105                 110 ggt gcc ttt gag atc ttc aag gag gcc ggc ttc acc ccg gac ttt gcc    384
Gly Ala Phe Glu Ile Phe Lys Glu Ala Gly Phe Thr Pro Asp Phe Ala
        115                 120                 125 gcc ggc cat tcg ctc ggt gag ttc gcc gcc ctc tac gcc gcg ggc tgc    432
Ala Gly His Ser Leu Gly Glu Phe Ala Ala Leu Tyr Ala Ala Gly Cys
    130                 135                 140 gtc gac cgc gac gag ctc ttt gag ctt gtc tgc cgc cgc gcc cgc atc    480
Val Asp Arg Asp Glu Leu Phe Glu Leu Val Cys Arg Arg Ala Arg Ile
145                 150                 155                 160 atg ggc ggc aag gac gca ccg gcc acc ccc aag gga tgc atg gcc gcc    528
Met Gly Gly Lys Asp Ala Pro Ala Thr Pro Lys Gly Cys Met Ala Ala
                165                 170                 175 gtc att ggc ccc aac gcc gag aac atc aag gtc cag gcc gcc aac gtc    576
Val Ile Gly Pro Asn Ala Glu Asn Ile Lys Val Gln Ala Ala Asn Val
            180                 185                 190
```

```
tgg ctc ggc aac tcc aac tcg cct tcg cag acc gtc atc acc ggc tcc      624
Trp Leu Gly Asn Ser Asn Ser Pro Ser Gln Thr Val Ile Thr Gly Ser
            195                 200                 205 gtc gaa ggt atc cag gcc gag agc gcc cgc ctc cag aag gag ggc ttc      672
Val Glu Gly Ile Gln Ala Glu Ser Ala Arg Leu Gln Lys Glu Gly Phe
    210                 215                 220 cgc gtc gtg cct ctt gcc tgc gag agc gcc ttc cac tcg ccc cag atg      720
Arg Val Val Pro Leu Ala Cys Glu Ser Ala Phe His Ser Pro Gln Met
225                 230                 235                 240 gag aac gcc tcg tcg gcc ttc aag gac gtc atc tcc aag gtc tcc ttc      768
Glu Asn Ala Ser Ser Ala Phe Lys Asp Val Ile Ser Lys Val Ser Phe
                245                 250                 255 cgc acc ccc aag gcc gag acc aag ctc ttc agc aac gtc tct ggc gag      816
Arg Thr Pro Lys Ala Glu Thr Lys Leu Phe Ser Asn Val Ser Gly Glu
            260                 265                 270 acc tac ccc acg gac gcc cgc gag atg ctt acg cag cac atg acc agc      864
Thr Tyr Pro Thr Asp Ala Arg Glu Met Leu Thr Gln His Met Thr Ser
    275                 280                 285 agc gtc aag ttc ctc acc cag gtc cgc aac atg cac cag gcc ggt gcg      912
Ser Val Lys Phe Leu Thr Gln Val Arg Asn Met His Gln Ala Gly Ala
290                 295                 300 cgc atc ttt gtc gag ttc gga ccc aag cag gtg ctc tcc aag ctt gtc      960
Arg Ile Phe Val Glu Phe Gly Pro Lys Gln Val Leu Ser Lys Leu Val
305                 310                 315                 320 tcc gag acc ctc aag gat gac ccc tcg gtt gtc acc gtc tct gtc aac     1008
Ser Glu Thr Leu Lys Asp Asp Pro Ser Val Val Thr Val Ser Val Asn
                325                 330                 335 ccg gcc tcg ggc acg gat tcg gac atc cag ctc cgc gac gcg gcc gtc     1056
Pro Ala Ser Gly Thr Asp Ser Asp Ile Gln Leu Arg Asp Ala Ala Val
            340                 345                 350 cag ctc gtt gtc gct ggc gtc aac ctt cag ggc ttt gac aag tgg gac     1104
Gln Leu Val Val Ala Gly Val Asn Leu Gln Gly Phe Asp Lys Trp Asp
    355                 360                 365 gcc ccc gat gcc acc cgc atg cag gcc atc aag aag aag cgc act acc     1152
Ala Pro Asp Ala Thr Arg Met Gln Ala Ile Lys Lys Lys Arg Thr Thr
370                 375                 380 ctc cgc ctt tcg gcc gcc acc tac gtc tcg gac aag acc aag aag gtc     1200
Leu Arg Leu Ser Ala Ala Thr Tyr Val Ser Asp Lys Thr Lys Lys Val
385                 390                 395                 400 cgc gac gcc gcc atg aac gat ggc cgc tgc gtc acc tac ctc aag ggc     1248
Arg Asp Ala Ala Met Asn Asp Gly Arg Cys Val Thr Tyr Leu Lys Gly
                405                 410                 415 gcc gca ccg ctc atc aag gcc ccg gag ccc                            1278
Ala Ala Pro Leu Ile Lys Ala Pro Glu Pro
            420                 425

<210> SEQ ID NO 10
<211> LENGTH: 426
<212> TYPE: PRT
<213> ORGANISM: Schizochytrium sp.

<400> SEQUENCE: 10

Asp Val Thr Lys Glu Ala Trp Arg Leu Pro Arg Glu Gly Val Ser Phe
1               5                   10                  15

Arg Ala Lys Gly Ile Ala Thr Asn Gly Ala Val Ala Ala Leu Phe Ser
            20                  25                  30

Gly Gln Gly Ala Gln Tyr Thr His Met Phe Ser Glu Val Ala Met Asn
        35                  40                  45

Trp Pro Gln Phe Arg Gln Ser Ile Ala Ala Met Asp Ala Ala Gln Ser
```

-continued

```
                50                  55                  60
Lys Val Ala Gly Ser Asp Lys Asp Phe Glu Arg Val Ser Gln Val Leu
 65                  70                  75                  80

Tyr Pro Arg Lys Pro Tyr Glu Arg Glu Pro Glu Gln Asn Pro Lys Lys
                 85                  90                  95

Ile Ser Leu Thr Ala Tyr Ser Gln Pro Ser Thr Leu Ala Cys Ala Leu
                100                 105                 110

Gly Ala Phe Glu Ile Phe Lys Glu Ala Gly Phe Thr Pro Asp Phe Ala
                115                 120                 125

Ala Gly His Ser Leu Gly Glu Phe Ala Ala Leu Tyr Ala Ala Gly Cys
                130                 135                 140

Val Asp Arg Asp Glu Leu Phe Glu Leu Val Cys Arg Arg Ala Arg Ile
145                 150                 155                 160

Met Gly Gly Lys Asp Ala Pro Ala Thr Pro Lys Gly Cys Met Ala Ala
                165                 170                 175

Val Ile Gly Pro Asn Ala Glu Asn Ile Lys Val Gln Ala Ala Asn Val
                180                 185                 190

Trp Leu Gly Asn Ser Asn Ser Pro Ser Gln Thr Val Ile Thr Gly Ser
                195                 200                 205

Val Glu Gly Ile Gln Ala Glu Ser Ala Arg Leu Gln Lys Glu Gly Phe
                210                 215                 220

Arg Val Val Pro Leu Ala Cys Glu Ser Ala Phe His Ser Pro Gln Met
225                 230                 235                 240

Glu Asn Ala Ser Ser Ala Phe Lys Asp Val Ile Ser Lys Val Ser Phe
                245                 250                 255

Arg Thr Pro Lys Ala Glu Thr Lys Leu Phe Ser Asn Val Ser Gly Glu
                260                 265                 270

Thr Tyr Pro Thr Asp Ala Arg Glu Met Leu Thr Gln His Met Thr Ser
                275                 280                 285

Ser Val Lys Phe Leu Thr Gln Val Arg Asn Met His Gln Ala Gly Ala
                290                 295                 300

Arg Ile Phe Val Glu Phe Gly Pro Lys Gln Val Leu Ser Lys Leu Val
305                 310                 315                 320

Ser Glu Thr Leu Lys Asp Asp Pro Ser Val Val Thr Val Ser Val Asn
                325                 330                 335

Pro Ala Ser Gly Thr Asp Ser Asp Ile Gln Leu Arg Asp Ala Ala Val
                340                 345                 350

Gln Leu Val Val Ala Gly Val Asn Leu Gln Gly Phe Asp Lys Trp Asp
                355                 360                 365

Ala Pro Asp Ala Thr Arg Met Gln Ala Ile Lys Lys Lys Arg Thr Thr
                370                 375                 380

Leu Arg Leu Ser Ala Ala Thr Tyr Val Ser Asp Lys Thr Lys Lys Val
385                 390                 395                 400

Arg Asp Ala Ala Met Asn Asp Gly Arg Cys Val Thr Tyr Leu Lys Gly
                405                 410                 415

Ala Ala Pro Leu Ile Lys Ala Pro Glu Pro
                420                 425

<210> SEQ ID NO 11
<211> LENGTH: 5
<212> TYPE: PRT
<213> ORGANISM: Schizochytrium sp.
<220> FEATURE:
<221> NAME/KEY: MISC_FEATURE
<222> LOCATION: (1)..(5)
```

<223> OTHER INFORMATION: Xaa = any amino acid

<400> SEQUENCE: 11

Gly His Ser Xaa Gly
1               5

<210> SEQ ID NO 12
<211> LENGTH: 258
<212> TYPE: DNA
<213> ORGANISM: Schizochytrium sp.
<220> FEATURE:
<221> NAME/KEY: CDS
<222> LOCATION: (1)..(258)

<400> SEQUENCE: 12

```
gct gtc tcg aac gag ctt ctt gag aag gcc gag act gtc gtc atg gag      48
Ala Val Ser Asn Glu Leu Leu Glu Lys Ala Glu Thr Val Val Met Glu
1               5                   10                  15 gtc ctc gcc gcc aag acc ggc tac gag acc gac atg atc gag gct gac      96
Val Leu Ala Ala Lys Thr Gly Tyr Glu Thr Asp Met Ile Glu Ala Asp
            20                  25                  30 atg gag ctc gag acc gag ctc ggc att gac tcc atc aag cgt gtc gag     144
Met Glu Leu Glu Thr Glu Leu Gly Ile Asp Ser Ile Lys Arg Val Glu
        35                  40                  45 atc ctc tcc gag gtc cag gcc atg ctc aat gtc gag gcc aag gat gtc     192
Ile Leu Ser Glu Val Gln Ala Met Leu Asn Val Glu Ala Lys Asp Val
    50                  55                  60 gat gcc ctc agc cgc act cgc act gtt ggt gag gtt gtc aac gcc atg     240
Asp Ala Leu Ser Arg Thr Arg Thr Val Gly Glu Val Val Asn Ala Met
65                  70                  75                  80 aag gcc gag atc gct ggc                                             258
Lys Ala Glu Ile Ala Gly
                85
```

<210> SEQ ID NO 13
<211> LENGTH: 86
<212> TYPE: PRT
<213> ORGANISM: Schizochytrium sp.

<400> SEQUENCE: 13

Ala Val Ser Asn Glu Leu Leu Glu Lys Ala Glu Thr Val Val Met Glu
1               5                   10                  15

Val Leu Ala Ala Lys Thr Gly Tyr Glu Thr Asp Met Ile Glu Ala Asp
            20                  25                  30

Met Glu Leu Glu Thr Glu Leu Gly Ile Asp Ser Ile Lys Arg Val Glu
        35                  40                  45

Ile Leu Ser Glu Val Gln Ala Met Leu Asn Val Glu Ala Lys Asp Val
    50                  55                  60

Asp Ala Leu Ser Arg Thr Arg Thr Val Gly Glu Val Val Asn Ala Met
65                  70                  75                  80

Lys Ala Glu Ile Ala Gly
                85

<210> SEQ ID NO 14
<211> LENGTH: 5
<212> TYPE: PRT
<213> ORGANISM: Schizochytrium sp.

<400> SEQUENCE: 14

Leu Gly Ile Asp Ser
1               5

```
<210> SEQ ID NO 15
<211> LENGTH: 21
<212> TYPE: PRT
<213> ORGANISM: Schizochytrium sp.

<400> SEQUENCE: 15

Ala Pro Ala Pro Val Lys Ala Ala Ala Pro Ala Ala Pro Val Ala Ser
1               5                   10                  15

Ala Pro Ala Pro Ala
            20

<210> SEQ ID NO 16
<211> LENGTH: 3006
<212> TYPE: DNA
<213> ORGANISM: Schizochytrium sp.

<400> SEQUENCE: 16
gcccccgccc cggtcaaggc tgctgcgcct gccgccccg ttgcctcggc ccctgccccg      60
gctgtctcga acgagcttct tgagaaggcc gagactgtcg tcatggaggt cctcgccgcc     120
aagaccggct acgagaccga catgatcgag gctgacatgg agctcgagac cgagctcggc     180
attgactcca tcaagcgtgt cgagatcctc tccgaggtcc aggccatgct caatgtcgag     240
gccaaggatg tcgatgccct cagccgcact cgcactgttg gtgaggttgt caacgccatg     300
aaggccgaga tcgctggcag ctctgccccg gcgcctgctg ccgctgctcc ggctccggcc     360
aaggctgccc ctgccgccgc tgcgcctgct gtctcgaacg agcttctcga aggccgag      420 accgtcgtca tggaggtcct cgccgccaag actggctacg agactgacat gatcgagtcc     480
gacatggagc tcgagactga gctcggcatt gactccatca agcgtgtcga gatcctctcc     540
gaggttcagg ccatgctcaa cgtcgaggcc aaggacgtcg acgctctcag ccgcactcgc     600
actgtgggtg aggtcgtcaa cgccatgaag gctgagatcc tggtggctc tgccccggcg     660 cctgccgccg ctgccccagg tccggctgct gccgcccctg cgcctgccgc cgccgcccct     720
gctgtctcga acgagcttct tgagaaggcc gagaccgtcg tcatggaggt cctcgccgcc     780
aagactggct acgagactga catgatcgag tccgacatgg agctcgagac cgagctcggc     840
attgactcca tcaagcgtgt cgagattctc tccgaggtcc aggccatgct caacgtcgag     900
gccaaggacg tcgacgctct cagccgcacc cgcactgttg gcgaggtcgt cgatgccatg     960
aaggccgaga tcgctggtgg ctctgccccg gcgcctgccg ccgctgctcc tgctccggct    1020
gctgccgccc ctgcgcctgc cgcccctgcg cctgctgtct cgagcgagct tctcgagaag    1080
gccgagactg tcgtcatgga ggtcctcgcc gccaagactg gctacgagac tgacatgatc    1140
gagtccgaca tggagctcga gaccgagctc ggcattgact ccatcaagcg tgtcgagatt    1200
ctctccgagg tccaggccat gctcaacgtc gaggccaagg acgtcgacgc tctcagccgc    1260
acccgcactt tggcgaggt cgtcgatgcc atgaaggccg agatcgctgg tggctctgcc    1320
ccggcgcctg ccgccgctgc tcctgctccg gctgctgccg cccctgcgcc tgccgcccct    1380
gcgcctgccg cccctgcgcc tgctgtctcg agcgagcttc tcgagaaggc cgagactgtc    1440
gtcatggagg tcctcgccgc caagactggc tacgagactg acatgattga gtccgacatg    1500
gagctcgaga ccgagctcgg cattgactcc atcaagcgtg tcgagattct ctccgaggtt    1560
caggccatgc tcaacgtcga ggccaaggac gtcgacgctc tcagccgcac tcgcactgtt    1620
ggtgaggtcg tcgatgccat gaaggctgag atcgctggca gctccgcctc ggcgcctgcc    1680
gccgctgctc ctgctccggc tgctgccgct cctgcgcccg ctgccgccgc ccctgctgtc    1740
```

-continued

```
tcgaacgagc ttctcgagaa agccgagact gtcgtcatgg aggtcctcgc cgccaagact      1800
ggctacgaga ctgacatgat cgagtccgac atggagctcg agactgagct cggcattgac      1860
tccatcaagc gtgtcgagat cctctccgag gttcaggcca tgctcaacgt cgaggccaag      1920
gacgtcgatg ccctcagccg cacccgcact gttggcgagg ttgtcgatgc catgaaggcc      1980
gagatcgctg gtggctctgc cccggcgcct gccgccgctg cccctgctcc ggctgccgcc      2040
gcccctgctg tctcgaacga gcttctcgag aaggccgaga ctgtcgtcat ggaggtcctc      2100
gccgccaaga ctggctacga gaccgacatg atcgagtccg acatggagct cgagaccgag      2160
ctcggcattg actccatcaa gcgtgtcgag attctctccg aggttcaggc catgctcaac      2220
gtcgaggcca aggacgtcga tgctctcagc cgcactcgca ctgttggcga ggtcgtcgat      2280
gccatgaagg ctgagatcgc cggcagctcc gccccggcgc ctgccgccgc tgctcctgct      2340
ccggctgctg ccgctcctgc gcccgctgcc gctgcccctg ctgtctcgag cgagcttctc      2400
gagaaggccg agaccgtcgt catggaggtc ctcgccgcca agactggcta cgagactgac      2460
atgattgagt ccgacatgga gctcgagact gagctcggca ttgactccat caagcgtgtc      2520
gagatcctct ccgaggttca ggccatgctc aacgtcgagg ccaaggacgt cgatgccctc      2580
agccgcaccc gcactgttgg cgaggttgtc gatgccatga aggccgagat cgctggtggc      2640
tctgccccgg cgcctgccgc cgctgcccct gctccggctg ccgccgcccc tgctgtctcg      2700
aacgagcttc ttgagaaggc cgagaccgtc gtcatggagg tcctcgccgc caagactggc      2760
tacgagaccg acatgatcga gtccgacatg gagctcgaga ccgagctcgg cattgactcc      2820
atcaagcgtg tcgagattct ctccgaggtt caggccatgc tcaacgtcga ggccaaggac      2880
gtcgacgctc tcagccgcac tcgcactgtt ggcgaggtcg tcgatgccat gaaggctgag      2940
atcgctggtg gctctgcccc ggcgcctgcc gccgctgctc ctgcctcggc tggcgccgcg      3000
cctgcg                                                                3006
```

```
<210> SEQ ID NO 17
<211> LENGTH: 2133
<212> TYPE: DNA
<213> ORGANISM: Schizochytrium sp.
<220> FEATURE:
<221> NAME/KEY: CDS
<222> LOCATION: (1)..(2133)

<400> SEQUENCE: 17
```

```
ttt ggc gct ctc ggc ggc ttc atc tcg cag cag gcg gag cgc ttc gag       48
Phe Gly Ala Leu Gly Gly Phe Ile Ser Gln Gln Ala Glu Arg Phe Glu
1               5                   10                  15 ccc gcc gaa atc ctc ggc ttc acg ctc atg tgc gcc aag ttc gcc aag       96
Pro Ala Glu Ile Leu Gly Phe Thr Leu Met Cys Ala Lys Phe Ala Lys
            20                  25                  30 gct tcc ctc tgc acg gct gtg gct ggc ggc cgc ccg gcc ttt atc ggt      144
Ala Ser Leu Cys Thr Ala Val Ala Gly Gly Arg Pro Ala Phe Ile Gly
        35                  40                  45 gtg gcg cgc ctt gac ggc cgc ctc gga ttc act tcg cag ggc act tct      192
Val Ala Arg Leu Asp Gly Arg Leu Gly Phe Thr Ser Gln Gly Thr Ser
    50                  55                  60 gac gcg ctc aag cgt gcc cag cgt ggt gcc atc ttt ggc ctc tgc aag      240
Asp Ala Leu Lys Arg Ala Gln Arg Gly Ala Ile Phe Gly Leu Cys Lys
65                  70                  75                  80 acc atc ggc ctc gag tgg tcc gag tct gac gtc ttt tcc cgc ggc gtg      288
Thr Ile Gly Leu Glu Trp Ser Glu Ser Asp Val Phe Ser Arg Gly Val
                85                  90                  95
```

-continued

```
gac att gct cag ggc atg cac ccc gag gat gcc gcc gtg gcg att gtg      336
Asp Ile Ala Gln Gly Met His Pro Glu Asp Ala Ala Val Ala Ile Val
        100                 105                 110 cgc gag atg gcg tgc gct gac att cgc att cgc gag gtc ggc att ggc      384
Arg Glu Met Ala Cys Ala Asp Ile Arg Ile Arg Glu Val Gly Ile Gly
            115                 120                 125 gca aac cag cag cgc tgc acg atc cgt gcc gcc aag ctc gag acc ggc      432
Ala Asn Gln Gln Arg Cys Thr Ile Arg Ala Ala Lys Leu Glu Thr Gly
    130                 135                 140 aac ccg cag cgc cag atc gcc aag gac gac gtg ctg ctc gtt tct ggc      480
Asn Pro Gln Arg Gln Ile Ala Lys Asp Asp Val Leu Leu Val Ser Gly
145                 150                 155                 160 ggc gct cgc ggc atc acg cct ctt tgc atc cgg gag atc acg cgc cag      528
Gly Ala Arg Gly Ile Thr Pro Leu Cys Ile Arg Glu Ile Thr Arg Gln
                165                 170                 175 atc gcg ggc ggc aag tac att ctg ctt ggc cgc agc aag gtc tct gcg      576
Ile Ala Gly Gly Lys Tyr Ile Leu Leu Gly Arg Ser Lys Val Ser Ala
            180                 185                 190 agc gaa ccg gca tgg tgc gct ggc atc act gac gag aag gct gtg caa      624
Ser Glu Pro Ala Trp Cys Ala Gly Ile Thr Asp Glu Lys Ala Val Gln
        195                 200                 205 aag gct gct acc cag gag ctc aag cgc gcc ttt agc gct ggc gag ggc      672
Lys Ala Ala Thr Gln Glu Leu Lys Arg Ala Phe Ser Ala Gly Glu Gly
    210                 215                 220 ccc aag ccc acg ccc cgc gct gtc act aag ctt gtg ggc tct gtt ctt      720
Pro Lys Pro Thr Pro Arg Ala Val Thr Lys Leu Val Gly Ser Val Leu
225                 230                 235                 240 ggc gct cgc gag gtg cgc agc tct att gct gcg att gaa gcg ctc ggc      768
Gly Ala Arg Glu Val Arg Ser Ser Ile Ala Ala Ile Glu Ala Leu Gly
                245                 250                 255 ggc aag gcc atc tac tcg tcg tgc gac gtg aac tct gcc gcc gac gtg      816
Gly Lys Ala Ile Tyr Ser Ser Cys Asp Val Asn Ser Ala Ala Asp Val
            260                 265                 270 gcc aag gcc gtg cgc gat gcc gag tcc cag ctc ggt gcc cgc gtc tcg      864
Ala Lys Ala Val Arg Asp Ala Glu Ser Gln Leu Gly Ala Arg Val Ser
        275                 280                 285 ggc atc gtt cat gcc tcg ggc gtg ctc cgc gac cgt ctc atc gag aag      912
Gly Ile Val His Ala Ser Gly Val Leu Arg Asp Arg Leu Ile Glu Lys
    290                 295                 300 aag ctc ccc gac gag ttc gac gcc gtc ttt ggc acc aag gtc acc ggt      960
Lys Leu Pro Asp Glu Phe Asp Ala Val Phe Gly Thr Lys Val Thr Gly
305                 310                 315                 320 ctc gag aac ctc ctc gcc gcc gtc gac cgc gcc aac ctc aag cac atg     1008
Leu Glu Asn Leu Leu Ala Ala Val Asp Arg Ala Asn Leu Lys His Met
                325                 330                 335 gtc ctc ttc agc tcg ctc gcc ggc ttc cac ggc aac gtc ggc cag tct     1056
Val Leu Phe Ser Ser Leu Ala Gly Phe His Gly Asn Val Gly Gln Ser
            340                 345                 350 gac tac gcc atg gcc aac gag gcc ctt aac aag atg ggc ctc gag ctc     1104
Asp Tyr Ala Met Ala Asn Glu Ala Leu Asn Lys Met Gly Leu Glu Leu
        355                 360                 365 gcc aag gac gtc tcg gtc aag tcg atc tgc ttc ggt ccc tgg gac ggt     1152
Ala Lys Asp Val Ser Val Lys Ser Ile Cys Phe Gly Pro Trp Asp Gly
    370                 375                 380 ggc atg gtg acg ccg cag ctc aag aag cag ttc cag gag atg ggc gtg     1200
Gly Met Val Thr Pro Gln Leu Lys Lys Gln Phe Gln Glu Met Gly Val
385                 390                 395                 400 cag atc atc ccc cgc gag ggc ggc gct gat acc gtg gcg cgc atc gtg     1248
Gln Ile Ile Pro Arg Glu Gly Gly Ala Asp Thr Val Ala Arg Ile Val
```

-continued

|  |  |  | 405 |  |  |  | 410 |  |  |  | 415 |  |  |  |  |
|---|---|---|---|---|---|---|---|---|---|---|---|---|---|---|---|

```
ctc ggc tcc tcg ccg gct gag atc ctt gtc ggc aac tgg cgc acc ccg    1296
Leu Gly Ser Ser Pro Ala Glu Ile Leu Val Gly Asn Trp Arg Thr Pro
            420                 425                 430 tcc aag aag gtc ggc tcg gac acc atc acc ctg cac cgc aag att tcc    1344
Ser Lys Lys Val Gly Ser Asp Thr Ile Thr Leu His Arg Lys Ile Ser
            435                 440                 445 gcc aag tcc aac ccc ttc ctc gag gac cac gtc atc cag ggc cgc cgc    1392
Ala Lys Ser Asn Pro Phe Leu Glu Asp His Val Ile Gln Gly Arg Arg
        450                 455                 460 gtg ctg ccc atg acg ctg gcc att ggc tcg ctc gcg gag acc tgc ctc    1440
Val Leu Pro Met Thr Leu Ala Ile Gly Ser Leu Ala Glu Thr Cys Leu
465                 470                 475                 480 ggc ctc ttc ccc ggc tac tcg ctc tgg gcc att gac gac gcc cag ctc    1488
Gly Leu Phe Pro Gly Tyr Ser Leu Trp Ala Ile Asp Asp Ala Gln Leu
                    485                 490                 495 ttc aag ggt gtc act gtc gac ggc gac gtc aac tgc gag gtg acc ctc    1536
Phe Lys Gly Val Thr Val Asp Gly Asp Val Asn Cys Glu Val Thr Leu
                500                 505                 510 acc ccg tcg acg gcg ccc tcg ggc cgc gtc aac gtc cag gcc acg ctc    1584
Thr Pro Ser Thr Ala Pro Ser Gly Arg Val Asn Val Gln Ala Thr Leu
            515                 520                 525 aag acc ttt tcc agc ggc aag ctg gtc ccg gcc tac cgc gcc gtc atc    1632
Lys Thr Phe Ser Ser Gly Lys Leu Val Pro Ala Tyr Arg Ala Val Ile
        530                 535                 540 gtg ctc tcc aac cag ggc gcg ccc ccg gcc aac gcc acc atg cag ccg    1680
Val Leu Ser Asn Gln Gly Ala Pro Pro Ala Asn Ala Thr Met Gln Pro
545                 550                 555                 560 ccc tcg ctc gat gcc gat ccg gcg ctc cag ggc tcc gtc tac gac ggc    1728
Pro Ser Leu Asp Ala Asp Pro Ala Leu Gln Gly Ser Val Tyr Asp Gly
                    565                 570                 575 aag acc ctc ttc cac ggc ccg gcc ttc cgc ggc atc gat gac gtg ctc    1776
Lys Thr Leu Phe His Gly Pro Ala Phe Arg Gly Ile Asp Asp Val Leu
                580                 585                 590 tcg tgc acc aag agc cag ctt gtg gcc aag tgc agc gct gtc ccc ggc    1824
Ser Cys Thr Lys Ser Gln Leu Val Ala Lys Cys Ser Ala Val Pro Gly
            595                 600                 605 tcc gac gcc gct cgc ggc gag ttt gcc acg gac act gac gcc cat gac    1872
Ser Asp Ala Ala Arg Gly Glu Phe Ala Thr Asp Thr Asp Ala His Asp
        610                 615                 620 ccc ttc gtg aac gac ctg gcc ttt cag gcc atg ctc gtc tgg gtg cgc    1920
Pro Phe Val Asn Asp Leu Ala Phe Gln Ala Met Leu Val Trp Val Arg
625                 630                 635                 640 cgc acg ctc ggc cag gct gcg ctc ccc aac tcg atc cag cgc atc gtc    1968
Arg Thr Leu Gly Gln Ala Ala Leu Pro Asn Ser Ile Gln Arg Ile Val
                    645                 650                 655 cag cac cgc ccg gtc ccg cag gac aag ccc ttc tac att acc ctc cgc    2016
Gln His Arg Pro Val Pro Gln Asp Lys Pro Phe Tyr Ile Thr Leu Arg
                660                 665                 670 tcc aac cag tcg ggc ggt cac tcc cag cac aag cac gcc ctt cag ttc    2064
Ser Asn Gln Ser Gly Gly His Ser Gln His Lys His Ala Leu Gln Phe
            675                 680                 685 cac aac gag cag ggc gat ctc ttc att gat gtc cag gct tcg gtc atc    2112
His Asn Glu Gln Gly Asp Leu Phe Ile Asp Val Gln Ala Ser Val Ile
        690                 695                 700 gcc acg gac agc ctt gcc ttc                                        2133
Ala Thr Asp Ser Leu Ala Phe
705                 710
```

-continued

```
<210> SEQ ID NO 18
<211> LENGTH: 711
<212> TYPE: PRT
<213> ORGANISM: Schizochytrium sp.

<400> SEQUENCE: 18
```

| | | | | | | | | | | | | | | |
|---|---|---|---|---|---|---|---|---|---|---|---|---|---|---|
| Phe | Gly | Ala | Leu | Gly | Gly | Phe | Ile | Ser | Gln | Gln | Ala | Glu | Arg | Phe | Glu |
| 1 | | | | 5 | | | | | 10 | | | | | 15 | |

Pro Ala Glu Ile Leu Gly Phe Thr Leu Met Cys Ala Lys Phe Ala Lys
            20                  25                  30

Ala Ser Leu Cys Thr Ala Val Ala Gly Gly Arg Pro Ala Phe Ile Gly
        35                  40                  45

Val Ala Arg Leu Asp Gly Arg Leu Gly Phe Thr Ser Gln Gly Thr Ser
 50                  55                  60

Asp Ala Leu Lys Arg Ala Gln Arg Gly Ala Ile Phe Gly Leu Cys Lys
 65                  70                  75                  80

Thr Ile Gly Leu Glu Trp Ser Glu Ser Asp Val Phe Ser Arg Gly Val
                85                  90                  95

Asp Ile Ala Gln Gly Met His Pro Glu Asp Ala Val Ala Ile Val
            100                 105                 110

Arg Glu Met Ala Cys Ala Asp Ile Arg Ile Arg Glu Val Gly Ile Gly
            115                 120                 125

Ala Asn Gln Gln Arg Cys Thr Ile Arg Ala Ala Lys Leu Glu Thr Gly
        130                 135                 140

Asn Pro Gln Arg Gln Ile Ala Lys Asp Asp Val Leu Leu Val Ser Gly
145                 150                 155                 160

Gly Ala Arg Gly Ile Thr Pro Leu Cys Ile Arg Glu Ile Thr Arg Gln
                165                 170                 175

Ile Ala Gly Gly Lys Tyr Ile Leu Leu Gly Arg Ser Lys Val Ser Ala
            180                 185                 190

Ser Glu Pro Ala Trp Cys Ala Gly Ile Thr Asp Glu Lys Ala Val Gln
        195                 200                 205

Lys Ala Ala Thr Gln Glu Leu Lys Arg Ala Phe Ser Ala Gly Glu Gly
    210                 215                 220

Pro Lys Pro Thr Pro Arg Ala Val Thr Lys Leu Val Gly Ser Val Leu
225                 230                 235                 240

Gly Ala Arg Glu Val Arg Ser Ser Ile Ala Ala Ile Glu Ala Leu Gly
                245                 250                 255

Gly Lys Ala Ile Tyr Ser Ser Cys Asp Val Asn Ser Ala Ala Asp Val
            260                 265                 270

Ala Lys Ala Val Arg Asp Ala Glu Ser Gln Leu Gly Ala Arg Val Ser
        275                 280                 285

Gly Ile Val His Ala Ser Gly Val Leu Arg Asp Arg Leu Ile Glu Lys
    290                 295                 300

Lys Leu Pro Asp Glu Phe Asp Ala Val Phe Gly Thr Lys Val Thr Gly
305                 310                 315                 320

Leu Glu Asn Leu Leu Ala Ala Val Asp Arg Ala Asn Leu Lys His Met
                325                 330                 335

Val Leu Phe Ser Ser Leu Ala Gly Phe His Gly Asn Val Gly Gln Ser
            340                 345                 350

Asp Tyr Ala Met Ala Asn Glu Ala Leu Asn Lys Met Gly Leu Glu Leu
        355                 360                 365

Ala Lys Asp Val Ser Val Lys Ser Ile Cys Phe Gly Pro Trp Asp Gly
    370                 375                 380

-continued

```
Gly Met Val Thr Pro Gln Leu Lys Lys Gln Phe Gln Glu Met Gly Val
385                 390                 395                 400

Gln Ile Ile Pro Arg Glu Gly Ala Asp Thr Val Ala Arg Ile Val
            405                 410                 415

Leu Gly Ser Ser Pro Ala Glu Ile Leu Val Gly Asn Trp Arg Thr Pro
            420                 425                 430

Ser Lys Lys Val Gly Ser Asp Thr Ile Thr Leu His Arg Lys Ile Ser
            435                 440                 445

Ala Lys Ser Asn Pro Phe Leu Glu Asp His Val Ile Gln Gly Arg Arg
        450                 455                 460

Val Leu Pro Met Thr Leu Ala Ile Gly Ser Leu Ala Glu Thr Cys Leu
465                 470                 475                 480

Gly Leu Phe Pro Gly Tyr Ser Leu Trp Ala Ile Asp Asp Ala Gln Leu
                485                 490                 495

Phe Lys Gly Val Thr Val Asp Gly Asp Val Asn Cys Glu Val Thr Leu
            500                 505                 510

Thr Pro Ser Thr Ala Pro Ser Gly Arg Val Asn Val Gln Ala Thr Leu
            515                 520                 525

Lys Thr Phe Ser Ser Gly Lys Leu Val Pro Ala Tyr Arg Ala Val Ile
    530                 535                 540

Val Leu Ser Asn Gln Gly Ala Pro Pro Ala Asn Ala Thr Met Gln Pro
545                 550                 555                 560

Pro Ser Leu Asp Ala Asp Pro Ala Leu Gln Gly Ser Val Tyr Asp Gly
                565                 570                 575

Lys Thr Leu Phe His Gly Pro Ala Phe Arg Gly Ile Asp Asp Val Leu
            580                 585                 590

Ser Cys Thr Lys Ser Gln Leu Val Ala Lys Cys Ser Ala Val Pro Gly
        595                 600                 605

Ser Asp Ala Ala Arg Gly Glu Phe Ala Thr Asp Thr Asp Ala His Asp
610                 615                 620

Pro Phe Val Asn Asp Leu Ala Phe Gln Ala Met Leu Val Trp Val Arg
625                 630                 635                 640

Arg Thr Leu Gly Gln Ala Ala Leu Pro Asn Ser Ile Gln Arg Ile Val
                645                 650                 655

Gln His Arg Pro Val Pro Gln Asp Lys Pro Phe Tyr Ile Thr Leu Arg
            660                 665                 670

Ser Asn Gln Ser Gly Gly His Ser Gln His Lys His Ala Leu Gln Phe
        675                 680                 685

His Asn Glu Gln Gly Asp Leu Phe Ile Asp Val Gln Ala Ser Val Ile
    690                 695                 700

Ala Thr Asp Ser Leu Ala Phe
705                 710

<210> SEQ ID NO 19
<211> LENGTH: 1350
<212> TYPE: DNA
<213> ORGANISM: Schizochytrium sp.
<220> FEATURE:
<221> NAME/KEY: CDS
<222> LOCATION: (1)..(1350)

<400> SEQUENCE: 19 atg gcc gct cgg aat gtg agc gcc gcg cat gag atg cac gat gaa aag      48
Met Ala Ala Arg Asn Val Ser Ala Ala His Glu Met His Asp Glu Lys
1               5                   10                  15 cgc atc gcc gtc gtc ggc atg gcc gtc cag tac gcc gga tgc aaa acc      96
```

```
                                                                          -continued Arg Ile Ala Val Val Gly Met Ala Val Gln Tyr Ala Gly Cys Lys Thr
            20                  25                  30 aag gac gag ttc tgg gag gtg ctc atg aac ggc aag gtc gag tcc aag        144
Lys Asp Glu Phe Trp Glu Val Leu Met Asn Gly Lys Val Glu Ser Lys
        35                  40                  45 gtg atc agc gac aaa cga ctc ggc tcc aac tac cgc gcc gag cac tac        192
Val Ile Ser Asp Lys Arg Leu Gly Ser Asn Tyr Arg Ala Glu His Tyr
 50                  55                  60 aaa gca gag cgc agc aag tat gcc gac acc ttt tgc aac gaa acg tac        240
Lys Ala Glu Arg Ser Lys Tyr Ala Asp Thr Phe Cys Asn Glu Thr Tyr
 65                  70                  75                  80 ggc acc ctt gac gag aac gag atc gac aac gag cac gaa ctc ctc ctc        288
Gly Thr Leu Asp Glu Asn Glu Ile Asp Asn Glu His Glu Leu Leu Leu
                 85                  90                  95 aac ctc gcc aag cag gca ctc gca gag aca tcc gtc aaa gac tcg aca        336
Asn Leu Ala Lys Gln Ala Leu Ala Glu Thr Ser Val Lys Asp Ser Thr
            100                 105                 110 cgc tgc ggc atc gtc agc ggc tgc ctc tcg ttc ccc atg gac aac ctc        384
Arg Cys Gly Ile Val Ser Gly Cys Leu Ser Phe Pro Met Asp Asn Leu
        115                 120                 125 cag ggt gaa ctc ctc aac gtg tac caa aac cat gtc gag aaa aag ctc        432
Gln Gly Glu Leu Leu Asn Val Tyr Gln Asn His Val Glu Lys Lys Leu
130                 135                 140 ggg gcc cgc gtc ttc aag gac gcc tcc cat tgg tcc gaa cgc gag cag        480
Gly Ala Arg Val Phe Lys Asp Ala Ser His Trp Ser Glu Arg Glu Gln
145                 150                 155                 160 tcc aac aaa ccc gag gcc ggt gac cgc cgc atc ttc atg gac ccg gcc        528
Ser Asn Lys Pro Glu Ala Gly Asp Arg Arg Ile Phe Met Asp Pro Ala
                165                 170                 175 tcc ttc gtc gcc gaa gaa ctc aac ctc ggc gcc ctt cac tac tcc gtc        576
Ser Phe Val Ala Glu Glu Leu Asn Leu Gly Ala Leu His Tyr Ser Val
            180                 185                 190 gac gca gca tgc gcc acg gcg ctc tac gtg ctc cgc ctc gcg cag gat        624
Asp Ala Ala Cys Ala Thr Ala Leu Tyr Val Leu Arg Leu Ala Gln Asp
        195                 200                 205 cat ctc gtc tcc ggc gcc gcc gac gtc atg ctc tgc ggt gcc acc tgc        672
His Leu Val Ser Gly Ala Ala Asp Val Met Leu Cys Gly Ala Thr Cys
    210                 215                 220 ctg ccg gag ccc ttt ttc atc ctt tcg ggc ttt tcc acc ttc cag gcc        720
Leu Pro Glu Pro Phe Phe Ile Leu Ser Gly Phe Ser Thr Phe Gln Ala
225                 230                 235                 240 atg ccc gtc ggc acg ggc cag aac gtg tcc atg ccg ctg cac aag gac        768
Met Pro Val Gly Thr Gly Gln Asn Val Ser Met Pro Leu His Lys Asp
                245                 250                 255 agc cag ggc ctc acc ccg ggt gag ggc ggc tcc atc atg gtc ctc aag        816
Ser Gln Gly Leu Thr Pro Gly Glu Gly Gly Ser Ile Met Val Leu Lys
            260                 265                 270 cgt ctc gat gat gcc atc cgc gac ggc gac cac att tac ggc acc ctt        864
Arg Leu Asp Asp Ala Ile Arg Asp Gly Asp His Ile Tyr Gly Thr Leu
        275                 280                 285 ctc ggc gcc aat gtc agc aac tcc ggc aca ggt ctg ccc ctc aag ccc        912
Leu Gly Ala Asn Val Ser Asn Ser Gly Thr Gly Leu Pro Leu Lys Pro
    290                 295                 300 ctt ctc ccc agc gag aaa aag tgc ctc atg gac acc tac acg cgc att        960
Leu Leu Pro Ser Glu Lys Lys Cys Leu Met Asp Thr Tyr Thr Arg Ile
305                 310                 315                 320 aac gtg cac ccg cac aag att cag tac gtc gag tgc cac gcc acc ggc       1008
Asn Val His Pro His Lys Ile Gln Tyr Val Glu Cys His Ala Thr Gly
                325                 330                 335
```

```
acg ccc cag ggt gat cgt gtg gaa atc gac gcc gtc aag gcc tgc ttt    1056
Thr Pro Gln Gly Asp Arg Val Glu Ile Asp Ala Val Lys Ala Cys Phe
        340                 345                 350 gaa ggc aag gtc ccc cgt ttc ggt acc aca aag ggc aac ttt gga cac    1104
Glu Gly Lys Val Pro Arg Phe Gly Thr Thr Lys Gly Asn Phe Gly His
355                 360                 365 acc cts gyc gca gcc ggc ttt gcc ggt atg tgc aag gtc ctc ctc tcc    1152
Thr Xaa Xaa Ala Ala Gly Phe Ala Gly Met Cys Lys Val Leu Leu Ser
    370                 375                 380 atg aag cat ggc atc atc ccg ccc acc ccg ggt atc gat gac gag acc    1200
Met Lys His Gly Ile Ile Pro Pro Thr Pro Gly Ile Asp Asp Glu Thr
385                 390                 395                 400 aag atg gac cct ctc gtc gtc tcc ggt gag gcc atc cca tgg cca gag    1248
Lys Met Asp Pro Leu Val Val Ser Gly Glu Ala Ile Pro Trp Pro Glu
                405                 410                 415 acc aac ggc gag ccc aag cgc gcc ggt ctc tcg gcc ttt ggc ttt ggt    1296
Thr Asn Gly Glu Pro Lys Arg Ala Gly Leu Ser Ala Phe Gly Phe Gly
            420                 425                 430 ggc acc aac gcc cat gcc gtc ttt gag gag cat gac ccc tcc aac gcc    1344
Gly Thr Asn Ala His Ala Val Phe Glu Glu His Asp Pro Ser Asn Ala
        435                 440                 445 gcc tgc                                                             1350
Ala Cys
    450

<210> SEQ ID NO 20
<211> LENGTH: 450
<212> TYPE: PRT
<213> ORGANISM: Schizochytrium sp.
<220> FEATURE:
<221> NAME/KEY: misc_feature
<222> LOCATION: (370)..(370)
<223> OTHER INFORMATION: The 'Xaa' at location 370 stands for Leu.
<220> FEATURE:
<221> NAME/KEY: misc_feature
<222> LOCATION: (371)..(371)
<223> OTHER INFORMATION: The 'Xaa' at location 371 stands for Ala, or
      Val.

<400> SEQUENCE: 20

Met Ala Ala Arg Asn Val Ser Ala Ala His Glu Met His Asp Glu Lys
1               5                   10                  15

Arg Ile Ala Val Val Gly Met Ala Val Gln Tyr Ala Gly Cys Lys Thr
            20                  25                  30

Lys Asp Glu Phe Trp Glu Val Leu Met Asn Gly Lys Val Glu Ser Lys
        35                  40                  45

Val Ile Ser Asp Lys Arg Leu Gly Ser Asn Tyr Arg Ala Glu His Tyr
    50                  55                  60

Lys Ala Glu Arg Ser Lys Tyr Ala Asp Thr Phe Cys Asn Glu Thr Tyr
65                  70                  75                  80

Gly Thr Leu Asp Glu Asn Glu Ile Asp Asn Glu His Glu Leu Leu Leu
                85                  90                  95

Asn Leu Ala Lys Gln Ala Leu Ala Glu Thr Ser Val Lys Asp Ser Thr
            100                 105                 110

Arg Cys Gly Ile Val Ser Gly Cys Leu Ser Phe Pro Met Asp Asn Leu
        115                 120                 125

Gln Gly Glu Leu Leu Asn Val Tyr Gln Asn His Val Glu Lys Lys Leu
    130                 135                 140

Gly Ala Arg Val Phe Lys Asp Ala Ser His Trp Ser Glu Arg Glu Gln
145                 150                 155                 160
```

-continued

```
Ser Asn Lys Pro Glu Ala Gly Asp Arg Arg Ile Phe Met Asp Pro Ala
            165                 170                 175

Ser Phe Val Ala Glu Glu Leu Asn Leu Gly Ala Leu His Tyr Ser Val
        180                 185                 190

Asp Ala Ala Cys Ala Thr Ala Leu Tyr Val Leu Arg Leu Ala Gln Asp
    195                 200                 205

His Leu Val Ser Gly Ala Ala Asp Val Met Leu Cys Gly Ala Thr Cys
210                 215                 220

Leu Pro Glu Pro Phe Phe Ile Leu Ser Gly Phe Ser Thr Phe Gln Ala
225                 230                 235                 240

Met Pro Val Gly Thr Gly Gln Asn Val Ser Met Pro Leu His Lys Asp
                245                 250                 255

Ser Gln Gly Leu Thr Pro Gly Glu Gly Gly Ser Ile Met Val Leu Lys
            260                 265                 270

Arg Leu Asp Asp Ala Ile Arg Asp Gly Asp His Ile Tyr Gly Thr Leu
        275                 280                 285

Leu Gly Ala Asn Val Ser Asn Ser Gly Thr Gly Leu Pro Leu Lys Pro
    290                 295                 300

Leu Leu Pro Ser Glu Lys Lys Cys Leu Met Asp Thr Tyr Thr Arg Ile
305                 310                 315                 320

Asn Val His Pro His Lys Ile Gln Tyr Val Glu Cys His Ala Thr Gly
                325                 330                 335

Thr Pro Gln Gly Asp Arg Val Glu Ile Asp Ala Val Lys Ala Cys Phe
            340                 345                 350

Glu Gly Lys Val Pro Arg Phe Gly Thr Thr Lys Gly Asn Phe Gly His
        355                 360                 365

Thr Xaa Xaa Ala Ala Gly Phe Ala Gly Met Cys Lys Val Leu Leu Ser
    370                 375                 380

Met Lys His Gly Ile Ile Pro Pro Thr Pro Gly Ile Asp Asp Glu Thr
385                 390                 395                 400

Lys Met Asp Pro Leu Val Val Ser Gly Glu Ala Ile Pro Trp Pro Glu
                405                 410                 415

Thr Asn Gly Glu Pro Lys Arg Ala Gly Leu Ser Ala Phe Gly Phe Gly
            420                 425                 430

Gly Thr Asn Ala His Ala Val Phe Glu Glu His Asp Pro Ser Asn Ala
        435                 440                 445

Ala Cys
    450

<210> SEQ ID NO 21
<211> LENGTH: 1323
<212> TYPE: DNA
<213> ORGANISM: Schizochytrium sp.
<220> FEATURE:
<221> NAME/KEY: CDS
<222> LOCATION: (1)..(1323)

<400> SEQUENCE: 21 tcg gcc cgc tgc ggc ggt gaa agc aac atg cgc atc gcc atc act ggt      48
Ser Ala Arg Cys Gly Gly Glu Ser Asn Met Arg Ile Ala Ile Thr Gly
1               5                   10                  15 atg gac gcc acc ttt ggc gct ctc aag gga ctc gac gcc ttc gag cgc      96
Met Asp Ala Thr Phe Gly Ala Leu Lys Gly Leu Asp Ala Phe Glu Arg
            20                  25                  30 gcc att tac acc ggc gct cac ggt gcc atc cca ctc cca gaa aag cgc     144
Ala Ile Tyr Thr Gly Ala His Gly Ala Ile Pro Leu Pro Glu Lys Arg
        35                  40                  45
```

| | |
|---|---|
| tgg cgc ttt ctc ggc aag gac aag gac ttt ctt gac ctc tgc ggc gtc<br>Trp Arg Phe Leu Gly Lys Asp Lys Asp Phe Leu Asp Leu Cys Gly Val<br>50                        55                     60 | 192 |
| aag gcc acc ccg cac ggc tgc tac att gaa gat gtt gag gtc gac ttc<br>Lys Ala Thr Pro His Gly Cys Tyr Ile Glu Asp Val Glu Val Asp Phe<br>65                        70                     75                     80 | 240 |
| cag cgc ctc cgc acg ccc atg acc cct gaa gac atg ctc ctc cct cag<br>Gln Arg Leu Arg Thr Pro Met Thr Pro Glu Asp Met Leu Leu Pro Gln<br>               85                     90                     95 | 288 |
| cag ctt ctg gcc gtc acc acc att gac cgc gcc atc ctc gac tcg gga<br>Gln Leu Leu Ala Val Thr Thr Ile Asp Arg Ala Ile Leu Asp Ser Gly<br>              100                   105                   110 | 336 |
| atg aaa aag ggt ggc aat gtc gcc gtc ttt gtc ggc ctc ggc acc gac<br>Met Lys Lys Gly Gly Asn Val Ala Val Phe Val Gly Leu Gly Thr Asp<br>              115                   120                   125 | 384 |
| ctc gag ctc tac cgt cac cgt gct cgc gtc gct ctc aag gag cgc gtc<br>Leu Glu Leu Tyr Arg His Arg Ala Arg Val Ala Leu Lys Glu Arg Val<br>130                       135                   140 | 432 |
| cgc cct gaa gcc tcc aag aag ctc aat gac atg atg cag tac att aac<br>Arg Pro Glu Ala Ser Lys Lys Leu Asn Asp Met Met Gln Tyr Ile Asn<br>145                       150                   155                   160 | 480 |
| gac tgc ggc aca tcc aca tcg tac acc tcg tac att ggc aac ctc gtc<br>Asp Cys Gly Thr Ser Thr Ser Tyr Thr Ser Tyr Ile Gly Asn Leu Val<br>                   165                   170                   175 | 528 |
| gcc acg cgc gtc tcg tcg cag tgg ggc ttc acg ggc ccc tcc ttt acg<br>Ala Thr Arg Val Ser Ser Gln Trp Gly Phe Thr Gly Pro Ser Phe Thr<br>                   180                   185                   190 | 576 |
| atc acc gag ggc aac aac tcc gtc tac cgc tgc gcc gag ctc ggc aag<br>Ile Thr Glu Gly Asn Asn Ser Val Tyr Arg Cys Ala Glu Leu Gly Lys<br>                   195                   200                   205 | 624 |
| tac ctc ctc gag acc ggc gag gtc gat ggc gtc gtc gtt gcg ggt gtc<br>Tyr Leu Leu Glu Thr Gly Glu Val Asp Gly Val Val Val Ala Gly Val<br>210                       215                   220 | 672 |
| gat ctc tgc ggc agt gcc gaa aac ctt tac gtc aag tct cgc cgc ttc<br>Asp Leu Cys Gly Ser Ala Glu Asn Leu Tyr Val Lys Ser Arg Arg Phe<br>225                       230                   235                   240 | 720 |
| aag gtg tcc acc tcc gat acc ccg cgc gcc agc ttt gac gcc gcc gcc<br>Lys Val Ser Thr Ser Asp Thr Pro Arg Ala Ser Phe Asp Ala Ala Ala<br>                   245                   250                   255 | 768 |
| gat ggc tac ttt gtc ggc gag ggc tgc ggt gcc ttt gtg ctc aag cgt<br>Asp Gly Tyr Phe Val Gly Glu Gly Cys Gly Ala Phe Val Leu Lys Arg<br>                   260                   265                   270 | 816 |
| gag act agc tgc acc aag gac gac cgt atc tac gct tgc atg gat gcc<br>Glu Thr Ser Cys Thr Lys Asp Asp Arg Ile Tyr Ala Cys Met Asp Ala<br>              275                   280                   285 | 864 |
| atc gtc cct ggc aac gtc cct agc gcc tgc ttg cgc gag gcc ctc gac<br>Ile Val Pro Gly Asn Val Pro Ser Ala Cys Leu Arg Glu Ala Leu Asp<br>290                       295                   300 | 912 |
| cag gcg cgc gtc aag ccg ggc gat atc gag atg ctc gag ctc agc gcc<br>Gln Ala Arg Val Lys Pro Gly Asp Ile Glu Met Leu Glu Leu Ser Ala<br>305                       310                   315                   320 | 960 |
| gac tcc gcc cgc cac ctc aag gac ccg tcc gtc ctg ccc aag gag ctc<br>Asp Ser Ala Arg His Leu Lys Asp Pro Ser Val Leu Pro Lys Glu Leu<br>                   325                   330                   335 | 1008 |
| act gcc gag gag gaa atc ggc ggc ctt cag acg atc ctt cgt gac gat<br>Thr Ala Glu Glu Glu Ile Gly Gly Leu Gln Thr Ile Leu Arg Asp Asp<br>              340                   345                   350 | 1056 |
| gac aag ctc ccg cgc aac gtc gca acg ggc agt gtc aag gcc acc gtc<br>Asp Lys Leu Pro Arg Asn Val Ala Thr Gly Ser Val Lys Ala Thr Val | 1104 |

```
                355                 360                 365
ggt gac acc ggt tat gcc tct ggt gct gcc agc ctc atc aag gct gcg      1152
Gly Asp Thr Gly Tyr Ala Ser Gly Ala Ala Ser Leu Ile Lys Ala Ala
    370                 375                 380 ctt tgc atc tac aac cgc tac ctg ccc agc aac ggc gac gac tgg gat      1200
Leu Cys Ile Tyr Asn Arg Tyr Leu Pro Ser Asn Gly Asp Asp Trp Asp
385                 390                 395                 400 gaa ccc gcc cct gag gcg ccc tgg gac agc acc ctc ttt gcg tgc cag      1248
Glu Pro Ala Pro Glu Ala Pro Trp Asp Ser Thr Leu Phe Ala Cys Gln
                405                 410                 415 acc tcg cgc gct tgg ctc aag aac cct ggc gag cgt cgc tat gcg gcc      1296
Thr Ser Arg Ala Trp Leu Lys Asn Pro Gly Glu Arg Arg Tyr Ala Ala
            420                 425                 430 gtc tcg ggc gtc tcc gag acg cgc tcg                                  1323
Val Ser Gly Val Ser Glu Thr Arg Ser
            435                 440

<210> SEQ ID NO 22
<211> LENGTH: 441
<212> TYPE: PRT
<213> ORGANISM: Schizochytrium sp.

<400> SEQUENCE: 22

Ser Ala Arg Cys Gly Gly Glu Ser Asn Met Arg Ile Ala Ile Thr Gly
1               5                   10                  15

Met Asp Ala Thr Phe Gly Ala Leu Lys Gly Leu Asp Ala Phe Glu Arg
            20                  25                  30

Ala Ile Tyr Thr Gly Ala His Gly Ala Ile Pro Leu Pro Glu Lys Arg
        35                  40                  45

Trp Arg Phe Leu Gly Lys Asp Lys Asp Phe Leu Asp Leu Cys Gly Val
    50                  55                  60

Lys Ala Thr Pro His Gly Cys Tyr Ile Glu Asp Val Glu Val Asp Phe
65                  70                  75                  80

Gln Arg Leu Arg Thr Pro Met Thr Pro Glu Asp Met Leu Leu Pro Gln
                85                  90                  95

Gln Leu Leu Ala Val Thr Thr Ile Asp Arg Ala Ile Leu Asp Ser Gly
            100                 105                 110

Met Lys Lys Gly Gly Asn Val Ala Val Phe Val Gly Leu Gly Thr Asp
        115                 120                 125

Leu Glu Leu Tyr Arg His Arg Ala Arg Val Ala Leu Lys Glu Arg Val
    130                 135                 140

Arg Pro Glu Ala Ser Lys Lys Leu Asn Asp Met Met Gln Tyr Ile Asn
145                 150                 155                 160

Asp Cys Gly Thr Ser Thr Ser Tyr Thr Ser Tyr Ile Gly Asn Leu Val
                165                 170                 175

Ala Thr Arg Val Ser Ser Gln Trp Gly Phe Thr Gly Pro Ser Phe Thr
            180                 185                 190

Ile Thr Glu Gly Asn Asn Ser Val Tyr Arg Cys Ala Glu Leu Gly Lys
        195                 200                 205

Tyr Leu Leu Glu Thr Gly Glu Val Asp Gly Val Val Ala Gly Val
    210                 215                 220

Asp Leu Cys Gly Ser Ala Glu Asn Leu Tyr Val Lys Ser Arg Arg Phe
225                 230                 235                 240

Lys Val Ser Thr Ser Asp Thr Pro Arg Ala Ser Phe Asp Ala Ala Ala
                245                 250                 255

Asp Gly Tyr Phe Val Gly Glu Gly Cys Gly Ala Phe Val Leu Lys Arg
```

```
                    260                 265                 270
Glu Thr Ser Cys Thr Lys Asp Asp Arg Ile Tyr Ala Cys Met Asp Ala
            275                 280                 285

Ile Val Pro Gly Asn Val Pro Ser Ala Cys Leu Arg Glu Ala Leu Asp
        290                 295                 300

Gln Ala Arg Val Lys Pro Gly Asp Ile Glu Met Leu Glu Leu Ser Ala
305                 310                 315                 320

Asp Ser Ala Arg His Leu Lys Asp Pro Ser Val Leu Pro Lys Glu Leu
                325                 330                 335

Thr Ala Glu Glu Ile Gly Gly Leu Gln Thr Ile Leu Arg Asp Asp
            340                 345                 350

Asp Lys Leu Pro Arg Asn Val Ala Thr Gly Ser Val Lys Ala Thr Val
                355                 360                 365

Gly Asp Thr Gly Tyr Ala Ser Gly Ala Ala Ser Leu Ile Lys Ala Ala
        370                 375                 380

Leu Cys Ile Tyr Asn Arg Tyr Leu Pro Ser Asn Gly Asp Asp Trp Asp
385                 390                 395                 400

Glu Pro Ala Pro Glu Ala Pro Trp Asp Ser Thr Leu Phe Ala Cys Gln
                405                 410                 415

Thr Ser Arg Ala Trp Leu Lys Asn Pro Gly Glu Arg Arg Tyr Ala Ala
            420                 425                 430

Val Ser Gly Val Ser Glu Thr Arg Ser
            435                 440

<210> SEQ ID NO 23
<211> LENGTH: 1500
<212> TYPE: DNA
<213> ORGANISM: Schizochytrium sp.
<220> FEATURE:
<221> NAME/KEY: CDS
<222> LOCATION: (1)..(1500)

<400> SEQUENCE: 23 tgc tat tcc gtg ctc ctc tcc gaa gcc gag ggc cac tac gag cgc gag       48
Cys Tyr Ser Val Leu Leu Ser Glu Ala Glu Gly His Tyr Glu Arg Glu
1               5                   10                  15 aac cgc atc tcg ctc gac gag gag gcg ccc aag ctc att gtg ctt cgc       96
Asn Arg Ile Ser Leu Asp Glu Glu Ala Pro Lys Leu Ile Val Leu Arg
            20                  25                  30 gcc gac tcc cac gag gag atc ctt ggt cgc ctc gac aag atc cgc gag      144
Ala Asp Ser His Glu Glu Ile Leu Gly Arg Leu Asp Lys Ile Arg Glu
        35                  40                  45 cgc ttc ttg cag ccc acg ggc gcc gcc ccg cgc gag tcc gag ctc aag      192
Arg Phe Leu Gln Pro Thr Gly Ala Ala Pro Arg Glu Ser Glu Leu Lys
    50                  55                  60 gcg cag gcc cgc cgc atc ttc ctc gag ctc ctc ggc gag acc ctt gcc      240
Ala Gln Ala Arg Arg Ile Phe Leu Glu Leu Leu Gly Glu Thr Leu Ala
65                  70                  75                  80 cag gat gcc gct tct tca ggc tcg caa aag ccc ctc gct ctc agc ctc      288
Gln Asp Ala Ala Ser Ser Gly Ser Gln Lys Pro Leu Ala Leu Ser Leu
                85                  90                  95 gtc tcc acg ccc tcc aag ctc cag cgc gag gtc gag ctc gcg gcc aag      336
Val Ser Thr Pro Ser Lys Leu Gln Arg Glu Val Glu Leu Ala Ala Lys
            100                 105                 110 ggt atc ccg cgc tgc ctc aag atg cgc cgc gat tgg agc tcc cct gct      384
Gly Ile Pro Arg Cys Leu Lys Met Arg Arg Asp Trp Ser Ser Pro Ala
        115                 120                 125 ggc agc cgc tac gcg cct gag ccg ctc gcc agc gac cgc gtc gcc ttc      432
```

-continued

| | | | | | | | | | | | | | | | |
|---|---|---|---|---|---|---|---|---|---|---|---|---|---|---|---|
| Gly | Ser | Arg | Tyr | Ala | Pro | Glu | Pro | Leu | Ala | Ser | Asp | Arg | Val | Ala | Phe |
| | 130 | | | | 135 | | | | 140 | | | | | | |

| atg | tac | ggc | gaa | ggt | cgc | agc | cct | tac | tac | ggc | atc | acc | caa | gac | att | 480 |
|---|---|---|---|---|---|---|---|---|---|---|---|---|---|---|---|---|
| Met | Tyr | Gly | Glu | Gly | Arg | Ser | Pro | Tyr | Tyr | Gly | Ile | Thr | Gln | Asp | Ile | |
| 145 | | | | | 150 | | | | | 155 | | | | | 160 | |

| cac | cgc | att | tgg | ccc | gaa | ctc | cac | gag | gtc | atc | aac | gaa | aag | acg | aac | 528 |
|---|---|---|---|---|---|---|---|---|---|---|---|---|---|---|---|---|
| His | Arg | Ile | Trp | Pro | Glu | Leu | His | Glu | Val | Ile | Asn | Glu | Lys | Thr | Asn | |
| | | | | 165 | | | | | 170 | | | | | 175 | | |

| cgt | ctc | tgg | gcc | gaa | ggc | gac | cgc | tgg | gtc | atg | ccg | cgc | gcc | agc | ttc | 576 |
|---|---|---|---|---|---|---|---|---|---|---|---|---|---|---|---|---|
| Arg | Leu | Trp | Ala | Glu | Gly | Asp | Arg | Trp | Val | Met | Pro | Arg | Ala | Ser | Phe | |
| | | | 180 | | | | | 185 | | | | | 190 | | | |

| aag | tcg | gag | ctc | gag | agc | cag | cag | caa | gag | ttt | gat | cgc | aac | atg | att | 624 |
|---|---|---|---|---|---|---|---|---|---|---|---|---|---|---|---|---|
| Lys | Ser | Glu | Leu | Glu | Ser | Gln | Gln | Gln | Glu | Phe | Asp | Arg | Asn | Met | Ile | |
| | | 195 | | | | | 200 | | | | | 205 | | | | |

| gaa | atg | ttc | cgt | ctt | gga | atc | ctc | acc | tca | att | gcc | ttc | acc | aat | ctg | 672 |
|---|---|---|---|---|---|---|---|---|---|---|---|---|---|---|---|---|
| Glu | Met | Phe | Arg | Leu | Gly | Ile | Leu | Thr | Ser | Ile | Ala | Phe | Thr | Asn | Leu | |
| 210 | | | | | 215 | | | | | 220 | | | | | | |

| gcg | cgc | gac | gtt | ctc | aac | atc | acg | ccc | aag | gcc | gcc | ttt | ggc | ctc | agt | 720 |
|---|---|---|---|---|---|---|---|---|---|---|---|---|---|---|---|---|
| Ala | Arg | Asp | Val | Leu | Asn | Ile | Thr | Pro | Lys | Ala | Ala | Phe | Gly | Leu | Ser | |
| 225 | | | | | 230 | | | | | 235 | | | | | 240 | |

| ctt | ggc | gag | att | tcc | atg | att | ttt | gcc | ttt | tcc | aag | aag | aac | ggt | ctc | 768 |
|---|---|---|---|---|---|---|---|---|---|---|---|---|---|---|---|---|
| Leu | Gly | Glu | Ile | Ser | Met | Ile | Phe | Ala | Phe | Ser | Lys | Lys | Asn | Gly | Leu | |
| | | | | 245 | | | | | 250 | | | | | 255 | | |

| atc | tcc | gac | cag | ctc | acc | aag | gat | ctt | cgc | gag | tcc | gac | gtg | tgg | aac | 816 |
|---|---|---|---|---|---|---|---|---|---|---|---|---|---|---|---|---|
| Ile | Ser | Asp | Gln | Leu | Thr | Lys | Asp | Leu | Arg | Glu | Ser | Asp | Val | Trp | Asn | |
| | | | 260 | | | | | 265 | | | | | 270 | | | |

| aag | gct | ctg | gcc | gtt | gaa | ttt | aat | gcg | ctg | cgc | gag | gcc | tgg | ggc | att | 864 |
|---|---|---|---|---|---|---|---|---|---|---|---|---|---|---|---|---|
| Lys | Ala | Leu | Ala | Val | Glu | Phe | Asn | Ala | Leu | Arg | Glu | Ala | Trp | Gly | Ile | |
| | | 275 | | | | | 280 | | | | | 285 | | | | |

| cca | cag | agt | gtc | ccc | aag | gac | gag | ttc | tgg | caa | ggc | tac | att | gtg | cgc | 912 |
|---|---|---|---|---|---|---|---|---|---|---|---|---|---|---|---|---|
| Pro | Gln | Ser | Val | Pro | Lys | Asp | Glu | Phe | Trp | Gln | Gly | Tyr | Ile | Val | Arg | |
| 290 | | | | | 295 | | | | | 300 | | | | | | |

| ggc | acc | aag | cag | gat | atc | gag | gcg | gcc | atc | gcc | ccg | gac | agc | aag | tac | 960 |
|---|---|---|---|---|---|---|---|---|---|---|---|---|---|---|---|---|
| Gly | Thr | Lys | Gln | Asp | Ile | Glu | Ala | Ala | Ile | Ala | Pro | Asp | Ser | Lys | Tyr | |
| 305 | | | | | 310 | | | | | 315 | | | | | 320 | |

| gtg | cgc | ctc | acc | atc | atc | aat | gat | gcc | aac | acc | gcc | ctc | att | agc | ggc | 1008 |
|---|---|---|---|---|---|---|---|---|---|---|---|---|---|---|---|---|
| Val | Arg | Leu | Thr | Ile | Ile | Asn | Asp | Ala | Asn | Thr | Ala | Leu | Ile | Ser | Gly | |
| | | | | 325 | | | | | 330 | | | | | 335 | | |

| aag | ccc | gac | gcc | tgc | aag | gct | gcg | atc | gcg | cgt | ctc | ggt | ggc | aac | att | 1056 |
|---|---|---|---|---|---|---|---|---|---|---|---|---|---|---|---|---|
| Lys | Pro | Asp | Ala | Cys | Lys | Ala | Ala | Ile | Ala | Arg | Leu | Gly | Gly | Asn | Ile | |
| | | | 340 | | | | | 345 | | | | | 350 | | | |

| cct | gcg | ctt | ccc | gtg | acc | cag | ggc | atg | tgc | ggc | cac | tgc | ccc | gag | gtg | 1104 |
|---|---|---|---|---|---|---|---|---|---|---|---|---|---|---|---|---|
| Pro | Ala | Leu | Pro | Val | Thr | Gln | Gly | Met | Cys | Gly | His | Cys | Pro | Glu | Val | |
| | | 355 | | | | | 360 | | | | | 365 | | | | |

| gga | cct | tat | acc | aag | gat | atc | gcc | aag | atc | cat | gcc | aac | ctt | gag | ttc | 1152 |
|---|---|---|---|---|---|---|---|---|---|---|---|---|---|---|---|---|
| Gly | Pro | Tyr | Thr | Lys | Asp | Ile | Ala | Lys | Ile | His | Ala | Asn | Leu | Glu | Phe | |
| | 370 | | | | | 375 | | | | | 380 | | | | | |

| ccc | gtt | gtc | gac | ggc | ctt | gac | ctc | tgg | acc | aca | atc | aac | cag | aag | cgc | 1200 |
|---|---|---|---|---|---|---|---|---|---|---|---|---|---|---|---|---|
| Pro | Val | Val | Asp | Gly | Leu | Asp | Leu | Trp | Thr | Thr | Ile | Asn | Gln | Lys | Arg | |
| 385 | | | | | 390 | | | | | 395 | | | | | 400 | |

| ctc | gtg | cca | cgc | gcc | acg | ggc | gcc | aag | gac | gaa | tgg | gcc | cct | tct | tcc | 1248 |
|---|---|---|---|---|---|---|---|---|---|---|---|---|---|---|---|---|
| Leu | Val | Pro | Arg | Ala | Thr | Gly | Ala | Lys | Asp | Glu | Trp | Ala | Pro | Ser | Ser | |
| | | | | 405 | | | | | 410 | | | | | 415 | | |

| ttt | ggc | gag | tac | gcc | ggc | cag | ctc | tac | gag | aag | cag | gct | aac | ttc | ccc | 1296 |
|---|---|---|---|---|---|---|---|---|---|---|---|---|---|---|---|---|
| Phe | Gly | Glu | Tyr | Ala | Gly | Gln | Leu | Tyr | Glu | Lys | Gln | Ala | Asn | Phe | Pro | |
| | | | 420 | | | | | 425 | | | | | 430 | | | |

| caa | atc | gtc | gag | acc | att | tac | aag | caa | aac | tac | gac | gtc | ttt | gtc | gag | 1344 |
|---|---|---|---|---|---|---|---|---|---|---|---|---|---|---|---|---|
| Gln | Ile | Val | Glu | Thr | Ile | Tyr | Lys | Gln | Asn | Tyr | Asp | Val | Phe | Val | Glu | |
| | | 435 | | | | | 440 | | | | | 445 | | | | |

```
gtt ggg ccc aac aac cac cgt agc acc gca gtg cgc acc acg ctt ggt    1392
Val Gly Pro Asn Asn His Arg Ser Thr Ala Val Arg Thr Thr Leu Gly
450                 455                 460 ccc cag cgc aac cac ctt gct ggc gcc atc gac aag cag aac gag gat    1440
Pro Gln Arg Asn His Leu Ala Gly Ala Ile Asp Lys Gln Asn Glu Asp
465                 470                 475                 480 gct tgg acg acc atc gtc aag ctt gtg gct tcg ctc aag gcc cac ctt    1488
Ala Trp Thr Thr Ile Val Lys Leu Val Ala Ser Leu Lys Ala His Leu
                485                 490                 495 gtt cct ggc gtc                                                    1500
Val Pro Gly Val
            500

<210> SEQ ID NO 24
<211> LENGTH: 500
<212> TYPE: PRT
<213> ORGANISM: Schizochytrium sp.

<400> SEQUENCE: 24

Cys Tyr Ser Val Leu Ser Glu Ala Glu Gly His Tyr Glu Arg Glu
1               5                   10                  15

Asn Arg Ile Ser Leu Asp Glu Glu Ala Pro Lys Leu Ile Val Leu Arg
            20                  25                  30

Ala Asp Ser His Glu Glu Ile Leu Gly Arg Leu Asp Lys Ile Arg Glu
        35                  40                  45

Arg Phe Leu Gln Pro Thr Gly Ala Ala Pro Arg Glu Ser Glu Leu Lys
    50                  55                  60

Ala Gln Ala Arg Arg Ile Phe Leu Glu Leu Leu Gly Glu Thr Leu Ala
65                  70                  75                  80

Gln Asp Ala Ala Ser Ser Gly Ser Gln Lys Pro Leu Ala Leu Ser Leu
                85                  90                  95

Val Ser Thr Pro Ser Lys Leu Gln Arg Glu Val Glu Leu Ala Ala Lys
            100                 105                 110

Gly Ile Pro Arg Cys Leu Lys Met Arg Arg Asp Trp Ser Ser Pro Ala
        115                 120                 125

Gly Ser Arg Tyr Ala Pro Glu Pro Leu Ala Ser Asp Arg Val Ala Phe
    130                 135                 140

Met Tyr Gly Glu Gly Arg Ser Pro Tyr Tyr Gly Ile Thr Gln Asp Ile
145                 150                 155                 160

His Arg Ile Trp Pro Glu Leu His Glu Val Ile Asn Glu Lys Thr Asn
                165                 170                 175

Arg Leu Trp Ala Glu Gly Asp Arg Trp Val Met Pro Arg Ala Ser Phe
            180                 185                 190

Lys Ser Glu Leu Glu Ser Gln Gln Gln Glu Phe Asp Arg Asn Met Ile
        195                 200                 205

Glu Met Phe Arg Leu Gly Ile Leu Thr Ser Ile Ala Phe Thr Asn Leu
    210                 215                 220

Ala Arg Asp Val Leu Asn Ile Thr Pro Lys Ala Ala Phe Gly Leu Ser
225                 230                 235                 240

Leu Gly Glu Ile Ser Met Ile Phe Ala Phe Ser Lys Lys Asn Gly Leu
                245                 250                 255

Ile Ser Asp Gln Leu Thr Lys Asp Leu Arg Glu Ser Asp Val Trp Asn
            260                 265                 270

Lys Ala Leu Ala Val Glu Phe Asn Ala Leu Arg Glu Ala Trp Gly Ile
        275                 280                 285

Pro Gln Ser Val Pro Lys Asp Glu Phe Trp Gln Gly Tyr Ile Val Arg
```

```
                290                  295                  300
Gly Thr Lys Gln Asp Ile Glu Ala Ala Ile Ala Pro Asp Ser Lys Tyr
305                 310                  315                  320

Val Arg Leu Thr Ile Ile Asn Asp Ala Asn Thr Ala Leu Ile Ser Gly
                325                  330                  335

Lys Pro Asp Ala Cys Lys Ala Ile Ala Arg Leu Gly Gly Asn Ile
                340                  345                  350

Pro Ala Leu Pro Val Thr Gln Gly Met Cys Gly His Cys Pro Glu Val
                355                  360                  365

Gly Pro Tyr Thr Lys Asp Ile Ala Lys Ile His Ala Asn Leu Glu Phe
370                 375                  380

Pro Val Val Asp Gly Leu Asp Leu Trp Thr Thr Ile Asn Gln Lys Arg
385                 390                  395                  400

Leu Val Pro Arg Ala Thr Gly Ala Lys Asp Glu Trp Ala Pro Ser Ser
                405                  410                  415

Phe Gly Glu Tyr Ala Gly Gln Leu Tyr Glu Lys Gln Ala Asn Phe Pro
                420                  425                  430

Gln Ile Val Glu Thr Ile Tyr Lys Gln Asn Tyr Asp Val Phe Val Glu
                435                  440                  445

Val Gly Pro Asn Asn His Arg Ser Thr Ala Val Arg Thr Thr Leu Gly
450                 455                  460

Pro Gln Arg Asn His Leu Ala Gly Ala Ile Asp Lys Gln Asn Glu Asp
465                 470                  475                  480

Ala Trp Thr Thr Ile Val Lys Leu Val Ala Ser Leu Lys Ala His Leu
                485                  490                  495

Val Pro Gly Val
            500

<210> SEQ ID NO 25
<211> LENGTH: 1530
<212> TYPE: DNA
<213> ORGANISM: Schizochytrium sp.
<220> FEATURE:
<221> NAME/KEY: CDS
<222> LOCATION: (1)..(1530)

<400> SEQUENCE: 25 ctg ctc gat ctc gac agt atg ctt gcg ctg agc tct gcc agt gcc tcc       48
Leu Leu Asp Leu Asp Ser Met Leu Ala Leu Ser Ser Ala Ser Ala Ser
1               5                   10                  15 ggc aac ctt gtt gag act gcg cct agc gac gcc tcg gtc att gtg ccg       96
Gly Asn Leu Val Glu Thr Ala Pro Ser Asp Ala Ser Val Ile Val Pro
                20                  25                  30 ccc tgc aac att gcg gat ctc ggc agc cgc gcc ttc atg aaa acg tac      144
Pro Cys Asn Ile Ala Asp Leu Gly Ser Arg Ala Phe Met Lys Thr Tyr
            35                  40                  45 ggt gtt tcg gcg cct ctg tac acg ggc gcc atg gcc aag ggc att gcc      192
Gly Val Ser Ala Pro Leu Tyr Thr Gly Ala Met Ala Lys Gly Ile Ala
        50                  55                  60 tct gcg gac ctc gtc att gcc gcc ggc cgc cag ggc atc ctt gcg tcc      240
Ser Ala Asp Leu Val Ile Ala Ala Gly Arg Gln Gly Ile Leu Ala Ser
65                  70                  75                  80 ttt ggc gcc ggc gga ctt ccc atg cag gtt gtg cgt gag tcc atc gaa      288
Phe Gly Ala Gly Gly Leu Pro Met Gln Val Val Arg Glu Ser Ile Glu
                85                  90                  95 aag att cag gcc gcc ctg ccc aat ggc ccg tac gct gtc aac ctt atc      336
Lys Ile Gln Ala Ala Leu Pro Asn Gly Pro Tyr Ala Val Asn Leu Ile
            100                 105                 110
```

|  |  |
|---|---|
| cat tct ccc ttt gac agc aac ctc gaa aag ggc aat gtc gat ctc ttc<br>His Ser Pro Phe Asp Ser Asn Leu Glu Lys Gly Asn Val Asp Leu Phe<br>115                    120                   125 | 384 |
| ctc gag aag ggt gtc acc ttt gtc gag gcc tcg gcc ttt atg acg ctc<br>Leu Glu Lys Gly Val Thr Phe Val Glu Ala Ser Ala Phe Met Thr Leu<br>130                   135                   140 | 432 |
| acc ccg cag gtc gtg cgg tac cgc gcg gct ggc ctc acg cgc aac gcc<br>Thr Pro Gln Val Val Arg Tyr Arg Ala Ala Gly Leu Thr Arg Asn Ala<br>145                    150                 155               160 | 480 |
| gac ggc tcg gtc aac atc cgc aac cgt atc att ggc aag gtc tcg cgc<br>Asp Gly Ser Val Asn Ile Arg Asn Arg Ile Ile Gly Lys Val Ser Arg<br>               165                 170                 175 | 528 |
| acc gag ctc gcc gag atg ttc atg cgt cct gcg ccc gag cac ctt ctt<br>Thr Glu Leu Ala Glu Met Phe Met Arg Pro Ala Pro Glu His Leu Leu<br>180                    185                   190 | 576 |
| cag aag ctc att gct tcc ggc gag atc aac cag gag cag gcc gag ctc<br>Gln Lys Leu Ile Ala Ser Gly Glu Ile Asn Gln Glu Gln Ala Glu Leu<br>               195                 200                 205 | 624 |
| gcc cgc cgt gtt ccc gtc gct gac gac atc gcg gtc gaa gct gac tcg<br>Ala Arg Arg Val Pro Val Ala Asp Asp Ile Ala Val Glu Ala Asp Ser<br>210                    215                   220 | 672 |
| ggt ggc cac acc gac aac cgc ccc atc cac gtc att ctg ccc ctc atc<br>Gly Gly His Thr Asp Asn Arg Pro Ile His Val Ile Leu Pro Leu Ile<br>225                    230                 235               240 | 720 |
| atc aac ctt cgc gac cgc ctt cac cgc gag tgc ggc tac ccg gcc aac<br>Ile Asn Leu Arg Asp Arg Leu His Arg Glu Cys Gly Tyr Pro Ala Asn<br>               245                 250                 255 | 768 |
| ctt cgc gtc cgt gtg ggc gcc ggc ggt ggc att ggg tgc ccc cag gcg<br>Leu Arg Val Arg Val Gly Ala Gly Gly Gly Ile Gly Cys Pro Gln Ala<br>             260                   265                 270 | 816 |
| gcg ctg gcc acc ttc aac atg ggt gcc tcc ttt att gtc acc ggc acc<br>Ala Leu Ala Thr Phe Asn Met Gly Ala Ser Phe Ile Val Thr Gly Thr<br>275                    280                 285 | 864 |
| gtg aac cag gtc gcc aag cag tcg ggc acg tgc gac aat gtg cgc aag<br>Val Asn Gln Val Ala Lys Gln Ser Gly Thr Cys Asp Asn Val Arg Lys<br>290                    295                   300 | 912 |
| cag ctc gcg aag gcc act tac tcg gac gta tgc atg gcc ccg gct gcc<br>Gln Leu Ala Lys Ala Thr Tyr Ser Asp Val Cys Met Ala Pro Ala Ala<br>305                    310                 315               320 | 960 |
| gac atg ttc gag gaa ggc gtc aag ctt cag gtc ctc aag aag gga acc<br>Asp Met Phe Glu Glu Gly Val Lys Leu Gln Val Leu Lys Lys Gly Thr<br>                    325                 330                 335 | 1008 |
| atg ttt ccc tcg cgc gcc aac aag ctc tac gag ctc ttt tgc aag tac<br>Met Phe Pro Ser Arg Ala Asn Lys Leu Tyr Glu Leu Phe Cys Lys Tyr<br>             340                   345                 350 | 1056 |
| gac tcg ttc gag tcc atg ccc ccc gca gag ctt gcg cgc gtc gag aag<br>Asp Ser Phe Glu Ser Met Pro Pro Ala Glu Leu Ala Arg Val Glu Lys<br>         355                   360                 365 | 1104 |
| cgc atc ttc agc cgc gcg ctc gaa gag gtc tgg gac gag acc aaa aac<br>Arg Ile Phe Ser Arg Ala Leu Glu Glu Val Trp Asp Glu Thr Lys Asn<br>370                    375                 380 | 1152 |
| ttt tac att aac cgt ctt cac aac ccg gag aag atc cag cgc gcc gag<br>Phe Tyr Ile Asn Arg Leu His Asn Pro Glu Lys Ile Gln Arg Ala Glu<br>385                    390                 395               400 | 1200 |
| cgc gac ccc aag ctc aag atg tcg ctg tgc ttt cgc tgg tac ctg agc<br>Arg Asp Pro Lys Leu Lys Met Ser Leu Cys Phe Arg Trp Tyr Leu Ser<br>               405                 410                 415 | 1248 |
| ctg gcg agc cgc tgg gcc aac act gga gct tcc gat cgc gtc atg gac<br>Leu Ala Ser Arg Trp Ala Asn Thr Gly Ala Ser Asp Arg Val Met Asp | 1296 |

```
                    420             425             430
tac cag gtc tgg tgc ggt cct gcc att ggt tcc ttc aac gat ttc atc    1344
Tyr Gln Val Trp Cys Gly Pro Ala Ile Gly Ser Phe Asn Asp Phe Ile
            435             440             445 aag gga act tac ctt gat ccg gcc gtc gca aac gag tac ccg tgc gtc    1392
Lys Gly Thr Tyr Leu Asp Pro Ala Val Ala Asn Glu Tyr Pro Cys Val
        450             455             460 gtt cag att aac aag cag atc ctt cgt gga gcg tgc ttc ttg cgc cgt    1440
Val Gln Ile Asn Lys Gln Ile Leu Arg Gly Ala Cys Phe Leu Arg Arg
465             470             475             480 ctc gaa att ctg cgc aac gca cgc ctt tcc gat ggc gct gcc gct ctt    1488
Leu Glu Ile Leu Arg Asn Ala Arg Leu Ser Asp Gly Ala Ala Ala Leu
                485             490             495 gtg gcc agc atc gat gac aca tac gtc ccg gcc gag aag ctg            1530
Val Ala Ser Ile Asp Asp Thr Tyr Val Pro Ala Glu Lys Leu
            500             505             510

<210> SEQ ID NO 26
<211> LENGTH: 510
<212> TYPE: PRT
<213> ORGANISM: Schizochytrium sp.

<400> SEQUENCE: 26

Leu Leu Asp Leu Asp Ser Met Leu Ala Leu Ser Ser Ala Ser Ala Ser
1               5                   10                  15

Gly Asn Leu Val Glu Thr Ala Pro Ser Asp Ala Ser Val Ile Val Pro
            20                  25                  30

Pro Cys Asn Ile Ala Asp Leu Gly Ser Arg Ala Phe Met Lys Thr Tyr
        35                  40                  45

Gly Val Ser Ala Pro Leu Tyr Thr Gly Ala Met Ala Lys Gly Ile Ala
    50                  55                  60

Ser Ala Asp Leu Val Ile Ala Ala Gly Arg Gln Gly Ile Leu Ala Ser
65                  70                  75                  80

Phe Gly Ala Gly Gly Leu Pro Met Gln Val Val Arg Glu Ser Ile Glu
                85                  90                  95

Lys Ile Gln Ala Ala Leu Pro Asn Gly Pro Tyr Ala Val Asn Leu Ile
            100                 105                 110

His Ser Pro Phe Asp Ser Asn Leu Glu Lys Gly Asn Val Asp Leu Phe
        115                 120                 125

Leu Glu Lys Gly Val Thr Phe Val Glu Ala Ser Ala Phe Met Thr Leu
    130                 135                 140

Thr Pro Gln Val Val Arg Tyr Arg Ala Ala Gly Leu Thr Arg Asn Ala
145                 150                 155                 160

Asp Gly Ser Val Asn Ile Arg Asn Arg Ile Ile Gly Lys Val Ser Arg
                165                 170                 175

Thr Glu Leu Ala Glu Met Phe Met Arg Pro Ala Pro Glu His Leu Leu
            180                 185                 190

Gln Lys Leu Ile Ala Ser Gly Glu Ile Asn Gln Glu Gln Ala Glu Leu
        195                 200                 205

Ala Arg Arg Val Pro Val Ala Asp Ile Ala Val Glu Ala Asp Ser
    210                 215                 220

Gly Gly His Thr Asp Asn Arg Pro Ile His Val Ile Leu Pro Leu Ile
225                 230                 235                 240

Ile Asn Leu Arg Asp Arg Leu His Arg Glu Cys Gly Tyr Pro Ala Asn
                245                 250                 255

Leu Arg Val Arg Val Gly Ala Gly Gly Gly Ile Gly Cys Pro Gln Ala
```

```
                260                 265                 270
Ala Leu Ala Thr Phe Asn Met Gly Ala Ser Phe Ile Val Thr Gly Thr
            275                 280                 285
Val Asn Gln Val Ala Lys Gln Ser Gly Thr Cys Asp Asn Val Arg Lys
        290                 295                 300
Gln Leu Ala Lys Ala Thr Tyr Ser Asp Val Cys Met Ala Pro Ala Ala
305                 310                 315                 320
Asp Met Phe Glu Glu Gly Val Lys Leu Gln Val Leu Lys Lys Gly Thr
                325                 330                 335
Met Phe Pro Ser Arg Ala Asn Lys Leu Tyr Glu Leu Phe Cys Lys Tyr
            340                 345                 350
Asp Ser Phe Glu Ser Met Pro Pro Ala Glu Leu Ala Arg Val Glu Lys
        355                 360                 365
Arg Ile Phe Ser Arg Ala Leu Glu Glu Val Trp Asp Glu Thr Lys Asn
    370                 375                 380
Phe Tyr Ile Asn Arg Leu His Asn Pro Glu Lys Ile Gln Arg Ala Glu
385                 390                 395                 400
Arg Asp Pro Lys Leu Lys Met Ser Leu Cys Phe Arg Trp Tyr Leu Ser
                405                 410                 415
Leu Ala Ser Arg Trp Ala Asn Thr Gly Ala Ser Asp Arg Val Met Asp
            420                 425                 430
Tyr Gln Val Trp Cys Gly Pro Ala Ile Gly Ser Phe Asn Asp Phe Ile
        435                 440                 445
Lys Gly Thr Tyr Leu Asp Pro Ala Val Ala Asn Glu Tyr Pro Cys Val
    450                 455                 460
Val Gln Ile Asn Lys Gln Ile Leu Arg Gly Ala Cys Phe Leu Arg Arg
465                 470                 475                 480
Leu Glu Ile Leu Arg Asn Ala Arg Leu Ser Asp Gly Ala Ala Ala Leu
                485                 490                 495
Val Ala Ser Ile Asp Asp Thr Tyr Val Pro Ala Glu Lys Leu
            500                 505                 510

<210> SEQ ID NO 27
<211> LENGTH: 4512
<212> TYPE: DNA
<213> ORGANISM: Schizochytrium sp.
<220> FEATURE:
<221> NAME/KEY: CDS
<222> LOCATION: (1)..(4512)

<400> SEQUENCE: 27 atg gcg ctc cgt gtc aag acg aac aag aag cca tgc tgg gag atg acc      48
Met Ala Leu Arg Val Lys Thr Asn Lys Lys Pro Cys Trp Glu Met Thr
1               5                   10                  15 aag gag gag ctg acc agc ggc aag acc gag gtg ttc aac tat gag gaa      96
Lys Glu Glu Leu Thr Ser Gly Lys Thr Glu Val Phe Asn Tyr Glu Glu
                20                  25                  30 ctc ctc gag ttc gca gag ggc gac atc gcc aag gtc ttc gga ccc gag     144
Leu Leu Glu Phe Ala Glu Gly Asp Ile Ala Lys Val Phe Gly Pro Glu
            35                  40                  45 ttc gcc gtc atc gac aag tac ccg cgc cgc gtg cgc ctg ccc gcc cgc     192
Phe Ala Val Ile Asp Lys Tyr Pro Arg Arg Val Arg Leu Pro Ala Arg
        50                  55                  60 gag tac ctg ctc gtg acc cgc gtc acc ctc atg gac gcc gag gtc aac     240
Glu Tyr Leu Leu Val Thr Arg Val Thr Leu Met Asp Ala Glu Val Asn
65                  70                  75                  80 aac tac cgc gtc ggc gcc cgc atg gtc acc gag tac gat ctc ccc gtc     288
```

-continued

```
                Asn Tyr Arg Val Gly Ala Arg Met Val Thr Glu Tyr Asp Leu Pro Val
                                 85                  90                  95 aac gga gag ctc tcc gag ggc gga gac tgc ccc tgg gcc gtc ctg gtc           336
Asn Gly Glu Leu Ser Glu Gly Gly Asp Cys Pro Trp Ala Val Leu Val
            100                 105                 110 gag agt ggc cag tgc gat ctc atg ctc atc tcc tac atg ggc att gac           384
Glu Ser Gly Gln Cys Asp Leu Met Leu Ile Ser Tyr Met Gly Ile Asp
        115                 120                 125 ttc cag aac cag ggc gac cgc gtc tac cgc ctg ctc aac acc acg ctc           432
Phe Gln Asn Gln Gly Asp Arg Val Tyr Arg Leu Leu Asn Thr Thr Leu
    130                 135                 140 acc ttt tac ggc gtg gcc cac gag ggc gag acc ctc gag tac gac att           480
Thr Phe Tyr Gly Val Ala His Glu Gly Glu Thr Leu Glu Tyr Asp Ile
145                 150                 155                 160 cgc gtc acc ggc ttc gcc aag cgt ctc gac ggc ggc atc tcc atg ttc           528
Arg Val Thr Gly Phe Ala Lys Arg Leu Asp Gly Gly Ile Ser Met Phe
                165                 170                 175 ttc ttc gag tac gac tgc tac gtc aac ggc cgc ctc ctc atc gag atg           576
Phe Phe Glu Tyr Asp Cys Tyr Val Asn Gly Arg Leu Leu Ile Glu Met
            180                 185                 190 cgc gat ggc tgc gcc ggc ttc ttc acc aac gag gag ctc gac gcc ggc           624
Arg Asp Gly Cys Ala Gly Phe Phe Thr Asn Glu Glu Leu Asp Ala Gly
        195                 200                 205 aag ggc gtc gtc ttc acc cgc ggc gac ctc gcc gcc cgc gcc aag atc           672
Lys Gly Val Val Phe Thr Arg Gly Asp Leu Ala Ala Arg Ala Lys Ile
    210                 215                 220 cca aag cag gac gtc tcc ccc tac gcc gtc gcc ccc tgc ctc cac aag           720
Pro Lys Gln Asp Val Ser Pro Tyr Ala Val Ala Pro Cys Leu His Lys
225                 230                 235                 240 acc aag ctc aac gaa aag gag atg cag acc ctc gtc gac aag gac tgg           768
Thr Lys Leu Asn Glu Lys Glu Met Gln Thr Leu Val Asp Lys Asp Trp
                245                 250                 255 gca tcc gtc ttt ggc tcc aag aac ggc atg ccg gaa atc aac tac aaa           816
Ala Ser Val Phe Gly Ser Lys Asn Gly Met Pro Glu Ile Asn Tyr Lys
            260                 265                 270 ctc tgc gcg cgt aag atg ctc atg att gac cgc gtc acc agc att gac           864
Leu Cys Ala Arg Lys Met Leu Met Ile Asp Arg Val Thr Ser Ile Asp
        275                 280                 285 cac aag ggc ggt gtc tac ggc ctc ggt cag ctc gtc ggt gaa aag atc           912
His Lys Gly Gly Val Tyr Gly Leu Gly Gln Leu Val Gly Glu Lys Ile
    290                 295                 300 ctc gag cgc gac cac tgg tac ttt ccc tgc cac ttt gtc aag gat cag           960
Leu Glu Arg Asp His Trp Tyr Phe Pro Cys His Phe Val Lys Asp Gln
305                 310                 315                 320 gtc atg gcc gga tcc ctc gtc tcc gac ggc tgc agc cag atg ctc aag          1008
Val Met Ala Gly Ser Leu Val Ser Asp Gly Cys Ser Gln Met Leu Lys
                325                 330                 335 atg tac atg atc tgg ctc ggc ctc cac ctc acc acc gga ccc ttt gac          1056
Met Tyr Met Ile Trp Leu Gly Leu His Leu Thr Thr Gly Pro Phe Asp
            340                 345                 350 ttc cgc ccg gtc aac ggc cac ccc aac aag gtc cgc tgc cgc ggc caa          1104
Phe Arg Pro Val Asn Gly His Pro Asn Lys Val Arg Cys Arg Gly Gln
        355                 360                 365 atc tcc ccg cac aag ggc aag ctc gtc tac gtc atg gag atc aag gag          1152
Ile Ser Pro His Lys Gly Lys Leu Val Tyr Val Met Glu Ile Lys Glu
    370                 375                 380 atg ggc ttc gac gag gac aac gac ccg tac gcc att gcc gac gtc aac          1200
Met Gly Phe Asp Glu Asp Asn Asp Pro Tyr Ala Ile Ala Asp Val Asn
385                 390                 395                 400
```

-continued

```
atc att gat gtc gac ttc gaa aag ggc cag gac ttt agc ctc gac cgc     1248
Ile Ile Asp Val Asp Phe Glu Lys Gly Gln Asp Phe Ser Leu Asp Arg
            405                 410                 415 atc agc gac tac ggc aag ggc gac ctc aac aag aag atc gtc gtc gac     1296
Ile Ser Asp Tyr Gly Lys Gly Asp Leu Asn Lys Lys Ile Val Val Asp
420                 425                 430 ttt aag ggc atc gct ctc aag atg cag aag cgc tcc acc aac aag aac     1344
Phe Lys Gly Ile Ala Leu Lys Met Gln Lys Arg Ser Thr Asn Lys Asn
    435                 440                 445 ccc tcc aag gtt cag ccc gtc ttt gcc aac ggc gcc gcc act gtc ggc     1392
Pro Ser Lys Val Gln Pro Val Phe Ala Asn Gly Ala Ala Thr Val Gly
        450                 455                 460 ccc gag gcc tcc aag gct tcc tcc ggc gcc agc gcc agc gcc agc gcc     1440
Pro Glu Ala Ser Lys Ala Ser Ser Gly Ala Ser Ala Ser Ala Ser Ala
465                 470                 475                 480 gcc ccg gcc aag cct gcc ttc agc gcc gat gtt ctt gcg ccc aag ccc     1488
Ala Pro Ala Lys Pro Ala Phe Ser Ala Asp Val Leu Ala Pro Lys Pro
                485                 490                 495 gtt gcc ctt ccc gag cac atc ctc aag ggc gac gcc ctc gcc ccc aag     1536
Val Ala Leu Pro Glu His Ile Leu Lys Gly Asp Ala Leu Ala Pro Lys
            500                 505                 510 gag atg tcc tgg cac ccc atg gcc cgc atc ccg ggc aac ccg acg ccc     1584
Glu Met Ser Trp His Pro Met Ala Arg Ile Pro Gly Asn Pro Thr Pro
        515                 520                 525 tct ttt gcg ccc tcg gcc tac aag ccg cgc aac atc gcc ttt acg ccc     1632
Ser Phe Ala Pro Ser Ala Tyr Lys Pro Arg Asn Ile Ala Phe Thr Pro
    530                 535                 540 ttc ccc ggc aac ccc aac gat aac gac cac acc ccg ggc aag atg ccg     1680
Phe Pro Gly Asn Pro Asn Asp Asn Asp His Thr Pro Gly Lys Met Pro
545                 550                 555                 560 ctc acc tgg ttc aac atg gcc gag ttc atg gcc ggc aag gtc agc atg     1728
Leu Thr Trp Phe Asn Met Ala Glu Phe Met Ala Gly Lys Val Ser Met
                565                 570                 575 tgc ctc ggc ccc gag ttc gcc aag ttc gac gac tcg aac acc agc cgc     1776
Cys Leu Gly Pro Glu Phe Ala Lys Phe Asp Asp Ser Asn Thr Ser Arg
            580                 585                 590 agc ccc gct tgg gac ctc gct ctc gtc acc cgc gcc gtg tct gtg tct     1824
Ser Pro Ala Trp Asp Leu Ala Leu Val Thr Arg Ala Val Ser Val Ser
        595                 600                 605 gac ctc aag cac gtc aac tac cgc aac atc gac ctc gac ccc tcc aag     1872
Asp Leu Lys His Val Asn Tyr Arg Asn Ile Asp Leu Asp Pro Ser Lys
    610                 615                 620 ggt acc atg gtc ggc gag ttc gac tgc ccc gcg gac gcc tgg ttc tac     1920
Gly Thr Met Val Gly Glu Phe Asp Cys Pro Ala Asp Ala Trp Phe Tyr
625                 630                 635                 640 aag ggc gcc tgc aac gat gcc cac atg ccg tac tcg atc ctc atg gag     1968
Lys Gly Ala Cys Asn Asp Ala His Met Pro Tyr Ser Ile Leu Met Glu
                645                 650                 655 atc gcc ctc cag acc tcg ggt gtg ctc acc tcg gtg ctc aag gcg ccc     2016
Ile Ala Leu Gln Thr Ser Gly Val Leu Thr Ser Val Leu Lys Ala Pro
            660                 665                 670 ctg acc atg gag aag gac gac atc ctc ttc cgc aac ctc gac gcc aac     2064
Leu Thr Met Glu Lys Asp Asp Ile Leu Phe Arg Asn Leu Asp Ala Asn
        675                 680                 685 gcc gag ttc gtg cgc gcc gac ctc gac tac cgc ggc aag act atc cgc     2112
Ala Glu Phe Val Arg Ala Asp Leu Asp Tyr Arg Gly Lys Thr Ile Arg
    690                 695                 700 aac gtc acc aag tgc act ggc tac agc atg ctc ggc gag atg ggc gtc     2160
Asn Val Thr Lys Cys Thr Gly Tyr Ser Met Leu Gly Glu Met Gly Val
705                 710                 715                 720
```

```
cac cgc ttc acc ttt gag ctc tac gtc gat gat gtg ctc ttt tac aag     2208
His Arg Phe Thr Phe Glu Leu Tyr Val Asp Asp Val Leu Phe Tyr Lys
            725                 730                 735 ggc tcg acc tcg ttc ggc tgg ttc gtg ccc gag gtc ttt gcc gcc cag     2256
Gly Ser Thr Ser Phe Gly Trp Phe Val Pro Glu Val Phe Ala Ala Gln
            740                 745                 750 gcc ggc ctc gac aac ggc cgc aag tcg gag ccc tgg ttc att gag aac     2304
Ala Gly Leu Asp Asn Gly Arg Lys Ser Glu Pro Trp Phe Ile Glu Asn
            755                 760                 765 aag gtt ccg gcc tcg cag gtc tcc tcc ttt gac gtg cgc ccc aac ggc     2352
Lys Val Pro Ala Ser Gln Val Ser Ser Phe Asp Val Arg Pro Asn Gly
            770                 775                 780 agc ggc cgc acc gcc atc ttc gcc aac gcc ccc agc ggc gcc cag ctc     2400
Ser Gly Arg Thr Ala Ile Phe Ala Asn Ala Pro Ser Gly Ala Gln Leu
785                 790                 795                 800 aac cgc cgc acg gac cag ggc cag tac ctc gac gcc gtc gac att gtc     2448
Asn Arg Arg Thr Asp Gln Gly Gln Tyr Leu Asp Ala Val Asp Ile Val
                805                 810                 815 tcc ggc agc ggc aag aag agc ctc ggc tac gcc cac ggt tcc aag acg     2496
Ser Gly Ser Gly Lys Lys Ser Leu Gly Tyr Ala His Gly Ser Lys Thr
            820                 825                 830 gtc aac ccg aac gac tgg ttc ttc tcg tgc cac ttt tgg ttt gac tcg     2544
Val Asn Pro Asn Asp Trp Phe Phe Ser Cys His Phe Trp Phe Asp Ser
            835                 840                 845 gtc atg ccc gga agt ctc ggt gtc gag tcc atg ttc cag ctc gtc gag     2592
Val Met Pro Gly Ser Leu Gly Val Glu Ser Met Phe Gln Leu Val Glu
850                 855                 860 gcc atc gcc gcc cac gag gat ctc gct ggc aaa gca cgg cat tgc caa     2640
Ala Ile Ala Ala His Glu Asp Leu Ala Gly Lys Ala Arg His Cys Gln
865                 870                 875                 880 ccc cac ctt tgt gca cgc ccc cgg gca aga tca agc tgg aag tac cgc     2688
Pro His Leu Cys Ala Arg Pro Arg Ala Arg Ser Ser Trp Lys Tyr Arg
                885                 890                 895 ggc cag ctc acg ccc aag agc aag aag atg gac tcg gag gtc cac atc     2736
Gly Gln Leu Thr Pro Lys Ser Lys Lys Met Asp Ser Glu Val His Ile
            900                 905                 910 gtg tcc gtg gac gcc cac gac ggc gtt gtc gac ctc gtc gcc gac ggc     2784
Val Ser Val Asp Ala His Asp Gly Val Val Asp Leu Val Ala Asp Gly
            915                 920                 925 ttc ctc tgg gcc gac agc ctc cgc gtc tac tcg gtg agc aac att cgc     2832
Phe Leu Trp Ala Asp Ser Leu Arg Val Tyr Ser Val Ser Asn Ile Arg
            930                 935                 940 gtg cgc atc gcc tcc ggt gag gcc cct gcc gcc gcc tcc tcc gcc gcc     2880
Val Arg Ile Ala Ser Gly Glu Ala Pro Ala Ala Ala Ser Ser Ala Ala
945                 950                 955                 960 tct gtg ggc tcc tcg gct tcg tcc gtc gag cgc acg cgc tcg agc ccc     2928
Ser Val Gly Ser Ser Ala Ser Ser Val Glu Arg Thr Arg Ser Ser Pro
                965                 970                 975 gct gtc gcc tcc ggc ccg gcc cag acc atc gac ctc aag cag ctc aag     2976
Ala Val Ala Ser Gly Pro Ala Gln Thr Ile Asp Leu Lys Gln Leu Lys
            980                 985                 990 acc gag ctc ctc gag ctc gat gcc  ccg ctc tac ctc tcg  cag gac ccg   3024
Thr Glu Leu Leu Glu Leu Asp Ala  Pro Leu Tyr Leu Ser  Gln Asp Pro
            995                 1000                1005 acc agc  ggc cag ctc aag aag  cac acc gac gtg gcc  tcc ggc cag      3069
Thr Ser  Gly Gln Leu Lys Lys  His Thr Asp Val Ala  Ser Gly Gln
    1010                1015                1020 gcc acc  atc gtg cag ccc tgc  acg ctc ggc gac ctc  ggt gac cgc      3114
Ala Thr  Ile Val Gln Pro Cys  Thr Leu Gly Asp Leu  Gly Asp Arg
```

-continued

|  |  |  |  |
|---|---|---|---|
| 1025 | 1030 | 1035 | |
| tcc ttc atg gag acc tac ggc gtc gtc gcc ccg ctg tac acg ggc<br>Ser Phe Met Glu Thr Tyr Gly Val Val Ala Pro Leu Tyr Thr Gly<br>1040          1045          1050 | | | 3159 |
| gcc atg gcc aag ggc att gcc tcg gcg gac ctc gtc atc gcc gcc<br>Ala Met Ala Lys Gly Ile Ala Ser Ala Asp Leu Val Ile Ala Ala<br>1055          1060          1065 | | | 3204 |
| ggc aag cgc aag atc ctc ggc tcc ttt ggc gcc ggc ggc ctc ccc<br>Gly Lys Arg Lys Ile Leu Gly Ser Phe Gly Ala Gly Gly Leu Pro<br>1070          1075          1080 | | | 3249 |
| atg cac cac gtg cgc gcc gcc ctc gag aag atc cag gcc gcc ctg<br>Met His His Val Arg Ala Ala Leu Glu Lys Ile Gln Ala Ala Leu<br>1085          1090          1095 | | | 3294 |
| cct cag ggc ccc tac gcc gtc aac ctc atc cac tcg cct ttt gac<br>Pro Gln Gly Pro Tyr Ala Val Asn Leu Ile His Ser Pro Phe Asp<br>1100          1105          1110 | | | 3339 |
| agc aac ctc gag aag ggc aac gtc gat ctc ttc ctc gag aag ggc<br>Ser Asn Leu Glu Lys Gly Asn Val Asp Leu Phe Leu Glu Lys Gly<br>1115          1120          1125 | | | 3384 |
| gtc act gtg gtg gag gcc tcg gca ttc atg acc ctc acc ccg cag<br>Val Thr Val Val Glu Ala Ser Ala Phe Met Thr Leu Thr Pro Gln<br>1130          1135          1140 | | | 3429 |
| gtc gtg cgc tac cgc gcc gcc ggc ctc tcg cgc aac gcc gac ggt<br>Val Val Arg Tyr Arg Ala Ala Gly Leu Ser Arg Asn Ala Asp Gly<br>1145          1150          1155 | | | 3474 |
| tcg gtc aac atc cgc aac cgc atc atc ggc aag gtc tcg cgc acc<br>Ser Val Asn Ile Arg Asn Arg Ile Ile Gly Lys Val Ser Arg Thr<br>1160          1165          1170 | | | 3519 |
| gag ctc gcc gag atg ttc atc cgc ccg gcc ccg gag cac ctc ctc<br>Glu Leu Ala Glu Met Phe Ile Arg Pro Ala Pro Glu His Leu Leu<br>1175          1180          1185 | | | 3564 |
| gag aag ctc atc gcc tcg ggc gag atc acc cag gag cag gcc gag<br>Glu Lys Leu Ile Ala Ser Gly Glu Ile Thr Gln Glu Gln Ala Glu<br>1190          1195          1200 | | | 3609 |
| ctc gcg cgc cgc gtt ccc gtc gcc gac gat atc gct gtc gag gct<br>Leu Ala Arg Arg Val Pro Val Ala Asp Asp Ile Ala Val Glu Ala<br>1205          1210          1215 | | | 3654 |
| gac tcg ggc ggc cac acc gac aac cgc ccc atc cac gtc atc ctc<br>Asp Ser Gly Gly His Thr Asp Asn Arg Pro Ile His Val Ile Leu<br>1220          1225          1230 | | | 3699 |
| ccg ctc atc atc aac ctc cgc aac cgc ctg cac cgc gag tgc ggc<br>Pro Leu Ile Ile Asn Leu Arg Asn Arg Leu His Arg Glu Cys Gly<br>1235          1240          1245 | | | 3744 |
| tac ccc gcg cac ctc cgc gtc cgc gtt ggc gcc ggc ggt ggc gtc<br>Tyr Pro Ala His Leu Arg Val Arg Val Gly Ala Gly Gly Gly Val<br>1250          1255          1260 | | | 3789 |
| ggc tgc ccg cag gcc gcc gcc gcc gcg ctc acc atg ggc gcc gcc<br>Gly Cys Pro Gln Ala Ala Ala Ala Ala Leu Thr Met Gly Ala Ala<br>1265          1270          1275 | | | 3834 |
| ttc atc gtc acc ggc act gtc aac cag gtc gcc aag cag tcc ggc<br>Phe Ile Val Thr Gly Thr Val Asn Gln Val Ala Lys Gln Ser Gly<br>1280          1285          1290 | | | 3879 |
| acc tgc gac aac gtg cgc aag cag ctc tcg cag gcc acc tac tcg<br>Thr Cys Asp Asn Val Arg Lys Gln Leu Ser Gln Ala Thr Tyr Ser<br>1295          1300          1305 | | | 3924 |
| gat atc tgc atg gcc ccg gcc gcc gac atg ttc gag gag ggc gtc<br>Asp Ile Cys Met Ala Pro Ala Ala Asp Met Phe Glu Glu Gly Val<br>1310          1315          1320 | | | 3969 |
| aag ctc cag gtc ctc aag aag gga acc atg ttc ccc tcg cgc gcc | | | 4014 |

```
Lys Leu Gln Val Leu Lys Lys Gly Thr Met Phe Pro Ser Arg Ala
1325                1330                1335 aac aag ctc tac gag ctc ttt tgc aag tac gac tcc ttc gac tcc    4059
Asn Lys Leu Tyr Glu Leu Phe Cys Lys Tyr Asp Ser Phe Asp Ser
    1340                1345                1350 atg cct cct gcc gag ctc gag cgc atc gag aag cgt atc ttc aag    4104
Met Pro Pro Ala Glu Leu Glu Arg Ile Glu Lys Arg Ile Phe Lys
1355                1360                1365 cgc gca ctc cag gag gtc tgg gag gag acc aag gac ttt tac att    4149
Arg Ala Leu Gln Glu Val Trp Glu Glu Thr Lys Asp Phe Tyr Ile
    1370                1375                1380 aac ggt ctc aag aac ccg gag aag atc cag cgc gcc gag cac gac    4194
Asn Gly Leu Lys Asn Pro Glu Lys Ile Gln Arg Ala Glu His Asp
1385                1390                1395 ccc aag ctc aag atg tcg ctc tgc ttc cgc tgg tac ctt ggt ctt    4239
Pro Lys Leu Lys Met Ser Leu Cys Phe Arg Trp Tyr Leu Gly Leu
    1400                1405                1410 gcc agc cgc tgg gcc aac atg ggc gcc ccg gac cgc gtc atg gac    4284
Ala Ser Arg Trp Ala Asn Met Gly Ala Pro Asp Arg Val Met Asp
1415                1420                1425 tac cag gtc tgg tgt ggc ccg gcc att ggc gcc ttc aac gac ttc    4329
Tyr Gln Val Trp Cys Gly Pro Ala Ile Gly Ala Phe Asn Asp Phe
    1430                1435                1440 atc aag ggc acc tac ctc gac ccc gct gtc tcc aac gag tac ccc    4374
Ile Lys Gly Thr Tyr Leu Asp Pro Ala Val Ser Asn Glu Tyr Pro
1445                1450                1455 tgt gtc gtc cag atc aac ctg caa atc ctc cgt ggt gcc tgc tac    4419
Cys Val Val Gln Ile Asn Leu Gln Ile Leu Arg Gly Ala Cys Tyr
    1460                1465                1470 ctg cgc cgt ctc aac gcc ctg cgc aac gac ccg cgc att gac ctc    4464
Leu Arg Arg Leu Asn Ala Leu Arg Asn Asp Pro Arg Ile Asp Leu
1475                1480                1485 gag acc gag gat gct gcc ttt gtc tac gag ccc acc aac gcg ctc    4509
Glu Thr Glu Asp Ala Ala Phe Val Tyr Glu Pro Thr Asn Ala Leu
    1490                1495                1500 taa                                                              4512

<210> SEQ ID NO 28
<211> LENGTH: 1503
<212> TYPE: PRT
<213> ORGANISM: Schizochytrium sp.

<400> SEQUENCE: 28

Met Ala Leu Arg Val Lys Thr Asn Lys Lys Pro Cys Trp Glu Met Thr
1               5                   10                  15

Lys Glu Glu Leu Thr Ser Gly Lys Thr Glu Val Phe Asn Tyr Glu Glu
            20                  25                  30

Leu Leu Glu Phe Ala Glu Gly Asp Ile Ala Lys Val Phe Gly Pro Glu
        35                  40                  45

Phe Ala Val Ile Asp Lys Tyr Pro Arg Arg Val Arg Leu Pro Ala Arg
    50                  55                  60

Glu Tyr Leu Leu Val Thr Arg Val Thr Leu Met Asp Ala Glu Val Asn
65                  70                  75                  80

Asn Tyr Arg Val Gly Ala Arg Met Val Thr Glu Tyr Asp Leu Pro Val
                85                  90                  95

Asn Gly Glu Leu Ser Glu Gly Gly Asp Cys Pro Trp Ala Val Leu Val
            100                 105                 110

Glu Ser Gly Gln Cys Asp Leu Met Leu Ile Ser Tyr Met Gly Ile Asp
```

-continued

```
            115                 120                 125
Phe Gln Asn Gln Gly Asp Arg Val Tyr Arg Leu Leu Asn Thr Thr Leu
    130                 135                 140
Thr Phe Tyr Gly Val Ala His Glu Gly Glu Thr Leu Glu Tyr Asp Ile
145                 150                 155                 160
Arg Val Thr Gly Phe Ala Lys Arg Leu Asp Gly Gly Ile Ser Met Phe
                165                 170                 175
Phe Phe Glu Tyr Asp Cys Tyr Val Asn Gly Arg Leu Leu Ile Glu Met
            180                 185                 190
Arg Asp Gly Cys Ala Gly Phe Phe Thr Asn Glu Glu Leu Asp Ala Gly
        195                 200                 205
Lys Gly Val Val Phe Thr Arg Gly Asp Leu Ala Ala Arg Ala Lys Ile
    210                 215                 220
Pro Lys Gln Asp Val Ser Pro Tyr Ala Val Ala Pro Cys Leu His Lys
225                 230                 235                 240
Thr Lys Leu Asn Glu Lys Glu Met Gln Thr Leu Val Asp Lys Asp Trp
                245                 250                 255
Ala Ser Val Phe Gly Ser Lys Asn Gly Met Pro Glu Ile Asn Tyr Lys
            260                 265                 270
Leu Cys Ala Arg Lys Met Leu Met Ile Asp Arg Val Thr Ser Ile Asp
        275                 280                 285
His Lys Gly Gly Val Tyr Gly Leu Gly Gln Leu Val Gly Glu Lys Ile
    290                 295                 300
Leu Glu Arg Asp His Trp Tyr Phe Pro Cys His Phe Val Lys Asp Gln
305                 310                 315                 320
Val Met Ala Gly Ser Leu Val Ser Asp Gly Cys Ser Gln Met Leu Lys
                325                 330                 335
Met Tyr Met Ile Trp Leu Gly Leu His Leu Thr Thr Gly Pro Phe Asp
            340                 345                 350
Phe Arg Pro Val Asn Gly His Pro Asn Lys Val Arg Cys Arg Gly Gln
        355                 360                 365
Ile Ser Pro His Lys Gly Lys Leu Val Tyr Val Met Glu Ile Lys Glu
    370                 375                 380
Met Gly Phe Asp Glu Asp Asn Asp Pro Tyr Ala Ile Ala Asp Val Asn
385                 390                 395                 400
Ile Ile Asp Val Asp Phe Glu Lys Gly Gln Asp Phe Ser Leu Asp Arg
                405                 410                 415
Ile Ser Asp Tyr Gly Lys Gly Asp Leu Asn Lys Ile Val Val Asp
            420                 425                 430
Phe Lys Gly Ile Ala Leu Lys Met Gln Lys Arg Ser Thr Asn Lys Asn
        435                 440                 445
Pro Ser Lys Val Gln Pro Val Phe Ala Asn Gly Ala Ala Thr Val Gly
    450                 455                 460
Pro Glu Ala Ser Lys Ala Ser Ser Gly Ala Ser Ala Ser Ala
465                 470                 475                 480
Ala Pro Ala Lys Pro Ala Phe Ser Ala Asp Val Leu Ala Pro Lys Pro
                485                 490                 495
Val Ala Leu Pro Glu His Ile Leu Lys Gly Asp Ala Leu Ala Pro Lys
            500                 505                 510
Glu Met Ser Trp His Pro Met Ala Arg Ile Pro Gly Asn Pro Thr Pro
        515                 520                 525
Ser Phe Ala Pro Ser Ala Tyr Lys Pro Arg Asn Ile Ala Phe Thr Pro
    530                 535                 540
```

```
Phe Pro Gly Asn Pro Asn Asp Asn Asp His Thr Pro Gly Lys Met Pro
545                 550                 555                 560

Leu Thr Trp Phe Asn Met Ala Glu Phe Met Ala Gly Lys Val Ser Met
                565                 570                 575

Cys Leu Gly Pro Glu Phe Ala Lys Phe Asp Asp Ser Asn Thr Ser Arg
                580                 585                 590

Ser Pro Ala Trp Asp Leu Ala Leu Val Thr Arg Ala Val Ser Val Ser
            595                 600                 605

Asp Leu Lys His Val Asn Tyr Arg Asn Ile Asp Leu Asp Pro Ser Lys
            610                 615                 620

Gly Thr Met Val Gly Glu Phe Asp Cys Pro Ala Asp Ala Trp Phe Tyr
625                 630                 635                 640

Lys Gly Ala Cys Asn Asp Ala His Met Pro Tyr Ser Ile Leu Met Glu
                645                 650                 655

Ile Ala Leu Gln Thr Ser Gly Val Leu Thr Ser Val Leu Lys Ala Pro
                660                 665                 670

Leu Thr Met Glu Lys Asp Asp Ile Leu Phe Arg Asn Leu Asp Ala Asn
            675                 680                 685

Ala Glu Phe Val Arg Ala Asp Leu Asp Tyr Arg Gly Lys Thr Ile Arg
690                 695                 700

Asn Val Thr Lys Cys Thr Gly Tyr Ser Met Leu Gly Glu Met Gly Val
705                 710                 715                 720

His Arg Phe Thr Phe Glu Leu Tyr Val Asp Asp Val Leu Phe Tyr Lys
                725                 730                 735

Gly Ser Thr Ser Phe Gly Trp Phe Val Pro Glu Val Phe Ala Ala Gln
            740                 745                 750

Ala Gly Leu Asp Asn Gly Arg Lys Ser Glu Pro Trp Phe Ile Glu Asn
            755                 760                 765

Lys Val Pro Ala Ser Gln Val Ser Ser Phe Asp Val Arg Pro Asn Gly
770                 775                 780

Ser Gly Arg Thr Ala Ile Phe Ala Asn Ala Pro Ser Gly Ala Gln Leu
785                 790                 795                 800

Asn Arg Arg Thr Asp Gln Gly Gln Tyr Leu Asp Ala Val Asp Ile Val
                805                 810                 815

Ser Gly Ser Gly Lys Lys Ser Leu Gly Tyr Ala His Gly Ser Lys Thr
            820                 825                 830

Val Asn Pro Asn Asp Trp Phe Phe Ser Cys His Phe Trp Phe Asp Ser
            835                 840                 845

Val Met Pro Gly Ser Leu Gly Val Glu Ser Met Phe Gln Leu Val Glu
850                 855                 860

Ala Ile Ala Ala His Glu Asp Leu Ala Gly Lys Ala Arg His Cys Gln
865                 870                 875                 880

Pro His Leu Cys Ala Arg Pro Arg Ala Arg Ser Ser Trp Lys Tyr Arg
                885                 890                 895

Gly Gln Leu Thr Pro Lys Ser Lys Lys Met Asp Ser Glu Val His Ile
            900                 905                 910

Val Ser Val Asp Ala His Asp Gly Val Val Asp Leu Val Ala Asp Gly
            915                 920                 925

Phe Leu Trp Ala Asp Ser Leu Arg Val Tyr Ser Val Ser Asn Ile Arg
930                 935                 940

Val Arg Ile Ala Ser Gly Glu Ala Pro Ala Ala Ser Ser Ala Ala
945                 950                 955                 960
```

-continued

Ser Val Gly Ser Ser Ala Ser Ser Val Glu Arg Thr Arg Ser Ser Pro
            965                 970                 975

Ala Val Ala Ser Gly Pro Ala Gln Thr Ile Asp Leu Lys Gln Leu Lys
            980                 985                 990

Thr Glu Leu Leu Glu Leu Asp Ala Pro Leu Tyr Leu Ser Gln Asp Pro
            995                 1000                1005

Thr Ser Gly Gln Leu Lys Lys His Thr Asp Val Ala Ser Gly Gln
    1010                1015                1020

Ala Thr Ile Val Gln Pro Cys Thr Leu Gly Asp Leu Gly Asp Arg
    1025                1030                1035

Ser Phe Met Glu Thr Tyr Gly Val Val Ala Pro Leu Tyr Thr Gly
    1040                1045                1050

Ala Met Ala Lys Gly Ile Ala Ser Ala Asp Leu Val Ile Ala Ala
    1055                1060                1065

Gly Lys Arg Lys Ile Leu Gly Ser Phe Gly Ala Gly Gly Leu Pro
    1070                1075                1080

Met His His Val Arg Ala Ala Leu Glu Lys Ile Gln Ala Ala Leu
    1085                1090                1095

Pro Gln Gly Pro Tyr Ala Val Asn Leu Ile His Ser Pro Phe Asp
    1100                1105                1110

Ser Asn Leu Glu Lys Gly Asn Val Asp Leu Phe Leu Glu Lys Gly
    1115                1120                1125

Val Thr Val Val Glu Ala Ser Ala Phe Met Thr Leu Thr Pro Gln
    1130                1135                1140

Val Val Arg Tyr Arg Ala Ala Gly Leu Ser Arg Asn Ala Asp Gly
    1145                1150                1155

Ser Val Asn Ile Arg Asn Arg Ile Ile Gly Lys Val Ser Arg Thr
    1160                1165                1170

Glu Leu Ala Glu Met Phe Ile Arg Pro Ala Pro Glu His Leu Leu
    1175                1180                1185

Glu Lys Leu Ile Ala Ser Gly Glu Ile Thr Gln Glu Gln Ala Glu
    1190                1195                1200

Leu Ala Arg Arg Val Pro Val Ala Asp Asp Ile Ala Val Glu Ala
    1205                1210                1215

Asp Ser Gly Gly His Thr Asn Arg Pro Ile His Val Ile Leu
    1220                1225                1230

Pro Leu Ile Ile Asn Leu Arg Asn Arg Leu His Arg Glu Cys Gly
    1235                1240                1245

Tyr Pro Ala His Leu Arg Val Arg Val Gly Ala Gly Gly Gly Val
    1250                1255                1260

Gly Cys Pro Gln Ala Ala Ala Ala Ala Leu Thr Met Gly Ala Ala
    1265                1270                1275

Phe Ile Val Thr Gly Thr Val Asn Gln Val Ala Lys Gln Ser Gly
    1280                1285                1290

Thr Cys Asp Asn Val Arg Lys Gln Leu Ser Gln Ala Thr Tyr Ser
    1295                1300                1305

Asp Ile Cys Met Ala Pro Ala Ala Asp Met Phe Glu Glu Gly Val
    1310                1315                1320

Lys Leu Gln Val Leu Lys Lys Gly Thr Met Phe Pro Ser Arg Ala
    1325                1330                1335

Asn Lys Leu Tyr Glu Leu Phe Cys Lys Tyr Asp Ser Phe Asp Ser
    1340                1345                1350

Met Pro Pro Ala Glu Leu Glu Arg Ile Glu Lys Arg Ile Phe Lys

```
                 1355                 1360                 1365

Arg Ala Leu Gln Glu Val Trp Glu Glu Thr Lys Asp Phe Tyr Ile
        1370                1375                1380

Asn Gly Leu Lys Asn Pro Glu Lys Ile Gln Arg Ala Glu His Asp
        1385                1390                1395

Pro Lys Leu Lys Met Ser Leu Cys Phe Arg Trp Tyr Leu Gly Leu
        1400                1405                1410

Ala Ser Arg Trp Ala Asn Met Gly Ala Pro Asp Arg Val Met Asp
        1415                1420                1425

Tyr Gln Val Trp Cys Gly Pro Ala Ile Gly Ala Phe Asn Asp Phe
        1430                1435                1440

Ile Lys Gly Thr Tyr Leu Asp Pro Ala Val Ser Asn Glu Tyr Pro
        1445                1450                1455

Cys Val Val Gln Ile Asn Leu Gln Ile Leu Arg Gly Ala Cys Tyr
        1460                1465                1470

Leu Arg Arg Leu Asn Ala Leu Arg Asn Asp Pro Arg Ile Asp Leu
        1475                1480                1485

Glu Thr Glu Asp Ala Ala Phe Val Tyr Glu Pro Thr Asn Ala Leu
        1490                1495                1500

<210> SEQ ID NO 29
<211> LENGTH: 1500
<212> TYPE: DNA
<213> ORGANISM: Schizochytrium sp.
<220> FEATURE:
<221> NAME/KEY: CDS
<222> LOCATION: (1)..(1500)

<400> SEQUENCE: 29 aag gtt cag ccc gtc ttt gcc aac ggc gcc gcc act gtc ggc ccc gag      48
Lys Val Gln Pro Val Phe Ala Asn Gly Ala Ala Thr Val Gly Pro Glu
1               5                   10                  15 gcc tcc aag gct tcc tcc ggc gcc agc gcc agc gcc agc gcc gcc ccg      96
Ala Ser Lys Ala Ser Ser Gly Ala Ser Ala Ser Ala Ser Ala Ala Pro
            20                  25                  30 gcc aag cct gcc ttc agc gcc gat gtt ctt gcg ccc aag ccc gtt gcc     144
Ala Lys Pro Ala Phe Ser Ala Asp Val Leu Ala Pro Lys Pro Val Ala
        35                  40                  45 ctt ccc gag cac atc ctc aag ggc gac gcc ctc gcc ccc aag gag atg     192
Leu Pro Glu His Ile Leu Lys Gly Asp Ala Leu Ala Pro Lys Glu Met
    50                  55                  60 tcc tgg cac ccc atg gcc cgc atc ccg ggc aac ccg acg ccc tct ttt     240
Ser Trp His Pro Met Ala Arg Ile Pro Gly Asn Pro Thr Pro Ser Phe
65                  70                  75                  80 gcg ccc tcg gcc tac aag ccg cgc aac atc gcc ttt acg ccc ttc ccc     288
Ala Pro Ser Ala Tyr Lys Pro Arg Asn Ile Ala Phe Thr Pro Phe Pro
                85                  90                  95 ggc aac ccc aac gat aac gac cac acc ccg ggc aag atg ccg ctc acc     336
Gly Asn Pro Asn Asp Asn Asp His Thr Pro Gly Lys Met Pro Leu Thr
            100                 105                 110 tgg ttc aac atg gcc gag ttc atg gcc ggc aag gtc agc atg tgc ctc     384
Trp Phe Asn Met Ala Glu Phe Met Ala Gly Lys Val Ser Met Cys Leu
        115                 120                 125 ggc ccc gag ttc gcc aag ttc gac gac tcg aac acc agc cgc agc ccc     432
Gly Pro Glu Phe Ala Lys Phe Asp Asp Ser Asn Thr Ser Arg Ser Pro
    130                 135                 140 gct tgg gac ctc gct ctc gtc acc cgc gcc gtg tct gtg tct gac ctc     480
Ala Trp Asp Leu Ala Leu Val Thr Arg Ala Val Ser Val Ser Asp Leu
145                 150                 155                 160
```

```
aag cac gtc aac tac cgc aac atc gac ctc gac ccc tcc aag ggt acc     528
Lys His Val Asn Tyr Arg Asn Ile Asp Leu Asp Pro Ser Lys Gly Thr
            165                 170                 175 atg gtc ggc gag ttc gac tgc ccc gcg gac gcc tgg ttc tac aag ggc     576
Met Val Gly Glu Phe Asp Cys Pro Ala Asp Ala Trp Phe Tyr Lys Gly
        180                 185                 190 gcc tgc aac gat gcc cac atg ccg tac tcg atc ctc atg gag atc gcc     624
Ala Cys Asn Asp Ala His Met Pro Tyr Ser Ile Leu Met Glu Ile Ala
            195                 200                 205 ctc cag acc tcg ggt gtg ctc acc tcg gtg ctc aag gcg ccc ctg acc     672
Leu Gln Thr Ser Gly Val Leu Thr Ser Val Leu Lys Ala Pro Leu Thr
        210                 215                 220 atg gag aag gac gac atc ctc ttc cgc aac ctc gac gcc aac gcc gag     720
Met Glu Lys Asp Asp Ile Leu Phe Arg Asn Leu Asp Ala Asn Ala Glu
225                 230                 235                 240 ttc gtg cgc gcc gac ctc gac tac cgc ggc aag act atc cgc aac gtc     768
Phe Val Arg Ala Asp Leu Asp Tyr Arg Gly Lys Thr Ile Arg Asn Val
                245                 250                 255 acc aag tgc act ggc tac agc atg ctc ggc gag atg ggc gtc cac cgc     816
Thr Lys Cys Thr Gly Tyr Ser Met Leu Gly Glu Met Gly Val His Arg
            260                 265                 270 ttc acc ttt gag ctc tac gtc gat gat gtg ctc ttt tac aag ggc tcg     864
Phe Thr Phe Glu Leu Tyr Val Asp Asp Val Leu Phe Tyr Lys Gly Ser
        275                 280                 285 acc tcg ttc ggc tgg ttc gtg ccc gag gtc ttt gcc gcc cag gcc ggc     912
Thr Ser Phe Gly Trp Phe Val Pro Glu Val Phe Ala Ala Gln Ala Gly
        290                 295                 300 ctc gac aac ggc cgc aag tcg gag ccc tgg ttc att gag aac aag gtt     960
Leu Asp Asn Gly Arg Lys Ser Glu Pro Trp Phe Ile Glu Asn Lys Val
305                 310                 315                 320 ccg gcc tcg cag gtc tcc tcc ttt gac gtg cgc ccc aac ggc agc ggc    1008
Pro Ala Ser Gln Val Ser Ser Phe Asp Val Arg Pro Asn Gly Ser Gly
                325                 330                 335 cgc acc gcc atc ttc gcc aac gcc ccc agc ggc gcc cag ctc aac cgc    1056
Arg Thr Ala Ile Phe Ala Asn Ala Pro Ser Gly Ala Gln Leu Asn Arg
            340                 345                 350 cgc acg gac cag ggc cag tac ctc gac gcc gtc gac att gtc tcc ggc    1104
Arg Thr Asp Gln Gly Gln Tyr Leu Asp Ala Val Asp Ile Val Ser Gly
        355                 360                 365 agc ggc aag aag agc ctc ggc tac gcc cac ggt tcc aag acg gtc aac    1152
Ser Gly Lys Lys Ser Leu Gly Tyr Ala His Gly Ser Lys Thr Val Asn
        370                 375                 380 ccg aac gac tgg ttc ttc tcg tgc cac ttt tgg ttt gac tcg gtc atg    1200
Pro Asn Asp Trp Phe Phe Ser Cys His Phe Trp Phe Asp Ser Val Met
385                 390                 395                 400 ccc gga agt ctc ggt gtc gag tcc atg ttc cag ctc gtc gag gcc atc    1248
Pro Gly Ser Leu Gly Val Glu Ser Met Phe Gln Leu Val Glu Ala Ile
                405                 410                 415 gcc gcc cac gag gat ctc gct ggc aaa gca cgg cat tgc caa ccc cac    1296
Ala Ala His Glu Asp Leu Ala Gly Lys Ala Arg His Cys Gln Pro His
            420                 425                 430 ctt tgt gca cgc ccc cgg gca aga tca agc tgg aag tac cgc ggc cag    1344
Leu Cys Ala Arg Pro Arg Ala Arg Ser Ser Trp Lys Tyr Arg Gly Gln
        435                 440                 445 ctc acg ccc aag agc aag aag atg gac tcg gag gtc cac atc gtg tcc    1392
Leu Thr Pro Lys Ser Lys Lys Met Asp Ser Glu Val His Ile Val Ser
450                 455                 460 gtg gac gcc cac gac ggc gtt gtc gac ctc gtc gcc gac ggc ttc ctc    1440
Val Asp Ala His Asp Gly Val Val Asp Leu Val Ala Asp Gly Phe Leu
```

```
                465                 470                 475                 480
tgg gcc gac agc ctc cgc gtc tac tcg gtg agc aac att cgc gtg cgc        1488
Trp Ala Asp Ser Leu Arg Val Tyr Ser Val Ser Asn Ile Arg Val Arg
                485                 490                 495 atc gcc tcc ggt                                                        1500
Ile Ala Ser Gly
        500

<210> SEQ ID NO 30
<211> LENGTH: 500
<212> TYPE: PRT
<213> ORGANISM: Schizochytrium sp.

<400> SEQUENCE: 30

Lys Val Gln Pro Val Phe Ala Asn Gly Ala Ala Thr Val Gly Pro Glu
1               5                   10                  15

Ala Ser Lys Ala Ser Ser Gly Ala Ser Ala Ser Ala Ser Ala Ala Pro
            20                  25                  30

Ala Lys Pro Ala Phe Ser Ala Asp Val Leu Ala Pro Lys Pro Val Ala
        35                  40                  45

Leu Pro Glu His Ile Leu Lys Gly Asp Ala Leu Ala Pro Lys Glu Met
    50                  55                  60

Ser Trp His Pro Met Ala Arg Ile Pro Gly Asn Pro Thr Pro Ser Phe
65                  70                  75                  80

Ala Pro Ser Ala Tyr Lys Pro Arg Asn Ile Ala Phe Thr Pro Phe Pro
                85                  90                  95

Gly Asn Pro Asn Asp Asn Asp His Thr Pro Gly Lys Met Pro Leu Thr
            100                 105                 110

Trp Phe Asn Met Ala Glu Phe Met Ala Gly Lys Val Ser Met Cys Leu
        115                 120                 125

Gly Pro Glu Phe Ala Lys Phe Asp Asp Ser Asn Thr Ser Arg Ser Pro
    130                 135                 140

Ala Trp Asp Leu Ala Leu Val Thr Arg Ala Val Ser Val Ser Asp Leu
145                 150                 155                 160

Lys His Val Asn Tyr Arg Asn Ile Asp Leu Asp Pro Ser Lys Gly Thr
                165                 170                 175

Met Val Gly Glu Phe Asp Cys Pro Ala Asp Ala Trp Phe Tyr Lys Gly
            180                 185                 190

Ala Cys Asn Asp Ala His Met Pro Tyr Ser Ile Leu Met Glu Ile Ala
        195                 200                 205

Leu Gln Thr Ser Gly Val Leu Thr Ser Val Leu Lys Ala Pro Leu Thr
    210                 215                 220

Met Glu Lys Asp Asp Ile Leu Phe Arg Asn Leu Asp Ala Asn Ala Glu
225                 230                 235                 240

Phe Val Arg Ala Asp Leu Asp Tyr Arg Gly Lys Thr Ile Arg Asn Val
                245                 250                 255

Thr Lys Cys Thr Gly Tyr Ser Met Leu Gly Glu Met Gly Val His Arg
            260                 265                 270

Phe Thr Phe Glu Leu Tyr Val Asp Asp Val Leu Phe Tyr Lys Gly Ser
        275                 280                 285

Thr Ser Phe Gly Trp Phe Val Pro Glu Val Phe Ala Ala Gln Ala Gly
    290                 295                 300

Leu Asp Asn Gly Arg Lys Ser Glu Pro Trp Phe Ile Glu Asn Lys Val
305                 310                 315                 320

Pro Ala Ser Gln Val Ser Ser Phe Asp Val Arg Pro Asn Gly Ser Gly
```

-continued

```
                    325                 330                 335
Arg Thr Ala Ile Phe Ala Asn Ala Pro Ser Gly Ala Gln Leu Asn Arg
            340                 345                 350
Arg Thr Asp Gln Gly Gln Tyr Leu Asp Ala Val Asp Ile Val Ser Gly
            355                 360                 365
Ser Gly Lys Lys Ser Leu Gly Tyr Ala His Gly Ser Lys Thr Val Asn
        370                 375                 380
Pro Asn Asp Trp Phe Phe Ser Cys His Phe Trp Phe Asp Ser Val Met
385                 390                 395                 400
Pro Gly Ser Leu Gly Val Glu Ser Met Phe Gln Leu Val Glu Ala Ile
                405                 410                 415
Ala Ala His Glu Asp Leu Ala Gly Lys Ala Arg His Cys Gln Pro His
            420                 425                 430
Leu Cys Ala Arg Pro Arg Ala Arg Ser Ser Trp Lys Tyr Arg Gly Gln
        435                 440                 445
Leu Thr Pro Lys Ser Lys Lys Met Asp Ser Glu Val His Ile Val Ser
    450                 455                 460
Val Asp Ala His Asp Gly Val Val Asp Leu Val Ala Asp Gly Phe Leu
465                 470                 475                 480
Trp Ala Asp Ser Leu Arg Val Tyr Ser Val Ser Asn Ile Arg Val Arg
                485                 490                 495
Ile Ala Ser Gly
            500

<210> SEQ ID NO 31
<211> LENGTH: 1512
<212> TYPE: DNA
<213> ORGANISM: Schizochytrium sp.
<220> FEATURE:
<221> NAME/KEY: CDS
<222> LOCATION: (1)..(1512)

<400> SEQUENCE: 31 gcc ccg ctc tac ctc tcg cag gac ccg acc agc ggc cag ctc aag aag      48
Ala Pro Leu Tyr Leu Ser Gln Asp Pro Thr Ser Gly Gln Leu Lys Lys
1               5                   10                  15 cac acc gac gtg gcc tcc ggc cag gcc acc atc gtg cag ccc tgc acg      96
His Thr Asp Val Ala Ser Gly Gln Ala Thr Ile Val Gln Pro Cys Thr
            20                  25                  30 ctc ggc gac ctc ggt gac cgc tcc ttc atg gag acc tac ggc gtc gtc     144
Leu Gly Asp Leu Gly Asp Arg Ser Phe Met Glu Thr Tyr Gly Val Val
        35                  40                  45 gcc ccg ctg tac acg ggc gcc atg gcc aag ggc att gcc tcg gcg gac     192
Ala Pro Leu Tyr Thr Gly Ala Met Ala Lys Gly Ile Ala Ser Ala Asp
    50                  55                  60 ctc gtc atc gcc gcc ggc aag cgc aag atc ctc ggc tcc ttt ggc gcc     240
Leu Val Ile Ala Ala Gly Lys Arg Lys Ile Leu Gly Ser Phe Gly Ala
65                  70                  75                  80 ggc ggc ctc ccc atg cac cac gtg cgc gcc gcc ctc gag aag atc cag     288
Gly Gly Leu Pro Met His His Val Arg Ala Ala Leu Glu Lys Ile Gln
                85                  90                  95 gcc gcc ctg cct cag ggc ccc tac gcc gtc aac ctc atc cac tcg cct     336
Ala Ala Leu Pro Gln Gly Pro Tyr Ala Val Asn Leu Ile His Ser Pro
            100                 105                 110 ttt gac agc aac ctc gag aag ggc aac gtc gat ctc ttc ctc gag aag     384
Phe Asp Ser Asn Leu Glu Lys Gly Asn Val Asp Leu Phe Leu Glu Lys
        115                 120                 125 ggc gtc act gtg gtg gag gcc tcg gca ttc atg acc ctc acc ccg cag     432
```

```
                    Gly Val Thr Val Val Glu Ala Ser Ala Phe Met Thr Leu Thr Pro Gln
                        130                 135                 140 gtc gtg cgc tac cgc gcc gcc ggc ctc tcg cgc aac gcc gac ggt tcg         480
Val Val Arg Tyr Arg Ala Ala Gly Leu Ser Arg Asn Ala Asp Gly Ser
145                 150                 155                 160 gtc aac atc cgc aac cgc atc atc ggc aag gtc tcg cgc acc gag ctc         528
Val Asn Ile Arg Asn Arg Ile Ile Gly Lys Val Ser Arg Thr Glu Leu
                165                 170                 175 gcc gag atg ttc atc cgc ccg gcc ccg gag cac ctc ctc gag aag ctc         576
Ala Glu Met Phe Ile Arg Pro Ala Pro Glu His Leu Leu Glu Lys Leu
            180                 185                 190 atc gcc tcg ggc gag atc acc cag gag cag gcc gag ctc gcg cgc cgc         624
Ile Ala Ser Gly Glu Ile Thr Gln Glu Gln Ala Glu Leu Ala Arg Arg
        195                 200                 205 gtt ccc gtc gcc gac gat atc gct gtc gag gct gac tcg ggc ggc cac         672
Val Pro Val Ala Asp Asp Ile Ala Val Glu Ala Asp Ser Gly Gly His
    210                 215                 220 acc gac aac cgc ccc atc cac gtc atc ctc ccg ctc atc atc aac ctc         720
Thr Asp Asn Arg Pro Ile His Val Ile Leu Pro Leu Ile Ile Asn Leu
225                 230                 235                 240 cgc aac cgc ctg cac cgc gag tgc ggc tac ccc gcg cac ctc cgc gtc         768
Arg Asn Arg Leu His Arg Glu Cys Gly Tyr Pro Ala His Leu Arg Val
                245                 250                 255 cgc gtt ggc gcc ggc ggt ggc gtc ggc tgc ccg cag gcc gcc gcc gcc         816
Arg Val Gly Ala Gly Gly Gly Val Gly Cys Pro Gln Ala Ala Ala Ala
            260                 265                 270 gcg ctc acc atg ggc gcc gcc ttc atc gtc acc ggc act gtc aac cag         864
Ala Leu Thr Met Gly Ala Ala Phe Ile Val Thr Gly Thr Val Asn Gln
        275                 280                 285 gtc gcc aag cag tcc ggc acc tgc gac aac gtg cgc aag cag ctc tcg         912
Val Ala Lys Gln Ser Gly Thr Cys Asp Asn Val Arg Lys Gln Leu Ser
    290                 295                 300 cag gcc acc tac tcg gat atc tgc atg gcc ccg gcc gcc gac atg ttc         960
Gln Ala Thr Tyr Ser Asp Ile Cys Met Ala Pro Ala Ala Asp Met Phe
305                 310                 315                 320 gag gag ggc gtc aag ctc cag gtc ctc aag aag gga acc atg ttc ccc        1008
Glu Glu Gly Val Lys Leu Gln Val Leu Lys Lys Gly Thr Met Phe Pro
                325                 330                 335 tcg cgc gcc aac aag ctc tac gag ctc ttt tgc aag tac gac tcc ttc        1056
Ser Arg Ala Asn Lys Leu Tyr Glu Leu Phe Cys Lys Tyr Asp Ser Phe
            340                 345                 350 gac tcc atg cct cct gcc gag ctc gag cgc atc gag aag cgt atc ttc        1104
Asp Ser Met Pro Pro Ala Glu Leu Glu Arg Ile Glu Lys Arg Ile Phe
        355                 360                 365 aag cgc gca ctc cag gag gtc tgg gag gag acc aag gac ttt tac att        1152
Lys Arg Ala Leu Gln Glu Val Trp Glu Glu Thr Lys Asp Phe Tyr Ile
    370                 375                 380 aac ggt ctc aag aac ccg gag aag atc cag cgc gcc gag cac gac ccc        1200
Asn Gly Leu Lys Asn Pro Glu Lys Ile Gln Arg Ala Glu His Asp Pro
385                 390                 395                 400 aag ctc aag atg tcg ctc tgc ttc cgc tgg tac ctt ggt ctt gcc agc        1248
Lys Leu Lys Met Ser Leu Cys Phe Arg Trp Tyr Leu Gly Leu Ala Ser
                405                 410                 415 cgc tgg gcc aac atg ggc gcc ccg gac cgc gtc atg gac tac cag gtc        1296
Arg Trp Ala Asn Met Gly Ala Pro Asp Arg Val Met Asp Tyr Gln Val
            420                 425                 430 tgg tgt ggc ccg gcc att ggc gcc ttc aac gac ttc atc aag ggc acc        1344
Trp Cys Gly Pro Ala Ile Gly Ala Phe Asn Asp Phe Ile Lys Gly Thr
        435                 440                 445
```

```
tac ctc gac ccc gct gtc tcc aac gag tac ccc tgt gtc gtc cag atc    1392
Tyr Leu Asp Pro Ala Val Ser Asn Glu Tyr Pro Cys Val Val Gln Ile
    450                 455                 460 aac ctg caa atc ctc cgt ggt gcc tgc tac ctg cgc gtc ctc aac gcc    1440
Asn Leu Gln Ile Leu Arg Gly Ala Cys Tyr Leu Arg Arg Leu Asn Ala
465                 470                 475                 480 ctg cgc aac gac ccg cgc att gac ctc gag acc gag gat gct gcc ttt    1488
Leu Arg Asn Asp Pro Arg Ile Asp Leu Glu Thr Glu Asp Ala Ala Phe
                485                 490                 495 gtc tac gag ccc acc aac gcg ctc                                     1512
Val Tyr Glu Pro Thr Asn Ala Leu
                500

<210> SEQ ID NO 32
<211> LENGTH: 504
<212> TYPE: PRT
<213> ORGANISM: Schizochytrium sp.

<400> SEQUENCE: 32

Ala Pro Leu Tyr Leu Ser Gln Asp Pro Thr Ser Gly Gln Leu Lys Lys
1               5                   10                  15

His Thr Asp Val Ala Ser Gly Gln Ala Thr Ile Val Gln Pro Cys Thr
            20                  25                  30

Leu Gly Asp Leu Gly Asp Arg Ser Phe Met Glu Thr Tyr Gly Val Val
        35                  40                  45

Ala Pro Leu Tyr Thr Gly Ala Met Ala Lys Gly Ile Ala Ser Ala Asp
    50                  55                  60

Leu Val Ile Ala Ala Gly Lys Arg Lys Ile Leu Gly Ser Phe Gly Ala
65                  70                  75                  80

Gly Gly Leu Pro Met His His Val Arg Ala Ala Leu Glu Lys Ile Gln
                85                  90                  95

Ala Ala Leu Pro Gln Gly Pro Tyr Ala Val Asn Leu Ile His Ser Pro
            100                 105                 110

Phe Asp Ser Asn Leu Glu Lys Gly Asn Val Asp Leu Phe Leu Glu Lys
        115                 120                 125

Gly Val Thr Val Val Glu Ala Ser Ala Phe Met Thr Leu Thr Pro Gln
    130                 135                 140

Val Val Arg Tyr Arg Ala Ala Gly Leu Ser Arg Asn Ala Asp Gly Ser
145                 150                 155                 160

Val Asn Ile Arg Asn Arg Ile Ile Gly Lys Val Ser Arg Thr Glu Leu
                165                 170                 175

Ala Glu Met Phe Ile Arg Pro Ala Pro Glu His Leu Leu Glu Lys Leu
            180                 185                 190

Ile Ala Ser Gly Glu Ile Thr Gln Glu Gln Ala Glu Leu Ala Arg Arg
        195                 200                 205

Val Pro Val Ala Asp Asp Ile Ala Val Glu Ala Asp Ser Gly Gly His
    210                 215                 220

Thr Asp Asn Arg Pro Ile His Val Ile Leu Pro Leu Ile Asn Leu
225                 230                 235                 240

Arg Asn Arg Leu His Arg Glu Cys Gly Tyr Pro Ala His Leu Arg Val
                245                 250                 255

Arg Val Gly Ala Gly Gly Val Gly Cys Pro Gln Ala Ala Ala
            260                 265                 270

Ala Leu Thr Met Gly Ala Ala Phe Ile Val Thr Gly Thr Val Asn Gln
        275                 280                 285

Val Ala Lys Gln Ser Gly Thr Cys Asp Asn Val Arg Lys Gln Leu Ser
```

```
                290             295             300
Gln Ala Thr Tyr Ser Asp Ile Cys Met Ala Pro Ala Ala Asp Met Phe
305                 310                 315                 320

Glu Glu Gly Val Lys Leu Gln Val Leu Lys Gly Thr Met Phe Pro
                325                 330                 335

Ser Arg Ala Asn Lys Leu Tyr Glu Leu Phe Cys Lys Tyr Asp Ser Phe
                340                 345                 350

Asp Ser Met Pro Pro Ala Glu Leu Glu Arg Ile Glu Lys Arg Ile Phe
                355                 360                 365

Lys Arg Ala Leu Gln Glu Val Trp Glu Thr Lys Asp Phe Tyr Ile
370                 375                 380

Asn Gly Leu Lys Asn Pro Glu Lys Ile Gln Arg Ala Glu His Asp Pro
385                 390                 395                 400

Lys Leu Lys Met Ser Leu Cys Phe Arg Trp Tyr Leu Gly Leu Ala Ser
                405                 410                 415

Arg Trp Ala Asn Met Gly Ala Pro Asp Arg Val Met Asp Tyr Gln Val
                420                 425                 430

Trp Cys Gly Pro Ala Ile Gly Ala Phe Asn Asp Phe Ile Lys Gly Thr
                435                 440                 445

Tyr Leu Asp Pro Ala Val Ser Asn Glu Tyr Pro Cys Val Val Gln Ile
450                 455                 460

Asn Leu Gln Ile Leu Arg Gly Ala Cys Tyr Leu Arg Arg Leu Asn Ala
465                 470                 475                 480

Leu Arg Asn Asp Pro Arg Ile Asp Leu Glu Thr Glu Asp Ala Ala Phe
                485                 490                 495

Val Tyr Glu Pro Thr Asn Ala Leu
                500

<210> SEQ ID NO 33
<211> LENGTH: 9
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (2)..(3)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = Ala or Ser
<220> FEATURE:
<221> NAME/KEY: MISC_FEATURE
<222> LOCATION: (7)..(8)
<223> OTHER INFORMATION: Xaa = any amino acid

<400> SEQUENCE: 33

Trp Xaa Xaa Lys Glu Xaa Xaa Xaa Lys
1               5

<210> SEQ ID NO 34
<211> LENGTH: 6
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (1)..(6)
<223> OTHER INFORMATION: Xaa = Ile or Leu or Val

<400> SEQUENCE: 34
```

Phe Asn Xaa Ser His Ser
1               5

<210> SEQ ID NO 35
<211> LENGTH: 5
<212> TYPE: PRT
<213> ORGANISM: Artificial sequence
<220> FEATURE:
<223> OTHER INFORMATION: motif
<220> FEATURE:
<221> NAME/KEY: MISC_FEATURE
<222> LOCATION: (1)..(5)
<223> OTHER INFORMATION: Xaa = Ile or Leu or Val

<400> SEQUENCE: 35

Xaa Gly Xaa Asp Xaa
1               5

<210> SEQ ID NO 36
<211> LENGTH: 4244
<212> TYPE: DNA
<213> ORGANISM: Schizochytrium sp.

<400> SEQUENCE: 36

```
tttctctctc tcgagctgtt gctgctgctg ctgctgctgc tgcttccttg ctggttctca     60
cgtccgttcg atcaagcgct cgctcgctcg accgatcggt gcgtgcgtgc gtgcgtgagt    120
cttgttgcca ggcagccgca ggctgtctgt ctgtttgtgt agttttaccc tcggggttcg    180
gggtctgcct gctccccgct cccgcccgcc gccgccgta tccacccogc tcgcctccgc    240
ccatcgggcc tcgcctcctc gcgccgcacg catcgcgcgc atcgcatgca tcatgctgcc    300
acgcacgggg ggacgcgcgc cccgcgtccc cgccgccgcc cgtcgtcgtc tggcgatgcc    360
gtcgccgccc tccttccttc cctcgcctcc tcttcctccc gagccccct gtcttccttc    420
gccccccgcag cggcgcgcag gaagcgagga gagcggggag gagagaagaa aagaaaagaa    480
aagaaaagaa aataacagcg ccgtctcgcg cagacgcgcg cggccgcgtg cgaggcggcg    540
tgatgggct tctcgtggcg cggctgcggc ctggccggc ctcgcctttg aggtgcaggc    600
tttgggagag aagagtggga cgcggagaag ataagatggt gccatggcgc aggacggaga    660
ggttgctgaa acttcttcga gcggcacagg cgatggcgag agaccgacag ctgccggcgc    720
ggaggggatg ataccctccc gaggctggca tggacgagct ggccgcgcgg atctggctgg    780
ccgcgcggcg gtgggtccgg aggcgcgagg ttggttttct tcatacctga taccatacgg    840
tattcattct tcctctccag gaaggaagca agtcacatag agtatcacta gcctaatgat    900
ggactctatg ttttagggca cgtcggagca gaaggcgcga gcgattcgaa tgcgagcgat    960
agatacagca cagagaccttt gccggcgacg cggatgcagg cgagcacgca cgcaccgcac   1020
gcacggcagc ggtgcacgcg ctcctcggca gatgcacggt tctgcgccgc gcctttacat   1080
tttttgattt taggtggtgt gcctgccact ttgaacatca tccacaagtc aacgcagcat   1140
caagaggcaa gcaagtacat acatccattc gaattcaagt tcaagagacg cagcaacagc   1200
cgccgctccg ctcaagctgc agctagctgg ctgacagggc tcgctggctg tagtggaaaa   1260
ttccattcac ttttctgcat ccgcggccag caggcccgta cgcacgttct ctcgttttgtt   1320
tgttcgttcg tgcgtgcgtg cgtgcgtccc agctgcctgt ctaatctgcc gcgcgatcca   1380
acgaccctcg gtcgtcgccg caagcgaaac ccgacgccga cctggccaat gccgcaagaa   1440
tgctaagcgc gcagcaatgc tgagagtaat cttcagccca ccaagtcatt atcgctgccc   1500
```

```
aagtctccat cgcagccaca ttcaggctttt ctctctctct ccctccctct ctttctgccg   1560
ggagagaagg aaagacccgc cgccgccgcc tctgcgcctg tgacgggctg tccgttgtaa   1620
gccctcttag acagttccta ggtgccgggc gccgccgcgc ctccgtcgca ggcacacgta   1680
ggcggccacg ggttccccccc gcaccttcca caccttcttc ccccgcagcc ggaccgcgcg   1740
ccgtctgctt acgcacttcg cgcggccgcc gcccgcgaac ccgagcgcgt gctgtgggcg   1800
ccgtcttccg gccgcgtcgg aggtcgtccc cgcgccgcgc tactccgggt cctgtgcggt   1860
acgtacttaa tattaacagt gggacctcgc acaggacctg acggcagcac agacgtcgcc   1920
gcctcgcatc gctggggacg caggcgaggc atcccgcgc ggccccgcac cggggaggct   1980
gcggggcggc ctcttccggc cggcggccgc atcaggcgga tgacgcaaga gccctcgcag   2040
tcgctcgctc gcgggagcgc agcgcggcgc cagcgtggcc aagctcccgc cccttctggc   2100
tggctgcatg cctgcctgcc tgcctgcctg cgtgcgtgcg tgcgtgcgtg ccttcgtgcg   2160
tgcctgcctt cgtgcgtgcg tgcgtgagtg cggcggaaga gggatcatgc gaggatcaat   2220
cacccgccgc acctcgactt ttgaagaagc cgcgatgcga tgcgatgcga tgcgatgcga   2280
cgcgataccg tgcgaggcta cgaagcgagt ctggccggcc gtcatacaac gcacgttttc   2340
gagaaggagg gctggcggag gcgtgcatgc cggcgaccat tgcgaacgcg cgtctcgtg   2400
gctggcgaag gtgcctggag gatctaacga tcgctgctat gatgctatag ctgtgctgat   2460
ccccggtcca ttccaccacg tctgtgcctg ccgcctgacc tgcgcttggc tttccttcaa   2520
gttctcctcc gccgggcctt caggaccgag acgagacctg cagctgcagc tagactcgcg   2580
ctcgctcgcg gaggattcgc cggccgccgg gccggacggg actcgcgagg tcacacggcc   2640
gccggcgatc gcgatggctg tgctgacgta ctccgtgcgtg gcagccgtac gtcagcgacg   2700
ccgcctccgt attgtggatt cgttagttgg ttgttggttg atttgttgat taattttttt   2760
gttcgtaggc ttggttatag ctaatagttt agtttatact ggtgctcttc ggtgctgatt   2820
tagctcgact tgggtccaca ccactgcccc tctactgtga atggatcaat ggacgcacga   2880
cgggccgacg aaagtgcgcg agtgaggtaa cctaagcaac ggcggtcttc agaggggacg   2940
cacgccctcc gtcgcagtca gtccagacag gcagaaaagc gtcttaggga ccacgcacgc   3000
acgcacgcac gcacgcacgc ccgcacgcac gctccctccc tcgcgtgcct attttttag   3060
gcttccttcc gcacgggcct acctctcgct ccctcgcctc gccgcaccag gcggcagcag   3120
cgatacctgc cggtgccgcc tccgtcacgc gctcagccgc agctcagccc agccgcgagc   3180
tagggtttgt tcgtcctgaa ttgtttgatt tgatttgatt tgatttgatc cgatccgatc   3240
cgatctgatc tgatttgctt tgctttgctt tgtctccctc ccggcgcgga ccaagcgtcc   3300
gtctgcgcgc cgcagcttcc cttcttctcc cagccctcct tctgctcccg cctctcgcgc   3360
aagcacgcag cttcgccgcc gcatccggtc ggtcggtcgg tcgatcgacc cgcctgccgc   3420
tgctgctgtg gccgggcttt tctccatcgg cgactcttcc ttctccatac gtcctactac   3480
gtacatacat actgccggct tcctcctctt ccagcgcggc gacggcggca ggctgcgacg   3540
tcgtcgccgc cgcgggcgcc gcgcgcgccg ccgccgccgc ccgcgtcgca gggcctcgtc   3600
gccgccgccg ctccgctccg ctccgaggcc gcgagagggc cgcggcggcg cgatggatgg   3660
atggatggat ggatgatgg atggattttg ttgatcgatg gcggcgcatg ggcggagatg   3720
agcgaggacg agcgcgcgag gcggcagcc ggattcgcag ggcctcgctc gcctcgcgcc   3780
cgctgccgcg cccgccttgc gagcctgcgc gcgagcgag cgagcgagcg agcggggctt   3840
tctttgtctc gcgcgccgct tggcctcgtg tgtcttgtgc ttgcgtagcg ggcgccgcgg   3900
```

| | |
|---|---:|
| tggaagatgg ctcattcaat cgacccattc acgcacgcac tccggcgcgc agagaaggcc | 3960 |
| gaggaggagc agcaagcaaa ccaaaagctc tcgcgctcgc ggtctcgggc tcgagcggtc | 4020 |
| tcggagagag agtcttgcgg cgaccaccgg cagcagcagc agcagcagca gcgctgtcga | 4080 |
| gcacgagcac gagcacgagc acgagcacga gcattcgagc aagaggacag acacggttgt | 4140 |
| cagcgcctag ctcgctcgat acagaaagag gcgggttggg cgtaaaaaaa aaggagcacg | 4200 |
| caagccgcca gccagccagc tagctagcca gcctgcctgc caaa | 4244 |

```
<210> SEQ ID NO 37
<211> LENGTH: 3886
<212> TYPE: DNA
<213> ORGANISM: Schizochytrium sp.
<220> FEATURE:
<221> NAME/KEY: misc_feature
<222> LOCATION: (1)..(3886)
<223> OTHER INFORMATION: n = a, c, g, or t

<400> SEQUENCE: 37
```

| | |
|---|---:|
| gatcttgatt gccaagctct ggattgtcga ttccgatgaa tcgagctctt tgttgtcgag | 60 |
| ctctggcttg ccgagctttc agaaatagac aaaattgccg agttcctgat tgcggggctc | 120 |
| tcgattgcca aggtctggtg gattctcgaa ctctcgattg tcaaaatctt ggtcgtctcg | 180 |
| tcggattctt tcctgatttg ttttgtcaag accttgagat tgtgcaaaac cttgatcgtt | 240 |
| gacaaaccct tgatcgacag cagcctttca tcacgctcag ctcttgtcat tgattatatt | 300 |
| cccccctgaca gccaacacct tgatgcaggg tctcaacctt gattttttgga ggccatcatc | 360 |
| agcatcacgc cccggcactc accctcaaca ttcgacagcc aacgcttttt tttcttcgac | 420 |
| taggatctga gaataaaagc aggtcaccac gaccgtaggc caacgcgaca accatggaaa | 480 |
| taaagtgaca cgaacgact tgcaagttta aatgtaaaga gcagcaattg cccgcccaca | 540 |
| gacaaatgaa agcaggcgcc gagtcttatt tgaggaggtg ggcctgtggc aatgggcgaa | 600 |
| agaaaatcaa ggacaaggag agcaggttac gtaccggtat actggtatac gtacatggat | 660 |
| ggttcttggc aagttgacgg gatgtgtgcg agtgaccgtg gtagttaacg aaagagccgc | 720 |
| aagggcaagg aaagcaagag aatgcagact tttccacagg atggatgggt ccgcagcttg | 780 |
| ccgcatgatg aaacgctgta tttcacctgg cacgtggtgg cgcacgcgcc cacatatgat | 840 |
| cgcggcggcg ggtgtattat acatttttccc cctcaggtct actgccatcc ctccatgcgt | 900 |
| cgctcgtgcg aacgacgcaa gccttttcgca tcgtgcagcc tctttctggt aaggcaagag | 960 |
| ctaaacccaa acctaaacga aagaacattt ttacctctct ctctctccca ttggtcgcgt | 1020 |
| gcgctccgcc gctcgctcct cctcctgcca gtgtcgcgcc ctaacttccc ccctccctcc | 1080 |
| ctccctccct ccctccctct ctcctgccac cgcccctctc tccgcgctgc gtgcggtgct | 1140 |
| gccctggacc aatggcatgc tgctgcacgc tcggcggatg acgcaagccg cttcgcaatt | 1200 |
| tccggatcag atctcggcgg ggcgtgcgcc gcggggtcac tgcggacctg ccgcggcccc | 1260 |
| tgcttctttc acatccatca tgtcctccaa acctccgcct cctccacgca cgtacgcacg | 1320 |
| cccgctcgca cgcgcgcact gccgctgcga aagcaagcgc ccgcccgccg cccggcgacg | 1380 |
| ggaaggcggc cgcggtctcc ctccgcggtt gcctcgctcc cgcgcggggc tgggcgggca | 1440 |
| gcagaaggcg ggtggcggcg gcggcttccg tcttcgtcag cggcctacgt cggcggcggc | 1500 |
| gcgcgagact acgcatgccc ttgcgtcatg cgctcgcagg tagccgccgc gggcctagcg | 1560 |
| tttccgctgg cgccgcgcct aagcccccgg cgcgcacggt attgccgcga taccgtacgg | 1620 |

-continued

```
ccaagaccgc cgcagacgtc ggccctctcg cggccagcca gccagcagcg cagcggagga      1680
agagcgcgca ggcgcggcgg gagggcggcc gcggagcagc gcagagcggg gcggagcagc      1740
gcggagcaga acgggcagac tcggagcggg cagggcgggc agagctttgg ggtttaagga      1800
ccgggttacc ggcgaagtga gcggctgcgg ggagcggctg tgggaggggt gagtacgcaa      1860
gcacgatgcg agcgagagag agacgctgcc gcgaatcaag aaggtaggcg cgctgcgagg      1920
cgcggcggcg gagcggagcg agggagaggg agagggagag agagggaggg agacgtcgcc      1980
gcggcggggc ctggcctggc ctggtttggc ttggtcagcg cggccttgtc cgagcgtgca      2040
gctggagttg ggtggattca tttgatttt cttttgtttt tgttttctc tctttcccgg        2100 aaagtgttgg ccggncggtg ttctttgttt tgatttcttc aaaagttttg gtggttggtt      2160
ctctctcttg gctctctgtc aggcggtccg gtccacgccc cggcctctcc tctcctctcc      2220
tctcctctcc tctccgtgcg tatacgtacg tacgtttgta tacgtacata catcccgccc      2280
gccgtgccgg cgagggtttg ctcagcctgg agcaatgcga tgcgatgcga tgcgatgcga      2340
cgcgacgcga cgcgagtcac tggttcgcgc tgtggctgtg gcttgcttgc ttacttgctt      2400
tcgagctctc ccgcttttctt ctttccttct cacgccacca caacgaaag aagatcggcc      2460 ccggcacgcc gctgagaagg gctggcggcg atgacggcac gcgcgcccgc tgccacgttg      2520
gcgctcgctc ctgctgctgc tgctgctgct gctgctgctg ctgctgctgc tgctgcttct      2580
gcgcgcaggc tttgccacga ggccggcgtg ctggccgctg ccgcttccag tccgcgtgga      2640
gagatcgaat gagagataaa ctggatggat tcatcgaggg atgaatgaac gatggttgga      2700
tgcctttttc cttttcagg tccacagcgg gaagcaggag cgcgtgaatc tgccgccatc       2760
cgcatacgtc tgcatcgcat cgcatcgcat gcacgcatcg ctcgccggga gccacagacg      2820
ggcgacaggg cggccagcca gccaggcagc cagccaggca ggcaccagag ggccagagag      2880
cgcgcctcac gcacgcgccg cagtgcgcgc atcgctcgca gtgcagacct tgattccccg      2940
cgcggatctc cgcgagcccg aaacgaagag cgccgtacgg gcccatccta gcgtcgcctc      3000
gcaccgcatc gcatcgcatc gcgttcccta gagagtagta ctcgacgaag gcaccatttc      3060
cgcgctcctc ttcggcgcga tcgaggcccc cggcgccgcg acgatcgcgg cggccgcggc      3120
gctggcggcg gccctggcgc tcgcgctggc ggccgccgcg ggcgtctggc cctggcgcgc      3180
gcgggcgccg caggaggagc ggcagcggct gctcgccgcc agagaagagc gcgccgggcc      3240
cggggaggga cggggaggag aaggagaagg cgcgcaaggc ggccccgaaa gagaagaccc      3300
tggacttgaa cgcgaagaag aagaagaagg agaagaagtt gaagaagaag aagaagaagg      3360
agaggaagtt gaagaagacg aggagcaggc gcgttccaag gcgcgttctc ttccggaggc      3420
gcgttccagc tgcggcggcg gggcgggctg cggggcgggc gcgggcgcgg gtgcgggcag      3480
aggggacgcg cgcgcggagg cggaggggc cgagcgggag ccctgctgc tgcggggcgc       3540 ccgggccgca ggtgtggcgc gcgcgacgac ggaggcgacg acgccagcgg ccgcgacgac      3600
aaggccggcg gcgtcggcgg gcggaaggcc ccgcgcggag caggggcggg agcaggacaa      3660
ggcgcaggag caggagcagg gccgggagcg ggagcgggag cggcggcgg agcccgaggc       3720 agaacccaat cgagatccag agcgagcaga ggccggccgc gagcccgagc ccgcgccgca      3780
gatcactagt accgctgcgg aatcacagca gcagcagcag cagcagcagc agcagcagca      3840
gcagcagcag ccacgagagg gagataaaga aaaagcggca gagacg                    3886
```

<210> SEQ ID NO 38
<211> LENGTH: 8436

```
<212> TYPE: DNA
<213> ORGANISM: Thraustochytrium sp.
<220> FEATURE:
<221> NAME/KEY: CDS
<222> LOCATION: (1)..(8433)

<400> SEQUENCE: 38
```

| | | | | | | | | | | | | | | | | |
|---|---|---|---|---|---|---|---|---|---|---|---|---|---|---|---|---|
| atg | aag | gac | atg | gaa | gat | aga | cgg | gtc | gct | att | gtg | ggc | atg | tca | gct | 48 |
| Met | Lys | Asp | Met | Glu | Asp | Arg | Arg | Val | Ala | Ile | Val | Gly | Met | Ser | Ala | |
| 1 | | | | 5 | | | | | 10 | | | | | 15 | | |
| cac | ttg | cct | tgt | ggg | aca | gat | gtg | aag | gaa | tca | tgg | cag | gct | att | cgc | 96 |
| His | Leu | Pro | Cys | Gly | Thr | Asp | Val | Lys | Glu | Ser | Trp | Gln | Ala | Ile | Arg | |
| | | 20 | | | | | 25 | | | | | 30 | | | | |
| gat | gga | atc | gac | tgt | cta | agt | gac | cta | ccc | gcg | gat | cgt | ctc | gac | gtt | 144 |
| Asp | Gly | Ile | Asp | Cys | Leu | Ser | Asp | Leu | Pro | Ala | Asp | Arg | Leu | Asp | Val | |
| | 35 | | | | | 40 | | | | | 45 | | | | | |
| aca | gct | tac | tac | aat | ccc | aac | aaa | gcc | acg | aaa | gac | aag | atc | tac | tgc | 192 |
| Thr | Ala | Tyr | Tyr | Asn | Pro | Asn | Lys | Ala | Thr | Lys | Asp | Lys | Ile | Tyr | Cys | |
| 50 | | | | | 55 | | | | | 60 | | | | | | |
| aaa | cgg | ggt | ggc | ttc | atc | ccg | aac | tat | gac | ttc | gac | ccc | cgc | gaa | ttt | 240 |
| Lys | Arg | Gly | Gly | Phe | Ile | Pro | Asn | Tyr | Asp | Phe | Asp | Pro | Arg | Glu | Phe | |
| 65 | | | | | 70 | | | | | 75 | | | | | 80 | |
| ggg | ctc | aac | atg | ttt | caa | atg | gaa | gac | tct | gat | gcg | aat | cag | aca | ctt | 288 |
| Gly | Leu | Asn | Met | Phe | Gln | Met | Glu | Asp | Ser | Asp | Ala | Asn | Gln | Thr | Leu | |
| | | | | 85 | | | | | 90 | | | | | 95 | | |
| acc | ttg | ctc | aaa | gtc | aaa | caa | gct | ctc | gaa | gat | gca | agc | ata | gag | cct | 336 |
| Thr | Leu | Leu | Lys | Val | Lys | Gln | Ala | Leu | Glu | Asp | Ala | Ser | Ile | Glu | Pro | |
| | | | 100 | | | | | 105 | | | | | 110 | | | |
| ttc | acc | aag | gag | aag | aag | aac | att | gga | tgt | gtt | tta | ggt | att | ggt | ggg | 384 |
| Phe | Thr | Lys | Glu | Lys | Lys | Asn | Ile | Gly | Cys | Val | Leu | Gly | Ile | Gly | Gly | |
| | | 115 | | | | | 120 | | | | | 125 | | | | |
| ggc | caa | aag | gcg | agt | cat | gag | ttc | tac | tct | cgt | ctc | aac | tac | gtt | gtc | 432 |
| Gly | Gln | Lys | Ala | Ser | His | Glu | Phe | Tyr | Ser | Arg | Leu | Asn | Tyr | Val | Val | |
| | 130 | | | | | 135 | | | | | 140 | | | | | |
| gtt | gaa | aag | gta | ctt | cgg | aaa | atg | ggt | tta | cca | gat | gct | gat | gtt | gaa | 480 |
| Val | Glu | Lys | Val | Leu | Arg | Lys | Met | Gly | Leu | Pro | Asp | Ala | Asp | Val | Glu | |
| 145 | | | | | 150 | | | | | 155 | | | | | 160 | |
| gaa | gct | gtg | gag | aaa | tac | aag | gca | aat | ttt | ccc | gag | tgg | cgc | cta | gac | 528 |
| Glu | Ala | Val | Glu | Lys | Tyr | Lys | Ala | Asn | Phe | Pro | Glu | Trp | Arg | Leu | Asp | |
| | | | | 165 | | | | | 170 | | | | | 175 | | |
| tct | ttc | cct | ggg | ttt | ctt | ggg | aat | gta | acg | gct | ggt | cgg | tgc | agt | aac | 576 |
| Ser | Phe | Pro | Gly | Phe | Leu | Gly | Asn | Val | Thr | Ala | Gly | Arg | Cys | Ser | Asn | |
| | | | 180 | | | | | 185 | | | | | 190 | | | |
| acc | ttc | aac | atg | gaa | ggt | atg | aac | tgc | gtt | gtg | gat | gct | gca | tgt | gcc | 624 |
| Thr | Phe | Asn | Met | Glu | Gly | Met | Asn | Cys | Val | Val | Asp | Ala | Ala | Cys | Ala | |
| | | 195 | | | | | 200 | | | | | 205 | | | | |
| agt | tct | cta | att | gca | atc | aag | gtt | gca | gtt | gaa | gag | cta | ctc | ttt | ggt | 672 |
| Ser | Ser | Leu | Ile | Ala | Ile | Lys | Val | Ala | Val | Glu | Glu | Leu | Leu | Phe | Gly | |
| | 210 | | | | | 215 | | | | | 220 | | | | | |
| gac | tgt | gac | acc | atg | att | gca | ggt | gcc | acc | tgc | acg | gac | aat | tca | ctt | 720 |
| Asp | Cys | Asp | Thr | Met | Ile | Ala | Gly | Ala | Thr | Cys | Thr | Asp | Asn | Ser | Leu | |
| 225 | | | | | 230 | | | | | 235 | | | | | 240 | |
| ggc | atg | tac | atg | gcc | ttc | tct | aaa | acg | cca | gtt | ttt | tct | act | gac | cca | 768 |
| Gly | Met | Tyr | Met | Ala | Phe | Ser | Lys | Thr | Pro | Val | Phe | Ser | Thr | Asp | Pro | |
| | | | | 245 | | | | | 250 | | | | | 255 | | |
| agt | gtc | cgc | gcg | tat | gat | gag | aaa | aca | aaa | ggg | atg | cta | att | gga | gaa | 816 |
| Ser | Val | Arg | Ala | Tyr | Asp | Glu | Lys | Thr | Lys | Gly | Met | Leu | Ile | Gly | Glu | |
| | | | 260 | | | | | 265 | | | | | 270 | | | |
| ggt | tca | gca | atg | ttc | gtt | ctt | aaa | cgc | tat | gcg | gat | gcc | gta | cgt | gat | 864 |
| Gly | Ser | Ala | Met | Phe | Val | Leu | Lys | Arg | Tyr | Ala | Asp | Ala | Val | Arg | Asp | |
| | | 275 | | | | | 280 | | | | | 285 | | | | |

```
ggc gac aca att cac gcg gtt ctg cgt tct tgc tct tcg tct agt gat      912
Gly Asp Thr Ile His Ala Val Leu Arg Ser Cys Ser Ser Ser Ser Asp
    290                 295                 300 gga aaa gcg gca gga att tat act cct act ata tct gga caa gaa gaa      960
Gly Lys Ala Ala Gly Ile Tyr Thr Pro Thr Ile Ser Gly Gln Glu Glu
305                 310                 315                 320 gct ttg cgt cga gcg tat gcc cgt gcg ggg gta tgt cca tct acg atc     1008
Ala Leu Arg Arg Ala Tyr Ala Arg Ala Gly Val Cys Pro Ser Thr Ile
                325                 330                 335 ggg ctt gtt gag ggt cac ggg aca ggg acc cct gtt gga gat cgc att     1056
Gly Leu Val Glu Gly His Gly Thr Gly Thr Pro Val Gly Asp Arg Ile
        340                 345                 350 gag tta aca gct ctg cgg aac ttg ttt gac aaa gct ttt ggt agc aag     1104
Glu Leu Thr Ala Leu Arg Asn Leu Phe Asp Lys Ala Phe Gly Ser Lys
    355                 360                 365 aag gaa caa ata gca gtt ggc agc ata aag tct cag ata ggt cac ctg     1152
Lys Glu Gln Ile Ala Val Gly Ser Ile Lys Ser Gln Ile Gly His Leu
370                 375                 380 aaa tct gtt gcc ggc ttt gcc ggc ttg gtc aaa gct gtg ctt gcg ctt     1200
Lys Ser Val Ala Gly Phe Ala Gly Leu Val Lys Ala Val Leu Ala Leu
385                 390                 395                 400 aaa cac aaa acg ctc cca ggt tcg att aat gtc gac cag cca cct ttg     1248
Lys His Lys Thr Leu Pro Gly Ser Ile Asn Val Asp Gln Pro Pro Leu
                405                 410                 415 ttg tat gac ggt act caa att caa gac tct tct tta tat atc aac aag     1296
Leu Tyr Asp Gly Thr Gln Ile Gln Asp Ser Ser Leu Tyr Ile Asn Lys
        420                 425                 430 aca aat aga cca tgg ttt acg caa aac aag ctt ccg cgt cgg gct ggt     1344
Thr Asn Arg Pro Trp Phe Thr Gln Asn Lys Leu Pro Arg Arg Ala Gly
    435                 440                 445 gtc tca agt ttt gga ttt gga ggt gca aac tac cac gcg gtt ctg gaa     1392
Val Ser Ser Phe Gly Phe Gly Gly Ala Asn Tyr His Ala Val Leu Glu
450                 455                 460 gaa ttc gag ccc gag cat gaa aaa cca tac cgc ctc aat act gtt gga     1440
Glu Phe Glu Pro Glu His Glu Lys Pro Tyr Arg Leu Asn Thr Val Gly
465                 470                 475                 480 cat cct gtc ctc ttg tac gct ccg tct gtg gaa gcc ctc aaa gta ctt     1488
His Pro Val Leu Leu Tyr Ala Pro Ser Val Glu Ala Leu Lys Val Leu
                485                 490                 495 tgc aac gac cag ctt gcg gag ctc aca att gca ttg gaa gag gca aaa     1536
Cys Asn Asp Gln Leu Ala Glu Leu Thr Ile Ala Leu Glu Glu Ala Lys
        500                 505                 510 aca cat aaa aat gtt gac aaa gtt tgt ggc tac aag ttt att gac gaa     1584
Thr His Lys Asn Val Asp Lys Val Cys Gly Tyr Lys Phe Ile Asp Glu
    515                 520                 525 ttt cag ctc caa gga agc tgt cct cca gaa aat ccg aga gta gga ttt     1632
Phe Gln Leu Gln Gly Ser Cys Pro Pro Glu Asn Pro Arg Val Gly Phe
530                 535                 540 tta gca aca ctg cct act tca aat atc att gtc gcg ctt aag gca att     1680
Leu Ala Thr Leu Pro Thr Ser Asn Ile Ile Val Ala Leu Lys Ala Ile
545                 550                 555                 560 ctc gcg cag ctt gat gca aaa cca gat gcg aag aaa tgg gat ttg cct     1728
Leu Ala Gln Leu Asp Ala Lys Pro Asp Ala Lys Lys Trp Asp Leu Pro
                565                 570                 575 cat aaa aag gct ttt ggg gct acc ttc gca tcg tct tca gtg aaa ggc     1776
His Lys Lys Ala Phe Gly Ala Thr Phe Ala Ser Ser Ser Val Lys Gly
        580                 585                 590 tct gtt gct gcg ctc ttc gca gga cag ggt acc cag tac tta aac atg     1824
Ser Val Ala Ala Leu Phe Ala Gly Gln Gly Thr Gln Tyr Leu Asn Met
```

```
                 595                 600                 605
ttc tct gat gtg gca atg aac tgg cca ccg ttc cgt gac agc att gtc   1872
Phe Ser Asp Val Ala Met Asn Trp Pro Pro Phe Arg Asp Ser Ile Val
        610                 615                 620 gca atg gaa gaa gct caa act gag gta ttt gag ggc caa gtt gaa cca   1920
Ala Met Glu Glu Ala Gln Thr Glu Val Phe Glu Gly Gln Val Glu Pro
625                 630                 635                 640 att agc aaa gtt ctg ttt cca cga gag cgc tat gca tcc gaa agt gaa   1968
Ile Ser Lys Val Leu Phe Pro Arg Glu Arg Tyr Ala Ser Glu Ser Glu
                645                 650                 655 cag ggg aat gaa ctt ctt tgc tta aca gag tac tct cag cca act acg   2016
Gln Gly Asn Glu Leu Leu Cys Leu Thr Glu Tyr Ser Gln Pro Thr Thr
            660                 665                 670 ata gca gcc gca gta ggg gcc ttc gat att ttc aaa gcg gct ggc ttt   2064
Ile Ala Ala Ala Val Gly Ala Phe Asp Ile Phe Lys Ala Ala Gly Phe
        675                 680                 685 aag cca gac atg gtt gga ggg cat tca ctt ggc gaa ttt gct gct ttg   2112
Lys Pro Asp Met Val Gly Gly His Ser Leu Gly Glu Phe Ala Ala Leu
690                 695                 700 tac gcg gct ggg tcc att tcg cgt gac gac ctg tac aag ctt gtg tgc   2160
Tyr Ala Ala Gly Ser Ile Ser Arg Asp Asp Leu Tyr Lys Leu Val Cys
705                 710                 715                 720 aaa cgg gca aag gca atg gcg aac gct agt gac gga gct atg gca gca   2208
Lys Arg Ala Lys Ala Met Ala Asn Ala Ser Asp Gly Ala Met Ala Ala
                725                 730                 735 gtg att ggc cca gat gca cgt cta gtt acg cca caa aat agt gac gtt   2256
Val Ile Gly Pro Asp Ala Arg Leu Val Thr Pro Gln Asn Ser Asp Val
            740                 745                 750 tat gtc gca aac ttc aac tcc gca act caa gta gtc atc agt ggc act   2304
Tyr Val Ala Asn Phe Asn Ser Ala Thr Gln Val Val Ile Ser Gly Thr
        755                 760                 765 gtt caa ggt gtg aaa gaa gag tcg aaa ttg ctc att tca aag ggg ttc   2352
Val Gln Gly Val Lys Glu Glu Ser Lys Leu Leu Ile Ser Lys Gly Phe
770                 775                 780 cgc gta ctg cca ctt aaa tgc cag ggc gcc ttc cat tct cct ttg atg   2400
Arg Val Leu Pro Leu Lys Cys Gln Gly Ala Phe His Ser Pro Leu Met
785                 790                 795                 800 ggg cct tct gag gat agt ttc aaa tca ctt gtg gag act tgt acc atc   2448
Gly Pro Ser Glu Asp Ser Phe Lys Ser Leu Val Glu Thr Cys Thr Ile
                805                 810                 815 tcg ccg cca aaa aat gtg aaa ttc ttt tgc aat gtt agt ggc aag gaa   2496
Ser Pro Pro Lys Asn Val Lys Phe Phe Cys Asn Val Ser Gly Lys Glu
            820                 825                 830 agc cca aac cca aaa cag acc ctc aag tca cac atg acg tct agc gtt   2544
Ser Pro Asn Pro Lys Gln Thr Leu Lys Ser His Met Thr Ser Ser Val
        835                 840                 845 cag ttc gag gag cag att cgt aac atg tac gat gcc gga gca cgt gtt   2592
Gln Phe Glu Glu Gln Ile Arg Asn Met Tyr Asp Ala Gly Ala Arg Val
850                 855                 860 ttt ctg gag ttt gga ccc cgc caa gtc ctt gca aag ctt atc gcg gaa   2640
Phe Leu Glu Phe Gly Pro Arg Gln Val Leu Ala Lys Leu Ile Ala Glu
865                 870                 875                 880 atg ttt ccc tcg tgt aca gct atc agc gtt aac ccc gcg agc agt ggt   2688
Met Phe Pro Ser Cys Thr Ala Ile Ser Val Asn Pro Ala Ser Ser Gly
                885                 890                 895 gac agt gac gtg caa ctc cgc ctc gcc gcc gta aaa ttc gcg gtc tcg   2736
Asp Ser Asp Val Gln Leu Arg Leu Ala Ala Val Lys Phe Ala Val Ser
            900                 905                 910 ggt gca gcc ctt agc acc ttt gat cca tgg gag tat cgc aag cca caa   2784
```

```
                                                         -continued

Gly Ala Ala Leu Ser Thr Phe Asp Pro Trp Glu Tyr Arg Lys Pro Gln
        915                 920                 925 gat ctt ctt att cga aaa cca cga aaa act gcc ctt gtt cta tca gca       2832
Asp Leu Leu Ile Arg Lys Pro Arg Lys Thr Ala Leu Val Leu Ser Ala
    930                 935                 940 gca aca tat gtt tcc cca aag act ctt gca gaa cgt aaa aag gct atg       2880
Ala Thr Tyr Val Ser Pro Lys Thr Leu Ala Glu Arg Lys Lys Ala Met
945                 950                 955                 960 gaa gat atc aag cta gta tcc att aca cca aga gat agt atg gta tca       2928
Glu Asp Ile Lys Leu Val Ser Ile Thr Pro Arg Asp Ser Met Val Ser
                965                 970                 975 att gga aaa atc gcg caa gaa gta cgg aca gct aaa cag cct tta gaa       2976
Ile Gly Lys Ile Ala Gln Glu Val Arg Thr Ala Lys Gln Pro Leu Glu
            980                 985                 990 acc gaa att cga aga ctc aac aaa  gaa tta gaa cat ctc  aag aga gag     3024
Thr Glu Ile Arg Arg Leu Asn Lys  Glu Leu Glu His Leu  Lys Arg Glu
        995                 1000                1005 cta gca gca gcc aaa gcg agt  gtc aag tct gca tca  aaa agc tct         3069
Leu Ala Ala Ala Lys Ala Ser  Val Lys Ser Ala Ser  Lys Ser Ser
    1010            1015                1020 aaa gag cga tct gtc cta tca  aag cac cgc gct ttg  ctt caa aac         3114
Lys Glu Arg Ser Val Leu Ser  Lys His Arg Ala Leu  Leu Gln Asn
1025            1030                1035 att ttg caa gac tac gat gat  ctt cgt gtg gtg cca  ttc gct gtt         3159
Ile Leu Gln Asp Tyr Asp Asp  Leu Arg Val Val Pro  Phe Ala Val
        1040            1045                1050 cgt tct gtt gca gtg gac aac  acc gcg ccg tat gct  gac caa gtt         3204
Arg Ser Val Ala Val Asp Asn  Thr Ala Pro Tyr Ala  Asp Gln Val
    1055            1060                1065 tcg acc cca gcg tca gag cgg  tcg gct tca ccg ctt  ttc gag aaa         3249
Ser Thr Pro Ala Ser Glu Arg  Ser Ala Ser Pro Leu  Phe Glu Lys
1070            1075                1080 cgc agt tcg gtt tcg tca gca  cgc ctc gct gaa gct  gaa gcc gcg         3294
Arg Ser Ser Val Ser Ser Ala  Arg Leu Ala Glu Ala  Glu Ala Ala
        1085            1090                1095 gta ctg agc gtt ctc gca gac  aag aca ggc tac gac  agc tca atg         3339
Val Leu Ser Val Leu Ala Asp  Lys Thr Gly Tyr Asp  Ser Ser Met
    1100            1105                1110 atc gag atg gac atg gac ctg  gag agt gag ctt ggc  gtt gat agc         3384
Ile Glu Met Asp Met Asp Leu  Glu Ser Glu Leu Gly  Val Asp Ser
1115            1120                1125 atc aaa cgc gtg gag atc atg  agc gag gtt caa acg  ctg ctc agc         3429
Ile Lys Arg Val Glu Ile Met  Ser Glu Val Gln Thr  Leu Leu Ser
        1130            1135                1140 gtg gaa gtc tcc gac gtt gac  gct ctg tca aga acc  aag act gtt         3474
Val Glu Val Ser Asp Val Asp  Ala Leu Ser Arg Thr  Lys Thr Val
    1145            1150                1155 ggc gac gtc atc gag gcg atg  aag ctg gaa ctc ggt  gga ccc caa         3519
Gly Asp Val Ile Glu Ala Met  Lys Leu Glu Leu Gly  Gly Pro Gln
1160            1165                1170 ggc cag act ttg acc gcg gaa  tcg atc cgt cag cca  ccg gtg tcc         3564
Gly Gln Thr Leu Thr Ala Glu  Ser Ile Arg Gln Pro  Pro Val Ser
        1175            1180                1185 gag cct gct gta ccg acc tca  tcg tca agc agt att  gct aat gtt         3609
Glu Pro Ala Val Pro Thr Ser  Ser Ser Ser Ser Ile  Ala Asn Val
    1190            1195                1200 tcg tca gca cgc ctc gct gaa  gct gaa gct gcg gta  ctg agc gtt         3654
Ser Ser Ala Arg Leu Ala Glu  Ala Glu Ala Ala Val  Leu Ser Val
1205            1210                1215
```

```
ctc gca gac aag aca ggc tac gac agc tca atg atc gag atg gac      3699
Leu Ala Asp Lys Thr Gly Tyr Asp Ser Ser Met Ile Glu Met Asp
    1220            1225                1230 atg gac ctg gag agc gag ctt ggc gtt gat agc atc aaa cgc gtg      3744
Met Asp Leu Glu Ser Glu Leu Gly Val Asp Ser Ile Lys Arg Val
    1235            1240                1245 gag atc atg agc gag gtt caa acg ctg ctc agc gtg gaa gtc tcc      3789
Glu Ile Met Ser Glu Val Gln Thr Leu Leu Ser Val Glu Val Ser
    1250            1255                1260 gac gtt gac gct ctg tca aga act aag act gtt ggc gac gtc atc      3834
Asp Val Asp Ala Leu Ser Arg Thr Lys Thr Val Gly Asp Val Ile
    1265            1270                1275 gag gcg atg aag ctg gaa ctc ggt gga ccc caa ggc cag act ttg      3879
Glu Ala Met Lys Leu Glu Leu Gly Gly Pro Gln Gly Gln Thr Leu
    1280            1285                1290 acc gcg gaa tcg atc cgt cag cca ccg gtg tct gag cct gct gta      3924
Thr Ala Glu Ser Ile Arg Gln Pro Pro Val Ser Glu Pro Ala Val
    1295            1300                1305 ccg acc tca tcg tca agc agt att gct aat gtt tcg tca gca cgc      3969
Pro Thr Ser Ser Ser Ser Ile Ala Asn Val Ser Ser Ala Arg
    1310            1315                1320 ctc gct gaa gct gaa gcg gcg gta ctg agc gtt ctc gca gac aag      4014
Leu Ala Glu Ala Glu Ala Ala Val Leu Ser Val Leu Ala Asp Lys
    1325            1330                1335 aca ggc tac gac agc tca atg atc gag atg gac atg gac ctg gag      4059
Thr Gly Tyr Asp Ser Ser Met Ile Glu Met Asp Met Asp Leu Glu
    1340            1345                1350 agc gag ctt ggc gtc gac agc atc aaa cgc gtg gag atc atg agc      4104
Ser Glu Leu Gly Val Asp Ser Ile Lys Arg Val Glu Ile Met Ser
    1355            1360                1365 gag gtt caa acg ctg ctc agc gtg gaa gtc tcc gac gtt gac gct      4149
Glu Val Gln Thr Leu Leu Ser Val Glu Val Ser Asp Val Asp Ala
    1370            1375                1380 ctg tca aga acc aag act gtt ggc gac gtc atc gag gcg atg aag      4194
Leu Ser Arg Thr Lys Thr Val Gly Asp Val Ile Glu Ala Met Lys
    1385            1390                1395 ctg gaa ctc ggt gga ccc caa ggc cag act ttg acc gcg gaa tcg      4239
Leu Glu Leu Gly Gly Pro Gln Gly Gln Thr Leu Thr Ala Glu Ser
    1400            1405                1410 atc cgt cag cca ccg gtg tcc gag cct gct gta ccg acc tca tcg      4284
Ile Arg Gln Pro Pro Val Ser Glu Pro Ala Val Pro Thr Ser Ser
    1415            1420                1425 tca agc agt att gct aat gtt ttg tca gca cgc ctc gct gaa gct      4329
Ser Ser Ser Ile Ala Asn Val Leu Ser Ala Arg Leu Ala Glu Ala
    1430            1435                1440 gaa gcc gcg gta ctg agc gtt ctc gca gac aag aca ggc tac gac      4374
Glu Ala Ala Val Leu Ser Val Leu Ala Asp Lys Thr Gly Tyr Asp
    1445            1450                1455 agc tca atg atc gag atg gac atg gac ctg gag agc gag ctt ggc      4419
Ser Ser Met Ile Glu Met Asp Met Asp Leu Glu Ser Glu Leu Gly
    1460            1465                1470 gtt gat agc atc aaa cgc gtg gag atc atg agc gag gtt caa acg      4464
Val Asp Ser Ile Lys Arg Val Glu Ile Met Ser Glu Val Gln Thr
    1475            1480                1485 ttg ctc agc gtg gaa gtc tcc gac gtt gac gct ctg tca aga acc      4509
Leu Leu Ser Val Glu Val Ser Asp Val Asp Ala Leu Ser Arg Thr
    1490            1495                1500 aag act gtt ggc gac gtc atc gag gcg atg aag ctg gaa ctc ggt      4554
Lys Thr Val Gly Asp Val Ile Glu Ala Met Lys Leu Glu Leu Gly
    1505            1510                1515
```

-continued

| | | |
|---|---|---|
| gga ccc caa ggc cag act ttg acc gcg gaa tcg atc cgt cag cca<br>Gly Pro Gln Gly Gln Thr Leu Thr Ala Glu Ser Ile Arg Gln Pro<br>1520                        1525                        1530 | 4599 |
| ccg gtg tct gag cct gct gta ccg acc tca tcg tca agc agt att<br>Pro Val Ser Glu Pro Ala Val Pro Thr Ser Ser Ser Ser Ser Ile<br>1535                        1540                        1545 | 4644 |
| gct aat gtt tcg tca gca cgc ctc gct gaa gct gaa gcc gcg gta<br>Ala Asn Val Ser Ser Ala Arg Leu Ala Glu Ala Glu Ala Ala Val<br>1550                        1555                        1560 | 4689 |
| ctg agc gtt ctc gca gac aag aca ggc tac gac agc tca atg atc<br>Leu Ser Val Leu Ala Asp Lys Thr Gly Tyr Asp Ser Ser Met Ile<br>1565                        1570                        1575 | 4734 |
| gag atg gac atg gac ctg gag agt gag ctt ggc gtc gac agc atc<br>Glu Met Asp Met Asp Leu Glu Ser Glu Leu Gly Val Asp Ser Ile<br>1580                        1585                        1590 | 4779 |
| aaa cgc gtg gag atc atg agc gag gtt caa acg ctg ctc agc gtg<br>Lys Arg Val Glu Ile Met Ser Glu Val Gln Thr Leu Leu Ser Val<br>1595                        1600                        1605 | 4824 |
| gaa gtc tcc gac gtt gac gct ctg tca aga acc aag act gtt ggc<br>Glu Val Ser Asp Val Asp Ala Leu Ser Arg Thr Lys Thr Val Gly<br>1610                        1615                        1620 | 4869 |
| gac gtc atc gag gcg atg aag ctg gaa ctc ggt gga ccc caa ggc<br>Asp Val Ile Glu Ala Met Lys Leu Glu Leu Gly Gly Pro Gln Gly<br>1625                        1630                        1635 | 4914 |
| cag act ttg acc tct gaa ccg atc cat cag cca cca gtg tcc gag<br>Gln Thr Leu Thr Ser Glu Pro Ile His Gln Pro Pro Val Ser Glu<br>1640                        1645                        1650 | 4959 |
| cct gct gta ccg acc tca tcg tca agc agt att gct aat gtt tct<br>Pro Ala Val Pro Thr Ser Ser Ser Ser Ser Ile Ala Asn Val Ser<br>1655                        1660                        1665 | 5004 |
| tca gca cgc ctc gct gaa gct gaa gcc gcg gta ctg agc gtt ctc<br>Ser Ala Arg Leu Ala Glu Ala Glu Ala Ala Val Leu Ser Val Leu<br>1670                        1675                        1680 | 5049 |
| gca gac aag aca ggc tac gac agc tca atg atc gag atg gac atg<br>Ala Asp Lys Thr Gly Tyr Asp Ser Ser Met Ile Glu Met Asp Met<br>1685                        1690                        1695 | 5094 |
| gac ctg gag agc gag ctt ggc gtt gat agc atc aaa cgc gtg gaa<br>Asp Leu Glu Ser Glu Leu Gly Val Asp Ser Ile Lys Arg Val Glu<br>1700                        1705                        1710 | 5139 |
| atc atg agc gag gtt caa acg ctg ctc agc gtg gaa gtc tcc gac<br>Ile Met Ser Glu Val Gln Thr Leu Leu Ser Val Glu Val Ser Asp<br>1715                        1720                        1725 | 5184 |
| gtt gac gct ctg tca aga acc aag act gtt ggc gac gtc atc gag<br>Val Asp Ala Leu Ser Arg Thr Lys Thr Val Gly Asp Val Ile Glu<br>1730                        1735                        1740 | 5229 |
| gcg atg aag atg gaa ctc ggt gga ccc caa ggc cag act ttg acc<br>Ala Met Lys Met Glu Leu Gly Gly Pro Gln Gly Gln Thr Leu Thr<br>1745                        1750                        1755 | 5274 |
| gcg gaa tcg atc cgt cag cca ccg gtg tct gag cct gct gta ccg<br>Ala Glu Ser Ile Arg Gln Pro Pro Val Ser Glu Pro Ala Val Pro<br>1760                        1765                        1770 | 5319 |
| acc tca tcg tca agc agt att gct aat gtt tcg tca gca cgc ctc<br>Thr Ser Ser Ser Ser Ser Ile Ala Asn Val Ser Ser Ala Arg Leu<br>1775                        1780                        1785 | 5364 |
| gct gaa gct gaa gcg gcg gta ctg agc gtt ctc gca gac aag aca<br>Ala Glu Ala Glu Ala Ala Val Leu Ser Val Leu Ala Asp Lys Thr<br>1790                        1795                        1800 | 5409 |
| ggc tac gac agc tca atg atc gag atg gac atg gac ctg gag agc<br>Gly Tyr Asp Ser Ser Met Ile Glu Met Asp Met Asp Leu Glu Ser | 5454 |

```
                             -continued
       1805                 1810                 1815
gag ctt ggc gtt gat agc atc aaa cgc gtg gag atc atg agc gag    5499
Glu Leu Gly Val Asp Ser Ile Lys Arg Val Glu Ile Met Ser Glu
    1820                1825                1830 gtt caa gcg ctg ctc agc gtg gaa gtc tcc gac gtt gac gct ctg    5544
Val Gln Ala Leu Leu Ser Val Glu Val Ser Asp Val Asp Ala Leu
    1835                1840                1845 tca aga acc aag act gtt ggc gac gtc atc gag gcg atg aag atg    5589
Ser Arg Thr Lys Thr Val Gly Asp Val Ile Glu Ala Met Lys Met
    1850                1855                1860 gaa ctc ggt gga ccc caa ggc cag act ttg acc gca gaa tcg atc    5634
Glu Leu Gly Gly Pro Gln Gly Gln Thr Leu Thr Ala Glu Ser Ile
    1865                1870                1875 cgt gag cca ccg gtg tct gag cct gct gta ccg acc tca tcg tca    5679
Arg Glu Pro Pro Val Ser Glu Pro Ala Val Pro Thr Ser Ser Ser
    1880                1885                1890 agt agt atc gct aat gtt tct tca gct cgc ctc gct gaa gct gaa    5724
Ser Ser Ile Ala Asn Val Ser Ser Ala Arg Leu Ala Glu Ala Glu
    1895                1900                1905 gcc gcg gta ctg agc gtt ctc gca gac aag aca ggc tac gac agc    5769
Ala Ala Val Leu Ser Val Leu Ala Asp Lys Thr Gly Tyr Asp Ser
    1910                1915                1920 tca atg atc gag atg gac atg gac ctg gag agt gag ctt ggc gtc    5814
Ser Met Ile Glu Met Asp Met Asp Leu Glu Ser Glu Leu Gly Val
    1925                1930                1935 gac agc atc aaa cgc gtg gag atc atg agc gag gtt caa acg ttg    5859
Asp Ser Ile Lys Arg Val Glu Ile Met Ser Glu Val Gln Thr Leu
    1940                1945                1950 ctc agc gtg gaa gtc tcc gac gtt gac gct ctg tca aga acc aag    5904
Leu Ser Val Glu Val Ser Asp Val Asp Ala Leu Ser Arg Thr Lys
    1955                1960                1965 act gtt ggc gac gtc atc gag gcg atg aag ctg gaa ctt ggg gaa    5949
Thr Val Gly Asp Val Ile Glu Ala Met Lys Leu Glu Leu Gly Glu
    1970                1975                1980 tca tca agt att gag act ctc aat tgt acc gag gtt gag cac acg    5994
Ser Ser Ser Ile Glu Thr Leu Asn Cys Thr Glu Val Glu His Thr
    1985                1990                1995 agc tac aaa agt gtc aag gct tca ggg tgt gag aat gta gat acc    6039
Ser Tyr Lys Ser Val Lys Ala Ser Gly Cys Glu Asn Val Asp Thr
    2000                2005                2010 cgt ttc gct aag gtt gta caa atc tcg ctt cct agc aag ctg aaa    6084
Arg Phe Ala Lys Val Val Gln Ile Ser Leu Pro Ser Lys Leu Lys
    2015                2020                2025 tcc act gtg tcg cac gat cga cct gta att gtt gta gat gat gga    6129
Ser Thr Val Ser His Asp Arg Pro Val Ile Val Val Asp Asp Gly
    2030                2035                2040 acg ccc tta acc acg gag ctt tgt aaa att ctt ggg ggt aat att    6174
Thr Pro Leu Thr Thr Glu Leu Cys Lys Ile Leu Gly Gly Asn Ile
    2045                2050                2055 gtg gtt ctc tct tat caa ggg aag ccc gct ggt cca cgg gga gtc    6219
Val Val Leu Ser Tyr Gln Gly Lys Pro Ala Gly Pro Arg Gly Val
    2060                2065                2070 gag gtg cca gat ctt tcc gag gaa gcc cta att caa gct ctt gca    6264
Glu Val Pro Asp Leu Ser Glu Glu Ala Leu Ile Gln Ala Leu Ala
    2075                2080                2085 ttg att cgg tct aca tat gga gtt cca att ggt ttt att tgt cag    6309
Leu Ile Arg Ser Thr Tyr Gly Val Pro Ile Gly Phe Ile Cys Gln
    2090                2095                2100 caa gtg tct aat gtg agc acc aag gca cag ctt tgt tgg gca ctc    6354
```

```
          Gln Val Ser Asn Val Ser Thr Lys Ala Gln Leu Cys Trp Ala Leu
              2105            2110            2115 ctc gca gcg aag cat ctc aag aag gat ttg aat gct gtc tta ccc            6399
Leu Ala Ala Lys His Leu Lys Lys Asp Leu Asn Ala Val Leu Pro
2120            2125            2130 gat tca aga tcc ttc ttc gtc gga gtt gta cgc ttg aac ggg aaa            6444
Asp Ser Arg Ser Phe Phe Val Gly Val Val Arg Leu Asn Gly Lys
        2135            2140            2145 ctt gga act ttc gaa aac atc agc gac ttc tct aaa ttt gat ttg            6489
Leu Gly Thr Phe Glu Asn Ile Ser Asp Phe Ser Lys Phe Asp Leu
    2150            2155            2160 acg aaa gcc cta gat tac gga cag cgt ggt tct ctc tta ggc ctg            6534
Thr Lys Ala Leu Asp Tyr Gly Gln Arg Gly Ser Leu Leu Gly Leu
    2165            2170            2175 tgc aag tca cta gac tta gaa tgg gaa cag gtg ttt tgc cgt gga            6579
Cys Lys Ser Leu Asp Leu Glu Trp Glu Gln Val Phe Cys Arg Gly
        2180            2185            2190 ata gat ctt gcg tgt gat ctt atg cca ctc cag gcc gca agg ata            6624
Ile Asp Leu Ala Cys Asp Leu Met Pro Leu Gln Ala Ala Arg Ile
    2195            2200            2205 ctc aga aat gag ctt cag tgt ccc aat atg cgc ctt cgc gag gtt            6669
Leu Arg Asn Glu Leu Gln Cys Pro Asn Met Arg Leu Arg Glu Val
    2210            2215            2220 ggg tac gat att tct ggc gcc agg tac acc att tca acc gat gac            6714
Gly Tyr Asp Ile Ser Gly Ala Arg Tyr Thr Ile Ser Thr Asp Asp
        2225            2230            2235 ctg cta tgt gga ccc tcg aag gct aaa gta gag gcc gca gac ttg            6759
Leu Leu Cys Gly Pro Ser Lys Ala Lys Val Glu Ala Ala Asp Leu
    2240            2245            2250 ttt ctt gtg aca ggt ggc gca cga ggt att aca cct cat tgt gtt            6804
Phe Leu Val Thr Gly Gly Ala Arg Gly Ile Thr Pro His Cys Val
    2255            2260            2265 cgt gag att gca agt cga tcc ccc gga acc aca ttt gtg ctg gtt            6849
Arg Glu Ile Ala Ser Arg Ser Pro Gly Thr Thr Phe Val Leu Val
        2270            2275            2280 gga aga agc gaa atg tcc gac gag cct gac tgg gct gtt ggc cac            6894
Gly Arg Ser Glu Met Ser Asp Glu Pro Asp Trp Ala Val Gly His
    2285            2290            2295 tac aat aaa gac ctg gac caa agc aca atg aaa cac ttg aaa gca            6939
Tyr Asn Lys Asp Leu Asp Gln Ser Thr Met Lys His Leu Lys Ala
    2300            2305            2310 acg cat gct gct gga ggg gta aaa cct acg cct aaa gca cat cgt            6984
Thr His Ala Ala Gly Gly Val Lys Pro Thr Pro Lys Ala His Arg
        2315            2320            2325 gca ctt gtg aac agg gtc act ggc tca cgg gag gta cga gaa tct            7029
Ala Leu Val Asn Arg Val Thr Gly Ser Arg Glu Val Arg Glu Ser
    2330            2335            2340 ctt aga gca atc cag gag gca ggg gca aat gtc gaa tat atc gcc            7074
Leu Arg Ala Ile Gln Glu Ala Gly Ala Asn Val Glu Tyr Ile Ala
    2345            2350            2355 tgt gat gtt tcg gat gaa aac aag gtc cgc caa ctt gtg caa aga            7119
Cys Asp Val Ser Asp Glu Asn Lys Val Arg Gln Leu Val Gln Arg
        2360            2365            2370 gtg gag caa aag tat ggc tgt gaa ata act ggg att tgg cat gca            7164
Val Glu Gln Lys Tyr Gly Cys Glu Ile Thr Gly Ile Trp His Ala
    2375            2380            2385 agc ggg gtt ctt cgt gac aaa ctt gtc gag caa aag act aca gac            7209
Ser Gly Val Leu Arg Asp Lys Leu Val Glu Gln Lys Thr Thr Asp
    2390            2395            2400
```

```
gac ttt gag gca gtt ttt ggg acc aag gtg act ggc ctt gta aac      7254
Asp Phe Glu Ala Val Phe Gly Thr Lys Val Thr Gly Leu Val Asn
    2405                2410                2415 atc gtg tca caa gtc aat atg tct aag cta cga cac ttc atc ctc      7299
Ile Val Ser Gln Val Asn Met Ser Lys Leu Arg His Phe Ile Leu
2420                2425                2430 ttc agt tct ttg gct gga ttt cat ggg aac aag ggc caa acg gat      7344
Phe Ser Ser Leu Ala Gly Phe His Gly Asn Lys Gly Gln Thr Asp
    2435                2440                2445 tat gca att gct aat gaa gcc ttg aac aaa atc gcg cat act ctc      7389
Tyr Ala Ile Ala Asn Glu Ala Leu Asn Lys Ile Ala His Thr Leu
2450                2455                2460 tca gcg ttt ttg ccc aaa ctg aat gca aag gtg cta gac ttc ggt      7434
Ser Ala Phe Leu Pro Lys Leu Asn Ala Lys Val Leu Asp Phe Gly
    2465                2470                2475 ccg tgg gta ggt tca gga atg gta acc gaa aca ctt gag aag cat      7479
Pro Trp Val Gly Ser Gly Met Val Thr Glu Thr Leu Glu Lys His
2480                2485                2490 ttt aaa gct atg ggg gtt cag act att cct ctc gag cca gga gca      7524
Phe Lys Ala Met Gly Val Gln Thr Ile Pro Leu Glu Pro Gly Ala
    2495                2500                2505 cgg act gtt gcg caa atc att ttg gca agt tcg cca ccg caa tcg      7569
Arg Thr Val Ala Gln Ile Ile Leu Ala Ser Ser Pro Pro Gln Ser
2510                2515                2520 ctt ttg ggg aac tgg ggc ttt cca gcc acc aaa ccg cta caa cgc      7614
Leu Leu Gly Asn Trp Gly Phe Pro Ala Thr Lys Pro Leu Gln Arg
    2525                2530                2535 tct aat gta gtc acg ggc aca ctc tct ccg gaa gag ata gaa ttc      7659
Ser Asn Val Val Thr Gly Thr Leu Ser Pro Glu Glu Ile Glu Phe
2540                2545                2550 atc gca gac cac aaa att caa ggc cgc aag gtg ctt ccc atg atg      7704
Ile Ala Asp His Lys Ile Gln Gly Arg Lys Val Leu Pro Met Met
    2555                2560                2565 gct gca atc ggg ttc atg gcc tct att gcg gaa gga ctc tac ccg      7749
Ala Ala Ile Gly Phe Met Ala Ser Ile Ala Glu Gly Leu Tyr Pro
2570                2575                2580 ggg tac aat ctg caa ggc gtg gaa aat gct cag ctc ttt caa ggc      7794
Gly Tyr Asn Leu Gln Gly Val Glu Asn Ala Gln Leu Phe Gln Gly
    2585                2590                2595 ttg act atc aac caa gag aca aaa ttt caa atc act ctc att gag      7839
Leu Thr Ile Asn Gln Glu Thr Lys Phe Gln Ile Thr Leu Ile Glu
2600                2605                2610 gag cac aac tct gag gaa aac ctg gat gtc ctg aca tcc ctt ggt      7884
Glu His Asn Ser Glu Glu Asn Leu Asp Val Leu Thr Ser Leu Gly
    2615                2620                2625 gta atg ttg gaa agc ggg aag gtg ctt ccc gct tac cga tgt gtt      7929
Val Met Leu Glu Ser Gly Lys Val Leu Pro Ala Tyr Arg Cys Val
2630                2635                2640 gta tgc ttg aat aca acc cag cag cag ccc aag cta tct cca aaa      7974
Val Cys Leu Asn Thr Thr Gln Gln Gln Pro Lys Leu Ser Pro Lys
    2645                2650                2655 att ctt aac ttg gaa gtt gac cct gca tgc gag gtt aac ccc tat      8019
Ile Leu Asn Leu Glu Val Asp Pro Ala Cys Glu Val Asn Pro Tyr
2660                2665                2670 gat gga aag tcg ttg ttc cac ggt ccg ctt ttg caa ttc gtt caa      8064
Asp Gly Lys Ser Leu Phe His Gly Pro Leu Leu Gln Phe Val Gln
    2675                2680                2685 caa gtg ttg cac tca agt acc aaa ggc ctc gtt gcc aag tgc cgc      8109
Gln Val Leu His Ser Ser Thr Lys Gly Leu Val Ala Lys Cys Arg
2690                2695                2700
```

-continued

```
gcg ctt cca atc aaa gaa gcc atc cga ggg cca ttt atc aag caa      8154
Ala Leu Pro Ile Lys Glu Ala Ile Arg Gly Pro Phe Ile Lys Gln
    2705                2710                2715 aca ctc cat gat cca att cta gac gac gtc att ttt cag cta atg      8199
Thr Leu His Asp Pro Ile Leu Asp Asp Val Ile Phe Gln Leu Met
    2720                2725                2730 ctc gtg tgg tgt cgt aat gct cta gga agt gca tcg cta ccc aac      8244
Leu Val Trp Cys Arg Asn Ala Leu Gly Ser Ala Ser Leu Pro Asn
    2735                2740                2745 aga att gaa aag atg tca tac ttt ggg aat gtc tca gaa ggt agc      8289
Arg Ile Glu Lys Met Ser Tyr Phe Gly Asn Val Ser Glu Gly Ser
    2750                2755                2760 act ttc ttt gcc tca gtt aca cct gtg gga cca aga gta cca aag      8334
Thr Phe Phe Ala Ser Val Thr Pro Val Gly Pro Arg Val Pro Lys
    2765                2770                2775 gat ccc gtg atc aaa atg cag ttt ctt ctc caa gat gaa tcc ggc      8379
Asp Pro Val Ile Lys Met Gln Phe Leu Leu Gln Asp Glu Ser Gly
    2780                2785                2790 aac aca ttt tca tcg ggg gag ggc tcg gtt gtg ctt agt gac gaa      8424
Asn Thr Phe Ser Ser Gly Glu Gly Ser Val Val Leu Ser Asp Glu
    2795                2800                2805 ctc gtc ttt tga                                                  8436
Leu Val Phe
    2810

<210> SEQ ID NO 39
<211> LENGTH: 2811
<212> TYPE: PRT
<213> ORGANISM: Thraustochytrium sp.

<400> SEQUENCE: 39

Met Lys Asp Met Glu Asp Arg Arg Val Ala Ile Val Gly Met Ser Ala
1               5                   10                  15

His Leu Pro Cys Gly Thr Asp Val Lys Glu Ser Trp Gln Ala Ile Arg
            20                  25                  30

Asp Gly Ile Asp Cys Leu Ser Asp Leu Pro Ala Asp Arg Leu Asp Val
        35                  40                  45

Thr Ala Tyr Tyr Asn Pro Asn Lys Ala Thr Lys Asp Lys Ile Tyr Cys
    50                  55                  60

Lys Arg Gly Gly Phe Ile Pro Asn Tyr Asp Phe Asp Pro Arg Glu Phe
65                  70                  75                  80

Gly Leu Asn Met Phe Gln Met Glu Asp Ser Asp Ala Asn Gln Thr Leu
                85                  90                  95

Thr Leu Leu Lys Val Lys Gln Ala Leu Glu Asp Ala Ser Ile Glu Pro
            100                 105                 110

Phe Thr Lys Glu Lys Lys Asn Ile Gly Cys Val Leu Gly Ile Gly Gly
        115                 120                 125

Gly Gln Lys Ala Ser His Glu Phe Tyr Ser Arg Leu Asn Tyr Val Val
    130                 135                 140

Val Glu Lys Val Leu Arg Lys Met Gly Leu Pro Asp Ala Asp Val Glu
145                 150                 155                 160

Glu Ala Val Glu Lys Tyr Lys Ala Asn Phe Pro Glu Trp Arg Leu Asp
                165                 170                 175

Ser Phe Pro Gly Phe Leu Gly Asn Val Thr Ala Gly Arg Cys Ser Asn
            180                 185                 190

Thr Phe Asn Met Glu Gly Met Asn Cys Val Val Asp Ala Ala Cys Ala
        195                 200                 205
```

-continued

```
Ser Ser Leu Ile Ala Ile Lys Val Ala Val Glu Glu Leu Leu Phe Gly
    210                 215                 220

Asp Cys Asp Thr Met Ile Ala Gly Ala Thr Cys Thr Asp Asn Ser Leu
225                 230                 235                 240

Gly Met Tyr Met Ala Phe Ser Lys Thr Pro Val Phe Ser Thr Asp Pro
                245                 250                 255

Ser Val Arg Ala Tyr Asp Glu Lys Thr Lys Gly Met Leu Ile Gly Glu
            260                 265                 270

Gly Ser Ala Met Phe Val Leu Lys Arg Tyr Ala Asp Ala Val Arg Asp
        275                 280                 285

Gly Asp Thr Ile His Ala Val Leu Arg Ser Cys Ser Ser Ser Ser Asp
    290                 295                 300

Gly Lys Ala Ala Gly Ile Tyr Thr Pro Thr Ile Ser Gly Gln Glu Glu
305                 310                 315                 320

Ala Leu Arg Arg Ala Tyr Ala Arg Ala Gly Val Cys Pro Ser Thr Ile
                325                 330                 335

Gly Leu Val Glu Gly His Gly Thr Gly Thr Pro Val Gly Asp Arg Ile
            340                 345                 350

Glu Leu Thr Ala Leu Arg Asn Leu Phe Asp Lys Ala Phe Gly Ser Lys
        355                 360                 365

Lys Glu Gln Ile Ala Val Gly Ser Ile Lys Ser Gln Ile Gly His Leu
    370                 375                 380

Lys Ser Val Ala Gly Phe Ala Gly Leu Val Lys Ala Val Leu Ala Leu
385                 390                 395                 400

Lys His Lys Thr Leu Pro Gly Ser Ile Asn Val Asp Gln Pro Pro Leu
                405                 410                 415

Leu Tyr Asp Gly Thr Gln Ile Gln Asp Ser Ser Leu Tyr Ile Asn Lys
            420                 425                 430

Thr Asn Arg Pro Trp Phe Thr Gln Asn Lys Leu Pro Arg Arg Ala Gly
        435                 440                 445

Val Ser Ser Phe Gly Phe Gly Gly Ala Asn Tyr His Ala Val Leu Glu
    450                 455                 460

Glu Phe Glu Pro Glu His Glu Lys Pro Tyr Arg Leu Asn Thr Val Gly
465                 470                 475                 480

His Pro Val Leu Leu Tyr Ala Pro Ser Val Glu Ala Leu Lys Val Leu
                485                 490                 495

Cys Asn Asp Gln Leu Ala Glu Leu Thr Ile Ala Leu Glu Glu Ala Lys
            500                 505                 510

Thr His Lys Asn Val Asp Lys Val Cys Gly Tyr Lys Phe Ile Asp Glu
        515                 520                 525

Phe Gln Leu Gln Gly Ser Cys Pro Pro Glu Asn Pro Arg Val Gly Phe
    530                 535                 540

Leu Ala Thr Leu Pro Thr Ser Asn Ile Ile Val Ala Leu Lys Ala Ile
545                 550                 555                 560

Leu Ala Gln Leu Asp Ala Lys Pro Asp Ala Lys Lys Trp Asp Leu Pro
                565                 570                 575

His Lys Lys Ala Phe Gly Ala Thr Phe Ala Ser Ser Val Lys Gly
            580                 585                 590

Ser Val Ala Ala Leu Phe Ala Gly Gln Gly Thr Gln Tyr Leu Asn Met
        595                 600                 605

Phe Ser Asp Val Ala Met Asn Trp Pro Pro Phe Arg Asp Ser Ile Val
    610                 615                 620
```

```
Ala Met Glu Glu Ala Gln Thr Glu Val Phe Glu Gly Gln Val Glu Pro
625                 630                 635                 640

Ile Ser Lys Val Leu Phe Pro Arg Glu Arg Tyr Ala Ser Glu Ser Glu
                645                 650                 655

Gln Gly Asn Glu Leu Leu Cys Leu Thr Glu Tyr Ser Gln Pro Thr Thr
            660                 665                 670

Ile Ala Ala Ala Val Gly Ala Phe Asp Ile Phe Lys Ala Ala Gly Phe
        675                 680                 685

Lys Pro Asp Met Val Gly Gly His Ser Leu Gly Glu Phe Ala Ala Leu
690                 695                 700

Tyr Ala Ala Gly Ser Ile Ser Arg Asp Asp Leu Tyr Lys Leu Val Cys
705                 710                 715                 720

Lys Arg Ala Lys Ala Met Ala Asn Ala Ser Asp Gly Ala Met Ala Ala
                725                 730                 735

Val Ile Gly Pro Asp Ala Arg Leu Val Thr Pro Gln Asn Ser Asp Val
            740                 745                 750

Tyr Val Ala Asn Phe Asn Ser Ala Thr Gln Val Val Ile Ser Gly Thr
        755                 760                 765

Val Gln Gly Val Lys Glu Ser Lys Leu Leu Ile Ser Lys Gly Phe
770                 775                 780

Arg Val Leu Pro Leu Lys Cys Gln Gly Ala Phe His Ser Pro Leu Met
785                 790                 795                 800

Gly Pro Ser Glu Asp Ser Phe Lys Ser Leu Val Glu Thr Cys Thr Ile
                805                 810                 815

Ser Pro Pro Lys Asn Val Lys Phe Phe Cys Asn Val Ser Gly Lys Glu
            820                 825                 830

Ser Pro Asn Pro Lys Gln Thr Leu Lys Ser His Met Thr Ser Ser Val
        835                 840                 845

Gln Phe Glu Glu Gln Ile Arg Asn Met Tyr Asp Ala Gly Ala Arg Val
850                 855                 860

Phe Leu Glu Phe Gly Pro Arg Gln Val Leu Ala Lys Leu Ile Ala Glu
865                 870                 875                 880

Met Phe Pro Ser Cys Thr Ala Ile Ser Val Asn Pro Ala Ser Ser Gly
                885                 890                 895

Asp Ser Asp Val Gln Leu Arg Leu Ala Ala Val Lys Phe Ala Val Ser
            900                 905                 910

Gly Ala Ala Leu Ser Thr Phe Asp Pro Trp Glu Tyr Arg Lys Pro Gln
        915                 920                 925

Asp Leu Leu Ile Arg Lys Pro Arg Lys Thr Ala Leu Val Leu Ser Ala
930                 935                 940

Ala Thr Tyr Val Ser Pro Lys Thr Leu Ala Glu Arg Lys Lys Ala Met
945                 950                 955                 960

Glu Asp Ile Lys Leu Val Ser Ile Thr Pro Arg Asp Ser Met Val Ser
                965                 970                 975

Ile Gly Lys Ile Ala Gln Glu Val Arg Thr Ala Lys Gln Pro Leu Glu
            980                 985                 990

Thr Glu Ile Arg Arg Leu Asn Lys  Glu Leu Glu His Leu  Lys Arg Glu
        995                 1000                1005

Leu Ala  Ala Ala Lys Ala Ser  Val Lys Ser Ala Ser  Lys Ser Ser
    1010                1015                1020

Lys Glu  Arg Ser Val Leu Ser  Lys His Arg Ala Leu  Leu Gln Asn
    1025                1030                1035

Ile Leu  Gln Asp Tyr Asp Asp  Leu Arg Val Val Pro  Phe Ala Val
```

-continued

```
              1040                1045                1050
Arg Ser Val Ala Val Asp Asn Thr Ala Pro Tyr Ala Asp Gln Val
    1055                1060                1065
Ser Thr Pro Ala Ser Glu Arg Ser Ala Ser Pro Leu Phe Glu Lys
    1070                1075                1080
Arg Ser Ser Val Ser Ser Ala Arg Leu Ala Glu Ala Glu Ala Ala
    1085                1090                1095
Val Leu Ser Val Leu Ala Asp Lys Thr Gly Tyr Asp Ser Ser Met
    1100                1105                1110
Ile Glu Met Asp Met Asp Leu Glu Ser Glu Leu Gly Val Asp Ser
    1115                1120                1125
Ile Lys Arg Val Glu Ile Met Ser Glu Val Gln Thr Leu Leu Ser
    1130                1135                1140
Val Glu Val Ser Asp Val Asp Ala Leu Ser Arg Thr Lys Thr Val
    1145                1150                1155
Gly Asp Val Ile Glu Ala Met Lys Leu Glu Leu Gly Gly Pro Gln
    1160                1165                1170
Gly Gln Thr Leu Thr Ala Glu Ser Ile Arg Gln Pro Pro Val Ser
    1175                1180                1185
Glu Pro Ala Val Pro Thr Ser Ser Ser Ser Ile Ala Asn Val
    1190                1195                1200
Ser Ser Ala Arg Leu Ala Glu Ala Glu Ala Ala Val Leu Ser Val
    1205                1210                1215
Leu Ala Asp Lys Thr Gly Tyr Asp Ser Ser Met Ile Glu Met Asp
    1220                1225                1230
Met Asp Leu Glu Ser Glu Leu Gly Val Asp Ser Ile Lys Arg Val
    1235                1240                1245
Glu Ile Met Ser Glu Val Gln Thr Leu Leu Ser Val Glu Val Ser
    1250                1255                1260
Asp Val Asp Ala Leu Ser Arg Thr Lys Thr Val Gly Asp Val Ile
    1265                1270                1275
Glu Ala Met Lys Leu Glu Leu Gly Gly Pro Gln Gly Gln Thr Leu
    1280                1285                1290
Thr Ala Glu Ser Ile Arg Gln Pro Pro Val Ser Glu Pro Ala Val
    1295                1300                1305
Pro Thr Ser Ser Ser Ser Ser Ile Ala Asn Val Ser Ser Ala Arg
    1310                1315                1320
Leu Ala Glu Ala Glu Ala Ala Val Leu Ser Val Leu Ala Asp Lys
    1325                1330                1335
Thr Gly Tyr Asp Ser Ser Met Ile Glu Met Asp Met Asp Leu Glu
    1340                1345                1350
Ser Glu Leu Gly Val Asp Ser Ile Lys Arg Val Glu Ile Met Ser
    1355                1360                1365
Glu Val Gln Thr Leu Leu Ser Val Glu Val Ser Asp Val Asp Ala
    1370                1375                1380
Leu Ser Arg Thr Lys Thr Val Gly Asp Val Ile Glu Ala Met Lys
    1385                1390                1395
Leu Glu Leu Gly Gly Pro Gln Gly Gln Thr Leu Thr Ala Glu Ser
    1400                1405                1410
Ile Arg Gln Pro Pro Val Ser Glu Pro Ala Val Pro Thr Ser Ser
    1415                1420                1425
Ser Ser Ser Ile Ala Asn Val Leu Ser Ala Arg Leu Ala Glu Ala
    1430                1435                1440
```

-continued

```
Glu Ala Ala Val Leu Ser Val Leu Ala Asp Lys Thr Gly Tyr Asp
    1445                1450                1455
Ser Ser Met Ile Glu Met Asp Met Asp Leu Glu Ser Glu Leu Gly
    1460                1465                1470
Val Asp Ser Ile Lys Arg Val Glu Ile Met Ser Glu Val Gln Thr
    1475                1480                1485
Leu Leu Ser Val Glu Val Ser Asp Val Asp Ala Leu Ser Arg Thr
    1490                1495                1500
Lys Thr Val Gly Asp Val Ile Glu Ala Met Lys Leu Glu Leu Gly
    1505                1510                1515
Gly Pro Gln Gly Gln Thr Leu Thr Ala Glu Ser Ile Arg Gln Pro
    1520                1525                1530
Pro Val Ser Glu Pro Ala Val Pro Thr Ser Ser Ser Ser Ser Ile
    1535                1540                1545
Ala Asn Val Ser Ser Ala Arg Leu Ala Glu Ala Glu Ala Ala Val
    1550                1555                1560
Leu Ser Val Leu Ala Asp Lys Thr Gly Tyr Asp Ser Ser Met Ile
    1565                1570                1575
Glu Met Asp Met Asp Leu Glu Ser Glu Leu Gly Val Asp Ser Ile
    1580                1585                1590
Lys Arg Val Glu Ile Met Ser Glu Val Gln Thr Leu Leu Ser Val
    1595                1600                1605
Glu Val Ser Asp Val Asp Ala Leu Ser Arg Thr Lys Thr Val Gly
    1610                1615                1620
Asp Val Ile Glu Ala Met Lys Leu Glu Leu Gly Gly Pro Gln Gly
    1625                1630                1635
Gln Thr Leu Thr Ser Glu Pro Ile His Gln Pro Pro Val Ser Glu
    1640                1645                1650
Pro Ala Val Pro Thr Ser Ser Ser Ser Ser Ile Ala Asn Val Ser
    1655                1660                1665
Ser Ala Arg Leu Ala Glu Ala Glu Ala Ala Val Leu Ser Val Leu
    1670                1675                1680
Ala Asp Lys Thr Gly Tyr Asp Ser Ser Met Ile Glu Met Asp Met
    1685                1690                1695
Asp Leu Glu Ser Glu Leu Gly Val Asp Ser Ile Lys Arg Val Glu
    1700                1705                1710
Ile Met Ser Glu Val Gln Thr Leu Leu Ser Val Glu Val Ser Asp
    1715                1720                1725
Val Asp Ala Leu Ser Arg Thr Lys Thr Val Gly Asp Val Ile Glu
    1730                1735                1740
Ala Met Lys Met Glu Leu Gly Gly Pro Gln Gly Gln Thr Leu Thr
    1745                1750                1755
Ala Glu Ser Ile Arg Gln Pro Pro Val Ser Glu Pro Ala Val Pro
    1760                1765                1770
Thr Ser Ser Ser Ser Ser Ile Ala Asn Val Ser Ser Ala Arg Leu
    1775                1780                1785
Ala Glu Ala Glu Ala Ala Val Leu Ser Val Leu Ala Asp Lys Thr
    1790                1795                1800
Gly Tyr Asp Ser Ser Met Ile Glu Met Asp Met Asp Leu Glu Ser
    1805                1810                1815
Glu Leu Gly Val Asp Ser Ile Lys Arg Val Glu Ile Met Ser Glu
    1820                1825                1830
```

-continued

```
Val Gln Ala Leu Leu Ser Val Glu Val Ser Asp Val Asp Ala Leu
1835                1840                1845

Ser Arg Thr Lys Thr Val Gly Asp Val Ile Glu Ala Met Lys Met
1850                1855                1860

Glu Leu Gly Gly Pro Gln Gly Gln Thr Leu Thr Ala Glu Ser Ile
1865                1870                1875

Arg Glu Pro Pro Val Ser Glu Pro Ala Val Pro Thr Ser Ser Ser
1880                1885                1890

Ser Ser Ile Ala Asn Val Ser Ser Ala Arg Leu Ala Glu Ala Glu
1895                1900                1905

Ala Ala Val Leu Ser Val Leu Ala Asp Lys Thr Gly Tyr Asp Ser
1910                1915                1920

Ser Met Ile Glu Met Asp Met Asp Leu Glu Ser Glu Leu Gly Val
1925                1930                1935

Asp Ser Ile Lys Arg Val Glu Ile Met Ser Glu Val Gln Thr Leu
1940                1945                1950

Leu Ser Val Glu Val Ser Asp Val Asp Ala Leu Ser Arg Thr Lys
1955                1960                1965

Thr Val Gly Asp Val Ile Glu Ala Met Lys Leu Glu Leu Gly Glu
1970                1975                1980

Ser Ser Ser Ile Glu Thr Leu Asn Cys Thr Glu Val Glu His Thr
1985                1990                1995

Ser Tyr Lys Ser Val Lys Ala Ser Gly Cys Glu Asn Val Asp Thr
2000                2005                2010

Arg Phe Ala Lys Val Val Gln Ile Ser Leu Pro Ser Lys Leu Lys
2015                2020                2025

Ser Thr Val Ser His Asp Arg Pro Val Ile Val Val Asp Asp Gly
2030                2035                2040

Thr Pro Leu Thr Thr Glu Leu Cys Lys Ile Leu Gly Gly Asn Ile
2045                2050                2055

Val Val Leu Ser Tyr Gln Gly Lys Pro Ala Gly Pro Arg Gly Val
2060                2065                2070

Glu Val Pro Asp Leu Ser Glu Glu Ala Leu Ile Gln Ala Leu Ala
2075                2080                2085

Leu Ile Arg Ser Thr Tyr Gly Val Pro Ile Gly Phe Ile Cys Gln
2090                2095                2100

Gln Val Ser Asn Val Ser Thr Lys Ala Gln Leu Cys Trp Ala Leu
2105                2110                2115

Leu Ala Ala Lys His Leu Lys Lys Asp Leu Asn Ala Val Leu Pro
2120                2125                2130

Asp Ser Arg Ser Phe Phe Val Gly Val Val Arg Leu Asn Gly Lys
2135                2140                2145

Leu Gly Thr Phe Glu Asn Ile Ser Asp Phe Ser Lys Phe Asp Leu
2150                2155                2160

Thr Lys Ala Leu Asp Tyr Gly Gln Arg Gly Ser Leu Leu Gly Leu
2165                2170                2175

Cys Lys Ser Leu Asp Leu Glu Trp Glu Gln Val Phe Cys Arg Gly
2180                2185                2190

Ile Asp Leu Ala Cys Asp Leu Met Pro Leu Gln Ala Ala Arg Ile
2195                2200                2205

Leu Arg Asn Glu Leu Gln Cys Pro Asn Met Arg Leu Arg Glu Val
2210                2215                2220

Gly Tyr Asp Ile Ser Gly Ala Arg Tyr Thr Ile Ser Thr Asp Asp
```

-continued

```
            2225                2230                2235
Leu Leu Cys Gly Pro Ser Lys Ala Lys Val Glu Ala Ala Asp Leu
    2240                2245                2250

Phe Leu Val Thr Gly Gly Ala Arg Gly Ile Thr Pro His Cys Val
    2255                2260                2265

Arg Glu Ile Ala Ser Arg Ser Pro Gly Thr Thr Phe Val Leu Val
    2270                2275                2280

Gly Arg Ser Glu Met Ser Asp Glu Pro Asp Trp Ala Val Gly His
    2285                2290                2295

Tyr Asn Lys Asp Leu Asp Gln Ser Thr Met Lys His Leu Lys Ala
    2300                2305                2310

Thr His Ala Ala Gly Gly Val Lys Pro Thr Pro Lys Ala His Arg
    2315                2320                2325

Ala Leu Val Asn Arg Val Thr Gly Ser Arg Glu Val Arg Glu Ser
    2330                2335                2340

Leu Arg Ala Ile Gln Glu Ala Gly Ala Asn Val Glu Tyr Ile Ala
    2345                2350                2355

Cys Asp Val Ser Asp Glu Asn Lys Val Arg Gln Leu Val Gln Arg
    2360                2365                2370

Val Glu Gln Lys Tyr Gly Cys Glu Ile Thr Gly Ile Trp His Ala
    2375                2380                2385

Ser Gly Val Leu Arg Asp Lys Leu Val Glu Gln Lys Thr Thr Asp
    2390                2395                2400

Asp Phe Glu Ala Val Phe Gly Thr Lys Val Thr Gly Leu Val Asn
    2405                2410                2415

Ile Val Ser Gln Val Asn Met Ser Lys Leu Arg His Phe Ile Leu
    2420                2425                2430

Phe Ser Ser Leu Ala Gly Phe His Gly Asn Lys Gly Gln Thr Asp
    2435                2440                2445

Tyr Ala Ile Ala Asn Glu Ala Leu Asn Lys Ile Ala His Thr Leu
    2450                2455                2460

Ser Ala Phe Leu Pro Lys Leu Asn Ala Lys Val Leu Asp Phe Gly
    2465                2470                2475

Pro Trp Val Gly Ser Gly Met Val Thr Glu Thr Leu Glu Lys His
    2480                2485                2490

Phe Lys Ala Met Gly Val Gln Thr Ile Pro Leu Glu Pro Gly Ala
    2495                2500                2505

Arg Thr Val Ala Gln Ile Ile Leu Ala Ser Ser Pro Pro Gln Ser
    2510                2515                2520

Leu Leu Gly Asn Trp Gly Phe Pro Ala Thr Lys Pro Leu Gln Arg
    2525                2530                2535

Ser Asn Val Val Thr Gly Thr Leu Ser Pro Glu Glu Ile Glu Phe
    2540                2545                2550

Ile Ala Asp His Lys Ile Gln Gly Arg Lys Val Leu Pro Met Met
    2555                2560                2565

Ala Ala Ile Gly Phe Met Ala Ser Ile Ala Glu Gly Leu Tyr Pro
    2570                2575                2580

Gly Tyr Asn Leu Gln Gly Val Glu Asn Ala Gln Leu Phe Gln Gly
    2585                2590                2595

Leu Thr Ile Asn Gln Glu Thr Lys Phe Gln Ile Thr Leu Ile Glu
    2600                2605                2610

Glu His Asn Ser Glu Glu Asn Leu Asp Val Leu Thr Ser Leu Gly
    2615                2620                2625
```

```
Val Met Leu Glu Ser Gly Lys Val Leu Pro Ala Tyr Arg Cys Val
    2630                2635                2640

Val Cys Leu Asn Thr Thr Gln Gln Gln Pro Lys Leu Ser Pro Lys
    2645                2650                2655

Ile Leu Asn Leu Glu Val Asp Pro Ala Cys Glu Val Asn Pro Tyr
    2660                2665                2670

Asp Gly Lys Ser Leu Phe His Gly Pro Leu Leu Gln Phe Val Gln
    2675                2680                2685

Gln Val Leu His Ser Ser Thr Lys Gly Leu Val Ala Lys Cys Arg
    2690                2695                2700

Ala Leu Pro Ile Lys Glu Ala Ile Arg Gly Pro Phe Ile Lys Gln
    2705                2710                2715

Thr Leu His Asp Pro Ile Leu Asp Asp Val Ile Phe Gln Leu Met
    2720                2725                2730

Leu Val Trp Cys Arg Asn Ala Leu Gly Ser Ala Ser Leu Pro Asn
    2735                2740                2745

Arg Ile Glu Lys Met Ser Tyr Phe Gly Asn Val Ser Glu Gly Ser
    2750                2755                2760

Thr Phe Phe Ala Ser Val Thr Pro Val Gly Pro Arg Val Pro Lys
    2765                2770                2775

Asp Pro Val Ile Lys Met Gln Phe Leu Leu Gln Asp Glu Ser Gly
    2780                2785                2790

Asn Thr Phe Ser Ser Gly Glu Gly Ser Val Val Leu Ser Asp Glu
    2795                2800                2805

Leu Val Phe
    2810

<210> SEQ ID NO 40
<211> LENGTH: 1500
<212> TYPE: DNA
<213> ORGANISM: Thraustochytrium sp.
<220> FEATURE:
<221> NAME/KEY: CDS
<222> LOCATION: (1)..(1500)

<400> SEQUENCE: 40 atg aag gac atg gaa gat aga cgg gtc gct att gtg ggc atg tca gct      48
Met Lys Asp Met Glu Asp Arg Arg Val Ala Ile Val Gly Met Ser Ala
1               5                   10                  15 cac ttg cct tgt ggg aca gat gtg aag gaa tca tgg cag gct att cgc      96
His Leu Pro Cys Gly Thr Asp Val Lys Glu Ser Trp Gln Ala Ile Arg
                20                  25                  30 gat gga atc gac tgt cta agt gac cta ccc gcg gat cgt ctc gac gtt     144
Asp Gly Ile Asp Cys Leu Ser Asp Leu Pro Ala Asp Arg Leu Asp Val
            35                  40                  45 aca gct tac tac aat ccc aac aaa gcc acg aaa gac aag atc tac tgc     192
Thr Ala Tyr Tyr Asn Pro Asn Lys Ala Thr Lys Asp Lys Ile Tyr Cys
        50                  55                  60 aaa cgg ggt ggc ttc atc ccg aac tat gac ttc gac ccc cgc gaa ttt     240
Lys Arg Gly Gly Phe Ile Pro Asn Tyr Asp Phe Asp Pro Arg Glu Phe
65                  70                  75                  80 ggg ctc aac atg ttt caa atg gaa gac tct gat gcg aat cag aca ctt     288
Gly Leu Asn Met Phe Gln Met Glu Asp Ser Asp Ala Asn Gln Thr Leu
                85                  90                  95 acc ttg ctc aaa gtc aaa caa gct ctc gaa gat gca agc ata gag cct     336
Thr Leu Leu Lys Val Lys Gln Ala Leu Glu Asp Ala Ser Ile Glu Pro
                100                 105                 110
```

```
ttc acc aag gag aag aag aac att gga tgt gtt tta ggt att ggt ggg      384
Phe Thr Lys Glu Lys Lys Asn Ile Gly Cys Val Leu Gly Ile Gly Gly
            115                 120                 125 ggc caa aag gcg agt cat gag ttc tac tct cgt ctc aac tac gtt gtc      432
Gly Gln Lys Ala Ser His Glu Phe Tyr Ser Arg Leu Asn Tyr Val Val
        130                 135                 140 gtt gaa aag gta ctt cgg aaa atg ggt tta cca gat gct gat gtt gaa      480
Val Glu Lys Val Leu Arg Lys Met Gly Leu Pro Asp Ala Asp Val Glu
145                 150                 155                 160 gaa gct gtg gag aaa tac aag gca aat ttt ccc gag tgg cgc cta gac      528
Glu Ala Val Glu Lys Tyr Lys Ala Asn Phe Pro Glu Trp Arg Leu Asp
                165                 170                 175 tct ttc cct ggg ttt ctt ggg aat gta acg gct ggt cgg tgc agt aac      576
Ser Phe Pro Gly Phe Leu Gly Asn Val Thr Ala Gly Arg Cys Ser Asn
            180                 185                 190 acc ttc aac atg gaa ggt atg aac tgc gtt gtg gat gct gca tgt gcc      624
Thr Phe Asn Met Glu Gly Met Asn Cys Val Val Asp Ala Ala Cys Ala
        195                 200                 205 agt tct cta att gca atc aag gtt gca gtt gaa gag cta ctc ttt ggt      672
Ser Ser Leu Ile Ala Ile Lys Val Ala Val Glu Glu Leu Leu Phe Gly
    210                 215                 220 gac tgt gac acc atg att gca ggt gcc acc tgc acg gac aat tca ctt      720
Asp Cys Asp Thr Met Ile Ala Gly Ala Thr Cys Thr Asp Asn Ser Leu
225                 230                 235                 240 ggc atg tac atg gcc ttc tct aaa acg cca gtt ttt tct act gac cca      768
Gly Met Tyr Met Ala Phe Ser Lys Thr Pro Val Phe Ser Thr Asp Pro
                245                 250                 255 agt gtc cgc gcg tat gat gag aaa aca aaa ggg atg cta att gga gaa      816
Ser Val Arg Ala Tyr Asp Glu Lys Thr Lys Gly Met Leu Ile Gly Glu
            260                 265                 270 ggt tca gca atg ttc gtt ctt aaa cgc tat gcg gat gcc gta cgt gat      864
Gly Ser Ala Met Phe Val Leu Lys Arg Tyr Ala Asp Ala Val Arg Asp
        275                 280                 285 ggc gac aca att cac gcg gtt ctg cgt tct tgc tct tcg tct agt gat      912
Gly Asp Thr Ile His Ala Val Leu Arg Ser Cys Ser Ser Ser Ser Asp
    290                 295                 300 gga aaa gcg gca gga att tat act cct act ata tct gga caa gaa gaa      960
Gly Lys Ala Ala Gly Ile Tyr Thr Pro Thr Ile Ser Gly Gln Glu Glu
305                 310                 315                 320 gct ttg cgt cga gcg tat gcc cgt gcg ggg gta tgt cca tct acg atc     1008
Ala Leu Arg Arg Ala Tyr Ala Arg Ala Gly Val Cys Pro Ser Thr Ile
                325                 330                 335 ggg ctt gtt gag ggt cac ggg aca ggg acc cct gtt gga gat cgc att     1056
Gly Leu Val Glu Gly His Gly Thr Gly Thr Pro Val Gly Asp Arg Ile
            340                 345                 350 gag tta aca gct ctg cgg aac ttg ttt gac aaa gct ttt ggt agc aag     1104
Glu Leu Thr Ala Leu Arg Asn Leu Phe Asp Lys Ala Phe Gly Ser Lys
        355                 360                 365 aag gaa caa ata gca gtt ggc agc ata aag tct cag ata ggt cac ctg     1152
Lys Glu Gln Ile Ala Val Gly Ser Ile Lys Ser Gln Ile Gly His Leu
    370                 375                 380 aaa tct gtt gcc ggc ttt gcc ggc ttg gtc aaa gct gtg ctt gcg ctt     1200
Lys Ser Val Ala Gly Phe Ala Gly Leu Val Lys Ala Val Leu Ala Leu
385                 390                 395                 400 aaa cac aaa acg ctc cca ggt tcg att aat gtc gac cag cca cct ttg     1248
Lys His Lys Thr Leu Pro Gly Ser Ile Asn Val Asp Gln Pro Pro Leu
                405                 410                 415 ttg tat gac ggt act caa att caa gac tct tct tta tat atc aac aag     1296
Leu Tyr Asp Gly Thr Gln Ile Gln Asp Ser Ser Leu Tyr Ile Asn Lys
            420                 425                 430
```

```
aca aat aga cca tgg ttt acg caa aac aag ctt ccg cgt cgg gct ggt    1344
Thr Asn Arg Pro Trp Phe Thr Gln Asn Lys Leu Pro Arg Arg Ala Gly
        435                 440                 445 gtc tca agt ttt gga ttt gga ggt gca aac tac cac gcg gtt ctg gaa    1392
Val Ser Ser Phe Gly Phe Gly Gly Ala Asn Tyr His Ala Val Leu Glu
450                 455                 460 gaa ttc gag ccc gag cat gaa aaa cca tac cgc ctc aat act gtt gga    1440
Glu Phe Glu Pro Glu His Glu Lys Pro Tyr Arg Leu Asn Thr Val Gly
465                 470                 475                 480 cat cct gtc ctc ttg tac gct ccg tct gtg gaa gcc ctc aaa gta ctt    1488
His Pro Val Leu Leu Tyr Ala Pro Ser Val Glu Ala Leu Lys Val Leu
            485                 490                 495 tgc aac gac cag                                                    1500
Cys Asn Asp Gln
        500

<210> SEQ ID NO 41
<211> LENGTH: 500
<212> TYPE: PRT
<213> ORGANISM: Thraustochytrium sp.

<400> SEQUENCE: 41

Met Lys Asp Met Glu Asp Arg Arg Val Ala Ile Val Gly Met Ser Ala
1               5                   10                  15

His Leu Pro Cys Gly Thr Asp Val Lys Glu Ser Trp Gln Ala Ile Arg
            20                  25                  30

Asp Gly Ile Asp Cys Leu Ser Asp Leu Pro Ala Asp Arg Leu Asp Val
        35                  40                  45

Thr Ala Tyr Tyr Asn Pro Asn Lys Ala Thr Lys Asp Lys Ile Tyr Cys
    50                  55                  60

Lys Arg Gly Gly Phe Ile Pro Asn Tyr Asp Phe Asp Pro Arg Glu Phe
65                  70                  75                  80

Gly Leu Asn Met Phe Gln Met Glu Asp Ser Asp Ala Asn Gln Thr Leu
                85                  90                  95

Thr Leu Leu Lys Val Lys Gln Ala Leu Glu Asp Ala Ser Ile Glu Pro
            100                 105                 110

Phe Thr Lys Glu Lys Lys Asn Ile Gly Cys Val Leu Gly Ile Gly Gly
        115                 120                 125

Gly Gln Lys Ala Ser His Glu Phe Tyr Ser Arg Leu Asn Tyr Val Val
    130                 135                 140

Val Glu Lys Val Leu Arg Lys Met Gly Leu Pro Asp Ala Asp Val Glu
145                 150                 155                 160

Glu Ala Val Glu Lys Tyr Lys Ala Asn Phe Pro Glu Trp Arg Leu Asp
                165                 170                 175

Ser Phe Pro Gly Phe Leu Gly Asn Val Thr Ala Gly Arg Cys Ser Asn
            180                 185                 190

Thr Phe Asn Met Glu Gly Met Asn Cys Val Val Asp Ala Ala Cys Ala
        195                 200                 205

Ser Ser Leu Ile Ala Ile Lys Val Ala Val Glu Glu Leu Leu Phe Gly
    210                 215                 220

Asp Cys Asp Thr Met Ile Ala Gly Ala Thr Cys Thr Asp Asn Ser Leu
225                 230                 235                 240

Gly Met Tyr Met Ala Phe Ser Lys Thr Pro Val Phe Ser Thr Asp Pro
                245                 250                 255

Ser Val Arg Ala Tyr Asp Glu Lys Thr Lys Gly Met Leu Ile Gly Glu
            260                 265                 270
```

```
Gly Ser Ala Met Phe Val Leu Lys Arg Tyr Ala Asp Ala Val Arg Asp
            275                 280                 285

Gly Asp Thr Ile His Ala Val Leu Arg Ser Cys Ser Ser Ser Ser Asp
        290                 295                 300

Gly Lys Ala Ala Gly Ile Tyr Thr Pro Thr Ile Ser Gly Gln Glu Glu
305                 310                 315                 320

Ala Leu Arg Arg Ala Tyr Ala Arg Ala Gly Val Cys Pro Ser Thr Ile
                325                 330                 335

Gly Leu Val Glu Gly His Gly Thr Gly Thr Pro Val Gly Asp Arg Ile
            340                 345                 350

Glu Leu Thr Ala Leu Arg Asn Leu Phe Asp Lys Ala Phe Gly Ser Lys
        355                 360                 365

Lys Glu Gln Ile Ala Val Gly Ser Ile Lys Ser Gln Ile Gly His Leu
    370                 375                 380

Lys Ser Val Ala Gly Phe Ala Gly Leu Val Lys Ala Val Leu Ala Leu
385                 390                 395                 400

Lys His Lys Thr Leu Pro Gly Ser Ile Asn Val Asp Gln Pro Pro Leu
                405                 410                 415

Leu Tyr Asp Gly Thr Gln Ile Gln Asp Ser Ser Leu Tyr Ile Asn Lys
            420                 425                 430

Thr Asn Arg Pro Trp Phe Thr Gln Asn Lys Leu Pro Arg Arg Ala Gly
        435                 440                 445

Val Ser Ser Phe Gly Phe Gly Gly Ala Asn Tyr His Ala Val Leu Glu
    450                 455                 460

Glu Phe Glu Pro Glu His Glu Lys Pro Tyr Arg Leu Asn Thr Val Gly
465                 470                 475                 480

His Pro Val Leu Leu Tyr Ala Pro Ser Val Glu Ala Leu Lys Val Leu
                485                 490                 495

Cys Asn Asp Gln
            500

<210> SEQ ID NO 42
<211> LENGTH: 1500
<212> TYPE: DNA
<213> ORGANISM: Thraustochytrium sp.
<220> FEATURE:
<221> NAME/KEY: CDS
<222> LOCATION: (1)..(1500)

<400> SEQUENCE: 42 ctt gcg gag ctc aca att gca ttg gaa gag gca aaa aca cat aaa aat    48
Leu Ala Glu Leu Thr Ile Ala Leu Glu Glu Ala Lys Thr His Lys Asn
1               5                   10                  15 gtt gac aaa gtt tgt ggc tac aag ttt att gac gaa ttt cag ctc caa    96
Val Asp Lys Val Cys Gly Tyr Lys Phe Ile Asp Glu Phe Gln Leu Gln
            20                  25                  30 gga agc tgt cct cca gaa aat ccg aga gta gga ttt tta gca aca ctg   144
Gly Ser Cys Pro Pro Glu Asn Pro Arg Val Gly Phe Leu Ala Thr Leu
        35                  40                  45 cct act tca aat atc att gtc gcg ctt aag gca att ctc gcg cag ctt   192
Pro Thr Ser Asn Ile Ile Val Ala Leu Lys Ala Ile Leu Ala Gln Leu
    50                  55                  60 gat gca aaa cca gat gcg aag aaa tgg gat ttg cct cat aaa aag gct   240
Asp Ala Lys Pro Asp Ala Lys Lys Trp Asp Leu Pro His Lys Lys Ala
65                  70                  75                  80 ttt ggg gct acc ttc gca tcg tct tca gtg aaa ggc tct gtt gct gcg   288
Phe Gly Ala Thr Phe Ala Ser Ser Ser Val Lys Gly Ser Val Ala Ala
```

-continued

```
              85                  90                  95
ctc ttc gca gga cag ggt acc cag tac tta aac atg ttc tct gat gtg    336
Leu Phe Ala Gly Gln Gly Thr Gln Tyr Leu Asn Met Phe Ser Asp Val
            100                 105                 110 gca atg aac tgg cca ccg ttc cgt gac agc att gtc gca atg gaa gaa    384
Ala Met Asn Trp Pro Pro Phe Arg Asp Ser Ile Val Ala Met Glu Glu
                115                 120                 125 gct caa act gag gta ttt gag ggc caa gtt gaa cca att agc aaa gtt    432
Ala Gln Thr Glu Val Phe Glu Gly Gln Val Glu Pro Ile Ser Lys Val
130                 135                 140 ctg ttt cca cga gag cgc tat gca tcc gaa agt gaa cag ggg aat gaa    480
Leu Phe Pro Arg Glu Arg Tyr Ala Ser Glu Ser Glu Gln Gly Asn Glu
            145                 150                 155                 160 ctt ctt tgc tta aca gag tac tct cag cca act acg ata gca gcc gca    528
Leu Leu Cys Leu Thr Glu Tyr Ser Gln Pro Thr Thr Ile Ala Ala Ala
                165                 170                 175 gta ggg gcc ttc gat att ttc aaa gcg gct ggc ttt aag cca gac atg    576
Val Gly Ala Phe Asp Ile Phe Lys Ala Ala Gly Phe Lys Pro Asp Met
                180                 185                 190 gtt gga ggg cat tca ctt ggc gaa ttt gct gct ttg tac gcg gct ggg    624
Val Gly Gly His Ser Leu Gly Glu Phe Ala Ala Leu Tyr Ala Ala Gly
            195                 200                 205 tcc att tcg cgt gac gac ctg tac aag ctt gtg tgc aaa cgg gca aag    672
Ser Ile Ser Arg Asp Asp Leu Tyr Lys Leu Val Cys Lys Arg Ala Lys
            210                 215                 220 gca atg gcg aac gct agt gac gga gct atg gca gca gtg att ggc cca    720
Ala Met Ala Asn Ala Ser Asp Gly Ala Met Ala Ala Val Ile Gly Pro
225                 230                 235                 240 gat gca cgt cta gtt acg cca caa aat agt gac gtt tat gtc gca aac    768
Asp Ala Arg Leu Val Thr Pro Gln Asn Ser Asp Val Tyr Val Ala Asn
                245                 250                 255 ttc aac tcc gca act caa gta gtc atc agt ggc act gtt caa ggt gtg    816
Phe Asn Ser Ala Thr Gln Val Val Ile Ser Gly Thr Val Gln Gly Val
                260                 265                 270 aaa gaa gag tcg aaa ttg ctc att tca aag ggg ttc cgc gta ctg cca    864
Lys Glu Glu Ser Lys Leu Leu Ile Ser Lys Gly Phe Arg Val Leu Pro
            275                 280                 285 ctt aaa tgc cag ggc gcc ttc cat tct cct ttg atg ggg cct tct gag    912
Leu Lys Cys Gln Gly Ala Phe His Ser Pro Leu Met Gly Pro Ser Glu
            290                 295                 300 gat agt ttc aaa tca ctt gtg gag act tgt acc atc tcg ccg cca aaa    960
Asp Ser Phe Lys Ser Leu Val Glu Thr Cys Thr Ile Ser Pro Pro Lys
305                 310                 315                 320 aat gtg aaa ttc ttt tgc aat gtt agt ggc aag gaa agc cca aac cca   1008
Asn Val Lys Phe Phe Cys Asn Val Ser Gly Lys Glu Ser Pro Asn Pro
                325                 330                 335 aaa cag acc ctc aag tca cac atg acg tct agc gtt cag ttc gag gag   1056
Lys Gln Thr Leu Lys Ser His Met Thr Ser Ser Val Gln Phe Glu Glu
            340                 345                 350 cag att cgt aac atg tac gat gcc gga gca cgt gtt ttt ctg gag ttt   1104
Gln Ile Arg Asn Met Tyr Asp Ala Gly Ala Arg Val Phe Leu Glu Phe
            355                 360                 365 gga ccc cgc caa gtc ctt gca aag ctt atc gcg gaa atg ttt ccc tcg   1152
Gly Pro Arg Gln Val Leu Ala Lys Leu Ile Ala Glu Met Phe Pro Ser
        370                 375                 380 tgt aca gct atc agc gtt aac ccc gcg agc agt ggt gac agt gac gtg   1200
Cys Thr Ala Ile Ser Val Asn Pro Ala Ser Ser Gly Asp Ser Asp Val
385                 390                 395                 400 caa ctc cgc ctc gcc gcc gta aaa ttc gcg gtc tcg ggt gca gcc ctt   1248
```

```
Gln Leu Arg Leu Ala Ala Val Lys Phe Ala Val Ser Gly Ala Ala Leu
            405                 410                 415 agc acc ttt gat cca tgg gag tat cgc aag cca caa gat ctt ctt att      1296
Ser Thr Phe Asp Pro Trp Glu Tyr Arg Lys Pro Gln Asp Leu Leu Ile
        420                 425                 430 cga aaa cca cga aaa act gcc ctt gtt cta tca gca gca aca tat gtt      1344
Arg Lys Pro Arg Lys Thr Ala Leu Val Leu Ser Ala Ala Thr Tyr Val
        435                 440                 445 tcc cca aag act ctt gca gaa cgt aaa aag gct atg gaa gat atc aag      1392
Ser Pro Lys Thr Leu Ala Glu Arg Lys Lys Ala Met Glu Asp Ile Lys
450                 455                 460 cta gta tcc att aca cca aga gat agt atg gta tca att gga aaa atc      1440
Leu Val Ser Ile Thr Pro Arg Asp Ser Met Val Ser Ile Gly Lys Ile
465                 470                 475                 480 gcg caa gaa gta cgg aca gct aaa cag cct tta gaa acc gaa att cga      1488
Ala Gln Glu Val Arg Thr Ala Lys Gln Pro Leu Glu Thr Glu Ile Arg
                485                 490                 495 aga ctc aac aaa                                                       1500
Arg Leu Asn Lys
500
```

<210> SEQ ID NO 43
<211> LENGTH: 500
<212> TYPE: PRT
<213> ORGANISM: Thraustochytrium sp.

<400> SEQUENCE: 43

```
Leu Ala Glu Leu Thr Ile Ala Leu Glu Glu Ala Lys Thr His Lys Asn
1               5                   10                  15

Val Asp Lys Val Cys Gly Tyr Lys Phe Ile Asp Glu Phe Gln Leu Gln
            20                  25                  30

Gly Ser Cys Pro Pro Glu Asn Pro Arg Val Gly Phe Leu Ala Thr Leu
        35                  40                  45

Pro Thr Ser Asn Ile Ile Val Ala Leu Lys Ala Ile Leu Ala Gln Leu
    50                  55                  60

Asp Ala Lys Pro Asp Ala Lys Lys Trp Asp Leu Pro His Lys Lys Ala
65                  70                  75                  80

Phe Gly Ala Thr Phe Ala Ser Ser Val Lys Gly Ser Val Ala Ala
                85                  90                  95

Leu Phe Ala Gly Gln Gly Thr Gln Tyr Leu Asn Met Phe Ser Asp Val
            100                 105                 110

Ala Met Asn Trp Pro Pro Phe Arg Asp Ser Ile Val Ala Met Glu Glu
        115                 120                 125

Ala Gln Thr Glu Val Phe Glu Gly Gln Val Glu Pro Ile Ser Lys Val
    130                 135                 140

Leu Phe Pro Arg Glu Arg Tyr Ala Ser Glu Ser Glu Gln Gly Asn Glu
145                 150                 155                 160

Leu Leu Cys Leu Thr Glu Tyr Ser Gln Pro Thr Thr Ile Ala Ala Ala
                165                 170                 175

Val Gly Ala Phe Asp Ile Phe Lys Ala Ala Gly Phe Lys Pro Asp Met
            180                 185                 190

Val Gly Gly His Ser Leu Gly Glu Phe Ala Ala Leu Tyr Ala Ala Gly
        195                 200                 205

Ser Ile Ser Arg Asp Asp Leu Tyr Lys Leu Val Cys Lys Arg Ala Lys
    210                 215                 220

Ala Met Ala Asn Ala Ser Asp Gly Ala Met Ala Ala Val Ile Gly Pro
225                 230                 235                 240
```

```
Asp Ala Arg Leu Val Thr Pro Gln Asn Ser Asp Val Tyr Val Ala Asn
                245                 250                 255

Phe Asn Ser Ala Thr Gln Val Val Ile Ser Gly Thr Val Gln Gly Val
                260                 265                 270

Lys Glu Glu Ser Lys Leu Leu Ile Ser Lys Gly Phe Arg Val Leu Pro
                275                 280                 285

Leu Lys Cys Gln Gly Ala Phe His Ser Pro Leu Met Gly Pro Ser Glu
                290                 295                 300

Asp Ser Phe Lys Ser Leu Val Glu Thr Cys Thr Ile Ser Pro Pro Lys
305                 310                 315                 320

Asn Val Lys Phe Phe Cys Asn Val Ser Gly Lys Glu Ser Pro Asn Pro
                325                 330                 335

Lys Gln Thr Leu Lys Ser His Met Thr Ser Ser Val Gln Phe Glu Glu
                340                 345                 350

Gln Ile Arg Asn Met Tyr Asp Ala Gly Ala Arg Val Phe Leu Glu Phe
                355                 360                 365

Gly Pro Arg Gln Val Leu Ala Lys Leu Ile Ala Glu Met Phe Pro Ser
            370                 375                 380

Cys Thr Ala Ile Ser Val Asn Pro Ala Ser Ser Gly Asp Ser Asp Val
385                 390                 395                 400

Gln Leu Arg Leu Ala Ala Val Lys Phe Ala Val Ser Gly Ala Ala Leu
                405                 410                 415

Ser Thr Phe Asp Pro Trp Glu Tyr Arg Lys Pro Gln Asp Leu Leu Ile
                420                 425                 430

Arg Lys Pro Arg Lys Thr Ala Leu Val Leu Ser Ala Ala Thr Tyr Val
                435                 440                 445

Ser Pro Lys Thr Leu Ala Glu Arg Lys Lys Ala Met Glu Asp Ile Lys
            450                 455                 460

Leu Val Ser Ile Thr Pro Arg Asp Ser Met Val Ser Ile Gly Lys Ile
465                 470                 475                 480

Ala Gln Glu Val Arg Thr Ala Lys Gln Pro Leu Glu Thr Glu Ile Arg
                485                 490                 495

Arg Leu Asn Lys
            500

<210> SEQ ID NO 44
<211> LENGTH: 351
<212> TYPE: DNA
<213> ORGANISM: Thraustochytrium sp.
<220> FEATURE:
<221> NAME/KEY: CDS
<222> LOCATION: (1)..(351)

<400> SEQUENCE: 44 tcg acc cca gcg tca gag cgg tcg gct tca ccg ctt ttc gag aaa cgc        48
Ser Thr Pro Ala Ser Glu Arg Ser Ala Ser Pro Leu Phe Glu Lys Arg
1               5                   10                  15 agt tcg gtt tcg tca gca cgc ctc gct gaa gct gaa gcc gcg gta ctg       96
Ser Ser Val Ser Ser Ala Arg Leu Ala Glu Ala Glu Ala Ala Val Leu
                20                  25                  30 agc gtt ctc gca gac aag aca ggc tac gac agc tca atg atc gag atg      144
Ser Val Leu Ala Asp Lys Thr Gly Tyr Asp Ser Ser Met Ile Glu Met
            35                  40                  45 gac atg gac ctg gag agt gag ctt ggc gtt gat agc atc aaa cgc gtg      192
Asp Met Asp Leu Glu Ser Glu Leu Gly Val Asp Ser Ile Lys Arg Val
50                  55                  60
```

```
gag atc atg agc gag gtt caa acg ctg ctc agc gtg gaa gtc tcc gac    240
Glu Ile Met Ser Glu Val Gln Thr Leu Leu Ser Val Glu Val Ser Asp
 65              70                  75                  80 gtt gac gct ctg tca aga acc aag act gtt ggc gac gtc atc gag gcg    288
Val Asp Ala Leu Ser Arg Thr Lys Thr Val Gly Asp Val Ile Glu Ala
                 85                  90                  95 atg aag ctg gaa ctc ggt gga ccc caa ggc cag act ttg acc gcg gaa    336
Met Lys Leu Glu Leu Gly Gly Pro Gln Gly Gln Thr Leu Thr Ala Glu
            100                 105                 110 tcg atc cgt cag cca                                                351
Ser Ile Arg Gln Pro
        115

<210> SEQ ID NO 45
<211> LENGTH: 117
<212> TYPE: PRT
<213> ORGANISM: Thraustochytrium sp.

<400> SEQUENCE: 45

Ser Thr Pro Ala Ser Glu Arg Ser Ala Ser Pro Leu Phe Glu Lys Arg
 1               5                  10                  15

Ser Ser Val Ser Ser Ala Arg Leu Ala Glu Ala Glu Ala Ala Val Leu
            20                  25                  30

Ser Val Leu Ala Asp Lys Thr Gly Tyr Asp Ser Ser Met Ile Glu Met
        35                  40                  45

Asp Met Asp Leu Glu Ser Glu Leu Gly Val Asp Ser Ile Lys Arg Val
 50                  55                  60

Glu Ile Met Ser Glu Val Gln Thr Leu Leu Ser Val Glu Val Ser Asp
 65              70                  75                  80

Val Asp Ala Leu Ser Arg Thr Lys Thr Val Gly Asp Val Ile Glu Ala
                 85                  90                  95

Met Lys Leu Glu Leu Gly Gly Pro Gln Gly Gln Thr Leu Thr Ala Glu
            100                 105                 110

Ser Ile Arg Gln Pro
        115

<210> SEQ ID NO 46
<211> LENGTH: 5
<212> TYPE: PRT
<213> ORGANISM: Thraustochytrium sp.
<220> FEATURE:
<221> NAME/KEY: MISC_FEATURE
<222> LOCATION: (1)..(5)
<223> OTHER INFORMATION: Xaa = any amino acid

<400> SEQUENCE: 46

Leu Gly Xaa Asp Ser
 1               5

<210> SEQ ID NO 47
<211> LENGTH: 2790
<212> TYPE: DNA
<213> ORGANISM: Thraustochytrium sp.
<220> FEATURE:
<221> NAME/KEY: CDS
<222> LOCATION: (1)..(2790)

<400> SEQUENCE: 47 tcg acc cca gcg tca gag cgg tcg gct tca ccg ctt ttc gag aaa cgc     48
Ser Thr Pro Ala Ser Glu Arg Ser Ala Ser Pro Leu Phe Glu Lys Arg
 1               5                  10                  15 agt tcg gtt tcg tca gca cgc ctc gct gaa gct gaa gcc gcg gta ctg     96
```

```
                Ser Ser Val Ser Ser Ala Arg Leu Ala Glu Ala Glu Ala Ala Val Leu
                        20                  25                  30 agc gtt ctc gca gac aag aca ggc tac gac agc tca atg atc gag atg       144
Ser Val Leu Ala Asp Lys Thr Gly Tyr Asp Ser Ser Met Ile Glu Met
         35                  40                  45 gac atg gac ctg gag agt gag ctt ggc gtt gat agc atc aaa cgc gtg       192
Asp Met Asp Leu Glu Ser Glu Leu Gly Val Asp Ser Ile Lys Arg Val
 50                  55                  60 gag atc atg agc gag gtt caa acg ctg ctc agc gtg gaa gtc tcc gac       240
Glu Ile Met Ser Glu Val Gln Thr Leu Leu Ser Val Glu Val Ser Asp
 65                  70                  75                  80 gtt gac gct ctg tca aga acc aag act gtt ggc gac gtc atc gag gcg       288
Val Asp Ala Leu Ser Arg Thr Lys Thr Val Gly Asp Val Ile Glu Ala
                 85                  90                  95 atg aag ctg gaa ctc ggt gga ccc caa ggc cag act ttg acc gcg gaa       336
Met Lys Leu Glu Leu Gly Gly Pro Gln Gly Gln Thr Leu Thr Ala Glu
            100                 105                 110 tcg atc cgt cag cca ccg gtg tcc gag cct gct gta ccg acc tca tcg       384
Ser Ile Arg Gln Pro Pro Val Ser Glu Pro Ala Val Pro Thr Ser Ser
        115                 120                 125 tca agc agt att gct aat gtt tcg tca gca cgc ctc gct gaa gct gaa       432
Ser Ser Ser Ile Ala Asn Val Ser Ser Ala Arg Leu Ala Glu Ala Glu
130                 135                 140 gct gcg gta ctg agc gtt ctc gca gac aag aca ggc tac gac agc tca       480
Ala Ala Val Leu Ser Val Leu Ala Asp Lys Thr Gly Tyr Asp Ser Ser
145                 150                 155                 160 atg atc gag atg gac atg gac ctg gag agc gag ctt ggc gtt gat agc       528
Met Ile Glu Met Asp Met Asp Leu Glu Ser Glu Leu Gly Val Asp Ser
                165                 170                 175 atc aaa cgc gtg gag atc atg agc gag gtt caa acg ctg ctc agc gtg       576
Ile Lys Arg Val Glu Ile Met Ser Glu Val Gln Thr Leu Leu Ser Val
            180                 185                 190 gaa gtc tcc gac gtt gac gct ctg tca aga act aag act gtt ggc gac       624
Glu Val Ser Asp Val Asp Ala Leu Ser Arg Thr Lys Thr Val Gly Asp
        195                 200                 205 gtc atc gag gcg atg aag ctg gaa ctc ggt gga ccc caa ggc cag act       672
Val Ile Glu Ala Met Lys Leu Glu Leu Gly Gly Pro Gln Gly Gln Thr
    210                 215                 220 ttg acc gcg gaa tcg atc cgt cag cca ccg gtg tct gag cct gct gta       720
Leu Thr Ala Glu Ser Ile Arg Gln Pro Pro Val Ser Glu Pro Ala Val
225                 230                 235                 240 ccg acc tca tcg tca agc agt att gct aat gtt tcg tca gca cgc ctc       768
Pro Thr Ser Ser Ser Ser Ile Ala Asn Val Ser Ser Ala Arg Leu
                245                 250                 255 gct gaa gct gaa gcg gcg gta ctg agc gtt ctc gca gac aag aca ggc       816
Ala Glu Ala Glu Ala Ala Val Leu Ser Val Leu Ala Asp Lys Thr Gly
            260                 265                 270 tac gac agc tca atg atc gag atg gac atg gac ctg gag agc gag ctt       864
Tyr Asp Ser Ser Met Ile Glu Met Asp Met Asp Leu Glu Ser Glu Leu
        275                 280                 285 ggc gtc gac agc atc aaa cgc gtg gag atc atg agc gag gtt caa acg       912
Gly Val Asp Ser Ile Lys Arg Val Glu Ile Met Ser Glu Val Gln Thr
290                 295                 300 ctg ctc agc gtg gaa gtc tcc gac gtt gac gct ctg tca aga acc aag       960
Leu Leu Ser Val Glu Val Ser Asp Val Asp Ala Leu Ser Arg Thr Lys
305                 310                 315                 320 act gtt ggc gac gtc atc gag gcg atg aag ctg gaa ctc ggt gga ccc      1008
Thr Val Gly Asp Val Ile Glu Ala Met Lys Leu Glu Leu Gly Gly Pro
                325                 330                 335
```

-continued

```
caa ggc cag act ttg acc gcg gaa tcg atc cgt cag cca ccg gtg tcc    1056
Gln Gly Gln Thr Leu Thr Ala Glu Ser Ile Arg Gln Pro Pro Val Ser
            340                 345                 350 gag cct gct gta ccg acc tca tcg tca agc agt att gct aat gtt ttg    1104
Glu Pro Ala Val Pro Thr Ser Ser Ser Ser Ser Ile Ala Asn Val Leu
        355                 360                 365 tca gca cgc ctc gct gaa gct gaa gcc gcg gta ctg agc gtt ctc gca    1152
Ser Ala Arg Leu Ala Glu Ala Glu Ala Ala Val Leu Ser Val Leu Ala
    370                 375                 380 gac aag aca ggc tac gac agc tca atg atc gag atg gac atg gac ctg    1200
Asp Lys Thr Gly Tyr Asp Ser Ser Met Ile Glu Met Asp Met Asp Leu
385                 390                 395                 400 gag agc gag ctt ggc gtt gat agc atc aaa cgc gtg gag atc atg agc    1248
Glu Ser Glu Leu Gly Val Asp Ser Ile Lys Arg Val Glu Ile Met Ser
            405                 410                 415 gag gtt caa acg ttg ctc agc gtg gaa gtc tcc gac gtt gac gct ctg    1296
Glu Val Gln Thr Leu Leu Ser Val Glu Val Ser Asp Val Asp Ala Leu
        420                 425                 430 tca aga acc aag act gtt ggc gac gtc atc gag gcg atg aag ctg gaa    1344
Ser Arg Thr Lys Thr Val Gly Asp Val Ile Glu Ala Met Lys Leu Glu
    435                 440                 445 ctc ggt gga ccc caa ggc cag act ttg acc gcg gaa tcg atc cgt cag    1392
Leu Gly Gly Pro Gln Gly Gln Thr Leu Thr Ala Glu Ser Ile Arg Gln
450                 455                 460 cca ccg gtg tct gag cct gct gta ccg acc tca tcg tca agc agt att    1440
Pro Pro Val Ser Glu Pro Ala Val Pro Thr Ser Ser Ser Ser Ser Ile
465                 470                 475                 480 gct aat gtt tcg tca gca cgc ctc gct gaa gct gaa gcc gcg gta ctg    1488
Ala Asn Val Ser Ser Ala Arg Leu Ala Glu Ala Glu Ala Ala Val Leu
            485                 490                 495 agc gtt ctc gca gac aag aca ggc tac gac agc tca atg atc gag atg    1536
Ser Val Leu Ala Asp Lys Thr Gly Tyr Asp Ser Ser Met Ile Glu Met
        500                 505                 510 gac atg gac ctg gag agt gag ctt ggc gtc gac agc atc aaa cgc gtg    1584
Asp Met Asp Leu Glu Ser Glu Leu Gly Val Asp Ser Ile Lys Arg Val
    515                 520                 525 gag atc atg agc gag gtt caa acg ctg ctc agc gtg gaa gtc tcc gac    1632
Glu Ile Met Ser Glu Val Gln Thr Leu Leu Ser Val Glu Val Ser Asp
530                 535                 540 gtt gac gct ctg tca aga acc aag act gtt ggc gac gtc atc gag gcg    1680
Val Asp Ala Leu Ser Arg Thr Lys Thr Val Gly Asp Val Ile Glu Ala
545                 550                 555                 560 atg aag ctg gaa ctc ggt gga ccc caa ggc cag act ttg acc tct gaa    1728
Met Lys Leu Glu Leu Gly Gly Pro Gln Gly Gln Thr Leu Thr Ser Glu
            565                 570                 575 ccg atc cat cag cca cca gtg tcc gag cct gct gta ccg acc tca tcg    1776
Pro Ile His Gln Pro Pro Val Ser Glu Pro Ala Val Pro Thr Ser Ser
        580                 585                 590 tca agc agt att gct aat gtt tct tca gca cgc ctc gct gaa gct gaa    1824
Ser Ser Ser Ile Ala Asn Val Ser Ser Ala Arg Leu Ala Glu Ala Glu
    595                 600                 605 gcc gcg gta ctg agc gtt ctc gca gac aag aca ggc tac gac agc tca    1872
Ala Ala Val Leu Ser Val Leu Ala Asp Lys Thr Gly Tyr Asp Ser Ser
610                 615                 620 atg atc gag atg gac atg gac ctg gag agc gag ctt ggc gtt gat agc    1920
Met Ile Glu Met Asp Met Asp Leu Glu Ser Glu Leu Gly Val Asp Ser
625                 630                 635                 640 atc aaa cgc gtg gaa atc atg agc gag gtt caa acg ctg ctc agc gtg    1968
Ile Lys Arg Val Glu Ile Met Ser Glu Val Gln Thr Leu Leu Ser Val
            645                 650                 655
```

```
gaa gtc tcc gac gtt gac gct ctg tca aga acc aag act gtt ggc gac    2016
Glu Val Ser Asp Val Asp Ala Leu Ser Arg Thr Lys Thr Val Gly Asp
        660                 665                 670 gtc atc gag gcg atg aag atg gaa ctc ggt gga ccc caa ggc cag act    2064
Val Ile Glu Ala Met Lys Met Glu Leu Gly Gly Pro Gln Gly Gln Thr
    675                 680                 685 ttg acc gcg gaa tcg atc cgt cag cca ccg gtg tct gag cct gct gta    2112
Leu Thr Ala Glu Ser Ile Arg Gln Pro Pro Val Ser Glu Pro Ala Val
690                 695                 700 ccg acc tca tcg tca agc agt att gct aat gtt tcg tca gca cgc ctc    2160
Pro Thr Ser Ser Ser Ser Ile Ala Asn Val Ser Ser Ala Arg Leu
705                 710                 715                 720 gct gaa gct gaa gcg gcg gta ctg agc gtt ctc gca gac aag aca ggc    2208
Ala Glu Ala Glu Ala Ala Val Leu Ser Val Leu Ala Asp Lys Thr Gly
                725                 730                 735 tac gac agc tca atg atc gag atg gac atg gac ctg gag agc gag ctt    2256
Tyr Asp Ser Ser Met Ile Glu Met Asp Met Asp Leu Glu Ser Glu Leu
            740                 745                 750 ggc gtt gat agc atc aaa cgc gtg gag atc atg agc gag gtt caa gcg    2304
Gly Val Asp Ser Ile Lys Arg Val Glu Ile Met Ser Glu Val Gln Ala
        755                 760                 765 ctg ctc agc gtg gaa gtc tcc gac gtt gac gct ctg tca aga acc aag    2352
Leu Leu Ser Val Glu Val Ser Asp Val Asp Ala Leu Ser Arg Thr Lys
770                 775                 780 act gtt ggc gac gtc atc gag gcg atg aag atg gaa ctc ggt gga ccc    2400
Thr Val Gly Asp Val Ile Glu Ala Met Lys Met Glu Leu Gly Gly Pro
785                 790                 795                 800 caa ggc cag act ttg acc gca gaa tcg atc cgt gag cca ccg gtg tct    2448
Gln Gly Gln Thr Leu Thr Ala Glu Ser Ile Arg Glu Pro Pro Val Ser
                805                 810                 815 gag cct gct gta ccg acc tca tcg tca agt agt atc gct aat gtt tct    2496
Glu Pro Ala Val Pro Thr Ser Ser Ser Ser Ile Ala Asn Val Ser
            820                 825                 830 tca gct cgc ctc gct gaa gct gaa gcc gcg gta ctg agc gtt ctc gca    2544
Ser Ala Arg Leu Ala Glu Ala Glu Ala Ala Val Leu Ser Val Leu Ala
        835                 840                 845 gac aag aca ggc tac gac agc tca atg atc gag atg gac atg gac ctg    2592
Asp Lys Thr Gly Tyr Asp Ser Ser Met Ile Glu Met Asp Met Asp Leu
850                 855                 860 gag agt gag ctt ggc gtc gac agc atc aaa cgc gtg gag atc atg agc    2640
Glu Ser Glu Leu Gly Val Asp Ser Ile Lys Arg Val Glu Ile Met Ser
865                 870                 875                 880 gag gtt caa acg ttg ctc agc gtg gaa gtc tcc gac gtt gac gct ctg    2688
Glu Val Gln Thr Leu Leu Ser Val Glu Val Ser Asp Val Asp Ala Leu
                885                 890                 895 tca aga acc aag act gtt ggc gac gtc atc gag gcg atg aag ctg gaa    2736
Ser Arg Thr Lys Thr Val Gly Asp Val Ile Glu Ala Met Lys Leu Glu
            900                 905                 910 ctt ggg gaa tca tca agt att gag act ctc aat tgt acc gag gtt gag    2784
Leu Gly Glu Ser Ser Ser Ile Glu Thr Leu Asn Cys Thr Glu Val Glu
        915                 920                 925 cac acg                                                             2790
His Thr
930

<210> SEQ ID NO 48
<211> LENGTH: 930
<212> TYPE: PRT
<213> ORGANISM: Thraustochytrium sp.
```

```
<400> SEQUENCE: 48

Ser Thr Pro Ala Ser Glu Arg Ser Ala Ser Pro Leu Phe Glu Lys Arg
1               5                   10                  15

Ser Ser Val Ser Ser Ala Arg Leu Ala Glu Ala Glu Ala Ala Val Leu
            20                  25                  30

Ser Val Leu Ala Asp Lys Thr Gly Tyr Asp Ser Ser Met Ile Glu Met
        35                  40                  45

Asp Met Asp Leu Glu Ser Glu Leu Gly Val Asp Ser Ile Lys Arg Val
    50                  55                  60

Glu Ile Met Ser Glu Val Gln Thr Leu Leu Ser Val Glu Val Ser Asp
65                  70                  75                  80

Val Asp Ala Leu Ser Arg Thr Lys Thr Val Gly Asp Val Ile Glu Ala
                85                  90                  95

Met Lys Leu Glu Leu Gly Gly Pro Gln Gly Gln Thr Leu Thr Ala Glu
            100                 105                 110

Ser Ile Arg Gln Pro Pro Val Ser Glu Pro Ala Val Pro Thr Ser Ser
        115                 120                 125

Ser Ser Ser Ile Ala Asn Val Ser Ser Ala Arg Leu Ala Glu Ala Glu
    130                 135                 140

Ala Ala Val Leu Ser Val Leu Ala Asp Lys Thr Gly Tyr Asp Ser Ser
145                 150                 155                 160

Met Ile Glu Met Asp Met Asp Leu Glu Ser Glu Leu Gly Val Asp Ser
                165                 170                 175

Ile Lys Arg Val Glu Ile Met Ser Glu Val Gln Thr Leu Leu Ser Val
            180                 185                 190

Glu Val Ser Asp Val Asp Ala Leu Ser Arg Thr Lys Thr Val Gly Asp
        195                 200                 205

Val Ile Glu Ala Met Lys Leu Glu Leu Gly Gly Pro Gln Gly Gln Thr
    210                 215                 220

Leu Thr Ala Glu Ser Ile Arg Gln Pro Pro Val Ser Glu Pro Ala Val
225                 230                 235                 240

Pro Thr Ser Ser Ser Ser Ser Ile Ala Asn Val Ser Ser Ala Arg Leu
                245                 250                 255

Ala Glu Ala Glu Ala Ala Val Leu Ser Val Leu Ala Asp Lys Thr Gly
            260                 265                 270

Tyr Asp Ser Ser Met Ile Glu Met Asp Met Asp Leu Glu Ser Glu Leu
        275                 280                 285

Gly Val Asp Ser Ile Lys Arg Val Glu Ile Met Ser Glu Val Gln Thr
    290                 295                 300

Leu Leu Ser Val Glu Val Ser Asp Val Asp Ala Leu Ser Arg Thr Lys
305                 310                 315                 320

Thr Val Gly Asp Val Ile Glu Ala Met Lys Leu Glu Leu Gly Gly Pro
                325                 330                 335

Gln Gly Gln Thr Leu Thr Ala Glu Ser Ile Arg Gln Pro Pro Val Ser
            340                 345                 350

Glu Pro Ala Val Pro Thr Ser Ser Ser Ser Ser Ile Ala Asn Val Leu
        355                 360                 365

Ser Ala Arg Leu Ala Glu Ala Glu Ala Ala Val Leu Ser Val Leu Ala
    370                 375                 380

Asp Lys Thr Gly Tyr Asp Ser Ser Met Ile Glu Met Asp Met Asp Leu
385                 390                 395                 400

Glu Ser Glu Leu Gly Val Asp Ser Ile Lys Arg Val Glu Ile Met Ser
                405                 410                 415
```

-continued

```
Glu Val Gln Thr Leu Leu Ser Val Glu Val Ser Asp Val Asp Ala Leu
            420                 425                 430
Ser Arg Thr Lys Thr Val Gly Asp Val Ile Glu Ala Met Lys Leu Glu
            435                 440                 445
Leu Gly Gly Pro Gln Gly Gln Thr Leu Thr Ala Glu Ser Ile Arg Gln
            450                 455                 460
Pro Pro Val Ser Glu Pro Ala Val Pro Thr Ser Ser Ser Ser Ser Ile
465                 470                 475                 480
Ala Asn Val Ser Ser Ala Arg Leu Ala Glu Ala Glu Ala Ala Val Leu
            485                 490                 495
Ser Val Leu Ala Asp Lys Thr Gly Tyr Asp Ser Ser Met Ile Glu Met
            500                 505                 510
Asp Met Asp Leu Glu Ser Glu Leu Gly Val Asp Ser Ile Lys Arg Val
            515                 520                 525
Glu Ile Met Ser Glu Val Gln Thr Leu Leu Ser Val Glu Val Ser Asp
            530                 535                 540
Val Asp Ala Leu Ser Arg Thr Lys Thr Val Gly Asp Val Ile Glu Ala
545                 550                 555                 560
Met Lys Leu Glu Leu Gly Gly Pro Gln Gly Gln Thr Leu Thr Ser Glu
            565                 570                 575
Pro Ile His Gln Pro Pro Val Ser Glu Pro Ala Val Pro Thr Ser Ser
            580                 585                 590
Ser Ser Ser Ile Ala Asn Val Ser Ser Ala Arg Leu Ala Glu Ala Glu
            595                 600                 605
Ala Ala Val Leu Ser Val Leu Ala Asp Lys Thr Gly Tyr Asp Ser Ser
            610                 615                 620
Met Ile Glu Met Asp Met Asp Leu Glu Ser Glu Leu Gly Val Asp Ser
625                 630                 635                 640
Ile Lys Arg Val Glu Ile Met Ser Glu Val Gln Thr Leu Leu Ser Val
            645                 650                 655
Glu Val Ser Asp Val Asp Ala Leu Ser Arg Thr Lys Thr Val Gly Asp
            660                 665                 670
Val Ile Glu Ala Met Lys Met Glu Leu Gly Gly Pro Gln Gly Gln Thr
            675                 680                 685
Leu Thr Ala Glu Ser Ile Arg Gln Pro Pro Val Ser Glu Pro Ala Val
            690                 695                 700
Pro Thr Ser Ser Ser Ser Ser Ile Ala Asn Val Ser Ser Ala Arg Leu
705                 710                 715                 720
Ala Glu Ala Glu Ala Ala Val Leu Ser Val Leu Ala Asp Lys Thr Gly
            725                 730                 735
Tyr Asp Ser Ser Met Ile Glu Met Asp Met Asp Leu Glu Ser Glu Leu
            740                 745                 750
Gly Val Asp Ser Ile Lys Arg Val Glu Ile Met Ser Glu Val Gln Ala
            755                 760                 765
Leu Leu Ser Val Glu Val Ser Asp Val Asp Ala Leu Ser Arg Thr Lys
            770                 775                 780
Thr Val Gly Asp Val Ile Glu Ala Met Lys Met Glu Leu Gly Gly Pro
785                 790                 795                 800
Gln Gly Gln Thr Leu Thr Ala Glu Ser Ile Arg Glu Pro Pro Val Ser
            805                 810                 815
Glu Pro Ala Val Pro Thr Ser Ser Ser Ser Ile Ala Asn Val Ser
            820                 825                 830
```

```
Ser Ala Arg Leu Ala Glu Ala Glu Ala Ala Val Leu Ser Val Leu Ala
        835                 840                 845

Asp Lys Thr Gly Tyr Asp Ser Ser Met Ile Glu Met Asp Met Asp Leu
    850                 855                 860

Glu Ser Glu Leu Gly Val Asp Ser Ile Lys Arg Val Glu Ile Met Ser
865                 870                 875                 880

Glu Val Gln Thr Leu Leu Ser Val Glu Val Ser Asp Val Asp Ala Leu
                885                 890                 895

Ser Arg Thr Lys Thr Val Gly Asp Val Ile Glu Ala Met Lys Leu Glu
            900                 905                 910

Leu Gly Glu Ser Ser Ile Glu Thr Leu Asn Cys Thr Glu Val Glu
        915                 920                 925

His Thr
    930

<210> SEQ ID NO 49
<211> LENGTH: 2433
<212> TYPE: DNA
<213> ORGANISM: Thraustochytrium sp.
<220> FEATURE:
<221> NAME/KEY: CDS
<222> LOCATION: (1)..(2433)

<400> SEQUENCE: 49 aaa agt gtc aag gct tca ggg tgt gag aat gta gat acc cgt ttc gct    48
Lys Ser Val Lys Ala Ser Gly Cys Glu Asn Val Asp Thr Arg Phe Ala
1               5                   10                  15 aag gtt gta caa atc tcg ctt cct agc aag ctg aaa tcc act gtg tcg    96
Lys Val Val Gln Ile Ser Leu Pro Ser Lys Leu Lys Ser Thr Val Ser
            20                  25                  30 cac gat cga cct gta att gtt gta gat gat gga acg ccc tta acc acg   144
His Asp Arg Pro Val Ile Val Val Asp Asp Gly Thr Pro Leu Thr Thr
        35                  40                  45 gag ctt tgt aaa att ctt ggg ggt aat att gtg gtt ctc tct tat caa   192
Glu Leu Cys Lys Ile Leu Gly Gly Asn Ile Val Val Leu Ser Tyr Gln
    50                  55                  60 ggg aag ccc gct ggt cca cgg gga gtc gag gtg cca gat ctt tcc gag   240
Gly Lys Pro Ala Gly Pro Arg Gly Val Glu Val Pro Asp Leu Ser Glu
65                  70                  75                  80 gaa gcc cta att caa gct ctt gca ttg att cgg tct aca tat gga gtt   288
Glu Ala Leu Ile Gln Ala Leu Ala Leu Ile Arg Ser Thr Tyr Gly Val
                85                  90                  95 cca att ggt ttt att tgt cag caa gtg tct aat gtg agc acc aag gca   336
Pro Ile Gly Phe Ile Cys Gln Gln Val Ser Asn Val Ser Thr Lys Ala
            100                 105                 110 cag ctt tgt tgg gca ctc ctc gca gcg aag cat ctc aag aag gat ttg   384
Gln Leu Cys Trp Ala Leu Leu Ala Ala Lys His Leu Lys Lys Asp Leu
        115                 120                 125 aat gct gtc tta ccc gat tca aga tcc ttc ttc gtc gga gtt gta cgc   432
Asn Ala Val Leu Pro Asp Ser Arg Ser Phe Phe Val Gly Val Val Arg
    130                 135                 140 ttg aac ggg aaa ctt gga act ttc gaa aac atc agc gac ttc tct aaa   480
Leu Asn Gly Lys Leu Gly Thr Phe Glu Asn Ile Ser Asp Phe Ser Lys
145                 150                 155                 160 ttt gat ttg acg aaa gcc cta gat tac gga cag cgt ggt tct ctc tta   528
Phe Asp Leu Thr Lys Ala Leu Asp Tyr Gly Gln Arg Gly Ser Leu Leu
                165                 170                 175 ggc ctg tgc aag tca cta gac tta gaa tgg gaa cag gtg ttt tgc cgt   576
Gly Leu Cys Lys Ser Leu Asp Leu Glu Trp Glu Gln Val Phe Cys Arg
            180                 185                 190
```

```
gga ata gat ctt gcg tgt gat ctt atg cca ctc cag gcc gca agg ata       624
Gly Ile Asp Leu Ala Cys Asp Leu Met Pro Leu Gln Ala Ala Arg Ile
        195                 200                 205 ctc aga aat gag ctt cag tgt ccc aat atg cgc ctt cgc gag gtt ggg       672
Leu Arg Asn Glu Leu Gln Cys Pro Asn Met Arg Leu Arg Glu Val Gly
210                 215                 220 tac gat att tct ggc gcc agg tac acc att tca acc gat gac ctg cta       720
Tyr Asp Ile Ser Gly Ala Arg Tyr Thr Ile Ser Thr Asp Asp Leu Leu
225                 230                 235                 240 tgt gga ccc tcg aag gct aaa gta gag gcc gca gac ttg ttt ctt gtg       768
Cys Gly Pro Ser Lys Ala Lys Val Glu Ala Ala Asp Leu Phe Leu Val
                245                 250                 255 aca ggt ggc gca cga ggt att aca cct cat tgt gtt cgt gag att gca       816
Thr Gly Gly Ala Arg Gly Ile Thr Pro His Cys Val Arg Glu Ile Ala
            260                 265                 270 agt cga tcc ccc gga acc aca ttt gtg ctg gtt gga aga agc gaa atg       864
Ser Arg Ser Pro Gly Thr Thr Phe Val Leu Val Gly Arg Ser Glu Met
        275                 280                 285 tcc gac gag cct gac tgg gct gtt ggc cac tac aat aaa gac ctg gac       912
Ser Asp Glu Pro Asp Trp Ala Val Gly His Tyr Asn Lys Asp Leu Asp
290                 295                 300 caa agc aca atg aaa cac ttg aaa gca acg cat gct gct gga ggg gta       960
Gln Ser Thr Met Lys His Leu Lys Ala Thr His Ala Ala Gly Gly Val
305                 310                 315                 320 aaa cct acg cct aaa gca cat cgt gca ctt gtg aac agg gtc act ggc      1008
Lys Pro Thr Pro Lys Ala His Arg Ala Leu Val Asn Arg Val Thr Gly
                325                 330                 335 tca cgg gag gta cga gaa tct ctt aga gca atc cag gag gca ggg gca      1056
Ser Arg Glu Val Arg Glu Ser Leu Arg Ala Ile Gln Glu Ala Gly Ala
            340                 345                 350 aat gtc gaa tat atc gcc tgt gat gtt tcg gat gaa aac aag gtc cgc      1104
Asn Val Glu Tyr Ile Ala Cys Asp Val Ser Asp Glu Asn Lys Val Arg
        355                 360                 365 caa ctt gtg caa aga gtg gag caa aag tat ggc tgt gaa ata act ggg      1152
Gln Leu Val Gln Arg Val Glu Gln Lys Tyr Gly Cys Glu Ile Thr Gly
370                 375                 380 att tgg cat gca agc ggg gtt ctt cgt gac aaa ctt gtc gag caa aag      1200
Ile Trp His Ala Ser Gly Val Leu Arg Asp Lys Leu Val Glu Gln Lys
385                 390                 395                 400 act aca gac gac ttt gag gca gtt ttt ggg acc aag gtg act ggc ctt      1248
Thr Thr Asp Asp Phe Glu Ala Val Phe Gly Thr Lys Val Thr Gly Leu
                405                 410                 415 gta aac atc gtg tca caa gtc aat atg tct aag cta cga cac ttc atc      1296
Val Asn Ile Val Ser Gln Val Asn Met Ser Lys Leu Arg His Phe Ile
            420                 425                 430 ctc ttc agt tct ttg gct gga ttt cat ggg aac aag ggc caa acg gat      1344
Leu Phe Ser Ser Leu Ala Gly Phe His Gly Asn Lys Gly Gln Thr Asp
        435                 440                 445 tat gca att gct aat gaa gcc ttg aac aaa atc gcg cat act ctc tca      1392
Tyr Ala Ile Ala Asn Glu Ala Leu Asn Lys Ile Ala His Thr Leu Ser
450                 455                 460 gcg ttt ttg ccc aaa ctg aat gca aag gtg cta gac ttc ggt ccg tgg      1440
Ala Phe Leu Pro Lys Leu Asn Ala Lys Val Leu Asp Phe Gly Pro Trp
465                 470                 475                 480 gta ggt tca gga atg gta acc gaa aca ctt gag aag cat ttt aaa gct      1488
Val Gly Ser Gly Met Val Thr Glu Thr Leu Glu Lys His Phe Lys Ala
                485                 490                 495 atg ggg gtt cag act att cct ctc gag cca gga gca cgg act gtt gcg      1536
Met Gly Val Gln Thr Ile Pro Leu Glu Pro Gly Ala Arg Thr Val Ala
```

```
                    500                 505                 510
caa atc att ttg gca agt tcg cca ccg caa tcg ctt ttg ggg aac tgg      1584
Gln Ile Ile Leu Ala Ser Ser Pro Pro Gln Ser Leu Leu Gly Asn Trp
            515                 520                 525 ggc ttt cca gcc acc aaa ccg cta caa cgc tct aat gta gtc acg ggc      1632
Gly Phe Pro Ala Thr Lys Pro Leu Gln Arg Ser Asn Val Val Thr Gly
    530                 535                 540 aca ctc tct ccg gaa gag ata gaa ttc atc gca gac cac aaa att caa      1680
Thr Leu Ser Pro Glu Glu Ile Glu Phe Ile Ala Asp His Lys Ile Gln
545                 550                 555                 560 ggc cgc aag gtg ctt ccc atg atg gct gca atc ggg ttc atg gcc tct      1728
Gly Arg Lys Val Leu Pro Met Met Ala Ala Ile Gly Phe Met Ala Ser
            565                 570                 575 att gcg gaa gga ctc tac ccg ggg tac aat ctg caa ggc gtg gaa aat      1776
Ile Ala Glu Gly Leu Tyr Pro Gly Tyr Asn Leu Gln Gly Val Glu Asn
    580                 585                 590 gct cag ctc ttt caa ggc ttg act atc aac caa gag aca aaa ttt caa      1824
Ala Gln Leu Phe Gln Gly Leu Thr Ile Asn Gln Glu Thr Lys Phe Gln
595                 600                 605 atc act ctc att gag gag cac aac tct gag gaa aac ctg gat gtc ctg      1872
Ile Thr Leu Ile Glu Glu His Asn Ser Glu Glu Asn Leu Asp Val Leu
            610                 615                 620 aca tcc ctt ggt gta atg ttg gaa agc ggg aag gtg ctt ccc gct tac      1920
Thr Ser Leu Gly Val Met Leu Glu Ser Gly Lys Val Leu Pro Ala Tyr
625                 630                 635                 640 cga tgt gtt gta tgc ttg aat aca acc cag cag cag ccc aag cta tct      1968
Arg Cys Val Val Cys Leu Asn Thr Thr Gln Gln Gln Pro Lys Leu Ser
            645                 650                 655 cca aaa att ctt aac ttg gaa gtt gac cct gca tgc gag gtt aac ccc      2016
Pro Lys Ile Leu Asn Leu Glu Val Asp Pro Ala Cys Glu Val Asn Pro
    660                 665                 670 tat gat gga aag tcg ttg ttc cac ggt ccg ctt ttg caa ttc gtt caa      2064
Tyr Asp Gly Lys Ser Leu Phe His Gly Pro Leu Leu Gln Phe Val Gln
675                 680                 685 caa gtg ttg cac tca agt acc aaa ggc ctc gtt gcc aag tgc cgc gcg      2112
Gln Val Leu His Ser Ser Thr Lys Gly Leu Val Ala Lys Cys Arg Ala
            690                 695                 700 ctt cca atc aaa gaa gcc atc cga ggg cca ttt atc aag caa aca ctc      2160
Leu Pro Ile Lys Glu Ala Ile Arg Gly Pro Phe Ile Lys Gln Thr Leu
705                 710                 715                 720 cat gat cca att cta gac gac gtc att ttt cag cta atg ctc gtg tgg      2208
His Asp Pro Ile Leu Asp Asp Val Ile Phe Gln Leu Met Leu Val Trp
            725                 730                 735 tgt cgt aat gct cta gga agt gca tcg cta ccc aac aga att gaa aag      2256
Cys Arg Asn Ala Leu Gly Ser Ala Ser Leu Pro Asn Arg Ile Glu Lys
    740                 745                 750 atg tca tac ttt ggg aat gtc tca gaa ggt agc act ttc ttt gcc tca      2304
Met Ser Tyr Phe Gly Asn Val Ser Glu Gly Ser Thr Phe Phe Ala Ser
755                 760                 765 gtt aca cct gtg gga cca aga gta cca aag gat ccc gtg atc aaa atg      2352
Val Thr Pro Val Gly Pro Arg Val Pro Lys Asp Pro Val Ile Lys Met
            770                 775                 780 cag ttt ctt ctc caa gat gaa tcc ggc aac aca ttt tca tcg ggg gag      2400
Gln Phe Leu Leu Gln Asp Glu Ser Gly Asn Thr Phe Ser Ser Gly Glu
785                 790                 795                 800 ggc tcg gtt gtg ctt agt gac gaa ctc gtc ttt                          2433
Gly Ser Val Val Leu Ser Asp Glu Leu Val Phe
            805                 810
```

<210> SEQ ID NO 50
<211> LENGTH: 811
<212> TYPE: PRT
<213> ORGANISM: Thraustochytrium sp.

<400> SEQUENCE: 50

```
Lys Ser Val Lys Ala Ser Gly Cys Glu Asn Val Asp Thr Arg Phe Ala
1               5                   10                  15

Lys Val Val Gln Ile Ser Leu Pro Ser Lys Leu Lys Ser Thr Val Ser
            20                  25                  30

His Asp Arg Pro Val Ile Val Asp Asp Gly Thr Pro Leu Thr Thr
        35                  40                  45

Glu Leu Cys Lys Ile Leu Gly Gly Asn Ile Val Val Leu Ser Tyr Gln
    50                  55                  60

Gly Lys Pro Ala Gly Pro Arg Gly Val Glu Val Pro Asp Leu Ser Glu
65                  70                  75                  80

Glu Ala Leu Ile Gln Ala Leu Ala Leu Ile Arg Ser Thr Tyr Gly Val
                85                  90                  95

Pro Ile Gly Phe Ile Cys Gln Gln Val Ser Asn Val Ser Thr Lys Ala
            100                 105                 110

Gln Leu Cys Trp Ala Leu Leu Ala Ala Lys His Leu Lys Lys Asp Leu
        115                 120                 125

Asn Ala Val Leu Pro Asp Ser Arg Ser Phe Phe Val Gly Val Val Arg
    130                 135                 140

Leu Asn Gly Lys Leu Gly Thr Phe Glu Asn Ile Ser Asp Phe Ser Lys
145                 150                 155                 160

Phe Asp Leu Thr Lys Ala Leu Asp Tyr Gly Gln Arg Gly Ser Leu Leu
                165                 170                 175

Gly Leu Cys Lys Ser Leu Asp Leu Glu Trp Glu Gln Val Phe Cys Arg
            180                 185                 190

Gly Ile Asp Leu Ala Cys Asp Leu Met Pro Leu Gln Ala Ala Arg Ile
        195                 200                 205

Leu Arg Asn Glu Leu Gln Cys Pro Asn Met Arg Leu Arg Glu Val Gly
    210                 215                 220

Tyr Asp Ile Ser Gly Ala Arg Tyr Thr Ile Ser Thr Asp Asp Leu Leu
225                 230                 235                 240

Cys Gly Pro Ser Lys Ala Lys Val Glu Ala Ala Asp Leu Phe Leu Val
                245                 250                 255

Thr Gly Gly Ala Arg Gly Ile Thr Pro His Cys Val Arg Glu Ile Ala
            260                 265                 270

Ser Arg Ser Pro Gly Thr Thr Phe Val Leu Val Gly Arg Ser Glu Met
        275                 280                 285

Ser Asp Glu Pro Asp Trp Ala Val Gly His Tyr Asn Lys Asp Leu Asp
    290                 295                 300

Gln Ser Thr Met Lys His Leu Lys Ala Thr His Ala Ala Gly Gly Val
305                 310                 315                 320

Lys Pro Thr Pro Lys Ala His Arg Ala Leu Val Asn Arg Val Thr Gly
                325                 330                 335

Ser Arg Glu Val Arg Glu Ser Leu Arg Ala Ile Gln Glu Ala Gly Ala
            340                 345                 350

Asn Val Glu Tyr Ile Ala Cys Asp Val Ser Asp Glu Asn Lys Val Arg
        355                 360                 365

Gln Leu Val Gln Arg Val Glu Gln Lys Tyr Gly Cys Glu Ile Thr Gly
    370                 375                 380
```

```
Ile Trp His Ala Ser Gly Val Leu Arg Asp Lys Leu Val Glu Gln Lys
385                 390                 395                 400

Thr Thr Asp Asp Phe Glu Ala Val Phe Gly Thr Lys Val Thr Gly Leu
            405                 410                 415

Val Asn Ile Val Ser Gln Val Asn Met Ser Lys Leu Arg His Phe Ile
        420                 425                 430

Leu Phe Ser Ser Leu Ala Gly Phe His Gly Asn Lys Gly Gln Thr Asp
    435                 440                 445

Tyr Ala Ile Ala Asn Glu Ala Leu Asn Lys Ile Ala His Thr Leu Ser
450                 455                 460

Ala Phe Leu Pro Lys Leu Asn Ala Lys Val Leu Asp Phe Gly Pro Trp
465                 470                 475                 480

Val Gly Ser Gly Met Val Thr Glu Thr Leu Glu Lys His Phe Lys Ala
                485                 490                 495

Met Gly Val Gln Thr Ile Pro Leu Glu Pro Gly Ala Arg Thr Val Ala
            500                 505                 510

Gln Ile Ile Leu Ala Ser Ser Pro Gln Ser Leu Leu Gly Asn Trp
        515                 520                 525

Gly Phe Pro Ala Thr Lys Pro Leu Gln Arg Ser Asn Val Val Thr Gly
530                 535                 540

Thr Leu Ser Pro Glu Glu Ile Glu Phe Ile Ala Asp His Lys Ile Gln
545                 550                 555                 560

Gly Arg Lys Val Leu Pro Met Met Ala Ala Ile Gly Phe Met Ala Ser
                565                 570                 575

Ile Ala Glu Gly Leu Tyr Pro Gly Tyr Asn Leu Gln Gly Val Glu Asn
            580                 585                 590

Ala Gln Leu Phe Gln Gly Leu Thr Ile Asn Gln Glu Thr Lys Phe Gln
        595                 600                 605

Ile Thr Leu Ile Glu Glu His Asn Ser Glu Glu Asn Leu Asp Val Leu
    610                 615                 620

Thr Ser Leu Gly Val Met Leu Glu Ser Gly Lys Val Leu Pro Ala Tyr
625                 630                 635                 640

Arg Cys Val Val Cys Leu Asn Thr Thr Gln Gln Pro Lys Leu Ser
                645                 650                 655

Pro Lys Ile Leu Asn Leu Glu Val Asp Pro Ala Cys Glu Val Asn Pro
            660                 665                 670

Tyr Asp Gly Lys Ser Leu Phe His Gly Pro Leu Leu Gln Phe Val Gln
        675                 680                 685

Gln Val Leu His Ser Ser Thr Lys Gly Leu Val Ala Lys Cys Arg Ala
    690                 695                 700

Leu Pro Ile Lys Glu Ala Ile Arg Gly Pro Phe Ile Lys Gln Thr Leu
705                 710                 715                 720

His Asp Pro Ile Leu Asp Val Ile Phe Gln Leu Met Leu Val Trp
                725                 730                 735

Cys Arg Asn Ala Leu Gly Ser Ala Ser Leu Pro Asn Arg Ile Glu Lys
            740                 745                 750

Met Ser Tyr Phe Gly Asn Val Ser Glu Gly Ser Thr Phe Phe Ala Ser
        755                 760                 765

Val Thr Pro Val Gly Pro Arg Val Pro Lys Asp Pro Val Ile Lys Met
    770                 775                 780

Gln Phe Leu Leu Gln Asp Glu Ser Gly Asn Thr Phe Ser Ser Gly Glu
785                 790                 795                 800

Gly Ser Val Val Leu Ser Asp Glu Leu Val Phe
```

<210> SEQ ID NO 51
<211> LENGTH: 5808
<212> TYPE: DNA
<213> ORGANISM: Thraustochytrium sp.
<220> FEATURE:
<221> NAME/KEY: CDS
<222> LOCATION: (1)..(5805)
<220> FEATURE:
<221> NAME/KEY: misc_feature
<222> LOCATION: (1)..(5808)
<223> OTHER INFORMATION: n = a c t or g

<400> SEQUENCE: 51

| | | | | | | | | | | | | | | | | |
|---|---|---|---|---|---|---|---|---|---|---|---|---|---|---|---|---|
| atg | caa | ctt | cct | cca | gcg | cat | tct | gcc | gat | gag | aat | cgc | atc | gcg | gtc | 48 |
| Met | Gln | Leu | Pro | Pro | Ala | His | Ser | Ala | Asp | Glu | Asn | Arg | Ile | Ala | Val | |
| 1 | | | | 5 | | | | | 10 | | | | | 15 | | |
| gtg | ggc | atg | gcc | gtc | aaa | tat | gcg | ggc | tgt | gac | aat | aaa | gaa | gag | ttt | 96 |
| Val | Gly | Met | Ala | Val | Lys | Tyr | Ala | Gly | Cys | Asp | Asn | Lys | Glu | Glu | Phe | |
| | | | 20 | | | | | 25 | | | | | 30 | | | |
| tgg | aag | act | ttg | atg | aat | ggt | agt | atc | aat | acc | aag | tcg | att | tcg | gca | 144 |
| Trp | Lys | Thr | Leu | Met | Asn | Gly | Ser | Ile | Asn | Thr | Lys | Ser | Ile | Ser | Ala | |
| | | | 35 | | | | | 40 | | | | | 45 | | | |
| gca | agg | ttg | ggc | agc | aat | aag | cgt | gac | gaa | cac | tat | gtt | cct | gaa | cga | 192 |
| Ala | Arg | Leu | Gly | Ser | Asn | Lys | Arg | Asp | Glu | His | Tyr | Val | Pro | Glu | Arg | |
| | 50 | | | | | 55 | | | | | 60 | | | | | |
| tcg | aaa | tat | gca | gat | acg | ttc | tgt | aac | gaa | agg | tac | ggt | tgt | atc | cag | 240 |
| Ser | Lys | Tyr | Ala | Asp | Thr | Phe | Cys | Asn | Glu | Arg | Tyr | Gly | Cys | Ile | Gln | |
| 65 | | | | | 70 | | | | | 75 | | | | | 80 | |
| caa | ggt | acg | gat | aat | gag | cat | gac | ctc | ctc | cta | ggt | ctt | gct | caa | gaa | 288 |
| Gln | Gly | Thr | Asp | Asn | Glu | His | Asp | Leu | Leu | Leu | Gly | Leu | Ala | Gln | Glu | |
| | | | | 85 | | | | | 90 | | | | | 95 | | |
| gct | ctc | gct | gac | gct | gcc | ggg | cgg | atg | gag | aaa | caa | cct | tcg | gag | gcg | 336 |
| Ala | Leu | Ala | Asp | Ala | Ala | Gly | Arg | Met | Glu | Lys | Gln | Pro | Ser | Glu | Ala | |
| | | | 100 | | | | | 105 | | | | | 110 | | | |
| ttc | gat | ctg | gaa | aat | act | ggc | atc | gtg | agt | ggg | tgc | tta | tct | ttt | cca | 384 |
| Phe | Asp | Leu | Glu | Asn | Thr | Gly | Ile | Val | Ser | Gly | Cys | Leu | Ser | Phe | Pro | |
| | | | 115 | | | | | 120 | | | | | 125 | | | |
| atg | gat | aac | ctg | caa | gga | gag | ttg | ttg | aac | ttg | tat | caa | agc | cat | gtg | 432 |
| Met | Asp | Asn | Leu | Gln | Gly | Glu | Leu | Leu | Asn | Leu | Tyr | Gln | Ser | His | Val | |
| | | | | 130 | | | | | 135 | | | | | 140 | | |
| gag | aaa | caa | ctt | cca | cct | agt | gcc | ttg | gta | gaa | gcc | gtg | aag | ctt | tgg | 480 |
| Glu | Lys | Gln | Leu | Pro | Pro | Ser | Ala | Leu | Val | Glu | Ala | Val | Lys | Leu | Trp | |
| 145 | | | | | 150 | | | | | 155 | | | | | 160 | |
| tct | gag | cga | cag | aaa | tct | acg | aaa | gca | cat | gca | ggg | gac | aag | cgc | cgg | 528 |
| Ser | Glu | Arg | Gln | Lys | Ser | Thr | Lys | Ala | His | Ala | Gly | Asp | Lys | Arg | Arg | |
| | | | | 165 | | | | | 170 | | | | | 175 | | |
| ttc | att | gac | cca | gct | tct | ttt | gta | gct | gat | aaa | ctg | aac | cta | ggc | cca | 576 |
| Phe | Ile | Asp | Pro | Ala | Ser | Phe | Val | Ala | Asp | Lys | Leu | Asn | Leu | Gly | Pro | |
| | | | 180 | | | | | 185 | | | | | 190 | | | |
| cta | cat | tat | gcg | atc | gat | gca | gca | tgc | gct | tct | gca | ttg | tac | gtg | tta | 624 |
| Leu | His | Tyr | Ala | Ile | Asp | Ala | Ala | Cys | Ala | Ser | Ala | Leu | Tyr | Val | Leu | |
| | | | | 195 | | | | | 200 | | | | | 205 | | |
| aaa | tta | gct | caa | gac | cac | ctt | gtt | tca | ggt | gcc | gtt | gat | atg | atg | tta | 672 |
| Lys | Leu | Ala | Gln | Asp | His | Leu | Val | Ser | Gly | Ala | Val | Asp | Met | Met | Leu | |
| | | | 210 | | | | | 215 | | | | | 220 | | | |
| tgt | gga | gcg | acg | tgc | ttc | cca | gaa | cca | ttc | ttc | atc | ttg | tct | ggg | ttc | 720 |
| Cys | Gly | Ala | Thr | Cys | Phe | Pro | Glu | Pro | Phe | Phe | Ile | Leu | Ser | Gly | Phe | |
| 225 | | | | | 230 | | | | | 235 | | | | | 240 | |
| tcg | act | ttt | caa | gcg | atg | cct | gnt | ggg | gca | gat | gga | gtc | tca | cta | cct | 768 |
| Ser | Thr | Phe | Gln | Ala | Met | Pro | Xaa | Gly | Ala | Asp | Gly | Val | Ser | Leu | Pro | |

-continued

```
                 245                 250                 255
ctc cat aaa acg agt gct ggg ctc act cca ggt gaa ggg ggg tcc att        816
Leu His Lys Thr Ser Ala Gly Leu Thr Pro Gly Glu Gly Gly Ser Ile
            260                 265                 270 atg gtg ctc aag cga ctg aaa gac gct atc aga gat gga aat cac att        864
Met Val Leu Lys Arg Leu Lys Asp Ala Ile Arg Asp Gly Asn His Ile
            275                 280                 285 tat ggt gtg ctc ctt gaa gca aat tta agt aac gca ggt tgt ggg ctt        912
Tyr Gly Val Leu Leu Glu Ala Asn Leu Ser Asn Ala Gly Cys Gly Leu
        290                 295                 300 cca ctc agc ccg cac tta ccg agc gaa gaa tca tgt att cgt gat acc        960
Pro Leu Ser Pro His Leu Pro Ser Glu Glu Ser Cys Ile Arg Asp Thr
305                 310                 315                 320 tac cgc cgt gct gga gtt gct gca gat caa agt att cag tat att gag       1008
Tyr Arg Arg Ala Gly Val Ala Ala Asp Gln Ser Ile Gln Tyr Ile Glu
                325                 330                 335 tgc cac gct acg gga acc cct cga ggg gat gtc gtg gaa att gag gcg       1056
Cys His Ala Thr Gly Thr Pro Arg Gly Asp Val Val Glu Ile Glu Ala
            340                 345                 350 gtt gaa aga gtt ttc aag aaa aac gtt cca cgc tta ggc tcg acg aaa       1104
Val Glu Arg Val Phe Lys Lys Asn Val Pro Arg Leu Gly Ser Thr Lys
        355                 360                 365 gga aat ttt ggt cac tcg tta gtt gcg gct ggt ttc gca ggt atg gca       1152
Gly Asn Phe Gly His Ser Leu Val Ala Ala Gly Phe Ala Gly Met Ala
370                 375                 380 aag ctt ctt ctt gca atg gaa cat gga gtg att cct ccc aca cca ggt       1200
Lys Leu Leu Leu Ala Met Glu His Gly Val Ile Pro Pro Thr Pro Gly
385                 390                 395                 400 ctt gat gct tcg aac cag gca agt gag cac gtt gtg aca aag gct atc       1248
Leu Asp Ala Ser Asn Gln Ala Ser Glu His Val Val Thr Lys Ala Ile
                405                 410                 415 act tgg cct gag aca cat ggg gct cca aaa cga gct ggc ctt tca gca       1296
Thr Trp Pro Glu Thr His Gly Ala Pro Lys Arg Ala Gly Leu Ser Ala
            420                 425                 430 ttt gga ttt ggt ggg act aat gcg cat gca ctc ttc gaa gag ttt aat       1344
Phe Gly Phe Gly Gly Thr Asn Ala His Ala Leu Phe Glu Glu Phe Asn
        435                 440                 445 gcc gag ggc ata agt tat cgc cct gga aag cct cca gtc gaa tcg aat       1392
Ala Glu Gly Ile Ser Tyr Arg Pro Gly Lys Pro Pro Val Glu Ser Asn
450                 455                 460 acc cgt cct tcc gtc gta ata act ggg atg gac tgt acc ttt ggg agc       1440
Thr Arg Pro Ser Val Val Ile Thr Gly Met Asp Cys Thr Phe Gly Ser
465                 470                 475                 480 ctt gaa ggg att gat gcg ttc gag act gcc ctg tac gag ggg cgt gac       1488
Leu Glu Gly Ile Asp Ala Phe Glu Thr Ala Leu Tyr Glu Gly Arg Asp
                485                 490                 495 gca gct cgt gac tta ccc gcc aaa cgt tgg agg ttc cta ggt gag gac       1536
Ala Ala Arg Asp Leu Pro Ala Lys Arg Trp Arg Phe Leu Gly Glu Asp
            500                 505                 510 ttg gag ttt ctc cga gcc atc agg ctc aag gaa aag cct agg ggt tgt       1584
Leu Glu Phe Leu Arg Ala Ile Arg Leu Lys Glu Lys Pro Arg Gly Cys
        515                 520                 525 ttt gtg gag agt gtt gac gtt aac ttt aga cgg ctg aaa acg ccc ttg       1632
Phe Val Glu Ser Val Asp Val Asn Phe Arg Arg Leu Lys Thr Pro Leu
530                 535                 540 aca cca gaa gat atg ttg cgg ccc caa caa ctc ttg gcg gtt tct acg       1680
Thr Pro Glu Asp Met Leu Arg Pro Gln Gln Leu Leu Ala Val Ser Thr
545                 550                 555                 560 atg gac cga gca att atc gat gca ggt cta aag aag ggc caa cat gta       1728
```

-continued

```
                Met Asp Arg Ala Ile Ile Asp Ala Gly Leu Lys Lys Gly Gln His Val
                            565                 570                 575 gca gtt ctt gtt ggc cta gga act gac ctg gaa ctt tac cgt cat cga          1776
Ala Val Leu Val Gly Leu Gly Thr Asp Leu Glu Leu Tyr Arg His Arg
            580                 585                 590 gca aga gtc gcg ctt aaa gag gtt ttg cac ccg agc tta aag tca gac          1824
Ala Arg Val Ala Leu Lys Glu Val Leu His Pro Ser Leu Lys Ser Asp
        595                 600                 605 act gca att ctc cag aaa ata atg caa tat gtg aat gat gca gga act          1872
Thr Ala Ile Leu Gln Lys Ile Met Gln Tyr Val Asn Asp Ala Gly Thr
    610                 615                 620 tcg act tca tac aca tct tac att gga aac ctc gtt gcc acg cgt att          1920
Ser Thr Ser Tyr Thr Ser Tyr Ile Gly Asn Leu Val Ala Thr Arg Ile
625                 630                 635                 640 tcg tct cag tgg gga ttc aca ggg ccg tcc ttt act gtc aca gaa gga          1968
Ser Ser Gln Trp Gly Phe Thr Gly Pro Ser Phe Thr Val Thr Glu Gly
            645                 650                 655 aat aat tcc gtg tac aga tgt gca caa cta gcc aaa gat atg ctt cag          2016
Asn Asn Ser Val Tyr Arg Cys Ala Gln Leu Ala Lys Asp Met Leu Gln
        660                 665                 670 gtt aac cga gtt gat gct gtc gtc atc gca ggc gtt gat ctc aac gga          2064
Val Asn Arg Val Asp Ala Val Val Ile Ala Gly Val Asp Leu Asn Gly
    675                 680                 685 agc gcc gaa agt ttt ttt gtc cga gca aat cgt caa aag ata tcc aag          2112
Ser Ala Glu Ser Phe Phe Val Arg Ala Asn Arg Gln Lys Ile Ser Lys
690                 695                 700 cta agt cat cca tgt gca agc ttc gac aga gat gca gat gga ttt ttc          2160
Leu Ser His Pro Cys Ala Ser Phe Asp Arg Asp Ala Asp Gly Phe Phe
705                 710                 715                 720 gca ggt gag ggc tgt ggt gcc cta gtt ttc aag agg tta gaa gac tgt          2208
Ala Gly Glu Gly Cys Gly Ala Leu Val Phe Lys Arg Leu Glu Asp Cys
            725                 730                 735 gct cct cag gaa aaa att tat gct agt ata gac tct atc gca ata gat          2256
Ala Pro Gln Glu Lys Ile Tyr Ala Ser Ile Asp Ser Ile Ala Ile Asp
        740                 745                 750 aaa gag cct act agc tca gct gtg aaa gct gtc tac caa agt gat tcg          2304
Lys Glu Pro Thr Ser Ser Ala Val Lys Ala Val Tyr Gln Ser Asp Ser
    755                 760                 765 agt ctc tcc gat att gag ctg tta gaa atc agt gga gac tcc aaa cgg          2352
Ser Leu Ser Asp Ile Glu Leu Leu Glu Ile Ser Gly Asp Ser Lys Arg
770                 775                 780 ttt gca gca ttc gaa ggc gct gtg gaa att caa tca agt gtg gaa gcc          2400
Phe Ala Ala Phe Glu Gly Ala Val Glu Ile Gln Ser Ser Val Glu Ala
785                 790                 795                 800 cag cta aaa gga ctt tcc aaa gtc ctt gaa cct gca aaa ggc caa ggc          2448
Gln Leu Lys Gly Leu Ser Lys Val Leu Glu Pro Ala Lys Gly Gln Gly
            805                 810                 815 gta gcg gtg gga agt act cga gca acc gtt ggg gat ata ggg tat gct          2496
Val Ala Val Gly Ser Thr Arg Ala Thr Val Gly Asp Ile Gly Tyr Ala
        820                 825                 830 aca gga gcg gca agc ctg att aaa act gca ctc tgc tta tat aat cgc          2544
Thr Gly Ala Ala Ser Leu Ile Lys Thr Ala Leu Cys Leu Tyr Asn Arg
    835                 840                 845 tac ctt ccg gca tta gca aac tgg agt ggc cca tgt gaa cag tcc gcc          2592
Tyr Leu Pro Ala Leu Ala Asn Trp Ser Gly Pro Cys Glu Gln Ser Ala
850                 855                 860 tgg ggc tca aac atg ttc gtt tgc cat gaa aca cgg ccg tgg atg aaa          2640
Trp Gly Ser Asn Met Phe Val Cys His Glu Thr Arg Pro Trp Met Lys
865                 870                 875                 880
```

```
aac cag aat gaa aag aga tgt gcc ctc att tct gga aca gat cca tct    2688
Asn Gln Asn Glu Lys Arg Cys Ala Leu Ile Ser Gly Thr Asp Pro Ser
                885                 890                 895 cat aca tgc ttt tcc ctc gta cta tcg gat act ggg tgt tat gaa gag    2736
His Thr Cys Phe Ser Leu Val Leu Ser Asp Thr Gly Cys Tyr Glu Glu
            900                 905                 910 cac aat cga acg tgc ttt gat gtg caa gcg cca cag cta gtt ctg ata    2784
His Asn Arg Thr Cys Phe Asp Val Gln Ala Pro Gln Leu Val Leu Ile
        915                 920                 925 cac gga ttc gat gga aaa act att gtg cgg cga ctt gaa gga tat ctc    2832
His Gly Phe Asp Gly Lys Thr Ile Val Arg Arg Leu Glu Gly Tyr Leu
    930                 935                 940 ctt gaa ctt gtt gaa ggg cat gca agc cct tca gag tat ttc cac aaa    2880
Leu Glu Leu Val Glu Gly His Ala Ser Pro Ser Glu Tyr Phe His Lys
945                 950                 955                 960 ctg att gga caa agt cta ctt gag aac tcg aaa gaa agt aaa ctc aca    2928
Leu Ile Gly Gln Ser Leu Leu Glu Asn Ser Lys Glu Ser Lys Leu Thr
                965                 970                 975 ctt tcg ctt gtg tgc aat ccg aac cag ctc caa aag gag ctc atg ctt    2976
Leu Ser Leu Val Cys Asn Pro Asn Gln Leu Gln Lys Glu Leu Met Leu
            980                 985                 990 gct atc aaa gga gta caa cga agc atg tta aca ggg aag gat tgg gtc    3024
Ala Ile Lys Gly Val Gln Arg Ser Met Leu Thr Gly Lys Asp Trp Val
        995                 1000                1005 agt cca tca gga agt tgt ttt gcc cca aat ccg tta tca agc gca       3069
Ser Pro Ser Gly Ser Cys Phe Ala Pro Asn Pro Leu Ser Ser Ala
    1010                1015                1020 aaa gtg gca ttc atg tac gga gaa ggc cga agc ccg tac tgt ggt       3114
Lys Val Ala Phe Met Tyr Gly Glu Gly Arg Ser Pro Tyr Cys Gly
1025                1030                1035 gta ggc ttg ggt cta cat cgt ttg tgg ccc ggt ctc cat gaa aat       3159
Val Gly Leu Gly Leu His Arg Leu Trp Pro Gly Leu His Glu Asn
    1040                1045                1050 gtg aac aat aag aca gtc gat tta tgg acg gaa gga gat ggt tgg       3204
Val Asn Asn Lys Thr Val Asp Leu Trp Thr Glu Gly Asp Gly Trp
1055                1060                1065 tta tat cct cga acg ttg aca cga gaa gag cat aca aaa gcc atc       3249
Leu Tyr Pro Arg Thr Leu Thr Arg Glu Glu His Thr Lys Ala Ile
    1070                1075                1080 gaa tct ttc aac gca aat caa att gaa atg ttt cgc gct ggg att       3294
Glu Ser Phe Asn Ala Asn Gln Ile Glu Met Phe Arg Ala Gly Ile
1085                1090                1095 ttc atc tca atg tgt cag aca gac tat gtc atg aat gtt ctc ggt       3339
Phe Ile Ser Met Cys Gln Thr Asp Tyr Val Met Asn Val Leu Gly
    1100                1105                1110 gtc cag cct aag gcc gga ttt ggg ctg agc ttg gga gaa att tca       3384
Val Gln Pro Lys Ala Gly Phe Gly Leu Ser Leu Gly Glu Ile Ser
1115                1120                1125 atg ctc ttt gcg atg tca aag gag aac tgc agg cag tca cag gaa       3429
Met Leu Phe Ala Met Ser Lys Glu Asn Cys Arg Gln Ser Gln Glu
    1130                1135                1140 atg acc aat cgt ttg cgc ggt tct cca gtg tgg tct aac gag ctt       3474
Met Thr Asn Arg Leu Arg Gly Ser Pro Val Trp Ser Asn Glu Leu
1145                1150                1155 gct atc aac ttc aat gca att cgc aag tta tgg aaa atc ccc cga       3519
Ala Ile Asn Phe Asn Ala Ile Arg Lys Leu Trp Lys Ile Pro Arg
    1160                1165                1170 gga gct ccc tta gaa tcc ttt tgg caa gga tac ttg gtt cac ggc       3564
Gly Ala Pro Leu Glu Ser Phe Trp Gln Gly Tyr Leu Val His Gly
1175                1180                1185
```

```
aca aga gaa gaa gta gag cat gct att ggt ctt tct gag cct tat        3609
Thr Arg Glu Glu Val Glu His Ala Ile Gly Leu Ser Glu Pro Tyr
    1190            1195                1200 gta cgt ctg ctt att gtg aac gat tca agg agt gcc ttg att gct        3654
Val Arg Leu Leu Ile Val Asn Asp Ser Arg Ser Ala Leu Ile Ala
    1205            1210                1215 gga aaa cca gac gcc tgt cag gca gta atc agt aga cta aac tcc        3699
Gly Lys Pro Asp Ala Cys Gln Ala Val Ile Ser Arg Leu Asn Ser
    1220            1225                1230 aag ttc cct tct ctg ccg gta aag caa gga atg att ggt cat tgc        3744
Lys Phe Pro Ser Leu Pro Val Lys Gln Gly Met Ile Gly His Cys
    1235            1240                1245 cca gaa gtt cgt gcg ttc atc aaa gat att ggg tac atc cat gaa        3789
Pro Glu Val Arg Ala Phe Ile Lys Asp Ile Gly Tyr Ile His Glu
    1250            1255                1260 aca ctc cga att tcc aat gac tat tcg gat tgt cag ctt ttc tca        3834
Thr Leu Arg Ile Ser Asn Asp Tyr Ser Asp Cys Gln Leu Phe Ser
    1265            1270                1275 gcg gta acc aag ggc gca ctt gac agc tcc aca atg gaa atc aaa        3879
Ala Val Thr Lys Gly Ala Leu Asp Ser Ser Thr Met Glu Ile Lys
    1280            1285                1290 cac ttt gtg gga gag gtc tac tcc cgg atc gca gac ttt cct caa        3924
His Phe Val Gly Glu Val Tyr Ser Arg Ile Ala Asp Phe Pro Gln
    1295            1300                1305 atc gtc aac acg gtg cat tcg gct ggt tat gac gta ttt ctt gag        3969
Ile Val Asn Thr Val His Ser Ala Gly Tyr Asp Val Phe Leu Glu
    1310            1315                1320 ctt ggc tgt gat gct tct aga tct gca gca gtt caa aac att ctt        4014
Leu Gly Cys Asp Ala Ser Arg Ser Ala Ala Val Gln Asn Ile Leu
    1325            1330                1335 ggt ggt caa gga aag ttc ttg tct aca gct att gac aaa aaa gga        4059
Gly Gly Gln Gly Lys Phe Leu Ser Thr Ala Ile Asp Lys Lys Gly
    1340            1345                1350 cac tcc gcc tgg tca caa gta ctt cgg gct acc gca tca tta gct        4104
His Ser Ala Trp Ser Gln Val Leu Arg Ala Thr Ala Ser Leu Ala
    1355            1360                1365 gca cat cga gta ccg gga atc tca att ttg gat ttg ttt cac cca        4149
Ala His Arg Val Pro Gly Ile Ser Ile Leu Asp Leu Phe His Pro
    1370            1375                1380 aat ttc cga gaa atg tgc tgt aca atg gca acc aca cct aaa gtg        4194
Asn Phe Arg Glu Met Cys Cys Thr Met Ala Thr Thr Pro Lys Val
    1385            1390                1395 gaa gat aag ttc ctg cgc acg att caa atc aat ggt cgg ttt gaa        4239
Glu Asp Lys Phe Leu Arg Thr Ile Gln Ile Asn Gly Arg Phe Glu
    1400            1405                1410 aaa gaa atg att cac cta gaa gat aca aca tta agt tgc tta ccc        4284
Lys Glu Met Ile His Leu Glu Asp Thr Thr Leu Ser Cys Leu Pro
    1415            1420                1425 gct cca agt gaa gca aat atc gca gct att caa tct cgg tca att        4329
Ala Pro Ser Glu Ala Asn Ile Ala Ala Ile Gln Ser Arg Ser Ile
    1430            1435                1440 cga tct gct gcg gcg cgt tct gga caa tcc cat gat tgt gca tcc        4374
Arg Ser Ala Ala Ala Arg Ser Gly Gln Ser His Asp Cys Ala Ser
    1445            1450                1455 cat agc cat gaa gaa aat aag gat tca tgc cct gaa aag ctg aag        4419
His Ser His Glu Glu Asn Lys Asp Ser Cys Pro Glu Lys Leu Lys
    1460            1465                1470 ctt gat tct gtg tcc gtc gcc ata aat ttc gac aat gat gac cgc        4464
Leu Asp Ser Val Ser Val Ala Ile Asn Phe Asp Asn Asp Asp Arg
```

-continued

|  |  |  |  |  |  |  |  |  |  |  |  |  |  |  |
|---|---|---|---|---|---|---|---|---|---|---|---|---|---|---|
|  | 1475 |  |  |  | 1480 |  |  |  | 1485 |  |  |  |  |  |
| att<br>Ile | cag<br>Gln | ctt<br>Leu<br>1490 | ggg<br>Gly | cac<br>His | gcg<br>Ala | ggt<br>Gly<br>1495 | ttt<br>Phe | cgg<br>Arg | gag<br>Glu | atg<br>Met<br>1500 | tac<br>Tyr | aat<br>Asn | aca<br>Thr | aga<br>Arg | 4509 |
| tat<br>Tyr | agc<br>Ser<br>1505 | ttg<br>Leu | tac<br>Tyr | aca<br>Thr | ggg<br>Gly<br>1510 | gcg<br>Ala | atg<br>Met | gca<br>Ala | aag<br>Lys<br>1515 | gga<br>Gly | att<br>Ile | gca<br>Ala | tct<br>Ser | gca<br>Ala | 4554 |
| gat<br>Asp | ctt<br>Leu<br>1520 | gtc<br>Val | att<br>Ile | gcc<br>Ala | gct<br>Ala<br>1525 | ggg<br>Gly | aaa<br>Lys | gag<br>Glu | ggc<br>Gly<br>1530 | atc<br>Ile | cta<br>Leu | gct<br>Ala | tcc<br>Ser | tat<br>Tyr | 4599 |
| gga<br>Gly | gct<br>Ala<br>1535 | gga<br>Gly | gga<br>Gly | cta<br>Leu | cct<br>Pro<br>1540 | ctt<br>Leu | gct<br>Ala | act<br>Thr | gtt<br>Val<br>1545 | cga<br>Arg | aag<br>Lys | gga<br>Gly | ata<br>Ile | gac<br>Asp | 4644 |
| aaa<br>Lys | att<br>Ile<br>1550 | caa<br>Gln | caa<br>Gln | gcc<br>Ala | ttg<br>Leu<br>1555 | cca<br>Pro | agt<br>Ser | ggc<br>Gly | cca<br>Pro<br>1560 | tat<br>Tyr | gct<br>Ala | gta<br>Val | aat<br>Asn | ctt<br>Leu | 4689 |
| att<br>Ile | cac<br>His<br>1565 | tct<br>Ser | ccc<br>Pro | ttt<br>Phe | gac<br>Asp<br>1570 | ggc<br>Gly | aac<br>Asn | ttg<br>Leu | gag<br>Glu<br>1575 | cag<br>Gln | gga<br>Gly | aac<br>Asn | gtc<br>Val | gat<br>Asp | 4734 |
| ttg<br>Leu | ttc<br>Phe<br>1580 | ttg<br>Leu | gaa<br>Glu | aag<br>Lys | aac<br>Asn<br>1585 | gtc<br>Val | cgc<br>Arg | gtg<br>Val | gcg<br>Ala<br>1590 | gaa<br>Glu | tgt<br>Cys | tcc<br>Ser | gcg<br>Ala | ttt<br>Phe | 4779 |
| aca<br>Thr | acg<br>Thr<br>1595 | cta<br>Leu | aca<br>Thr | gtg<br>Val | cca<br>Pro<br>1600 | gta<br>Val | cac<br>His | tat<br>Tyr | cgt<br>Arg<br>1605 | gct<br>Ala | gca<br>Ala | ggg<br>Gly | ctt<br>Leu |  | 4824 |
| gtt<br>Val | cgg<br>Arg<br>1610 | cgc<br>Arg | caa<br>Gln | gat<br>Asp | gga<br>Gly<br>1615 | agc<br>Ser | att<br>Ile | ttg<br>Leu | atc<br>Ile<br>1620 | aag<br>Lys | aac<br>Asn | cga<br>Arg | atc<br>Ile | att<br>Ile | 4869 |
| gct<br>Ala | aaa<br>Lys<br>1625 | gta<br>Val | tct<br>Ser | agg<br>Arg | aca<br>Thr<br>1630 | gaa<br>Glu | ctc<br>Leu | gct<br>Ala | gag<br>Glu<br>1635 | atg<br>Met | ttc<br>Phe | ctt<br>Leu | cgt<br>Arg | ccg<br>Pro | 4914 |
| gca<br>Ala | cct<br>Pro<br>1640 | caa<br>Gln | atc<br>Ile | atc<br>Ile | ctc<br>Leu<br>1645 | gaa<br>Glu | aaa<br>Lys | ctg<br>Leu | gta<br>Val<br>1650 | gca<br>Ala | gca<br>Ala | gaa<br>Glu | atc<br>Ile | att<br>Ile | 4959 |
| tca<br>Ser | tct<br>Ser<br>1655 | gac<br>Asp | caa<br>Gln | gcg<br>Ala | cgt<br>Arg<br>1660 | atg<br>Met | gca<br>Ala | gcc<br>Ala | aaa<br>Lys<br>1665 | gtt<br>Val | ccc<br>Pro | atg<br>Met | gcg<br>Ala | gac<br>Asp | 5004 |
| gac<br>Asp | atc<br>Ile<br>1670 | gca<br>Ala | gtc<br>Val | gaa<br>Glu | gcc<br>Ala<br>1675 | gac<br>Asp | tct<br>Ser | ggt<br>Gly | ggg<br>Gly<br>1680 | cac<br>His | acg<br>Thr | gat<br>Asp | aat<br>Asn | cgg<br>Arg | 5049 |
| cct<br>Pro | atg<br>Met<br>1685 | cac<br>His | gtc<br>Val | att<br>Ile | ttg<br>Leu<br>1690 | ccc<br>Pro | ctg<br>Leu | ata<br>Ile | att<br>Ile<br>1695 | caa<br>Gln | ctc<br>Leu | cgc<br>Arg | aat<br>Asn | act<br>Thr | 5094 |
| ata<br>Ile | ctt<br>Leu<br>1700 | gca<br>Ala | gag<br>Glu | tat<br>Tyr | ggc<br>Gly<br>1705 | tgt<br>Cys | gcc<br>Ala | acg<br>Thr | gct<br>Ala<br>1710 | ttt<br>Phe | cgt<br>Arg | acc<br>Thr | cgt<br>Arg | ata<br>Ile | 5139 |
| ggc<br>Gly | gct<br>Ala<br>1715 | gga<br>Gly | gga<br>Gly | ggc<br>Gly | att<br>Ile<br>1720 | ggt<br>Gly | tgt<br>Cys | cct<br>Pro | tca<br>Ser<br>1725 | gcg<br>Ala | gcc<br>Ala | ctc<br>Leu | gca<br>Ala | gcc<br>Ala | 5184 |
| ttt<br>Phe | gat<br>Asp<br>1730 | atg<br>Met | ggt<br>Gly | gcg<br>Ala | agt<br>Ser<br>1735 | ttt<br>Phe | gtc<br>Val | gtg<br>Val | act<br>Thr<br>1740 | gga<br>Gly | agc<br>Ser | ata<br>Ile | aat<br>Asn | caa<br>Gln | 5229 |
| att<br>Ile | tgc<br>Cys<br>1745 | cgc<br>Arg | gag<br>Glu | gca<br>Ala | ggg<br>Gly<br>1750 | act<br>Thr | tgc<br>Cys | gat<br>Asp | act<br>Thr<br>1755 | gtt<br>Val | cgg<br>Arg | gag<br>Glu | cta<br>Leu | ctt<br>Leu | 5274 |
| gcc<br>Ala | aac<br>Asn<br>1760 | tca<br>Ser | agc<br>Ser | tac<br>Tyr | tcg<br>Ser<br>1765 | gac<br>Asp | gtg<br>Val | acg<br>Thr | atg<br>Met<br>1770 | gcg<br>Ala | cca<br>Pro | gca<br>Ala | gca<br>Ala | gac<br>Asp | 5319 |
| atg<br>Met | ttt<br>Phe | gac<br>Asp | caa<br>Gln | ggt<br>Gly | gtg<br>Val | aaa<br>Lys | ctc<br>Leu | caa<br>Gln | gtc<br>Val | tta<br>Leu | aaa<br>Lys | cga<br>Arg | gga<br>Gly | acg<br>Thr | 5364 |

-continued

```
atg ttt cca agc aga gca aat aaa ctc cgg aag ctc ttt gtg aac      5409
Met Phe Pro Ser Arg Ala Asn Lys Leu Arg Lys Leu Phe Val Asn
    1775                1780                1785 atg ttt cca agc aga gca aat aaa ctc cgg aag ctc ttt gtg aac      5409
Met Phe Pro Ser Arg Ala Asn Lys Leu Arg Lys Leu Phe Val Asn
    1790                1795                1800 tac gaa tct cta gaa aca ctc ccg tcg aaa gag ttg aaa tac ctg      5454
Tyr Glu Ser Leu Glu Thr Leu Pro Ser Lys Glu Leu Lys Tyr Leu
    1805                1810                1815 gaa aac atc ata ttc aag caa gca gta gac cag gtg tgg gag gaa      5499
Glu Asn Ile Ile Phe Lys Gln Ala Val Asp Gln Val Trp Glu Glu
    1820                1825                1830 aca aag cgc ttt tac tgt gaa aaa ctg aac aat cca gat aaa att      5544
Thr Lys Arg Phe Tyr Cys Glu Lys Leu Asn Asn Pro Asp Lys Ile
    1835                1840                1845 gca agg gcc atg aaa gat cct aaa ttg aag atg tcg ctt tgc ttt      5589
Ala Arg Ala Met Lys Asp Pro Lys Leu Lys Met Ser Leu Cys Phe
    1850                1855                1860 cgg tgg tat ctc tcc aag agc tct ggg tgg gcc aac gca gga att      5634
Arg Trp Tyr Leu Ser Lys Ser Ser Gly Trp Ala Asn Ala Gly Ile
    1865                1870                1875 aaa tct cgt gca ctc gac tac cag atc tgg tgt ggc ccg gca atg      5679
Lys Ser Arg Ala Leu Asp Tyr Gln Ile Trp Cys Gly Pro Ala Met
    1880                1885                1890 ggc tcg ttc aac aat ttc gcc agc ggc aca tcc ctc gat tgg aaa      5724
Gly Ser Phe Asn Asn Phe Ala Ser Gly Thr Ser Leu Asp Trp Lys
    1895                1900                1905 gtg act ggg gtt ttc cct ggc gtt gcg gaa gta aac atg gcc att      5769
Val Thr Gly Val Phe Pro Gly Val Ala Glu Val Asn Met Ala Ile
    1910                1915                1920 tta gat ggc gcg cga gaa cta gct gct aaa cga aat taa              5808
Leu Asp Gly Ala Arg Glu Leu Ala Ala Lys Arg Asn
    1925                1930                1935

<210> SEQ ID NO 52
<211> LENGTH: 1935
<212> TYPE: PRT
<213> ORGANISM: Thraustochytrium sp.
<220> FEATURE:
<221> NAME/KEY: misc_feature
<222> LOCATION: (248)..(248)
<223> OTHER INFORMATION: The 'Xaa' at location 248 stands for Asp, Gly,
      Ala, or Val.

<400> SEQUENCE: 52

Met Gln Leu Pro Pro Ala His Ser Ala Asp Glu Asn Arg Ile Ala Val
1               5                   10                  15

Val Gly Met Ala Val Lys Tyr Ala Gly Cys Asp Asn Lys Glu Glu Phe
            20                  25                  30

Trp Lys Thr Leu Met Asn Gly Ser Ile Asn Thr Lys Ser Ile Ser Ala
        35                  40                  45

Ala Arg Leu Gly Ser Asn Lys Arg Asp Glu His Tyr Val Pro Glu Arg
    50                  55                  60

Ser Lys Tyr Ala Asp Thr Phe Cys Asn Glu Arg Tyr Gly Cys Ile Gln
65                  70                  75                  80

Gln Gly Thr Asp Asn Glu His Asp Leu Leu Leu Gly Leu Ala Gln Glu
                85                  90                  95

Ala Leu Ala Asp Ala Ala Gly Arg Met Glu Lys Gln Pro Ser Glu Ala
            100                 105                 110

Phe Asp Leu Glu Asn Thr Gly Ile Val Ser Gly Cys Leu Ser Phe Pro
        115                 120                 125
```

```
Met Asp Asn Leu Gln Gly Glu Leu Leu Asn Leu Tyr Gln Ser His Val
130                 135                 140

Glu Lys Gln Leu Pro Pro Ser Ala Leu Val Glu Ala Val Lys Leu Trp
145                 150                 155                 160

Ser Glu Arg Gln Lys Ser Thr Lys Ala His Ala Gly Asp Lys Arg Arg
                165                 170                 175

Phe Ile Asp Pro Ala Ser Phe Val Ala Asp Lys Leu Asn Leu Gly Pro
                180                 185                 190

Leu His Tyr Ala Ile Asp Ala Ala Cys Ala Ser Ala Leu Tyr Val Leu
            195                 200                 205

Lys Leu Ala Gln Asp His Leu Val Ser Gly Ala Val Asp Met Met Leu
210                 215                 220

Cys Gly Ala Thr Cys Phe Pro Glu Pro Phe Ile Leu Ser Gly Phe
225                 230                 235                 240

Ser Thr Phe Gln Ala Met Pro Xaa Gly Ala Asp Gly Val Ser Leu Pro
                245                 250                 255

Leu His Lys Thr Ser Ala Gly Leu Thr Pro Gly Glu Gly Ser Ile
                260                 265                 270

Met Val Leu Lys Arg Leu Lys Asp Ala Ile Arg Asp Gly Asn His Ile
            275                 280                 285

Tyr Gly Val Leu Leu Glu Ala Asn Leu Ser Asn Ala Gly Cys Gly Leu
290                 295                 300

Pro Leu Ser Pro His Leu Pro Ser Glu Glu Ser Cys Ile Arg Asp Thr
305                 310                 315                 320

Tyr Arg Arg Ala Gly Val Ala Ala Asp Gln Ser Ile Gln Tyr Ile Glu
                325                 330                 335

Cys His Ala Thr Gly Thr Pro Arg Gly Asp Val Val Glu Ile Glu Ala
                340                 345                 350

Val Glu Arg Val Phe Lys Lys Asn Val Pro Arg Leu Gly Ser Thr Lys
            355                 360                 365

Gly Asn Phe Gly His Ser Leu Val Ala Ala Gly Phe Ala Gly Met Ala
370                 375                 380

Lys Leu Leu Leu Ala Met Glu His Gly Val Ile Pro Pro Thr Pro Gly
385                 390                 395                 400

Leu Asp Ala Ser Asn Gln Ala Ser Glu His Val Val Thr Lys Ala Ile
                405                 410                 415

Thr Trp Pro Glu Thr His Gly Ala Pro Lys Arg Ala Gly Leu Ser Ala
                420                 425                 430

Phe Gly Phe Gly Gly Thr Asn Ala His Ala Leu Phe Glu Glu Phe Asn
            435                 440                 445

Ala Glu Gly Ile Ser Tyr Arg Pro Gly Lys Pro Pro Val Glu Ser Asn
450                 455                 460

Thr Arg Pro Ser Val Val Ile Thr Gly Met Asp Cys Thr Phe Gly Ser
465                 470                 475                 480

Leu Glu Gly Ile Asp Ala Phe Glu Thr Ala Leu Tyr Glu Gly Arg Asp
                485                 490                 495

Ala Ala Arg Asp Leu Pro Ala Lys Arg Trp Arg Phe Leu Gly Glu Asp
                500                 505                 510

Leu Glu Phe Leu Arg Ala Ile Arg Leu Lys Glu Lys Pro Arg Gly Cys
            515                 520                 525

Phe Val Glu Ser Val Asp Val Asn Phe Arg Arg Leu Lys Thr Pro Leu
530                 535                 540
```

-continued

```
Thr Pro Glu Asp Met Leu Arg Pro Gln Gln Leu Leu Ala Val Ser Thr
545                 550                 555                 560

Met Asp Arg Ala Ile Ile Asp Ala Gly Leu Lys Lys Gly Gln His Val
            565                 570                 575

Ala Val Leu Val Gly Leu Gly Thr Asp Leu Glu Leu Tyr Arg His Arg
        580                 585                 590

Ala Arg Val Ala Leu Lys Glu Val Leu His Pro Ser Leu Lys Ser Asp
    595                 600                 605

Thr Ala Ile Leu Gln Lys Ile Met Gln Tyr Val Asn Asp Ala Gly Thr
610                 615                 620

Ser Thr Ser Tyr Thr Ser Tyr Ile Gly Asn Leu Val Ala Thr Arg Ile
625                 630                 635                 640

Ser Ser Gln Trp Gly Phe Thr Gly Pro Ser Phe Thr Val Thr Glu Gly
            645                 650                 655

Asn Asn Ser Val Tyr Arg Cys Ala Gln Leu Ala Lys Asp Met Leu Gln
        660                 665                 670

Val Asn Arg Val Asp Ala Val Ile Ala Gly Val Asp Leu Asn Gly
    675                 680                 685

Ser Ala Glu Ser Phe Phe Val Arg Ala Asn Arg Gln Lys Ile Ser Lys
690                 695                 700

Leu Ser His Pro Cys Ala Ser Phe Asp Arg Asp Ala Asp Gly Phe Phe
705                 710                 715                 720

Ala Gly Glu Gly Cys Gly Ala Leu Val Phe Lys Arg Leu Glu Asp Cys
            725                 730                 735

Ala Pro Gln Glu Lys Ile Tyr Ala Ser Ile Asp Ser Ile Ala Ile Asp
        740                 745                 750

Lys Glu Pro Thr Ser Ser Ala Val Lys Ala Val Tyr Gln Ser Asp Ser
    755                 760                 765

Ser Leu Ser Asp Ile Glu Leu Leu Glu Ile Ser Gly Asp Ser Lys Arg
770                 775                 780

Phe Ala Ala Phe Glu Gly Ala Val Glu Ile Gln Ser Ser Val Glu Ala
785                 790                 795                 800

Gln Leu Lys Gly Leu Ser Lys Val Leu Glu Pro Ala Lys Gly Gln Gly
            805                 810                 815

Val Ala Val Gly Ser Thr Arg Ala Thr Val Gly Asp Ile Gly Tyr Ala
        820                 825                 830

Thr Gly Ala Ala Ser Leu Ile Lys Thr Ala Leu Cys Leu Tyr Asn Arg
    835                 840                 845

Tyr Leu Pro Ala Leu Ala Asn Trp Ser Gly Pro Cys Glu Gln Ser Ala
850                 855                 860

Trp Gly Ser Asn Met Phe Val Cys His Glu Thr Arg Pro Trp Met Lys
865                 870                 875                 880

Asn Gln Asn Glu Lys Arg Cys Ala Leu Ile Ser Gly Thr Asp Pro Ser
            885                 890                 895

His Thr Cys Phe Ser Leu Val Leu Ser Asp Thr Gly Cys Tyr Glu Glu
        900                 905                 910

His Asn Arg Thr Cys Phe Asp Val Gln Ala Pro Gln Leu Val Leu Ile
    915                 920                 925

His Gly Phe Asp Gly Lys Thr Ile Val Arg Arg Leu Glu Gly Tyr Leu
930                 935                 940

Leu Glu Leu Val Glu Gly His Ala Ser Pro Ser Glu Tyr Phe His Lys
945                 950                 955                 960

Leu Ile Gly Gln Ser Leu Leu Glu Asn Ser Lys Glu Ser Lys Leu Thr
```

-continued

```
                965                 970                 975
Leu Ser Leu Val Cys Asn Pro Asn Gln Leu Gln Lys Glu Leu Met Leu
            980                 985                 990
Ala Ile Lys Gly Val Gln Arg Ser Met Leu Thr Gly Lys Asp Trp Val
            995                 1000                1005
Ser Pro Ser Gly Ser Cys Phe Ala Pro Asn Pro Leu Ser Ser Ala
        1010                1015                1020
Lys Val Ala Phe Met Tyr Gly Glu Gly Arg Ser Pro Tyr Cys Gly
        1025                1030                1035
Val Gly Leu Gly Leu His Arg Leu Trp Pro Gly Leu His Glu Asn
        1040                1045                1050
Val Asn Asn Lys Thr Val Asp Leu Trp Thr Glu Gly Asp Gly Trp
        1055                1060                1065
Leu Tyr Pro Arg Thr Leu Thr Arg Glu Glu His Thr Lys Ala Ile
        1070                1075                1080
Glu Ser Phe Asn Ala Asn Gln Ile Glu Met Phe Arg Ala Gly Ile
        1085                1090                1095
Phe Ile Ser Met Cys Gln Thr Asp Tyr Val Met Asn Val Leu Gly
        1100                1105                1110
Val Gln Pro Lys Ala Gly Phe Gly Leu Ser Leu Gly Glu Ile Ser
        1115                1120                1125
Met Leu Phe Ala Met Ser Lys Glu Asn Cys Arg Gln Ser Gln Glu
        1130                1135                1140
Met Thr Asn Arg Leu Arg Gly Ser Pro Val Trp Ser Asn Glu Leu
        1145                1150                1155
Ala Ile Asn Phe Asn Ala Ile Arg Lys Leu Trp Lys Ile Pro Arg
        1160                1165                1170
Gly Ala Pro Leu Glu Ser Phe Trp Gln Gly Tyr Leu Val His Gly
        1175                1180                1185
Thr Arg Glu Glu Val Glu His Ala Ile Gly Leu Ser Glu Pro Tyr
        1190                1195                1200
Val Arg Leu Leu Ile Val Asn Asp Ser Arg Ser Ala Leu Ile Ala
        1205                1210                1215
Gly Lys Pro Asp Ala Cys Gln Ala Val Ile Ser Arg Leu Asn Ser
        1220                1225                1230
Lys Phe Pro Ser Leu Pro Val Lys Gln Gly Met Ile Gly His Cys
        1235                1240                1245
Pro Glu Val Arg Ala Phe Ile Lys Asp Ile Gly Tyr Ile His Glu
        1250                1255                1260
Thr Leu Arg Ile Ser Asn Asp Tyr Ser Asp Cys Gln Leu Phe Ser
        1265                1270                1275
Ala Val Thr Lys Gly Ala Leu Asp Ser Ser Thr Met Glu Ile Lys
        1280                1285                1290
His Phe Val Gly Glu Val Tyr Ser Arg Ile Ala Asp Phe Pro Gln
        1295                1300                1305
Ile Val Asn Thr Val His Ser Ala Gly Tyr Asp Val Phe Leu Glu
        1310                1315                1320
Leu Gly Cys Asp Ala Ser Arg Ser Ala Ala Val Gln Asn Ile Leu
        1325                1330                1335
Gly Gly Gln Gly Lys Phe Leu Ser Thr Ala Ile Asp Lys Lys Gly
        1340                1345                1350
His Ser Ala Trp Ser Gln Val Leu Arg Ala Thr Ala Ser Leu Ala
        1355                1360                1365
```

-continued

```
Ala His Arg Val Pro Gly Ile Ser Ile Leu Asp Leu Phe His Pro
    1370                1375                1380

Asn Phe Arg Glu Met Cys Cys Thr Met Ala Thr Thr Pro Lys Val
    1385                1390                1395

Glu Asp Lys Phe Leu Arg Thr Ile Gln Ile Asn Gly Arg Phe Glu
    1400                1405                1410

Lys Glu Met Ile His Leu Glu Asp Thr Thr Leu Ser Cys Leu Pro
    1415                1420                1425

Ala Pro Ser Glu Ala Asn Ile Ala Ala Ile Gln Ser Arg Ser Ile
    1430                1435                1440

Arg Ser Ala Ala Ala Arg Ser Gly Gln Ser His Asp Cys Ala Ser
    1445                1450                1455

His Ser His Glu Glu Asn Lys Asp Ser Cys Pro Glu Lys Leu Lys
    1460                1465                1470

Leu Asp Ser Val Ser Val Ala Ile Asn Phe Asp Asn Asp Asp Arg
    1475                1480                1485

Ile Gln Leu Gly His Ala Gly Phe Arg Glu Met Tyr Asn Thr Arg
    1490                1495                1500

Tyr Ser Leu Tyr Thr Gly Ala Met Ala Lys Gly Ile Ala Ser Ala
    1505                1510                1515

Asp Leu Val Ile Ala Ala Gly Lys Glu Gly Ile Leu Ala Ser Tyr
    1520                1525                1530

Gly Ala Gly Gly Leu Pro Leu Ala Thr Val Arg Lys Gly Ile Asp
    1535                1540                1545

Lys Ile Gln Gln Ala Leu Pro Ser Gly Pro Tyr Ala Val Asn Leu
    1550                1555                1560

Ile His Ser Pro Phe Asp Gly Asn Leu Glu Gln Gly Asn Val Asp
    1565                1570                1575

Leu Phe Leu Glu Lys Asn Val Arg Val Ala Glu Cys Ser Ala Phe
    1580                1585                1590

Thr Thr Leu Thr Val Pro Val His Tyr Arg Ala Ala Gly Leu
    1595                1600                1605

Val Arg Arg Gln Asp Gly Ser Ile Leu Ile Lys Asn Arg Ile Ile
    1610                1615                1620

Ala Lys Val Ser Arg Thr Glu Leu Ala Glu Met Phe Leu Arg Pro
    1625                1630                1635

Ala Pro Gln Ile Ile Leu Glu Lys Leu Val Ala Ala Glu Ile Ile
    1640                1645                1650

Ser Ser Asp Gln Ala Arg Met Ala Ala Lys Val Pro Met Ala Asp
    1655                1660                1665

Asp Ile Ala Val Glu Ala Asp Ser Gly Gly His Thr Asp Asn Arg
    1670                1675                1680

Pro Met His Val Ile Leu Pro Leu Ile Ile Gln Leu Arg Asn Thr
    1685                1690                1695

Ile Leu Ala Glu Tyr Gly Cys Ala Thr Ala Phe Arg Thr Arg Ile
    1700                1705                1710

Gly Ala Gly Gly Gly Ile Gly Cys Pro Ser Ala Ala Leu Ala Ala
    1715                1720                1725

Phe Asp Met Gly Ala Ser Phe Val Val Thr Gly Ser Ile Asn Gln
    1730                1735                1740

Ile Cys Arg Glu Ala Gly Thr Cys Asp Thr Val Arg Glu Leu Leu
    1745                1750                1755
```

```
Ala Asn Ser Ser Tyr Ser Asp Val Thr Met Ala Pro Ala Ala Asp
        1760                1765                1770

Met Phe Asp Gln Gly Val Lys Leu Gln Val Leu Lys Arg Gly Thr
1775                1780                1785

Met Phe Pro Ser Arg Ala Asn Lys Leu Arg Lys Leu Phe Val Asn
1790                1795                1800

Tyr Glu Ser Leu Glu Thr Leu Pro Ser Lys Glu Leu Lys Tyr Leu
1805                1810                1815

Glu Asn Ile Ile Phe Lys Gln Ala Val Asp Gln Val Trp Glu Glu
1820                1825                1830

Thr Lys Arg Phe Tyr Cys Glu Lys Leu Asn Asn Pro Asp Lys Ile
1835                1840                1845

Ala Arg Ala Met Lys Asp Pro Lys Leu Lys Met Ser Leu Cys Phe
1850                1855                1860

Arg Trp Tyr Leu Ser Lys Ser Ser Gly Trp Ala Asn Ala Gly Ile
1865                1870                1875

Lys Ser Arg Ala Leu Asp Tyr Gln Ile Trp Cys Gly Pro Ala Met
1880                1885                1890

Gly Ser Phe Asn Asn Phe Ala Ser Gly Thr Ser Leu Asp Trp Lys
1895                1900                1905

Val Thr Gly Val Phe Pro Gly Val Ala Glu Val Asn Met Ala Ile
1910                1915                1920

Leu Asp Gly Ala Arg Glu Leu Ala Ala Lys Arg Asn
1925                1930                1935

<210> SEQ ID NO 53
<211> LENGTH: 1500
<212> TYPE: DNA
<213> ORGANISM: Thraustochytrium sp.
<220> FEATURE:
<221> NAME/KEY: CDS
<222> LOCATION: (1)..(1500)
<220> FEATURE:
<221> NAME/KEY: misc_feature
<222> LOCATION: (1)..(1500)
<223> OTHER INFORMATION: n = a c t or g

<400> SEQUENCE: 53 atg caa ctt cct cca gcg cat tct gcc gat gag aat cgc atc gcg gtc     48
Met Gln Leu Pro Pro Ala His Ser Ala Asp Glu Asn Arg Ile Ala Val
1               5                   10                  15 gtg ggc atg gcc gtc aaa tat gcg ggc tgt gac aat aaa gaa gag ttt     96
Val Gly Met Ala Val Lys Tyr Ala Gly Cys Asp Asn Lys Glu Glu Phe
            20                  25                  30 tgg aag act ttg atg aat ggt agt atc aat acc aag tcg att tcg gca    144
Trp Lys Thr Leu Met Asn Gly Ser Ile Asn Thr Lys Ser Ile Ser Ala
        35                  40                  45 gca agg ttg ggc agc aat aag cgt gac gaa cac tat gtt cct gaa cga    192
Ala Arg Leu Gly Ser Asn Lys Arg Asp Glu His Tyr Val Pro Glu Arg
    50                  55                  60 tcg aaa tat gca gat acg ttc tgt aac gaa agg tac ggt tgt atc cag    240
Ser Lys Tyr Ala Asp Thr Phe Cys Asn Glu Arg Tyr Gly Cys Ile Gln
65                  70                  75                  80 caa ggt acg gat aat gag cat gac ctc ctc cta ggt ctt gct caa gaa    288
Gln Gly Thr Asp Asn Glu His Asp Leu Leu Leu Gly Leu Ala Gln Glu
                85                  90                  95 gct ctc gct gac gct gcc ggg cgg atg gag aaa caa cct tcg gag gcg    336
Ala Leu Ala Asp Ala Ala Gly Arg Met Glu Lys Gln Pro Ser Glu Ala
            100                 105                 110
```

-continued

| | |
|---|---|
| ttc gat ctg gaa aat act ggc atc gtg agt ggg tgc tta tct ttt cca<br>Phe Asp Leu Glu Asn Thr Gly Ile Val Ser Gly Cys Leu Ser Phe Pro<br>115                 120                 125 | 384 |
| atg gat aac ctg caa gga gag ttg ttg aac ttg tat caa agc cat gtg<br>Met Asp Asn Leu Gln Gly Glu Leu Leu Asn Leu Tyr Gln Ser His Val<br>130                 135                 140 | 432 |
| gag aaa caa ctt cca cct agt gcc ttg gta gaa gcc gtg aag ctt tgg<br>Glu Lys Gln Leu Pro Pro Ser Ala Leu Val Glu Ala Val Lys Leu Trp<br>145                 150                 155                 160 | 480 |
| tct gag cga cag aaa tct acg aaa gca cat gca ggg gac aag cgc cgg<br>Ser Glu Arg Gln Lys Ser Thr Lys Ala His Ala Gly Asp Lys Arg Arg<br>165                 170                 175 | 528 |
| ttc att gac cca gct tct ttt gta gct gat aaa ctg aac cta ggc cca<br>Phe Ile Asp Pro Ala Ser Phe Val Ala Asp Lys Leu Asn Leu Gly Pro<br>180                 185                 190 | 576 |
| cta cat tat gcg atc gat gca gca tgc gct tct gca ttg tac gtg tta<br>Leu His Tyr Ala Ile Asp Ala Ala Cys Ala Ser Ala Leu Tyr Val Leu<br>195                 200                 205 | 624 |
| aaa tta gct caa gac cac ctt gtt tca ggt gcc gtt gat atg atg tta<br>Lys Leu Ala Gln Asp His Leu Val Ser Gly Ala Val Asp Met Met Leu<br>210                 215                 220 | 672 |
| tgt gga gcg acg tgc ttc cca gaa cca ttc ttc atc ttg tct ggg ttc<br>Cys Gly Ala Thr Cys Phe Pro Glu Pro Phe Phe Ile Leu Ser Gly Phe<br>225                 230                 235                 240 | 720 |
| tcg act ttt caa gcg atg cct gnt ggg gca gat gga gtc tca cta cct<br>Ser Thr Phe Gln Ala Met Pro Xaa Gly Ala Asp Gly Val Ser Leu Pro<br>245                 250                 255 | 768 |
| ctc cat aaa acg agt gct ggg ctc act cca ggt gaa ggg ggg tcc att<br>Leu His Lys Thr Ser Ala Gly Leu Thr Pro Gly Glu Gly Gly Ser Ile<br>260                 265                 270 | 816 |
| atg gtg ctc aag cga ctg aaa gac gct atc aga gat gga aat cac att<br>Met Val Leu Lys Arg Leu Lys Asp Ala Ile Arg Asp Gly Asn His Ile<br>275                 280                 285 | 864 |
| tat ggt gtg ctc ctt gaa gca aat tta agt aac gca ggt tgt ggg ctt<br>Tyr Gly Val Leu Leu Glu Ala Asn Leu Ser Asn Ala Gly Cys Gly Leu<br>290                 295                 300 | 912 |
| cca ctc agc ccg cac tta ccg agc gaa gaa tca tgt att cgt gat acc<br>Pro Leu Ser Pro His Leu Pro Ser Glu Glu Ser Cys Ile Arg Asp Thr<br>305                 310                 315                 320 | 960 |
| tac cgc cgt gct gga gtt gct gca gat caa agt att cag tat att gag<br>Tyr Arg Arg Ala Gly Val Ala Ala Asp Gln Ser Ile Gln Tyr Ile Glu<br>325                 330                 335 | 1008 |
| tgc cac gct acg gga acc cct cga ggg gat gtc gtg gaa att gag gcg<br>Cys His Ala Thr Gly Thr Pro Arg Gly Asp Val Val Glu Ile Glu Ala<br>340                 345                 350 | 1056 |
| gtt gaa aga gtt ttc aag aaa aac gtt cca cgc tta ggc tcg acg aaa<br>Val Glu Arg Val Phe Lys Lys Asn Val Pro Arg Leu Gly Ser Thr Lys<br>355                 360                 365 | 1104 |
| gga aat ttt ggt cac tcg tta gtt gcg gct ggt ttc gca ggt atg gca<br>Gly Asn Phe Gly His Ser Leu Val Ala Ala Gly Phe Ala Gly Met Ala<br>370                 375                 380 | 1152 |
| aag ctt ctt ctt gca atg gaa cat gga gtg att cct ccc aca cca ggt<br>Lys Leu Leu Leu Ala Met Glu His Gly Val Ile Pro Pro Thr Pro Gly<br>385                 390                 395                 400 | 1200 |
| ctt gat gct tcg aac cag gca agt gag cac gtt gtg aca aag gct atc<br>Leu Asp Ala Ser Asn Gln Ala Ser Glu His Val Val Thr Lys Ala Ile<br>405                 410                 415 | 1248 |
| act tgg cct gag aca cat ggg gct cca aaa cga gct ggc ctt tca gca<br>Thr Trp Pro Glu Thr His Gly Ala Pro Lys Arg Ala Gly Leu Ser Ala<br>420                 425                 430 | 1296 |

-continued

```
ttt gga ttt ggt ggg act aat gcg cat gca ctc ttc gaa gag ttt aat    1344
Phe Gly Phe Gly Gly Thr Asn Ala His Ala Leu Phe Glu Glu Phe Asn
            435                 440                 445 gcc gag ggc ata agt tat cgc cct gga aag cct cca gtc gaa tcg aat    1392
Ala Glu Gly Ile Ser Tyr Arg Pro Gly Lys Pro Pro Val Glu Ser Asn
450                 455                 460 acc cgt cct tcc gtc gta ata act ggg atg gac tgt acc ttt ggg agc    1440
Thr Arg Pro Ser Val Val Ile Thr Gly Met Asp Cys Thr Phe Gly Ser
465                 470                 475                 480 ctt gaa ggg att gat gcg ttc gag act gcc ctg tac gag ggg cgt gac    1488
Leu Glu Gly Ile Asp Ala Phe Glu Thr Ala Leu Tyr Glu Gly Arg Asp
                485                 490                 495 gca gct cgt gac                                                    1500
Ala Ala Arg Asp
            500
```

<210> SEQ ID NO 54
<211> LENGTH: 500
<212> TYPE: PRT
<213> ORGANISM: Thraustochytrium sp.
<220> FEATURE:
<221> NAME/KEY: misc_feature
<222> LOCATION: (248)..(248)
<223> OTHER INFORMATION: The 'Xaa' at location 248 stands for Asp, Gly, Ala, or Val.

<400> SEQUENCE: 54

```
Met Gln Leu Pro Pro Ala His Ser Ala Asp Glu Asn Arg Ile Ala Val
1               5                   10                  15

Val Gly Met Ala Val Lys Tyr Ala Gly Cys Asp Asn Lys Glu Glu Phe
            20                  25                  30

Trp Lys Thr Leu Met Asn Gly Ser Ile Asn Thr Lys Ser Ile Ser Ala
        35                  40                  45

Ala Arg Leu Gly Ser Asn Lys Arg Asp Glu His Tyr Val Pro Glu Arg
    50                  55                  60

Ser Lys Tyr Ala Asp Thr Phe Cys Asn Glu Arg Tyr Gly Cys Ile Gln
65                  70                  75                  80

Gln Gly Thr Asp Asn Glu His Asp Leu Leu Gly Leu Ala Gln Glu
                85                  90                  95

Ala Leu Ala Asp Ala Ala Gly Arg Met Glu Lys Gln Pro Ser Glu Ala
            100                 105                 110

Phe Asp Leu Glu Asn Thr Gly Ile Val Ser Gly Cys Leu Ser Phe Pro
        115                 120                 125

Met Asp Asn Leu Gln Gly Glu Leu Leu Asn Leu Tyr Gln Ser His Val
    130                 135                 140

Glu Lys Gln Leu Pro Pro Ser Ala Leu Val Glu Ala Val Lys Leu Trp
145                 150                 155                 160

Ser Glu Arg Gln Lys Ser Thr Lys Ala His Ala Gly Asp Lys Arg Arg
                165                 170                 175

Phe Ile Asp Pro Ala Ser Phe Val Ala Asp Lys Leu Asn Leu Gly Pro
            180                 185                 190

Leu His Tyr Ala Ile Asp Ala Ala Cys Ala Ser Ala Leu Tyr Val Leu
        195                 200                 205

Lys Leu Ala Gln Asp His Leu Val Ser Gly Ala Val Asp Met Met Leu
    210                 215                 220

Cys Gly Ala Thr Cys Phe Pro Glu Pro Phe Phe Ile Leu Ser Gly Phe
225                 230                 235                 240
```

```
Ser Thr Phe Gln Ala Met Pro Xaa Gly Ala Asp Gly Val Ser Leu Pro
                245                 250                 255

Leu His Lys Thr Ser Ala Gly Leu Thr Pro Gly Glu Gly Gly Ser Ile
            260                 265                 270

Met Val Leu Lys Arg Leu Lys Asp Ala Ile Arg Asp Gly Asn His Ile
        275                 280                 285

Tyr Gly Val Leu Leu Glu Ala Asn Leu Ser Asn Ala Gly Cys Gly Leu
    290                 295                 300

Pro Leu Ser Pro His Leu Pro Ser Glu Glu Ser Cys Ile Arg Asp Thr
305                 310                 315                 320

Tyr Arg Arg Ala Gly Val Ala Ala Asp Gln Ser Ile Gln Tyr Ile Glu
                325                 330                 335

Cys His Ala Thr Gly Thr Pro Arg Gly Asp Val Val Glu Ile Glu Ala
            340                 345                 350

Val Glu Arg Val Phe Lys Lys Asn Val Pro Arg Leu Gly Ser Thr Lys
        355                 360                 365

Gly Asn Phe Gly His Ser Leu Val Ala Ala Gly Phe Ala Gly Met Ala
    370                 375                 380

Lys Leu Leu Leu Ala Met Glu His Gly Val Ile Pro Pro Thr Pro Gly
385                 390                 395                 400

Leu Asp Ala Ser Asn Gln Ala Ser Glu His Val Val Thr Lys Ala Ile
                405                 410                 415

Thr Trp Pro Glu Thr His Gly Ala Pro Lys Arg Ala Gly Leu Ser Ala
            420                 425                 430

Phe Gly Phe Gly Gly Thr Asn Ala His Ala Leu Phe Glu Glu Phe Asn
        435                 440                 445

Ala Glu Gly Ile Ser Tyr Arg Pro Gly Lys Pro Pro Val Glu Ser Asn
    450                 455                 460

Thr Arg Pro Ser Val Val Ile Thr Gly Met Asp Cys Thr Phe Gly Ser
465                 470                 475                 480

Leu Glu Gly Ile Asp Ala Phe Glu Thr Ala Leu Tyr Glu Gly Arg Asp
                485                 490                 495

Ala Ala Arg Asp
            500

<210> SEQ ID NO 55
<211> LENGTH: 1500
<212> TYPE: DNA
<213> ORGANISM: Thraustochytrium sp.
<220> FEATURE:
<221> NAME/KEY: CDS
<222> LOCATION: (1)..(1500)

<400> SEQUENCE: 55 tta ccc gcc aaa cgt tgg agg ttc cta ggt gag gac ttg gag ttt ctc      48
Leu Pro Ala Lys Arg Trp Arg Phe Leu Gly Glu Asp Leu Glu Phe Leu
1               5                   10                  15 cga gcc atc agg ctc aag gaa aag cct agg ggt tgt ttt gtg gag agt      96
Arg Ala Ile Arg Leu Lys Glu Lys Pro Arg Gly Cys Phe Val Glu Ser
            20                  25                  30 gtt gac gtt aac ttt aga cgg ctg aaa acg ccc ttg aca cca gaa gat     144
Val Asp Val Asn Phe Arg Arg Leu Lys Thr Pro Leu Thr Pro Glu Asp
        35                  40                  45 atg ttg cgg ccc caa caa ctc ttg gcg gtt tct acg atg gac cga gca     192
Met Leu Arg Pro Gln Gln Leu Leu Ala Val Ser Thr Met Asp Arg Ala
    50                  55                  60 att atc gat gca ggt cta aag aag ggc caa cat gta gca gtt ctt gtt     240
```

```
                                                                -continued

Ile Ile Asp Ala Gly Leu Lys Lys Gly Gln His Val Ala Val Leu Val
65                  70                  75                  80 ggc cta gga act gac ctg gaa ctt tac cgt cat cga gca aga gtc gcg      288
Gly Leu Gly Thr Asp Leu Glu Leu Tyr Arg His Arg Ala Arg Val Ala
                85                  90                  95 ctt aaa gag gtt ttg cac ccg agc tta aag tca gac act gca att ctc      336
Leu Lys Glu Val Leu His Pro Ser Leu Lys Ser Asp Thr Ala Ile Leu
            100                 105                 110 cag aaa ata atg caa tat gtg aat gat gca gga act tcg act tca tac      384
Gln Lys Ile Met Gln Tyr Val Asn Asp Ala Gly Thr Ser Thr Ser Tyr
        115                 120                 125 aca tct tac att gga aac ctc gtt gcc acg cgt att tcg tct cag tgg      432
Thr Ser Tyr Ile Gly Asn Leu Val Ala Thr Arg Ile Ser Ser Gln Trp
    130                 135                 140 gga ttc aca ggg ccg tcc ttt act gtc aca gaa gga aat aat tcc gtg      480
Gly Phe Thr Gly Pro Ser Phe Thr Val Thr Glu Gly Asn Asn Ser Val
145                 150                 155                 160 tac aga tgt gca caa cta gcc aaa gat atg ctt cag gtt aac cga gtt      528
Tyr Arg Cys Ala Gln Leu Ala Lys Asp Met Leu Gln Val Asn Arg Val
                165                 170                 175 gat gct gtc gtc atc gca ggc gtt gat ctc aac gga agc gcc gaa agt      576
Asp Ala Val Val Ile Ala Gly Val Asp Leu Asn Gly Ser Ala Glu Ser
            180                 185                 190 ttt ttt gtc cga gca aat cgt caa aag ata tcc aag cta agt cat cca      624
Phe Phe Val Arg Ala Asn Arg Gln Lys Ile Ser Lys Leu Ser His Pro
        195                 200                 205 tgt gca agc ttc gac aga gat gca gat gga ttt ttc gca ggt gag ggc      672
Cys Ala Ser Phe Asp Arg Asp Ala Asp Gly Phe Phe Ala Gly Glu Gly
    210                 215                 220 tgt ggt gcc cta gtt ttc aag agg tta gaa gac tgt gct cct cag gaa      720
Cys Gly Ala Leu Val Phe Lys Arg Leu Glu Asp Cys Ala Pro Gln Glu
225                 230                 235                 240 aaa att tat gct agt ata gac tct atc gca ata gat aaa gag cct act      768
Lys Ile Tyr Ala Ser Ile Asp Ser Ile Ala Ile Asp Lys Glu Pro Thr
                245                 250                 255 agc tca gct gtg aaa gct gtc tac caa agt gat tcg agt ctc tcc gat      816
Ser Ser Ala Val Lys Ala Val Tyr Gln Ser Asp Ser Ser Leu Ser Asp
            260                 265                 270 att gag ctg tta gaa atc agt gga gac tcc aaa cgg ttt gca gca ttc      864
Ile Glu Leu Leu Glu Ile Ser Gly Asp Ser Lys Arg Phe Ala Ala Phe
        275                 280                 285 gaa ggc gct gtg gaa att caa tca agt gtg gaa gcc cag cta aaa gga      912
Glu Gly Ala Val Glu Ile Gln Ser Ser Val Glu Ala Gln Leu Lys Gly
    290                 295                 300 ctt tcc aaa gtc ctt gaa cct gca aaa ggc caa ggc gta gcg gtg gga      960
Leu Ser Lys Val Leu Glu Pro Ala Lys Gly Gln Gly Val Ala Val Gly
305                 310                 315                 320 agt act cga gca acc gtt ggg gat ata ggg tat gct aca gga gcg gca     1008
Ser Thr Arg Ala Thr Val Gly Asp Ile Gly Tyr Ala Thr Gly Ala Ala
                325                 330                 335 agc ctg att aaa act gca ctc tgc tta tat aat cgc tac ctt ccg gca     1056
Ser Leu Ile Lys Thr Ala Leu Cys Leu Tyr Asn Arg Tyr Leu Pro Ala
            340                 345                 350 tta gca aac tgg agt ggc cca tgt gaa cag tcc gcc tgg ggc tca aac     1104
Leu Ala Asn Trp Ser Gly Pro Cys Glu Gln Ser Ala Trp Gly Ser Asn
        355                 360                 365 atg ttc gtt tgc cat gaa aca cgg ccg tgg atg aaa aac cag aat gaa     1152
Met Phe Val Cys His Glu Thr Arg Pro Trp Met Lys Asn Gln Asn Glu
    370                 375                 380
```

-continued

```
aag aga tgt gcc ctc att tct gga aca gat cca tct cat aca tgc ttt        1200
Lys Arg Cys Ala Leu Ile Ser Gly Thr Asp Pro Ser His Thr Cys Phe
385                 390                 395                 400 tcc ctc gta cta tcg gat act ggg tgt tat gaa gag cac aat cga acg        1248
Ser Leu Val Leu Ser Asp Thr Gly Cys Tyr Glu Glu His Asn Arg Thr
                405                 410                 415 tgc ttt gat gtg caa gcg cca cag cta gtt ctg ata cac gga ttc gat        1296
Cys Phe Asp Val Gln Ala Pro Gln Leu Val Leu Ile His Gly Phe Asp
        420                 425                 430 gga aaa act att gtg cgg cga ctt gaa gga tat ctc ctt gaa ctt gtt        1344
Gly Lys Thr Ile Val Arg Arg Leu Glu Gly Tyr Leu Leu Glu Leu Val
435                 440                 445 gaa ggg cat gca agc cct tca gag tat ttc cac aaa ctg att gga caa        1392
Glu Gly His Ala Ser Pro Ser Glu Tyr Phe His Lys Leu Ile Gly Gln
    450                 455                 460 agt cta ctt gag aac tcg aaa gaa agt aaa ctc aca ctt tcg ctt gtg        1440
Ser Leu Leu Glu Asn Ser Lys Glu Ser Lys Leu Thr Leu Ser Leu Val
465                 470                 475                 480 tgc aat ccg aac cag ctc caa aag gag ctc atg ctt gct atc aaa gga        1488
Cys Asn Pro Asn Gln Leu Gln Lys Glu Leu Met Leu Ala Ile Lys Gly
                485                 490                 495 gta caa cga agc                                                        1500
Val Gln Arg Ser
            500
```

<210> SEQ ID NO 56
<211> LENGTH: 500
<212> TYPE: PRT
<213> ORGANISM: Thraustochytrium sp.

<400> SEQUENCE: 56

```
Leu Pro Ala Lys Arg Trp Arg Phe Leu Gly Glu Asp Leu Glu Phe Leu
1               5                   10                  15

Arg Ala Ile Arg Leu Lys Glu Lys Pro Arg Gly Cys Phe Val Glu Ser
            20                  25                  30

Val Asp Val Asn Phe Arg Arg Leu Lys Thr Pro Leu Thr Pro Glu Asp
        35                  40                  45

Met Leu Arg Pro Gln Gln Leu Leu Ala Val Ser Thr Met Asp Arg Ala
    50                  55                  60

Ile Ile Asp Ala Gly Leu Lys Lys Gly Gln His Val Ala Val Leu Val
65                  70                  75                  80

Gly Leu Gly Thr Asp Leu Glu Leu Tyr Arg His Arg Ala Arg Val Ala
                85                  90                  95

Leu Lys Glu Val Leu His Pro Ser Leu Lys Ser Asp Thr Ala Ile Leu
            100                 105                 110

Gln Lys Ile Met Gln Tyr Val Asn Asp Ala Gly Thr Ser Thr Ser Tyr
        115                 120                 125

Thr Ser Tyr Ile Gly Asn Leu Val Ala Thr Arg Ile Ser Ser Gln Trp
    130                 135                 140

Gly Phe Thr Gly Pro Ser Phe Thr Val Thr Glu Gly Asn Asn Ser Val
145                 150                 155                 160

Tyr Arg Cys Ala Gln Leu Ala Lys Asp Met Leu Gln Val Asn Arg Val
                165                 170                 175

Asp Ala Val Val Ile Ala Gly Val Asp Leu Asn Gly Ser Ala Glu Ser
            180                 185                 190

Phe Phe Val Arg Ala Asn Arg Gln Lys Ile Ser Lys Leu Ser His Pro
        195                 200                 205
```

```
Cys Ala Ser Phe Asp Arg Asp Ala Asp Gly Phe Phe Ala Gly Glu Gly
        210                 215                 220

Cys Gly Ala Leu Val Phe Lys Arg Leu Glu Asp Cys Ala Pro Gln Glu
225                 230                 235                 240

Lys Ile Tyr Ala Ser Ile Asp Ser Ile Ala Ile Asp Lys Glu Pro Thr
            245                 250                 255

Ser Ser Ala Val Lys Ala Val Tyr Gln Ser Asp Ser Ser Leu Ser Asp
                260                 265                 270

Ile Glu Leu Leu Glu Ile Ser Gly Asp Ser Lys Arg Phe Ala Ala Phe
            275                 280                 285

Glu Gly Ala Val Glu Ile Gln Ser Ser Val Glu Ala Gln Leu Lys Gly
        290                 295                 300

Leu Ser Lys Val Leu Glu Pro Ala Lys Gly Gln Gly Val Ala Val Gly
305                 310                 315                 320

Ser Thr Arg Ala Thr Val Gly Asp Ile Gly Tyr Ala Thr Gly Ala Ala
                325                 330                 335

Ser Leu Ile Lys Thr Ala Leu Cys Leu Tyr Asn Arg Tyr Leu Pro Ala
            340                 345                 350

Leu Ala Asn Trp Ser Gly Pro Cys Glu Gln Ser Ala Trp Gly Ser Asn
        355                 360                 365

Met Phe Val Cys His Glu Thr Arg Pro Trp Met Lys Asn Gln Asn Glu
370                 375                 380

Lys Arg Cys Ala Leu Ile Ser Gly Thr Asp Pro Ser His Thr Cys Phe
385                 390                 395                 400

Ser Leu Val Leu Ser Asp Thr Gly Cys Tyr Glu Glu His Asn Arg Thr
                405                 410                 415

Cys Phe Asp Val Gln Ala Pro Gln Leu Val Leu Ile His Gly Phe Asp
            420                 425                 430

Gly Lys Thr Ile Val Arg Arg Leu Glu Gly Tyr Leu Leu Glu Leu Val
        435                 440                 445

Glu Gly His Ala Ser Pro Ser Glu Tyr Phe His Lys Leu Ile Gly Gln
        450                 455                 460

Ser Leu Leu Glu Asn Ser Lys Glu Ser Lys Leu Thr Leu Ser Leu Val
465                 470                 475                 480

Cys Asn Pro Asn Gln Leu Gln Lys Glu Leu Met Leu Ala Ile Lys Gly
                485                 490                 495

Val Gln Arg Ser
            500

<210> SEQ ID NO 57
<211> LENGTH: 1500
<212> TYPE: DNA
<213> ORGANISM: Thraustochytrium sp.
<220> FEATURE:
<221> NAME/KEY: CDS
<222> LOCATION: (1)..(1500)

<400> SEQUENCE: 57 atg tta aca ggg aag gat tgg gtc agt cca tca gga agt tgt ttt gcc     48
Met Leu Thr Gly Lys Asp Trp Val Ser Pro Ser Gly Ser Cys Phe Ala
1               5                   10                  15 cca aat ccg tta tca agc gca aaa gtg gca ttc atg tac gga gaa ggc     96
Pro Asn Pro Leu Ser Ser Ala Lys Val Ala Phe Met Tyr Gly Glu Gly
                20                  25                  30 cga agc ccg tac tgt ggt gta ggc ttg ggt cta cat cgt ttg tgg ccc    144
Arg Ser Pro Tyr Cys Gly Val Gly Leu Gly Leu His Arg Leu Trp Pro
            35                  40                  45
```

-continued

| | |
|---|---|
| ggt ctc cat gaa aat gtg aac aat aag aca gtc gat tta tgg acg gaa<br>Gly Leu His Glu Asn Val Asn Asn Lys Thr Val Asp Leu Trp Thr Glu<br>50                              55                          60 | 192 |
| gga gat ggt tgg tta tat cct cga acg ttg aca cga gaa gag cat aca<br>Gly Asp Gly Trp Leu Tyr Pro Arg Thr Leu Thr Arg Glu Glu His Thr<br>65                             70                          75                          80 | 240 |
| aaa gcc atc gaa tct ttc aac gca aat caa att gaa atg ttt cgc gct<br>Lys Ala Ile Glu Ser Phe Asn Ala Asn Gln Ile Glu Met Phe Arg Ala<br>                         85                          90                          95 | 288 |
| ggg att ttc atc tca atg tgt cag aca gac tat gtc atg aat gtt ctc<br>Gly Ile Phe Ile Ser Met Cys Gln Thr Asp Tyr Val Met Asn Val Leu<br>              100                        105                      110 | 336 |
| ggt gtc cag cct aag gcc gga ttt ggg ctg agc ttg gaa gaa att tca<br>Gly Val Gln Pro Lys Ala Gly Phe Gly Leu Ser Leu Gly Glu Ile Ser<br>              115                        120                      125 | 384 |
| atg ctc ttt gcg atg tca aag gag aac tgc agg cag tca cag gaa atg<br>Met Leu Phe Ala Met Ser Lys Glu Asn Cys Arg Gln Ser Gln Glu Met<br>130                              135                        140 | 432 |
| acc aat cgt ttg cgc ggt tct cca gtg tgg tct aac gag ctt gct atc<br>Thr Asn Arg Leu Arg Gly Ser Pro Val Trp Ser Asn Glu Leu Ala Ile<br>145                          150                        155                      160 | 480 |
| aac ttc aat gca att cgc aag tta tgg aaa atc ccc cga gga gct ccc<br>Asn Phe Asn Ala Ile Arg Lys Leu Trp Lys Ile Pro Arg Gly Ala Pro<br>              165                        170                      175 | 528 |
| tta gaa tcc ttt tgg caa gga tac ttg gtt cac ggc aca aga gaa gaa<br>Leu Glu Ser Phe Trp Gln Gly Tyr Leu Val His Gly Thr Arg Glu Glu<br>                  180                        185                      190 | 576 |
| gta gag cat gct att ggt ctt tct gag cct tat gta cgt ctg ctt att<br>Val Glu His Ala Ile Gly Leu Ser Glu Pro Tyr Val Arg Leu Leu Ile<br>              195                        200                      205 | 624 |
| gtg aac gat tca agg agt gcc ttg att gct gga aaa cca gac gcc tgt<br>Val Asn Asp Ser Arg Ser Ala Leu Ile Ala Gly Lys Pro Asp Ala Cys<br>210                              215                        220 | 672 |
| cag gca gta atc agt aga cta aac tcc aag ttc cct tct ctg ccg gta<br>Gln Ala Val Ile Ser Arg Leu Asn Ser Lys Phe Pro Ser Leu Pro Val<br>225                              230                        235                      240 | 720 |
| aag caa gga atg att ggt cat tgc cca gaa gtt cgt gcg ttc atc aaa<br>Lys Gln Gly Met Ile Gly His Cys Pro Glu Val Arg Ala Phe Ile Lys<br>                      245                        250                      255 | 768 |
| gat att ggg tac atc cat gaa aca ctc cga att tcc aat gac tat tcg<br>Asp Ile Gly Tyr Ile His Glu Thr Leu Arg Ile Ser Asn Asp Tyr Ser<br>                  260                        265                      270 | 816 |
| gat tgt cag ctt ttc tca gcg gta acc aag ggc gca ctt gac agc tcc<br>Asp Cys Gln Leu Phe Ser Ala Val Thr Lys Gly Ala Leu Asp Ser Ser<br>              275                        280                      285 | 864 |
| aca atg gaa atc aaa cac ttt gtg gga gag gtc tac tcc cgg atc gca<br>Thr Met Glu Ile Lys His Phe Val Gly Glu Val Tyr Ser Arg Ile Ala<br>290                              295                        300 | 912 |
| gac ttt cct caa atc gtc aac acg gtg cat tcg gct ggt tat gac gta<br>Asp Phe Pro Gln Ile Val Asn Thr Val His Ser Ala Gly Tyr Asp Val<br>305                              310                        315                      320 | 960 |
| ttt ctt gag ctt ggc tgt gat gct tct aga tct gca gca gtt caa aac<br>Phe Leu Glu Leu Gly Cys Asp Ala Ser Arg Ser Ala Ala Val Gln Asn<br>                  325                        330                      335 | 1008 |
| att ctt ggt ggt caa gga aag ttc ttg tct aca gct att gac aaa aaa<br>Ile Leu Gly Gly Gln Gly Lys Phe Leu Ser Thr Ala Ile Asp Lys Lys<br>                  340                        345                      350 | 1056 |
| gga cac tcc gcc tgg tca caa gta ctt cgg gct acc gca tca tta gct<br>Gly His Ser Ala Trp Ser Gln Val Leu Arg Ala Thr Ala Ser Leu Ala | 1104 |

-continued

```
              355                 360                 365
gca cat cga gta ccg gga atc tca att ttg gat ttg ttt cac cca aat    1152
Ala His Arg Val Pro Gly Ile Ser Ile Leu Asp Leu Phe His Pro Asn
        370                 375                 380 ttc cga gaa atg tgc tgt aca atg gca acc aca cct aaa gtg gaa gat    1200
Phe Arg Glu Met Cys Cys Thr Met Ala Thr Thr Pro Lys Val Glu Asp
385                 390                 395                 400 aag ttc ctg cgc acg att caa atc aat ggt cgg ttt gaa aaa gaa atg    1248
Lys Phe Leu Arg Thr Ile Gln Ile Asn Gly Arg Phe Glu Lys Glu Met
                405                 410                 415 att cac cta gaa gat aca aca tta agt tgc tta ccc gct cca agt gaa    1296
Ile His Leu Glu Asp Thr Thr Leu Ser Cys Leu Pro Ala Pro Ser Glu
            420                 425                 430 gca aat atc gca gct att caa tct cgg tca att cga tct gct gcg gcg    1344
Ala Asn Ile Ala Ala Ile Gln Ser Arg Ser Ile Arg Ser Ala Ala Ala
        435                 440                 445 cgt tct gga caa tcc cat gat tgt gca tcc cat agc cat gaa gaa aat    1392
Arg Ser Gly Gln Ser His Asp Cys Ala Ser His Ser His Glu Glu Asn
    450                 455                 460 aag gat tca tgc cct gaa aag ctg aag ctt gat tct gtg tcc gtc gcc    1440
Lys Asp Ser Cys Pro Glu Lys Leu Lys Leu Asp Ser Val Ser Val Ala
465                 470                 475                 480 ata aat ttc gac aat gat gac cgc att cag ctt ggg cac gcg ggt ttt    1488
Ile Asn Phe Asp Asn Asp Asp Arg Ile Gln Leu Gly His Ala Gly Phe
                485                 490                 495 cgg gag atg tac                                                    1500
Arg Glu Met Tyr
            500

<210> SEQ ID NO 58
<211> LENGTH: 500
<212> TYPE: PRT
<213> ORGANISM: Thraustochytrium sp.

<400> SEQUENCE: 58

Met Leu Thr Gly Lys Asp Trp Val Ser Pro Gly Ser Cys Phe Ala
1               5                   10                  15

Pro Asn Pro Leu Ser Ser Ala Lys Val Ala Phe Met Tyr Gly Glu Gly
                20                  25                  30

Arg Ser Pro Tyr Cys Gly Val Gly Leu Gly Leu His Arg Leu Trp Pro
            35                  40                  45

Gly Leu His Glu Asn Val Asn Asn Lys Thr Val Asp Leu Trp Thr Glu
        50                  55                  60

Gly Asp Gly Trp Leu Tyr Pro Arg Thr Leu Thr Arg Glu Glu His Thr
65                  70                  75                  80

Lys Ala Ile Glu Ser Phe Asn Ala Asn Gln Ile Glu Met Phe Arg Ala
                85                  90                  95

Gly Ile Phe Ile Ser Met Cys Gln Thr Asp Tyr Val Met Asn Val Leu
            100                 105                 110

Gly Val Gln Pro Lys Ala Gly Phe Gly Leu Ser Leu Gly Glu Ile Ser
        115                 120                 125

Met Leu Phe Ala Met Ser Lys Glu Asn Cys Arg Gln Ser Gln Glu Met
    130                 135                 140

Thr Asn Arg Leu Arg Gly Ser Pro Val Trp Ser Asn Glu Leu Ala Ile
145                 150                 155                 160

Asn Phe Asn Ala Ile Arg Lys Leu Trp Lys Ile Pro Arg Gly Ala Pro
                165                 170                 175
```

```
Leu Glu Ser Phe Trp Gln Gly Tyr Leu Val His Gly Thr Arg Glu Glu
            180                 185                 190

Val Glu His Ala Ile Gly Leu Ser Glu Pro Tyr Val Arg Leu Leu Ile
        195                 200                 205

Val Asn Asp Ser Arg Ser Ala Leu Ile Ala Gly Lys Pro Asp Ala Cys
    210                 215                 220

Gln Ala Val Ile Ser Arg Leu Asn Ser Lys Phe Pro Ser Leu Pro Val
225                 230                 235                 240

Lys Gln Gly Met Ile Gly His Cys Pro Glu Val Arg Ala Phe Ile Lys
                245                 250                 255

Asp Ile Gly Tyr Ile His Glu Thr Leu Arg Ile Ser Asn Asp Tyr Ser
            260                 265                 270

Asp Cys Gln Leu Phe Ser Ala Val Thr Lys Gly Ala Leu Asp Ser Ser
        275                 280                 285

Thr Met Glu Ile Lys His Phe Val Gly Glu Val Tyr Ser Arg Ile Ala
    290                 295                 300

Asp Phe Pro Gln Ile Val Asn Thr Val His Ser Ala Gly Tyr Asp Val
305                 310                 315                 320

Phe Leu Glu Leu Gly Cys Asp Ala Ser Arg Ser Ala Ala Val Gln Asn
                325                 330                 335

Ile Leu Gly Gly Gln Gly Lys Phe Leu Ser Thr Ala Ile Asp Lys Lys
            340                 345                 350

Gly His Ser Ala Trp Ser Gln Val Leu Arg Ala Thr Ala Ser Leu Ala
        355                 360                 365

Ala His Arg Val Pro Gly Ile Ser Ile Leu Asp Leu Phe His Pro Asn
    370                 375                 380

Phe Arg Glu Met Cys Cys Thr Met Ala Thr Thr Pro Lys Val Glu Asp
385                 390                 395                 400

Lys Phe Leu Arg Thr Ile Gln Ile Asn Gly Arg Phe Glu Lys Glu Met
                405                 410                 415

Ile His Leu Glu Asp Thr Thr Leu Ser Cys Leu Pro Ala Pro Ser Glu
            420                 425                 430

Ala Asn Ile Ala Ala Ile Gln Ser Arg Ser Ile Arg Ser Ala Ala Ala
        435                 440                 445

Arg Ser Gly Gln Ser His Asp Cys Ala Ser His Ser Glu Glu Asn
    450                 455                 460

Lys Asp Ser Cys Pro Glu Lys Leu Lys Leu Asp Ser Val Ser Val Ala
465                 470                 475                 480

Ile Asn Phe Asp Asn Asp Arg Ile Gln Leu Gly His Ala Gly Phe
                485                 490                 495

Arg Glu Met Tyr
            500

<210> SEQ ID NO 59
<211> LENGTH: 1305
<212> TYPE: DNA
<213> ORGANISM: Thraustochytrium sp.
<220> FEATURE:
<221> NAME/KEY: CDS
<222> LOCATION: (1)..(1305)

<400> SEQUENCE: 59 aat aca aga tat agc ttg tac aca ggg gcg atg gca aag gga att gca      48
Asn Thr Arg Tyr Ser Leu Tyr Thr Gly Ala Met Ala Lys Gly Ile Ala
1               5                   10                  15 tct gca gat ctt gtc att gcc gct ggg aaa gag ggc atc cta gct tcc     96
```

-continued

```
Ser Ala Asp Leu Val Ile Ala Ala Gly Lys Glu Gly Ile Leu Ala Ser
            20                  25                  30 tat gga gct gga gga cta cct ctt gct act gtt cga aag gga ata gac    144
Tyr Gly Ala Gly Gly Leu Pro Leu Ala Thr Val Arg Lys Gly Ile Asp
        35                  40                  45 aaa att caa caa gcc ttg cca agt ggc cca tat gct gta aat ctt att    192
Lys Ile Gln Gln Ala Leu Pro Ser Gly Pro Tyr Ala Val Asn Leu Ile
 50                  55                  60 cac tct ccc ttt gac ggc aac ttg gag cag gga aac gtc gat ttg ttc    240
His Ser Pro Phe Asp Gly Asn Leu Glu Gln Gly Asn Val Asp Leu Phe
 65                  70                  75                  80 ttg gaa aag aac gtc cgc gtg gcg gaa tgt tcc gcg ttt aca acg cta    288
Leu Glu Lys Asn Val Arg Val Ala Glu Cys Ser Ala Phe Thr Thr Leu
                 85                  90                  95 aca gtg cca gta gta cac tat cgt gct gca ggg ctt gtt cgg cgc caa    336
Thr Val Pro Val Val His Tyr Arg Ala Ala Gly Leu Val Arg Arg Gln
            100                 105                 110 gat gga agc att ttg atc aag aac cga atc att gct aaa gta tct agg    384
Asp Gly Ser Ile Leu Ile Lys Asn Arg Ile Ile Ala Lys Val Ser Arg
        115                 120                 125 aca gaa ctc gct gag atg ttc ctt cgt ccg gca cct caa atc atc ctc    432
Thr Glu Leu Ala Glu Met Phe Leu Arg Pro Ala Pro Gln Ile Ile Leu
130                 135                 140 gaa aaa ctg gta gca gca gaa atc att tca tct gac caa gcg cgt atg    480
Glu Lys Leu Val Ala Ala Glu Ile Ile Ser Ser Asp Gln Ala Arg Met
145                 150                 155                 160 gca gcc aaa gtt ccc atg gcg gac gac atc gca gtc gaa gcc gac tct    528
Ala Ala Lys Val Pro Met Ala Asp Asp Ile Ala Val Glu Ala Asp Ser
                165                 170                 175 ggt ggg cac acg gat aat cgg cct atg cac gtc att ttg ccc ctg ata    576
Gly Gly His Thr Asp Asn Arg Pro Met His Val Ile Leu Pro Leu Ile
            180                 185                 190 att caa ctc cgc aat act ata ctt gca gag tat ggc tgt gcc acg gct    624
Ile Gln Leu Arg Asn Thr Ile Leu Ala Glu Tyr Gly Cys Ala Thr Ala
        195                 200                 205 ttt cgt acc cgt ata ggc gct gga gga ggc att ggt tgt cct tca gcg    672
Phe Arg Thr Arg Ile Gly Ala Gly Gly Gly Ile Gly Cys Pro Ser Ala
    210                 215                 220 gcc ctc gca gcc ttt gat atg ggt gcg agt ttt gtc gtg act gga agc    720
Ala Leu Ala Ala Phe Asp Met Gly Ala Ser Phe Val Val Thr Gly Ser
225                 230                 235                 240 ata aat caa att tgc cgc gag gca ggg act tgc gat act gtt cgg gag    768
Ile Asn Gln Ile Cys Arg Glu Ala Gly Thr Cys Asp Thr Val Arg Glu
                245                 250                 255 cta ctt gcc aac tca agc tac tcg gac gtg acg atg gcg cca gca gca    816
Leu Leu Ala Asn Ser Ser Tyr Ser Asp Val Thr Met Ala Pro Ala Ala
            260                 265                 270 gac atg ttt gac caa ggt gtg aaa ctc caa gtc tta aaa cga gga acg    864
Asp Met Phe Asp Gln Gly Val Lys Leu Gln Val Leu Lys Arg Gly Thr
        275                 280                 285 atg ttt cca agc aga gca aat aaa ctc cgg aag ctc ttt gtg aac tac    912
Met Phe Pro Ser Arg Ala Asn Lys Leu Arg Lys Leu Phe Val Asn Tyr
    290                 295                 300 gaa tct cta gaa aca ctc ccg tcg aaa gag ttg aaa tac ctg gaa aac    960
Glu Ser Leu Glu Thr Leu Pro Ser Lys Glu Leu Lys Tyr Leu Glu Asn
305                 310                 315                 320 atc ata ttc aag caa gca gta gac cag gtg tgg gag gaa aca aag cgc    1008
Ile Ile Phe Lys Gln Ala Val Asp Gln Val Trp Glu Glu Thr Lys Arg
                325                 330                 335
```

```
ttt tac tgt gaa aaa ctg aac aat cca gat aaa att gca agg gcc atg    1056
Phe Tyr Cys Glu Lys Leu Asn Asn Pro Asp Lys Ile Ala Arg Ala Met
        340                 345                 350 aaa gat cct aaa ttg aag atg tcg ctt tgc ttt cgg tgg tat ctc tcc    1104
Lys Asp Pro Lys Leu Lys Met Ser Leu Cys Phe Arg Trp Tyr Leu Ser
            355                 360                 365 aag agc tct ggg tgg gcc aac gca gga att aaa tct cgt gca ctc gac    1152
Lys Ser Ser Gly Trp Ala Asn Ala Gly Ile Lys Ser Arg Ala Leu Asp
370                 375                 380 tac cag atc tgg tgt ggc ccg gca atg ggc tcg ttc aac aat ttc gcc    1200
Tyr Gln Ile Trp Cys Gly Pro Ala Met Gly Ser Phe Asn Asn Phe Ala
385                 390                 395                 400 agc ggc aca tcc ctc gat tgg aaa gtg act ggg gtt ttc cct ggc gtt    1248
Ser Gly Thr Ser Leu Asp Trp Lys Val Thr Gly Val Phe Pro Gly Val
                405                 410                 415 gcg gaa gta aac atg gcc att tta gat ggc gcg cga gaa cta gct gct    1296
Ala Glu Val Asn Met Ala Ile Leu Asp Gly Ala Arg Glu Leu Ala Ala
            420                 425                 430 aaa cga aat                                                        1305
Lys Arg Asn
        435

<210> SEQ ID NO 60
<211> LENGTH: 435
<212> TYPE: PRT
<213> ORGANISM: Thraustochytrium sp.

<400> SEQUENCE: 60

Asn Thr Arg Tyr Ser Leu Tyr Thr Gly Ala Met Ala Lys Gly Ile Ala
1               5                   10                  15

Ser Ala Asp Leu Val Ile Ala Ala Gly Lys Glu Gly Ile Leu Ala Ser
            20                  25                  30

Tyr Gly Ala Gly Gly Leu Pro Leu Ala Thr Val Arg Lys Gly Ile Asp
        35                  40                  45

Lys Ile Gln Gln Ala Leu Pro Ser Gly Pro Tyr Ala Val Asn Leu Ile
    50                  55                  60

His Ser Pro Phe Asp Gly Asn Leu Glu Gln Gly Asn Val Asp Leu Phe
65                  70                  75                  80

Leu Glu Lys Asn Val Arg Val Ala Glu Cys Ser Ala Phe Thr Thr Leu
                85                  90                  95

Thr Val Pro Val Val His Tyr Arg Ala Ala Gly Leu Val Arg Arg Gln
            100                 105                 110

Asp Gly Ser Ile Leu Ile Lys Asn Arg Ile Ile Ala Lys Val Ser Arg
        115                 120                 125

Thr Glu Leu Ala Glu Met Phe Leu Arg Pro Ala Pro Gln Ile Ile Leu
    130                 135                 140

Glu Lys Leu Val Ala Ala Glu Ile Ile Ser Ser Asp Gln Ala Arg Met
145                 150                 155                 160

Ala Ala Lys Val Pro Met Ala Asp Asp Ile Ala Val Glu Ala Asp Ser
                165                 170                 175

Gly Gly His Thr Asp Asn Arg Pro Met His Val Ile Leu Pro Leu Ile
            180                 185                 190

Ile Gln Leu Arg Asn Thr Ile Leu Ala Glu Tyr Gly Cys Ala Thr Ala
        195                 200                 205

Phe Arg Thr Arg Ile Gly Ala Gly Gly Ile Gly Cys Pro Ser Ala
    210                 215                 220

Ala Leu Ala Ala Phe Asp Met Gly Ala Ser Phe Val Val Thr Gly Ser
```

```
                225                 230                 235                 240
Ile Asn Gln Ile Cys Arg Glu Ala Gly Thr Cys Asp Thr Val Arg Glu
            245                 250                 255

Leu Leu Ala Asn Ser Ser Tyr Ser Asp Val Thr Met Ala Pro Ala Ala
            260                 265                 270

Asp Met Phe Asp Gln Gly Val Lys Leu Gln Val Leu Lys Arg Gly Thr
            275                 280                 285

Met Phe Pro Ser Arg Ala Asn Lys Leu Arg Lys Leu Phe Val Asn Tyr
            290                 295                 300

Glu Ser Leu Glu Thr Leu Pro Ser Lys Glu Leu Lys Tyr Leu Glu Asn
305                 310                 315                 320

Ile Ile Phe Lys Gln Ala Val Asp Gln Val Trp Glu Thr Lys Arg
                325                 330                 335

Phe Tyr Cys Glu Lys Leu Asn Asn Pro Asp Lys Ile Ala Arg Ala Met
            340                 345                 350

Lys Asp Pro Lys Leu Lys Met Ser Leu Cys Phe Arg Trp Tyr Leu Ser
            355                 360                 365

Lys Ser Ser Gly Trp Ala Asn Ala Gly Ile Lys Ser Arg Ala Leu Asp
            370                 375                 380

Tyr Gln Ile Trp Cys Gly Pro Ala Met Gly Ser Phe Asn Asn Phe Ala
385                 390                 395                 400

Ser Gly Thr Ser Leu Asp Trp Lys Val Thr Gly Val Phe Pro Gly Val
                405                 410                 415

Ala Glu Val Asn Met Ala Ile Leu Asp Gly Ala Arg Glu Leu Ala Ala
            420                 425                 430

Lys Arg Asn
        435

<210> SEQ ID NO 61
<211> LENGTH: 4410
<212> TYPE: DNA
<213> ORGANISM: Thraustochytrium sp.
<220> FEATURE:
<221> NAME/KEY: CDS
<222> LOCATION: (1)..(4410)

<400> SEQUENCE: 61 atg ggc ccg cga gtg gcg tca ggc aag gtg ccg gct tgg gag atg agc         48
Met Gly Pro Arg Val Ala Ser Gly Lys Val Pro Ala Trp Glu Met Ser
1               5                   10                  15 aag tcc gag ctg tgt gat gac cgc acg gta gtc ttt gac tat gag gag         96
Lys Ser Glu Leu Cys Asp Asp Arg Thr Val Val Phe Asp Tyr Glu Glu
            20                  25                  30 ctg ctg gag ttc gct gag ggc gat atc agt aag gtt ttt ggg ccg gag        144
Leu Leu Glu Phe Ala Glu Gly Asp Ile Ser Lys Val Phe Gly Pro Glu
        35                  40                  45 ttc aaa gtg gtg gac ggg ttt agg cgc agg gtg agg ttg ccc gct cga        192
Phe Lys Val Val Asp Gly Phe Arg Arg Arg Val Arg Leu Pro Ala Arg
    50                  55                  60 gag tac ctg ctg gtg acc cgg gtt acg ctg atg gat gcc gag gtg ggc        240
Glu Tyr Leu Leu Val Thr Arg Val Thr Leu Met Asp Ala Glu Val Gly
65                  70                  75                  80 aac ttt cga gtg gga gca cgt atg gtg aca gag tat gac gta cct gtg        288
Asn Phe Arg Val Gly Ala Arg Met Val Thr Glu Tyr Asp Val Pro Val
                85                  90                  95 aac gga gag ctc tcg gaa ggg gga gat gtg ccg tgg gct gtg ttg gtg        336
Asn Gly Glu Leu Ser Glu Gly Gly Asp Val Pro Trp Ala Val Leu Val
            100                 105                 110
```

-continued

```
gaa gcc ggg cag tgc gac ttg ctg cta att tct tac atg ggc atc gat        384
Glu Ala Gly Gln Cys Asp Leu Leu Leu Ile Ser Tyr Met Gly Ile Asp
            115                 120                 125 ttc cag tgc aaa gga gag cgg gtc tac cgg ctg ctg aac acc acc ttg        432
Phe Gln Cys Lys Gly Glu Arg Val Tyr Arg Leu Leu Asn Thr Thr Leu
130                 135                 140 acg ttt ttt ggc gtc gcg aaa gaa ggg gaa acg ctt gtg tac gat att        480
Thr Phe Phe Gly Val Ala Lys Glu Gly Glu Thr Leu Val Tyr Asp Ile
145                 150                 155                 160 cgc gtc acg ggt ttc gcc aag agg ccg gac gga gat atc tcc atg ttc        528
Arg Val Thr Gly Phe Ala Lys Arg Pro Asp Gly Asp Ile Ser Met Phe
                165                 170                 175 ttt ttc gaa tat gat tgc tac tgc aat ggc aag ctt ctc atc gaa atg        576
Phe Phe Glu Tyr Asp Cys Tyr Cys Asn Gly Lys Leu Leu Ile Glu Met
                    180                 185                 190 cga gat ggc tct gca ggc ttc ttc acg gac gaa gag ctc gct gcc ggc        624
Arg Asp Gly Ser Ala Gly Phe Phe Thr Asp Glu Glu Leu Ala Ala Gly
                        195                 200                 205 aaa gga gtg gtc gtc act cgt gca cag caa aac atg cgg gac aaa att        672
Lys Gly Val Val Val Thr Arg Ala Gln Gln Asn Met Arg Asp Lys Ile
210                 215                 220 gta cgg cag tcc att gag cct ttt gca ctg gcg gct tgc acg cac aaa        720
Val Arg Gln Ser Ile Glu Pro Phe Ala Leu Ala Ala Cys Thr His Lys
225                 230                 235                 240 acg act ctg aac gag agt gac atg cag tcc ctt gtg gag cga aac tgg        768
Thr Thr Leu Asn Glu Ser Asp Met Gln Ser Leu Val Glu Arg Asn Trp
                245                 250                 255 gca aac gtt ttt ggc acc agt aac aag atg gcg gag ctc aac tat aaa        816
Ala Asn Val Phe Gly Thr Ser Asn Lys Met Ala Glu Leu Asn Tyr Lys
                    260                 265                 270 att tgc gcc agg aaa atg ctc atg atc gac agg gtt acc cac att gac        864
Ile Cys Ala Arg Lys Met Leu Met Ile Asp Arg Val Thr His Ile Asp
                        275                 280                 285 cac cac ggt ggg gcg tat ggc ctc gga cta ctt gtt gga gag aag atc        912
His His Gly Gly Ala Tyr Gly Leu Gly Leu Leu Val Gly Glu Lys Ile
290                 295                 300 ttg gat cga aac cat tgg tac ttt cct tgt cac ttt gtc aat gat caa        960
Leu Asp Arg Asn His Trp Tyr Phe Pro Cys His Phe Val Asn Asp Gln
305                 310                 315                 320 gtc atg gca ggg tca ctg gtc agc gat ggt tgc agc cag ctc tta aaa       1008
Val Met Ala Gly Ser Leu Val Ser Asp Gly Cys Ser Gln Leu Leu Lys
                325                 330                 335 ctc tat atg atc tgg ctt ggc ctc cac ctg aaa atg gag gaa ttt gat       1056
Leu Tyr Met Ile Trp Leu Gly Leu His Leu Lys Met Glu Glu Phe Asp
                    340                 345                 350 ttt ctc cca gtt agc ggc cac aaa aac aag gtg cga tgc agg gga caa       1104
Phe Leu Pro Val Ser Gly His Lys Asn Lys Val Arg Cys Arg Gly Gln
                        355                 360                 365 att tca ccg cat aaa ggc aag ctt gtc tac gtc atg gaa atc aaa aag       1152
Ile Ser Pro His Lys Gly Lys Leu Val Tyr Val Met Glu Ile Lys Lys
370                 375                 380 atg ggt tac gat caa gca tct gga agc cca tac gcc atc gcg gac gtt       1200
Met Gly Tyr Asp Gln Ala Ser Gly Ser Pro Tyr Ala Ile Ala Asp Val
385                 390                 395                 400 gat atc att gac gtc aac gaa gag ctg ggt caa agt ttt gac atc aac       1248
Asp Ile Ile Asp Val Asn Glu Glu Leu Gly Gln Ser Phe Asp Ile Asn
                405                 410                 415 gac ctt gcg agc tac gga aaa ggt gac ctg agc aaa aaa atc gtg gtt       1296
Asp Leu Ala Ser Tyr Gly Lys Gly Asp Leu Ser Lys Lys Ile Val Val
```

-continued

```
                 420                 425                 430
gac ttc aaa gga att gct ttg cag ctc aaa ggc cgc gct ttt tca cgc    1344
Asp Phe Lys Gly Ile Ala Leu Gln Leu Lys Gly Arg Ala Phe Ser Arg
        435                 440                 445 atg agt tcc agc tcg tcc ttg aac gaa gga tgg caa tgt gtt cca aaa    1392
Met Ser Ser Ser Ser Leu Asn Glu Gly Trp Gln Cys Val Pro Lys
450                 455                 460 cca agc cag aga atg gaa cac gaa cag ccc cct gct cac tgc ctt gca    1440
Pro Ser Gln Arg Met Glu His Glu Gln Pro Pro Ala His Cys Leu Ala
465                 470                 475                 480 agc gac ccc gaa gcc cct tca act gtg acc tgg cac cca atg tca aag    1488
Ser Asp Pro Glu Ala Pro Ser Thr Val Thr Trp His Pro Met Ser Lys
                485                 490                 495 ctt cct ggc aac cct acg ccg ttc ttc tcc cct tca tct tac cct ccg    1536
Leu Pro Gly Asn Pro Thr Pro Phe Phe Ser Pro Ser Ser Tyr Pro Pro
            500                 505                 510 agg gca att tgc ttc atc cct ttc ccg ggc aat ccc ctt gac aac aac    1584
Arg Ala Ile Cys Phe Ile Pro Phe Pro Gly Asn Pro Leu Asp Asn Asn
        515                 520                 525 tgc aag gct gga gaa atg ccc ctg aac tgg tac aac atg tca gag ttc    1632
Cys Lys Ala Gly Glu Met Pro Leu Asn Trp Tyr Asn Met Ser Glu Phe
530                 535                 540 atg tgt ggc aag gtt tct aac tgc ttg ggc cca gaa ttc gca cgc ttt    1680
Met Cys Gly Lys Val Ser Asn Cys Leu Gly Pro Glu Phe Ala Arg Phe
545                 550                 555                 560 gac aag tcg aac acc agc cgg agc cct gct ttt gac ttg gct ctg gtg    1728
Asp Lys Ser Asn Thr Ser Arg Ser Pro Ala Phe Asp Leu Ala Leu Val
                565                 570                 575 acc cga gtt gtt gaa gtc aca aac atg gaa cac ggc aag ttt cta aac    1776
Thr Arg Val Val Glu Val Thr Asn Met Glu His Gly Lys Phe Leu Asn
            580                 585                 590 gtt gat tgc aat cca agc aaa ggc aca atg gtg ggg gag ttt gac tgt    1824
Val Asp Cys Asn Pro Ser Lys Gly Thr Met Val Gly Glu Phe Asp Cys
        595                 600                 605 ccc caa gac gcg tgg ttc ttt gat ggt tcg tgc aac gac ggc cat atg    1872
Pro Gln Asp Ala Trp Phe Phe Asp Gly Ser Cys Asn Asp Gly His Met
610                 615                 620 ccg tat tcc att atc atg gaa atc gga ctg caa acc tca ggt gtt ctc    1920
Pro Tyr Ser Ile Ile Met Glu Ile Gly Leu Gln Thr Ser Gly Val Leu
625                 630                 635                 640 acc tcg gtg ttg aag gca ccg ctg act atg gac aag gat gac att ctc    1968
Thr Ser Val Leu Lys Ala Pro Leu Thr Met Asp Lys Asp Asp Ile Leu
                645                 650                 655 ttt cga aac ctc gat gca agt gct gaa atg gtg cgt cca gac gtg gat    2016
Phe Arg Asn Leu Asp Ala Ser Ala Glu Met Val Arg Pro Asp Val Asp
            660                 665                 670 gtt cgc ggc aaa acg att cga aac gtg acc aag tgt acc ggc tat gca    2064
Val Arg Gly Lys Thr Ile Arg Asn Val Thr Lys Cys Thr Gly Tyr Ala
        675                 680                 685 atg ttg gga aag atg ggg att cac cgg ttc acg ttt gag ttg agc gtt    2112
Met Leu Gly Lys Met Gly Ile His Arg Phe Thr Phe Glu Leu Ser Val
690                 695                 700 gac ggc gtg gta ttt tat aaa gga tcc act tcc ttt gga tgg ttc act    2160
Asp Gly Val Val Phe Tyr Lys Gly Ser Thr Ser Phe Gly Trp Phe Thr
705                 710                 715                 720 ccc gag gtg ttt gct cag caa gct gga ctc gac aac ggg aaa aag acg    2208
Pro Glu Val Phe Ala Gln Gln Ala Gly Leu Asp Asn Gly Lys Lys Thr
                725                 730                 735 gag ccc tgg tgc aag act aac aac acc tcg gtt cga aga gtt gaa atc    2256
```

```
                Glu Pro Trp Cys Lys Thr Asn Asn Thr Ser Val Arg Arg Val Glu Ile
                                    740                 745                 750 gca tcc gcc aaa gga aaa gag cag ctg act gag aag ctt ccc gac gca       2304
Ala Ser Ala Lys Gly Lys Glu Gln Leu Thr Glu Lys Leu Pro Asp Ala
            755                 760                 765 act aat gct caa gtt ctt cgg cgt tca gag cag tgt gaa tac ctc gat       2352
Thr Asn Ala Gln Val Leu Arg Arg Ser Glu Gln Cys Glu Tyr Leu Asp
        770                 775                 780 tac ctc aat att gcc cct gac tct ggg ctg cat ggg aag ggc tac gcc       2400
Tyr Leu Asn Ile Ala Pro Asp Ser Gly Leu His Gly Lys Gly Tyr Ala
785                 790                 795                 800 cac gga cac aaa gac gtt aac ccg caa gac tgg ttc ttc tct tgc cac       2448
His Gly His Lys Asp Val Asn Pro Gln Asp Trp Phe Phe Ser Cys His
                805                 810                 815 ttt tgg ttc gat cct gta atg cca gga tct tta gga att gaa tca atg       2496
Phe Trp Phe Asp Pro Val Met Pro Gly Ser Leu Gly Ile Glu Ser Met
            820                 825                 830 ttc cag ctt atc gag gcc ttt gcg gtg gac caa aac att cct gga gag       2544
Phe Gln Leu Ile Glu Ala Phe Ala Val Asp Gln Asn Ile Pro Gly Glu
        835                 840                 845 tac aac gta tcc aat ccg acc ttt gcc cat gca cca ggc aaa acg gcg       2592
Tyr Asn Val Ser Asn Pro Thr Phe Ala His Ala Pro Gly Lys Thr Ala
    850                 855                 860 tgg aaa tac cga ggc cag ctc aca cca aag aac cgt gcg atg gac tgc       2640
Trp Lys Tyr Arg Gly Gln Leu Thr Pro Lys Asn Arg Ala Met Asp Cys
865                 870                 875                 880 gag gtg cat atc gtt tca att acc gcc tcc ccc gag aac ggg ggc tac       2688
Glu Val His Ile Val Ser Ile Thr Ala Ser Pro Glu Asn Gly Gly Tyr
                885                 890                 895 gtt gac atc gtg gcc gat gga gcg ctt tgg gta gat gga ctt cgc gtg       2736
Val Asp Ile Val Ala Asp Gly Ala Leu Trp Val Asp Gly Leu Arg Val
            900                 905                 910 tac gaa gcc aaa gag ctt cga gtt cgt gtc gtt tcg gca aaa cct caa       2784
Tyr Glu Ala Lys Glu Leu Arg Val Arg Val Val Ser Ala Lys Pro Gln
        915                 920                 925 gca att ccg gat gta caa caa cag cca cct agc gca aag gcg gac ccg       2832
Ala Ile Pro Asp Val Gln Gln Gln Pro Pro Ser Ala Lys Ala Asp Pro
    930                 935                 940 ggg aaa aca gga gtt gca ctt tcg ccc act cag cta cgc gac gtc ctg       2880
Gly Lys Thr Gly Val Ala Leu Ser Pro Thr Gln Leu Arg Asp Val Leu
945                 950                 955                 960 ctt gaa gtg gac aat cca ttg tat ctt ggt gta gag aac tcc aat ttg       2928
Leu Glu Val Asp Asn Pro Leu Tyr Leu Gly Val Glu Asn Ser Asn Leu
                965                 970                 975 gtg cag ttt gag tcg aaa cct gca act tct tca cgt atc gtt tcg atc       2976
Val Gln Phe Glu Ser Lys Pro Ala Thr Ser Ser Arg Ile Val Ser Ile
            980                 985                 990 aaa ccg tgc tcg att agt gac ctt  ggc gat aag tct ttt  atg gaa acg    3024
Lys Pro Cys Ser Ile Ser Asp Leu  Gly Asp Lys Ser Phe  Met Glu Thr
        995                 1000                 1005 tac aac  gtg tca gca cct ctg  tat act gga gca atg  gcc aag ggc        3069
Tyr Asn  Val Ser Ala Pro Leu  Tyr Thr Gly Ala Met  Ala Lys Gly
    1010                 1015                 1020 att gca  tcc gcc gac ttg gtc  att gct gct ggg aaa  cgc aag ata        3114
Ile Ala  Ser Ala Asp Leu Val  Ile Ala Ala Gly Lys  Arg Lys Ile
    1025                 1030                 1035 ctt gga  tcg ttt ggt gcg gga  ggg ctg cct att tcc  ata gtc cgt        3159
Leu Gly  Ser Phe Gly Ala Gly  Gly Leu Pro Ile Ser  Ile Val Arg
    1040                 1045                 1050
```

```
gaa gca ctg gag aaa att caa caa cac ctg ccc cac ggc ccc tac       3204
Glu Ala Leu Glu Lys Ile Gln Gln His Leu Pro His Gly Pro Tyr
    1055                1060                1065 gct gtt aac ctc att cac tcg cct ttc gac agc aac ttg gaa aag       3249
Ala Val Asn Leu Ile His Ser Pro Phe Asp Ser Asn Leu Glu Lys
    1070                1075                1080 ggc aac gtt gac ctc ttt ctc gag atg ggc gtg aca gtg gta gaa       3294
Gly Asn Val Asp Leu Phe Leu Glu Met Gly Val Thr Val Val Glu
    1085                1090                1095 tgc agc gcg ttc atg gaa ctc acg gcc cag gtt gtc cgg tac cgc       3339
Cys Ser Ala Phe Met Glu Leu Thr Ala Gln Val Val Arg Tyr Arg
    1100                1105                1110 gcg tct ggt cta agc aaa agt gcg gac ggt tcg att cgc att gct       3384
Ala Ser Gly Leu Ser Lys Ser Ala Asp Gly Ser Ile Arg Ile Ala
    1115                1120                1125 cac cgt att att ggc aag gtt tcc aga acc gag ctg gca gaa atg       3429
His Arg Ile Ile Gly Lys Val Ser Arg Thr Glu Leu Ala Glu Met
    1130                1135                1140 ttt att cgt cca gca cca cag cac ctc ctc caa aaa ctc gta gcc       3474
Phe Ile Arg Pro Ala Pro Gln His Leu Leu Gln Lys Leu Val Ala
    1145                1150                1155 tcc ggc gag ctg aca gct gag caa gcc gag ctt gca aca cag gtt       3519
Ser Gly Glu Leu Thr Ala Glu Gln Ala Glu Leu Ala Thr Gln Val
    1160                1165                1170 ccg gtg gcg gat gac att gcg gtc gaa gcc gac tcg ggg ggg cat       3564
Pro Val Ala Asp Asp Ile Ala Val Glu Ala Asp Ser Gly Gly His
    1175                1180                1185 acc gac aac agg cct att cac gtc att ctt cct cta atc atc aac       3609
Thr Asp Asn Arg Pro Ile His Val Ile Leu Pro Leu Ile Ile Asn
    1190                1195                1200 cta cgc aac cgt ttg cat aaa gag ctt gac tac cct tcg cat ctc       3654
Leu Arg Asn Arg Leu His Lys Glu Leu Asp Tyr Pro Ser His Leu
    1205                1210                1215 cgg gta cgt gtg ggt gct ggt ggt ggt att gga tgt cct caa gcc       3699
Arg Val Arg Val Gly Ala Gly Gly Gly Ile Gly Cys Pro Gln Ala
    1220                1225                1230 gct ctt gca gca ttt caa atg ggg gca gcg ttt tta atc act gga       3744
Ala Leu Ala Ala Phe Gln Met Gly Ala Ala Phe Leu Ile Thr Gly
    1235                1240                1245 acg gtg aac cag ctt gct cgt gaa agt ggc act tgt gac aac gtc       3789
Thr Val Asn Gln Leu Ala Arg Glu Ser Gly Thr Cys Asp Asn Val
    1250                1255                1260 cgg tta cag ctc tca aag gcc acg tat agc gac gtg tgt atg gct       3834
Arg Leu Gln Leu Ser Lys Ala Thr Tyr Ser Asp Val Cys Met Ala
    1265                1270                1275 cct gct gcc gat atg ttt gac caa ggc gtg gag ctg caa gta ttg       3879
Pro Ala Ala Asp Met Phe Asp Gln Gly Val Glu Leu Gln Val Leu
    1280                1285                1290 aag aaa ggc acg ctg ttc cca agt cgt gct aag aag ctg tac gag       3924
Lys Lys Gly Thr Leu Phe Pro Ser Arg Ala Lys Lys Leu Tyr Glu
    1295                1300                1305 ctg ttc tgc aag tat gac tcg ttt gag gca atg ccg gct gaa gaa       3969
Leu Phe Cys Lys Tyr Asp Ser Phe Glu Ala Met Pro Ala Glu Glu
    1310                1315                1320 ttg caa cgg gtt gaa aag cgg att ttt caa aag tcg ctt gct gaa       4014
Leu Gln Arg Val Glu Lys Arg Ile Phe Gln Lys Ser Leu Ala Glu
    1325                1330                1335 gtt tgg cag gag acc agt gac ttt tac att cat cgt atc aag aac       4059
Val Trp Gln Glu Thr Ser Asp Phe Tyr Ile His Arg Ile Lys Asn
    1340                1345                1350
```

```
cct gag aaa atc aat cgt gct gca agc gat ggc aaa ctg aaa atg      4104
Pro Glu Lys Ile Asn Arg Ala Ala Ser Asp Gly Lys Leu Lys Met
    1355                1360                1365 tcg ctt tgc ttt cgc tgg tac ctt ggg ctt tcc tca ttt tgg gcc      4149
Ser Leu Cys Phe Arg Trp Tyr Leu Gly Leu Ser Ser Phe Trp Ala
1370                1375                1380 aac tct ggg gca caa gat cgc gtc atg gac tat caa att tgg tgt      4194
Asn Ser Gly Ala Gln Asp Arg Val Met Asp Tyr Gln Ile Trp Cys
    1385                1390                1395 ggc cct gct att ggc gct ttc aat gat ttt acc aag ggc acg tac      4239
Gly Pro Ala Ile Gly Ala Phe Asn Asp Phe Thr Lys Gly Thr Tyr
1400                1405                1410 ctt gac gtg act gtt gca aag agt tac cct tgt gtg gca cag atc      4284
Leu Asp Val Thr Val Ala Lys Ser Tyr Pro Cys Val Ala Gln Ile
    1415                1420                1425 aat ttg caa att ttg caa gga gct gcg tat ctg aaa cgc ctt ggt      4329
Asn Leu Gln Ile Leu Gln Gly Ala Ala Tyr Leu Lys Arg Leu Gly
1430                1435                1440 gtc att cgt ttt gac cgc atg ctg ctg cag gcc gtc gat atc gac      4374
Val Ile Arg Phe Asp Arg Met Leu Leu Gln Ala Val Asp Ile Asp
    1445                1450                1455 gat cct gta ttt act tac gtg ccg acc cag cca ctt                  4410
Asp Pro Val Phe Thr Tyr Val Pro Thr Gln Pro Leu
1460                1465                1470

<210> SEQ ID NO 62
<211> LENGTH: 1470
<212> TYPE: PRT
<213> ORGANISM: Thraustochytrium sp.

<400> SEQUENCE: 62

Met Gly Pro Arg Val Ala Ser Gly Lys Val Pro Ala Trp Glu Met Ser
1               5                   10                  15

Lys Ser Glu Leu Cys Asp Asp Arg Thr Val Phe Asp Tyr Glu Glu
            20                  25                  30

Leu Leu Glu Phe Ala Glu Gly Asp Ile Ser Lys Val Phe Gly Pro Glu
        35                  40                  45

Phe Lys Val Val Asp Gly Phe Arg Arg Val Arg Leu Pro Ala Arg
    50                  55                  60

Glu Tyr Leu Leu Val Thr Arg Val Thr Leu Met Asp Ala Glu Val Gly
65                  70                  75                  80

Asn Phe Arg Val Gly Ala Arg Met Val Thr Glu Tyr Asp Val Pro Val
                85                  90                  95

Asn Gly Glu Leu Ser Glu Gly Gly Asp Val Pro Trp Ala Val Leu Val
            100                 105                 110

Glu Ala Gly Gln Cys Asp Leu Leu Leu Ile Ser Tyr Met Gly Ile Asp
        115                 120                 125

Phe Gln Cys Lys Gly Glu Arg Val Tyr Arg Leu Leu Asn Thr Thr Leu
    130                 135                 140

Thr Phe Phe Gly Val Ala Lys Glu Gly Glu Thr Leu Val Tyr Asp Ile
145                 150                 155                 160

Arg Val Thr Gly Phe Ala Lys Arg Pro Asp Gly Asp Ile Ser Met Phe
                165                 170                 175

Phe Phe Glu Tyr Asp Cys Tyr Cys Asn Gly Lys Leu Leu Ile Glu Met
            180                 185                 190

Arg Asp Gly Ser Ala Gly Phe Phe Thr Asp Glu Glu Leu Ala Ala Gly
```

-continued

```
              195                 200                 205
Lys Gly Val Val Thr Arg Ala Gln Gln Asn Met Arg Asp Lys Ile
    210                 215                 220
Val Arg Gln Ser Ile Glu Pro Phe Ala Leu Ala Ala Cys Thr His Lys
225                 230                 235                 240
Thr Thr Leu Asn Glu Ser Asp Met Gln Ser Leu Val Glu Arg Asn Trp
                245                 250                 255
Ala Asn Val Phe Gly Thr Ser Asn Lys Met Ala Glu Leu Asn Tyr Lys
                260                 265                 270
Ile Cys Ala Arg Lys Met Leu Met Ile Asp Arg Val Thr His Ile Asp
                275                 280                 285
His His Gly Gly Ala Tyr Gly Leu Gly Leu Leu Val Gly Glu Lys Ile
    290                 295                 300
Leu Asp Arg Asn His Trp Tyr Phe Pro Cys His Phe Val Asn Asp Gln
305                 310                 315                 320
Val Met Ala Gly Ser Leu Val Ser Asp Gly Cys Ser Gln Leu Leu Lys
                325                 330                 335
Leu Tyr Met Ile Trp Leu Gly Leu His Leu Lys Met Glu Glu Phe Asp
                340                 345                 350
Phe Leu Pro Val Ser Gly His Lys Asn Lys Val Arg Cys Arg Gly Gln
                355                 360                 365
Ile Ser Pro His Lys Gly Lys Leu Val Tyr Val Met Glu Ile Lys Lys
    370                 375                 380
Met Gly Tyr Asp Gln Ala Ser Gly Ser Pro Tyr Ala Ile Ala Asp Val
385                 390                 395                 400
Asp Ile Ile Asp Val Asn Glu Glu Leu Gly Gln Ser Phe Asp Ile Asn
                405                 410                 415
Asp Leu Ala Ser Tyr Gly Lys Gly Asp Leu Ser Lys Lys Ile Val Val
                420                 425                 430
Asp Phe Lys Gly Ile Ala Leu Gln Leu Lys Gly Arg Ala Phe Ser Arg
                435                 440                 445
Met Ser Ser Ser Ser Leu Asn Glu Gly Trp Gln Cys Val Pro Lys
    450                 455                 460
Pro Ser Gln Arg Met Glu His Glu Gln Pro Ala His Cys Leu Ala
465                 470                 475                 480
Ser Asp Pro Glu Ala Pro Ser Thr Val Thr Trp His Pro Met Ser Lys
                485                 490                 495
Leu Pro Gly Asn Pro Thr Pro Phe Phe Ser Pro Ser Tyr Pro Pro
                500                 505                 510
Arg Ala Ile Cys Phe Ile Pro Phe Pro Gly Asn Pro Leu Asp Asn Asn
                515                 520                 525
Cys Lys Ala Gly Glu Met Pro Leu Asn Trp Tyr Asn Met Ser Glu Phe
    530                 535                 540
Met Cys Gly Lys Val Ser Asn Cys Leu Gly Pro Glu Phe Ala Arg Phe
545                 550                 555                 560
Asp Lys Ser Asn Thr Ser Arg Ser Pro Ala Phe Asp Leu Ala Leu Val
                565                 570                 575
Thr Arg Val Val Glu Val Thr Asn Met Glu His Gly Lys Phe Leu Asn
                580                 585                 590
Val Asp Cys Asn Pro Ser Lys Gly Thr Met Val Gly Glu Phe Asp Cys
    595                 600                 605
Pro Gln Asp Ala Trp Phe Phe Asp Gly Ser Cys Asn Asp Gly His Met
    610                 615                 620
```

```
Pro Tyr Ser Ile Ile Met Glu Ile Gly Leu Gln Thr Ser Gly Val Leu
625                 630                 635                 640

Thr Ser Val Leu Lys Ala Pro Leu Thr Met Asp Lys Asp Ile Leu
        645                 650                 655

Phe Arg Asn Leu Asp Ala Ser Ala Glu Met Val Arg Pro Asp Val Asp
            660                 665                 670

Val Arg Gly Lys Thr Ile Arg Asn Val Thr Lys Cys Thr Gly Tyr Ala
            675                 680                 685

Met Leu Gly Lys Met Gly Ile His Arg Phe Thr Phe Glu Leu Ser Val
            690                 695                 700

Asp Gly Val Val Phe Tyr Lys Gly Ser Thr Ser Phe Gly Trp Phe Thr
705                 710                 715                 720

Pro Glu Val Phe Ala Gln Gln Ala Gly Leu Asp Asn Gly Lys Lys Thr
                725                 730                 735

Glu Pro Trp Cys Lys Thr Asn Asn Thr Ser Val Arg Arg Val Glu Ile
                740                 745                 750

Ala Ser Ala Lys Gly Lys Glu Gln Leu Thr Glu Lys Leu Pro Asp Ala
        755                 760                 765

Thr Asn Ala Gln Val Leu Arg Arg Ser Glu Gln Cys Glu Tyr Leu Asp
770                 775                 780

Tyr Leu Asn Ile Ala Pro Asp Ser Gly Leu His Gly Lys Gly Tyr Ala
785                 790                 795                 800

His Gly His Lys Asp Val Asn Pro Gln Asp Trp Phe Phe Ser Cys His
                805                 810                 815

Phe Trp Phe Asp Pro Val Met Pro Gly Ser Leu Gly Ile Glu Ser Met
                820                 825                 830

Phe Gln Leu Ile Glu Ala Phe Ala Val Asp Gln Asn Ile Pro Gly Glu
            835                 840                 845

Tyr Asn Val Ser Asn Pro Thr Phe Ala His Ala Pro Gly Lys Thr Ala
850                 855                 860

Trp Lys Tyr Arg Gly Gln Leu Thr Pro Lys Asn Arg Ala Met Asp Cys
865                 870                 875                 880

Glu Val His Ile Val Ser Ile Thr Ala Ser Pro Glu Asn Gly Gly Tyr
                885                 890                 895

Val Asp Ile Val Ala Asp Gly Ala Leu Trp Val Asp Gly Leu Arg Val
            900                 905                 910

Tyr Glu Ala Lys Glu Leu Arg Val Arg Val Ser Ala Lys Pro Gln
            915                 920                 925

Ala Ile Pro Asp Val Gln Gln Gln Pro Pro Ser Ala Lys Ala Asp Pro
930                 935                 940

Gly Lys Thr Gly Val Ala Leu Ser Pro Thr Gln Leu Arg Asp Val Leu
945                 950                 955                 960

Leu Glu Val Asp Asn Pro Leu Tyr Leu Gly Val Glu Asn Ser Asn Leu
                965                 970                 975

Val Gln Phe Glu Ser Lys Pro Ala Thr Ser Ser Arg Ile Val Ser Ile
            980                 985                 990

Lys Pro Cys Ser Ile Ser Asp Leu Gly Asp Lys Ser Phe Met Glu Thr
            995                 1000                1005

Tyr Asn Val Ser Ala Pro Leu Tyr Thr Gly Ala Met Ala Lys Gly
        1010                1015                1020

Ile Ala Ser Ala Asp Leu Val Ile Ala Ala Gly Lys Arg Lys Ile
        1025                1030                1035
```

-continued

| | | | | | | | | | | | |
|---|---|---|---|---|---|---|---|---|---|---|---|
| Leu | Gly | Ser | Phe | Gly | Ala | Gly | Gly | Leu | Pro | Ile | Ser | Ile | Val | Arg |
| | 1040 | | | | 1045 | | | | 1050 | | |

Leu Gly Ser Phe Gly Ala Gly Gly Leu Pro Ile Ser Ile Val Arg
    1040                1045                1050

Glu Ala Leu Glu Lys Ile Gln Gln His Leu Pro His Gly Pro Tyr
    1055                1060                1065

Ala Val Asn Leu Ile His Ser Pro Phe Asp Ser Asn Leu Glu Lys
    1070                1075                1080

Gly Asn Val Asp Leu Phe Leu Glu Met Gly Val Thr Val Val Glu
    1085                1090                1095

Cys Ser Ala Phe Met Glu Leu Thr Ala Gln Val Val Arg Tyr Arg
    1100                1105                1110

Ala Ser Gly Leu Ser Lys Ser Ala Asp Gly Ser Ile Arg Ile Ala
    1115                1120                1125

His Arg Ile Ile Gly Lys Val Ser Arg Thr Glu Leu Ala Glu Met
    1130                1135                1140

Phe Ile Arg Pro Ala Pro Gln His Leu Leu Gln Lys Leu Val Ala
    1145                1150                1155

Ser Gly Glu Leu Thr Ala Glu Gln Ala Glu Leu Ala Thr Gln Val
    1160                1165                1170

Pro Val Ala Asp Asp Ile Ala Val Glu Ala Asp Ser Gly Gly His
    1175                1180                1185

Thr Asp Asn Arg Pro Ile His Val Ile Leu Pro Leu Ile Ile Asn
    1190                1195                1200

Leu Arg Asn Arg Leu His Lys Glu Leu Asp Tyr Pro Ser His Leu
    1205                1210                1215

Arg Val Arg Val Gly Ala Gly Gly Gly Ile Gly Cys Pro Gln Ala
    1220                1225                1230

Ala Leu Ala Ala Phe Gln Met Gly Ala Ala Phe Leu Ile Thr Gly
    1235                1240                1245

Thr Val Asn Gln Leu Ala Arg Glu Ser Gly Thr Cys Asp Asn Val
    1250                1255                1260

Arg Leu Gln Leu Ser Lys Ala Thr Tyr Ser Asp Val Cys Met Ala
    1265                1270                1275

Pro Ala Ala Asp Met Phe Asp Gln Gly Val Glu Leu Gln Val Leu
    1280                1285                1290

Lys Lys Gly Thr Leu Phe Pro Ser Arg Ala Lys Lys Leu Tyr Glu
    1295                1300                1305

Leu Phe Cys Lys Tyr Asp Ser Phe Glu Ala Met Pro Ala Glu Glu
    1310                1315                1320

Leu Gln Arg Val Glu Lys Arg Ile Phe Gln Lys Ser Leu Ala Glu
    1325                1330                1335

Val Trp Gln Glu Thr Ser Asp Phe Tyr Ile His Arg Ile Lys Asn
    1340                1345                1350

Pro Glu Lys Ile Asn Arg Ala Ala Ser Asp Gly Lys Leu Lys Met
    1355                1360                1365

Ser Leu Cys Phe Arg Trp Tyr Leu Gly Leu Ser Ser Phe Trp Ala
    1370                1375                1380

Asn Ser Gly Ala Gln Asp Arg Val Met Asp Tyr Gln Ile Trp Cys
    1385                1390                1395

Gly Pro Ala Ile Gly Ala Phe Asn Asp Phe Thr Lys Gly Thr Tyr
    1400                1405                1410

Leu Asp Val Thr Val Ala Lys Ser Tyr Pro Cys Val Ala Gln Ile
    1415                1420                1425

Asn Leu Gln Ile Leu Gln Gly Ala Ala Tyr Leu Lys Arg Leu Gly

```
                     1430                  1435                 1440
Val Ile Arg Phe Asp Arg Met  Leu Leu Gln Ala Val  Asp Ile Asp
       1445                 1450                 1455

Asp Pro  Val Phe Thr Tyr Val  Pro Thr Gln Pro Leu
    1460                 1465                 1470

<210> SEQ ID NO 63
<211> LENGTH: 1500
<212> TYPE: DNA
<213> ORGANISM: Thraustochytrium sp.
<220> FEATURE:
<221> NAME/KEY: CDS
<222> LOCATION: (1)..(1500)

<400> SEQUENCE: 63 atg ggc ccg cga gtg gcg tca ggc aag gtg ccg gct tgg gag atg agc      48
Met Gly Pro Arg Val Ala Ser Gly Lys Val Pro Ala Trp Glu Met Ser
1               5                  10                  15 aag tcc gag ctg tgt gat gac cgc acg gta gtc ttt gac tat gag gag      96
Lys Ser Glu Leu Cys Asp Asp Arg Thr Val Val Phe Asp Tyr Glu Glu
            20                  25                  30 ctg ctg gag ttc gct gag ggc gat atc agt aag gtt ttt ggg ccg gag     144
Leu Leu Glu Phe Ala Glu Gly Asp Ile Ser Lys Val Phe Gly Pro Glu
        35                  40                  45 ttc aaa gtg gtg gac ggg ttt agg cgc agg gtg agg ttg ccc gct cga     192
Phe Lys Val Val Asp Gly Phe Arg Arg Arg Val Arg Leu Pro Ala Arg
    50                  55                  60 gag tac ctg ctg gtg acc cgg gtt acg ctg atg gat gcc gag gtg ggc     240
Glu Tyr Leu Leu Val Thr Arg Val Thr Leu Met Asp Ala Glu Val Gly
65                  70                  75                  80 aac ttt cga gtg gga gca cgt atg gtg aca gag tat gac gta cct gtg     288
Asn Phe Arg Val Gly Ala Arg Met Val Thr Glu Tyr Asp Val Pro Val
                85                  90                  95 aac gga gag ctc tcg gaa ggg gga gat gtg ccg tgg gct gtg ttg gtg     336
Asn Gly Glu Leu Ser Glu Gly Gly Asp Val Pro Trp Ala Val Leu Val
            100                 105                 110 gaa gcc ggg cag tgc gac ttg ctg cta att tct tac atg ggc atc gat     384
Glu Ala Gly Gln Cys Asp Leu Leu Leu Ile Ser Tyr Met Gly Ile Asp
        115                 120                 125 ttc cag tgc aaa gga gag cgg gtc tac cgg ctg ctg aac acc acc ttg     432
Phe Gln Cys Lys Gly Glu Arg Val Tyr Arg Leu Leu Asn Thr Thr Leu
    130                 135                 140 acg ttt ttt ggc gtc gcg aaa gaa ggg gaa acg ctt gtg tac gat att     480
Thr Phe Phe Gly Val Ala Lys Glu Gly Glu Thr Leu Val Tyr Asp Ile
145                 150                 155                 160 cgc gtc acg ggt ttc gcc aag agg ccg gac gga gat atc tcc atg ttc     528
Arg Val Thr Gly Phe Ala Lys Arg Pro Asp Gly Asp Ile Ser Met Phe
                165                 170                 175 ttt ttc gaa tat gat tgc tac tgc aat ggc aag ctt ctc atc gaa atg     576
Phe Phe Glu Tyr Asp Cys Tyr Cys Asn Gly Lys Leu Leu Ile Glu Met
            180                 185                 190 cga gat ggc tct gca ggc ttc ttc acg gac gaa gag ctc gct gcc ggc     624
Arg Asp Gly Ser Ala Gly Phe Phe Thr Asp Glu Glu Leu Ala Ala Gly
        195                 200                 205 aaa gga gtg gtc gtc act cgt gca cag caa aac atg cgg gac aaa att     672
Lys Gly Val Val Val Thr Arg Ala Gln Gln Asn Met Arg Asp Lys Ile
    210                 215                 220 gta cgg cag tcc att gag cct ttt gca ctg gcg gct tgc acg cac aaa     720
Val Arg Gln Ser Ile Glu Pro Phe Ala Leu Ala Ala Cys Thr His Lys
225                 230                 235                 240
```

```
acg act ctg aac gag agt gac atg cag tcc ctt gtg gag cga aac tgg      768
Thr Thr Leu Asn Glu Ser Asp Met Gln Ser Leu Val Glu Arg Asn Trp
            245                 250                 255 gca aac gtt ttt ggc acc agt aac aag atg gcg gag ctc aac tat aaa      816
Ala Asn Val Phe Gly Thr Ser Asn Lys Met Ala Glu Leu Asn Tyr Lys
        260                 265                 270 att tgc gcc agg aaa atg ctc atg atc gac agg gtt acc cac att gac      864
Ile Cys Ala Arg Lys Met Leu Met Ile Asp Arg Val Thr His Ile Asp
    275                 280                 285 cac cac ggt ggg gcg tat ggc ctc gga cta ctt gtt gga gag aag atc      912
His His Gly Gly Ala Tyr Gly Leu Gly Leu Leu Val Gly Glu Lys Ile
290                 295                 300 ttg gat cga aac cat tgg tac ttt cct tgt cac ttt gtc aat gat caa      960
Leu Asp Arg Asn His Trp Tyr Phe Pro Cys His Phe Val Asn Asp Gln
305                 310                 315                 320 gtc atg gca ggg tca ctg gtc agc gat ggt tgc agc cag ctc tta aaa     1008
Val Met Ala Gly Ser Leu Val Ser Asp Gly Cys Ser Gln Leu Leu Lys
                325                 330                 335 ctc tat atg atc tgg ctt ggc ctc cac ctg aaa atg gag gaa ttt gat     1056
Leu Tyr Met Ile Trp Leu Gly Leu His Leu Lys Met Glu Glu Phe Asp
            340                 345                 350 ttt ctc cca gtt agc ggc cac aaa aac aag gtg cga tgc agg gga caa     1104
Phe Leu Pro Val Ser Gly His Lys Asn Lys Val Arg Cys Arg Gly Gln
        355                 360                 365 att tca ccg cat aaa ggc aag ctt gtc tac gtc atg gaa atc aaa aag     1152
Ile Ser Pro His Lys Gly Lys Leu Val Tyr Val Met Glu Ile Lys Lys
    370                 375                 380 atg ggt tac gat caa gca tct gga agc cca tac gcc atc gcg gac gtt     1200
Met Gly Tyr Asp Gln Ala Ser Gly Ser Pro Tyr Ala Ile Ala Asp Val
385                 390                 395                 400 gat atc att gac gtc aac gaa gag ctg ggt caa agt ttt gac atc aac     1248
Asp Ile Ile Asp Val Asn Glu Glu Leu Gly Gln Ser Phe Asp Ile Asn
                405                 410                 415 gac ctt gcg agc tac gga aaa ggt gac ctg agc aaa aaa atc gtg gtt     1296
Asp Leu Ala Ser Tyr Gly Lys Gly Asp Leu Ser Lys Lys Ile Val Val
            420                 425                 430 gac ttc aaa gga att gct ttg cag ctc aaa ggc cgc gct ttt tca cgc     1344
Asp Phe Lys Gly Ile Ala Leu Gln Leu Lys Gly Arg Ala Phe Ser Arg
        435                 440                 445 atg agt tcc agc tcg tcc ttg aac gaa gga tgg caa tgt gtt cca aaa     1392
Met Ser Ser Ser Ser Leu Asn Glu Gly Trp Gln Cys Val Pro Lys
    450                 455                 460 cca agc cag aga atg gaa cac gaa cag ccc cct gct cac tgc ctt gca     1440
Pro Ser Gln Arg Met Glu His Glu Gln Pro Pro Ala His Cys Leu Ala
465                 470                 475                 480 agc gac ccc gaa gcc cct tca act gtg acc tgg cac cca atg tca aag     1488
Ser Asp Pro Glu Ala Pro Ser Thr Val Thr Trp His Pro Met Ser Lys
                485                 490                 495 ctt cct ggc aac                                                     1500
Leu Pro Gly Asn
            500

<210> SEQ ID NO 64
<211> LENGTH: 500
<212> TYPE: PRT
<213> ORGANISM: Thraustochytrium sp.

<400> SEQUENCE: 64

Met Gly Pro Arg Val Ala Ser Gly Lys Val Pro Ala Trp Glu Met Ser
1               5                   10                  15
```

```
Lys Ser Glu Leu Cys Asp Asp Arg Thr Val Val Phe Asp Tyr Glu Glu
         20                  25                  30

Leu Leu Glu Phe Ala Glu Gly Asp Ile Ser Lys Val Phe Gly Pro Glu
         35                  40                  45

Phe Lys Val Val Asp Gly Phe Arg Arg Val Arg Leu Pro Ala Arg
     50                  55                  60

Glu Tyr Leu Leu Val Thr Arg Val Thr Leu Met Asp Ala Glu Val Gly
65                   70                  75                  80

Asn Phe Arg Val Gly Ala Arg Met Val Thr Glu Tyr Asp Val Pro Val
                 85                  90                  95

Asn Gly Glu Leu Ser Glu Gly Gly Asp Val Pro Trp Ala Val Leu Val
             100                 105                 110

Glu Ala Gly Gln Cys Asp Leu Leu Leu Ile Ser Tyr Met Gly Ile Asp
             115                 120                 125

Phe Gln Cys Lys Gly Glu Arg Val Tyr Arg Leu Leu Asn Thr Thr Leu
     130                 135                 140

Thr Phe Phe Gly Val Ala Lys Glu Gly Glu Thr Leu Val Tyr Asp Ile
145                 150                 155                 160

Arg Val Thr Gly Phe Ala Lys Arg Pro Asp Gly Asp Ile Ser Met Phe
                165                 170                 175

Phe Phe Glu Tyr Asp Cys Tyr Cys Asn Gly Lys Leu Leu Ile Glu Met
             180                 185                 190

Arg Asp Gly Ser Ala Gly Phe Phe Thr Asp Glu Glu Leu Ala Ala Gly
         195                 200                 205

Lys Gly Val Val Val Thr Arg Ala Gln Gln Asn Met Arg Asp Lys Ile
210                 215                 220

Val Arg Gln Ser Ile Glu Pro Phe Ala Leu Ala Ala Cys Thr His Lys
225                 230                 235                 240

Thr Thr Leu Asn Glu Ser Asp Met Gln Ser Leu Val Glu Arg Asn Trp
                245                 250                 255

Ala Asn Val Phe Gly Thr Ser Asn Lys Met Ala Glu Leu Asn Tyr Lys
             260                 265                 270

Ile Cys Ala Arg Lys Met Leu Met Ile Asp Arg Val Thr His Ile Asp
         275                 280                 285

His His Gly Gly Ala Tyr Gly Leu Gly Leu Leu Val Gly Glu Lys Ile
290                 295                 300

Leu Asp Arg Asn His Trp Tyr Phe Pro Cys His Phe Val Asn Asp Gln
305                 310                 315                 320

Val Met Ala Gly Ser Leu Val Ser Asp Gly Cys Ser Gln Leu Leu Lys
                325                 330                 335

Leu Tyr Met Ile Trp Leu Gly Leu His Leu Lys Met Glu Glu Phe Asp
             340                 345                 350

Phe Leu Pro Val Ser Gly His Lys Asn Lys Val Arg Cys Arg Gly Gln
         355                 360                 365

Ile Ser Pro His Lys Gly Lys Leu Val Tyr Val Met Glu Ile Lys Lys
     370                 375                 380

Met Gly Tyr Asp Gln Ala Ser Gly Ser Pro Tyr Ala Ile Ala Asp Val
385                 390                 395                 400

Asp Ile Ile Asp Val Asn Glu Glu Leu Gly Gln Ser Phe Asp Ile Asn
                405                 410                 415

Asp Leu Ala Ser Tyr Gly Lys Gly Asp Leu Ser Lys Lys Ile Val Val
             420                 425                 430

Asp Phe Lys Gly Ile Ala Leu Gln Leu Lys Gly Arg Ala Phe Ser Arg
```

```
                 435                  440                   445
Met Ser Ser Ser Ser Leu Asn Glu Gly Trp Gln Cys Val Pro Lys
    450                   455                   460

Pro Ser Gln Arg Met Glu His Glu Gln Pro Ala His Cys Leu Ala
465                   470                   475                   480

Ser Asp Pro Glu Ala Pro Ser Thr Val Thr Trp His Pro Met Ser Lys
                    485                   490                   495

Leu Pro Gly Asn
            500

<210> SEQ ID NO 65
<211> LENGTH: 1500
<212> TYPE: DNA
<213> ORGANISM: Thraustochytrium sp.
<220> FEATURE:
<221> NAME/KEY: CDS
<222> LOCATION: (1)..(1500)

<400> SEQUENCE: 65
```

| | | |
|---|---|---|
| cct acg ccg ttc ttc tcc cct tca tct tac cct ccg agg gca att tgc<br>Pro Thr Pro Phe Phe Ser Pro Ser Ser Tyr Pro Pro Arg Ala Ile Cys<br>1               5                  10                  15 | 48 |
| ttc atc cct ttc ccg ggc aat ccc ctt gac aac aac tgc aag gct gga<br>Phe Ile Pro Phe Pro Gly Asn Pro Leu Asp Asn Asn Cys Lys Ala Gly<br>            20                  25                  30 | 96 |
| gaa atg ccc ctg aac tgg tac aac atg tca gag ttc atg tgt ggc aag<br>Glu Met Pro Leu Asn Trp Tyr Asn Met Ser Glu Phe Met Cys Gly Lys<br>        35                  40                  45 | 144 |
| gtt tct aac tgc ttg ggc cca gaa ttc gca cgc ttt gac aag tcg aac<br>Val Ser Asn Cys Leu Gly Pro Glu Phe Ala Arg Phe Asp Lys Ser Asn<br>    50                  55                  60 | 192 |
| acc agc cgg agc cct gct ttt gac ttg gct ctg gtg acc cga gtt gtt<br>Thr Ser Arg Ser Pro Ala Phe Asp Leu Ala Leu Val Thr Arg Val Val<br>65                  70                  75                  80 | 240 |
| gaa gtc aca aac atg gaa cac ggc aag ttt cta aac gtt gat tgc aat<br>Glu Val Thr Asn Met Glu His Gly Lys Phe Leu Asn Val Asp Cys Asn<br>                85                  90                  95 | 288 |
| cca agc aaa ggc aca atg gtg ggg gag ttt gac tgt ccc caa gac gcg<br>Pro Ser Lys Gly Thr Met Val Gly Glu Phe Asp Cys Pro Gln Asp Ala<br>            100                 105                 110 | 336 |
| tgg ttc ttt gat ggt tcg tgc aac gac ggc cat atg ccg tat tcc att<br>Trp Phe Phe Asp Gly Ser Cys Asn Asp Gly His Met Pro Tyr Ser Ile<br>        115                 120                 125 | 384 |
| atc atg gaa atc gga ctg caa acc tca ggt gtt ctc acc tcg gtg ttg<br>Ile Met Glu Ile Gly Leu Gln Thr Ser Gly Val Leu Thr Ser Val Leu<br>    130                 135                 140 | 432 |
| aag gca ccg ctg act atg gac aag gat gac att ctc ttt cga aac ctc<br>Lys Ala Pro Leu Thr Met Asp Lys Asp Asp Ile Leu Phe Arg Asn Leu<br>145                 150                 155                 160 | 480 |
| gat gca agt gct gaa atg gtg cgt cca gac gtg gat gtt cgc ggc aaa<br>Asp Ala Ser Ala Glu Met Val Arg Pro Asp Val Asp Val Arg Gly Lys<br>                165                 170                 175 | 528 |
| acg att cga aac gtg acc aag tgt acc ggc tat gca atg ttg gga aag<br>Thr Ile Arg Asn Val Thr Lys Cys Thr Gly Tyr Ala Met Leu Gly Lys<br>            180                 185                 190 | 576 |
| atg ggg att cac cgg ttc acg ttt gag ttg agc gtt gac ggc gtg gta<br>Met Gly Ile His Arg Phe Thr Phe Glu Leu Ser Val Asp Gly Val Val<br>        195                 200                 205 | 624 |
| ttt tat aaa gga tcc act tcc ttt gga tgg ttc act ccc gag gtg ttt<br>Phe Tyr Lys Gly Ser Thr Ser Phe Gly Trp Phe Thr Pro Glu Val Phe | 672 |

-continued

```
                210                 215                 220
gct cag caa gct gga ctc gac aac ggg aaa aag acg gag ccc tgg tgc       720
Ala Gln Gln Ala Gly Leu Asp Asn Gly Lys Lys Thr Glu Pro Trp Cys
225                 230                 235                 240 aag act aac aac acc tcg gtt cga aga gtt gaa atc gca tcc gcc aaa       768
Lys Thr Asn Asn Thr Ser Val Arg Arg Val Glu Ile Ala Ser Ala Lys
                245                 250                 255 gga aaa gag cag ctg act gag aag ctt ccc gac gca act aat gct caa       816
Gly Lys Glu Gln Leu Thr Glu Lys Leu Pro Asp Ala Thr Asn Ala Gln
            260                 265                 270 gtt ctt cgg cgt tca gag cag tgt gaa tac ctc gat tac ctc aat att       864
Val Leu Arg Arg Ser Glu Gln Cys Glu Tyr Leu Asp Tyr Leu Asn Ile
        275                 280                 285 gcc cct gac tct ggg ctg cat ggg aag ggc tac gcc cac gga cac aaa       912
Ala Pro Asp Ser Gly Leu His Gly Lys Gly Tyr Ala His Gly His Lys
    290                 295                 300 gac gtt aac ccg caa gac tgg ttc ttc tct tgc cac ttt tgg ttc gat       960
Asp Val Asn Pro Gln Asp Trp Phe Phe Ser Cys His Phe Trp Phe Asp
305                 310                 315                 320 cct gta atg cca gga tct tta gga att gaa tca atg ttc cag ctt atc      1008
Pro Val Met Pro Gly Ser Leu Gly Ile Glu Ser Met Phe Gln Leu Ile
                325                 330                 335 gag gcc ttt gcg gtg gac caa aac att cct gga gag tac aac gta tcc      1056
Glu Ala Phe Ala Val Asp Gln Asn Ile Pro Gly Glu Tyr Asn Val Ser
            340                 345                 350 aat ccg acc ttt gcc cat gca cca ggc aaa acg gcg tgg aaa tac cga      1104
Asn Pro Thr Phe Ala His Ala Pro Gly Lys Thr Ala Trp Lys Tyr Arg
        355                 360                 365 ggc cag ctc aca cca aag aac cgt gcg atg gac tgc gag gtg cat atc      1152
Gly Gln Leu Thr Pro Lys Asn Arg Ala Met Asp Cys Glu Val His Ile
    370                 375                 380 gtt tca att acc gcc tcc ccc gag aac ggg ggc tac gtt gac atc gtg      1200
Val Ser Ile Thr Ala Ser Pro Glu Asn Gly Gly Tyr Val Asp Ile Val
385                 390                 395                 400 gcc gat gga gcg ctt tgg gta gat gga ctt cgc gtg tac gaa gcc aaa      1248
Ala Asp Gly Ala Leu Trp Val Asp Gly Leu Arg Val Tyr Glu Ala Lys
                405                 410                 415 gag ctt cga gtt cgt gtc gtt tcg gca aaa cct caa gca att ccg gat      1296
Glu Leu Arg Val Arg Val Val Ser Ala Lys Pro Gln Ala Ile Pro Asp
            420                 425                 430 gta caa caa cag cca cct agc gca aag gcg gac ccg ggg aaa aca gga      1344
Val Gln Gln Gln Pro Pro Ser Ala Lys Ala Asp Pro Gly Lys Thr Gly
        435                 440                 445 gtt gca ctt tcg ccc act cag cta cgc gac gtc ctg ctt gaa gtg gac      1392
Val Ala Leu Ser Pro Thr Gln Leu Arg Asp Val Leu Leu Glu Val Asp
    450                 455                 460 aat cca ttg tat ctt ggt gta gag aac tcc aat ttg gtg cag ttt gag      1440
Asn Pro Leu Tyr Leu Gly Val Glu Asn Ser Asn Leu Val Gln Phe Glu
465                 470                 475                 480 tcg aaa cct gca act tct tca cgt atc gtt tcg atc aaa ccg tgc tcg      1488
Ser Lys Pro Ala Thr Ser Ser Arg Ile Val Ser Ile Lys Pro Cys Ser
                485                 490                 495 att agt gac ctt                                                      1500
Ile Ser Asp Leu
            500

<210> SEQ ID NO 66
<211> LENGTH: 500
<212> TYPE: PRT
<213> ORGANISM: Thraustochytrium sp.
```

<400> SEQUENCE: 66

```
Pro Thr Pro Phe Phe Ser Pro Ser Ser Tyr Pro Arg Ala Ile Cys
1               5                   10                  15

Phe Ile Pro Phe Pro Gly Asn Pro Leu Asp Asn Asn Cys Lys Ala Gly
            20                  25                  30

Glu Met Pro Leu Asn Trp Tyr Asn Met Ser Glu Phe Met Cys Gly Lys
        35                  40                  45

Val Ser Asn Cys Leu Gly Pro Glu Phe Ala Arg Phe Asp Lys Ser Asn
    50                  55                  60

Thr Ser Arg Ser Pro Ala Phe Asp Leu Ala Leu Val Thr Arg Val Val
65                  70                  75                  80

Glu Val Thr Asn Met Glu His Gly Lys Phe Leu Asn Val Asp Cys Asn
                85                  90                  95

Pro Ser Lys Gly Thr Met Val Gly Glu Phe Asp Cys Pro Gln Asp Ala
            100                 105                 110

Trp Phe Phe Asp Gly Ser Cys Asn Asp Gly His Met Pro Tyr Ser Ile
        115                 120                 125

Ile Met Glu Ile Gly Leu Gln Thr Ser Gly Val Leu Thr Ser Val Leu
    130                 135                 140

Lys Ala Pro Leu Thr Met Asp Lys Asp Ile Leu Phe Arg Asn Leu
145                 150                 155                 160

Asp Ala Ser Ala Glu Met Val Arg Pro Asp Val Asp Val Arg Gly Lys
                165                 170                 175

Thr Ile Arg Asn Val Thr Lys Cys Thr Gly Tyr Ala Met Leu Gly Lys
            180                 185                 190

Met Gly Ile His Arg Phe Thr Phe Glu Leu Ser Val Asp Gly Val Val
        195                 200                 205

Phe Tyr Lys Gly Ser Thr Ser Phe Gly Trp Phe Thr Pro Glu Val Phe
    210                 215                 220

Ala Gln Gln Ala Gly Leu Asp Asn Gly Lys Lys Thr Glu Pro Trp Cys
225                 230                 235                 240

Lys Thr Asn Asn Thr Ser Val Arg Arg Val Glu Ile Ala Ser Ala Lys
                245                 250                 255

Gly Lys Glu Gln Leu Thr Glu Lys Leu Pro Asp Ala Thr Asn Ala Gln
            260                 265                 270

Val Leu Arg Arg Ser Glu Gln Cys Glu Tyr Leu Asp Tyr Leu Asn Ile
        275                 280                 285

Ala Pro Asp Ser Gly Leu His Gly Lys Gly Tyr Ala His Gly His Lys
    290                 295                 300

Asp Val Asn Pro Gln Asp Trp Phe Phe Ser Cys His Phe Trp Phe Asp
305                 310                 315                 320

Pro Val Met Pro Gly Ser Leu Gly Ile Glu Ser Met Phe Gln Leu Ile
                325                 330                 335

Glu Ala Phe Ala Val Asp Gln Asn Ile Pro Gly Glu Tyr Asn Val Ser
            340                 345                 350

Asn Pro Thr Phe Ala His Ala Pro Gly Lys Thr Ala Trp Lys Tyr Arg
        355                 360                 365

Gly Gln Leu Thr Pro Lys Asn Arg Ala Met Asp Cys Glu Val His Ile
    370                 375                 380

Val Ser Ile Thr Ala Ser Pro Glu Asn Gly Gly Tyr Val Asp Ile Val
385                 390                 395                 400

Ala Asp Gly Ala Leu Trp Val Asp Gly Leu Arg Val Tyr Glu Ala Lys
```

```
                    405                 410                 415
Glu Leu Arg Val Arg Val Val Ser Ala Lys Pro Gln Ala Ile Pro Asp
            420                 425                 430

Val Gln Gln Pro Pro Ser Ala Lys Ala Asp Pro Gly Lys Thr Gly
        435                 440                 445

Val Ala Leu Ser Pro Thr Gln Leu Arg Asp Val Leu Glu Val Asp
    450                 455                 460

Asn Pro Leu Tyr Leu Gly Val Glu Asn Ser Asn Leu Val Gln Phe Glu
465                 470                 475                 480

Ser Lys Pro Ala Thr Ser Ser Arg Ile Val Ser Ile Lys Pro Cys Ser
                485                 490                 495

Ile Ser Asp Leu
            500

<210> SEQ ID NO 67
<211> LENGTH: 1410
<212> TYPE: DNA
<213> ORGANISM: Thraustochytrium sp.
<220> FEATURE:
<221> NAME/KEY: CDS
<222> LOCATION: (1)..(1410)

<400> SEQUENCE: 67 ggc gat aag tct ttt atg gaa acg tac aac gtg tca gca cct ctg tat       48
Gly Asp Lys Ser Phe Met Glu Thr Tyr Asn Val Ser Ala Pro Leu Tyr
1               5                   10                  15 act gga gca atg gcc aag ggc att gca tcc gcc gac ttg gtc att gct       96
Thr Gly Ala Met Ala Lys Gly Ile Ala Ser Ala Asp Leu Val Ile Ala
                20                  25                  30 gct ggg aaa cgc aag ata ctt gga tcg ttt ggt gcg gga ggg ctg cct      144
Ala Gly Lys Arg Lys Ile Leu Gly Ser Phe Gly Ala Gly Gly Leu Pro
            35                  40                  45 att tcc ata gtc cgt gaa gca ctg gag aaa att caa caa cac ctg ccc      192
Ile Ser Ile Val Arg Glu Ala Leu Glu Lys Ile Gln Gln His Leu Pro
        50                  55                  60 cac ggc ccc tac gct gtt aac ctc att cac tcg cct ttc gac agc aac      240
His Gly Pro Tyr Ala Val Asn Leu Ile His Ser Pro Phe Asp Ser Asn
65                  70                  75                  80 ttg gaa aag ggc aac gtt gac ctc ttt ctc gag atg ggc gtg aca gtg      288
Leu Glu Lys Gly Asn Val Asp Leu Phe Leu Glu Met Gly Val Thr Val
                85                  90                  95 gta gaa tgc agc gcg ttc atg gaa ctc acg gcc cag gtt gtc cgg tac      336
Val Glu Cys Ser Ala Phe Met Glu Leu Thr Ala Gln Val Val Arg Tyr
                100                 105                 110 cgc gcg tct ggt cta agc aaa agt gcg gac ggt tcg att cgc att gct      384
Arg Ala Ser Gly Leu Ser Lys Ser Ala Asp Gly Ser Ile Arg Ile Ala
            115                 120                 125 cac cgt att att ggc aag gtt tcc aga acc gag ctg gca gaa atg ttt      432
His Arg Ile Ile Gly Lys Val Ser Arg Thr Glu Leu Ala Glu Met Phe
        130                 135                 140 att cgt cca gca cca cag cac ctc ctc caa aaa ctc gta gcc tcc ggc      480
Ile Arg Pro Ala Pro Gln His Leu Leu Gln Lys Leu Val Ala Ser Gly
145                 150                 155                 160 gag ctg aca gct gag caa gcc gag ctt gca aca cag gtt ccg gtg gcg      528
Glu Leu Thr Ala Glu Gln Ala Glu Leu Ala Thr Gln Val Pro Val Ala
                165                 170                 175 gat gac att gcg gtc gaa gcc gac tcg ggg ggg cat acc gac aac agg      576
Asp Asp Ile Ala Val Glu Ala Asp Ser Gly Gly His Thr Asp Asn Arg
                180                 185                 190
```

```
cct att cac gtc att ctt cct cta atc atc aac cta cgc aac cgt ttg      624
Pro Ile His Val Ile Leu Pro Leu Ile Ile Asn Leu Arg Asn Arg Leu
            195                 200                 205 cat aaa gag ctt gac tac cct tcg cat ctc cgg gta cgt gtg ggt gct      672
His Lys Glu Leu Asp Tyr Pro Ser His Leu Arg Val Arg Val Gly Ala
        210                 215                 220 ggt ggt ggt att gga tgt cct caa gcc gct ctt gca gca ttt caa atg      720
Gly Gly Gly Ile Gly Cys Pro Gln Ala Ala Leu Ala Ala Phe Gln Met
225                 230                 235                 240 ggg gca gcg ttt tta atc act gga acg gtg aac cag ctt gct cgt gaa      768
Gly Ala Ala Phe Leu Ile Thr Gly Thr Val Asn Gln Leu Ala Arg Glu
                245                 250                 255 agt ggc act tgt gac aac gtc cgg tta cag ctc tca aag gcc acg tat      816
Ser Gly Thr Cys Asp Asn Val Arg Leu Gln Leu Ser Lys Ala Thr Tyr
            260                 265                 270 agc gac gtg tgt atg gct cct gct gcc gat atg ttt gac caa ggc gtg      864
Ser Asp Val Cys Met Ala Pro Ala Ala Asp Met Phe Asp Gln Gly Val
        275                 280                 285 gag ctg caa gta ttg aag aaa ggc acg ctg ttc cca agt cgt gct aag      912
Glu Leu Gln Val Leu Lys Lys Gly Thr Leu Phe Pro Ser Arg Ala Lys
290                 295                 300 aag ctg tac gag ctg ttc tgc aag tat gac tcg ttt gag gca atg ccg      960
Lys Leu Tyr Glu Leu Phe Cys Lys Tyr Asp Ser Phe Glu Ala Met Pro
305                 310                 315                 320 gct gaa gaa ttg caa cgg gtt gaa aag cgg att ttt caa aag tcg ctt     1008
Ala Glu Glu Leu Gln Arg Val Glu Lys Arg Ile Phe Gln Lys Ser Leu
                325                 330                 335 gct gaa gtt tgg cag gag acc agt gac ttt tac att cat cgt atc aag     1056
Ala Glu Val Trp Gln Glu Thr Ser Asp Phe Tyr Ile His Arg Ile Lys
            340                 345                 350 aac cct gag aaa atc aat cgt gct gca agc gat ggc aaa ctg aaa atg     1104
Asn Pro Glu Lys Ile Asn Arg Ala Ala Ser Asp Gly Lys Leu Lys Met
        355                 360                 365 tcg ctt tgc ttt cgc tgg tac ctt ggg ctt tcc tca ttt tgg gcc aac     1152
Ser Leu Cys Phe Arg Trp Tyr Leu Gly Leu Ser Ser Phe Trp Ala Asn
370                 375                 380 tct ggg gca caa gat cgc gtc atg gac tat caa att tgg tgt ggc cct     1200
Ser Gly Ala Gln Asp Arg Val Met Asp Tyr Gln Ile Trp Cys Gly Pro
385                 390                 395                 400 gct att ggc gct ttc aat gat ttt acc aag ggc acg tac ctt gac gtg     1248
Ala Ile Gly Ala Phe Asn Asp Phe Thr Lys Gly Thr Tyr Leu Asp Val
                405                 410                 415 act gtt gca aag agt tac cct tgt gtg gca cag atc aat ttg caa att     1296
Thr Val Ala Lys Ser Tyr Pro Cys Val Ala Gln Ile Asn Leu Gln Ile
            420                 425                 430 ttg caa gga gct gcg tat ctg aaa cgc ctt ggt gtc att cgt ttt gac     1344
Leu Gln Gly Ala Ala Tyr Leu Lys Arg Leu Gly Val Ile Arg Phe Asp
        435                 440                 445 cgc atg ctg ctg cag gcc gtc gat atc gac gat cct gta ttt act tac     1392
Arg Met Leu Leu Gln Ala Val Asp Ile Asp Asp Pro Val Phe Thr Tyr
450                 455                 460 gtg ccg acc cag cca ctt                                              1410
Val Pro Thr Gln Pro Leu
465                 470

<210> SEQ ID NO 68
<211> LENGTH: 470
<212> TYPE: PRT
<213> ORGANISM: Thraustochytrium sp.

<400> SEQUENCE: 68
```

-continued

```
Gly Asp Lys Ser Phe Met Glu Thr Tyr Asn Val Ser Ala Pro Leu Tyr
1               5                   10                  15

Thr Gly Ala Met Ala Lys Gly Ile Ala Ser Ala Asp Leu Val Ile Ala
                20                  25                  30

Ala Gly Lys Arg Lys Ile Leu Gly Ser Phe Gly Ala Gly Gly Leu Pro
            35                  40                  45

Ile Ser Ile Val Arg Glu Ala Leu Glu Lys Ile Gln Gln His Leu Pro
    50                  55                  60

His Gly Pro Tyr Ala Val Asn Leu Ile His Ser Pro Phe Asp Ser Asn
65                  70                  75                  80

Leu Glu Lys Gly Asn Val Asp Leu Phe Leu Glu Met Gly Val Thr Val
                85                  90                  95

Val Glu Cys Ser Ala Phe Met Glu Leu Thr Ala Gln Val Val Arg Tyr
                100                 105                 110

Arg Ala Ser Gly Leu Ser Lys Ser Ala Asp Gly Ser Ile Arg Ile Ala
            115                 120                 125

His Arg Ile Ile Gly Lys Val Ser Arg Thr Glu Leu Ala Glu Met Phe
130                 135                 140

Ile Arg Pro Ala Pro Gln His Leu Leu Gln Lys Leu Val Ala Ser Gly
145                 150                 155                 160

Glu Leu Thr Ala Glu Gln Ala Glu Leu Ala Thr Gln Val Pro Val Ala
                165                 170                 175

Asp Asp Ile Ala Val Glu Ala Asp Ser Gly Gly His Thr Asp Asn Arg
            180                 185                 190

Pro Ile His Val Ile Leu Pro Leu Ile Ile Asn Leu Arg Asn Arg Leu
    195                 200                 205

His Lys Glu Leu Asp Tyr Pro Ser His Leu Arg Val Arg Val Gly Ala
210                 215                 220

Gly Gly Gly Ile Gly Cys Pro Gln Ala Ala Leu Ala Ala Phe Gln Met
225                 230                 235                 240

Gly Ala Ala Phe Leu Ile Thr Gly Thr Val Asn Gln Leu Ala Arg Glu
                245                 250                 255

Ser Gly Thr Cys Asp Asn Val Arg Leu Gln Leu Ser Lys Ala Thr Tyr
            260                 265                 270

Ser Asp Val Cys Met Ala Pro Ala Ala Asp Met Phe Asp Gln Gly Val
        275                 280                 285

Glu Leu Gln Val Leu Lys Lys Gly Thr Leu Phe Pro Ser Arg Ala Lys
    290                 295                 300

Lys Leu Tyr Glu Leu Phe Cys Lys Tyr Asp Ser Phe Glu Ala Met Pro
305                 310                 315                 320

Ala Glu Glu Leu Gln Arg Val Glu Lys Arg Ile Phe Gln Lys Ser Leu
                325                 330                 335

Ala Glu Val Trp Gln Glu Thr Ser Asp Phe Tyr Ile His Arg Ile Lys
            340                 345                 350

Asn Pro Glu Lys Ile Asn Arg Ala Ala Ser Asp Gly Lys Leu Lys Met
        355                 360                 365

Ser Leu Cys Phe Arg Trp Tyr Leu Gly Leu Ser Ser Phe Trp Ala Asn
    370                 375                 380

Ser Gly Ala Gln Asp Arg Val Met Asp Tyr Gln Ile Trp Cys Gly Pro
385                 390                 395                 400

Ala Ile Gly Ala Phe Asn Asp Phe Thr Lys Gly Thr Tyr Leu Asp Val
                405                 410                 415
```

```
Thr Val Ala Lys Ser Tyr Pro Cys Val Ala Gln Ile Asn Leu Gln Ile
            420                 425                 430

Leu Gln Gly Ala Ala Tyr Leu Lys Arg Leu Gly Val Ile Arg Phe Asp
        435                 440                 445

Arg Met Leu Leu Gln Ala Val Asp Ile Asp Pro Val Phe Thr Tyr
    450                 455                 460

Val Pro Thr Gln Pro Leu
465             470
```

<210> SEQ ID NO 69
<211> LENGTH: 20
<212> TYPE: DNA
<213> ORGANISM: Artificial sequence
<220> FEATURE:
<223> OTHER INFORMATION: primer

<400> SEQUENCE: 69
ggyatgmtgr ttggtgaagg                                              20

<210> SEQ ID NO 70
<211> LENGTH: 22
<212> TYPE: DNA
<213> ORGANISM: Artificial sequence
<220> FEATURE:
<223> OTHER INFORMATION: primer

<400> SEQUENCE: 70
trttsasrta ytgygaacct tg                                           22

<210> SEQ ID NO 71
<211> LENGTH: 20
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: n = a c g or t

<400> SEQUENCE: 71
atgkcngaag gttgtggcca                                              20

<210> SEQ ID NO 72
<211> LENGTH: 23
<212> TYPE: DNA
<213> ORGANISM: Artificial sequence
<220> FEATURE:
<223> OTHER INFORMATION: primer

<400> SEQUENCE: 72
ccwgaratra agccrttdgg ttg                                          23

<210> SEQ ID NO 73
<211> LENGTH: 30
<212> TYPE: DNA
<213> ORGANISM: Artificial Sequence
<220> FEATURE:
<223> OTHER INFORMATION: primer

<400> SEQUENCE: 73
cggggtaccc gggagccgcc ttggctttgt                                   30

<210> SEQ ID NO 74
<211> LENGTH: 35

```
<212> TYPE: DNA
<213> ORGANISM: Artificial Sequence
<220> FEATURE:
<223> OTHER INFORMATION: primer

<400> SEQUENCE: 74
aaactgcagc ccgggtccag ctggcaggca ccctg                          35

<210> SEQ ID NO 75
<211> LENGTH: 798
<212> TYPE: DNA
<213> ORGANISM: Shewanella olleyana

<400> SEQUENCE: 75
atggcagaag gttgtggcca attattgcag ttcttcatgc tgcacattgg tatgcacacc    60
ttagttgaaa acgacgtttt ccagccttta gaaaatgctt cacaaaaagt acgttgtcgt   120
ggccaagtac tgccacaaca tggtgaactg acgtaccgca tggaagtcac agaaattggt   180
actcaccctc gcccatacgc caaagccaat attgaaatat tgctcaatgg taaagcggtc   240
gtggacttcc aaaatcttgg ggtgatgatt aagaagaag gtgaatgtac tcgttacact    300
gccgactcta ctgaaacaca tacaacctca ggcacagtcc aaaaaaacaa cagccacaac   360
acaccagcat cattaaatgc accgttaatg cacaagtgc cagacttaag tgaaccagcc    420
aataaaggcg ttatcccgct gcaacatgtt gaagcgccta tgctgccaga ctacccaaat   480
cgaacccctg atacgctgcc gttcaccgcg taccatatgt tgagtttgc aacaggtgac    540
atcgaaaact gttttggacc tgactttagt atttaccggg ctttattcc gccgcgcacg    600
ccatgtggtg acttacagct aacaacccgt gttgttgata ttcaaggtaa acgtggcgag   660
cttaaaaaac cgtcatcgtg tatcgctgaa atgaagtgc caaccgatgc gtggtatttt   720
gctaaaaaca gtcacgcttc agtgatgcct tactcggtat taatggaaat atcactgcaa   780
cccaacggct tcatctca                                                 798

<210> SEQ ID NO 76
<211> LENGTH: 1042
<212> TYPE: DNA
<213> ORGANISM: Shewanella olleyana

<400> SEQUENCE: 76
ggcatgatgg ttggtgaagg tatcggcatg gtagcactta agcgcctaga agatgctgag    60
cgtgatggcg accgtattta ttctgtgatt aaaggtgtcg gcgcttcatc agacggtaaa   120
tttaagagta tttatgcacc gcgccctgaa ggccaagcaa agcattaaa acgagcttat    180
gatgacgctg gttttgcccc tgaaacagtt ggcttaatcg aagctcacgg tacgggtact    240
gctgcaggtg atgtagccga atttaacggc cttaaatctg tatttggtga aaacgatcca    300
actaagcaac acatcgcttt aggttcagtg aaatcacaag tgggtcacac gaaatcaacc   360
gctggtactg ctggcgtgat taagctgcc cttgccctgc accataaagt attgccaccg   420
accattaacg tctctaagcc aaaccctaag cttaatgttg aggattcacc gtttttcgtt   480
aataccgaaa cacgcccatg gatgcctcgc cctgacggca ctcctcgccg tgctggtatt   540
agctcgttcg gttttggtgg aactaacttc cacttagtat tagaagaata cacccctgag   600
cacagccatg atgagaaata ccgtcaacgc caagtggctc aaagcttatt aatgagtgct   660
gataataaag cagccttgat tgcagaagtg aataagctaa ctgcagacat cagcgcgctt   720
aaaggcacag ataacagcag cattgaacaa gctgaacttg ctcgcattgc taaactatat   780
```

```
gctgttcgca ccatagatac ttcagcagcc cgtttaggtc ttgtggtatc aagccttaat    840
gaattaacca ctcagcttgg tttagcgtta aagcagctta ataatgatgt tgatgcatgg    900
caactgccat cagggactag ctaccgctct tcagcactca tcacgattaa tgcaaaccaa    960
aaggcgacta aagtaaaaaa agcgactaac gcaccgaaag ttgcagcatt gtttgcaggt   1020
caaggttcac aatacctcaa ca                                            1042
```

<210> SEQ ID NO 77  
<211> LENGTH: 806  
<212> TYPE: DNA  
<213> ORGANISM: Shewanella japonica

<400> SEQUENCE: 77

```
atggcggaag gttgtggcca attactgcaa ttctttatgc tgcacattgg tatgcacacg     60
ctcgttgaaa atggccgttt ccaaccactt gaaaatgctt cacaaaaagt gcgttgtcgt    120
ggtcaagttc tgccgcagca cggtgaactg acttaccgga tggaaatcac tgaaattggc    180
attcaccctc gcccatatgc caaagcgaat attgatattt gcttaacgg taaagcggtt     240 gtcgacttcc aaaacttagg tgtcatgatc aaagaagaaa gcgaatgtac gcgctacctt    300
aatgatacgc ccgctgtcga tgcctcagct gatcgaatta ttcagcaac caataatatt     360 ctatacccag cggcttcaac caatgcgcca ctcatggctc aactgcctga tttgaatgcc    420
ccaacgaata aaggcgttat cccactgcaa catgttgaag cgccgataat tccagattat    480
ccaaatcgta ctcctgatac cctgccattc acggcgtatc acatgttcga atttgccact    540
ggcaatattg aaaactgctt tggaccggac tttagtattt accgtggttt cattccaccg    600
cgcacaccat gtggcgactt acagctaacg actcgtattg ttgatattca aggtaaacgt    660
ggcgaattga aaaagccatc atcgtgtatc gcagaatatg aagtgccaac tgatgcatgg    720
tatttcgcta aaaacagcca cgcctcggtc ataccttatt cagtgttgat ggaaatttca    780
ctgcaaccca atggcttcat ctcagg                                         806
```

<210> SEQ ID NO 78  
<211> LENGTH: 1042  
<212> TYPE: DNA  
<213> ORGANISM: Shewanella japonica

<400> SEQUENCE: 78

```
ggtatgctgg ttggtgaagg cattggcatg gtggcattaa aacgtcttga agatgctgag     60
cgtgacggtg accgtattta ctcagtcatt aaagggggtcg cgcttcatc tgatggtaag    120 ttcaaatcaa tttatgcacc tcgacctgaa ggccaagcta aagcgctgaa gcgtgcttat    180
gatgacgccg gctttgcacc tgaaaccgtt ggcttaattg aagctcacgg aacaggcact    240
gcagcgggtg atgtggcaga atttaatggt cttaaatctg tatttggtga gaatgactca    300
acaaagcaac acattgcttt aggttcagtt aagtcacaag tgggccatac taaatcaact    360
gcgggaaccg cgggtgtgat taagcggcg ttagcactgc atcataaagt gctgccgcca    420
accatcaacg tctctaagcc taaccctaag cttaatgttg aggattcacc gttttttcatt    480 aacactgaaa ctcgccccttg gatgcctcgc cctgatggca caccacgccg agctggtata    540
agttcgttcg gttttggtgg cacaaactcc cacttagtac tagaagaata cagcccagag    600
cacagccgtg atgagaaata tcgtcagcgc caagtagcac aaagcttatt gattagcgct    660
gacaataaag ctgagctcat tgcagaaatc aacaagctta acgctgacat cagcgcgctt    720
aaaggcacag ataacagcag catcgaacaa gctgaacttg cccgcattgc taaactatat    780
```

-continued

```
gctgttcgca ctttagatac ttcagcagtc cgtttgggtc ttgtggtctc aagccttaat      840
gaattaacca ctcaacttgg tttagcgtta aagcagctaa gtaacgacgc tgaagcatgg      900
caattaccat caggtacgag ctatcgctca tctgcgctca tcacgattaa tgccaaccaa      960
aagacgacta aaggtaaaaa agcagctaac acaccgaaag tagcagcatt atttgcaggt     1020
caaggttcgc aatatctcaa ca                                              1042

<210> SEQ ID NO 79
<211> LENGTH: 6
<212> TYPE: DNA
<213> ORGANISM: Artificial Sequence
<220> FEATURE:
<223> OTHER INFORMATION: restriction enzyme site

<400> SEQUENCE: 79 catatg                                                                   6

<210> SEQ ID NO 80
<211> LENGTH: 192
<212> TYPE: DNA
<213> ORGANISM: Schizochytrium sp.
<220> FEATURE:
<221> NAME/KEY: misc_feature
<222> LOCATION: (1)..(7)
<223> OTHER INFORMATION: BspHI restriction site
<220> FEATURE:
<221> NAME/KEY: misc_feature
<222> LOCATION: (188)..(192)
<223> OTHER INFORMATION: SacII restriction site

<400> SEQUENCE: 80
tcatgaagcc ggttgctccg aagttctacg cgcgtctcaa cattgacgag caggacgaga       60
cccgtgatcc gatcctcaac aaggacaacg cgccgtcttc cagctctagc tcctcttcca      120
gctcttccag ctcttccagc ccgtcgccag ctccgtccgc cccagtgcaa agaaggctg       180 ctccggccgc gg                                                          192

<210> SEQ ID NO 81
<211> LENGTH: 717
<212> TYPE: DNA
<213> ORGANISM: Nostoc sp.
<220> FEATURE:
<221> NAME/KEY: CDS
<222> LOCATION: (4)..(714)

<400> SEQUENCE: 81 taa ttg ttg cag cat act tgg cta cca aaa ccc cca aat tta acc tta        48
    Leu Leu Gln His Thr Trp Leu Pro Lys Pro Pro Asn Leu Thr Leu
    1               5                   10                  15 ttg tca gat gaa gtt cat ctc tgg cgc att ccc ctt gac caa cca gaa        96
Leu Ser Asp Glu Val His Leu Trp Arg Ile Pro Leu Asp Gln Pro Glu
                20                  25                  30 tca cag cta cag gat tta gcc gct acc tta tct agt gac gaa tta gcc       144
Ser Gln Leu Gln Asp Leu Ala Ala Thr Leu Ser Ser Asp Glu Leu Ala
            35                  40                  45 cgt gca aac aga ttt tat ttt ccc gaa cat cgc cgg cgt ttt act gct       192
Arg Ala Asn Arg Phe Tyr Phe Pro Glu His Arg Arg Arg Phe Thr Ala
        50                  55                  60 ggt cgt ggt att ctc cgc agt atc ttg ggg ggc tat ttg ggt gtg gaa       240
Gly Arg Gly Ile Leu Arg Ser Ile Leu Gly Gly Tyr Leu Gly Val Glu
    65                  70                  75 cca ggg caa gtt aaa ttt gat tat gaa tcc cgt ggt aaa cca ata tta       288
```

```
Pro Gly Gln Val Lys Phe Asp Tyr Glu Ser Arg Gly Lys Pro Ile Leu
 80              85                  90                  95 ggc gat cgc ttt gcc gag agt ggt tta tta ttt aac ttg tca cac tcc      336
Gly Asp Arg Phe Ala Glu Ser Gly Leu Leu Phe Asn Leu Ser His Ser
            100                 105                 110 cag aac ttg gcc ttg tgt gca gtc aat tac acg cgc caa atc ggc atc      384
Gln Asn Leu Ala Leu Cys Ala Val Asn Tyr Thr Arg Gln Ile Gly Ile
            115                 120                 125 gat tta gaa tat ctc cgc ccc aca tct gat tta gaa tcc ctt gcc aaa      432
Asp Leu Glu Tyr Leu Arg Pro Thr Ser Asp Leu Glu Ser Leu Ala Lys
            130                 135                 140 agg ttc ttt tta ccg cga gaa tat gaa tta ttg cga tcg cta ccc gat      480
Arg Phe Phe Leu Pro Arg Glu Tyr Glu Leu Leu Arg Ser Leu Pro Asp
145                 150                 155 gag caa aaa caa aaa att ttc ttt cgt tac tgg act tgt aaa gag gct      528
Glu Gln Lys Gln Lys Ile Phe Phe Arg Tyr Trp Thr Cys Lys Glu Ala
160                 165                 170                 175 tat ctt aaa gca acg ggt gac ggc atc gct aaa tta gag gaa att gaa      576
Tyr Leu Lys Ala Thr Gly Asp Gly Ile Ala Lys Leu Glu Glu Ile Glu
                180                 185                 190 ata gca cta act ccc aca gaa cca gct aag tta cag aca gct cca gcg      624
Ile Ala Leu Thr Pro Thr Glu Pro Ala Lys Leu Gln Thr Ala Pro Ala
            195                 200                 205 tgg agt ctc cta gag cta gtg cca gat gat aat tgt gtt gct gct gtt      672
Trp Ser Leu Leu Glu Leu Val Pro Asp Asp Asn Cys Val Ala Ala Val
            210                 215                 220 gcc gtg gcg ggt ttt ggc tgg cag cca aaa ttc tgg cat tat tga          717
Ala Val Ala Gly Phe Gly Trp Gln Pro Lys Phe Trp His Tyr
225                 230                 235

<210> SEQ ID NO 82
<211> LENGTH: 237
<212> TYPE: PRT
<213> ORGANISM: Nostoc sp.

<400> SEQUENCE: 82

Leu Leu Gln His Thr Trp Leu Pro Lys Pro Asn Leu Thr Leu Leu
1               5                   10                  15

Ser Asp Glu Val His Leu Trp Arg Ile Pro Leu Asp Gln Pro Glu Ser
            20                  25                  30

Gln Leu Gln Asp Leu Ala Ala Thr Leu Ser Ser Asp Glu Leu Ala Arg
        35                  40                  45

Ala Asn Arg Phe Tyr Phe Pro Glu His Arg Arg Phe Thr Ala Gly
    50                  55                  60

Arg Gly Ile Leu Arg Ser Ile Leu Gly Gly Tyr Leu Gly Val Glu Pro
65                  70                  75                  80

Gly Gln Val Lys Phe Asp Tyr Glu Ser Arg Gly Lys Pro Ile Leu Gly
                85                  90                  95

Asp Arg Phe Ala Glu Ser Gly Leu Leu Phe Asn Leu Ser His Ser Gln
            100                 105                 110

Asn Leu Ala Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175
```

```
-continued

Leu Lys Ala Thr Gly Asp Gly Ile Ala Lys Leu Glu Glu Ile Glu Ile
            180             185                 190

Ala Leu Thr Pro Thr Glu Pro Ala Lys Leu Gln Thr Ala Pro Ala Trp
        195             200                 205

Ser Leu Leu Glu Leu Val Pro Asp Asp Asn Cys Val Ala Ala Val Ala
    210             215                 220

Val Ala Gly Phe Gly Trp Gln Pro Lys Phe Trp His Tyr
225             230                 235
```